(12) United States Patent
Schiller et al.

(10) Patent No.: US 12,139,487 B2
(45) Date of Patent: Nov. 12, 2024

(54) COMPOUNDS AND USES THEREOF

(71) Applicant: Foghorn Therapeutics Inc., Indianapolis, IN (US)

(72) Inventors: Shawn E. R. Schiller, Haverhill, MA (US); Solymar Negretti, Watertown, MA (US); David S. Huang, Cambridge, MA (US); Kevin J. Wilson, Roslindale, MA (US); Melek Nihan Ucisik, Medford, MA (US); Richard Caldwell, Melrose, MA (US)

(73) Assignee: Foghorn Therapeutics Inc., Cambridge, MA (US)

( * ) Notice: Subject to any disclaimer, the term of this patent is extended or adjusted under 35 U.S.C. 154(b) by 0 days.

(21) Appl. No.: 18/315,526

(22) Filed: May 11, 2023

(65) Prior Publication Data

US 2023/0365560 A1    Nov. 16, 2023

Related U.S. Application Data

(60) Provisional application No. 63/340,927, filed on May 11, 2022.

(51) Int. Cl.
| | |
|---|---|
| *C07D 471/04* | (2006.01) |
| *A61K 45/06* | (2006.01) |
| *C07D 519/00* | (2006.01) |

(52) U.S. Cl.
CPC ............ *C07D 471/04* (2013.01); *A61K 45/06* (2013.01); *C07D 519/00* (2013.01); *C07B 2200/05* (2013.01)

(58) Field of Classification Search
CPC .. C07D 471/04; C07D 519/00; C07D 411/14; A61K 45/06; C07B 2200/05; A61P 35/00
See application file for complete search history.

(56) References Cited

U.S. PATENT DOCUMENTS

2014/0256719 A1    9/2014   Finlay et al.

FOREIGN PATENT DOCUMENTS

| WO | 2007/127183 A1 | 11/2007 | | |
|---|---|---|---|---|
| WO | 2015/095788 A1 | 6/2015 | | |
| WO | 2016/016316 A1 | 2/2016 | | |
| WO | 2021/155316 A1 | 8/2021 | | |
| WO | WO-2021155320 A1 | * | 8/2021 | ......... A61K 31/4433 |
| WO | WO-2022103899 A1 | * | 5/2022 | ............. A61P 35/00 |

OTHER PUBLICATIONS

Luo et al. Principles of Cancer Therapy: Oncogene and Non-oncogene Addiction (Cell, 136, pp. 823-837) (Year: 2009).*
Wang et al. Molecular Pathways: SWI/SNF (BAF) Complexes Are Frequently Mutated in Cancer—Mechanisms and Potential Therapeutic Insights (Clin Cancer Res; 20:1, 21-27) (Year: 2014).*
PCT International Search Report and the Written Opinion of the International Searching Authority pertaining to international Application No. PCT/2021/058865; Date of Mailing: Mar. 17, 2022, 9 pages.
National Center for Biotechnology Information. "PubChem Compound Summary for CID 90386125" PubChem, https://pubchem.ncbi.nlm.nih.gov/compound/90386125. Accessed Apr. 17, 2023.

* cited by examiner

*Primary Examiner* — Matthew P Coughlin
*Assistant Examiner* — Meghan C Heasley
(74) *Attorney, Agent, or Firm* — Bradley W. Crawford

(57) ABSTRACT

The present disclosure features compounds of Formula I,

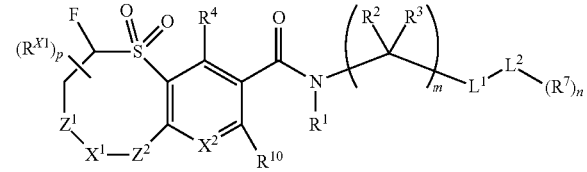

Formula I or pharmaceutically acceptable salts thereof, and formulations containing the same. Methods of treating BAF complex-related disorders, such as cancer, are also disclosed.

102 Claims, 14 Drawing Sheets

COMPOUNDS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In one aspect, the invention provides a compound having the structure:

Formula I

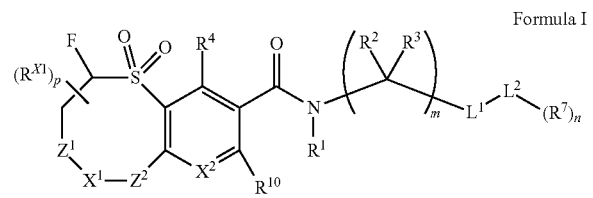

where m is 0, 1, 2, or 3;

n is 0, 1, 2, 3, or 4;

p is 0, 1, 2, or 3;

$X^1$ is O, $NR^5$, or $(C(R^5)(R^8))$, and each of $Z^1$ and $Z^2$ is independently absent or $(C(R^9)_2)$ or O, provided that, if $X^1$ is O, then each of $Z^1$ and $Z^2$ is independently absent or $(C(R^9)_2)$;

$X^2$ is N or $CR^8$;

each $R^{X1}$ is independently deuterium, optionally substituted $C_1$-$C_6$ alkyl, or halo, or two geminal $R^{X1}$ groups, together with the atom to which they are attached, combine to form a carbonyl;

$L^1$ is optionally substituted 9- or 10-membered bicyclic heterocyclyl, optionally substituted 9- or 10-membered bicyclic heteroaryl, optionally substituted monocyclic 6-membered heteroarylvinyl, optionally substituted monocyclic 6-membered heteroaryl-$C_3$-$C_8$-cycloalkyl, or optionally substituted monocyclic 6-membered heteroarylethynyl;

$L^2$ is absent, optionally substituted $C_3$-$C_{10}$ cycloalkyl, optionally substituted $C_6$-$C_{10}$ aryl, optionally substituted 5- to 10-membered heteroaryl, or optionally substituted 4- to 10-membered heterocyclyl;

$R^1$ is hydrogen or optionally substituted $C_1$-$C_6$ alkyl;

each $R^2$ and each $R^3$ are independently hydrogen, optionally substituted $C_1$-$C_6$ alkyl, or optionally substituted $C_1$-$C_6$ heteroalkyl;

$R^4$ is hydrogen, halo, optionally substituted $C_1$-$C_6$ alkyl, or optionally substituted $C_3$-$C_{10}$ cycloalkyl;

$R^5$ is hydrogen, deuterium, or optionally substituted $C_1$-$C_6$ alkyl;

$R^6$ is hydrogen, deuterium, optionally substituted $C_1$-$C_6$ alkyl, or halo, and each $R^9$ is independently hydrogen, deuterium, optionally substituted $C_1$-$C_6$ alkyl, or halo; or $R^6$ and one vicinal $R^9$, together with the atoms to which they are attached combine to form optionally substituted $C_3$-$C_8$ cycloalkyl, and the remaining $R^9$ groups, if present, are independently deuterium, optionally substituted $C_1$-$C_6$ alkyl, or halo;

each $R^7$ is independently optionally substituted $C_1$-$C_6$ alkyl, optionally substituted $C_1$-$C_6$ heteroalkyl, halo, optionally substituted $C_3$-$C_{10}$ cycloalkyl, optionally substituted 5- to 10-membered heteroaryl, optionally substituted 4- to 10-membered heterocyclyl, $—N(R^{7A})_2$, or $—OR^{7A}$, wherein each $R^{7A}$ is independently H, optionally substituted $C_1$-$C_6$ alkyl, optionally substituted $C_1$-$C_6$ heteroalkyl, optionally substituted $C_3$-$C_{10}$ cycloalkyl, optionally substituted $C_6$-$C_{10}$ aryl, optionally substituted 5- to 10-membered heteroaryl, or optionally substituted 4- to 10-membered heterocyclyl, or two geminal $R^{7A}$ groups, together with the atom to which they are attached, combine to form optionally substituted 5- to 10-membered heteroaryl or optionally substituted 4- to 10-membered heterocyclyl;

$R^8$ is hydrogen, halo, cyano, optionally substituted $C_1$-$C_6$ alkyl, optionally substituted $C_2$-$C_6$ alkynyl, optionally substituted $C_1$-$C_6$ heteroalkyl, or optionally substituted $C_3$-$C_{10}$ cycloalkyl; and $R^{10}$ is hydrogen or halo;

or a pharmaceutically acceptable salt thereof.

In some embodiments, $Z^1$ is $(C(R^9)_2)$. In some embodiments, $Z^1$ is absent. In some embodiments, $Z^1$ is O.

In some embodiments, $Z^2$ is $(C(R^9)_2)$. In some embodiments, $Z^2$ is absent. In some embodiments, $Z^2$ is O.

In some embodiments, $X^1$ is O. In some embodiments, $X^1$ is $NR^5$. In some embodiments, $X^1$ is $(C(R^5)(R^6))$.

In some embodiments, $X^2$ is $CR^8$.

In some embodiments, the group

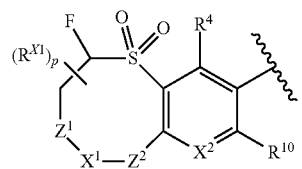

is a group of the following structure

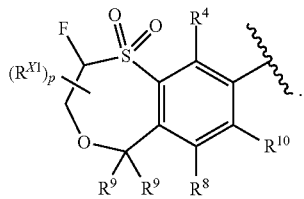

In some embodiments, the group

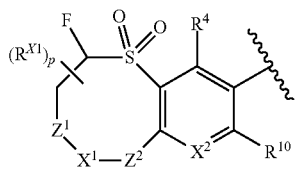

is a group of the following structure

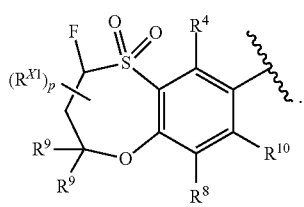

In some embodiments, the group

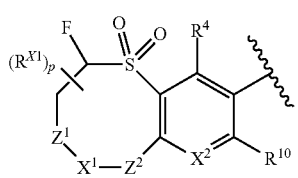

is a group of the following structure

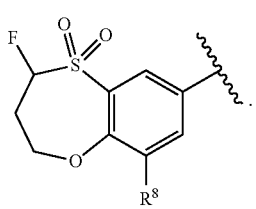

In some embodiments, the group

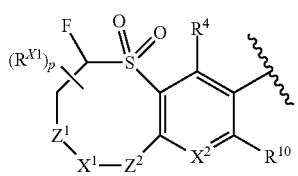

is a group of the following structure

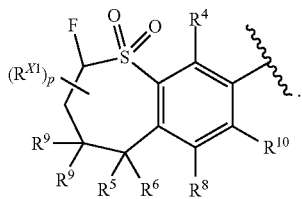

In some embodiments, the group

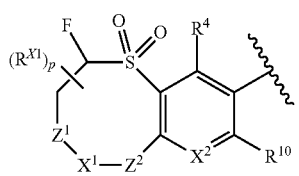

In some embodiments, the group

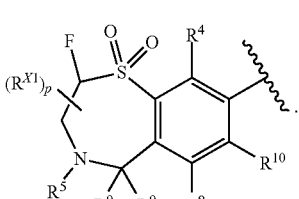

In some embodiments, the group

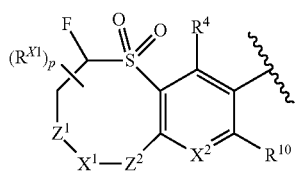

is a group of the following structure

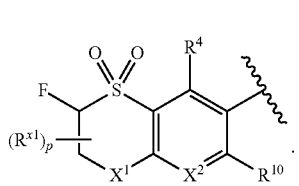

In some embodiments, the group

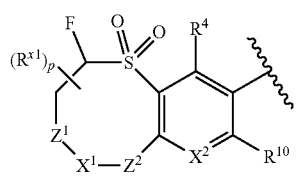

is a group of the following structure

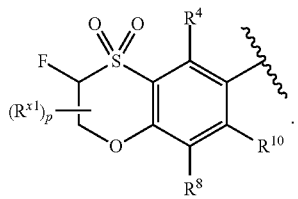

In some embodiments, the group

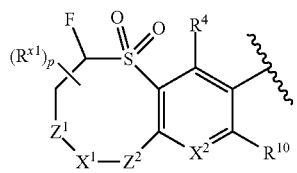

is a group of the following structure

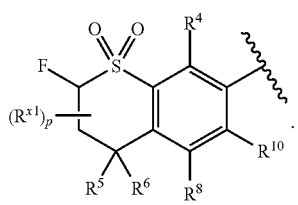

In some embodiments, the group

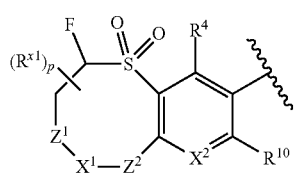

is a group of the following structure

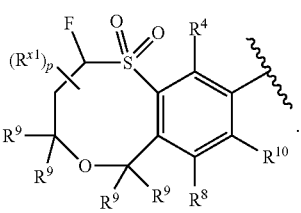

In some embodiments, the group

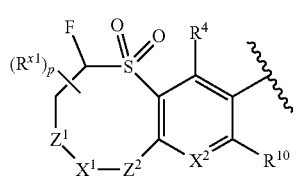

is a group of the following structure

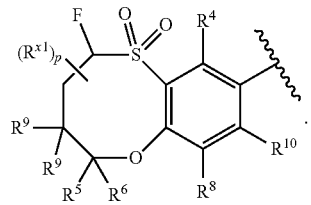

In some embodiments, $R^8$ is hydrogen. In some embodiments, $R^8$ is halo (e.g., fluoro). In some embodiments, $R^8$ is optionally substituted $C_2$-$C_6$ alkynyl. In some embodiments, $R^8$ is optionally substituted $C_1$-$C_6$ heteroalkyl. In some embodiments, $R^8$ is optionally substituted $C_3$-$C_{10}$ cycloalkyl.

In some embodiments, $X^2$ is N.

In some embodiments, the group

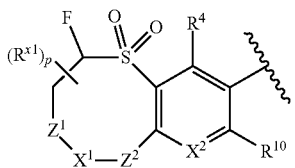

is a group of the following structure

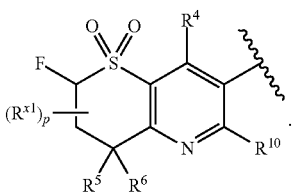

In some embodiments, $R^4$ is hydrogen. In some embodiments, $R^4$ is halogen.

In some embodiments, $R^{10}$ is hydrogen. In some embodiments, $R^{10}$ is halogen.

In some embodiments, at least one $R^{X1}$ is optionally substituted $C_1$-$C_6$ alkyl. In some embodiments, at least one $R^{X1}$ is halo. In some embodiments, at least one $R^{X1}$ is deuterium.

In some embodiments, p is 3. In some embodiments, p is 2. In some embodiments, p is 1. In some embodiments, p is 0.

In some embodiments, $L^1$ is optionally substituted 9- or 10-membered bicyclic heteroaryl. In some embodiments, $L^1$ is Formula A

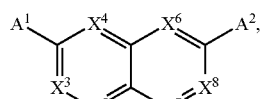

wherein
  each of $X^3$, $X^4$, $X^5$, $X^6$, $X^7$, and $X^8$ is independently N or $CR^{L1}$;
  each $R^{L1}$ is independently H, halo, optionally substituted $C_1$-$C_6$ alkyl;
  $A^1$ is a bond to —$(C(R^2)(R^3))_m$—; and
  $A^2$ is a bond to $L^2$.

In some embodiments, $L^1$ is

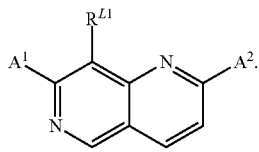

In some embodiments, $R^{L1}$ is hydrogen.

In some embodiments, $L^1$ is

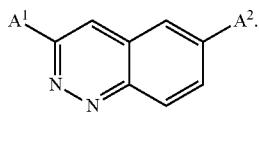

In some embodiments, $L^1$ is

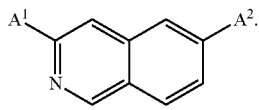

In some embodiments, $L^1$ is optionally substituted monocyclic 6-membered heteroarylvinyl.

In some embodiments, $L^1$ is

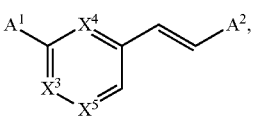
Formula B wherein
  each of $X^3$, $X^4$, and $X^5$ is independently N or $CR^{L1}$;
  each $R^{L1}$ is independently H, halo, optionally substituted $C_1$-$C_6$ alkyl;
  $A^1$ is a bond to —$(C(R^2)(R^3))_m$—; and
  $A^2$ is a bond to $L^2$.

In some embodiments, $L^1$ is

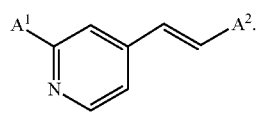

In some embodiments, $L^1$ is optionally substituted monocyclic 6-membered heteroarylethynyl.

In some embodiments, $L^1$ is

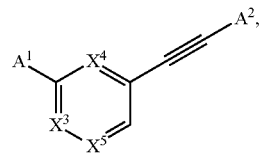
Formula C wherein
  each of $X^3$, $X^4$, and $X^5$ is independently N or $CR^{L1}$;
  each $R^{L1}$ is independently H, halo, optionally substituted $C_1$-$C_6$ alkyl;
  $A^1$ is a bond to —$(C(R^2)(R^3))_m$—; and
  $A^2$ is a bond to $L^2$.

In some embodiments, $L^1$ is

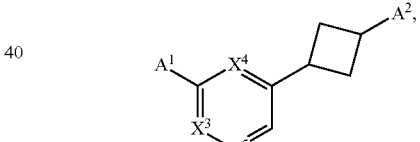

In some embodiments, $L^1$ is optionally substituted monocyclic 6-membered heteroaryl-$C_3$-$C_8$-cycloalkyl.

In some embodiments, $L^1$ is

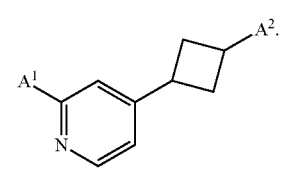
Formula D wherein
  each of $X^3$, $X^4$, and $X^5$ is independently N or $CR^{L1}$;
  each $R^{L1}$ is independently H, halo, optionally substituted $C_1$-$C_6$ alkyl;
  $A^1$ is a bond to —$(C(R^2)(R^3))_m$—; and
  $A^2$ is a bond to $L^2$.

In some embodiments, $L^1$ is

In some embodiments, $L^1$ is optionally substituted 9- or 10-membered bicyclic heterocyclyl.

In some embodiments, the compound has the structure:
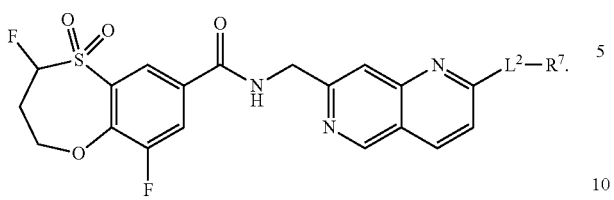
In some embodiments, $L^2$ is optionally substituted 5- to 10-membered heteroaryl.
In some embodiments, $-L^2-(R^7)_n$ is a group of the following structure:
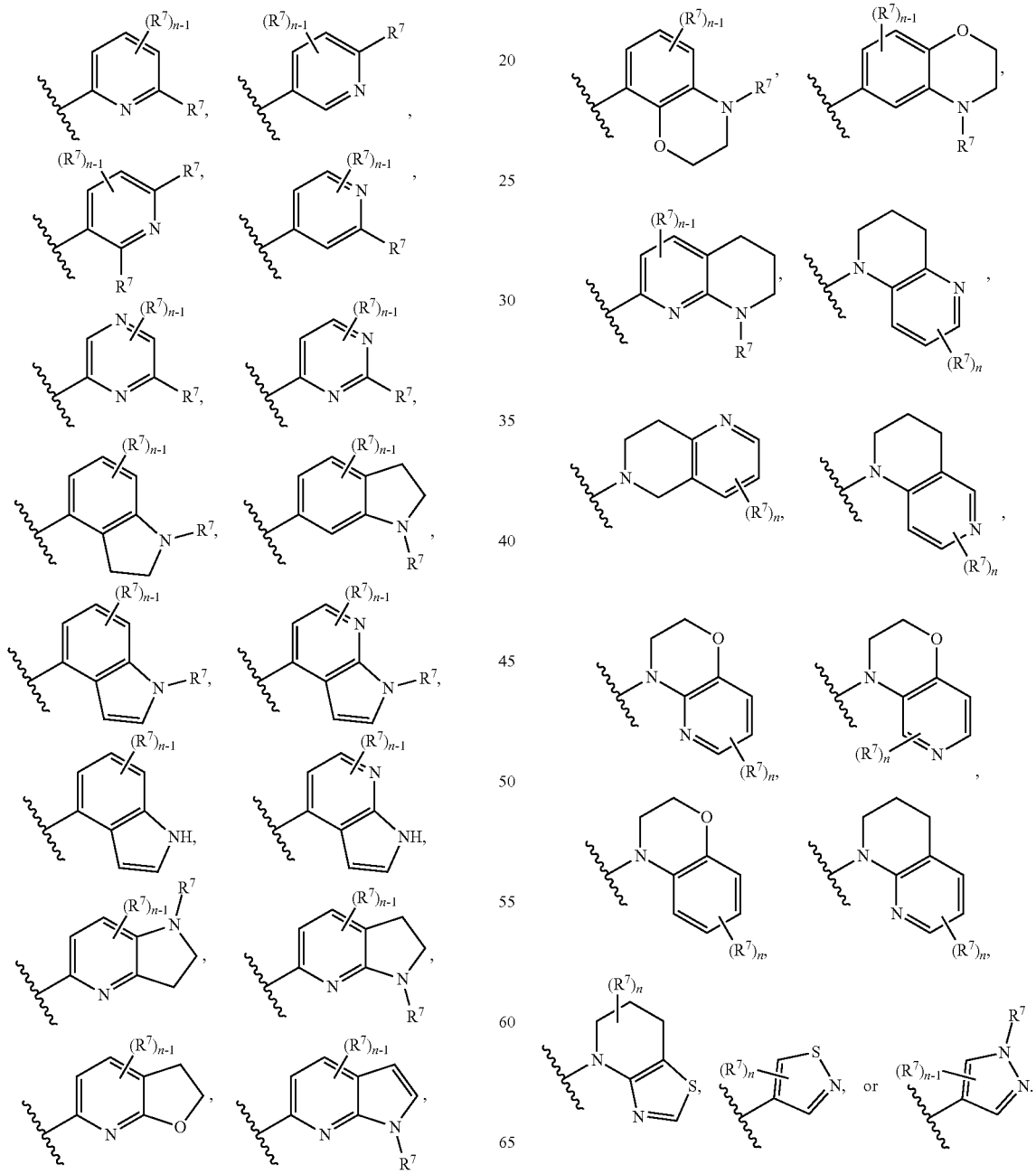
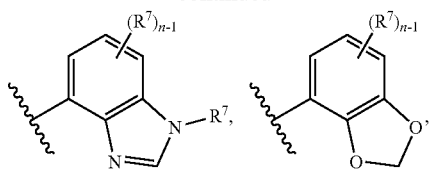
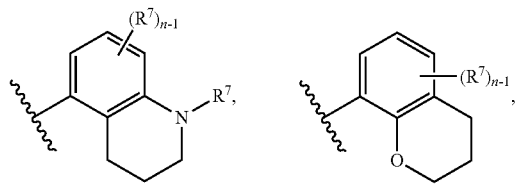
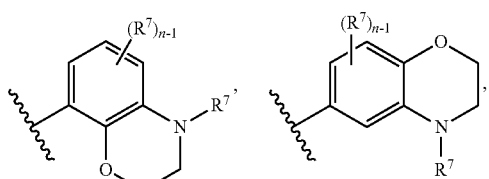
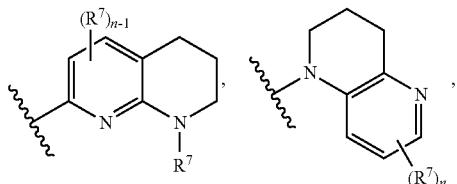
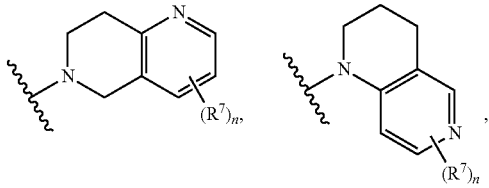
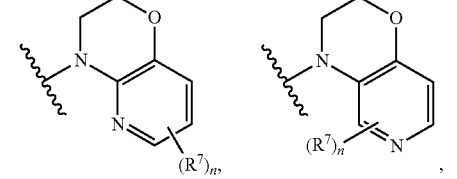
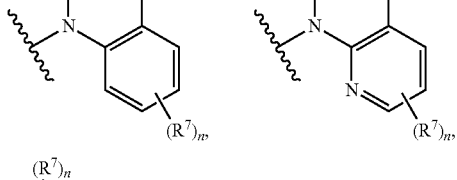
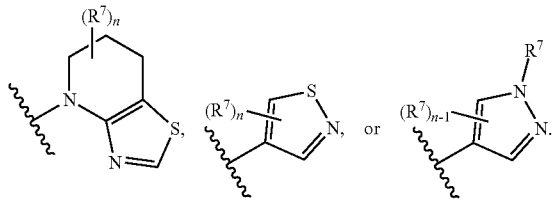

In some embodiments, -L²-(R⁷)ₙ is a group of the following structure:
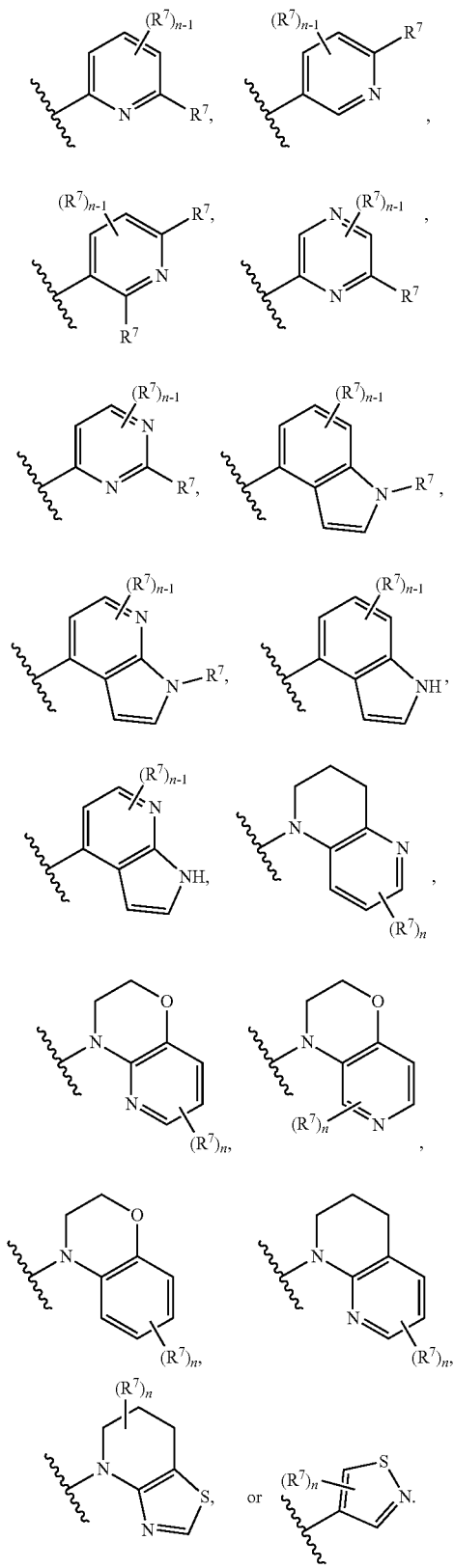
In some embodiments, -L²-(R⁷)ₙ is a group of the following structure:
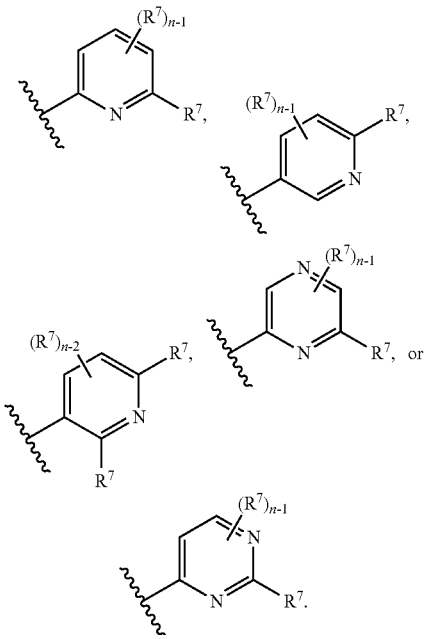
In some embodiments, -L²-(R⁷)ₙ is a group of the following structure:
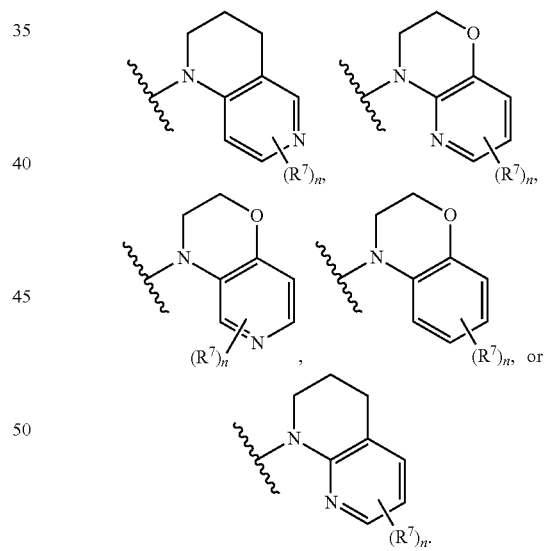
In some embodiments, -L²-(R⁷)ₙ is a group of the following structure:
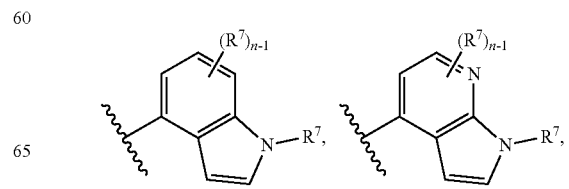

-continued

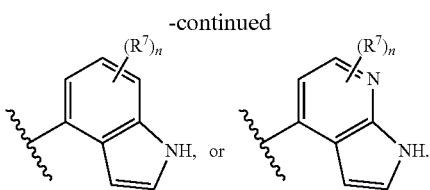

In some embodiments, -L²-(R⁷)ₙ is a group of the following structure:

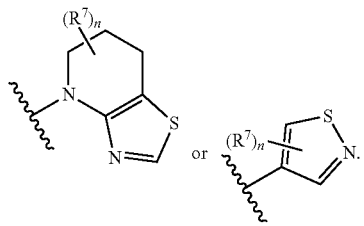

In some embodiments, L² is optionally substituted $C_6$-$C_{10}$ aryl. In some embodiments, L² is optionally substituted phenyl.

In some embodiments, n is 1. In some embodiments, n is 2. In some embodiments, n is 3.

In some embodiments, R⁷ is optionally substituted $C_1$-$C_6$ alkyl. In some embodiments, R⁷ is optionally substituted $C_1$-$C_6$ heteroalkyl. In some embodiments, R⁷ is optionally substituted 4- to 10-membered heterocyclyl. In some embodiments, R⁷ is optionally substituted azetidinyl or optionally substituted morpholinyl. In some embodiments, R⁷ is optionally substituted $C_3$-$C_{10}$ cycloalkyl. In some embodiments, R⁷ is optionally substituted cyclopropyl or optionally substituted cyclobutyl. In some embodiments, R⁷ is —N(R$^{7A}$)₂. In some embodiments, R⁷ is optionally substituted N-azetidinyl or optionally substituted N-morpholinyl. In some embodiments, two geminal R⁷ groups, together with the atom to which they are attached, combine to form optionally substituted 4- to 10-membered heterocyclyl. In some embodiments, at least one R⁷ is —OR$^{7A}$. In some embodiments, R$^{7A}$ is optionally substituted $C_{1-6}$ alkyl.

In some embodiments, n is 0.

In some embodiments, at least one R⁷ is difluoromethyl, cyclopropyl, 2,2-difluorocyclopropyl, difluoromethoxy, 2,6-dimethylmorpholin-4-yl, N-azetidinyl, 3-fluorocyclobutyl, 2-methoxyethyl, ethoxy, methoxy, 2,2-difluoroethoxy, 2,2-difluoroethyl, trifluoromethyl, isopropyl, methyl, acetyl, fluoro, chloro, 1-methylpyrazol-3-yl, dimethylamino, N-methyl-N-(2-methoxyethyl)-amino, N-ethyl-N-(2-methoxyethyl)-amino, N-(2-propyl)-N-(2-methoxyethyl)-amino, 2-methoxyethylamino, 3-aza-8-oxa-bicyclo[4.3.0]non-3-yl, 3-aza-7-oxa-bicyclo[4.3.0]non-3-yl, 1-fluorocyclobut-1-yl, 3-fluoropyrrolidin-1-yl, 3-methoxypyrrolidin-1-yl, oxetan-3-yl, N-methylindolin-4-yl, 2,2-difluoro-3-methylcycloprop-1-yl, 3-methoxyazetidin-1-yl, 3-methoxypiperidin-1-yl, 1,2-dimethyl-7-azaindol-4-yl, 1-methyl-7-azaindol-4-yl, 2,3-methylenedioxyphenyl, N-methyl-N-(3-oxetanyl)amino, 3-oxetanyloxy, 1,1-difluoro-5-azaspiro[2.3]hex-5-yl, 1-fluoromethyl-cyclopropyl, N-(3-tetrahydrofuranyl)methylamino, N-indolinyl, N-1,4-oxazepanyl, 2-fluoro-2-propyl, 1,1-difluoro-2-propyl, 2,2-difluoro-1-methylcycloprop-1-yl, 1-methylcyclopropyl, 4,4-difluoropiperidin-1-yl, 2-methoxyethoxy, 3,3-difluorocyclobut-1-yl, N-methyl-N-1-methoxyprop-2-ylamino, 1-methoxyprop-2-ylamino, 1-methoxyethyl, 4-methylpiperazinyl, 3-methylmorpholinyl, 2,2-difluoropropoxy, 3-methoxycyclobutyl, methylamino, 4-dimethylamino-3,3-difluoropiperidinyl, 4-methylamino-3,3-difluoropiperidinyl, 3,3-difluoropyrrolidinyl, N-methyl-N-3-methoxycyclobutylamino, 1-methylpyrazol-5-yl, 6-oxa-3-azabicyclo[3.1.1]hept-3-yl, cyclopropyloxy, 2,6-dimethylpyrid-4-yl, 2-methylpyrrolidinyl, 4-oxabicyclo[4.1.0]hept-1-yl, N-methyl-N-(2,6-dimethyltetrahydropyran-4-yl)amino, or N-methyl-N-3-methyloxetan-3-ylmethylamino.

In some embodiments, R¹ is hydrogen.
In some embodiments, the group

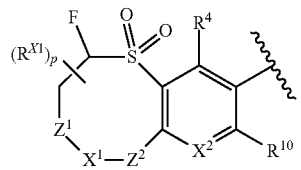

is a group of the following structure

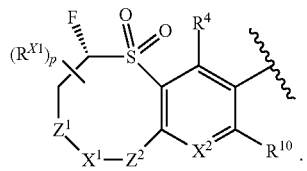

In some embodiments, the group

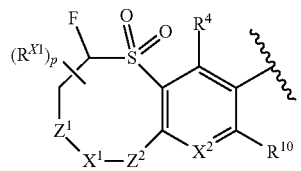

is a group of the following structure

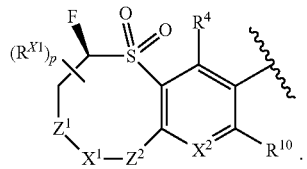

In some embodiments, the compound is selected from the group consisting of compounds 1-523 and pharmaceutically acceptable salts thereof.

TABLE 1
Compounds of the invention
| # | Structure |
|---|---|
| 1 | 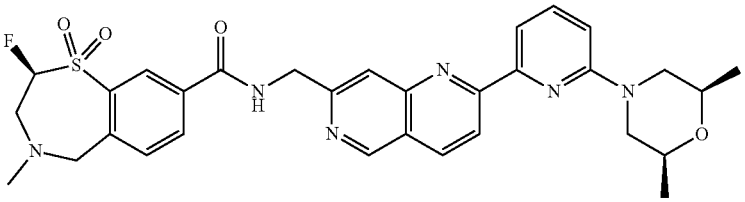 |
| 2 | 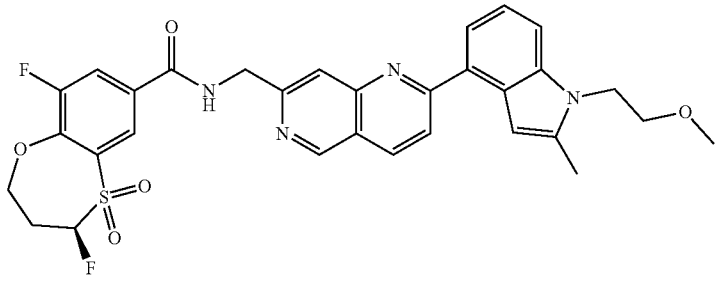 [SMILES: COCCn1c(C)cc2c(-c3ccc4cnc(CNC(=O)c5cc(F)c6c(c5)S(=O)(=O)[C@@H](F)CCO6)cc4n3)cccc21] |
| 3 | 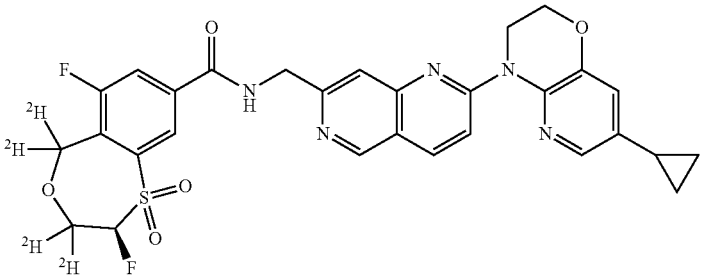 [SMILES: [2H]C1([2H])OC([2H])([2H])[C@H](F)S(=O)(=O)c2cc(C(=O)NCc3cc4nc(N5CCOc6cc(C7CC7)cnc65)ccc4cn3)cc(F)c21] |
| 4 | 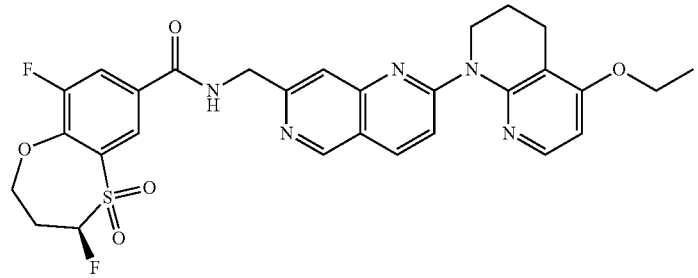 [SMILES: CCOc1ccnc2c1CCCN2c1ccc2cnc(CNC(=O)c3cc(F)c4c(c3)S(=O)(=O)[C@@H](F)CCO4)cc2n1] |
| 5 | 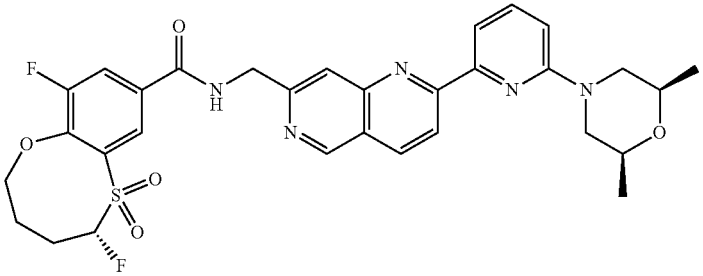 [SMILES: C[C@@H]1CN(c2cccc(-c3ccc4cnc(CNC(=O)c5cc(F)c6c(c5)S(=O)(=O)[C@H](F)CCCO6)cc4n3)n2)C[C@H](C)O1] |

TABLE 1-continued

Compounds of the invention

| # | Structure |
|---|---|
| 6 | 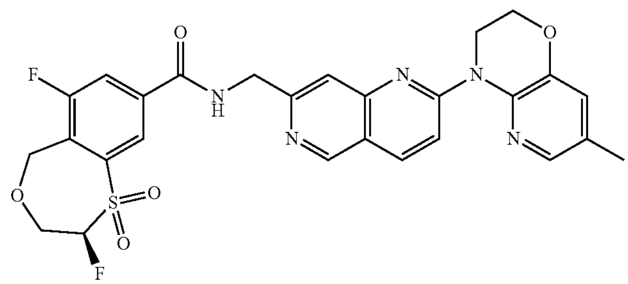 [SMILES: Cc1cnc2c(c1)OCCN2c1ccc2cnc(CNC(=O)c3cc(F)c4c(c3)S(=O)(=O)[C@@H](F)COC4)cc2n1] |
| 7 | 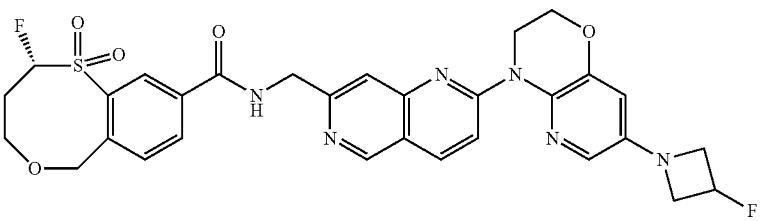 [SMILES: O=C(NCc1cc2nc(N3CCOc4cc(N5CC(F)C5)cnc43)ccc2cn1)c1ccc2c(c1)S(=O)(=O)[C@@H](F)CCOC2] |
| 8 | 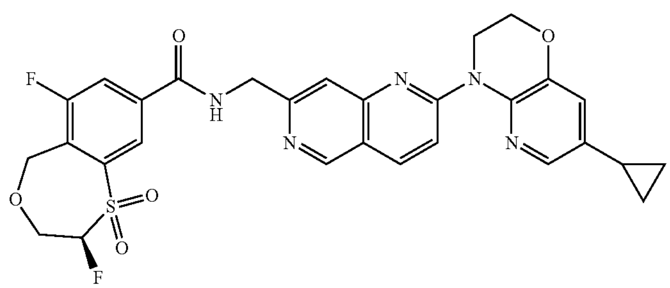 [SMILES: O=C(NCc1cc2nc(N3CCOc4cc(C5CC5)cnc43)ccc2cn1)c1cc(F)c2c(c1)S(=O)(=O)[C@@H](F)COC2] |
| 9 | 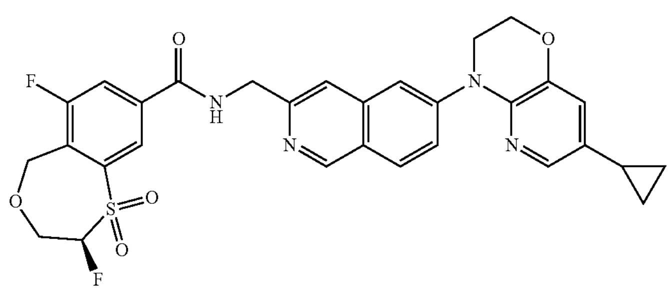 [SMILES: O=C(NCc1cc2cc(N3CCOc4cc(C5CC5)cnc43)ccc2cn1)c1cc(F)c2c(c1)S(=O)(=O)[C@@H](F)COC2] |
| 10 | 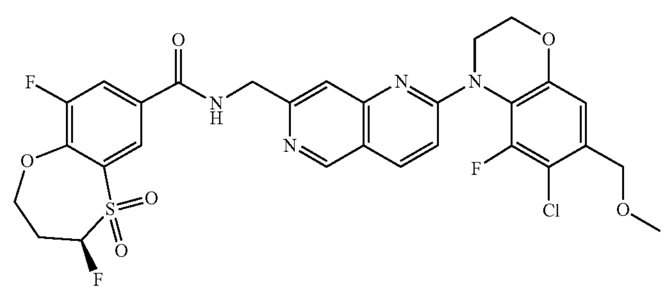 [SMILES: COCc1cc2c(c(F)c1Cl)N(c1ccc3cnc(CNC(=O)c4cc(F)c5c(c4)S(=O)(=O)[C@@H](F)CCO5)cc3n1)CCO2] |

TABLE 1-continued
Compounds of the invention
| # | Structure |
|---|-----------|
| 11 | 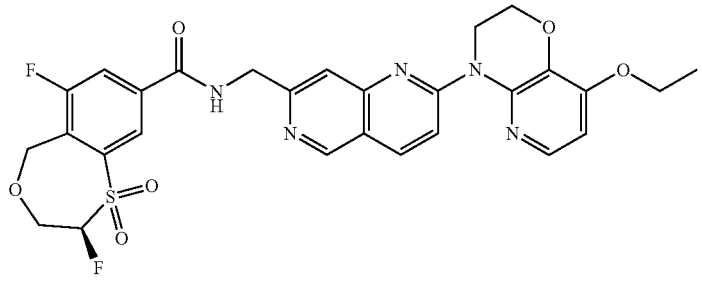 [SMILES: CCOc1ccnc2c1OCCN2c1ccc2cnc(CNC(=O)c3cc(F)c4c(c3)S(=O)(=O)[C@@H](F)COC4)cc2n1] |
| 12 | 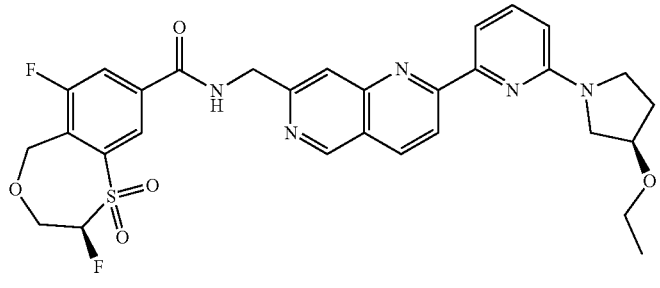 [SMILES: CCO[C@@H]1CCN(c2cccc(-c3ccc4cnc(CNC(=O)c5cc(F)c6c(c5)S(=O)(=O)[C@@H](F)COC6)cc4n3)n2)C1] |
| 13 | 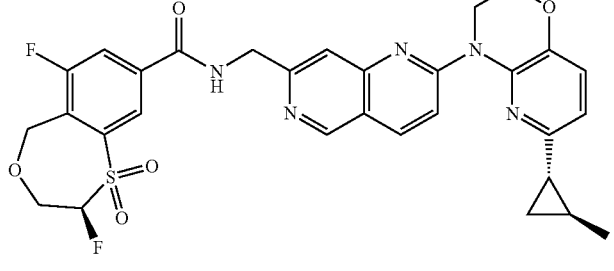 |
| 14 | 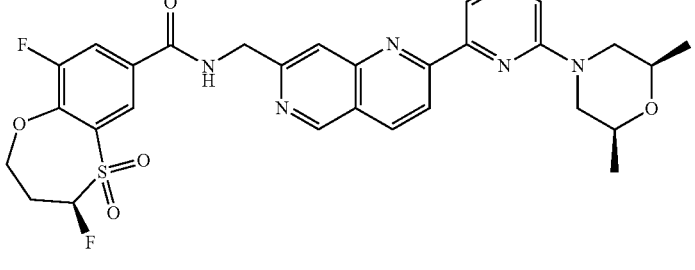 |
| 15 | 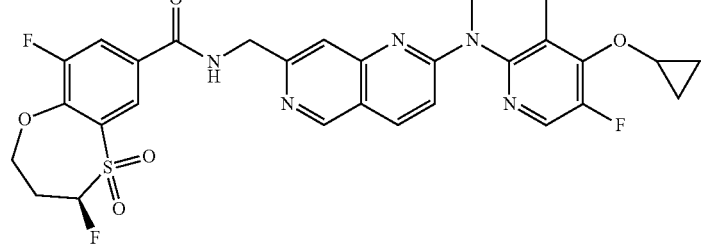 |

TABLE 1-continued

Compounds of the invention

| # | Structure |
|---|---|
| 16 | 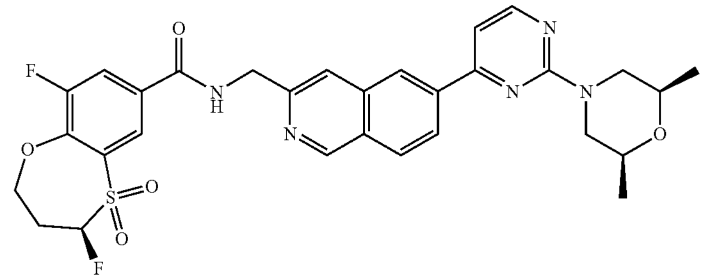 [SMILES: C[C@@H]1CN(c2nccc(-c3ccc4cnc(CNC(=O)c5cc(F)c6c(c5)S(=O)(=O)[C@@H](F)CCO6)cc4c3)n2)C[C@H](C)O1] |
| 17 | 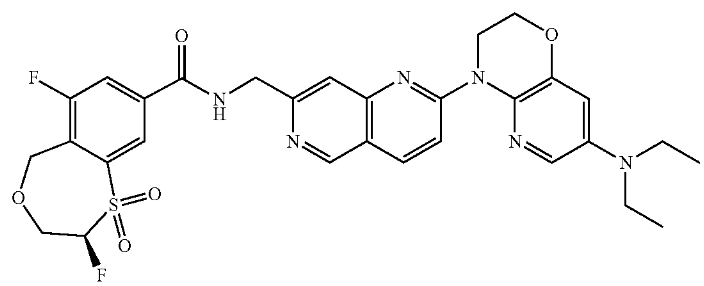 [SMILES: CCN(CC)c1cnc2c(c1)OCCN2c1ccc2cnc(CNC(=O)c3cc(F)c4c(c3)S(=O)(=O)[C@@H](F)COC4)cc2n1] |
| 18 | 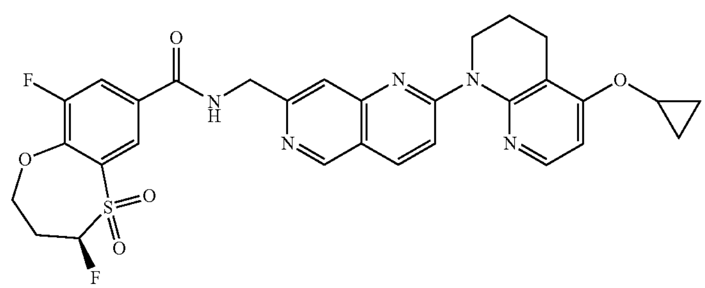 [SMILES: O=C(NCc1cc2nc(N3CCCc4c(OC5CC5)ccnc43)ccc2cn1)c1cc(F)c2c(c1)S(=O)(=O)[C@@H](F)CCO2] |
| 19 | 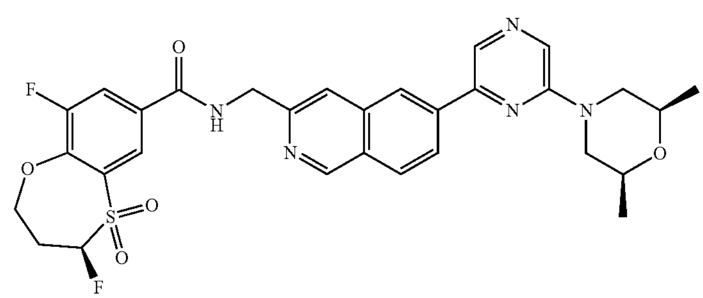 [SMILES: C[C@@H]1CN(c2cncc(-c3ccc4cnc(CNC(=O)c5cc(F)c6c(c5)S(=O)(=O)[C@@H](F)CCO6)cc4c3)n2)C[C@H](C)O1] |
| 20 | 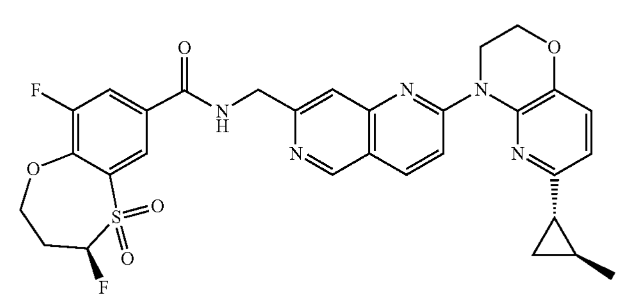 [SMILES: C[C@H]1C[C@@H]1c1ccc2c(n1)N(c1ccc3cnc(CNC(=O)c4cc(F)c5c(c4)S(=O)(=O)[C@@H](F)CCO5)cc3n1)CCO2] |

US 12,139,487 B2

TABLE 1-continued

Compounds of the invention

| # | Structure |
|---|-----------|
| 21 | 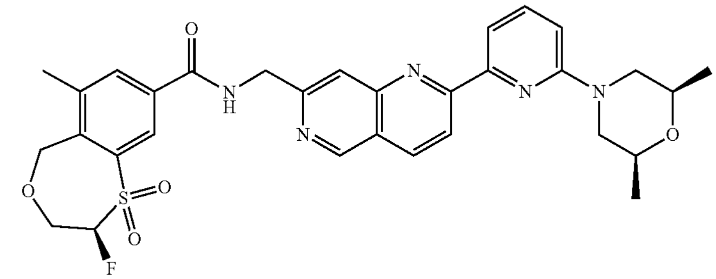 [SMILES: Cc1cc(C(=O)NCc2cc3nc(-c4cccc(N5C[C@@H](C)O[C@@H](C)C5)n4)ccc3cn2)cc2c1COC[C@H](F)S2(=O)=O] |
| 22 | 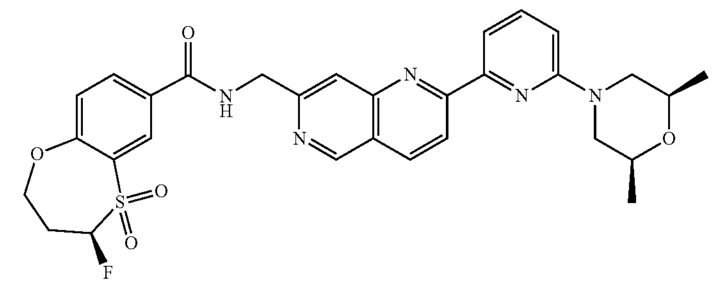 [SMILES: C[C@@H]1CN(c2cccc(-c3ccc4cnc(CNC(=O)c5ccc6c(c5)S(=O)(=O)[C@@H](F)CCO6)cc4n3)n2)C[C@H](C)O1] |
| 23 | 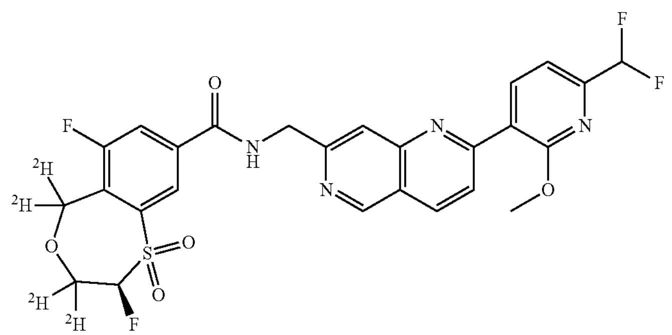 [SMILES: [2H]C1([2H])OC([2H])([2H])[C@H](F)S(=O)(=O)c2cc(C(=O)NCc3cc4nc(-c5ccc(C(F)F)nc5OC)ccc4cn3)cc(F)c21] |
| 24 | 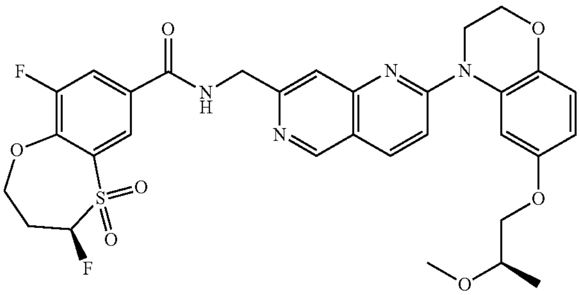 [SMILES: CO[C@H](C)COc1ccc2c(c1)N(c1ccc3cnc(CNC(=O)c4cc(F)c5c(c4)S(=O)(=O)[C@@H](F)CCO5)cc3n1)CCO2] |
| 25 | 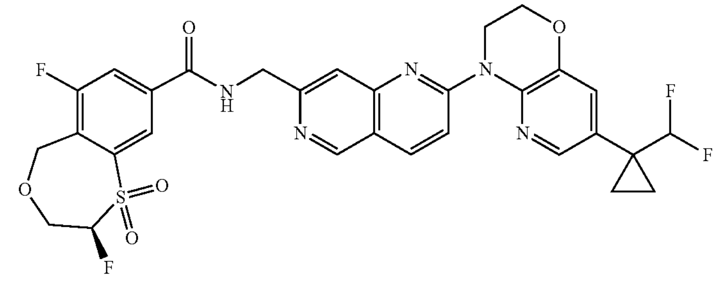 [SMILES: O=C(NCc1cc2nc(N3CCOc4cc(C5(C(F)F)CC5)cnc43)ccc2cn1)c1cc(F)c2c(c1)S(=O)(=O)[C@@H](F)COC2] |

TABLE 1-continued

Compounds of the invention

| # | Structure |
|---|-----------|
| 26 | 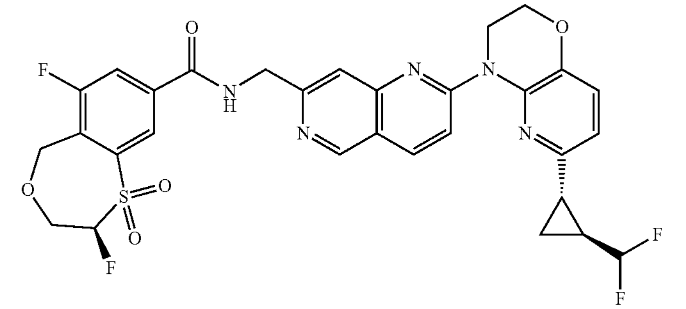 [SMILES: O=C(NCc1cc2nc(N3CCOc4ccc([C@H]5C[C@@H]5C(F)F)nc43)ccc2cn1)c1cc(F)c2c(c1)S(=O)(=O)[C@@H](F)COC2] |
| 27 | 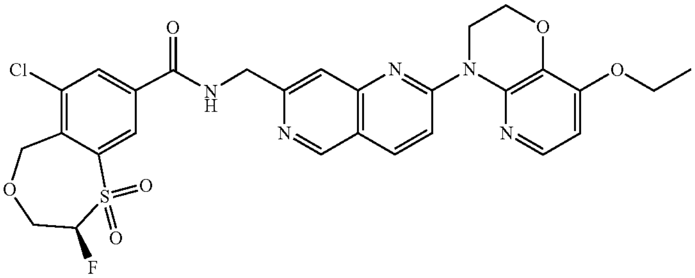 [SMILES: CCOc1ccnc2c1OCCN2c1ccc2cnc(CNC(=O)c3cc(Cl)c4c(c3)S(=O)(=O)[C@@H](F)COC4)cc2n1] |
| 28 | 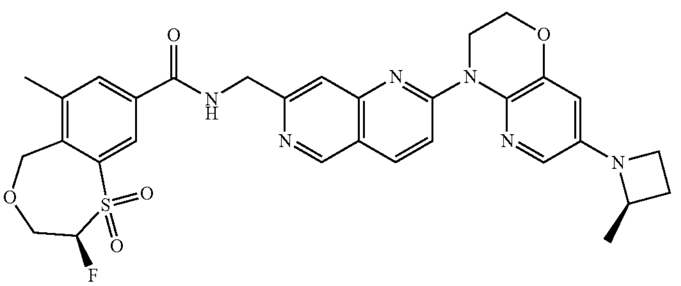 [SMILES: Cc1cc(C(=O)NCc2cc3nc(N4CCOc5cc(N6CC[C@H]6C)cnc54)ccc3cn2)cc2c1COC[C@H](F)S2(=O)=O] |
| 29 | 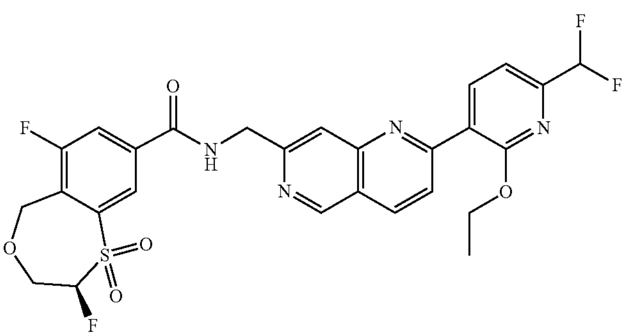 [SMILES: CCOc1nc(C(F)F)ccc1-c1ccc2cnc(CNC(=O)c3cc(F)c4c(c3)S(=O)(=O)[C@@H](F)COC4)cc2n1] |
| 30 | 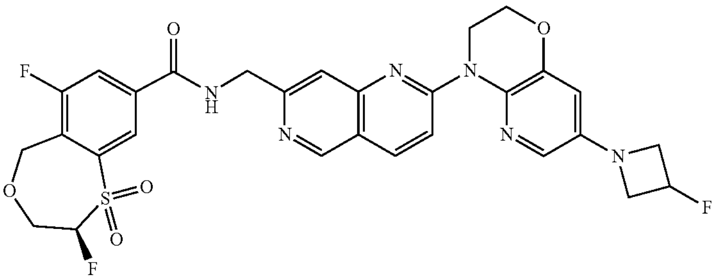 [SMILES: O=C(NCc1cc2nc(N3CCOc4cc(N5CC(F)C5)cnc43)ccc2cn1)c1cc(F)c2c(c1)S(=O)(=O)[C@@H](F)COC2] |

TABLE 1-continued

Compounds of the invention

| # | Structure |
|---|---|
| 31 | 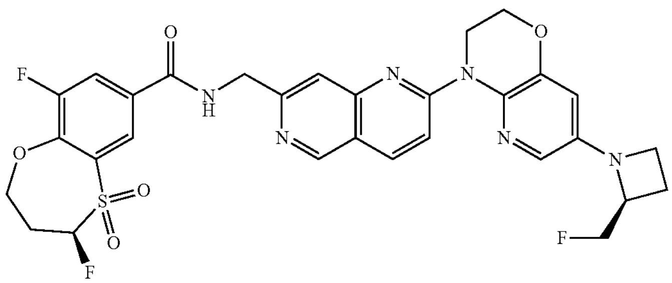 [SMILES: O=C(NCc1cc2nc(N3CCOc4cc(N5CC[C@H]5CF)cnc43)ccc2cn1)c1cc(F)c2c(c1)S(=O)(=O)[C@@H](F)CCO2] |
| 32 | 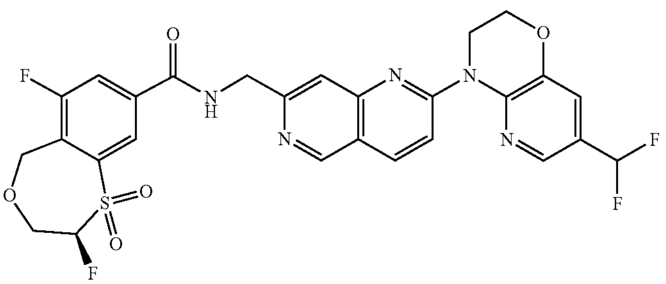 [SMILES: O=C(NCc1cc2nc(N3CCOc4cc(C(F)F)cnc43)ccc2cn1)c1cc(F)c2c(c1)S(=O)(=O)[C@@H](F)COC2] |
| 33 | 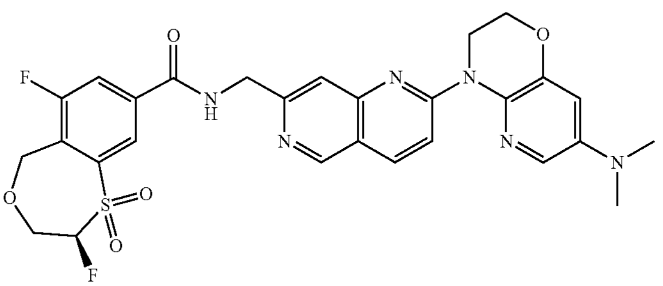 [SMILES: CN(C)c1cnc2c(c1)OCCN2c1ccc2cnc(CNC(=O)c3cc(F)c4c(c3)S(=O)(=O)[C@@H](F)COC4)cc2n1] |
| 34 | 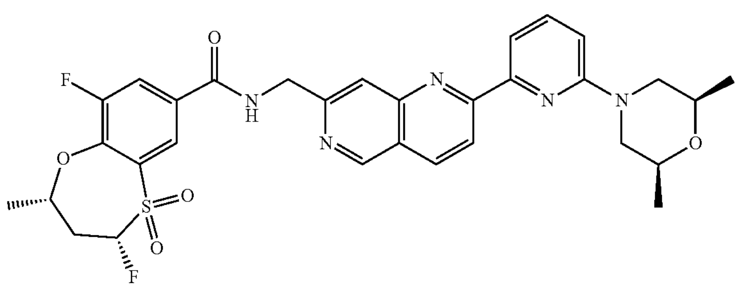 |
| 35 | 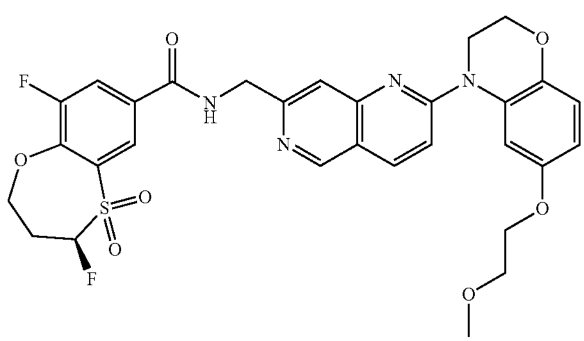 [SMILES: COCCOc1ccc2c(c1)N(c1ccc3cnc(CNC(=O)c4cc(F)c5c(c4)S(=O)(=O)[C@@H](F)CCO5)cc3n1)CCO2] |

TABLE 1-continued
Compounds of the invention
| # | Structure |
|---|---|
| 36 | 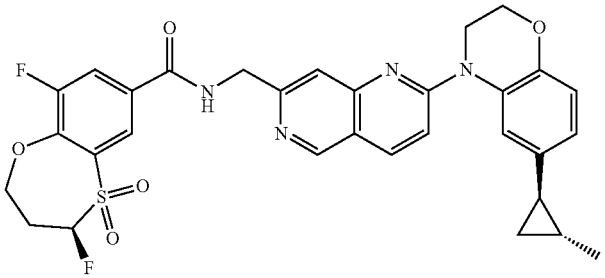 [SMILES: C[C@@H]1C[C@H]1c1ccc2c(c1)N(c1ccc3cnc(CNC(=O)c4cc(F)c5c(c4)S(=O)(=O)[C@@H](F)CCO5)cc3n1)CCO2] |
| 37 | 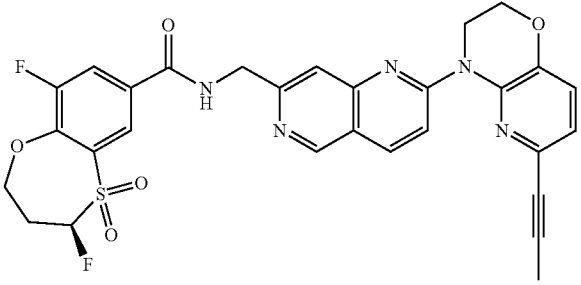 [SMILES: CC#Cc1ccc2c(n1)N(c1ccc3cnc(CNC(=O)c4cc(F)c5c(c4)S(=O)(=O)[C@@H](F)CCO5)cc3n1)CCO2] |
| 38 | 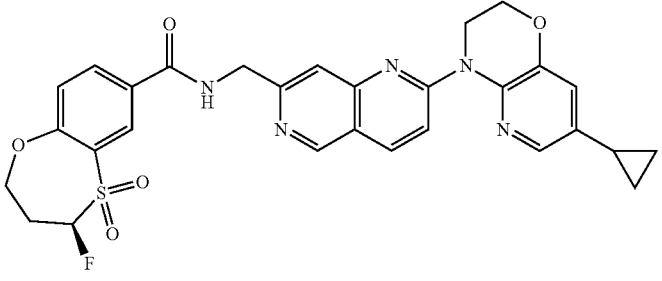 [SMILES: O=C(NCc1cc2nc(N3CCOc4cc(C5CC5)cnc43)ccc2cn1)c1ccc2c(c1)S(=O)(=O)[C@@H](F)CCO2] |
| 39 | 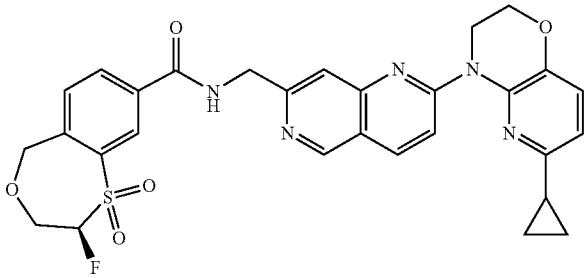 [SMILES: O=C(NCc1cc2nc(N3CCOc4ccc(C5CC5)nc43)ccc2cn1)c1ccc2c(c1)S(=O)(=O)[C@@H](F)COC2] |
| 40 | 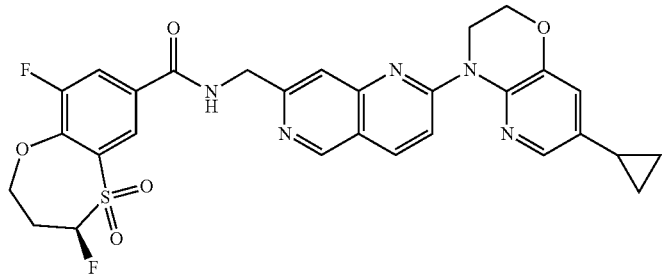 [SMILES: O=C(NCc1cc2nc(N3CCOc4cc(C5CC5)cnc43)ccc2cn1)c1cc(F)c2c(c1)S(=O)(=O)[C@@H](F)CCO2] |

TABLE 1-continued

Compounds of the invention

| # | Structure |
|---|---|
| 41 | 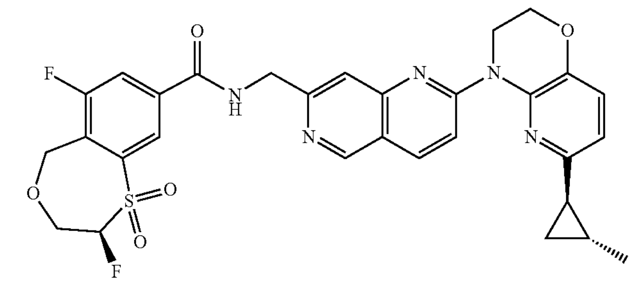 [SMILES: C[C@@H]1C[C@H]1c1ccc2c(n1)N(c1ccc3cnc(CNC(=O)c4cc(F)c5c(c4)S(=O)(=O)[C@@H](F)COC5)cc3n1)CCO2] |
| 42 | 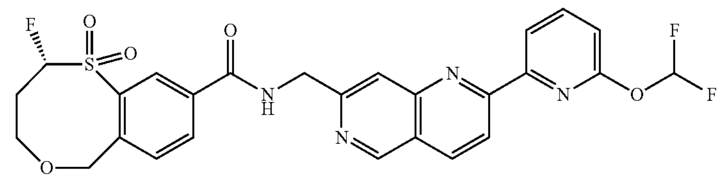 [SMILES: O=C(NCc1cc2nc(-c3cccc(OC(F)F)n3)ccc2cn1)c1ccc2c(c1)S(=O)(=O)[C@@H](F)CCOC2] |
| 43 | 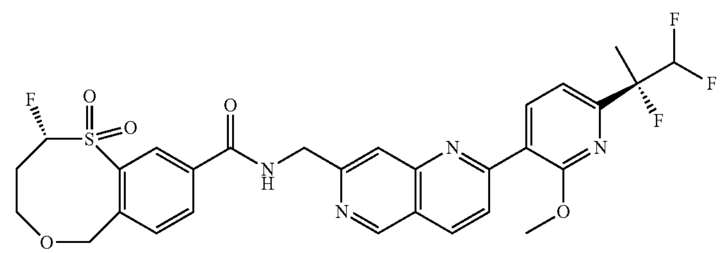 [SMILES: COc1nc([C@](C)(F)C(F)F)ccc1-c1ccc2cnc(CNC(=O)c3ccc4c(c3)S(=O)(=O)[C@@H](F)CCOC4)cc2n1] |
| 44 | 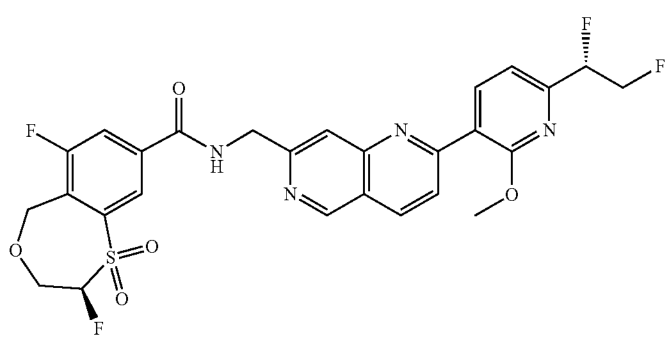 [SMILES: COc1nc([C@H](F)CF)ccc1-c1ccc2cnc(CNC(=O)c3cc(F)c4c(c3)S(=O)(=O)[C@@H](F)COC4)cc2n1] |
| 45 | 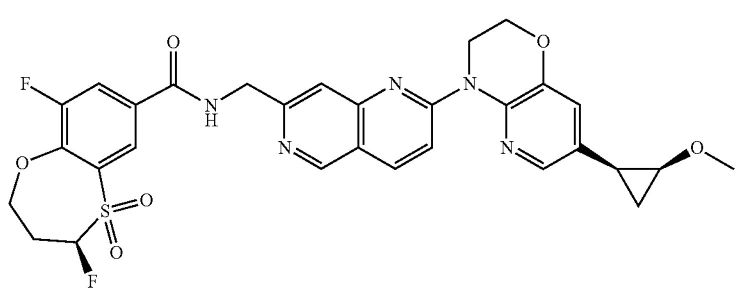 [SMILES: CO[C@H]1C[C@H]1c1cnc2c(c1)OCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|-----------|
| 46 | 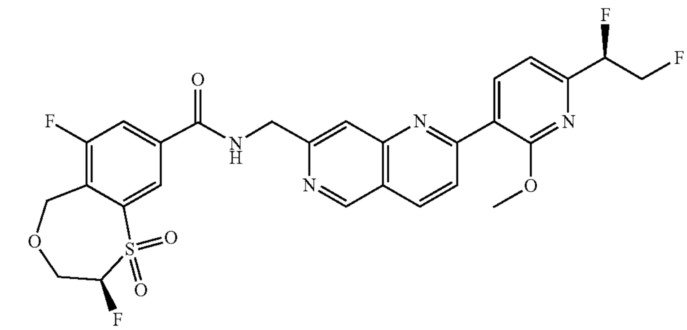 [SMILES: COc1nc([C@@H](F)CF)ccc1-c1ccc2cnc(CNC(=O)c3cc(F)c4c(c3)S(=O)(=O)[C@@H](F)COC4)cc2n1] |
| 47 | 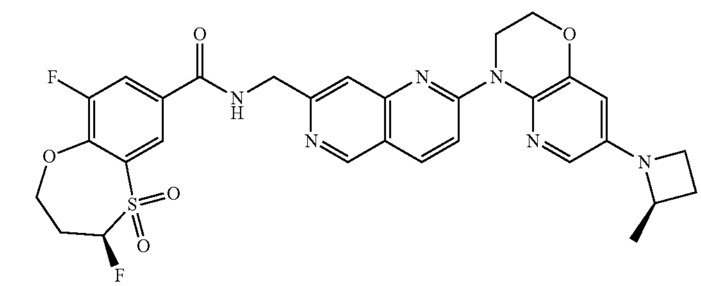 [SMILES: C[C@@H]1CCN1c1cnc2c(c1)OCCN2c1ccc2cnc(CNC(=O)c3cc(F)c4c(c3)S(=O)(=O)[C@@H](F)CCO4)cc2n1] |
| 48 | 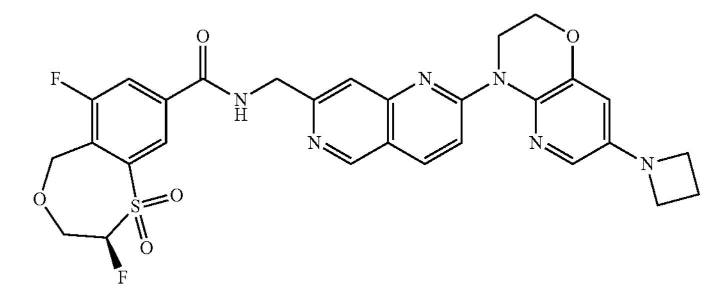 [SMILES: O=C(NCc1cc2nc(N3CCOc4cc(N5CCC5)cnc43)ccc2cn1)c1cc(F)c2c(c1)S(=O)(=O)[C@@H](F)COC2] |
| 49 | 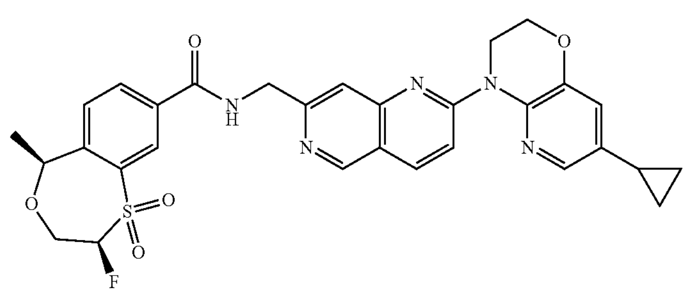 [SMILES: C[C@@H]1OC[C@H](F)S(=O)(=O)c2cc(C(=O)NCc3cc4nc(N5CCOc6cc(C7CC7)cnc65)ccc4cn3)ccc21] |
| 50 | 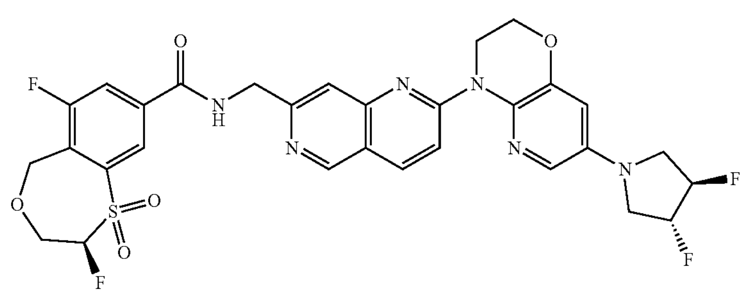 [SMILES: O=C(NCc1cc2nc(N3CCOc4cc(N5C[C@@H](F)[C@H](F)C5)cnc43)ccc2cn1)c1cc(F)c2c(c1)S(=O)(=O)[C@@H](F)COC2] |

TABLE 1-continued
Compounds of the invention
| # | Structure |
|---|---|
| 51 | 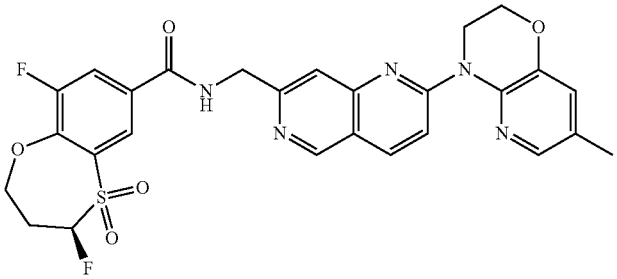 [SMILES: Cc1cnc2c(c1)OCCN2c1ccc2cnc(CNC(=O)c3cc(F)c4c(c3)S(=O)(=O)[C@@H](F)CCO4)cc2n1] |
| 52 | 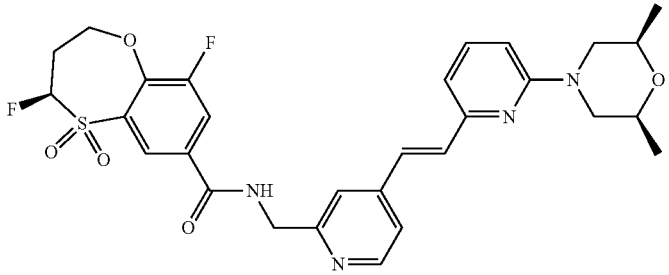 [SMILES: C[C@@H]1CN(c2cccc(/C=C/c3ccnc(CNC(=O)c4cc(F)c5c(c4)S(=O)(=O)[C@@H](F)CCO5)c3)n2)C[C@H](C)O1] |
| 53 | 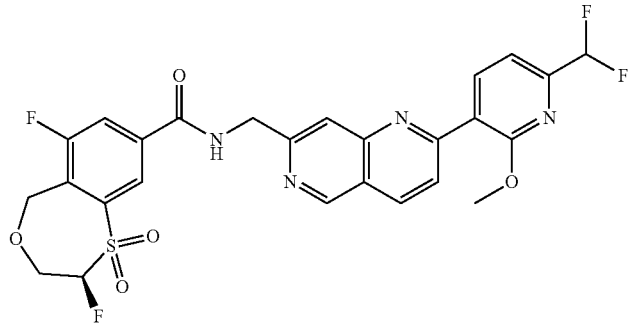 [SMILES: COc1nc(C(F)F)ccc1-c1ccc2cnc(CNC(=O)c3cc(F)c4c(c3)S(=O)(=O)[C@@H](F)COC4)cc2n1] |
| 54 | 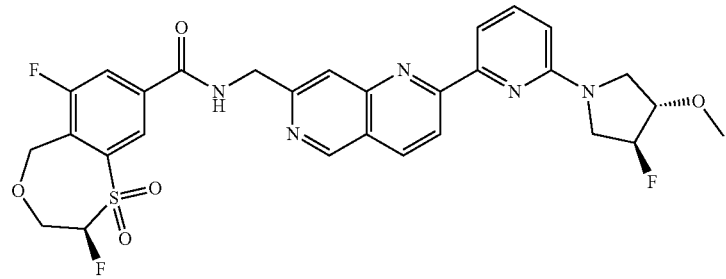 [SMILES: CO[C@H]1CN(c2cccc(-c3ccc4cnc(CNC(=O)c5cc(F)c6c(c5)S(=O)(=O)[C@@H](F)COC6)cc4n3)n2)C[C@@H]1F] |
| 55 | 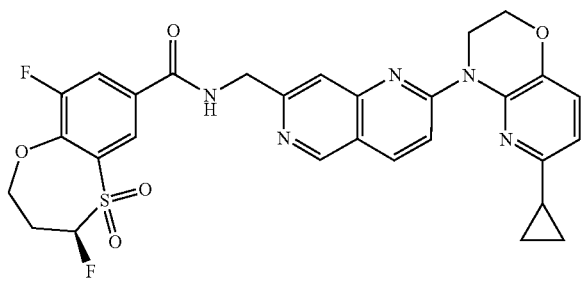 [SMILES: O=C(NCc1cc2nc(N3CCOc4ccc(C5CC5)nc43)ccc2cn1)c1cc(F)c2c(c1)S(=O)(=O)[C@@H](F)CCO2] |

TABLE 1-continued

Compounds of the invention

| # | Structure |
|---|---|
| 56 | 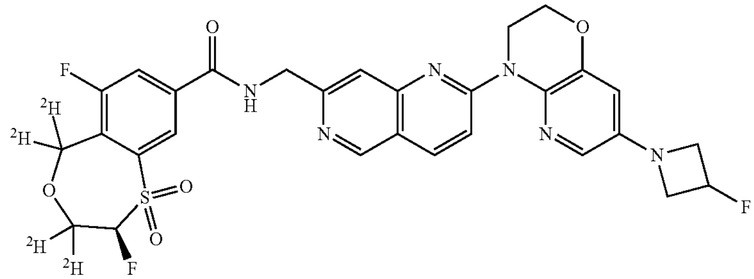 [SMILES: [2H]C1([2H])OC([2H])([2H])[C@H](F)S(=O)(=O)c2cc(C(=O)NCc3cc4nc(N5CCOc6cc(N7CC(F)C7)cnc65)ccc4cn3)cc(F)c21] |
| 57 | 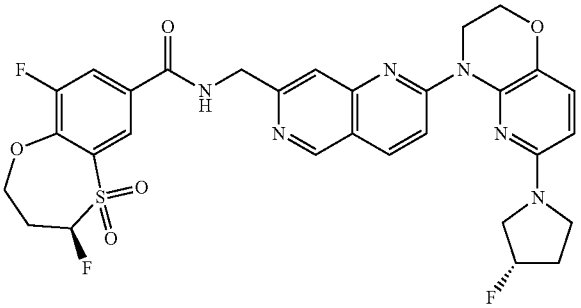 [SMILES: O=C(NCc1cc2nc(N3CCOc4ccc(N5CC[C@H](F)C5)nc43)ccc2cn1)c1cc(F)c2c(c1)S(=O)(=O)[C@@H](F)CCO2] |
| 58 | 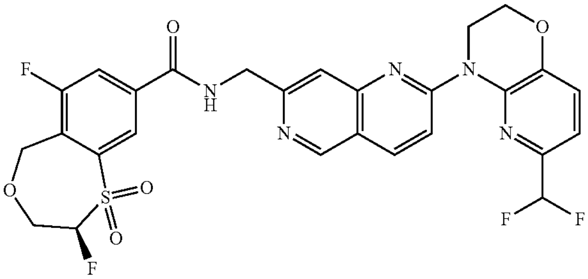 [SMILES: O=C(NCc1cc2nc(N3CCOc4ccc(C(F)F)nc43)ccc2cn1)c1cc(F)c2c(c1)S(=O)(=O)[C@@H](F)COC2] |
| 59 | 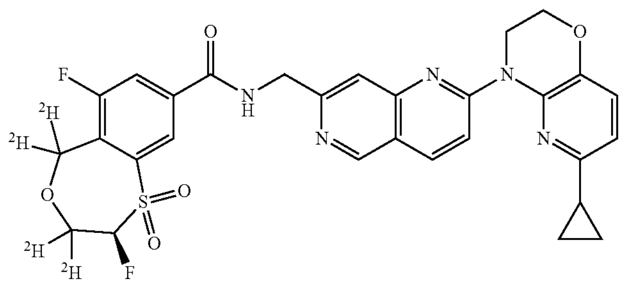 [SMILES: [2H]C1([2H])OC([2H])([2H])[C@H](F)S(=O)(=O)c2cc(C(=O)NCc3cc4nc(N5CCOc6ccc(C7CC7)nc65)ccc4cn3)cc(F)c21] |
| 60 | 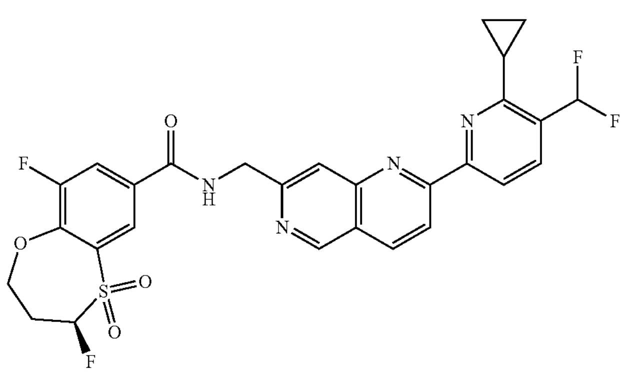 [SMILES: O=C(NCc1cc2nc(-c3ccc(C(F)F)c(C4CC4)n3)ccc2cn1)c1cc(F)c2c(c1)S(=O)(=O)[C@@H](F)CCO2] |

TABLE 1-continued
Compounds of the invention
| # | Structure |
|---|---|
| 61 | 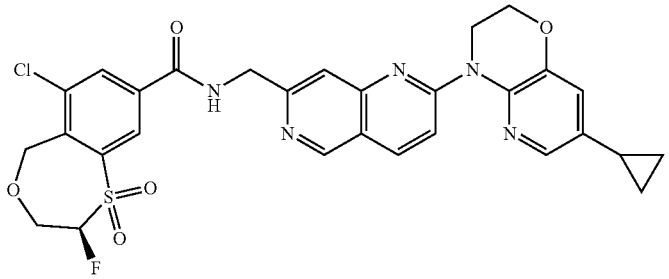 [SMILES: O=C(NCc1cc2nc(N3CCOc4cc(C5CC5)cnc43)ccc2cn1)c1cc(Cl)c2c(c1)S(=O)(=O)[C@@H](F)COC2] |
| 62 | 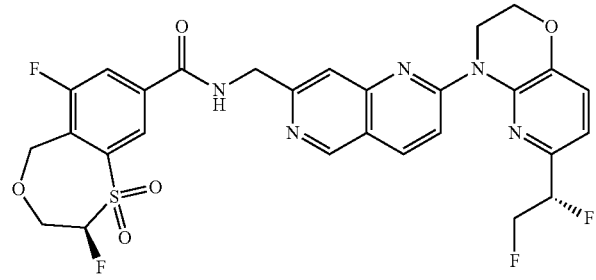 [SMILES: O=C(NCc1cc2nc(N3CCOc4ccc([C@H](F)CF)nc43)ccc2cn1)c1cc(F)c2c(c1)S(=O)(=O)[C@@H](F)COC2] |
| 63 | 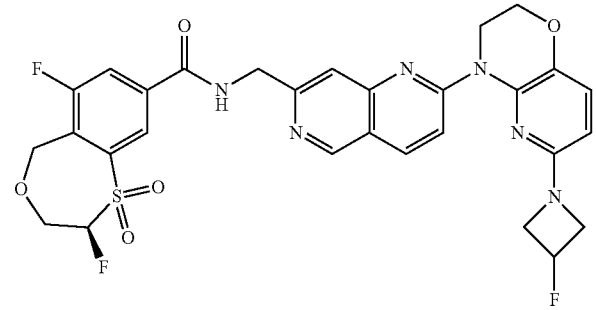 [SMILES: O=C(NCc1cc2nc(N3CCOc4ccc(N5CC(F)C5)nc43)ccc2cn1)c1cc(F)c2c(c1)S(=O)(=O)[C@@H](F)COC2] |
| 64 | 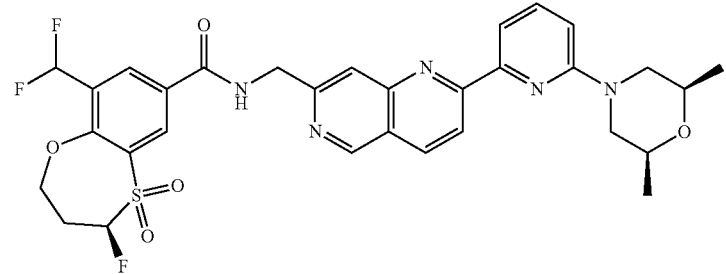 [SMILES: C[C@@H]1CN(c2cccc(-c3ccc4cnc(CNC(=O)c5cc(C(F)F)c6c(c5)S(=O)(=O)[C@@H](F)CCO6)cc4n3)n2)C[C@H](C)O1] |
| 65 | 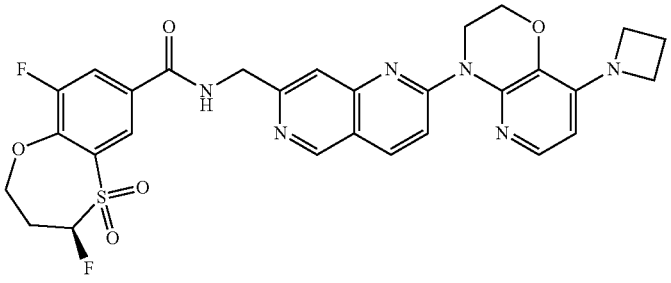 [SMILES: O=C(NCc1cc2nc(N3CCOc4c(N5CCC5)ccnc43)ccc2cn1)c1cc(F)c2c(c1)S(=O)(=O)[C@@H](F)CCO2] |

TABLE 1-continued

Compounds of the invention

| # | Structure |
|---|---|
| 66 | 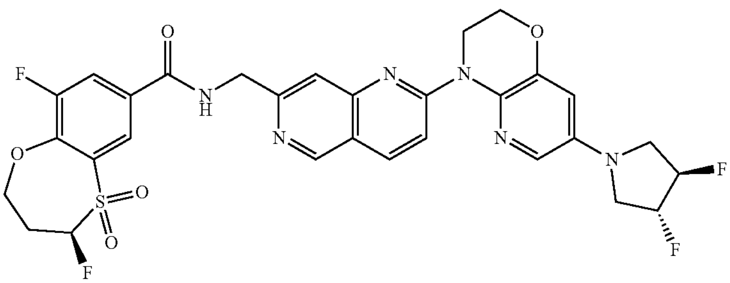 [SMILES: O=C(NCc1cc2nc(N3CCOc4cc(N5C[C@@H](F)[C@H](F)C5)cnc43)ccc2cn1)c1cc(F)c2c(c1)S(=O)(=O)[C@@H](F)CCO2] |
| 67 | 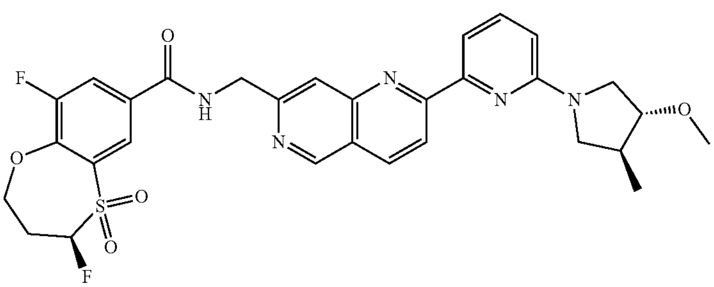 [SMILES: CO[C@H]1CN(c2cccc(-c3ccc4cnc(CNC(=O)c5cc(F)c6c(c5)S(=O)(=O)[C@@H](F)CCO6)cc4n3)n2)C[C@@H]1C] |
| 68 | 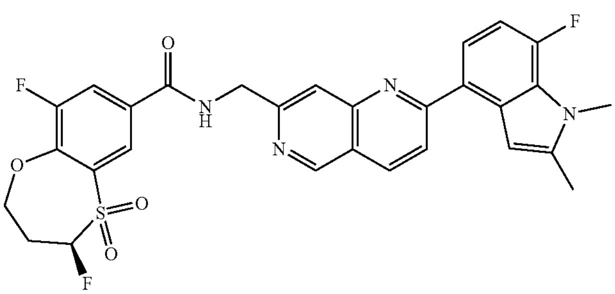 [SMILES: Cc1cc2c(-c3ccc4cnc(CNC(=O)c5cc(F)c6c(c5)S(=O)(=O)[C@@H](F)CCO6)cc4n3)ccc(F)c2n1C] |
| 69 | 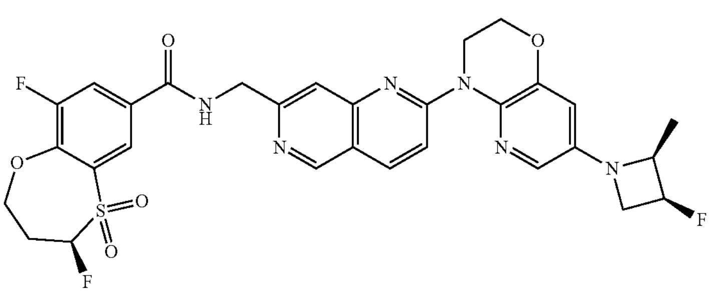 [SMILES: C[C@H]1[C@@H](F)CN1c1cnc2c(c1)OCCN2c1ccc2cnc(CNC(=O)c3cc(F)c4c(c3)S(=O)(=O)[C@@H](F)CCO4)cc2n1] |
| 70 | 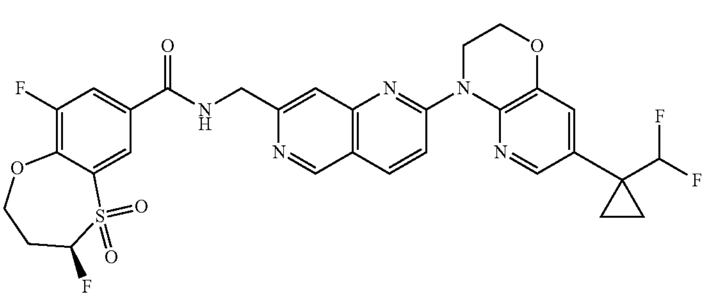 [SMILES: O=C(NCc1cc2nc(N3CCOc4cc(C5(C(F)F)CC5)cnc43)ccc2cn1)c1cc(F)c2c(c1)S(=O)(=O)[C@@H](F)CCO2] |

TABLE 1-continued
Compounds of the invention
| # | Structure |
|---|---|
| 71 | 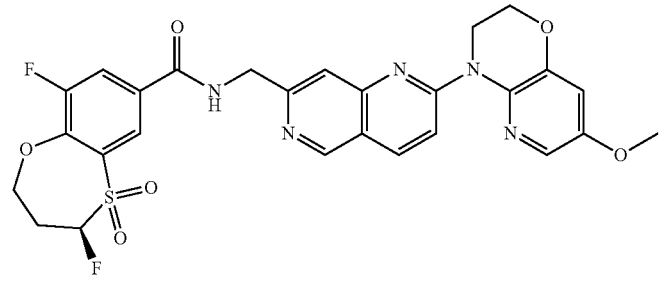 [SMILES: COc1cnc2c(c1)OCCN2c1ccc2cnc(CNC(=O)c3cc(F)c4c(c3)S(=O)(=O)[C@@H](F)CCO4)cc2n1] |
| 72 | 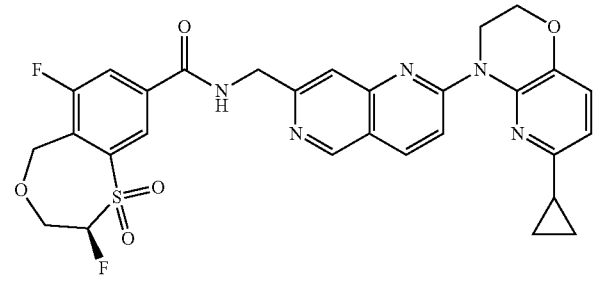 [SMILES: O=C(NCc1cc2nc(N3CCOc4ccc(C5CC5)nc43)ccc2cn1)c1cc(F)c2c(c1)S(=O)(=O)[C@@H](F)COC2] |
| 73 | 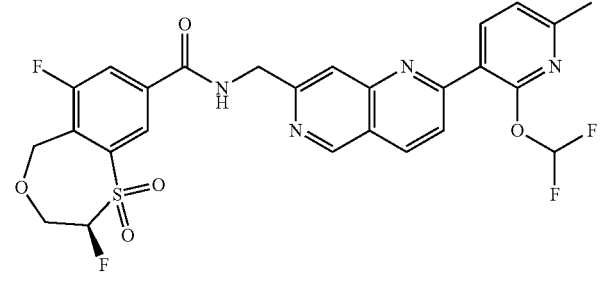 [SMILES: Cc1ccc(-c2ccc3cnc(CNC(=O)c4cc(F)c5c(c4)S(=O)(=O)[C@@H](F)COC5)cc3n2)c(OC(F)F)n1] |
| 74 | 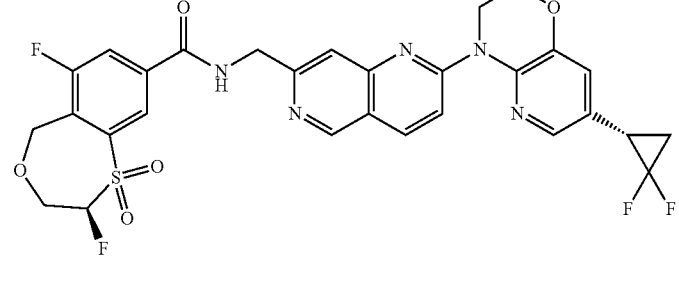 |
| 75 | 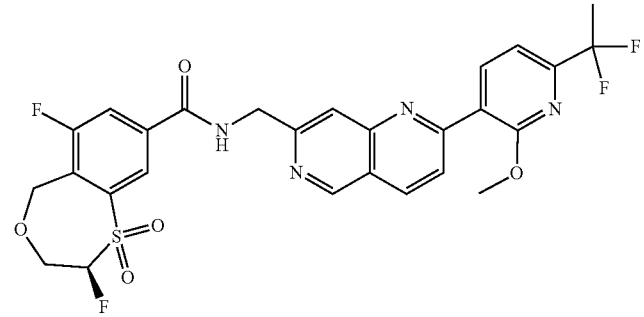 [SMILES: COc1nc(C(C)(F)F)ccc1-c1ccc2cnc(CNC(=O)c3cc(F)c4c(c3)S(=O)(=O)[C@@H](F)COC4)cc2n1] |

TABLE 1-continued

Compounds of the invention

| # | Structure |
|---|---|
| 76 | 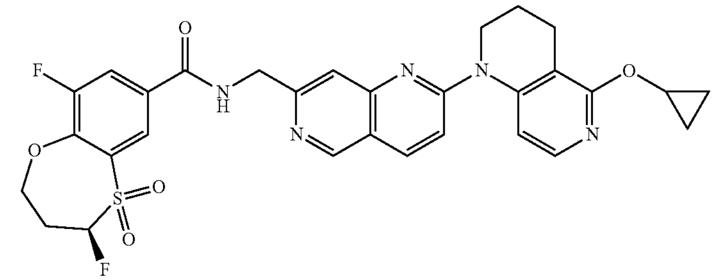 [SMILES: O=C(NCc1cc2nc(N3CCCc4c3ccnc4OC3CC3)ccc2cn1)c1cc(F)c2c(c1)S(=O)(=O)[C@@H](F)CCO2] |
| 77 | 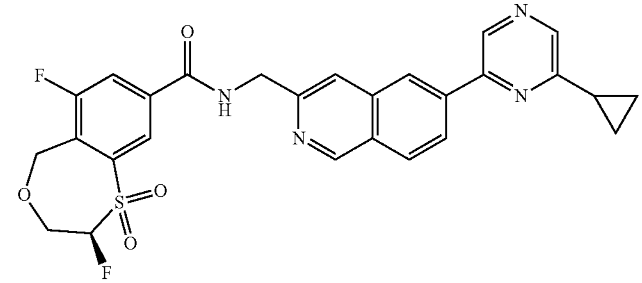 [SMILES: O=C(NCc1cc2cc(-c3cncc(C4CC4)n3)ccc2cn1)c1cc(F)c2c(c1)S(=O)(=O)[C@@H](F)COC2] |
| 78 | 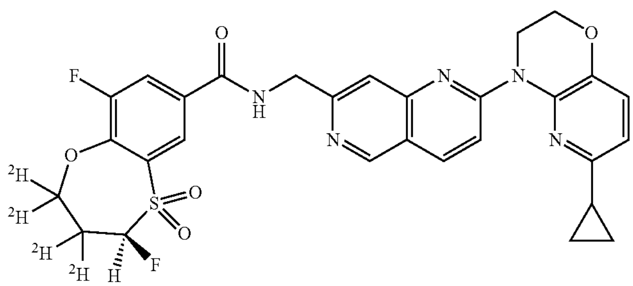 [SMILES: [2H]C1([2H])Oc2c(F)cc(C(=O)NCc3cc4nc(N5CCOc6ccc(C7CC7)nc65)ccc4cn3)cc2S(=O)(=O)[C@@H](F)C1([2H])[2H]] |
| 79 | 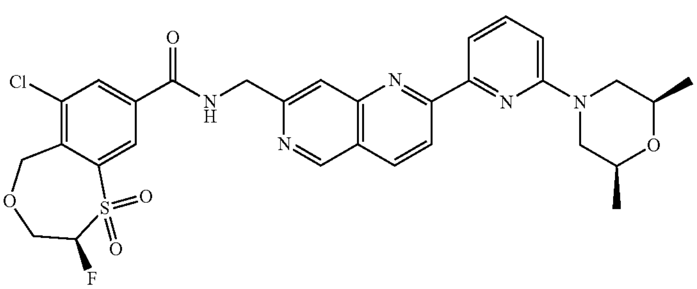 [SMILES: C[C@@H]1CN(c2cccc(-c3ccc4cnc(CNC(=O)c5cc(Cl)c6c(c5)S(=O)(=O)[C@@H](F)COC6)cc4n3)n2)C[C@H](C)O1] |
| 80 | 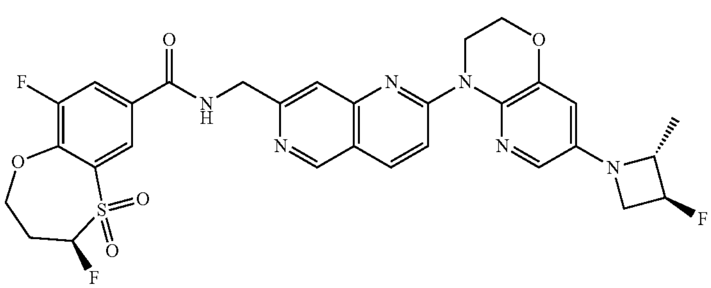 [SMILES: C[C@@H]1[C@@H](F)CN1c1cnc2c(c1)OCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|-----------|
| 81 | 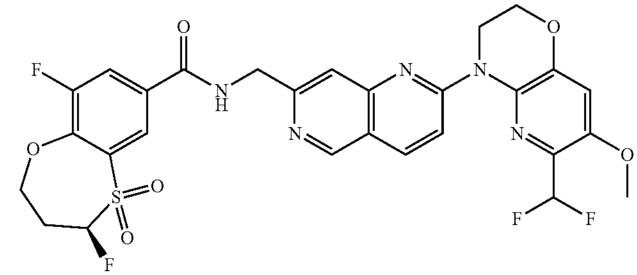 [SMILES: COc1cc2c(nc1C(F)F)N(c1ccc3cnc(CNC(=O)c4cc(F)c5c(c4)S(=O)(=O)[C@@H](F)CCO5)cc3n1)CCO2] |
| 82 | 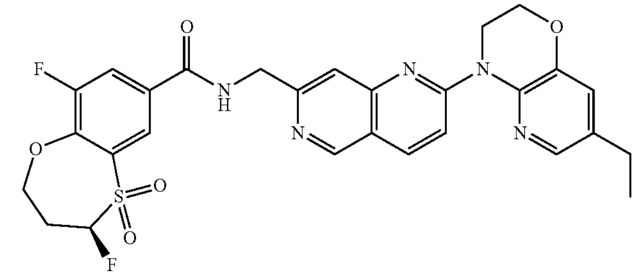 [SMILES: CCc1cnc2c(c1)OCCN2c1ccc2cnc(CNC(=O)c3cc(F)c4c(c3)S(=O)(=O)[C@@H](F)CCO4)cc2n1] |
| 83 | 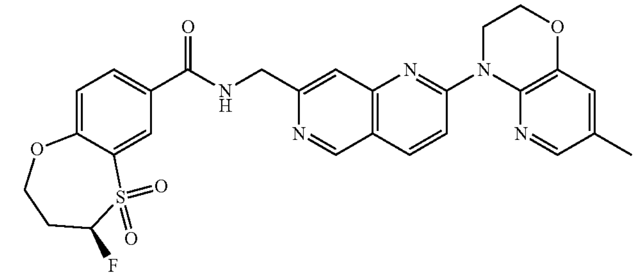 [SMILES: Cc1cnc2c(c1)OCCN2c1ccc2cnc(CNC(=O)c3ccc4c(c3)S(=O)(=O)[C@@H](F)CCO4)cc2n1] |
| 84 | 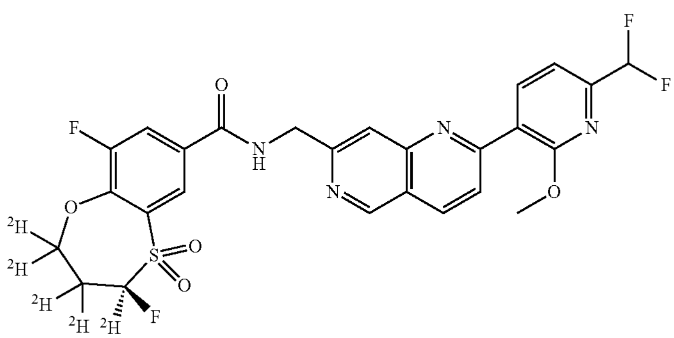 [SMILES: [2H]C1([2H])Oc2c(F)cc(C(=O)NCc3cc4nc(-c5ccc(C(F)F)nc5OC)ccc4cn3)cc2S(=O)(=O)[C@@]([2H])(F)C1([2H])[2H]] |
| 85 | 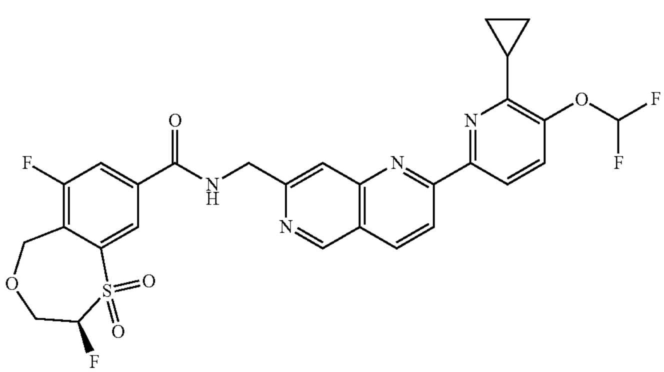 [SMILES: O=C(NCc1cc2nc(-c3ccc(OC(F)F)c(C4CC4)n3)ccc2cn1)c1cc(F)c2c(c1)S(=O)(=O)[C@@H](F)COC2] |

TABLE 1-continued
Compounds of the invention
| # | Structure |
|---|---|
| 86 | 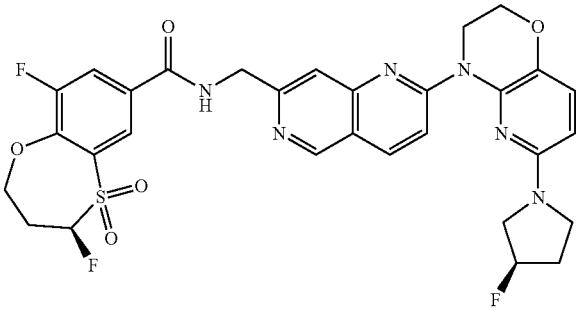 [SMILES: O=C(NCc1cc2nc(N3CCOc4ccc(N5CC[C@@H](F)C5)nc43)ccc2cn1)c1cc(F)c2c(c1)S(=O)(=O)[C@@H](F)CCO2] |
| 87 | 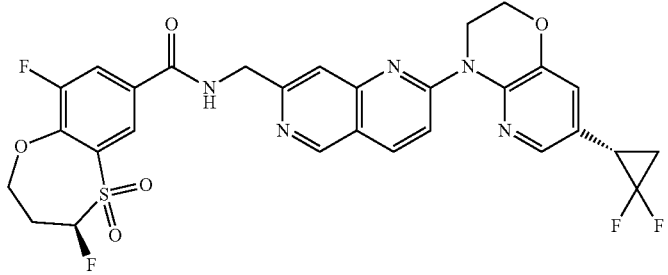 [SMILES: O=C(NCc1cc2nc(N3CCOc4cc([C@@H]5CC5(F)F)cnc43)ccc2cn1)c1cc(F)c2c(c1)S(=O)(=O)[C@@H](F)CCO2] |
| 88 | 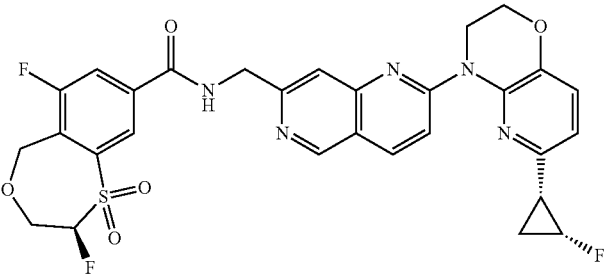 [SMILES: O=C(NCc1cc2nc(N3CCOc4ccc([C@H]5C[C@H]5F)nc43)ccc2cn1)c1cc(F)c2c(c1)S(=O)(=O)[C@@H](F)COC2] |
| 89 | 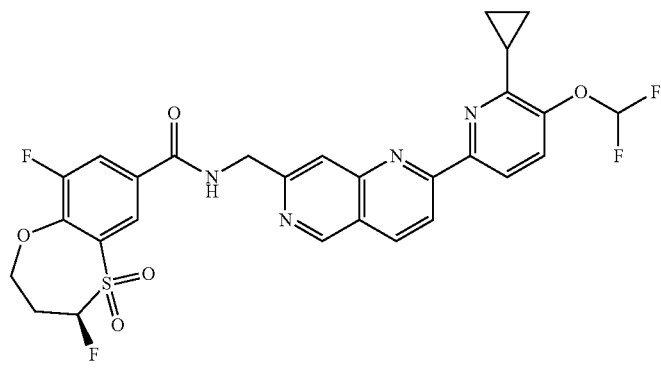 [SMILES: O=C(NCc1cc2nc(-c3ccc(OC(F)F)c(C4CC4)n3)ccc2cn1)c1cc(F)c2c(c1)S(=O)(=O)[C@@H](F)CCO2] |
| 90 | 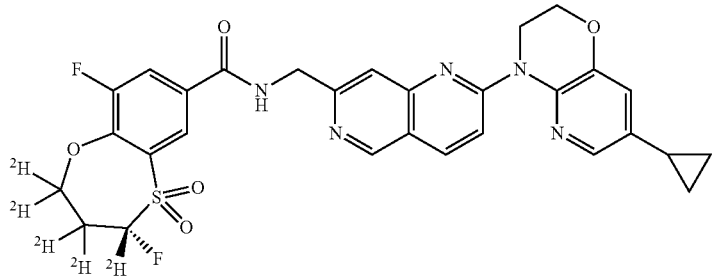 [SMILES: [2H]C1([2H])Oc2c(F)cc(C(=O)NCc3cc4nc(N5CCOc6cc(C7CC7)cnc65)ccc4cn3)cc2S(=O)(=O)[C@]([2H])(F)C1([2H])[2H]] |

TABLE 1-continued

Compounds of the invention

| # | Structure |
|---|---|
| 91 | 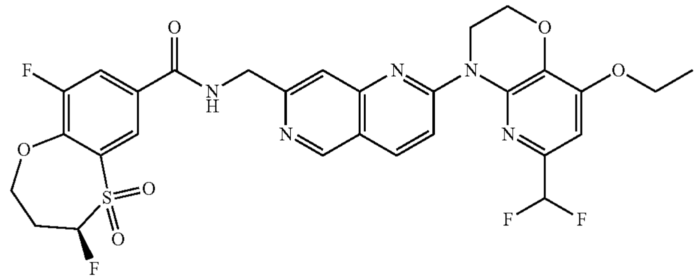 [SMILES: CCOc1cc(C(F)F)nc2c1OCCN2c1ccc2cnc(CNC(=O)c3cc(F)c4c(c3)S(=O)(=O)[C@@H](F)CCO4)cc2n1] |
| 92 | 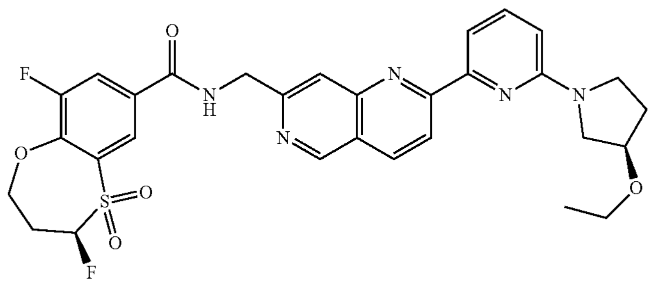 [SMILES: CCO[C@@H]1CCN(c2cccc(-c3ccc4cnc(CNC(=O)c5cc(F)c6c(c5)S(=O)(=O)[C@@H](F)CCO6)cc4n3)n2)C1] |
| 93 | 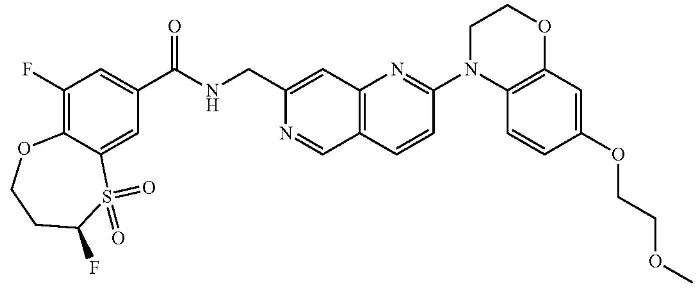 [SMILES: COCCOc1ccc2c(c1)OCCN2c1ccc2cnc(CNC(=O)c3cc(F)c4c(c3)S(=O)(=O)[C@@H](F)CCO4)cc2n1] |
| 94 | 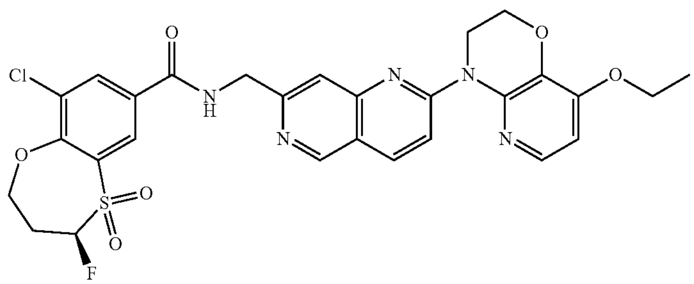 |
| 95 | 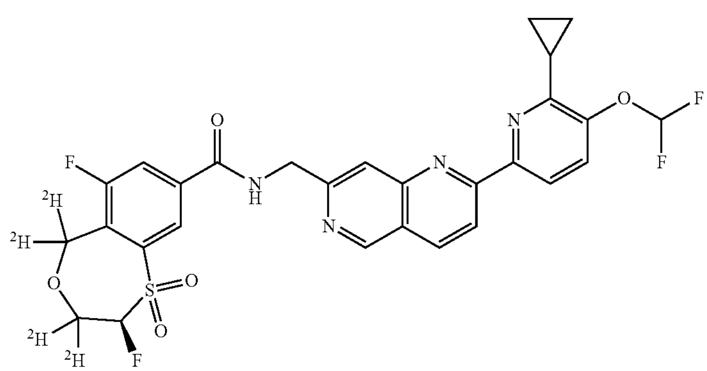 [SMILES: [2H]C1([2H])OC([2H])([2H])[C@H](F)S(=O)(=O)c2cc(C(=O)NCc3cc4nc(-c5ccc(OC(F)F)c(C6CC6)n5)ccc4cn3)cc(F)c21] |

TABLE 1-continued

Compounds of the invention

| # | Structure |
|---|---|
| 96 | 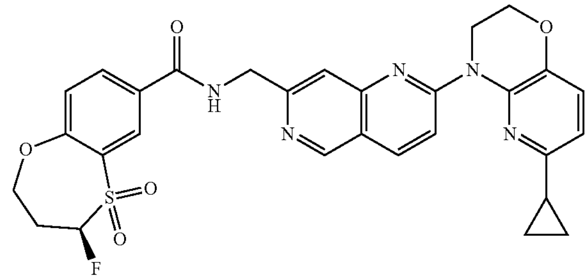 [SMILES: O=C(NCc1cc2nc(N3CCOc4ccc(C5CC5)nc43)ccc2cn1)c1ccc2c(c1)S(=O)(=O)[C@@H](F)CCO2] |
| 97 | 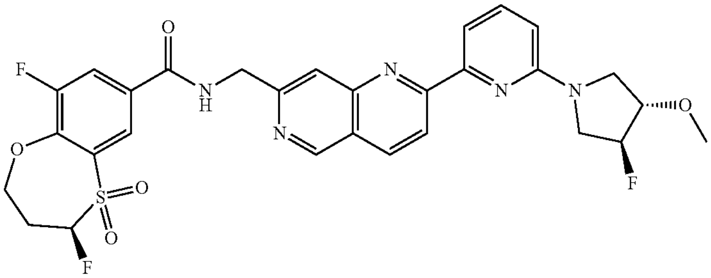 [SMILES: CO[C@H]1CN(c2cccc(-c3ccc4cnc(CNC(=O)c5cc(F)c6c(c5)S(=O)(=O)[C@@H](F)CCO6)cc4n3)n2)C[C@@H]1F] |
| 98 | 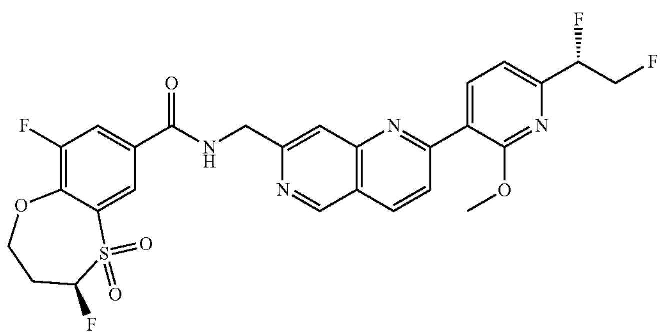 [SMILES: COc1nc([C@H](F)CF)ccc1-c1ccc2cnc(CNC(=O)c3cc(F)c4c(c3)S(=O)(=O)[C@@H](F)CCO4)cc2n1] |
| 99 | 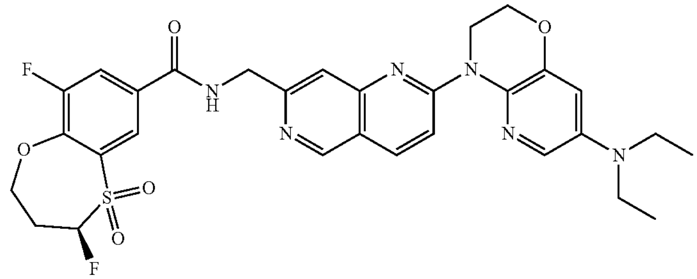 [SMILES: CCN(CC)c1cnc2c(c1)OCCN2c1ccc2cnc(CNC(=O)c3cc(F)c4c(c3)S(=O)(=O)[C@@H](F)CCO4)cc2n1] |
| 100 | 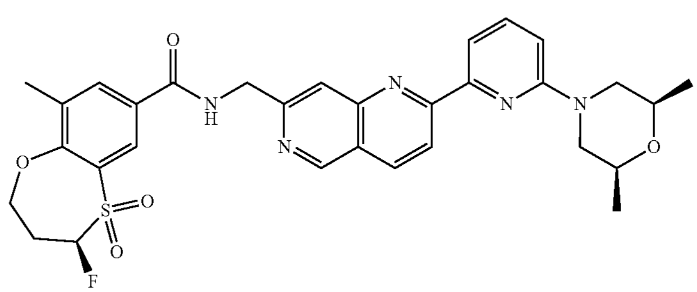 [SMILES: Cc1cc(C(=O)NCc2cc3nc(-c4cccc(N5C[C@@H](C)O[C@@H](C)C5)n4)ccc3cn2)cc2c1OCC[C@H](F)S2(=O)=O] |

TABLE 1-continued

Compounds of the invention

| # | Structure |
|---|-----------|
| 101 | 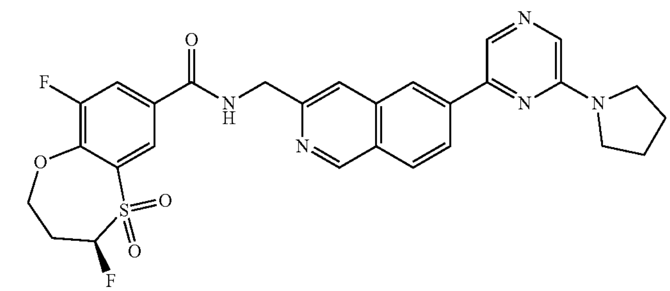 [SMILES: O=C(NCc1cc2cc(-c3cncc(N4CCCC4)n3)ccc2cn1)c1cc(F)c2c(c1)S(=O)(=O)[C@@H](F)CCO2] |
| 102 | 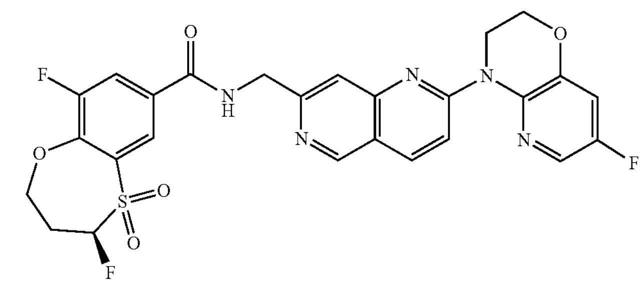 [SMILES: O=C(NCc1cc2nc(N3CCOc4cc(F)cnc43)ccc2cn1)c1cc(F)c2c(c1)S(=O)(=O)[C@@H](F)CCO2] |
| 103 | 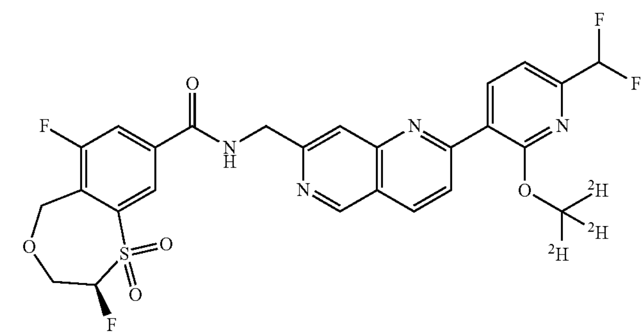 [SMILES: [2H]C([2H])([2H])Oc1nc(C(F)F)ccc1-c1ccc2cnc(CNC(=O)c3cc(F)c4c(c3)S(=O)(=O)[C@@H](F)COC4)cc2n1] |
| 104 | 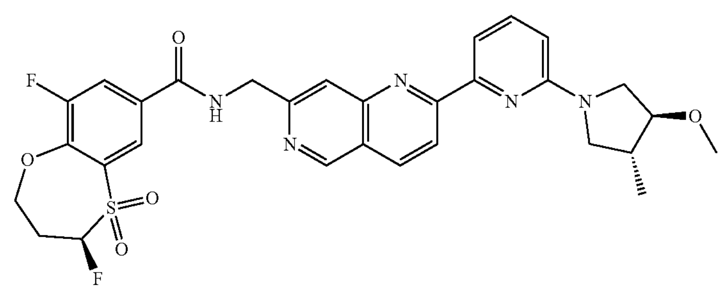 [SMILES: CO[C@@H]1CN(c2cccc(-c3ccc4cnc(CNC(=O)c5cc(F)c6c(c5)S(=O)(=O)[C@@H](F)CCO6)cc4n3)n2)C[C@H]1C] |
| 105 | 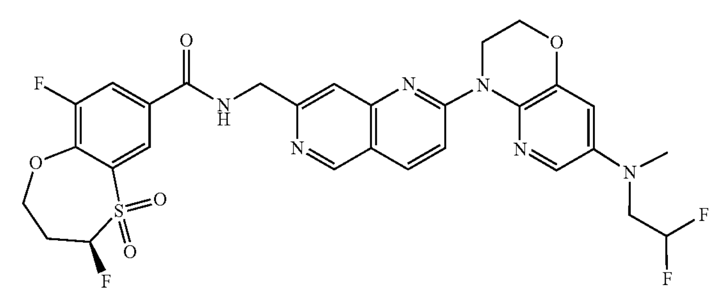 [SMILES: CN(CC(F)F)c1cnc2c(c1)OCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|-----------|
| 106 | 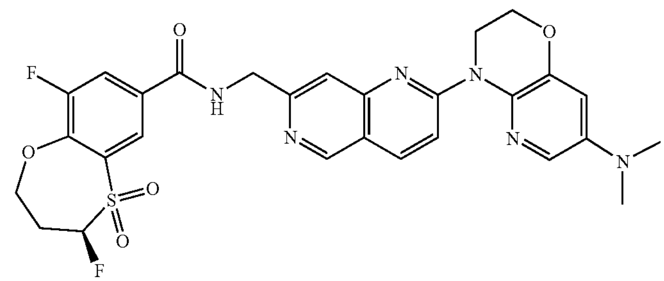 [SMILES: CN(C)c1cnc2c(c1)OCCN2c1ccc2cnc(CNC(=O)c3cc(F)c4c(c3)S(=O)(=O)[C@@H](F)CCO4)cc2n1] |
| 107 | 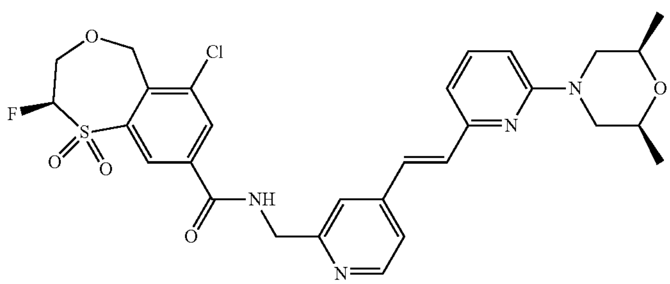 [SMILES: C[C@@H]1CN(c2cccc(/C=C/c3ccnc(CNC(=O)c4cc(Cl)c5c(c4)S(=O)(=O)[C@@H](F)COC5)c3)n2)C[C@H](C)O1] |
| 108 | 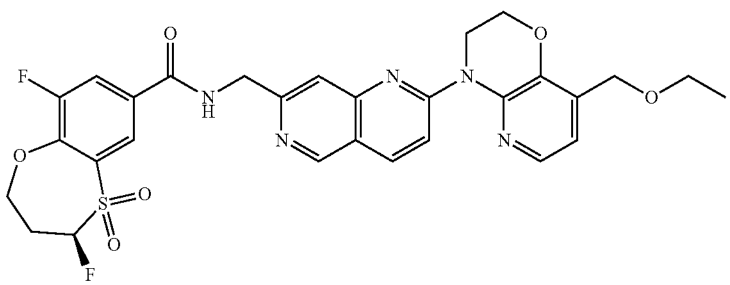 [SMILES: CCOCc1ccnc2c1OCCN2c1ccc2cnc(CNC(=O)c3cc(F)c4c(c3)S(=O)(=O)[C@@H](F)CCO4)cc2n1] |
| 109 | 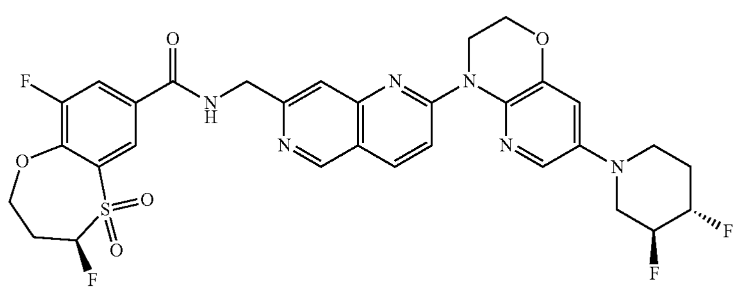 [SMILES: O=C(NCc1cc2nc(N3CCOc4cc(N5CC[C@H](F)[C@@H](F)C5)cnc43)ccc2cn1)c1cc(F)c2c(c1)S(=O)(=O)[C@@H](F)CCO2] |
| 110 | 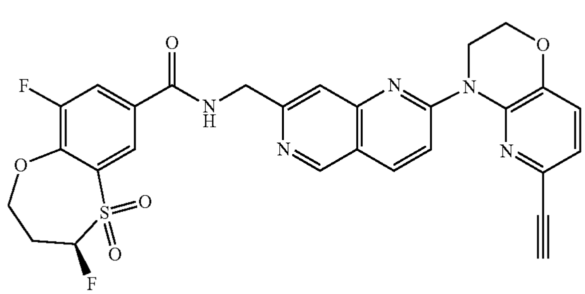 [SMILES: C#Cc1ccc2c(n1)N(c1ccc3cnc(CNC(=O)c4cc(F)c5c(c4)S(=O)(=O)[C@@H](F)CCO5)cc3n1)CCO2] |

TABLE 1-continued

Compounds of the invention

| # | Structure |
|---|-----------|
| 111 | 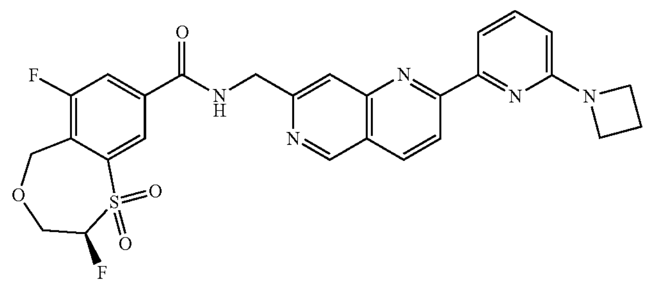 [SMILES: O=C(NCc1cc2nc(-c3cccc(N4CCC4)n3)ccc2cn1)c1cc(F)c2c(c1)S(=O)(=O)[C@@H](F)COC2] |
| 112 | 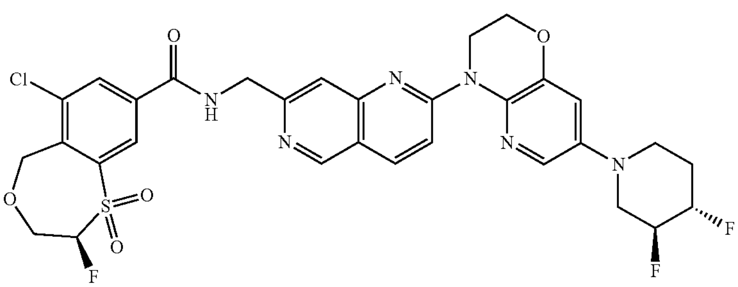 [SMILES: O=C(NCc1cc2nc(N3CCOc4cc(N5CC[C@H](F)[C@@H](F)C5)cnc43)ccc2cn1)c1cc(Cl)c2c(c1)S(=O)(=O)[C@@H](F)COC2] |
| 113 | 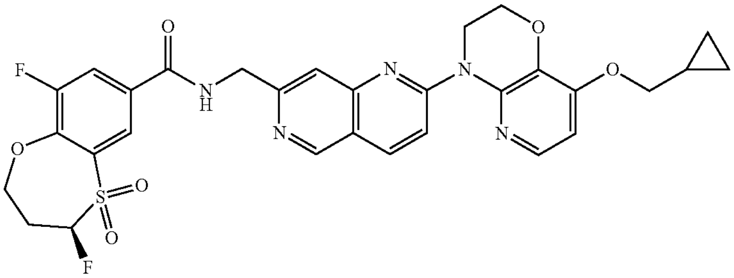 [SMILES: O=C(NCc1cc2nc(N3CCOc4c(OCC5CC5)ccnc43)ccc2cn1)c1cc(F)c2c(c1)S(=O)(=O)[C@@H](F)CCO2] |
| 114 | 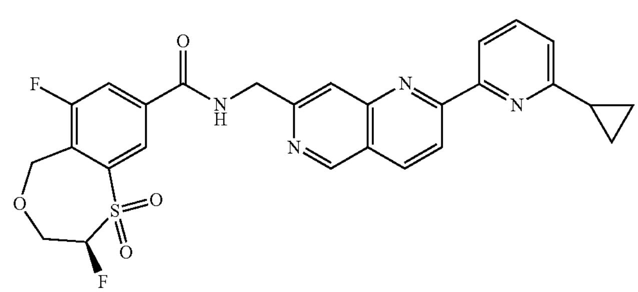 [SMILES: O=C(NCc1cc2nc(-c3cccc(C4CC4)n3)ccc2cn1)c1cc(F)c2c(c1)S(=O)(=O)[C@@H](F)COC2] |
| 115 | 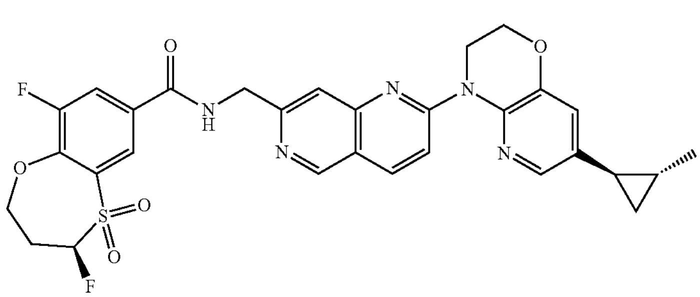 [SMILES: C[C@@H]1C[C@H]1c1cnc2c(c1)OCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|---|
| 116 | 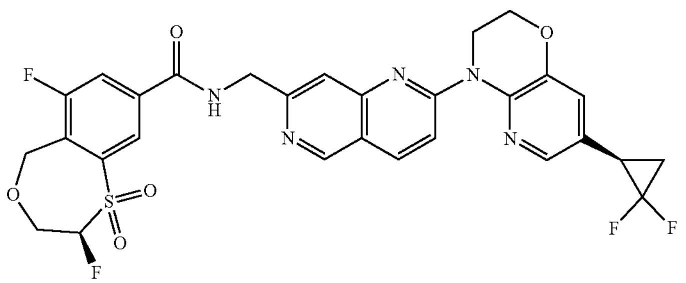 [SMILES: O=C(NCc1cc2nc(N3CCOc4cc([C@H]5CC5(F)F)cnc43)ccc2cn1)c1cc(F)c2c(c1)S(=O)(=O)[C@@H](F)COC2] |
| 117 | 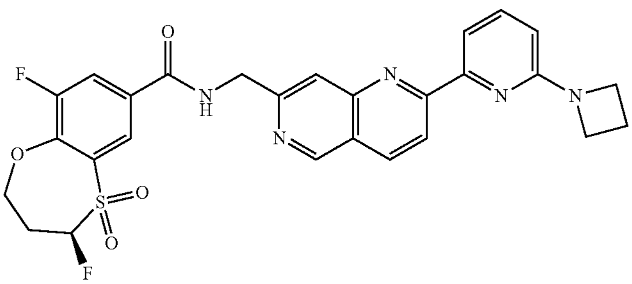 [SMILES: O=C(NCc1cc2nc(-c3cccc(N4CCC4)n3)ccc2cn1)c1cc(F)c2c(c1)S(=O)(=O)[C@@H](F)CCO2] |
| 118 | 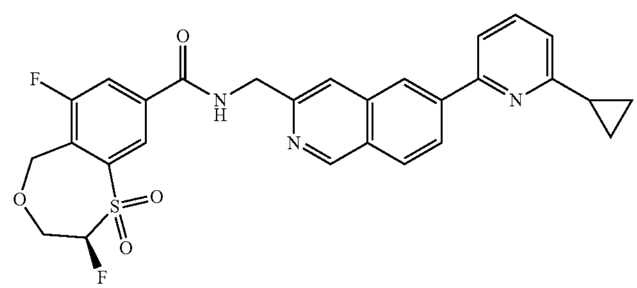 [SMILES: O=C(NCc1cc2cc(-c3cccc(C4CC4)n3)ccc2cn1)c1cc(F)c2c(c1)S(=O)(=O)[C@@H](F)COC2] |
| 119 | 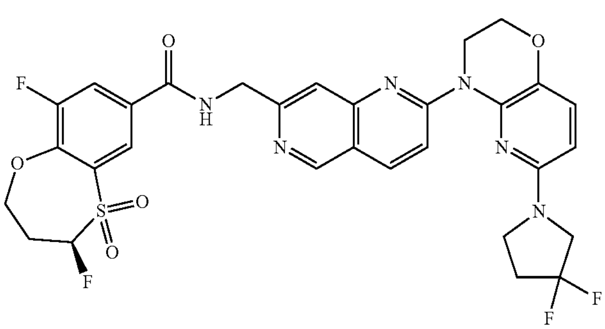 [SMILES: O=C(NCc1cc2nc(N3CCOc4ccc(N5CCC(F)(F)C5)nc43)ccc2cn1)c1cc(F)c2c(c1)S(=O)(=O)[C@@H](F)CCO2] |
| 120 | 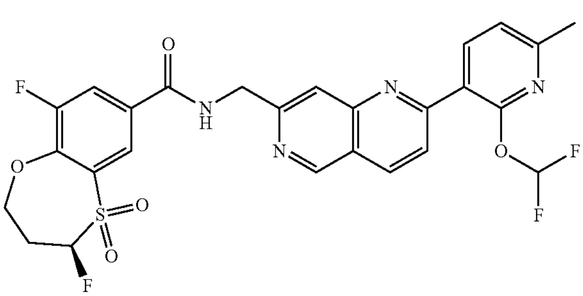 [SMILES: Cc1ccc(-c2ccc3cnc(CNC(=O)c4cc(F)c5c(c4)S(=O)(=O)[C@@H](F)CCO5)cc3n2)c(OC(F)F)n1] |

TABLE 1-continued
Compounds of the invention
| # | Structure |
|---|---|
| 121 | 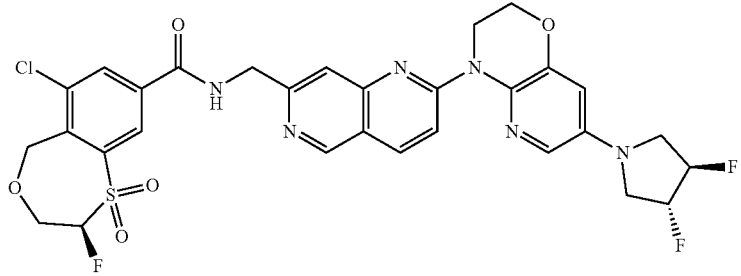 [SMILES: O=C(NCc1cc2nc(N3CCOc4cc(N5C[C@@H](F)[C@H](F)C5)cnc43)ccc2cn1)c1cc(Cl)c2c(c1)S(=O)(=O)[C@@H](F)COC2] |
| 122 | 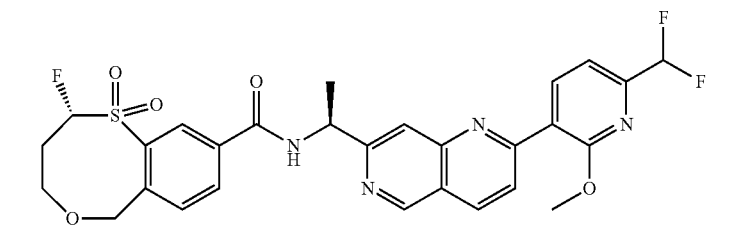 [SMILES: COc1nc(C(F)F)ccc1-c1ccc2cnc([C@H](C)NC(=O)c3ccc4c(c3)S(=O)(=O)[C@@H](F)CCOC4)cc2n1] |
| 123 | 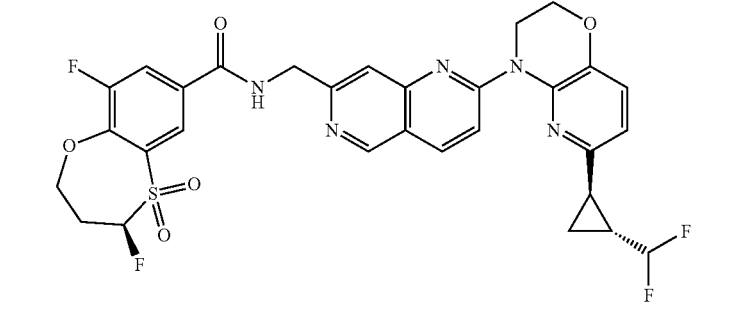 [SMILES: O=C(NCc1cc2nc(N3CCOc4ccc([C@@H]5C[C@H]5C(F)F)nc43)ccc2cn1)c1cc(F)c2c(c1)S(=O)(=O)[C@@H](F)CCO2] |
| 124 | 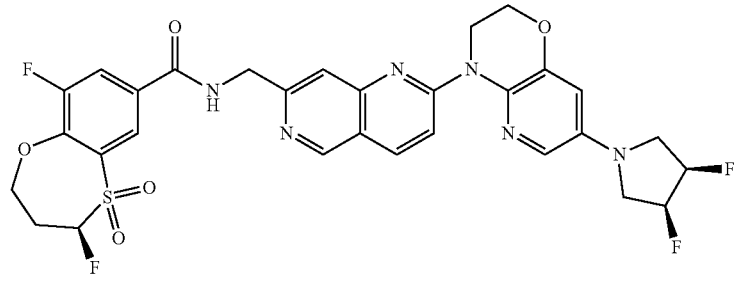 [SMILES: O=C(NCc1cc2nc(N3CCOc4cc(N5C[C@@H](F)[C@@H](F)C5)cnc43)ccc2cn1)c1cc(F)c2c(c1)S(=O)(=O)[C@@H](F)CCO2] |
| 125 | 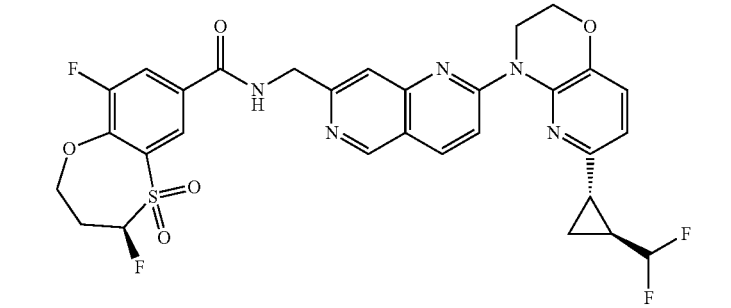 [SMILES: O=C(NCc1cc2nc(N3CCOc4ccc([C@H]5C[C@@H]5C(F)F)nc43)ccc2cn1)c1cc(F)c2c(c1)S(=O)(=O)[C@@H](F)CCO2] |

TABLE 1-continued

Compounds of the invention

| # | Structure |
|---|---|
| 126 | 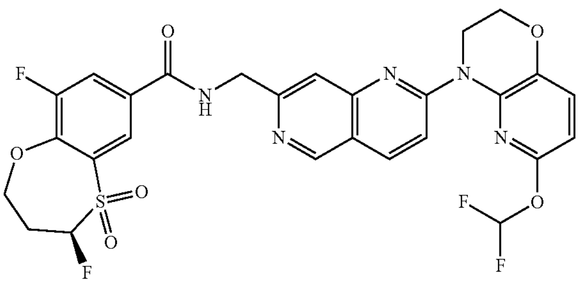 [SMILES: O=C(NCc1cc2nc(N3CCOc4ccc(OC(F)F)nc43)ccc2cn1)c1cc(F)c2c(c1)S(=O)(=O)[C@@H](F)CCO2] |
| 127 | 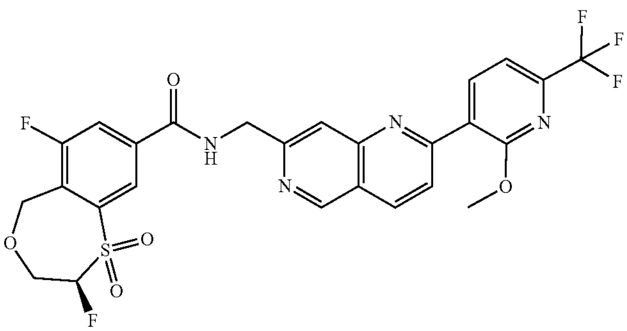 [SMILES: COc1nc(C(F)(F)F)ccc1-c1ccc2cnc(CNC(=O)c3cc(F)c4c(c3)S(=O)(=O)[C@@H](F)COC4)cc2n1] |
| 128 | 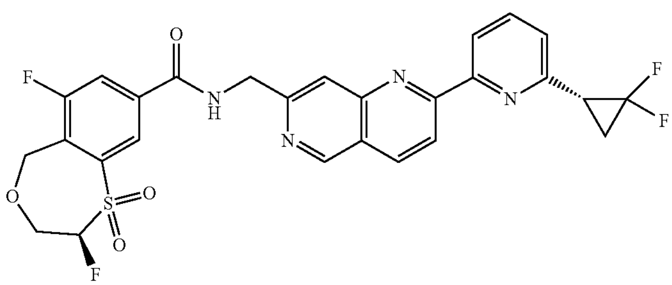 [SMILES: O=C(NCc1cc2nc(-c3cccc([C@H]4CC4(F)F)n3)ccc2cn1)c1cc(F)c2c(c1)S(=O)(=O)[C@@H](F)COC2] |
| 129 | 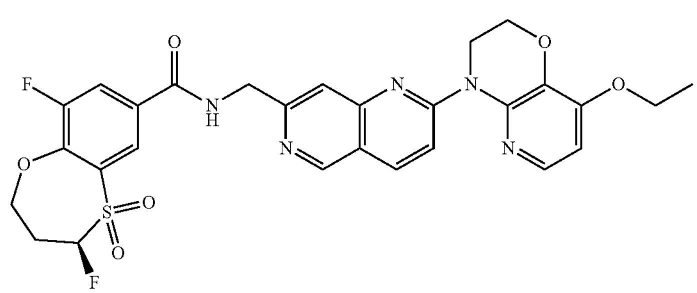 [SMILES: CCOc1ccnc2c1OCCN2c1ccc2cnc(CNC(=O)c3cc(F)c4c(c3)S(=O)(=O)[C@@H](F)CCO4)cc2n1] |
| 130 | 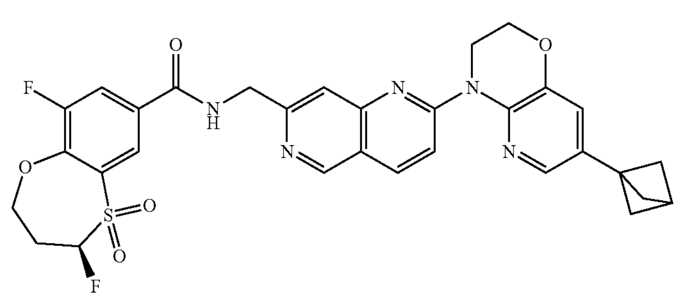 [SMILES: O=C(NCc1cc2nc(N3CCOc4cc(C56CC(C5)C6)cnc43)ccc2cn1)c1cc(F)c2c(c1)S(=O)(=O)[C@@H](F)CCO2] |

TABLE 1-continued
Compounds of the invention
| # | Structure |
|---|---|
| 131 | 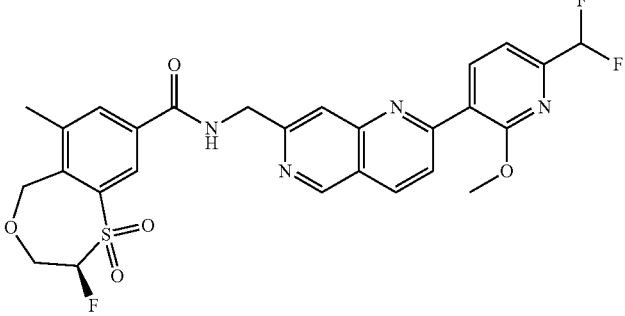 |
| 132 | 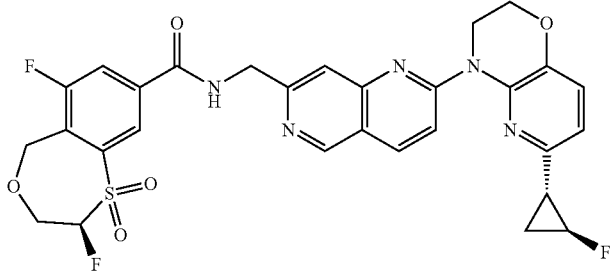 [SMILES: O=C(NCc1cc2nc(N3CCOc4ccc([C@H]5C[C@@H]5F)nc43)ccc2cn1)c1cc(F)c2c(c1)S(=O)(=O)[C@@H](F)COC2] |
| 133 | 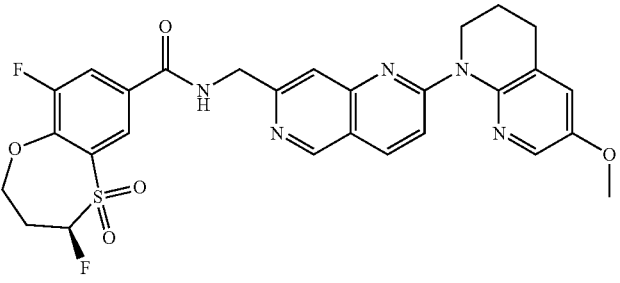 [SMILES: COc1cnc2c(c1)CCCN2c1ccc2cnc(CNC(=O)c3cc(F)c4c(c3)S(=O)(=O)[C@@H](F)CCO4)cc2n1] |
| 134 | 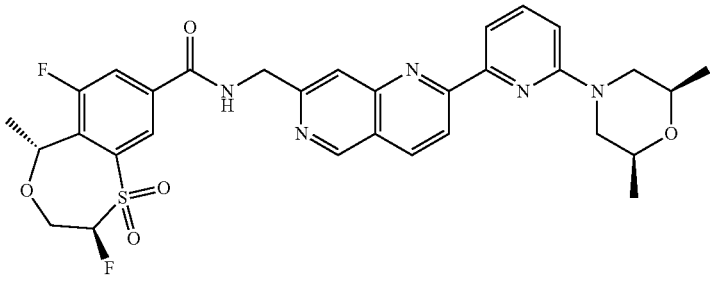 |
| 135 | 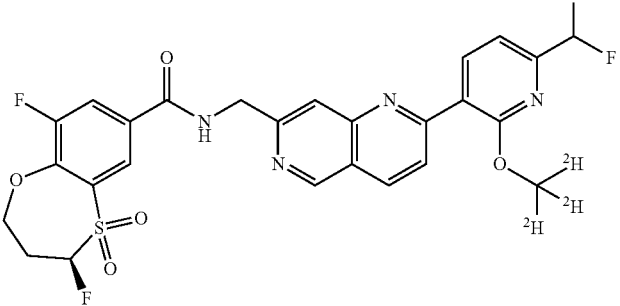 |

TABLE 1-continued

Compounds of the invention

| # | Structure |
|---|---|
| 136 | 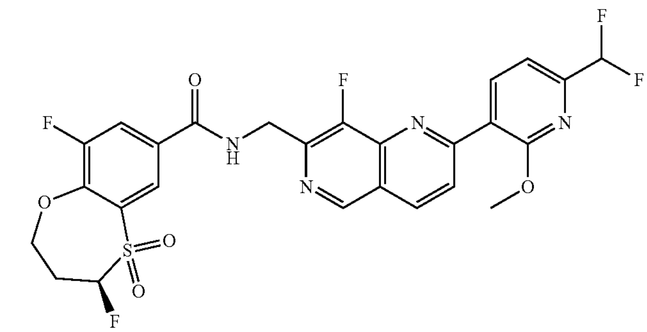 [SMILES: COc1nc(C(F)F)ccc1-c1ccc2cnc(CNC(=O)c3cc(F)c4c(c3)S(=O)(=O)[C@@H](F)CCO4)c(F)c2n1] |
| 137 | 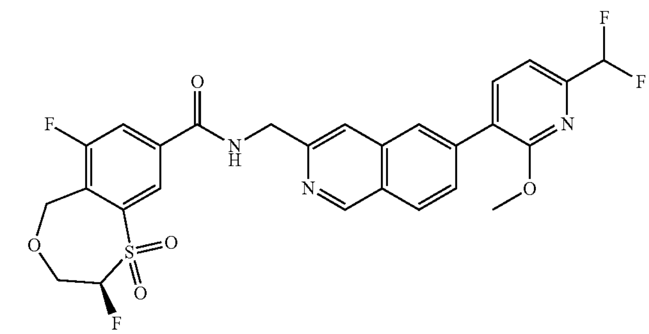 [SMILES: COc1nc(C(F)F)ccc1-c1ccc2cnc(CNC(=O)c3cc(F)c4c(c3)S(=O)(=O)[C@@H](F)COC4)cc2c1] |
| 138 | 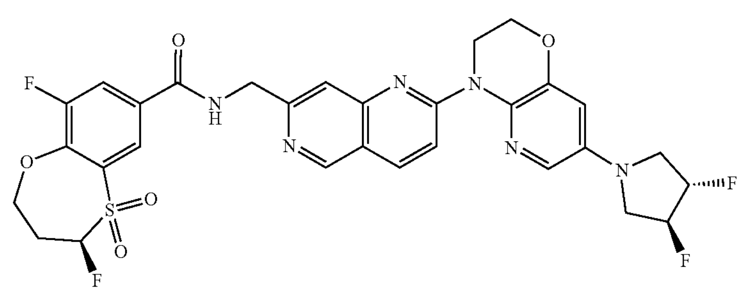 [SMILES: O=C(NCc1cc2nc(N3CCOc4cc(N5C[C@H](F)[C@@H](F)C5)cnc43)ccc2cn1)c1cc(F)c2c(c1)S(=O)(=O)[C@@H](F)CCO2] |
| 139 | 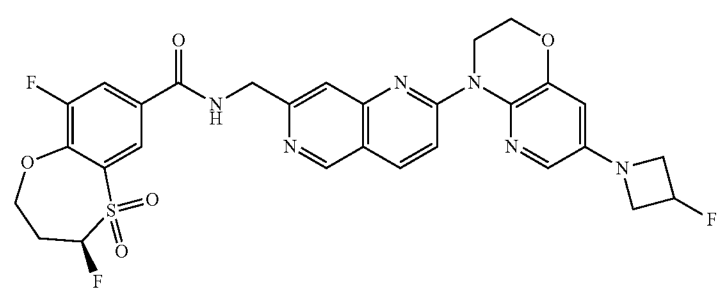 [SMILES: O=C(NCc1cc2nc(N3CCOc4cc(N5CC(F)C5)cnc43)ccc2cn1)c1cc(F)c2c(c1)S(=O)(=O)[C@@H](F)CCO2] |
| 140 | 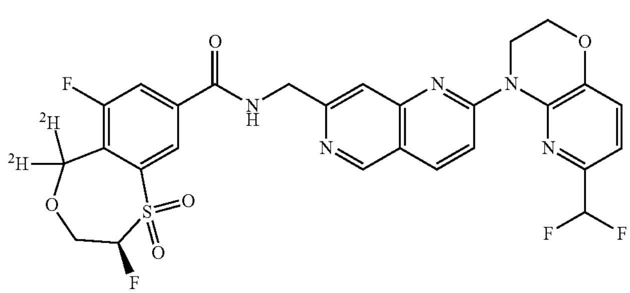 [SMILES: [2H]C1([2H])OC[C@H](F)S(=O)(=O)c2cc(C(=O)NCc3cc4nc(N5CCOc6ccc(C(F)F)nc65)ccc4cn3)cc(F)c21] |

TABLE 1-continued
Compounds of the invention
| # | Structure |
|---|---|
| 141 | 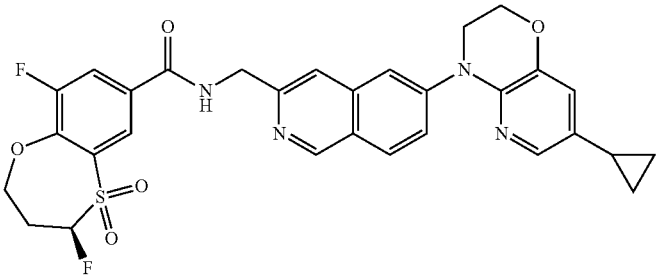 [SMILES: O=C(NCc1cc2cc(N3CCOc4cc(C5CC5)cnc43)ccc2cn1)c1cc(F)c2c(c1)S(=O)(=O)[C@@H](F)CCO2] |
| 142 | 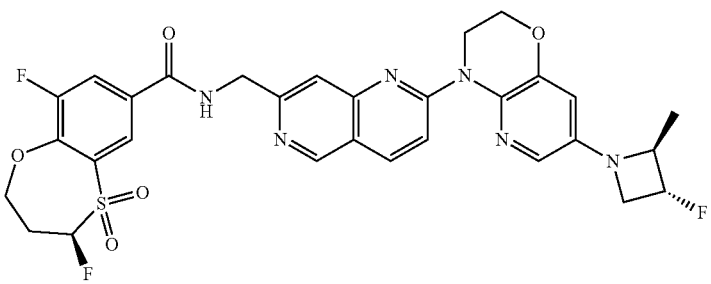 [SMILES: C[C@H]1[C@H](F)CN1c1cnc2c(c1)OCCN2c1ccc2cnc(CNC(=O)c3cc(F)c4c(c3)S(=O)(=O)[C@@H](F)CCO4)cc2n1] |
| 143 | 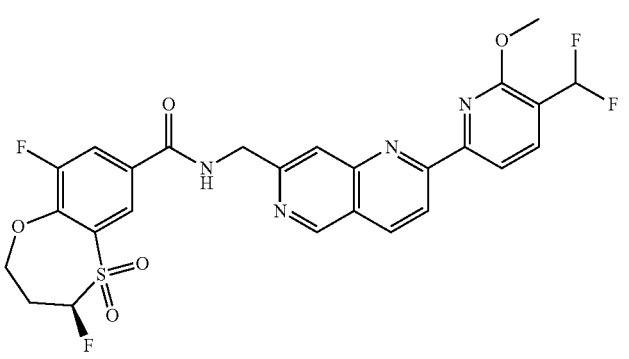 [SMILES: COc1nc(-c2ccc3cnc(CNC(=O)c4cc(F)c5c(c4)S(=O)(=O)[C@@H](F)CCO5)cc3n2)ccc1C(F)F] |
| 144 | 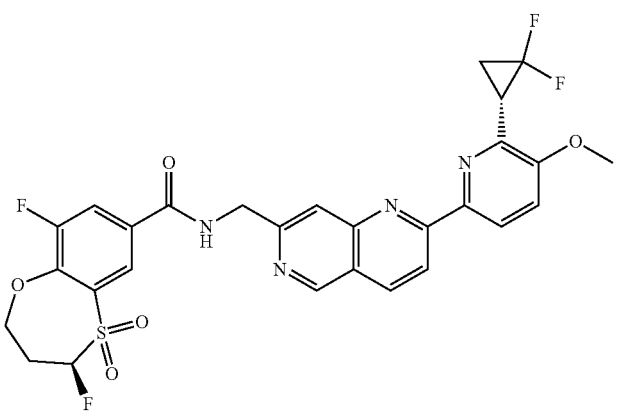 [SMILES: COc1ccc(-c2ccc3cnc(CNC(=O)c4cc(F)c5c(c4)S(=O)(=O)[C@@H](F)CCO5)cc3n2)nc1[C@@H]1CC1(F)F] |

TABLE 1-continued

Compounds of the invention

| # | Structure |
|---|---|
| 145 | 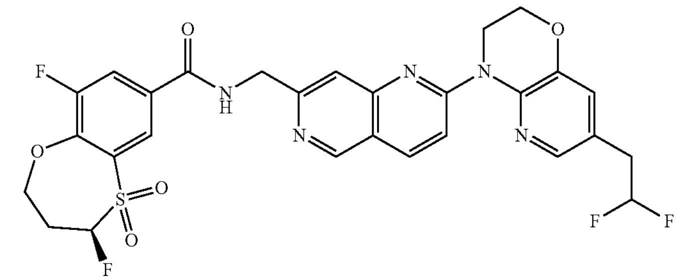 [SMILES: O=C(NCc1cc2nc(N3CCOc4cc(CC(F)F)cnc43)ccc2cn1)c1cc(F)c2c(c1)S(=O)(=O)[C@@H](F)CCO2] |
| 146 | 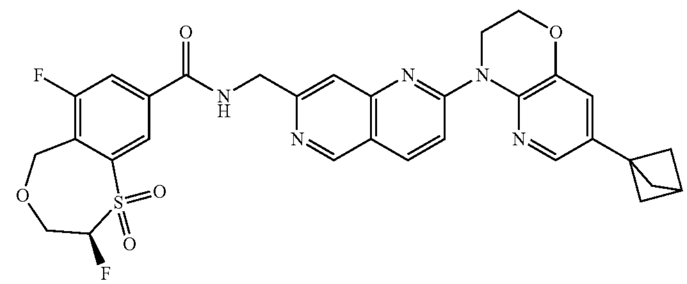 [SMILES: O=C(NCc1cc2nc(N3CCOc4cc(C56CC(C5)C6)cnc43)ccc2cn1)c1cc(F)c2c(c1)S(=O)(=O)[C@@H](F)COC2] |
| 147 | 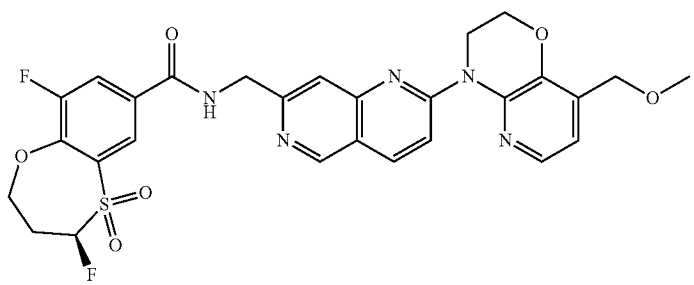 [SMILES: COCc1ccnc2c1OCCN2c1ccc2cnc(CNC(=O)c3cc(F)c4c(c3)S(=O)(=O)[C@@H](F)CCO4)cc2n1] |
| 148 | 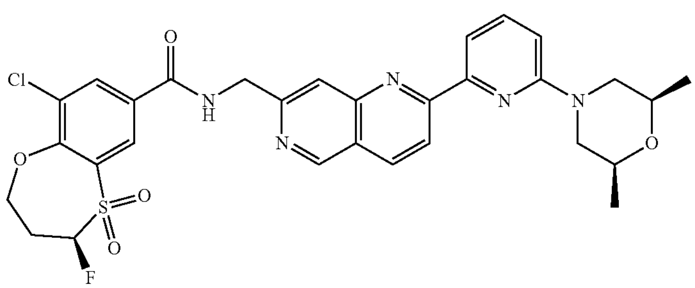 [SMILES: C[C@@H]1CN(c2cccc(-c3ccc4cnc(CNC(=O)c5cc(Cl)c6c(c5)S(=O)(=O)[C@@H](F)CCO6)cc4n3)n2)C[C@H](C)O1] |
| 149 | 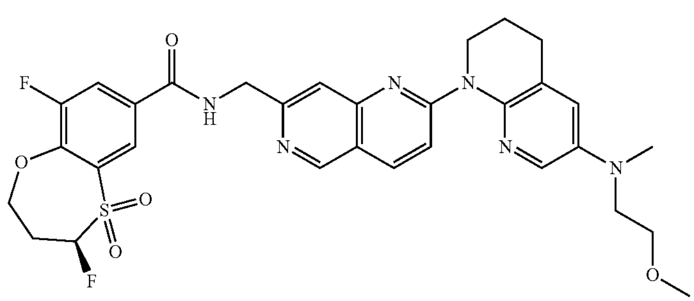 [SMILES: COCCN(C)c1cnc2c(c1)CCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|---|
| 150 | 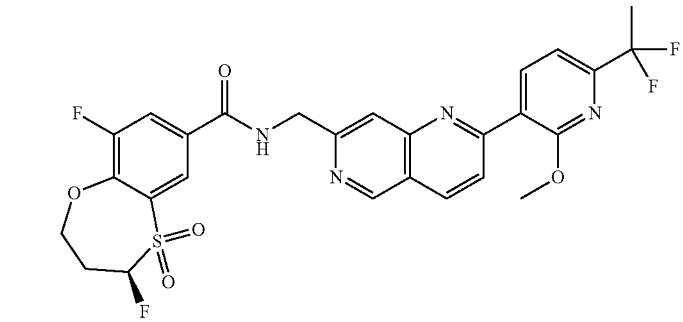 [SMILES: COc1nc(C(C)(F)F)ccc1-c1ccc2cnc(CNC(=O)c3cc(F)c4c(c3)S(=O)(=O)[C@@H](F)CCO4)cc2n1] |
| 151 | 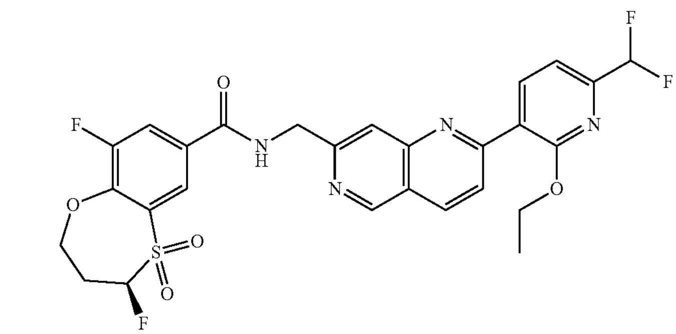 [SMILES: CCOc1nc(C(F)F)ccc1-c1ccc2cnc(CNC(=O)c3cc(F)c4c(c3)S(=O)(=O)[C@@H](F)CCO4)cc2n1] |
| 152 | 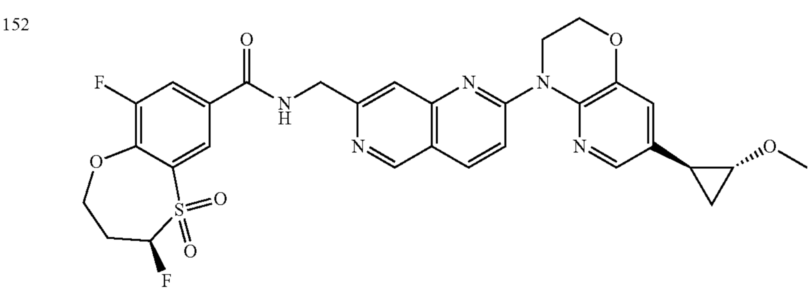 |
| 153 | 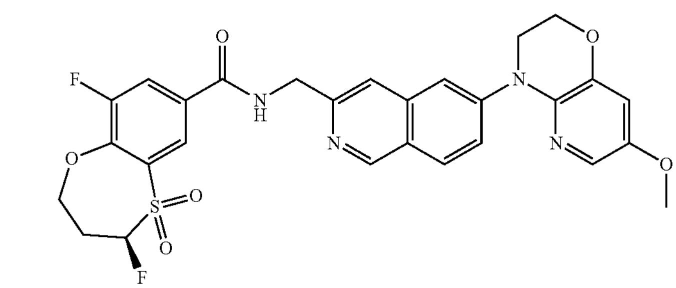 [SMILES: COc1cnc2c(c1)OCCN2c1ccc2cnc(CNC(=O)c3cc(F)c4c(c3)S(=O)(=O)[C@@H](F)CCO4)cc2c1] |
| 154 | 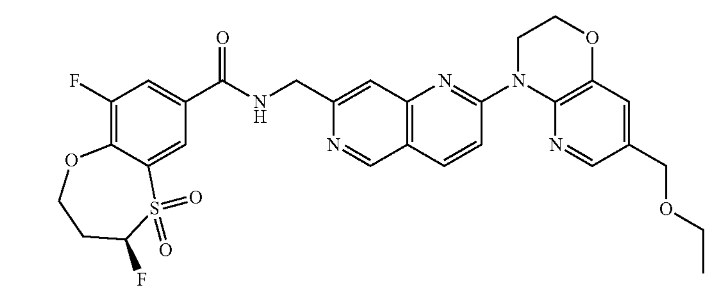 [SMILES: CCOCc1cnc2c(c1)OCCN2c1ccc2cnc(CNC(=O)c3cc(F)c4c(c3)S(=O)(=O)[C@@H](F)CCO4)cc2n1] |

TABLE 1-continued
Compounds of the invention
| # | Structure |
|---|---|
| 155 | 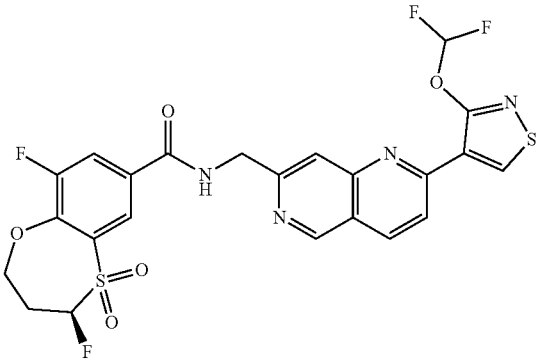 [SMILES: O=C(NCc1cc2nc(-c3csnc3OC(F)F)ccc2cn1)c1cc(F)c2c(c1)S(=O)(=O)[C@@H](F)CCO2] |
| 156 | 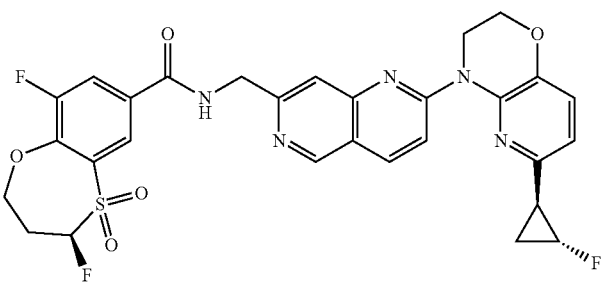 [SMILES: O=C(NCc1cc2nc(N3CCOc4ccc([C@@H]5C[C@H]5F)nc43)ccc2cn1)c1cc(F)c2c(c1)S(=O)(=O)[C@@H](F)CCO2] |
| 157 | 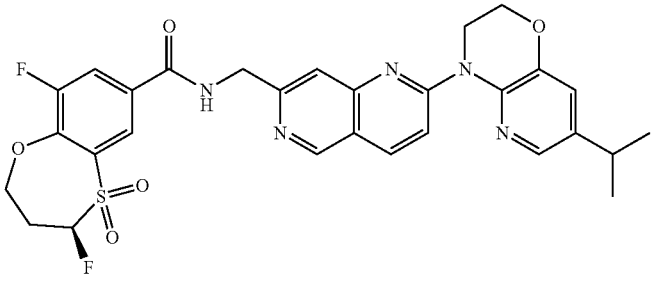 [SMILES: CC(C)c1cnc2c(c1)OCCN2c1ccc2cnc(CNC(=O)c3cc(F)c4c(c3)S(=O)(=O)[C@@H](F)CCO4)cc2n1] |
| 158 | 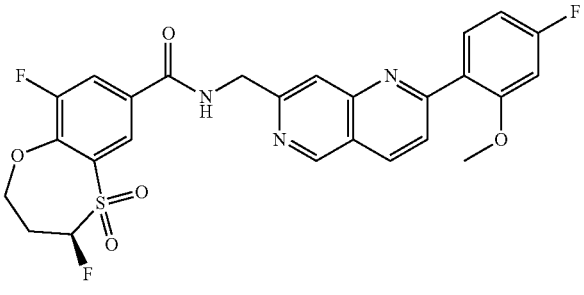 [SMILES: COc1cc(F)ccc1-c1ccc2cnc(CNC(=O)c3cc(F)c4c(c3)S(=O)(=O)[C@@H](F)CCO4)cc2n1] |
| 159 | 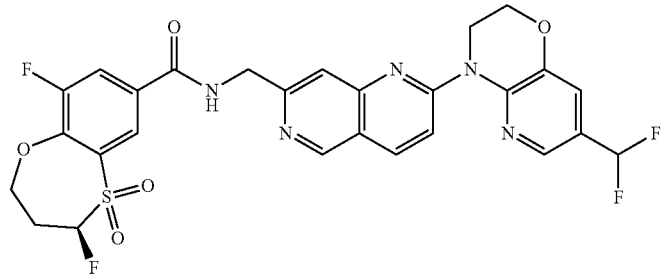 [SMILES: O=C(NCc1cc2nc(N3CCOc4cc(C(F)F)cnc43)ccc2cn1)c1cc(F)c2c(c1)S(=O)(=O)[C@@H](F)CCO2] |

TABLE 1-continued

Compounds of the invention

| # | Structure |
|---|---|
| 160 | 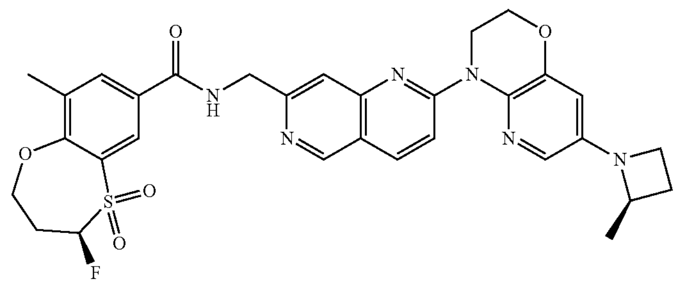 [SMILES: Cc1cc(C(=O)NCc2cc3nc(N4CCOc5cc(N6CC[C@H]6C)cnc54)ccc3cn2)cc2c1OCC[C@H](F)S2(=O)=O] |
| 161 | 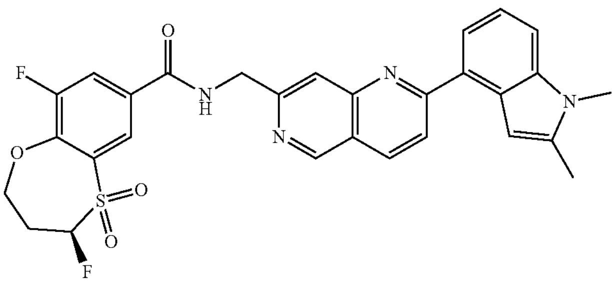 [SMILES: Cc1cc2c(-c3ccc4cnc(CNC(=O)c5cc(F)c6c(c5)S(=O)(=O)[C@@H](F)CCO6)cc4n3)cccc2n1C] |
| 162 | 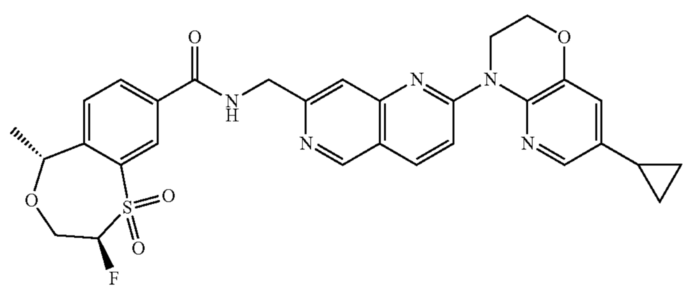 [SMILES: C[C@H]1OC[C@H](F)S(=O)(=O)c2cc(C(=O)NCc3cc4nc(N5CCOc6cc(C7CC7)cnc65)ccc4cn3)ccc21] |
| 163 | 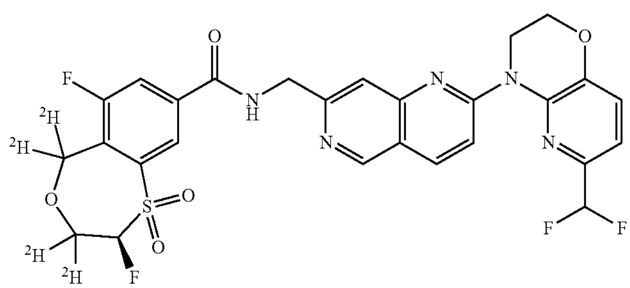 [SMILES: [2H]C1([2H])OC([2H])([2H])[C@H](F)S(=O)(=O)c2cc(C(=O)NCc3cc4nc(N5CCOc6ccc(C(F)F)nc65)ccc4cn3)cc(F)c21] |
| 164 | 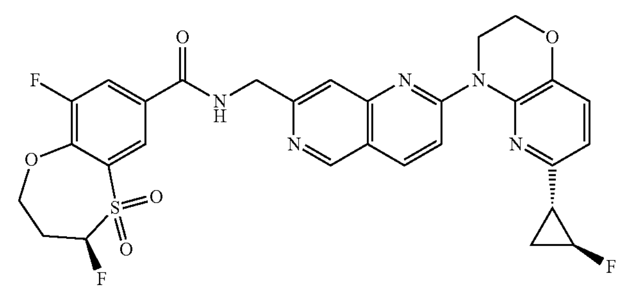 [SMILES: O=C(NCc1cc2nc(N3CCOc4ccc([C@H]5C[C@@H]5F)nc43)ccc2cn1)c1cc(F)c2c(c1)S(=O)(=O)[C@@H](F)CCO2] |

TABLE 1-continued

Compounds of the invention

| # | Structure |
|---|---|
| 165 | 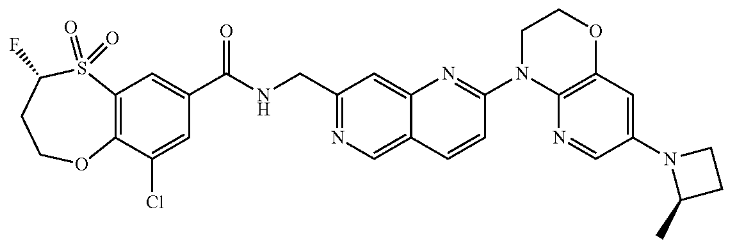 [SMILES: C[C@@H]1CCN1c1cnc2c(c1)OCCN2c1ccc2cnc(CNC(=O)c3cc(Cl)c4c(c3)S(=O)(=O)[C@@H](F)CCO4)cc2n1] |
| 166 | 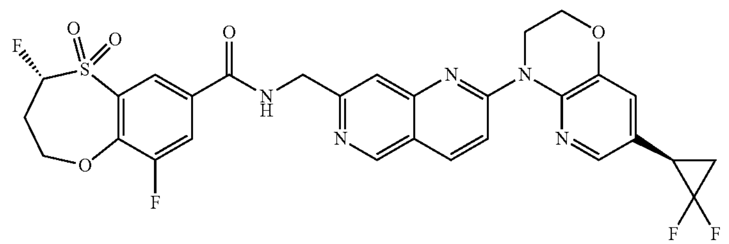 [SMILES: O=C(NCc1cc2nc(N3CCOc4cc([C@H]5CC5(F)F)cnc43)ccc2cn1)c1cc(F)c2c(c1)S(=O)(=O)[C@@H](F)CCO2] |
| 167 | 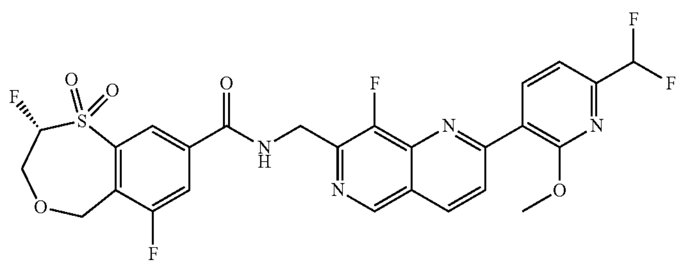 [SMILES: COc1nc(C(F)F)ccc1-c1ccc2cnc(CNC(=O)c3cc(F)c4c(c3)S(=O)(=O)[C@@H](F)COC4)c(F)c2n1] |
| 168 | 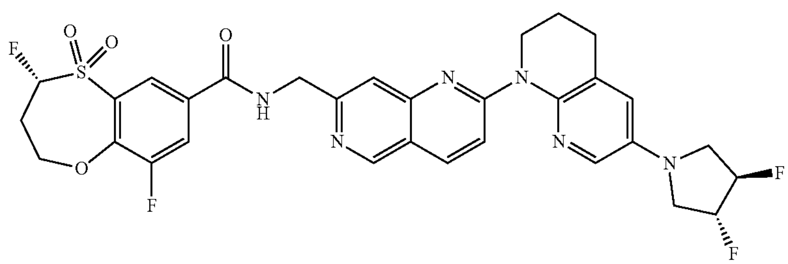 [SMILES: O=C(NCc1cc2nc(N3CCCc4cc(N5C[C@@H](F)[C@H](F)C5)cnc43)ccc2cn1)c1cc(F)c2c(c1)S(=O)(=O)[C@@H](F)CCO2] |
| 169 | 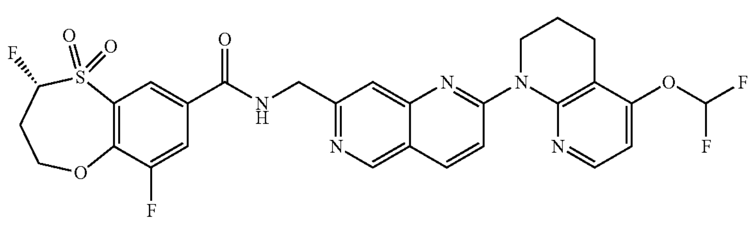 [SMILES: O=C(NCc1cc2nc(N3CCCc4c(OC(F)F)ccnc43)ccc2cn1)c1cc(F)c2c(c1)S(=O)(=O)[C@@H](F)CCO2] |
| 170 | 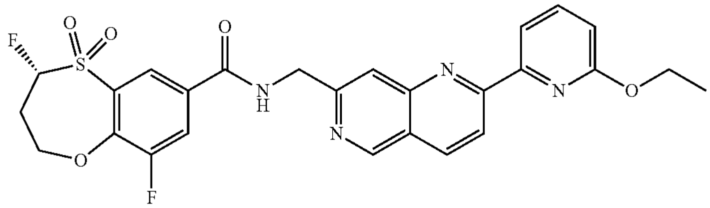 [SMILES: CCOc1cccc(-c2ccc3cnc(CNC(=O)c4cc(F)c5c(c4)S(=O)(=O)[C@@H](F)CCO5)cc3n2)n1] |

TABLE 1-continued

Compounds of the invention

| # | Structure |
|---|-----------|
| 171 | 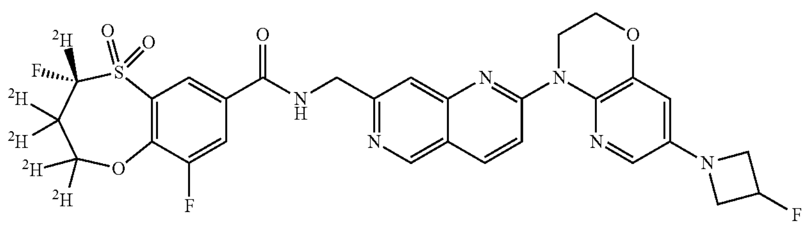 [SMILES: [2H]C1([2H])Oc2c(F)cc(C(=O)NCc3cc4nc(N5CCOc6cc(N7CC(F)C7)cnc65)ccc4cn3)cc2S(=O)(=O)[C@@]([2H])(F)C1([2H])[2H]] |
| 172 | 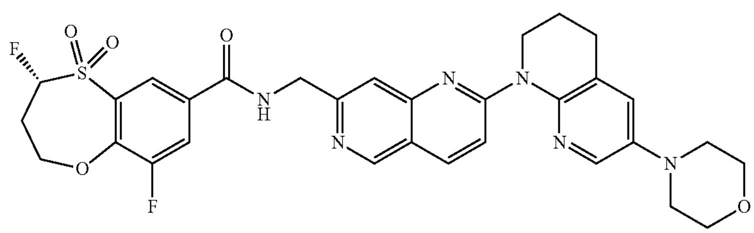 [SMILES: O=C(NCc1cc2nc(N3CCCc4cc(N5CCOCC5)cnc43)ccc2cn1)c1cc(F)c2c(c1)S(=O)(=O)[C@@H](F)CCO2] |
| 173 | 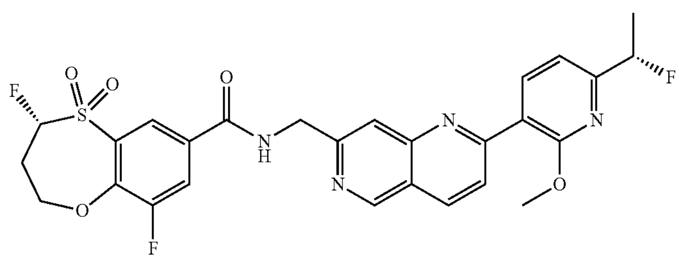 [SMILES: COc1nc([C@H](C)F)ccc1-c1ccc2cnc(CNC(=O)c3cc(F)c4c(c3)S(=O)(=O)[C@@H](F)CCO4)cc2n1] |
| 174 | 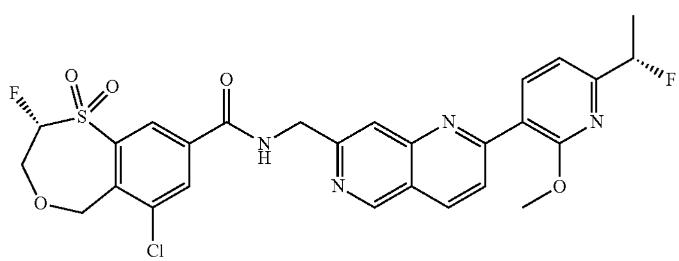 [SMILES: COc1nc([C@H](C)F)ccc1-c1ccc2cnc(CNC(=O)c3cc(Cl)c4c(c3)S(=O)(=O)[C@@H](F)COC4)cc2n1] |
| 175 | 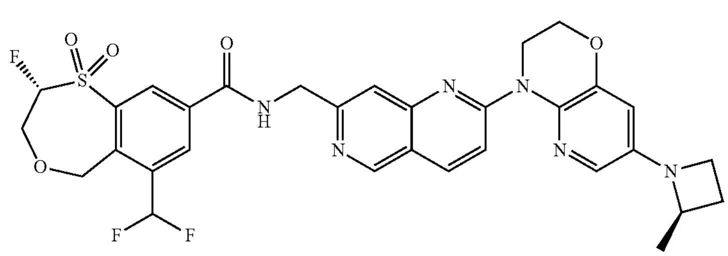 [SMILES: C[C@@H]1CCN1c1cnc2c(c1)OCCN2c1ccc2cnc(CNC(=O)c3cc(C(F)F)c4c(c3)S(=O)(=O)[C@@H](F)COC4)cc2n1] |
| 176 | 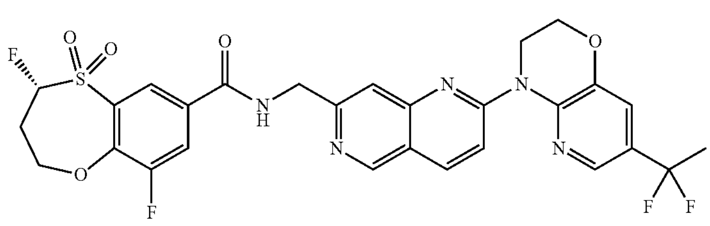 [SMILES: CC(F)(F)c1cnc2c(c1)OCCN2c1ccc2cnc(CNC(=O)c3cc(F)c4c(c3)S(=O)(=O)[C@@H](F)CCO4)cc2n1] |

TABLE 1-continued
Compounds of the invention
| # | Structure |
|---|---|
| 177 | 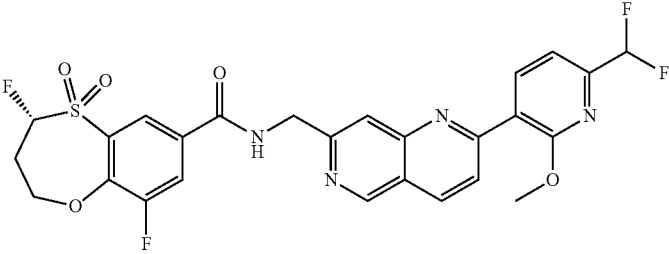 [SMILES: COc1nc(C(F)F)ccc1-c1ccc2cnc(CNC(=O)c3cc(F)c4c(c3)S(=O)(=O)[C@@H](F)CCO4)cc2n1] |
| 178 | 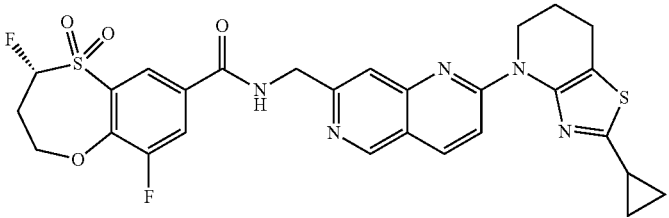 [SMILES: O=C(NCc1cc2nc(N3CCCc4sc(C5CC5)nc43)ccc2cn1)c1cc(F)c2c(c1)S(=O)(=O)[C@@H](F)CCO2] |
| 179 | 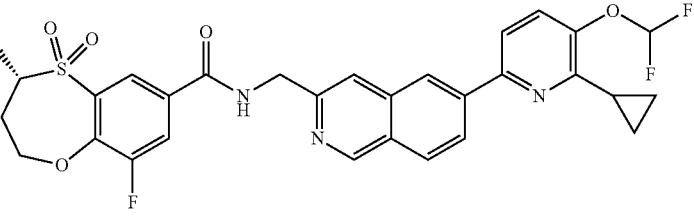 |
| 180 | 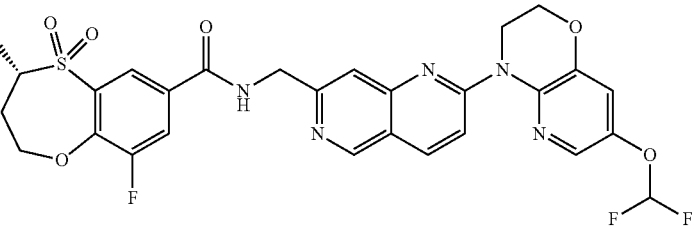 |
| 181 | 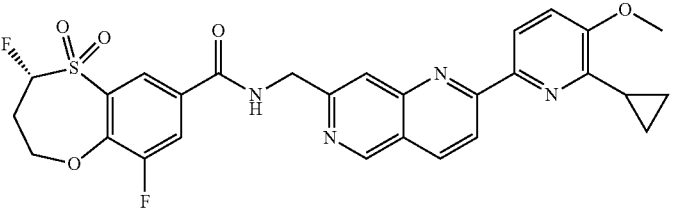 [SMILES: COc1ccc(-c2ccc3cnc(CNC(=O)c4cc(F)c5c(c4)S(=O)(=O)[C@@H](F)CCO5)cc3n2)nc1C1CC1] |
| 182 | 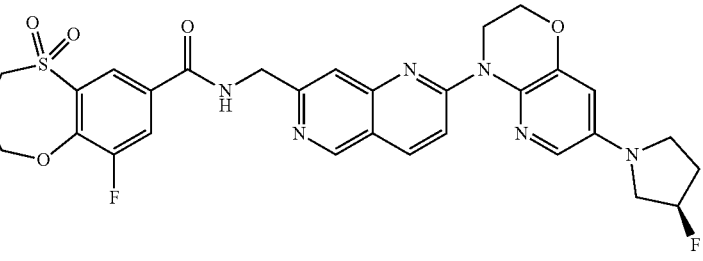 |

TABLE 1-continued

Compounds of the invention

| # | Structure |
|---|---|
| 183 | 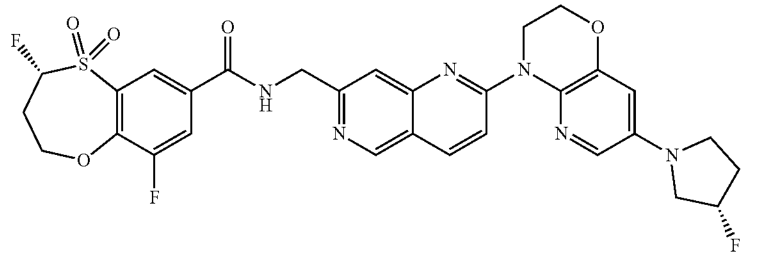 [SMILES: O=C(NCc1cc2nc(N3CCOc4cc(N5CC[C@H](F)C5)cnc43)ccc2cn1)c1cc(F)c2c(c1)S(=O)(=O)[C@@H](F)CCO2] |
| 184 | 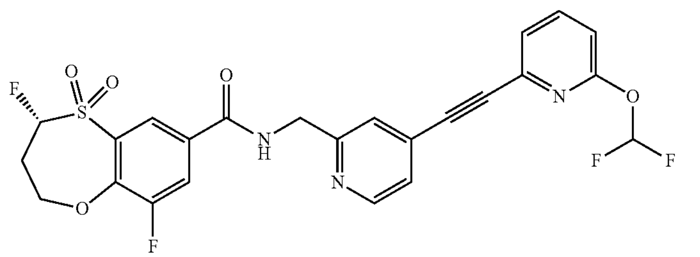 [SMILES: O=C(NCc1cc(C#Cc2cccc(OC(F)F)n2)ccn1)c1cc(F)c2c(c1)S(=O)(=O)[C@@H](F)CCO2] |
| 185 | 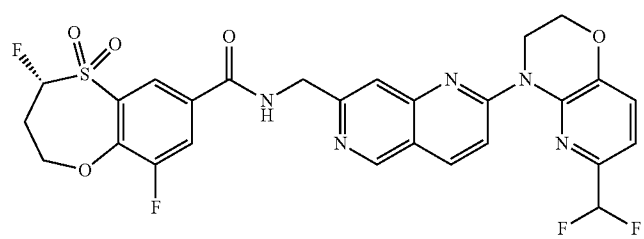 [SMILES: O=C(NCc1cc2nc(N3CCOc4ccc(C(F)F)nc43)ccc2cn1)c1cc(F)c2c(c1)S(=O)(=O)[C@@H](F)CCO2] |
| 186 | 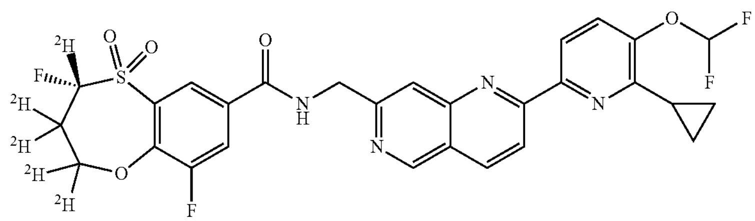 [SMILES: [2H]C1([2H])Oc2c(F)cc(C(=O)NCc3cc4nc(-c5ccc(OC(F)F)c(C6CC6)n5)ccc4cn3)cc2S(=O)(=O)[C@@]([2H])(F)C1([2H])[2H]] |
| 187 | 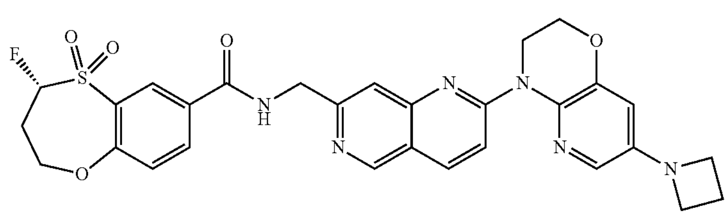 [SMILES: O=C(NCc1cc2nc(N3CCOc4cc(N5CCC5)cnc43)ccc2cn1)c1ccc2c(c1)S(=O)(=O)[C@@H](F)CCO2] |
| 188 | 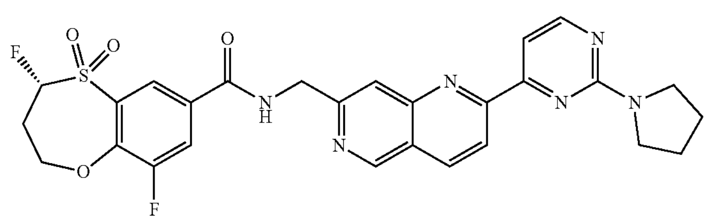 [SMILES: O=C(NCc1cc2nc(-c3ccnc(N4CCCC4)n3)ccc2cn1)c1cc(F)c2c(c1)S(=O)(=O)[C@@H](F)CCO2] |

TABLE 1-continued

Compounds of the invention

| # | Structure |
|---|---|
| 189 | 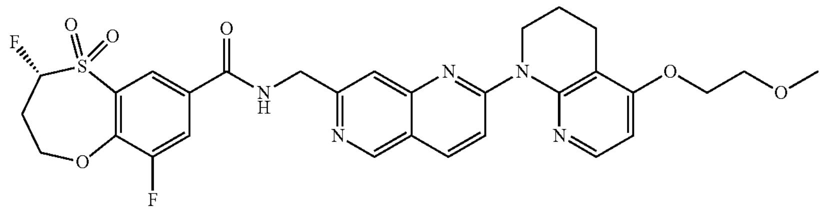 [SMILES: COCCOc1ccnc2c1CCCN2c1ccc2cnc(CNC(=O)c3cc(F)c4c(c3)S(=O)(=O)[C@@H](F)CCO4)cc2n1] |
| 190 | 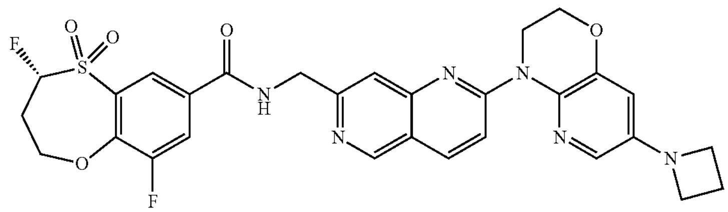 [SMILES: O=C(NCc1cc2nc(N3CCOc4cc(N5CCC5)cnc43)ccc2cn1)c1cc(F)c2c(c1)S(=O)(=O)[C@@H](F)CCO2] |
| 191 | 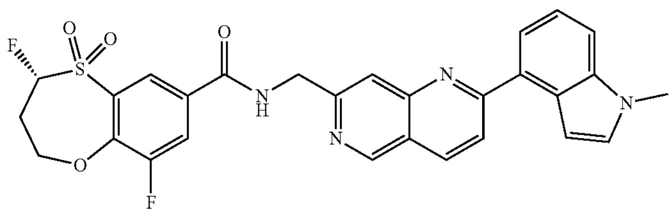 [SMILES: Cn1ccc2c(-c3ccc4cnc(CNC(=O)c5cc(F)c6c(c5)S(=O)(=O)[C@@H](F)CCO6)cc4n3)cccc21] |
| 192 | 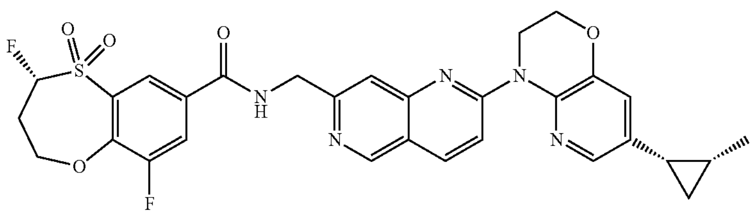 [SMILES: C[C@@H]1C[C@@H]1c1cnc2c(c1)OCCN2c1ccc2cnc(CNC(=O)c3cc(F)c4c(c3)S(=O)(=O)[C@@H](F)CCO4)cc2n1] |
| 193 | 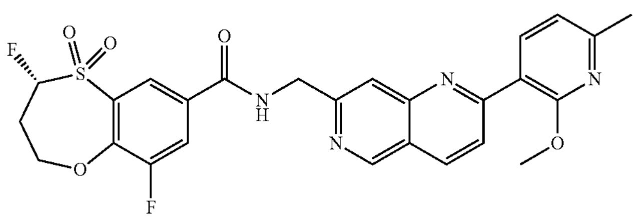 [SMILES: COc1nc(C)ccc1-c1ccc2cnc(CNC(=O)c3cc(F)c4c(c3)S(=O)(=O)[C@@H](F)CCO4)cc2n1] |
| 194 | 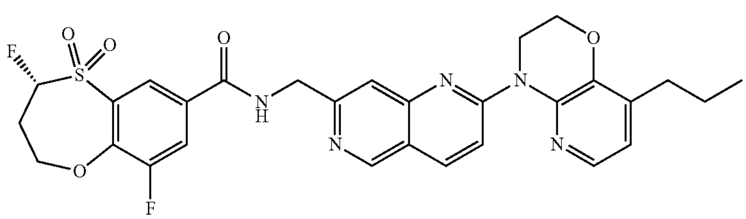 [SMILES: CCCc1ccnc2c1OCCN2c1ccc2cnc(CNC(=O)c3cc(F)c4c(c3)S(=O)(=O)[C@@H](F)CCO4)cc2n1] |
| 195 | 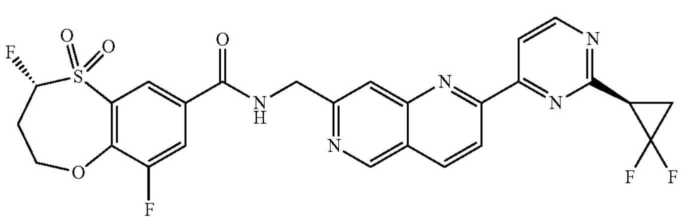 [SMILES: O=C(NCc1cc2nc(-c3ccnc([C@H]4CC4(F)F)n3)ccc2cn1)c1cc(F)c2c(c1)S(=O)(=O)[C@@H](F)CCO2] |

TABLE 1-continued

Compounds of the invention

| # | Structure |
|---|---|
| 196 | 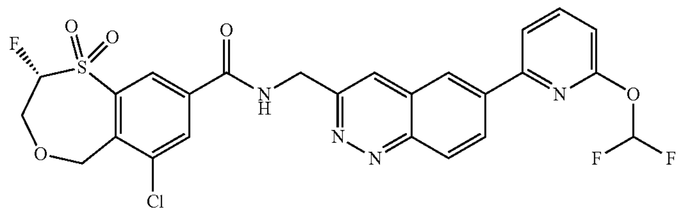 [SMILES: O=C(NCc1cc2cc(-c3cccc(OC(F)F)n3)ccc2nn1)c1cc(Cl)c2c(c1)S(=O)(=O)[C@@H](F)COC2] |
| 197 | 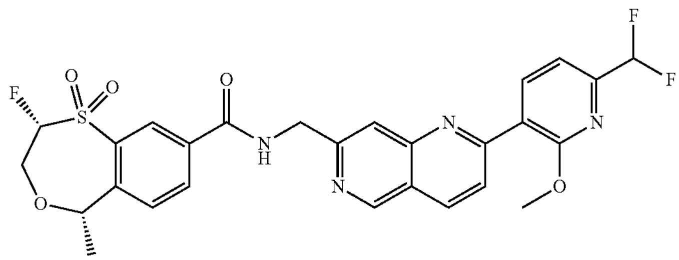 [SMILES: COc1nc(C(F)F)ccc1-c1ccc2cnc(CNC(=O)c3ccc4c(c3)S(=O)(=O)[C@@H](F)CO[C@H]4C)cc2n1] |
| 198 | 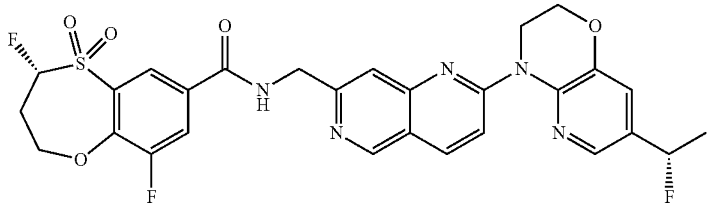 [SMILES: C[C@H](F)c1cnc2c(c1)OCCN2c1ccc2cnc(CNC(=O)c3cc(F)c4c(c3)S(=O)(=O)[C@@H](F)CCO4)cc2n1] |
| 199 | 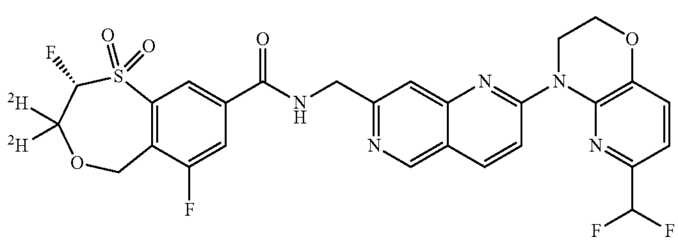 [SMILES: [2H]C1([2H])OCc2c(F)cc(C(=O)NCc3cc4nc(N5CCOc6ccc(C(F)F)nc65)ccc4cn3)cc2S(=O)(=O)[C@H]1F] |
| 200 | 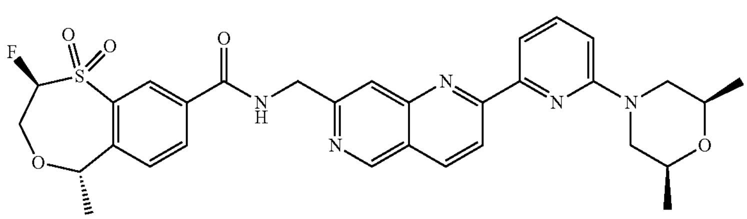 [SMILES: C[C@@H]1CN(c2cccc(-c3ccc4cnc(CNC(=O)c5ccc6c(c5)S(=O)(=O)[C@H](F)CO[C@H]6C)cc4n3)n2)C[C@H](C)O1] |
| 201 | 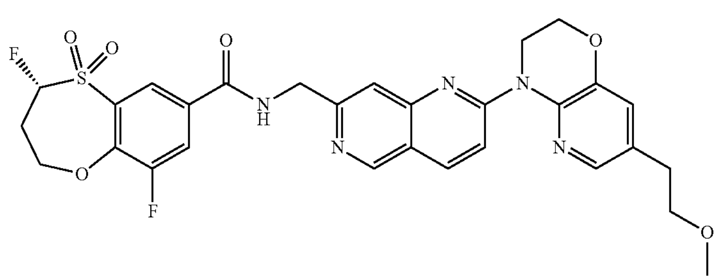 [SMILES: COCCc1cnc2c(c1)OCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|---|
| 202 | 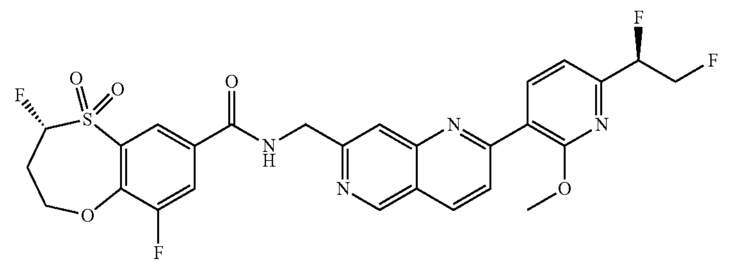 [SMILES: COc1nc([C@@H](F)CF)ccc1-c1ccc2cnc(CNC(=O)c3cc(F)c4c(c3)S(=O)(=O)[C@@H](F)CCO4)cc2n1] |
| 203 | 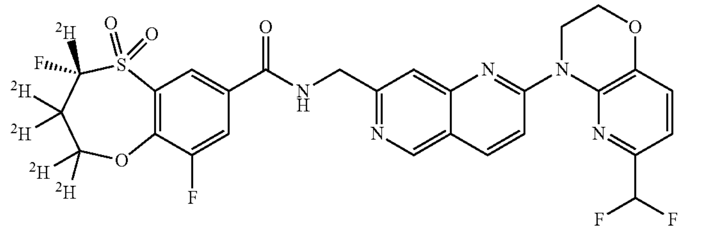 [SMILES: [2H]C1([2H])Oc2c(F)cc(C(=O)NCc3cc4nc(N5CCOc6ccc(C(F)F)nc65)ccc4cn3)cc2S(=O)(=O)[C@@]([2H])(F)C1([2H])[2H]] |
| 204 | 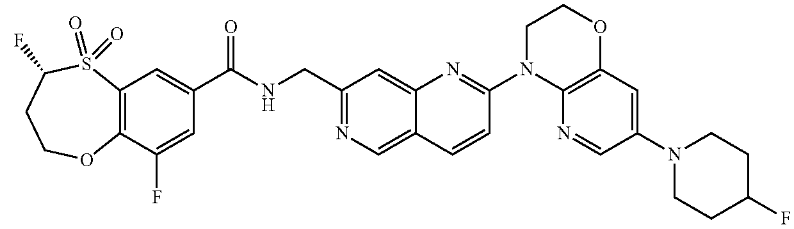 [SMILES: O=C(NCc1cc2nc(N3CCOc4cc(N5CCC(F)CC5)cnc43)ccc2cn1)c1cc(F)c2c(c1)S(=O)(=O)[C@@H](F)CCO2] |
| 205 | 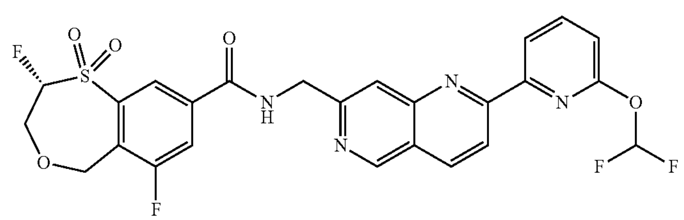 [SMILES: O=C(NCc1cc2nc(-c3cccc(OC(F)F)n3)ccc2cn1)c1cc(F)c2c(c1)S(=O)(=O)[C@@H](F)COC2] |
| 206 | 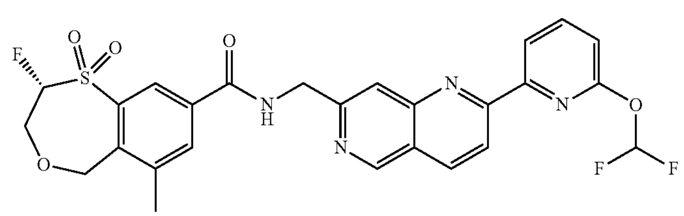 [SMILES: Cc1cc(C(=O)NCc2cc3nc(-c4cccc(OC(F)F)n4)ccc3cn2)cc2c1COC[C@H](F)S2(=O)=O] |
| 207 | 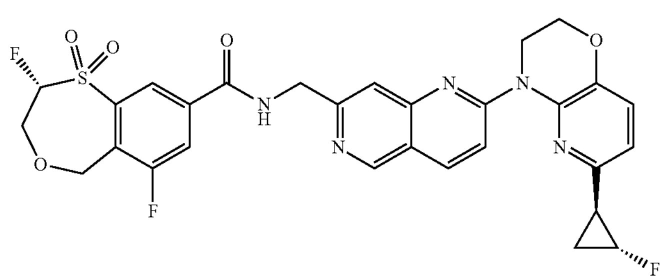 [SMILES: O=C(NCc1cc2nc(N3CCOc4ccc([C@@H]5C[C@H]5F)nc43)ccc2cn1)c1cc(F)c2c(c1)S(=O)(=O)[C@@H](F)COC2] |

TABLE 1-continued

Compounds of the invention

| # | Structure |
|---|---|
| 208 | 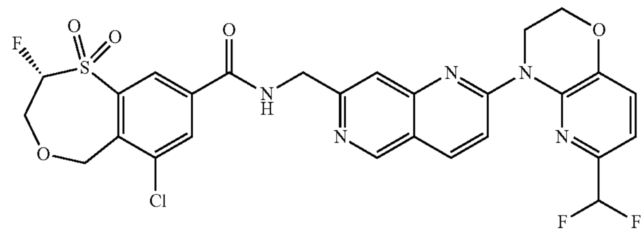 [SMILES: O=C(NCc1cc2nc(N3CCOc4ccc(C(F)F)nc43)ccc2cn1)c1cc(Cl)c2c(c1)S(=O)(=O)[C@@H](F)COC2] |
| 209 | 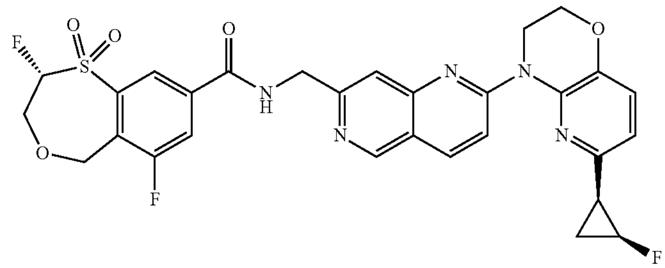 [SMILES: O=C(NCc1cc2nc(N3CCOc4ccc([C@@H]5C[C@@H]5F)nc43)ccc2cn1)c1cc(F)c2c(c1)S(=O)(=O)[C@@H](F)COC2] |
| 210 | 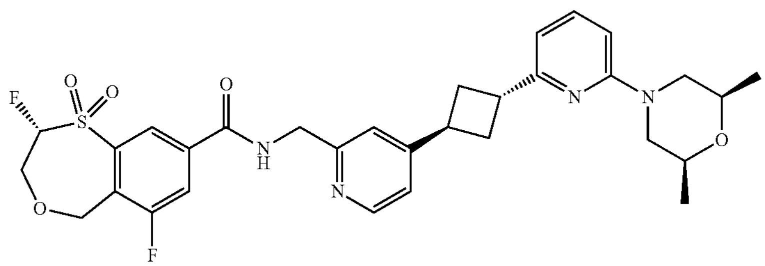 [SMILES: C[C@@H]1CN(c2cccc([C@H]3C[C@H](c4ccnc(CNC(=O)c5cc(F)c6c(c5)S(=O)(=O)[C@@H](F)COC6)c4)C3)n2)C[C@H](C)O1] |
| 211 | 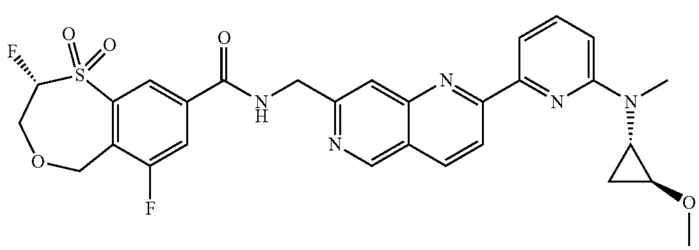 [SMILES: CO[C@H]1C[C@@H]1N(C)c1cccc(-c2ccc3cnc(CNC(=O)c4cc(F)c5c(c4)S(=O)(=O)[C@@H](F)COC5)cc3n2)n1] |
| 212 | 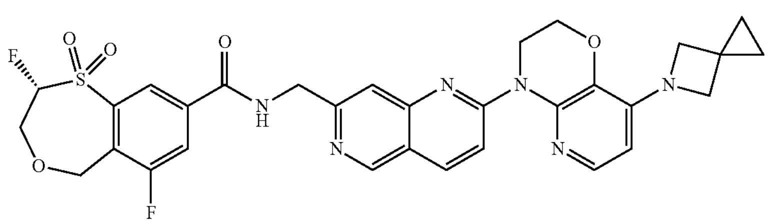 [SMILES: O=C(NCc1cc2nc(N3CCOc4c(N5CC6(CC6)C5)ccnc43)ccc2cn1)c1cc(F)c2c(c1)S(=O)(=O)[C@@H](F)COC2] |
| 213 | 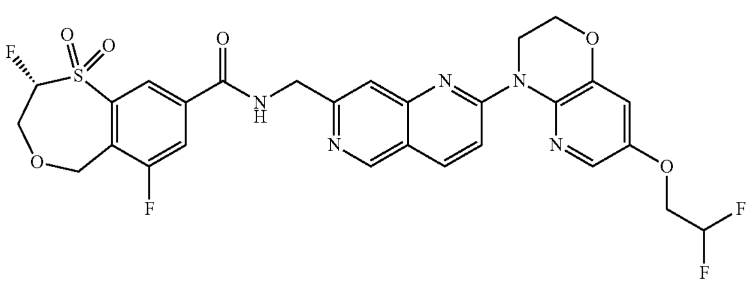 [SMILES: O=C(NCc1cc2nc(N3CCOc4cc(OCC(F)F)cnc43)ccc2cn1)c1cc(F)c2c(c1)S(=O)(=O)[C@@H](F)COC2] |

TABLE 1-continued
Compounds of the invention
| # | Structure |
|---|---|
| 214 | 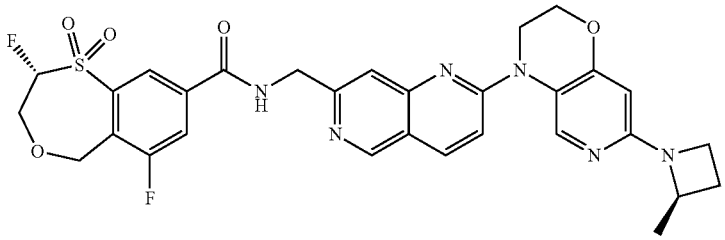 [SMILES: C[C@@H]1CCN1c1cc2c(cn1)N(c1ccc3cnc(CNC(=O)c4cc(F)c5c(c4)S(=O)(=O)[C@@H](F)COC5)cc3n1)CCO2] |
| 215 | 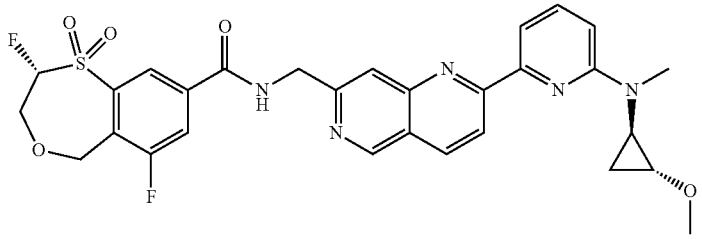 [SMILES: CO[C@@H]1C[C@H]1N(C)c1cccc(-c2ccc3cnc(CNC(=O)c4cc(F)c5c(c4)S(=O)(=O)[C@@H](F)COC5)cc3n2)n1] |
| 216 | 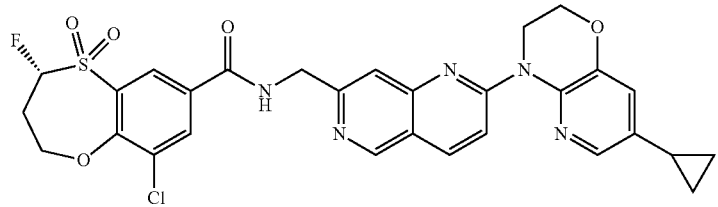 |
| 217 | 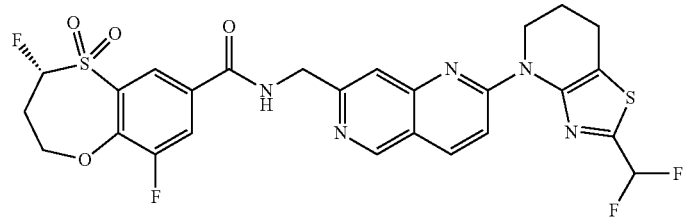 [SMILES: O=C(NCc1cc2nc(N3CCCc4sc(C(F)F)nc43)ccc2cn1)c1cc(F)c2c(c1)S(=O)(=O)[C@@H](F)CCO2] |
| 218 | 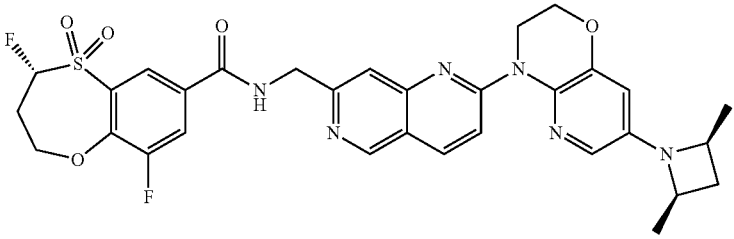 [SMILES: C[C@@H]1C[C@H](C)N1c1cnc2c(c1)OCCN2c1ccc2cnc(CNC(=O)c3cc(F)c4c(c3)S(=O)(=O)[C@@H](F)CCO4)cc2n1] |
| 219 | 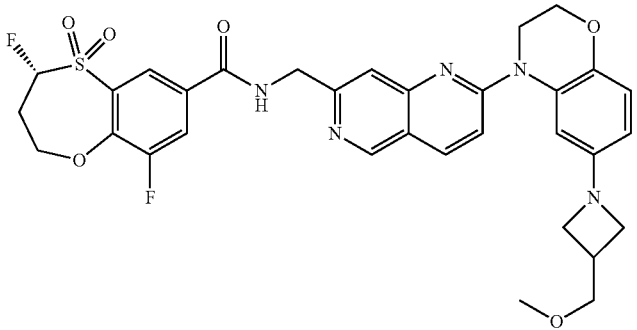 [SMILES: COCC1CN(c2ccc3c(c2)N(c2ccc4cnc(CNC(=O)c5cc(F)c6c(c5)S(=O)(=O)[C@@H](F)CCO6)cc4n2)CCO3)C1] |

TABLE 1-continued

Compounds of the invention

| # | Structure |
|---|---|
| 220 | 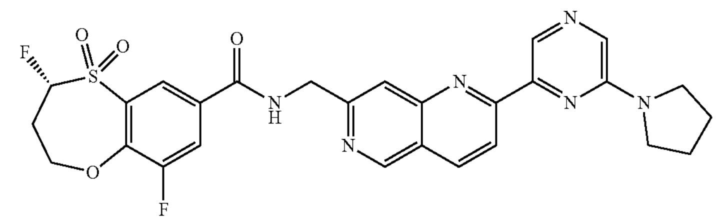 [SMILES: O=C(NCc1cc2nc(-c3cncc(N4CCCC4)n3)ccc2cn1)c1cc(F)c2c(c1)S(=O)(=O)[C@@H](F)CCO2] |
| 221 | 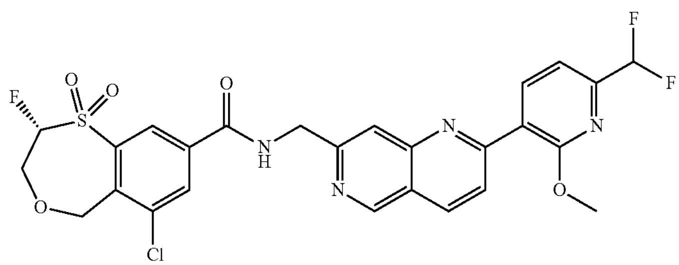 [SMILES: COc1nc(C(F)F)ccc1-c1ccc2cnc(CNC(=O)c3cc(Cl)c4c(c3)S(=O)(=O)[C@@H](F)COC4)cc2n1] |
| 222 | 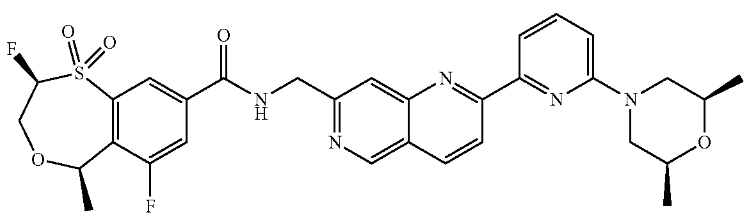 [SMILES: C[C@@H]1CN(c2cccc(-c3ccc4cnc(CNC(=O)c5cc(F)c6c(c5)S(=O)(=O)[C@H](F)CO[C@@H]6C)cc4n3)n2)C[C@H](C)O1] |
| 223 | 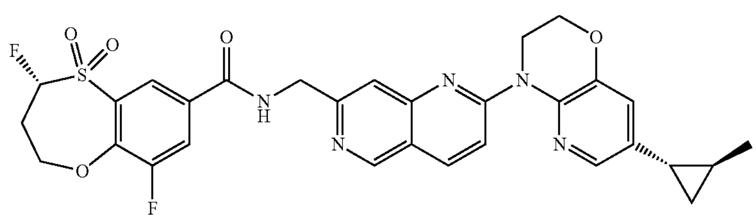 [SMILES: C[C@H]1C[C@@H]1c1cnc2c(c1)OCCN2c1ccc2cnc(CNC(=O)c3cc(F)c4c(c3)S(=O)(=O)[C@@H](F)CCO4)cc2n1] |
| 224 | 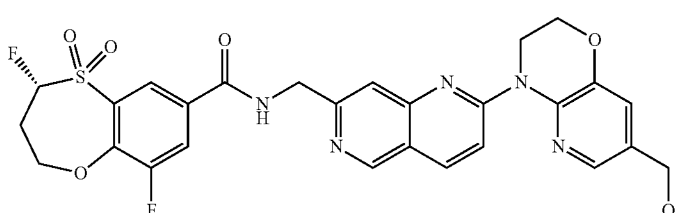 |
| 225 | 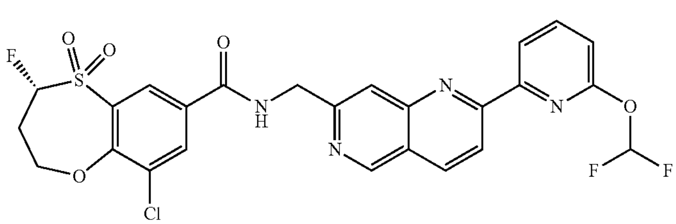 [SMILES: O=C(NCc1cc2nc(-c3cccc(OC(F)F)n3)ccc2cn1)c1cc(Cl)c2c(c1)S(=O)(=O)[C@@H](F)CCO2] |

TABLE 1-continued

Compounds of the invention

| # | Structure |
|---|---|
| 226 | 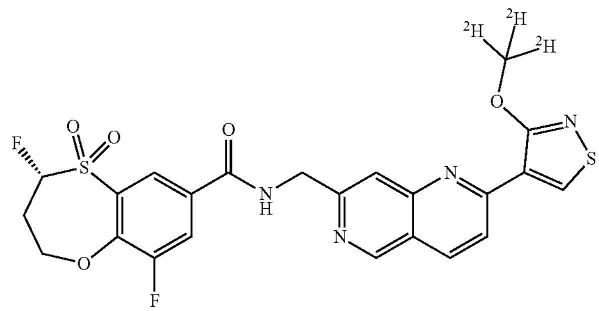 [SMILES: [2H]C([2H])([2H])Oc1nscc1-c1ccc2cnc(CNC(=O)c3cc(F)c4c(c3)S(=O)(=O)[C@@H](F)CCO4)cc2n1] |
| 227 | 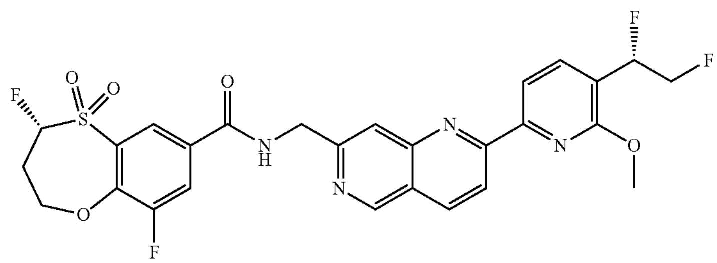 [SMILES: COc1nc(-c2ccc3cnc(CNC(=O)c4cc(F)c5c(c4)S(=O)(=O)[C@@H](F)CCO5)cc3n2)ccc1[C@H](F)CF] |
| 228 | 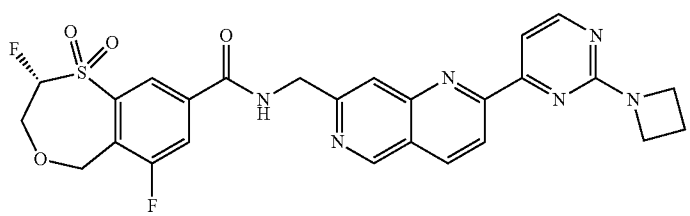 [SMILES: O=C(NCc1cc2nc(-c3ccnc(N4CCC4)n3)ccc2cn1)c1cc(F)c2c(c1)S(=O)(=O)[C@@H](F)COC2] |
| 229 | 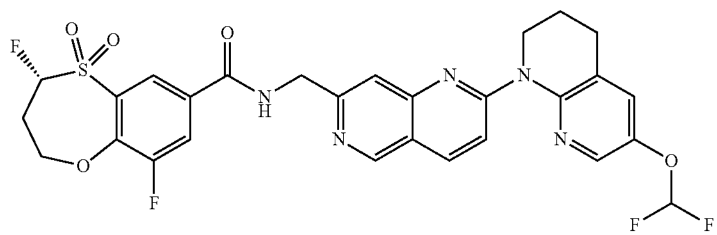 [SMILES: O=C(NCc1cc2nc(N3CCCc4cc(OC(F)F)cnc43)ccc2cn1)c1cc(F)c2c(c1)S(=O)(=O)[C@@H](F)CCO2] |
| 230 | 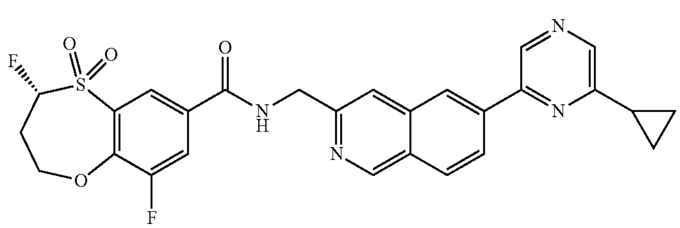 [SMILES: O=C(NCc1cc2cc(-c3cncc(C4CC4)n3)ccc2cn1)c1cc(F)c2c(c1)S(=O)(=O)[C@@H](F)CCO2] |
| 231 | 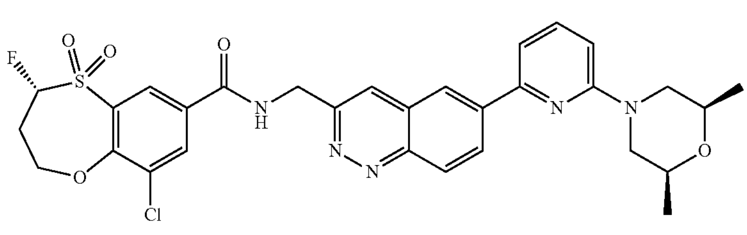 [SMILES: C[C@@H]1CN(c2cccc(-c3ccc4nnc(CNC(=O)c5cc(Cl)c6c(c5)S(=O)(=O)[C@@H](F)CCO6)cc4c3)n2)C[C@H](C)O1] |

TABLE 1-continued
Compounds of the invention
| # | Structure |
|---|---|
| 232 | 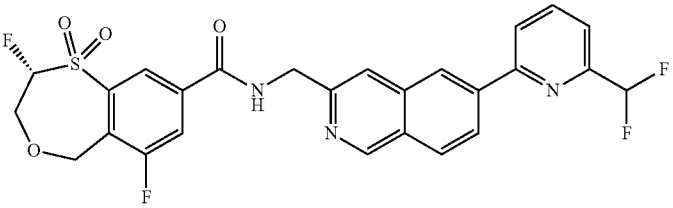 [SMILES: O=C(NCc1cc2cc(-c3cccc(C(F)F)n3)ccc2cn1)c1cc(F)c2c(c1)S(=O)(=O)[C@@H](F)COC2] |
| 233 | 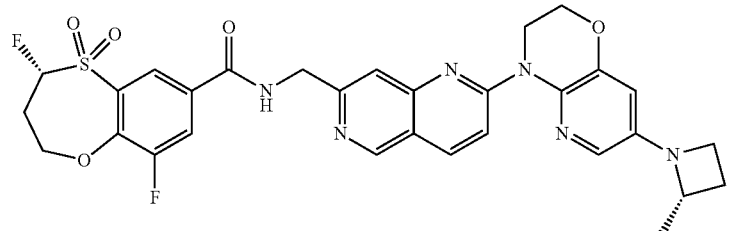 |
| 234 | 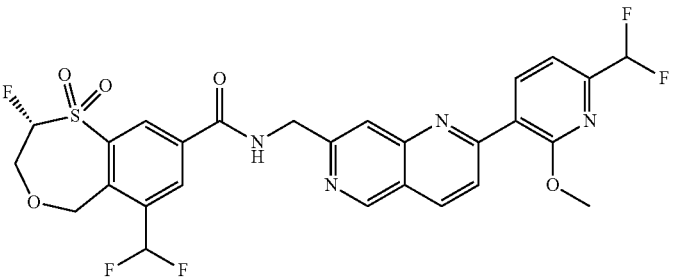 [SMILES: COc1nc(C(F)F)ccc1-c1ccc2cnc(CNC(=O)c3cc(C(F)F)c4c(c3)S(=O)(=O)[C@@H](F)COC4)cc2n1] |
| 235 | 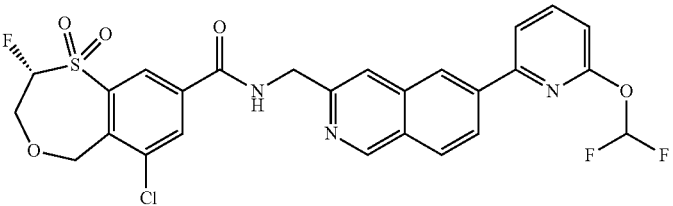 [SMILES: O=C(NCc1cc2cc(-c3cccc(OC(F)F)n3)ccc2cn1)c1cc(Cl)c2c(c1)S(=O)(=O)[C@@H](F)COC2] |
| 236 | 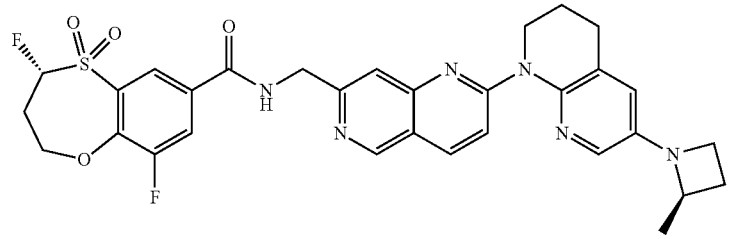 |
| 237 | 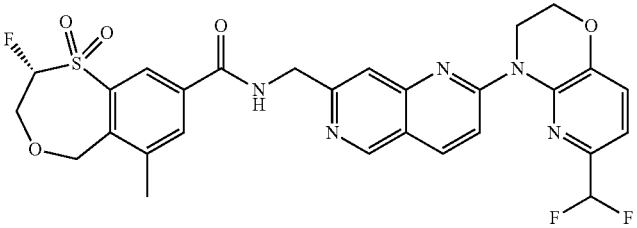 [SMILES: Cc1cc(C(=O)NCc2cc3nc(N4CCOc5ccc(C(F)F)nc54)ccc3cn2)cc2c1COC[C@H](F)S2(=O)=O] |

TABLE 1-continued

Compounds of the invention

| # | Structure |
|---|---|
| 238 | 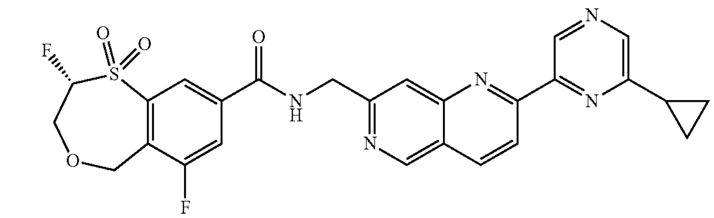 [SMILES: O=C(NCc1cc2nc(-c3cncc(C4CC4)n3)ccc2cn1)c1cc(F)c2c(c1)S(=O)(=O)[C@@H](F)COC2] |
| 239 | 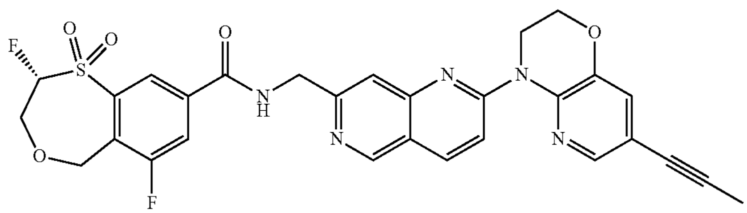 [SMILES: CC#Cc1cnc2c(c1)OCCN2c1ccc2cnc(CNC(=O)c3cc(F)c4c(c3)S(=O)(=O)[C@@H](F)COC4)cc2n1] |
| 240 | 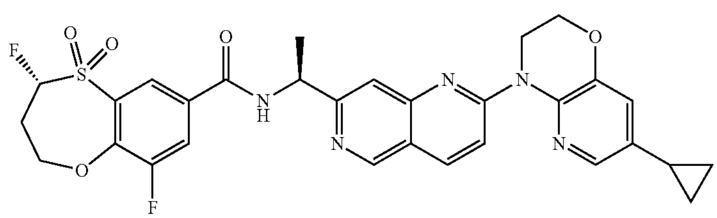 [SMILES: C[C@H](NC(=O)c1cc(F)c2c(c1)S(=O)(=O)[C@@H](F)CCO2)c1cc2nc(N3CCOc4cc(C5CC5)cnc43)ccc2cn1] |
| 241 | 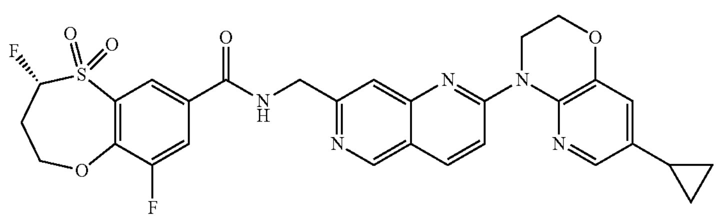 [SMILES: O=C(NCc1cc2nc(N3CCOc4cc(C5CC5)cnc43)ccc2cn1)c1cc(F)c2c(c1)S(=O)(=O)[C@@H](F)CCO2] |
| 242 | 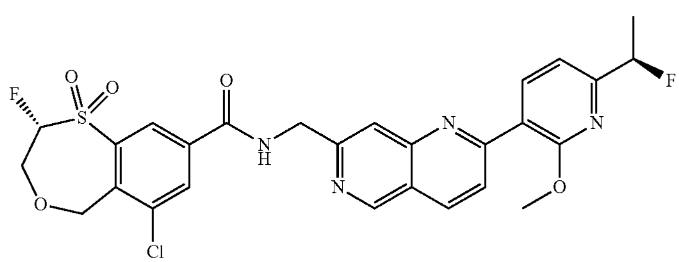 [SMILES: COc1nc([C@@H](C)F)ccc1-c1ccc2cnc(CNC(=O)c3cc(Cl)c4c(c3)S(=O)(=O)[C@@H](F)COC4)cc2n1] |
| 243 | 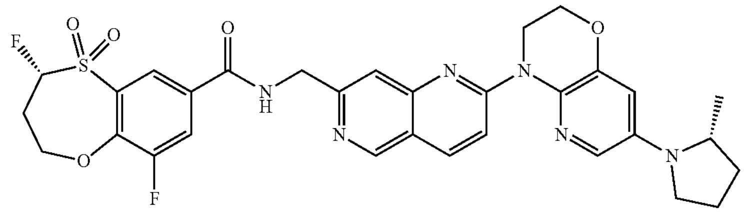 [SMILES: C[C@@H]1CCCN1c1cnc2c(c1)OCCN2c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|---|
| 244 | 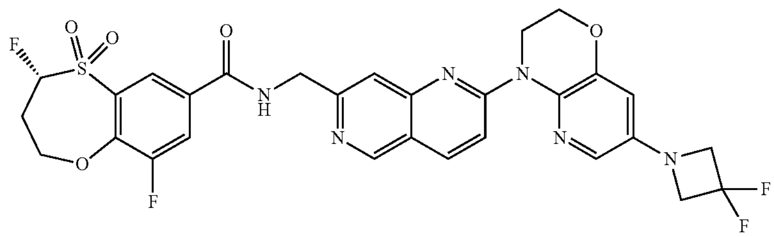 [SMILES: O=C(NCc1cc2nc(N3CCOc4cc(N5CC(F)(F)C5)cnc43)ccc2cn1)c1cc(F)c2c(c1)S(=O)(=O)[C@@H](F)CCO2] |
| 245 | 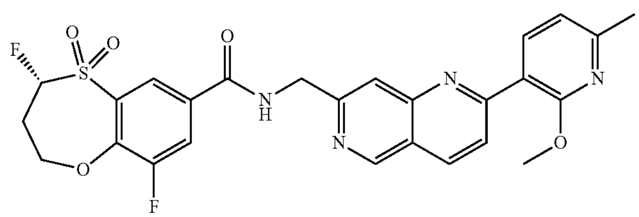 [SMILES: COc1nc(C)ccc1-c1ccc2cnc(CNC(=O)c3cc(F)c4c(c3)S(=O)(=O)[C@@H](F)CCO4)cc2n1] |
| 246 | 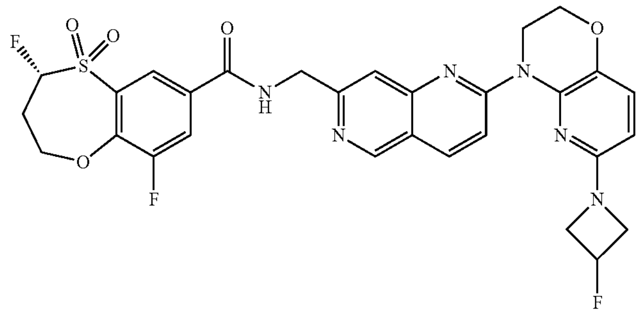 [SMILES: O=C(NCc1cc2nc(N3CCOc4ccc(N5CC(F)C5)nc43)ccc2cn1)c1cc(F)c2c(c1)S(=O)(=O)[C@@H](F)CCO2] |
| 247 | 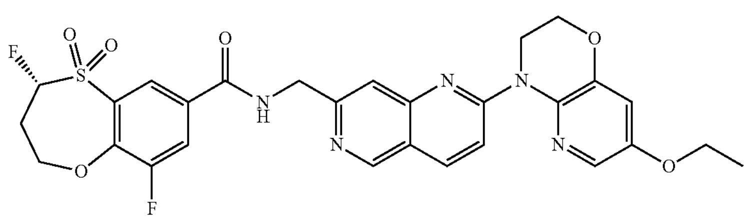 [SMILES: CCOc1cnc2c(c1)OCCN2c1ccc2cnc(CNC(=O)c3cc(F)c4c(c3)S(=O)(=O)[C@@H](F)CCO4)cc2n1] |
| 248 | 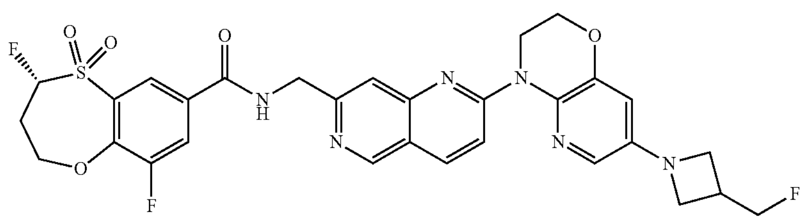 [SMILES: O=C(NCc1cc2nc(N3CCOc4cc(N5CC(CF)C5)cnc43)ccc2cn1)c1cc(F)c2c(c1)S(=O)(=O)[C@@H](F)CCO2] |
| 249 | 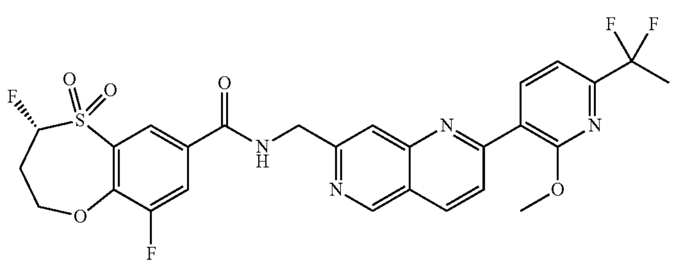 [SMILES: COc1nc(C(C)(F)F)ccc1-c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|-----------|
| 250 | 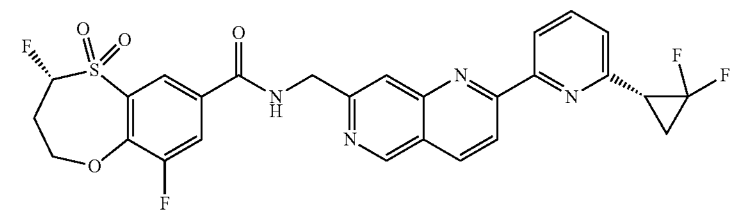 [SMILES: O=C(NCc1cc2nc(-c3cccc([C@H]4CC4(F)F)n3)ccc2cn1)c1cc(F)c2c(c1)S(=O)(=O)[C@@H](F)CCO2] |
| 251 | 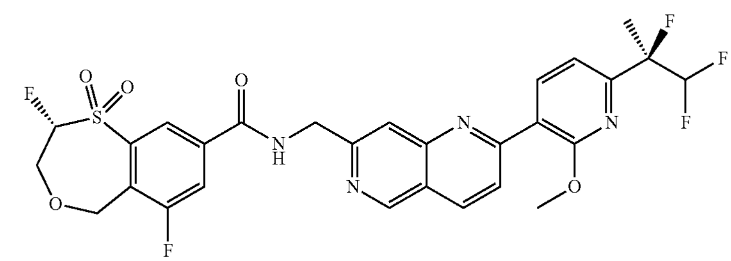 [SMILES: COc1nc([C@@](C)(F)C(F)F)ccc1-c1ccc2cnc(CNC(=O)c3cc(F)c4c(c3)S(=O)(=O)[C@@H](F)COC4)cc2n1] |
| 252 | 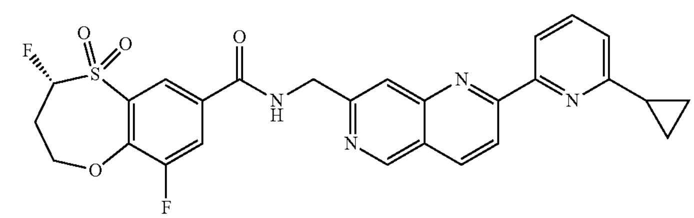 [SMILES: O=C(NCc1cc2nc(-c3cccc(C4CC4)n3)ccc2cn1)c1cc(F)c2c(c1)S(=O)(=O)[C@@H](F)CCO2] |
| 253 | 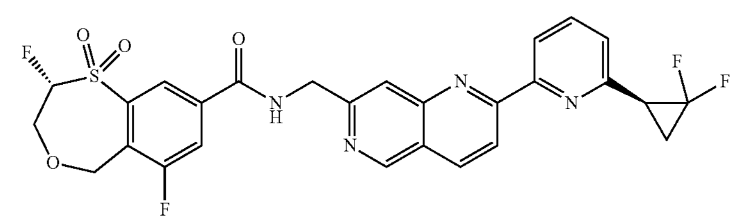 [SMILES: O=C(NCc1cc2nc(-c3cccc([C@@H]4CC4(F)F)n3)ccc2cn1)c1cc(F)c2c(c1)S(=O)(=O)[C@@H](F)COC2] |
| 254 | 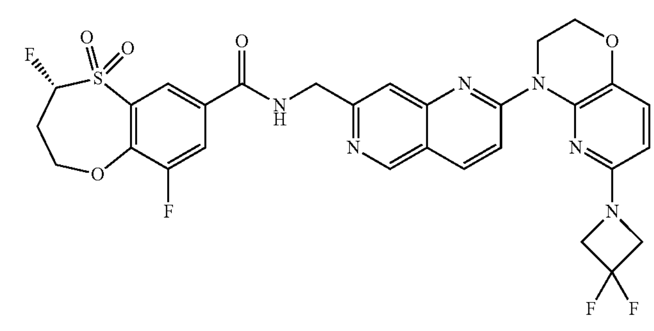 [SMILES: O=C(NCc1cc2nc(N3CCOc4ccc(N5CC(F)(F)C5)nc43)ccc2cn1)c1cc(F)c2c(c1)S(=O)(=O)[C@@H](F)CCO2] |
| 255 | 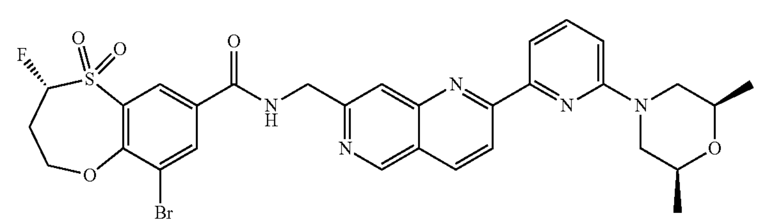 |

US 12,139,487 B2
111
112
TABLE 1-continued
Compounds of the invention
| # | Structure |
|---|---|
| 256 | 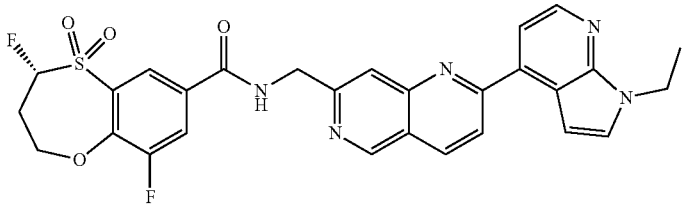 [SMILES: CCn1ccc2c(-c3ccc4cnc(CNC(=O)c5cc(F)c6c(c5)S(=O)(=O)[C@@H](F)CCO6)cc4n3)ccnc21] |
| 257 | 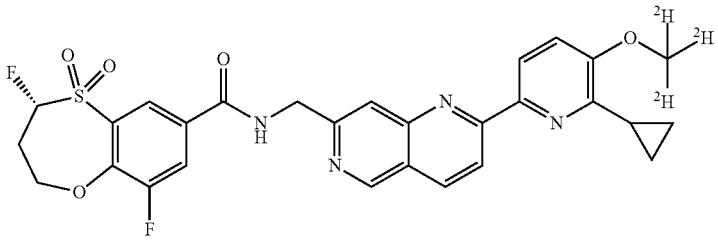 [SMILES: [2H]C([2H])([2H])Oc1ccc(-c2ccc3cnc(CNC(=O)c4cc(F)c5c(c4)S(=O)(=O)[C@@H](F)CCO5)cc3n2)nc1C1CC1] |
| 258 | 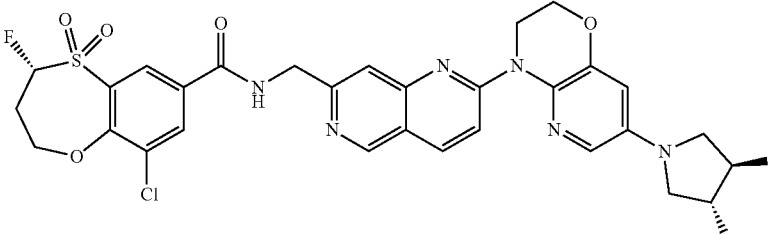 |
| 259 | 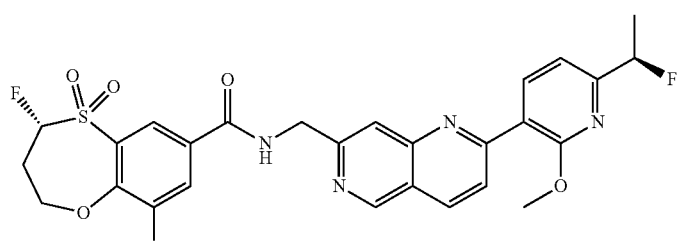 |
| 260 | 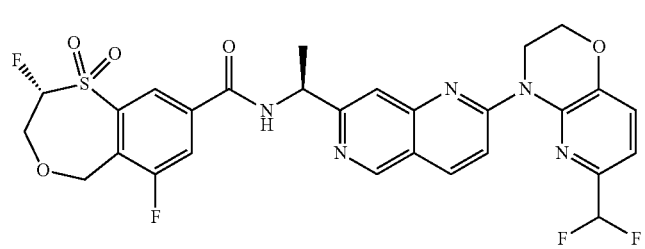 [SMILES: C[C@H](NC(=O)c1cc(F)c2c(c1)S(=O)(=O)[C@@H](F)COC2)c1cc2nc(N3CCOc4ccc(C(F)F)nc43)ccc2cn1] |
| 261 | 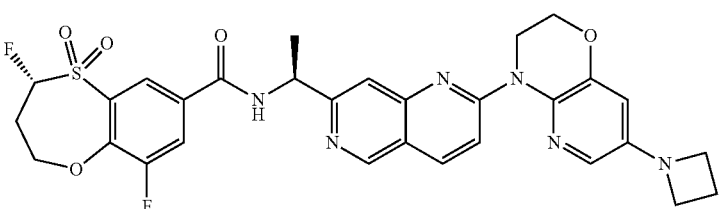 [SMILES: C[C@H](NC(=O)c1cc(F)c2c(c1)S(=O)(=O)[C@@H](F)CCO2)c1cc2nc(N3CCOc4cc(N5CCC5)cnc43)ccc2cn1] |

TABLE 1-continued

Compounds of the invention

| # | Structure |
|---|---|
| 262 | 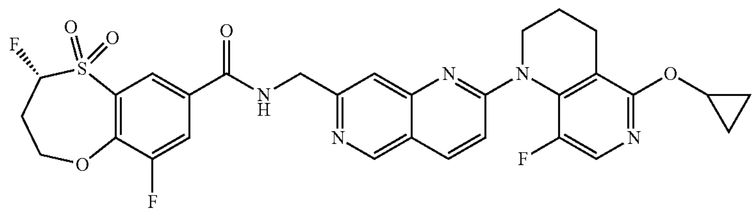 [SMILES: O=C(NCc1cc2nc(N3CCCc4c(OC5CC5)ncc(F)c43)ccc2cn1)c1cc(F)c2c(c1)S(=O)(=O)[C@@H](F)CCO2] |
| 263 | 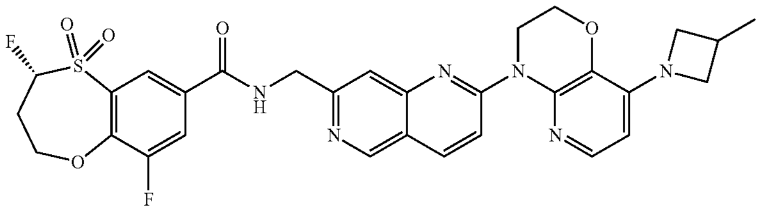 [SMILES: CC1CN(c2ccnc3c2OCCN3c2ccc3cnc(CNC(=O)c4cc(F)c5c(c4)S(=O)(=O)[C@@H](F)CCO5)cc3n2)C1] |
| 264 | 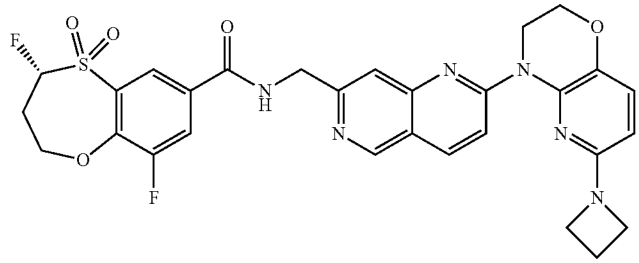 [SMILES: O=C(NCc1cc2nc(N3CCOc4ccc(N5CCC5)nc43)ccc2cn1)c1cc(F)c2c(c1)S(=O)(=O)[C@@H](F)CCO2] |
| 265 | 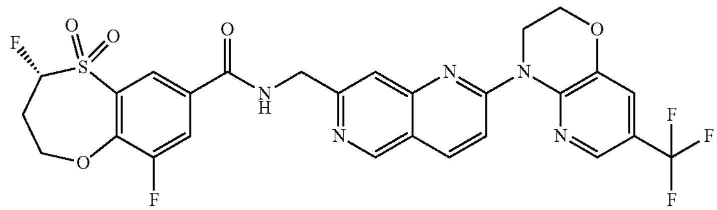 [SMILES: O=C(NCc1cc2nc(N3CCOc4cc(C(F)(F)F)cnc43)ccc2cn1)c1cc(F)c2c(c1)S(=O)(=O)[C@@H](F)CCO2] |
| 266 | 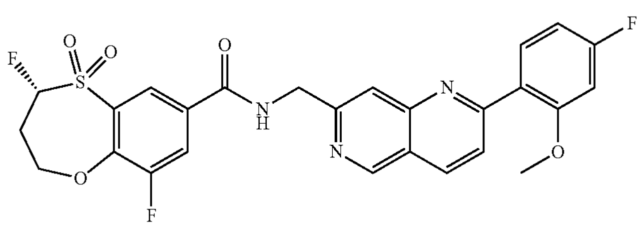 [SMILES: COc1cc(F)ccc1-c1ccc2cnc(CNC(=O)c3cc(F)c4c(c3)S(=O)(=O)[C@@H](F)CCO4)cc2n1] |
| 267 | 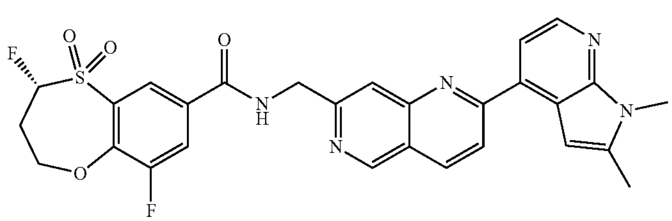 [SMILES: Cc1cc2c(-c3ccc4cnc(CNC(=O)c5cc(F)c6c(c5)S(=O)(=O)[C@@H](F)CCO6)cc4n3)ccnc2n1C] |

TABLE 1-continued
Compounds of the invention
| # | Structure |
|---|---|
| 268 | 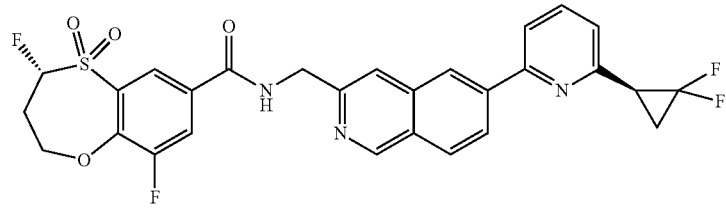 [SMILES: O=C(NCc1cc2cc(-c3cccc([C@@H]4CC4(F)F)n3)ccc2cn1)c1cc(F)c2c(c1)S(=O)(=O)[C@@H](F)CCO2] |
| 269 | 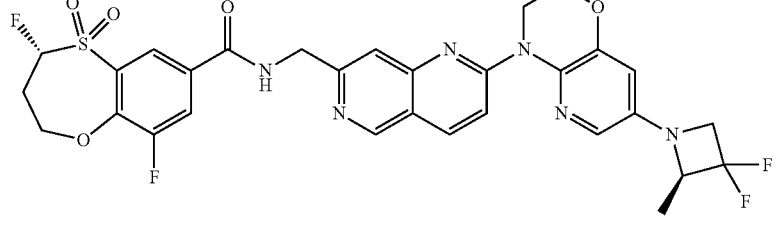 |
| 270 | 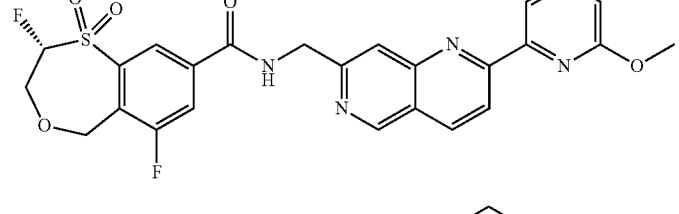 |
| 271 | 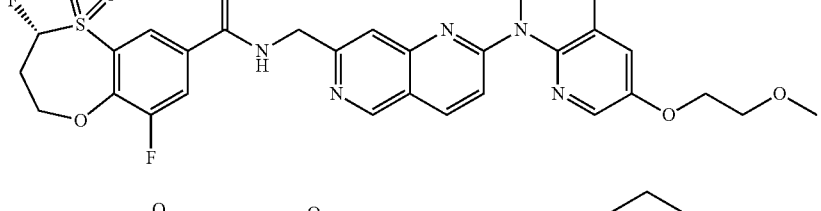 |
| 272 | 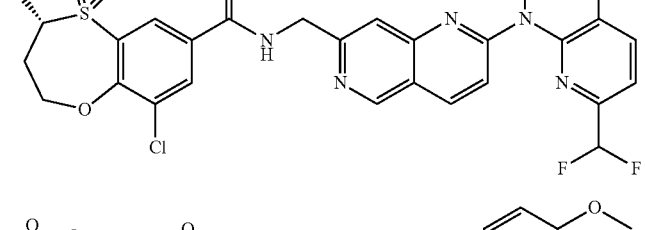 |
| 273 | 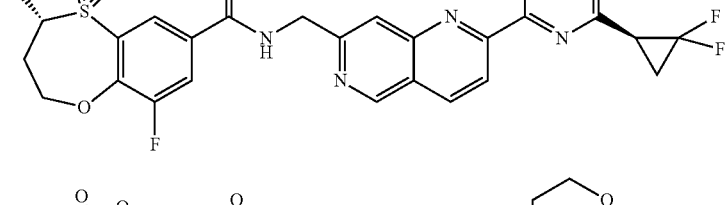 |
| 274 | 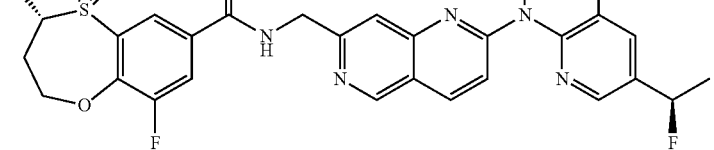 |

TABLE 1-continued

Compounds of the invention

| # | Structure |
|---|-----------|
| 275 | 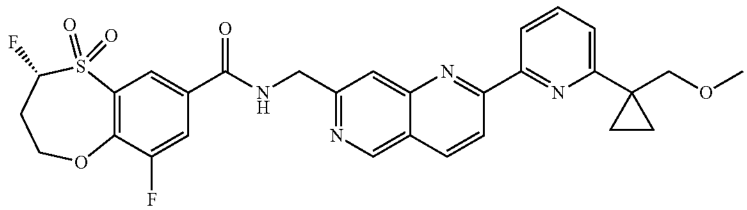 [SMILES: COCC1(c2cccc(-c3ccc4cnc(CNC(=O)c5cc(F)c6c(c5)S(=O)(=O)[C@@H](F)CCO6)cc4n3)n2)CC1] |
| 276 | 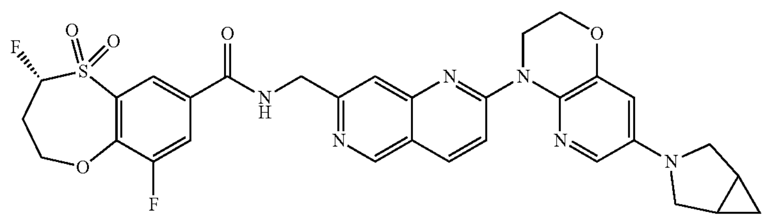 [SMILES: O=C(NCc1cc2nc(N3CCOc4cc(N5CC6CC6C5)cnc43)ccc2cn1)c1cc(F)c2c(c1)S(=O)(=O)[C@@H](F)CCO2] |
| 277 | 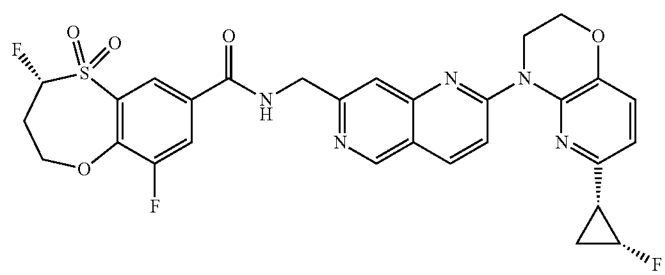 [SMILES: O=C(NCc1cc2nc(N3CCOc4ccc([C@H]5C[C@H]5F)nc43)ccc2cn1)c1cc(F)c2c(c1)S(=O)(=O)[C@@H](F)CCO2] |
| 278 | 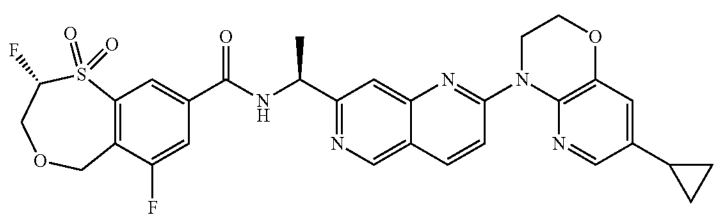 [SMILES: C[C@H](NC(=O)c1cc(F)c2c(c1)S(=O)(=O)[C@@H](F)COC2)c1cc2nc(N3CCOc4cc(C5CC5)cnc43)ccc2cn1] |
| 279 | 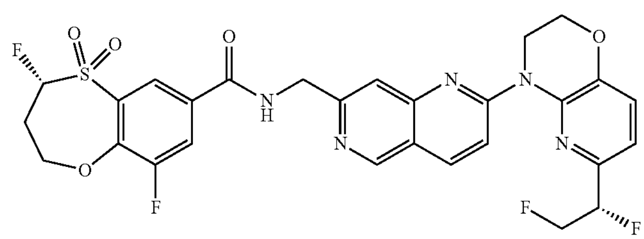 [SMILES: O=C(NCc1cc2nc(N3CCOc4ccc([C@H](F)CF)nc43)ccc2cn1)c1cc(F)c2c(c1)S(=O)(=O)[C@@H](F)CCO2] |
| 280 | 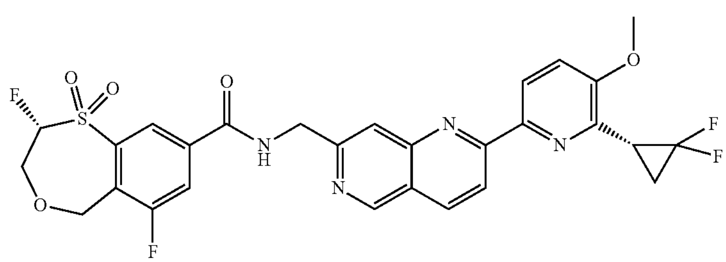 [SMILES: COc1ccc(-c2ccc3cnc(CNC(=O)c4cc(F)c5c(c4)S(=O)(=O)[C@@H](F)COC5)cc3n2)nc1[C@H]1CC1(F)F] |

119
TABLE 1-continued

Compounds of the invention

| # | Structure |
|---|---|
| 281 | 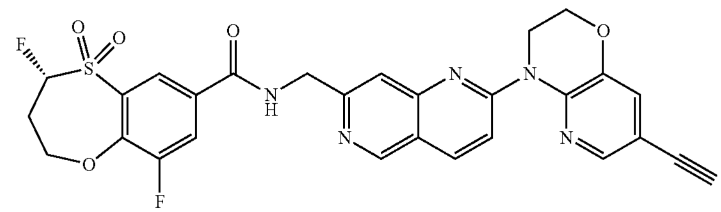 [SMILES: C#Cc1cnc2c(c1)OCCN2c1ccc2cnc(CNC(=O)c3cc(F)c4c(c3)S(=O)(=O)[C@@H](F)CCO4)cc2n1] |
| 282 | 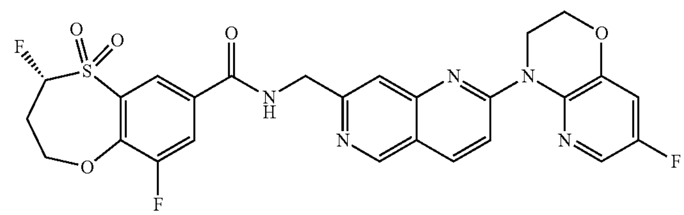 [SMILES: O=C(NCc1cc2nc(N3CCOc4cc(F)cnc43)ccc2cn1)c1cc(F)c2c(c1)S(=O)(=O)[C@@H](F)CCO2] |
| 283 | 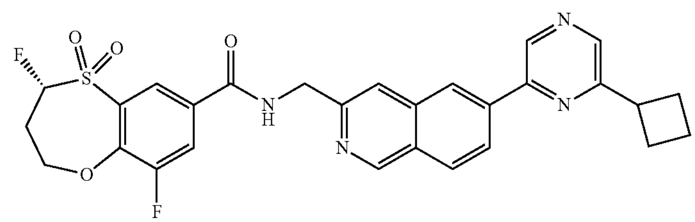 [SMILES: O=C(NCc1cc2cc(-c3cncc(C4CCC4)n3)ccc2cn1)c1cc(F)c2c(c1)S(=O)(=O)[C@@H](F)CCO2] |
| 284 | 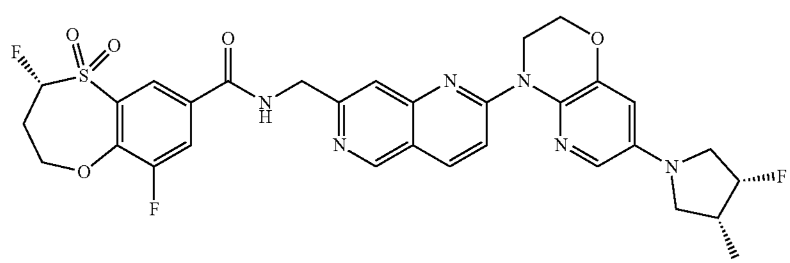 [SMILES: C[C@@H]1CN(c2cnc3c(c2)OCCN3c2ccc3cnc(CNC(=O)c4cc(F)c5c(c4)S(=O)(=O)[C@@H](F)CCO5)cc3n2)C[C@@H]1F] |
| 285 | 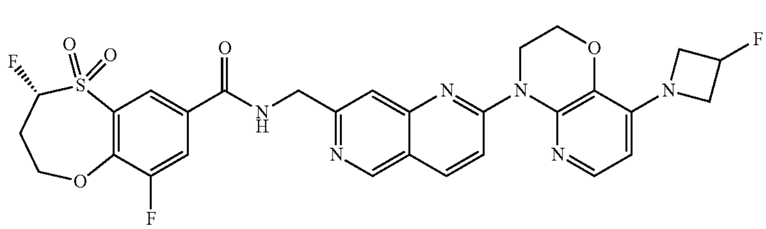 [SMILES: O=C(NCc1cc2nc(N3CCOc4c(N5CC(F)C5)ccnc43)ccc2cn1)c1cc(F)c2c(c1)S(=O)(=O)[C@@H](F)CCO2] |
| 286 | 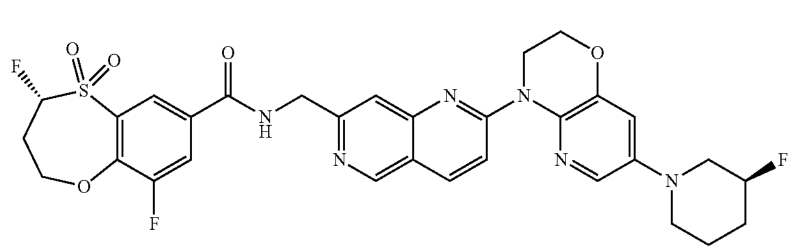 [SMILES: O=C(NCc1cc2nc(N3CCOc4cc(N5CCC[C@H](F)C5)cnc43)ccc2cn1)c1cc(F)c2c(c1)S(=O)(=O)[C@@H](F)CCO2] |

TABLE 1-continued

Compounds of the invention

| # | Structure |
|---|---|
| 287 | 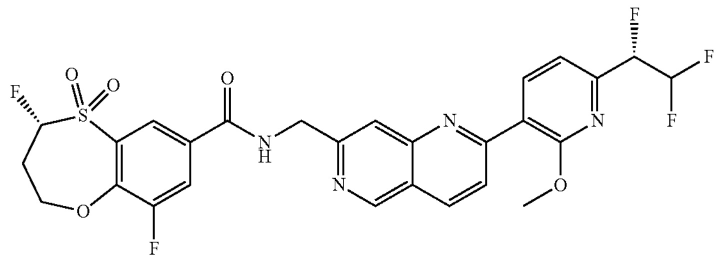 [SMILES: COc1nc([C@H](F)C(F)F)ccc1-c1ccc2cnc(CNC(=O)c3cc(F)c4c(c3)S(=O)(=O)[C@@H](F)CCO4)cc2n1] |
| 288 | 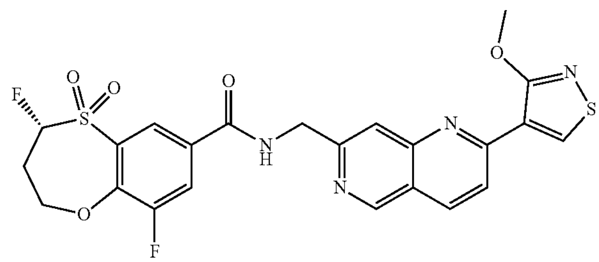 [SMILES: COc1nscc1-c1ccc2cnc(CNC(=O)c3cc(F)c4c(c3)S(=O)(=O)[C@@H](F)CCO4)cc2n1] |
| 289 | 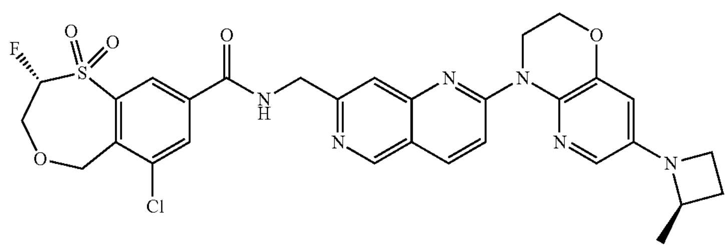 [SMILES: C[C@@H]1CCN1c1cnc2c(c1)OCCN2c1ccc2cnc(CNC(=O)c3cc(Cl)c4c(c3)S(=O)(=O)[C@@H](F)COC4)cc2n1] |
| 290 | 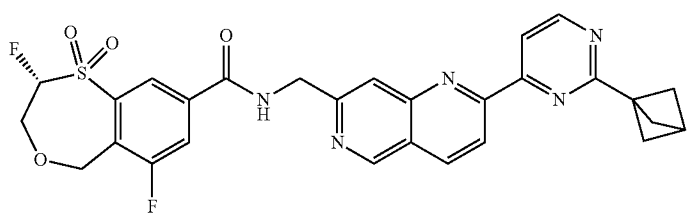 [SMILES: O=C(NCc1cc2nc(-c3ccnc(C45CC(C4)C5)n3)ccc2cn1)c1cc(F)c2c(c1)S(=O)(=O)[C@@H](F)COC2] |
| 291 | 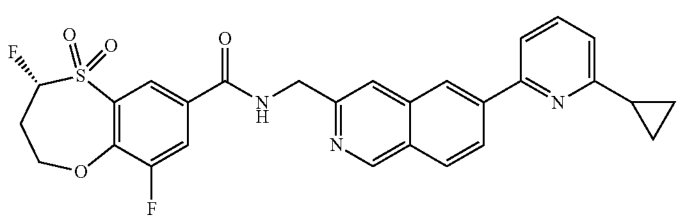 [SMILES: O=C(NCc1cc2cc(-c3cccc(C4CC4)n3)ccc2cn1)c1cc(F)c2c(c1)S(=O)(=O)[C@@H](F)CCO2] |
| 292 | 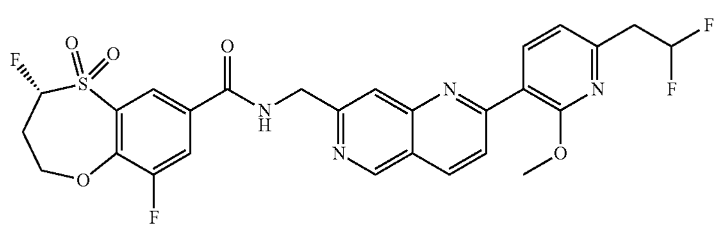 [SMILES: COc1nc(CC(F)F)ccc1-c1ccc2cnc(CNC(=O)c3cc(F)c4c(c3)S(=O)(=O)[C@@H](F)CCO4)cc2n1] |

TABLE 1-continued
Compounds of the invention
| # | Structure |
|---|---|
| 293 | 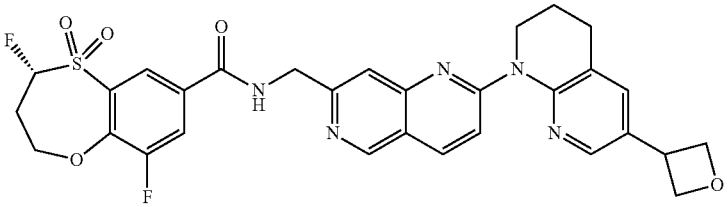 [SMILES: O=C(NCc1cc2nc(N3CCCc4cc(C5COC5)cnc43)ccc2cn1)c1cc(F)c2c(c1)S(=O)(=O)[C@@H](F)CCO2] |
| 294 | 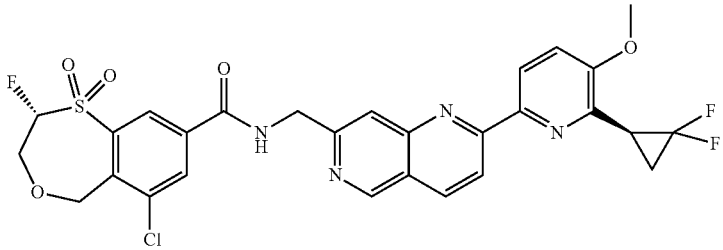 [SMILES: COc1ccc(-c2ccc3cnc(CNC(=O)c4cc(Cl)c5c(c4)S(=O)(=O)[C@@H](F)COC5)cc3n2)nc1[C@@H]1CC1(F)F] |
| 295 | 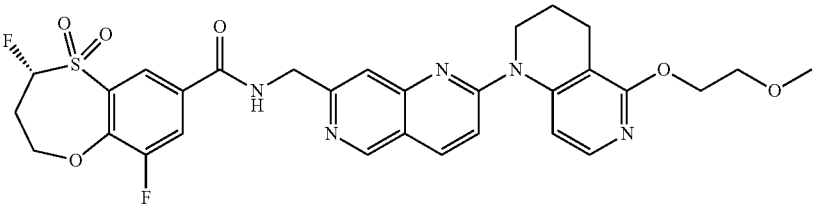 |
| 296 | 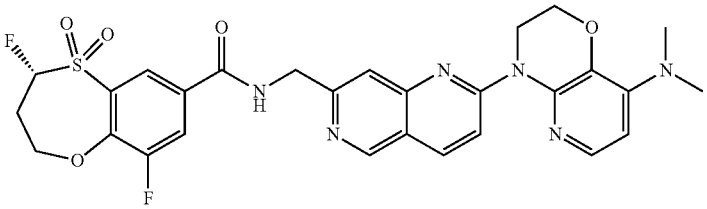 [SMILES: CN(C)c1ccnc2c1OCCN2c1ccc2cnc(CNC(=O)c3cc(F)c4c(c3)S(=O)(=O)[C@@H](F)CCO4)cc2n1] |
| 297 | 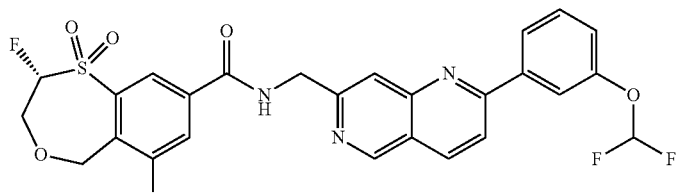 |
| 298 | 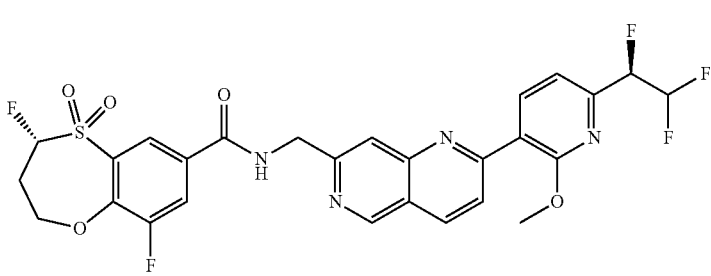 [SMILES: COc1nc([C@@H](F)C(F)F)ccc1-c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|---|
| 299 | 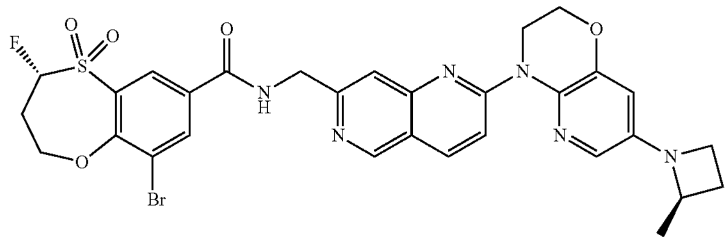 [SMILES: C[C@@H]1CCN1c1cnc2c(c1)OCCN2c1ccc2cnc(CNC(=O)c3cc(Br)c4c(c3)S(=O)(=O)[C@@H](F)CCO4)cc2n1] |
| 300 | 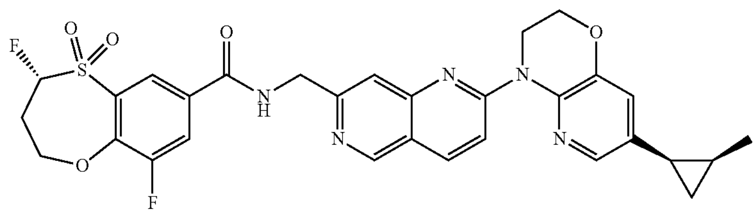 [SMILES: C[C@H]1C[C@H]1c1cnc2c(c1)OCCN2c1ccc2cnc(CNC(=O)c3cc(F)c4c(c3)S(=O)(=O)[C@@H](F)CCO4)cc2n1] |
| 301 | 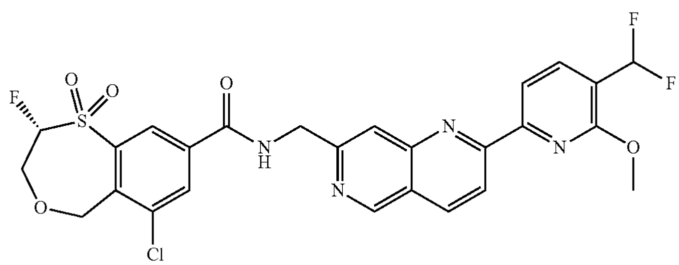 [SMILES: COc1nc(-c2ccc3cnc(CNC(=O)c4cc(Cl)c5c(c4)S(=O)(=O)[C@@H](F)COC5)cc3n2)ccc1C(F)F] |
| 302 | 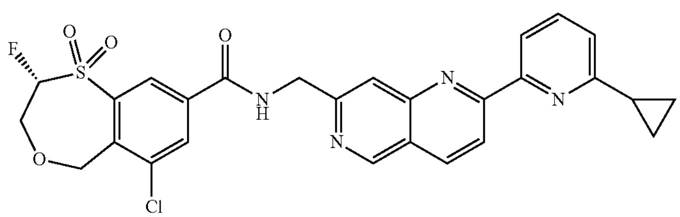 [SMILES: O=C(NCc1cc2nc(-c3cccc(C4CC4)n3)ccc2cn1)c1cc(Cl)c2c(c1)S(=O)(=O)[C@@H](F)COC2] |
| 303 | 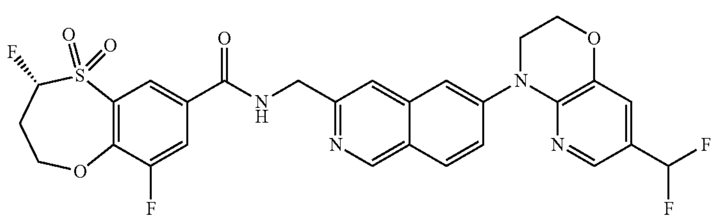 [SMILES: O=C(NCc1cc2cc(N3CCOc4cc(C(F)F)cnc43)ccc2cn1)c1cc(F)c2c(c1)S(=O)(=O)[C@@H](F)CCO2] |
| 304 | 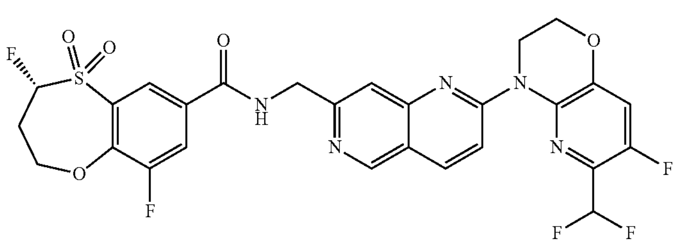 [SMILES: O=C(NCc1cc2nc(N3CCOc4cc(F)c(C(F)F)nc43)ccc2cn1)c1cc(F)c2c(c1)S(=O)(=O)[C@@H](F)CCO2] |

TABLE 1-continued

Compounds of the invention

| # | Structure |
|---|---|
| 305 | 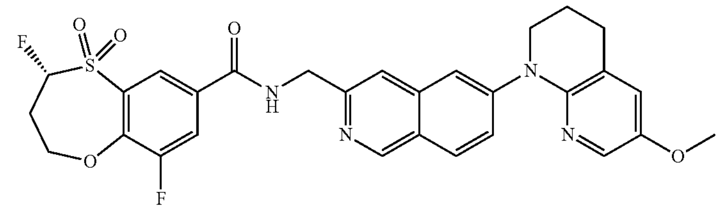 [SMILES: COc1cnc2c(c1)CCCN2c1ccc2cnc(CNC(=O)c3cc(F)c4c(c3)S(=O)(=O)[C@@H](F)CCO4)cc2c1] |
| 306 | 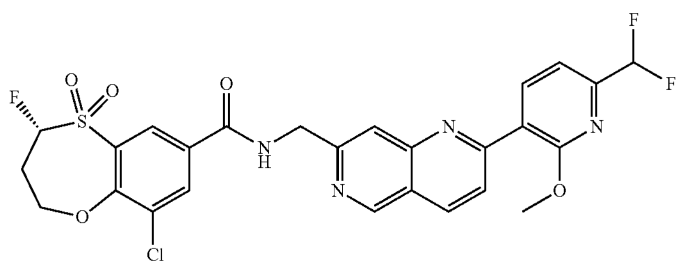 [SMILES: COc1nc(C(F)F)ccc1-c1ccc2cnc(CNC(=O)c3cc(Cl)c4c(c3)S(=O)(=O)[C@@H](F)CCO4)cc2n1] |
| 307 | 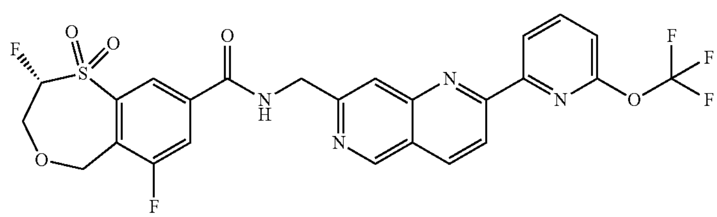 [SMILES: O=C(NCc1cc2nc(-c3cccc(OC(F)(F)F)n3)ccc2cn1)c1cc(F)c2c(c1)S(=O)(=O)[C@@H](F)COC2] |
| 308 | 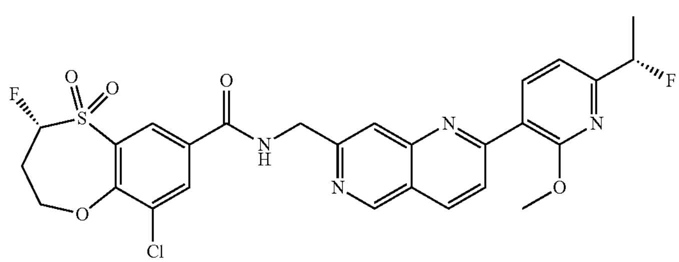 [SMILES: COc1nc([C@H](C)F)ccc1-c1ccc2cnc(CNC(=O)c3cc(Cl)c4c(c3)S(=O)(=O)[C@@H](F)CCO4)cc2n1] |
| 309 | 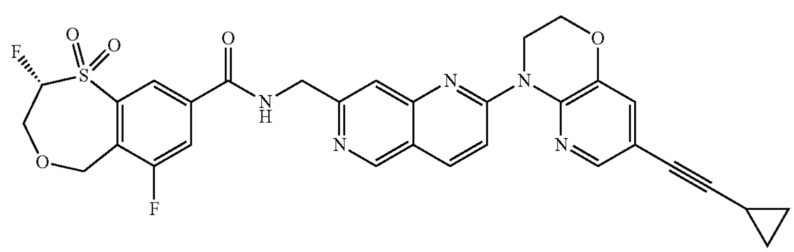 [SMILES: O=C(NCc1cc2nc(N3CCOc4cc(C#CC5CC5)cnc43)ccc2cn1)c1cc(F)c2c(c1)S(=O)(=O)[C@@H](F)COC2] |
| 310 | 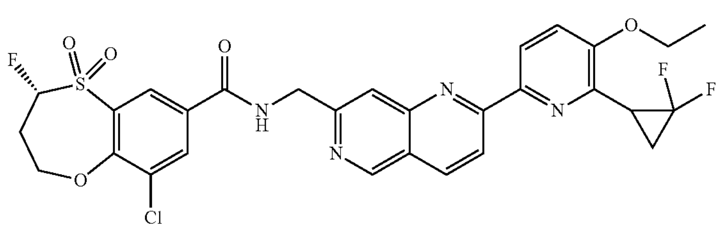 [SMILES: CCOc1ccc(-c2ccc3cnc(CNC(=O)c4cc(Cl)c5c(c4)S(=O)(=O)[C@@H](F)CCO5)cc3n2)nc1C1CC1(F)F] |

TABLE 1-continued

Compounds of the invention

| # | Structure |
|---|---|
| 311 | 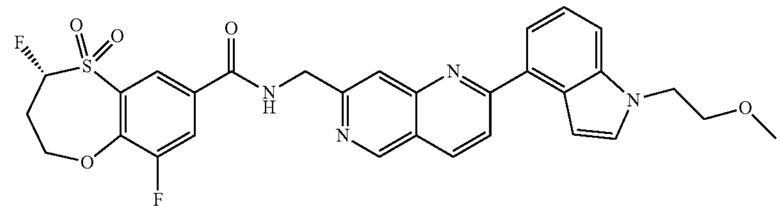 [SMILES: COCCn1ccc2c(-c3ccc4cnc(CNC(=O)c5cc(F)c6c(c5)S(=O)(=O)[C@@H](F)CCO6)cc4n3)cccc21] |
| 312 | 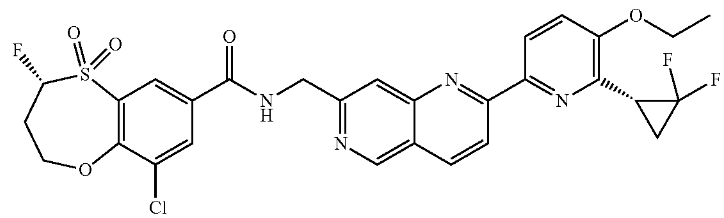 [SMILES: CCOc1ccc(-c2ccc3cnc(CNC(=O)c4cc(Cl)c5c(c4)S(=O)(=O)[C@@H](F)CCO5)cc3n2)nc1[C@H]1CC1(F)F] |
| 313 | 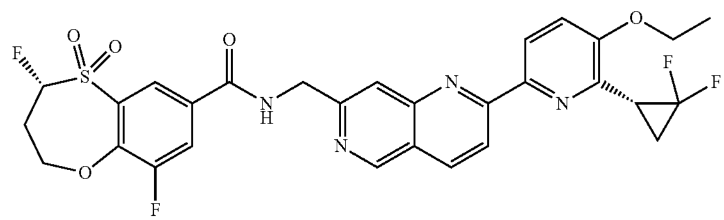 [SMILES: CCOc1ccc(-c2ccc3cnc(CNC(=O)c4cc(F)c5c(c4)S(=O)(=O)[C@@H](F)CCO5)cc3n2)nc1[C@H]1CC1(F)F] |
| 314 | 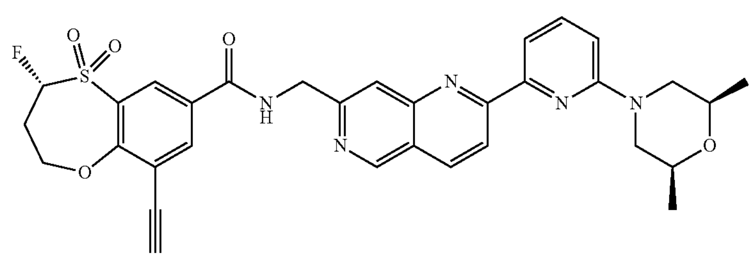 [SMILES: C#Cc1cc(C(=O)NCc2cc3nc(-c4cccc(N5C[C@@H](C)O[C@@H](C)C5)n4)ccc3cn2)cc2c1OCC[C@H](F)S2(=O)=O] |
| 315 | 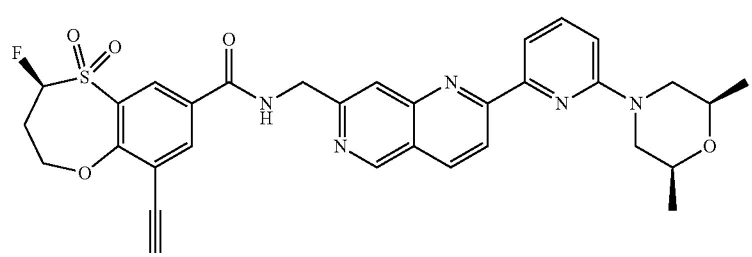 [SMILES: C#Cc1cc(C(=O)NCc2cc3nc(-c4cccc(N5C[C@@H](C)O[C@@H](C)C5)n4)ccc3cn2)cc2c1OCC[C@@H](F)S2(=O)=O] |
| 316 | 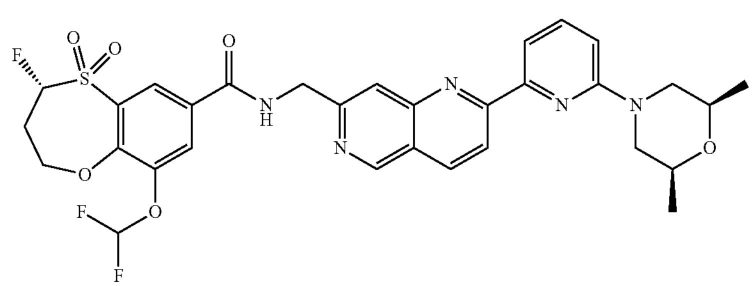 [SMILES: C[C@@H]1CN(c2cccc(-c3ccc4cnc(CNC(=O)c5cc(OC(F)F)c6c(c5)S(=O)(=O)[C@@H](F)CCO6)cc4n3)n2)C[C@H](C)O1] |

TABLE 1-continued
Compounds of the invention
| # | Structure |
|---|---|
| 317 | 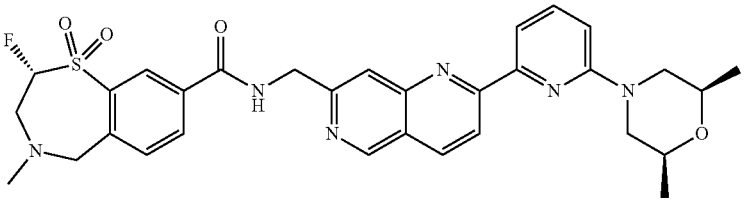 [SMILES: C[C@@H]1CN(c2cccc(-c3ccc4cnc(CNC(=O)c5ccc6c(c5)S(=O)(=O)[C@@H](F)CN(C)C6)cc4n3)n2)C[C@H](C)O1] |
| 318 | 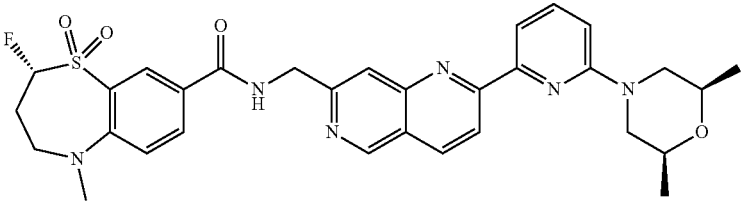 [SMILES: C[C@@H]1CN(c2cccc(-c3ccc4cnc(CNC(=O)c5ccc6c(c5)S(=O)(=O)[C@@H](F)CCN6C)cc4n3)n2)C[C@H](C)O1] |
| 319 | 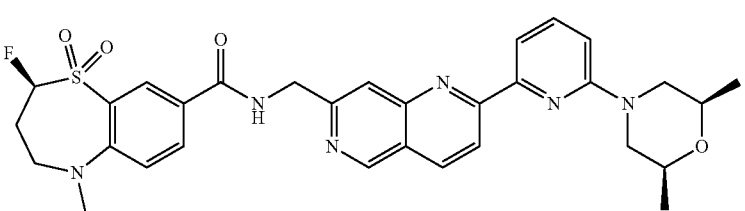 [SMILES: C[C@@H]1CN(c2cccc(-c3ccc4cnc(CNC(=O)c5ccc6c(c5)S(=O)(=O)[C@H](F)CN(C)C6)cc4n3)n2)C[C@H](C)O1] |
| 320 | 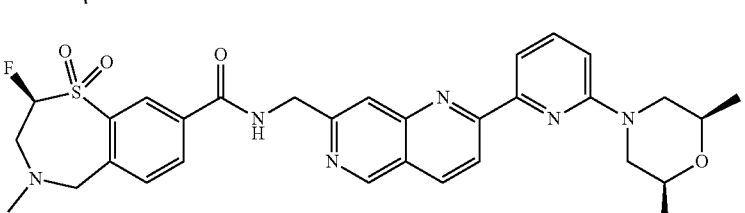 |
| 321 | 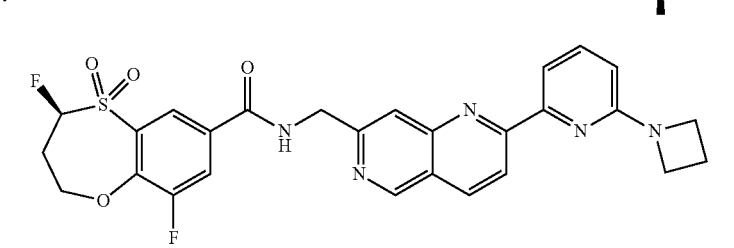 |
| 322 | 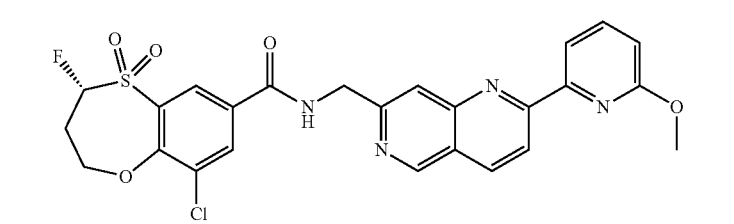 [SMILES: COc1cccc(-c2ccc3cnc(CNC(=O)c4cc(Cl)c5c(c4)S(=O)(=O)[C@@H](F)CCO5)cc3n2)n1] |
| 323 | 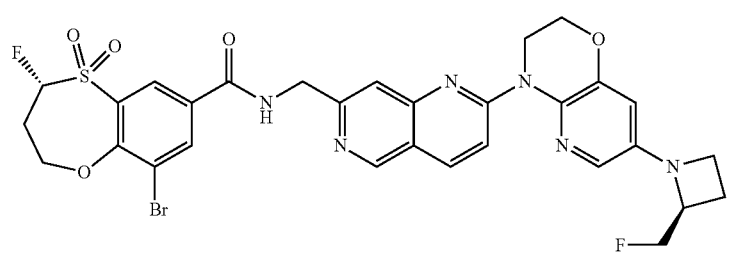 [SMILES: O=C(NCc1cc2nc(N3CCOc4cc(N5CC[C@H]5CF)cnc43)ccc2cn1)c1cc(Br)c2c(c1)S(=O)(=O)[C@@H](F)CCO2] |

US 12,139,487 B2
TABLE 1-continued
Compounds of the invention
| # | Structure |
|---|---|
| 324 | 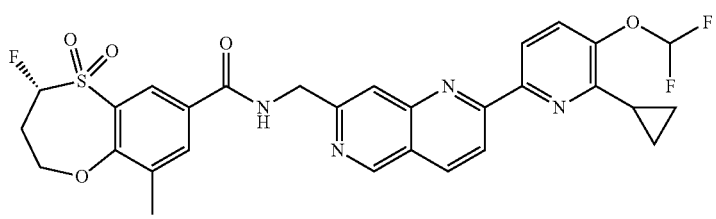 [SMILES: Cc1cc(C(=O)NCc2cc3nc(-c4ccc(OC(F)F)c(C5CC5)n4)ccc3cn2)cc2c1OCC[C@H](F)S2(=O)=O] |
| 325 | 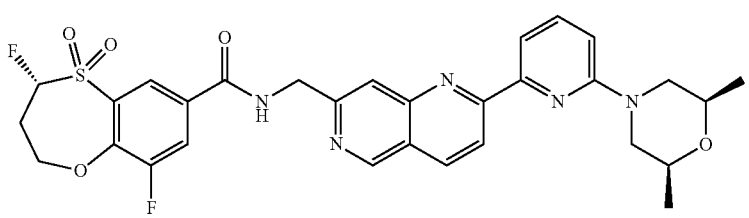 [SMILES: C[C@@H]1CN(c2cccc(-c3ccc4cnc(CNC(=O)c5cc(F)c6c(c5)S(=O)(=O)[C@@H](F)CCO6)cc4n3)n2)C[C@H](C)O1] |
| 326 | 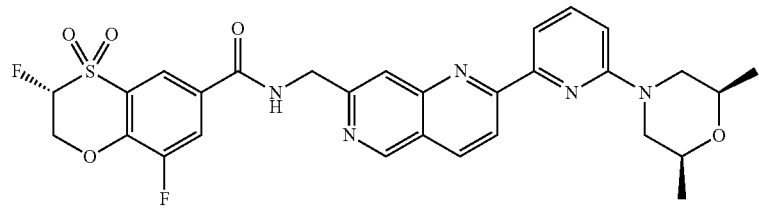 [SMILES: C[C@@H]1CN(c2cccc(-c3ccc4cnc(CNC(=O)c5cc(F)c6c(c5)S(=O)(=O)[C@@H](F)CO6)cc4n3)n2)C[C@H](C)O1] |
| 327 | 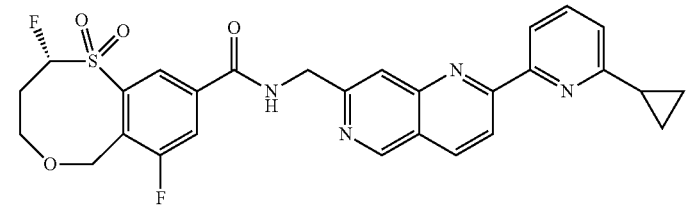 [SMILES: O=C(NCc1cc2nc(-c3cccc(C4CC4)n3)ccc2cn1)c1cc(F)c2c(c1)S(=O)(=O)[C@@H](F)CCOC2] |
| 328 | 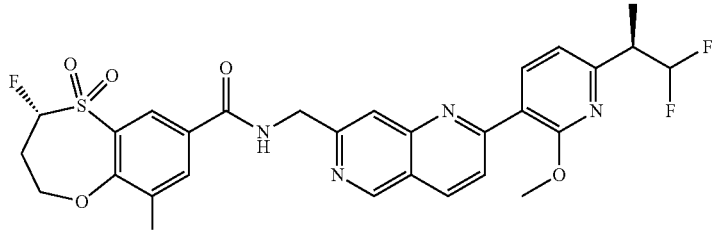 |
| 329 | 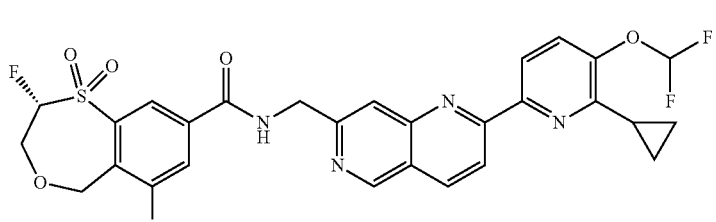 |

TABLE 1-continued
Compounds of the invention
| # | Structure |
|---|---|
| 330 | 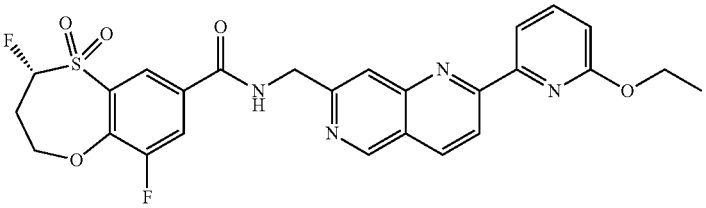 [SMILES: CCOc1cccc(-c2ccc3cnc(CNC(=O)c4cc(F)c5c(c4)S(=O)(=O)[C@@H](F)CCO5)cc3n2)n1] |
| 331 | 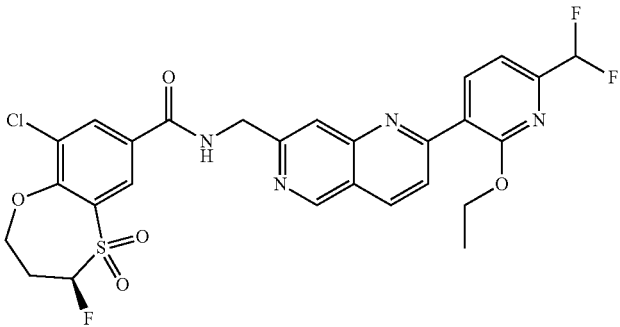 [SMILES: CCOc1nc(C(F)F)ccc1-c1ccc2cnc(CNC(=O)c3cc(Cl)c4c(c3)S(=O)(=O)[C@@H](F)CCO4)cc2n1] |
| 332 | 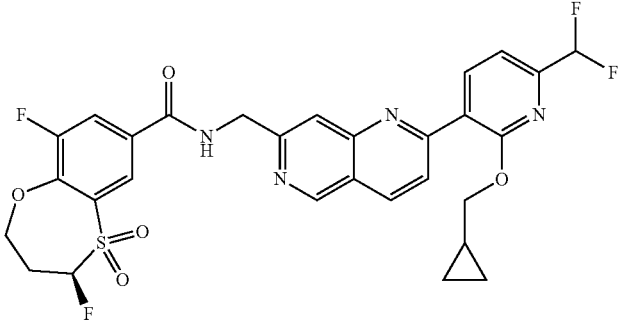 [SMILES: O=C(NCc1cc2nc(-c3ccc(C(F)F)nc3OCC3CC3)ccc2cn1)c1cc(F)c2c(c1)S(=O)(=O)[C@@H](F)CCO2] |
| 333 | 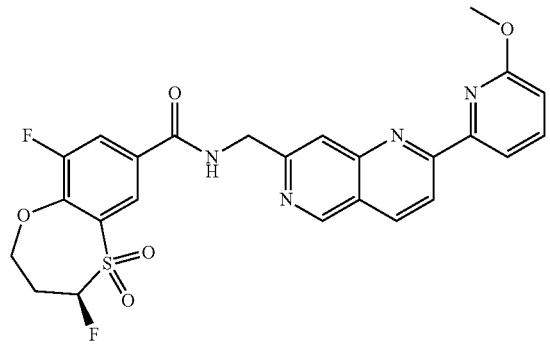 [SMILES: COc1cccc(-c2ccc3cnc(CNC(=O)c4cc(F)c5c(c4)S(=O)(=O)[C@@H](F)CCO5)cc3n2)n1] |

TABLE 1-continued
Compounds of the invention
| # | Structure |
|---|---|
| 334 | 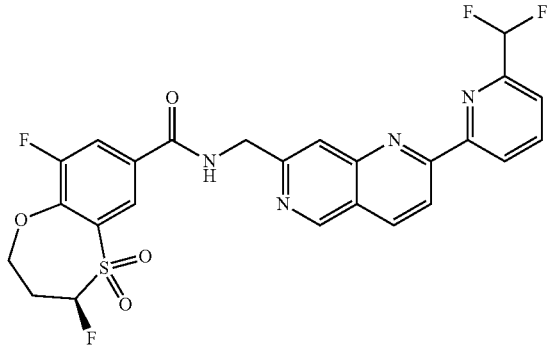 [SMILES: O=C(NCc1cc2nc(-c3cccc(C(F)F)n3)ccc2cn1)c1cc(F)c2c(c1)S(=O)(=O)[C@@H](F)CCO2] |
| 335 | 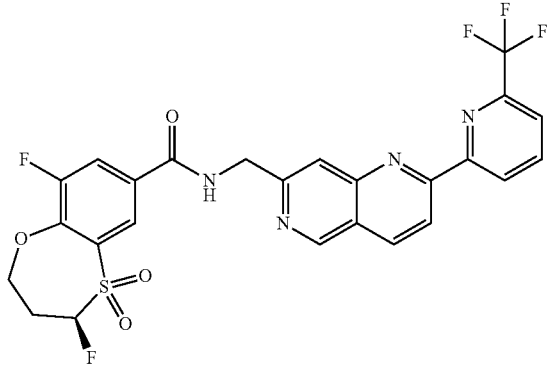 [SMILES: O=C(NCc1cc2nc(-c3cccc(C(F)(F)F)n3)ccc2cn1)c1cc(F)c2c(c1)S(=O)(=O)[C@@H](F)CCO2] |
| 336 | 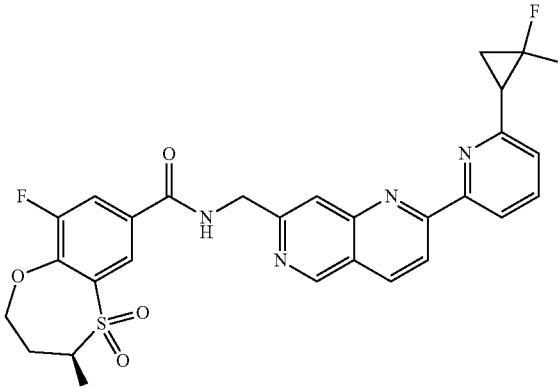 |
| 337 | 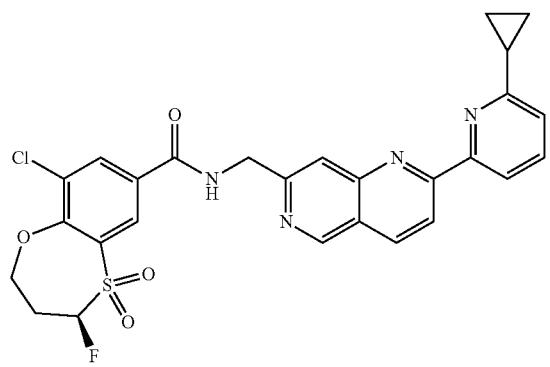 [SMILES: O=C(NCc1cc2nc(-c3cccc(C4CC4)n3)ccc2cn1)c1cc(Cl)c2c(c1)S(=O)(=O)[C@@H](F)CCO2] |

TABLE 1-continued
Compounds of the invention
| # | Structure |
|---|---|
| 338 | 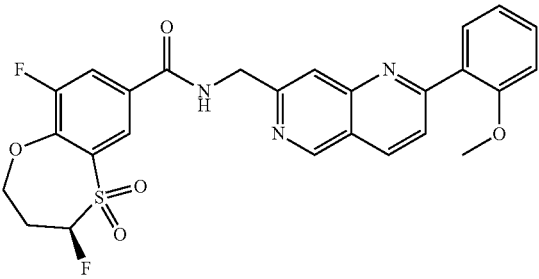 [SMILES: COc1ccccc1-c1ccc2cnc(CNC(=O)c3cc(F)c4c(c3)S(=O)(=O)[C@@H](F)CCO4)cc2n1] |
| 339 | 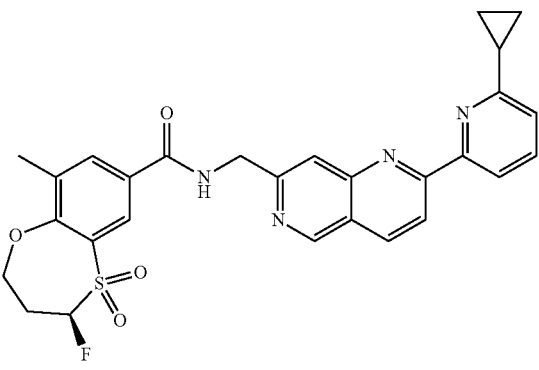 [SMILES: Cc1cc(C(=O)NCc2cc3nc(-c4cccc(C5CC5)n4)ccc3cn2)cc2c1OCC[C@H](F)S2(=O)=O] |
| 340 | 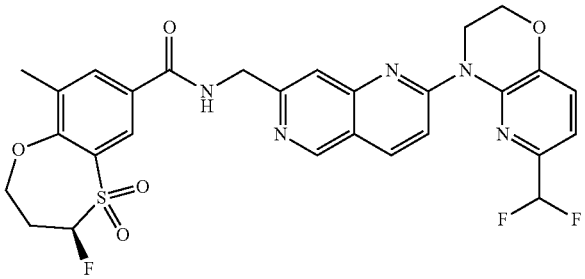 [SMILES: Cc1cc(C(=O)NCc2cc3nc(N4CCOc5ccc(C(F)F)nc54)ccc3cn2)cc2c1OCC[C@H](F)S2(=O)=O] |
| 341 | 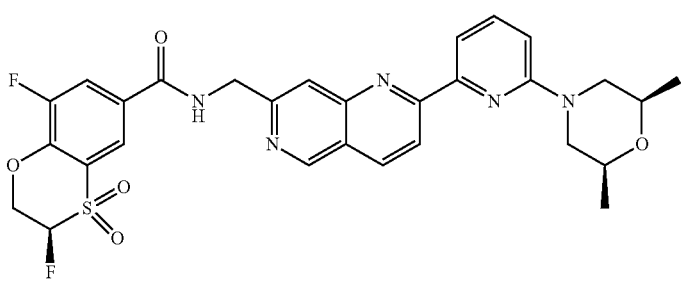 [SMILES: C[C@@H]1CN(c2cccc(-c3ccc4cnc(CNC(=O)c5cc(F)c6c(c5)S(=O)(=O)[C@@H](F)CO6)cc4n3)n2)C[C@H](C)O1] |
| 342 | 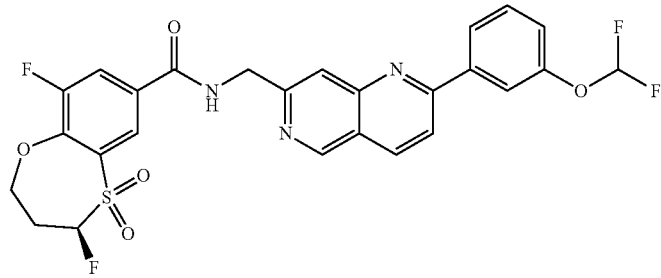 [SMILES: O=C(NCc1cc2nc(-c3cccc(OC(F)F)c3)ccc2cn1)c1cc(F)c2c(c1)S(=O)(=O)[C@@H](F)CCO2] |

TABLE 1-continued

Compounds of the invention

| # | Structure |
|---|-----------|
| 343 | 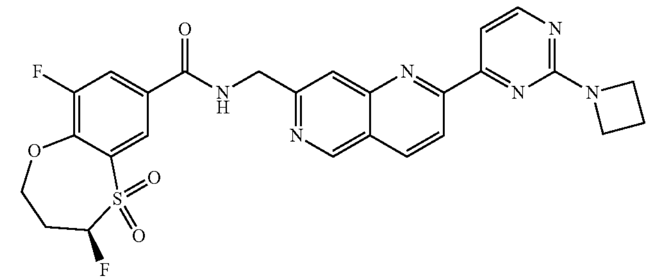 [SMILES: O=C(NCc1cc2nc(-c3ccnc(N4CCC4)n3)ccc2cn1)c1cc(F)c2c(c1)S(=O)(=O)[C@@H](F)CCO2] |
| 344 | 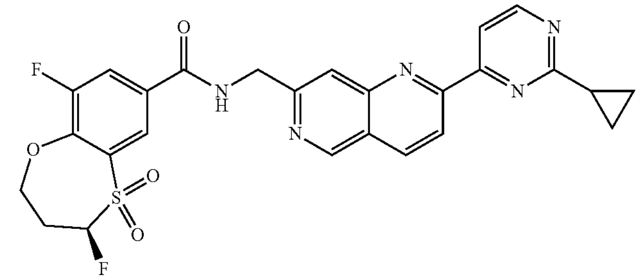 [SMILES: O=C(NCc1cc2nc(-c3ccnc(C4CC4)n3)ccc2cn1)c1cc(F)c2c(c1)S(=O)(=O)[C@@H](F)CCO2] |
| 345 | 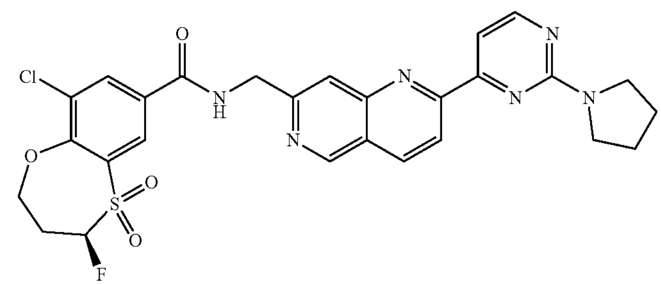 [SMILES: O=C(NCc1cc2nc(-c3ccnc(N4CCCC4)n3)ccc2cn1)c1cc(Cl)c2c(c1)S(=O)(=O)[C@@H](F)CCO2] |
| 346 | 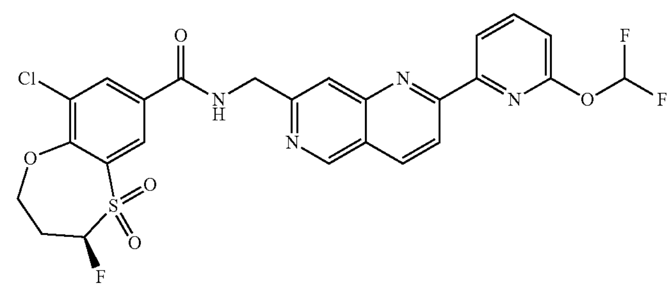 [SMILES: O=C(NCc1cc2nc(-c3cccc(OC(F)F)n3)ccc2cn1)c1cc(Cl)c2c(c1)S(=O)(=O)[C@@H](F)CCO2] |
| 347 | 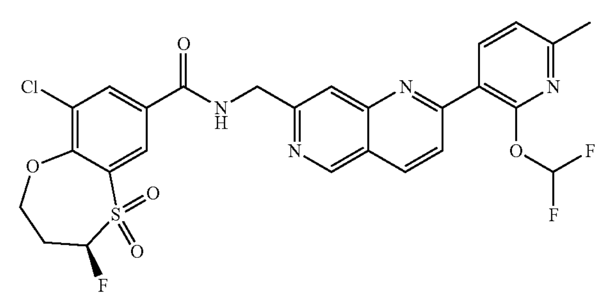 [SMILES: Cc1ccc(-c2ccc3cnc(CNC(=O)c4cc(Cl)c5c(c4)S(=O)(=O)[C@@H](F)CCO5)cc3n2)c(OC(F)F)n1] |

TABLE 1-continued

Compounds of the invention

| # | Structure |
|---|-----------|
| 348 | 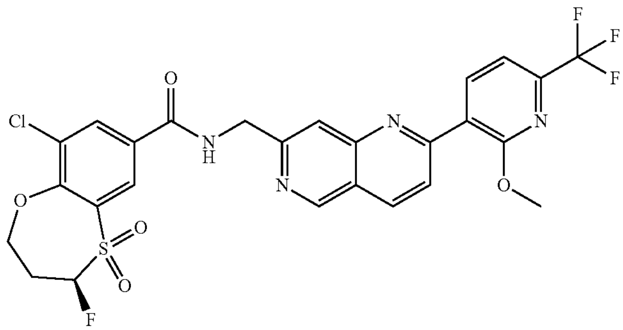 [SMILES: COc1nc(C(F)(F)F)ccc1-c1ccc2cnc(CNC(=O)c3cc(Cl)c4c(c3)S(=O)(=O)[C@@H](F)CCO4)cc2n1] |
| 349 | 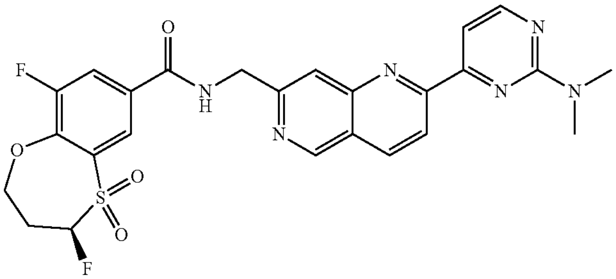 [SMILES: CN(C)c1nccc(-c2ccc3cnc(CNC(=O)c4cc(F)c5c(c4)S(=O)(=O)[C@@H](F)CCO5)cc3n2)n1] |
| 350 | 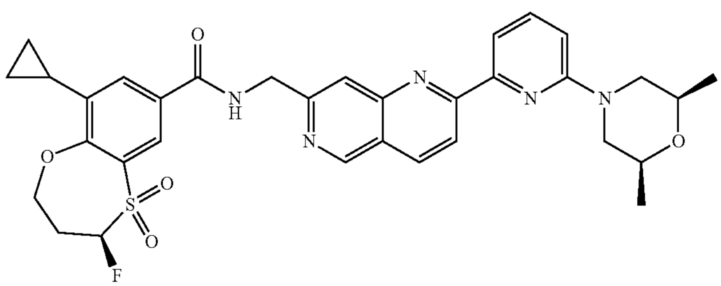 [SMILES: C[C@@H]1CN(c2cccc(-c3ccc4cnc(CNC(=O)c5cc(C6CC6)c6c(c5)S(=O)(=O)[C@@H](F)CCO6)cc4n3)n2)C[C@H](C)O1] |
| 351 | 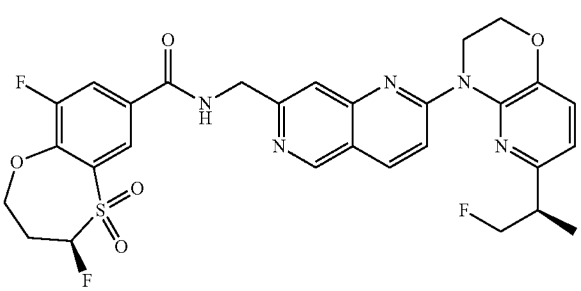 [SMILES: C[C@@H](CF)c1ccc2c(n1)N(c1ccc3cnc(CNC(=O)c4cc(F)c5c(c4)S(=O)(=O)[C@@H](F)CCO5)cc3n1)CCO2] |
| 352 | 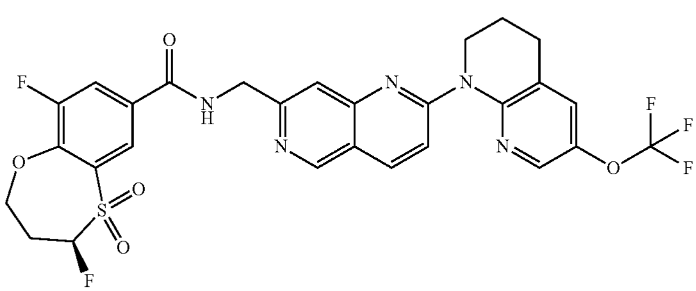 [SMILES: O=C(NCc1cc2nc(N3CCCc4cc(OC(F)(F)F)cnc43)ccc2cn1)c1cc(F)c2c(c1)S(=O)(=O)[C@@H](F)CCO2] |

TABLE 1-continued

Compounds of the invention

| # | Structure |
|---|---|
| 353 | 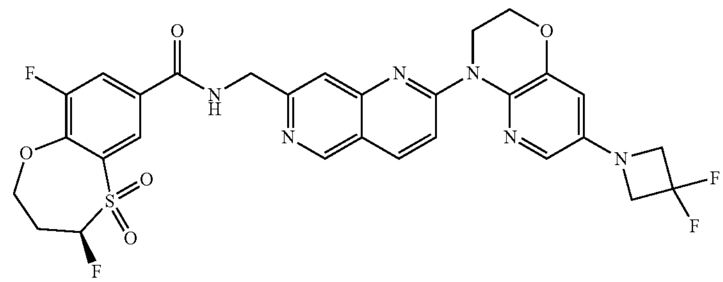 [SMILES: O=C(NCc1cc2nc(N3CCOc4cc(N5CC(F)(F)C5)cnc43)ccc2cn1)c1cc(F)c2c(c1)S(=O)(=O)[C@@H](F)CCO2] |
| 354 | 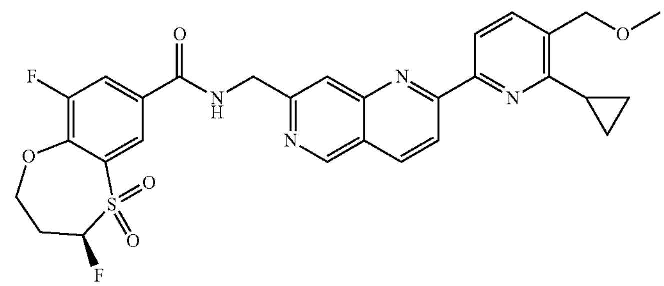 [SMILES: COCc1ccc(-c2ccc3cnc(CNC(=O)c4cc(F)c5c(c4)S(=O)(=O)[C@@H](F)CCO5)cc3n2)nc1C1CC1] |
| 355 | 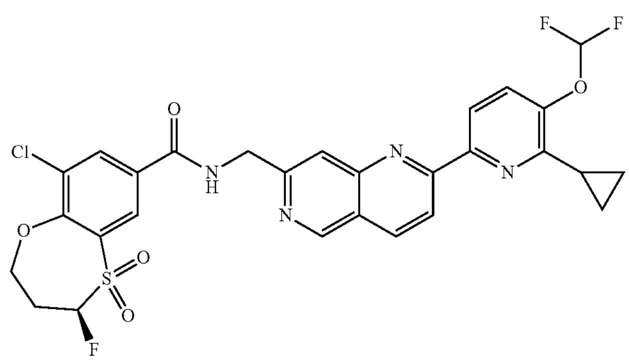 [SMILES: O=C(NCc1cc2nc(-c3ccc(OC(F)F)c(C4CC4)n3)ccc2cn1)c1cc(Cl)c2c(c1)S(=O)(=O)[C@@H](F)CCO2] |
| 356 | 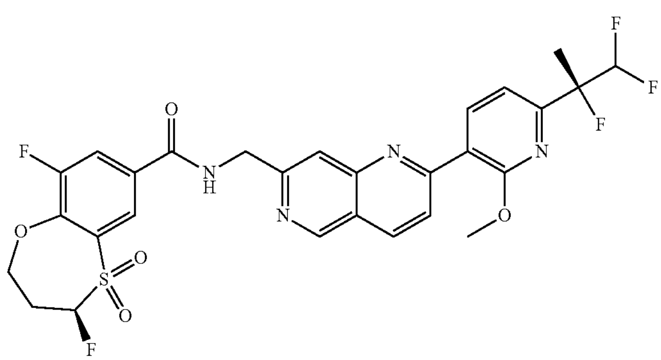 [SMILES: COc1nc([C@@](C)(F)C(F)F)ccc1-c1ccc2cnc(CNC(=O)c3cc(F)c4c(c3)S(=O)(=O)[C@@H](F)CCO4)cc2n1] |

TABLE 1-continued

Compounds of the invention

| # | Structure |
|---|---|
| 357 | 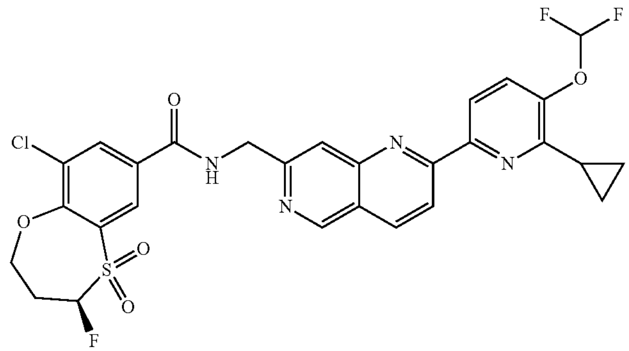 [SMILES: O=C(NCc1cc2nc(-c3ccc(OC(F)F)c(C4CC4)n3)ccc2cn1)c1cc(Cl)c2c(c1)S(=O)(=O)[C@@H](F)CCO2] |
| 358 | 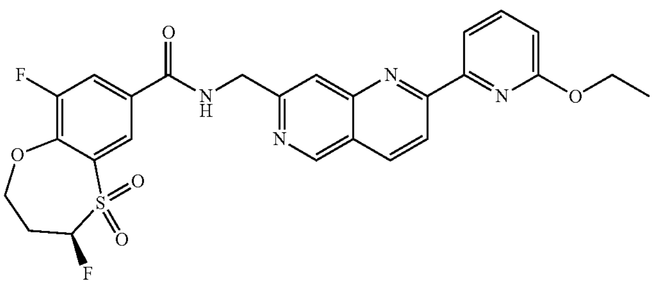 |
| 359 | 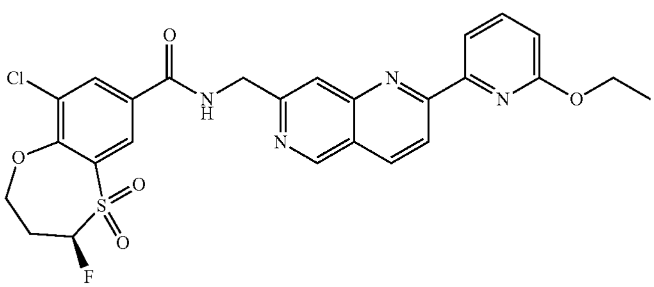 [SMILES: CCOc1cccc(-c2ccc3cnc(CNC(=O)c4cc(F)c5c(c4)S(=O)(=O)[C@@H](F)CCO5)cc3n2)n1] |
| 360 | 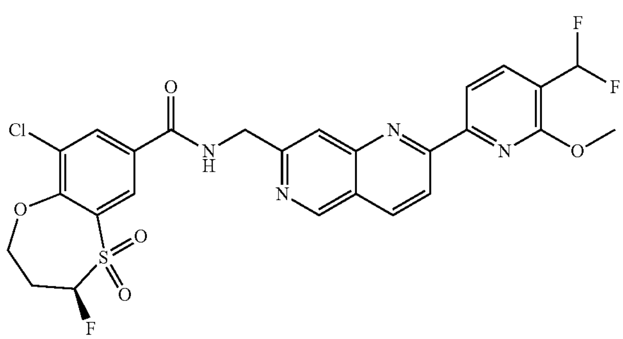 [SMILES: COc1nc(-c2ccc3cnc(CNC(=O)c4cc(Cl)c5c(c4)S(=O)(=O)[C@@H](F)CCO5)cc3n2)ccc1C(F)F] |
| 361 | 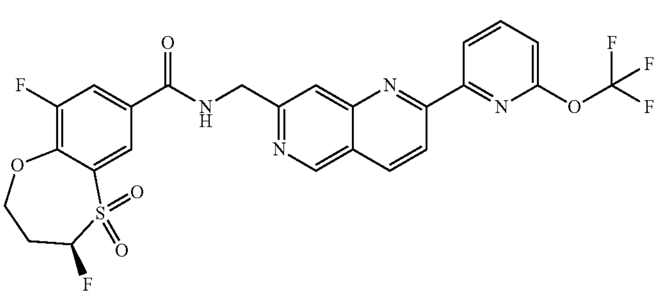 [SMILES: O=C(NCc1cc2nc(-c3cccc(OC(F)(F)F)n3)ccc2cn1)c1cc(F)c2c(c1)S(=O)(=O)[C@@H](F)CCO2] |

TABLE 1-continued

Compounds of the invention

| # | Structure |
|---|---|
| 362 | 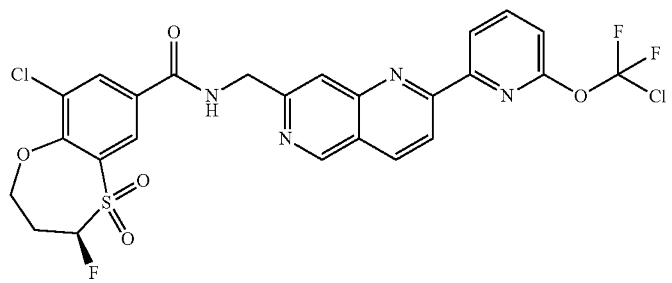 [SMILES: O=C(NCc1cc2nc(-c3cccc(OC(F)(F)Cl)n3)ccc2cn1)c1cc(Cl)c2c(c1)S(=O)(=O)[C@@H](F)CCO2] |
| 363 | 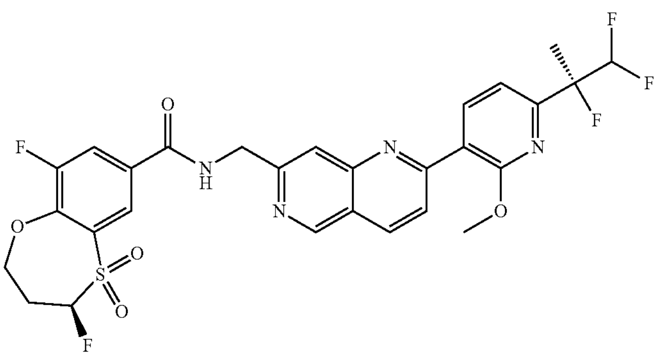 [SMILES: COc1nc([C@](C)(F)C(F)F)ccc1-c1ccc2cnc(CNC(=O)c3cc(F)c4c(c3)S(=O)(=O)[C@@H](F)CCO4)cc2n1] |
| 364 | 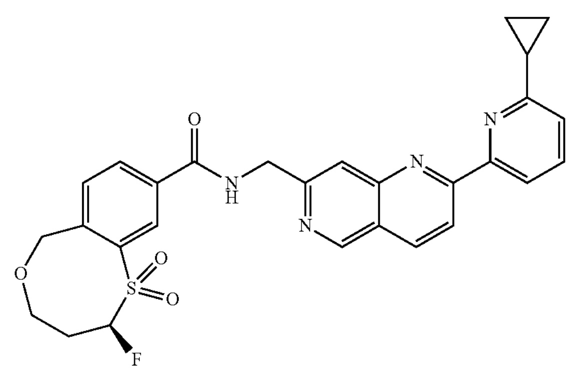 [SMILES: O=C(NCc1cc2nc(-c3cccc(C4CC4)n3)ccc2cn1)c1ccc2c(c1)S(=O)(=O)[C@@H](F)CCOC2] |
| 365 | 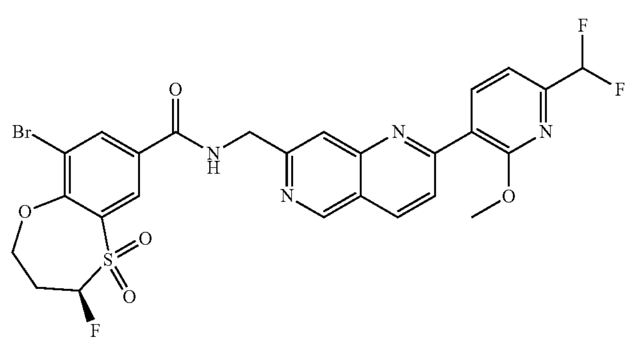 [SMILES: COc1nc(C(F)F)ccc1-c1ccc2cnc(CNC(=O)c3cc(Br)c4c(c3)S(=O)(=O)[C@@H](F)CCO4)cc2n1] |

TABLE 1-continued

Compounds of the invention

| # | Structure |
|---|-----------|
| 366 | 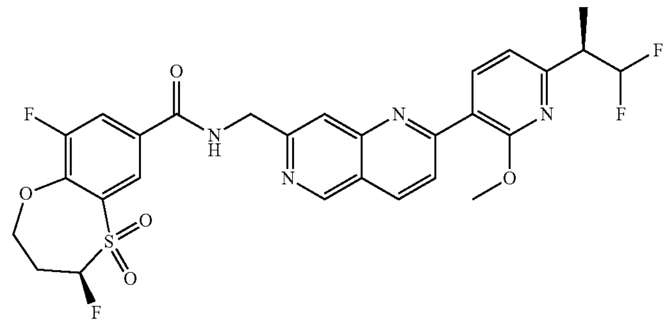 [SMILES: COc1nc([C@@H](C)C(F)F)ccc1-c1ccc2cnc(CNC(=O)c3cc(F)c4c(c3)S(=O)(=O)[C@@H](F)CCO4)cc2n1] |
| 367 | 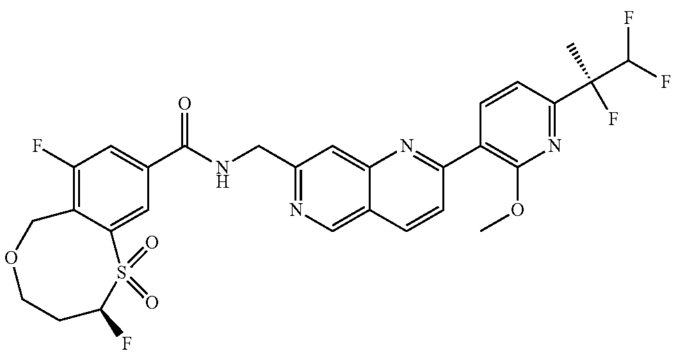 [SMILES: COc1nc([C@](C)(F)C(F)F)ccc1-c1ccc2cnc(CNC(=O)c3cc(F)c4c(c3)S(=O)(=O)[C@@H](F)CCOC4)cc2n1] |
| 368 | 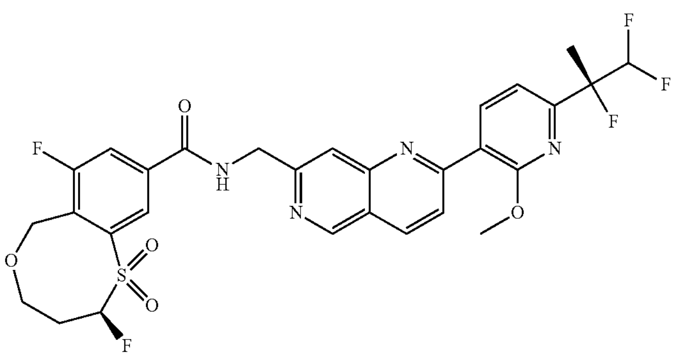 [SMILES: COc1nc([C@@](C)(F)C(F)F)ccc1-c1ccc2cnc(CNC(=O)c3cc(F)c4c(c3)S(=O)(=O)[C@@H](F)CCOC4)cc2n1] |
| 369 | 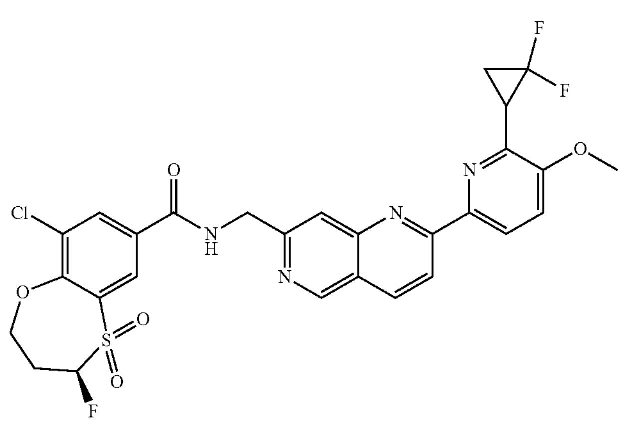 [SMILES: COc1ccc(-c2ccc3cnc(CNC(=O)c4cc(Cl)c5c(c4)S(=O)(=O)[C@@H](F)CCO5)cc3n2)nc1C1CC1(F)F] |

TABLE 1-continued
Compounds of the invention
| # | Structure |
|---|---|
| 370 | 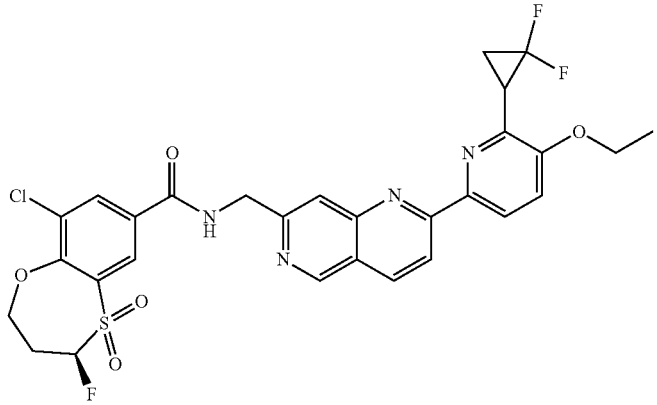 [SMILES: CCOc1ccc(-c2ccc3cnc(CNC(=O)c4cc(Cl)c5c(c4)S(=O)(=O)[C@@H](F)CCO5)cc3n2)nc1C1CC1(F)F] |
| 371 | 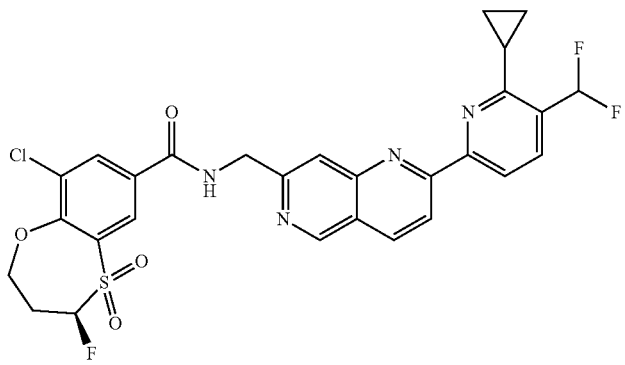 [SMILES: O=C(NCc1cc2nc(-c3ccc(C(F)F)c(C4CC4)n3)ccc2cn1)c1cc(Cl)c2c(c1)S(=O)(=O)[C@@H](F)CCO2] |
| 372 | 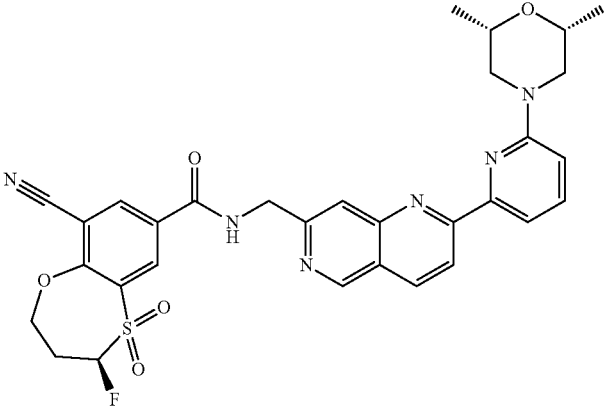 [SMILES: C[C@@H]1CN(c2cccc(-c3ccc4cnc(CNC(=O)c5cc(C#N)c6c(c5)S(=O)(=O)[C@@H](F)CCO6)cc4n3)n2)C[C@H](C)O1] |
| 373 | 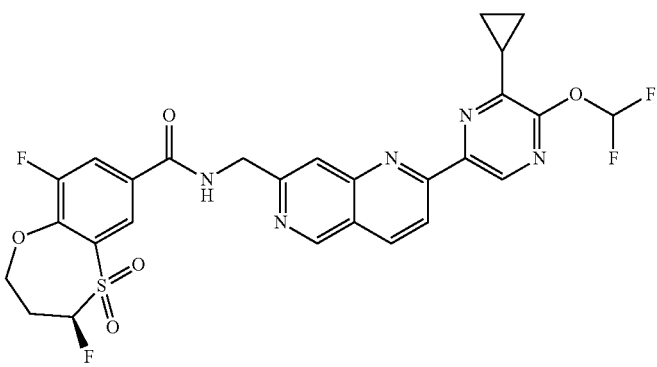 [SMILES: O=C(NCc1cc2nc(-c3cnc(OC(F)F)c(C4CC4)n3)ccc2cn1)c1cc(F)c2c(c1)S(=O)(=O)[C@@H](F)CCO2] |

TABLE 1-continued

Compounds of the invention

| # | Structure |
|---|-----------|
| 374 | 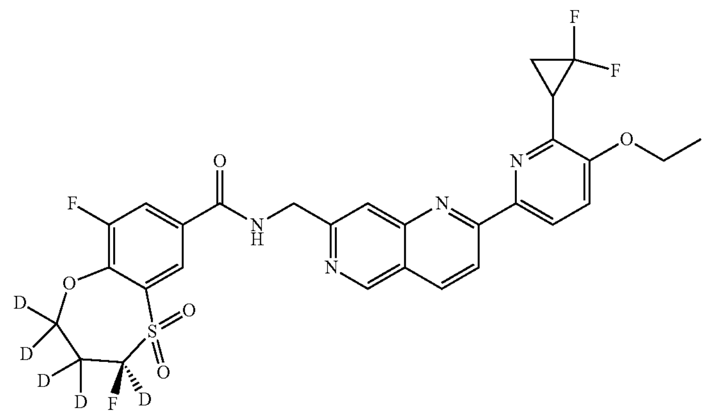 [SMILES: [2H]C1([2H])Oc2c(F)cc(C(=O)NCc3cc4nc(-c5ccc(OCC)c(C6CC6(F)F)n5)ccc4cn3)cc2S(=O)(=O)[C@@]([2H])(F)C1([2H])[2H]] |
| 375 | 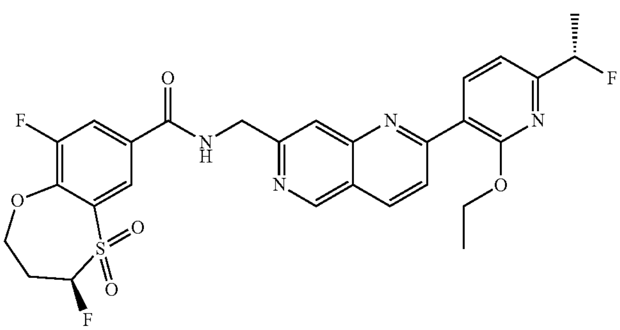 [SMILES: CCOc1nc([C@H](C)F)ccc1-c1ccc2cnc(CNC(=O)c3cc(F)c4c(c3)S(=O)(=O)[C@@H](F)CCO4)cc2n1] |
| 376 | 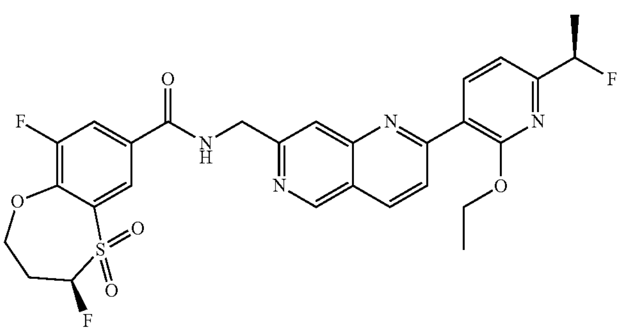 [SMILES: CCOc1nc([C@@H](C)F)ccc1-c1ccc2cnc(CNC(=O)c3cc(F)c4c(c3)S(=O)(=O)[C@@H](F)CCO4)cc2n1] |
| 377 | 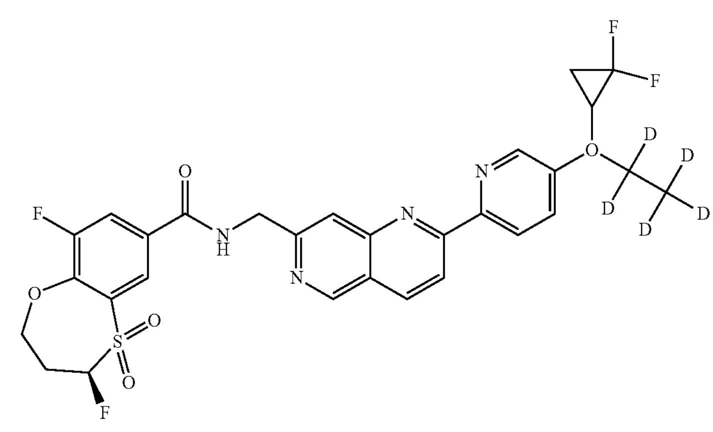 |

TABLE 1-continued

Compounds of the invention

| # | Structure |
|---|---|
| 378 | 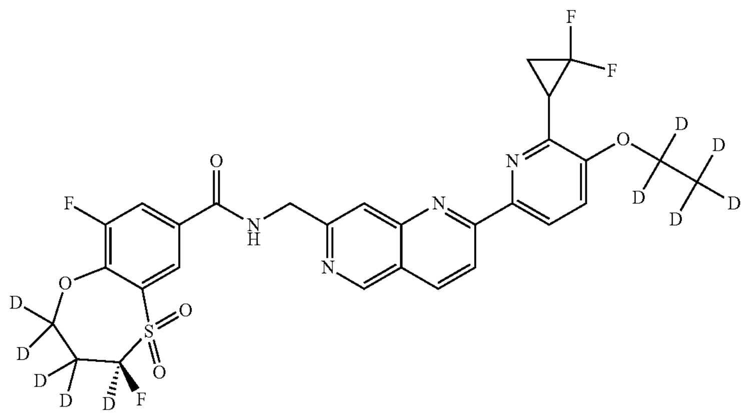 [SMILES: [2H]C([2H])([2H])C([2H])([2H])Oc1ccc(-c2ccc3cnc(CNC(=O)c4cc(F)c5c(c4)S(=O)(=O)[C@@]([2H])(F)C([2H])([2H])C([2H])([2H])O5)cc3n2)nc1C1CC1(F)F] |
| 379 | 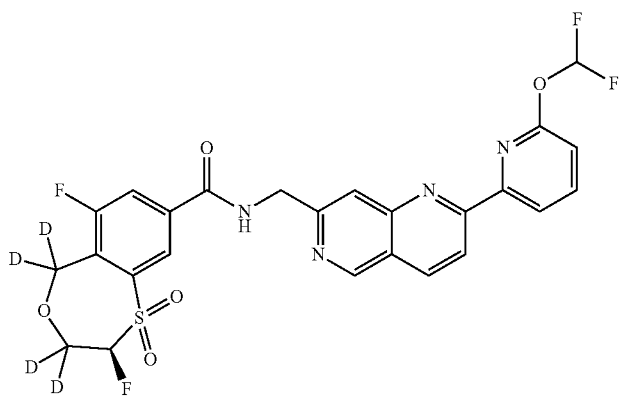 [SMILES: [2H]C1([2H])OC([2H])([2H])[C@H](F)S(=O)(=O)c2cc(C(=O)NCc3cc4nc(-c5cccc(OC(F)F)n5)ccc4cn3)cc(F)c21] |
| 380 | 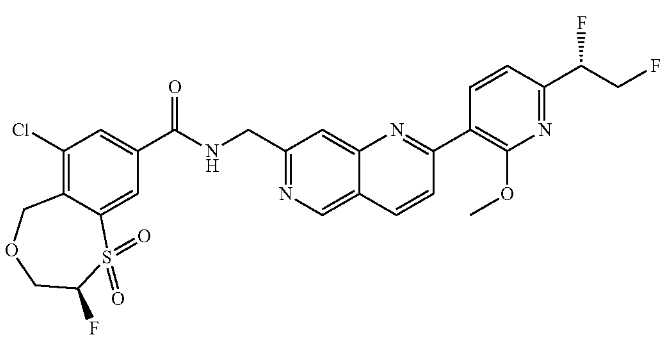 [SMILES: COc1nc([C@H](F)CF)ccc1-c1ccc2cnc(CNC(=O)c3cc(Cl)c4c(c3)S(=O)(=O)[C@@H](F)COC4)cc2n1] |
| 381 | 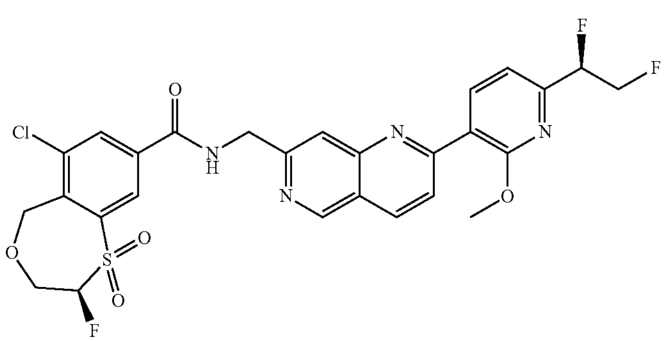 [SMILES: COc1nc([C@@H](F)CF)ccc1-c1ccc2cnc(CNC(=O)c3cc(Cl)c4c(c3)S(=O)(=O)[C@@H](F)COC4)cc2n1] |

TABLE 1-continued

Compounds of the invention

| # | Structure |
|---|-----------|
| 382 | 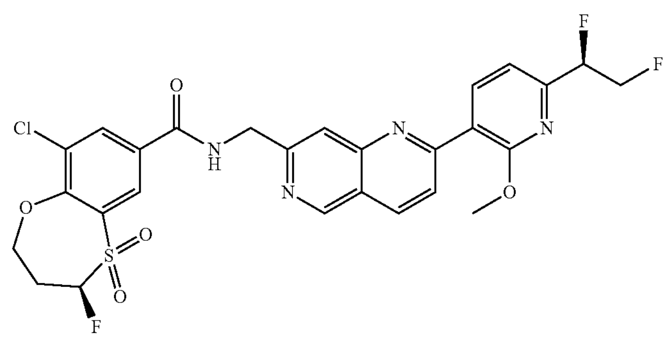 [SMILES: COc1nc([C@@H](F)CF)ccc1-c1ccc2cnc(CNC(=O)c3cc(Cl)c4c(c3)S(=O)(=O)[C@@H](F)CCO4)cc2n1] |
| 383 | 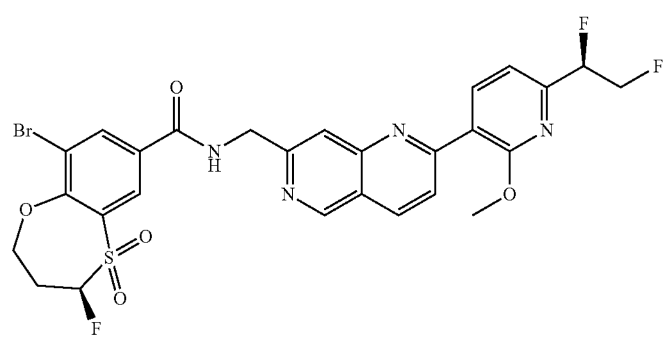 [SMILES: COc1nc([C@@H](F)CF)ccc1-c1ccc2cnc(CNC(=O)c3cc(Br)c4c(c3)S(=O)(=O)[C@@H](F)CCO4)cc2n1] |
| 384 | 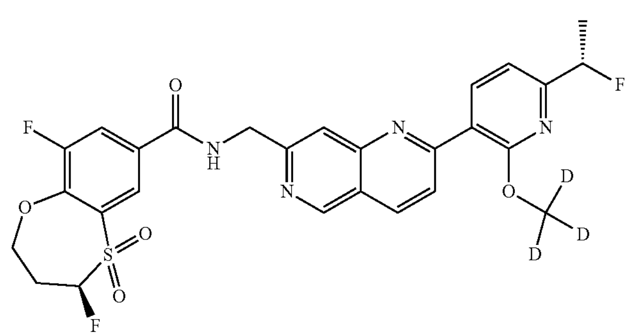 [SMILES: [2H]C([2H])([2H])Oc1nc([C@H](C)F)ccc1-c1ccc2cnc(CNC(=O)c3cc(F)c4c(c3)S(=O)(=O)[C@@H](F)CCO4)cc2n1] |
| 385 | 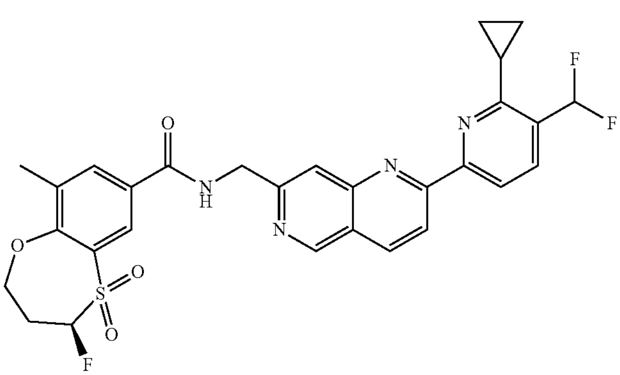 [SMILES: Cc1cc(C(=O)NCc2cc3nc(-c4ccc(C(F)F)c(C5CC5)n4)ccc3cn2)cc2c1OCC[C@H](F)S2(=O)=O] |

TABLE 1-continued
Compounds of the invention
| # | Structure |
|---|---|
| 386 | 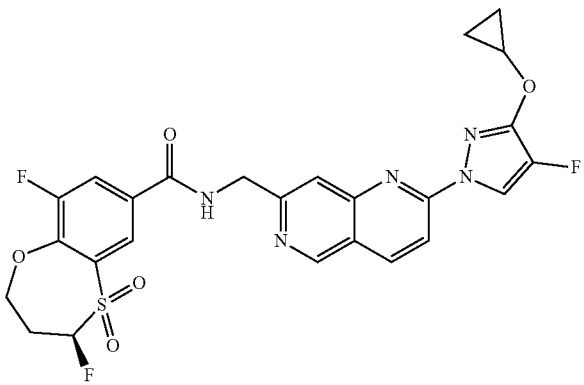 [SMILES: O=C(NCc1cc2nc(-n3cc(F)c(OC4CC4)n3)ccc2cn1)c1cc(F)c2c(c1)S(=O)(=O)[C@@H](F)CCO2] |
| 387 | 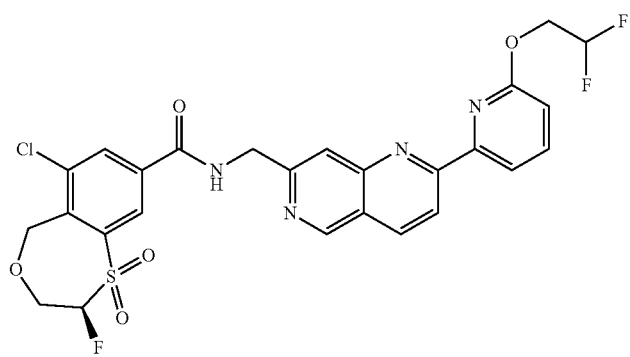 [SMILES: O=C(NCc1cc2nc(-c3cccc(OCC(F)F)n3)ccc2cn1)c1cc(Cl)c2c(c1)S(=O)(=O)[C@@H](F)COC2] |
| 388 | 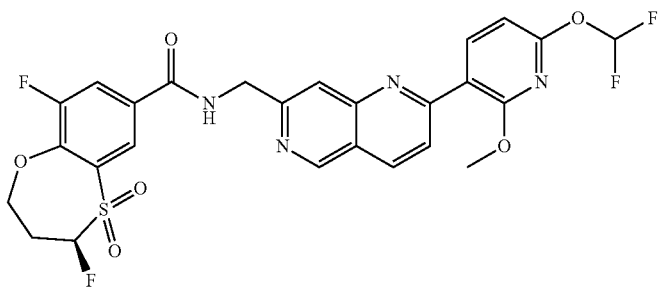 [SMILES: COc1nc(OC(F)F)ccc1-c1ccc2cnc(CNC(=O)c3cc(F)c4c(c3)S(=O)(=O)[C@@H](F)CCO4)cc2n1] |
| 389 | 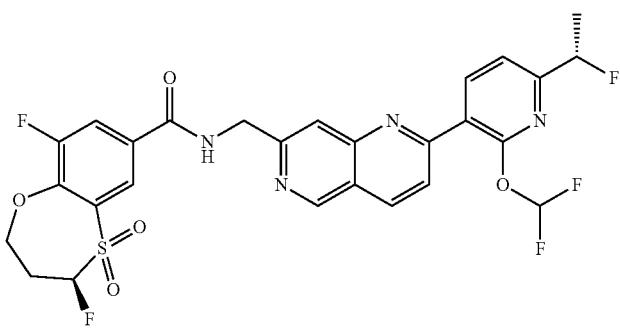 [SMILES: C[C@H](F)c1ccc(-c2ccc3cnc(CNC(=O)c4cc(F)c5c(c4)S(=O)(=O)[C@@H](F)CCO5)cc3n2)c(OC(F)F)n1] |

TABLE 1-continued
Compounds of the invention
| # | Structure |
|---|---|
| 390 | 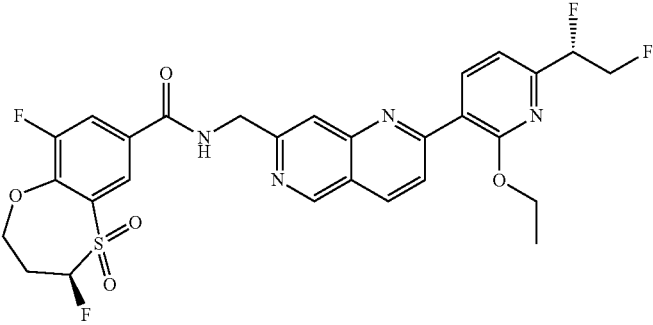 [SMILES: CCOc1nc([C@H](F)CF)ccc1-c1ccc2cnc(CNC(=O)c3cc(F)c4c(c3)S(=O)(=O)[C@@H](F)CCO4)cc2n1] |
| 391 | 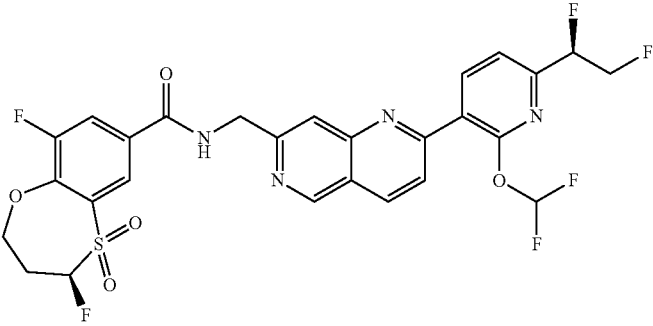 [SMILES: O=C(NCc1cc2nc(-c3ccc([C@@H](F)CF)nc3OC(F)F)ccc2cn1)c1cc(F)c2c(c1)S(=O)(=O)[C@@H](F)CCO2] |
| 392 | 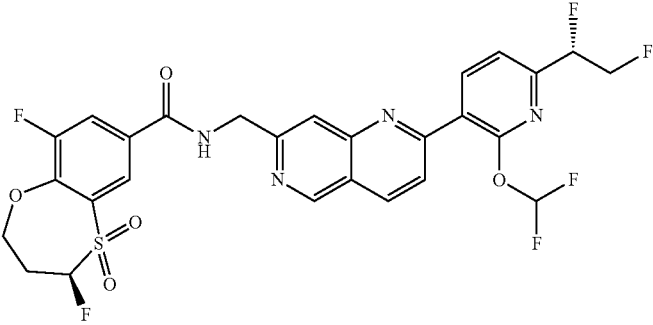 [SMILES: O=C(NCc1cc2nc(-c3ccc([C@H](F)CF)nc3OC(F)F)ccc2cn1)c1cc(F)c2c(c1)S(=O)(=O)[C@@H](F)CCO2] |
| 393 | 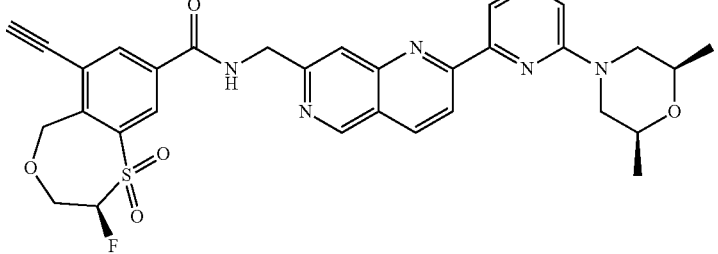 |

TABLE 1-continued

Compounds of the invention

| # | Structure |
|---|---|
| 394 | 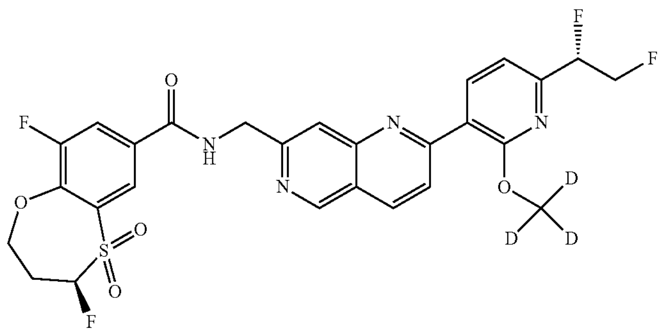 [SMILES: [2H]C([2H])([2H])Oc1nc([C@H](F)CF)ccc1-c1ccc2cnc(CNC(=O)c3cc(F)c4c(c3)S(=O)(=O)[C@@H](F)CCO4)cc2n1] |
| 395 | 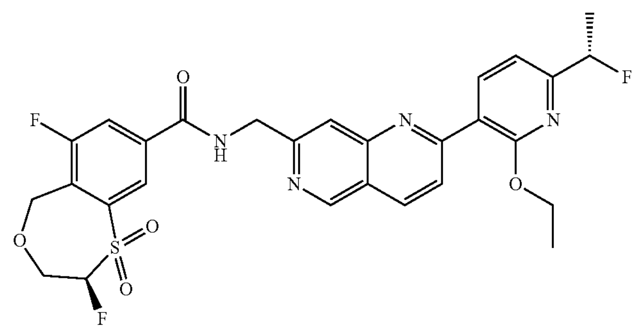 [SMILES: CCOc1nc([C@H](C)F)ccc1-c1ccc2cnc(CNC(=O)c3cc(F)c4c(c3)S(=O)(=O)[C@@H](F)COC4)cc2n1] |
| 396 | 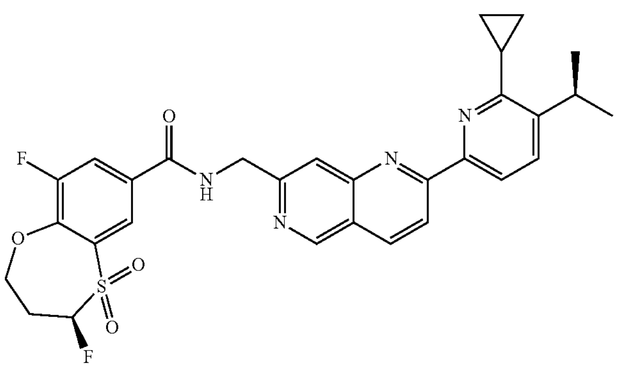 |
| 397 | 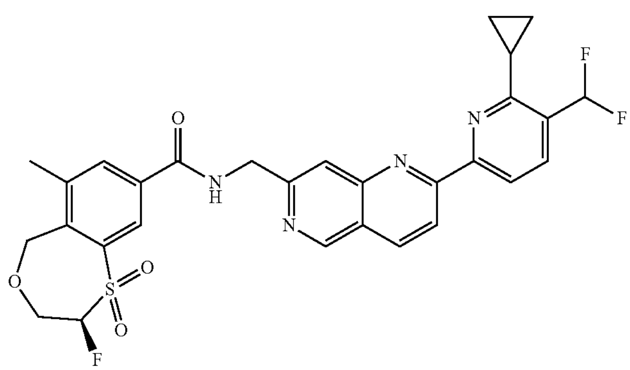 [SMILES: Cc1cc(C(=O)NCc2cc3nc(-c4ccc(C(F)F)c(C5CC5)n4)ccc3cn2)cc2c1COC[C@H](F)S2(=O)=O] |

TABLE 1-continued
Compounds of the invention
| # | Structure |
|---|---|
| 398 | 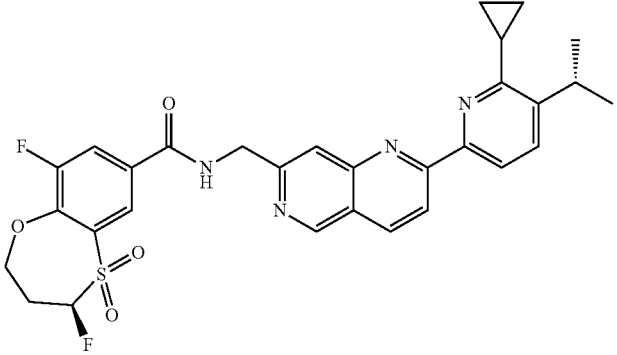 |
| 399 | 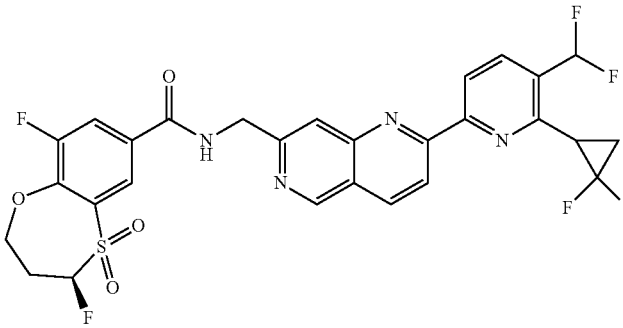 |
| 400 | 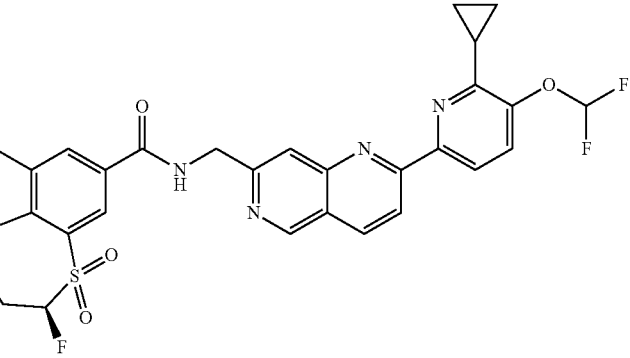 |
| 401 | 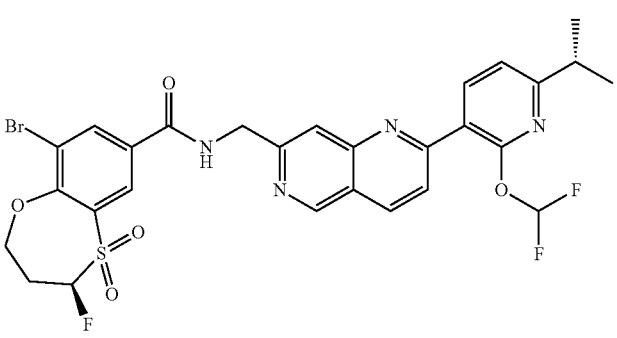 |

TABLE 1-continued

Compounds of the invention

| # | Structure |
|---|---|
| 402 | 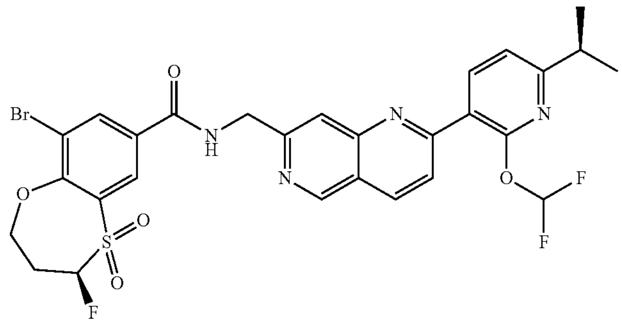 |
| 403 | 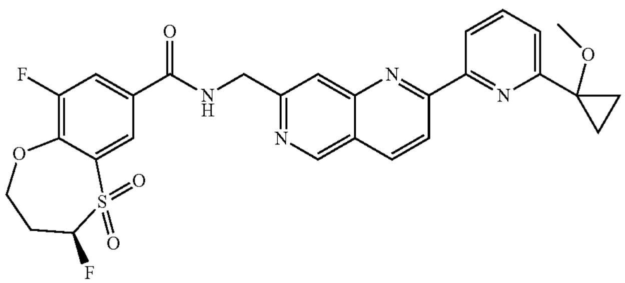 [SMILES: COC1(c2cccc(-c3ccc4cnc(CNC(=O)c5cc(F)c6c(c5)S(=O)(=O)[C@@H](F)CCO6)cc4n3)n2)CC1] |
| 404 | 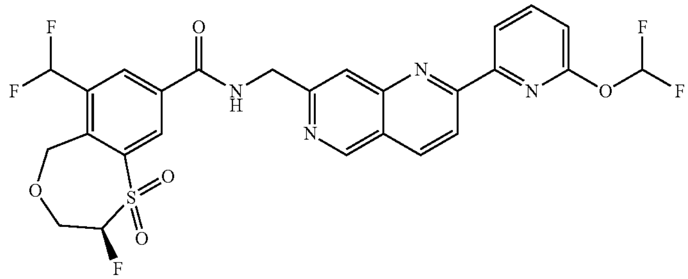 [SMILES: O=C(NCc1cc2nc(-c3cccc(OC(F)F)n3)ccc2cn1)c1cc(C(F)F)c2c(c1)S(=O)(=O)[C@@H](F)COC2] |
| 405 | 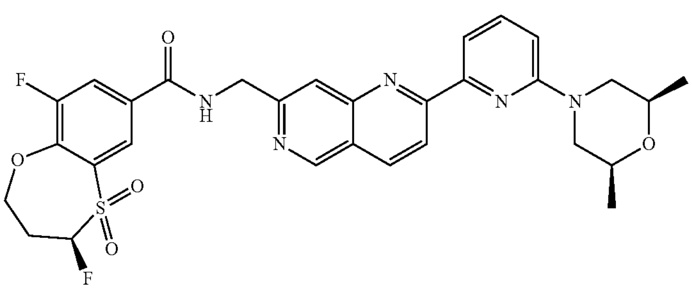 [SMILES: C[C@@H]1CN(c2cccc(-c3ccc4cnc(CNC(=O)c5cc(F)c6c(c5)S(=O)(=O)[C@@H](F)CCO6)cc4n3)n2)C[C@H](C)O1] |
| 406 | 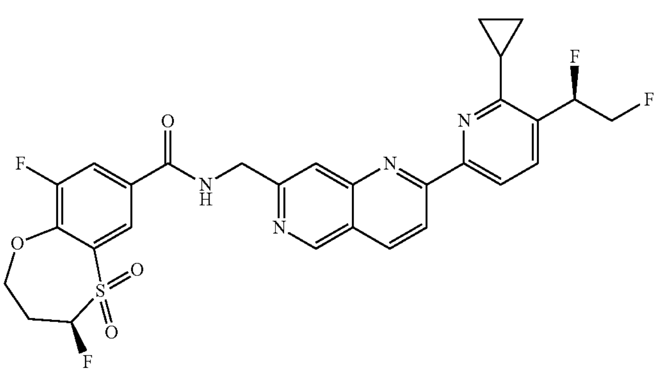 [SMILES: O=C(NCc1cc2nc(-c3ccc([C@@H](F)CF)c(C4CC4)n3)ccc2cn1)c1cc(F)c2c(c1)S(=O)(=O)[C@@H](F)CCO2] |

TABLE 1-continued

Compounds of the invention

| # | Structure |
|---|---|
| 407 | 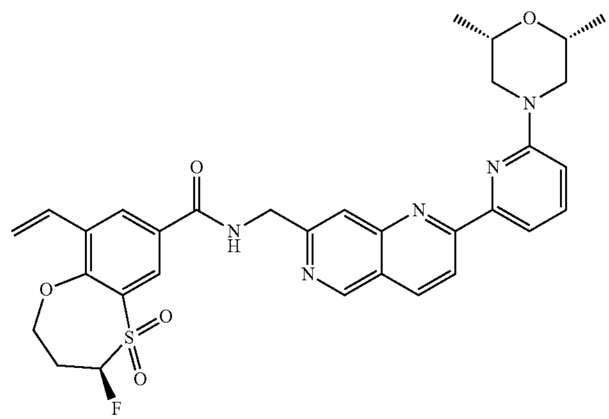 [SMILES: C=Cc1cc(C(=O)NCc2cc3nc(-c4cccc(N5C[C@@H](C)O[C@@H](C)C5)n4)ccc3cn2)cc2c1OCC[C@H](F)S2(=O)=O] |
| 408 | 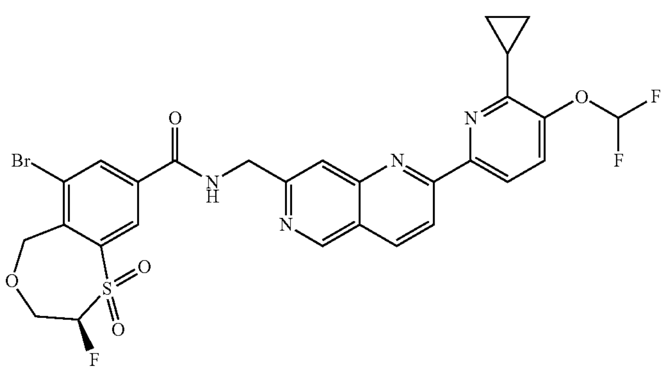 [SMILES: O=C(NCc1cc2nc(-c3ccc(OC(F)F)c(C4CC4)n3)ccc2cn1)c1cc(Br)c2c(c1)S(=O)(=O)[C@@H](F)COC2] |
| 409 | 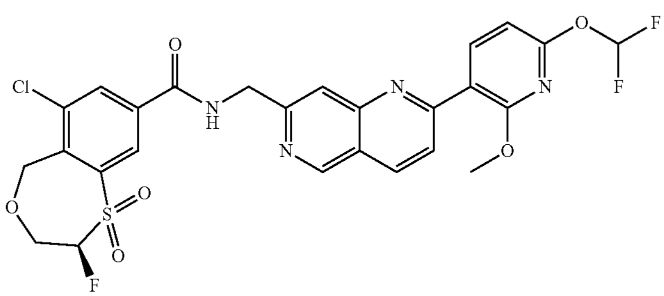 [SMILES: COc1nc(OC(F)F)ccc1-c1ccc2cnc(CNC(=O)c3cc(Cl)c4c(c3)S(=O)(=O)[C@@H](F)COC4)cc2n1] |
| 410 | 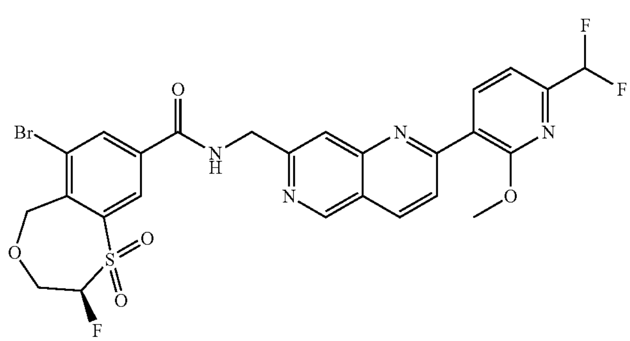 [SMILES: COc1nc(C(F)F)ccc1-c1ccc2cnc(CNC(=O)c3cc(Br)c4c(c3)S(=O)(=O)[C@@H](F)COC4)cc2n1] |

TABLE 1-continued

Compounds of the invention

| # | Structure |
|---|---|
| 411 | (structure) |
| 412 | (structure) |
| 413 | (structure) |
| 414 | (structure) |

US 12,139,487 B2
175 176
TABLE 1-continued
Compounds of the invention
| # | Structure |
|---|---|
| 415 | 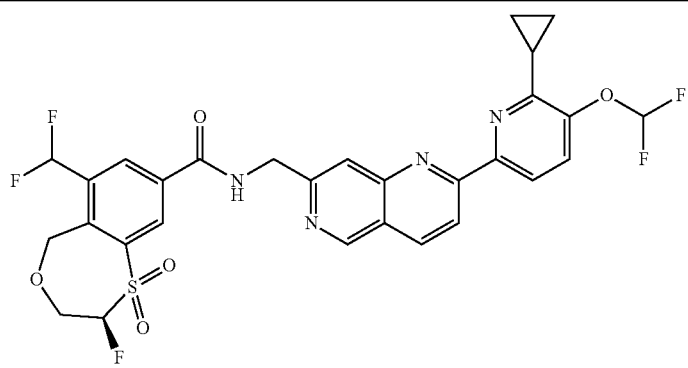 |
| 416 | 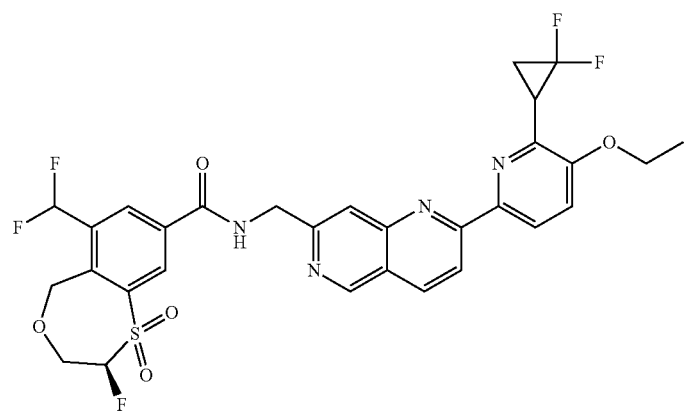 [SMILES: CCOc1ccc(-c2ccc3cnc(CNC(=O)c4cc(C(F)F)c5c(c4)S(=O)(=O)[C@@H](F)COC5)cc3n2)nc1C1CC1(F)F] |
| 417 | 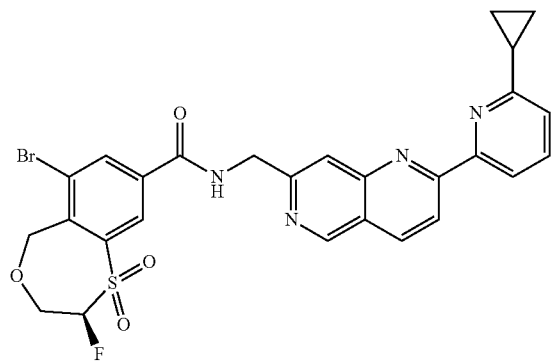 [SMILES: O=C(NCc1cc2nc(-c3cccc(C4CC4)n3)ccc2cn1)c1cc(Br)c2c(c1)S(=O)(=O)[C@@H](F)COC2] |
| 418 | 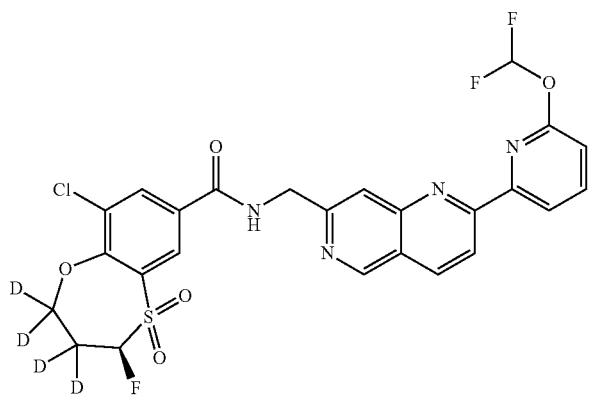 [SMILES: [2H]C1([2H])Oc2c(Cl)cc(C(=O)NCc3cc4nc(-c5cccc(OC(F)F)n5)ccc4cn3)cc2S(=O)(=O)[C@@H](F)C1([2H])[2H]] |

TABLE 1-continued

Compounds of the invention

| # | Structure |
|---|---|
| 419 | 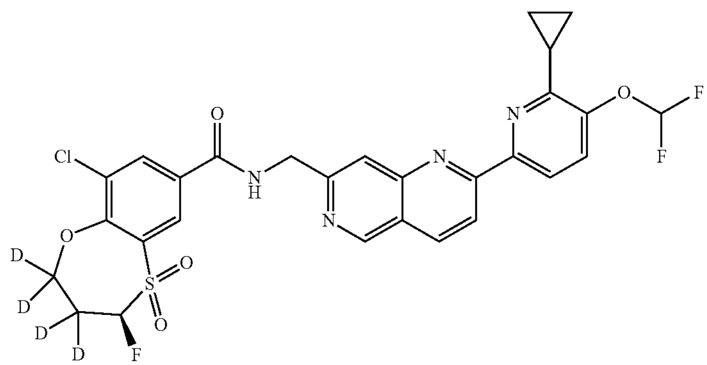 [SMILES: [2H]C1([2H])Oc2c(Cl)cc(C(=O)NCc3cc4nc(-c5ccc(OC(F)F)c(C6CC6)n5)ccc4cn3)cc2S(=O)(=O)[C@@H](F)C1([2H])[2H]] |
| 420 | 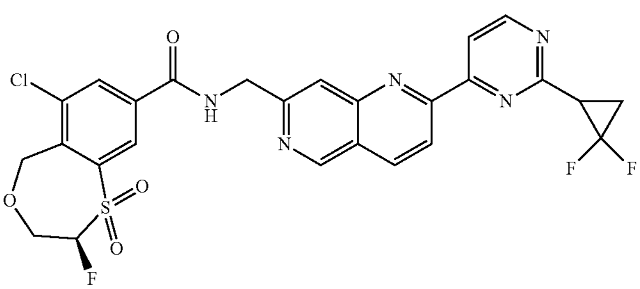 [SMILES: O=C(NCc1cc2nc(-c3ccnc(C4CC4(F)F)n3)ccc2cn1)c1cc(Cl)c2c(c1)S(=O)(=O)[C@@H](F)COC2] |
| 421 | 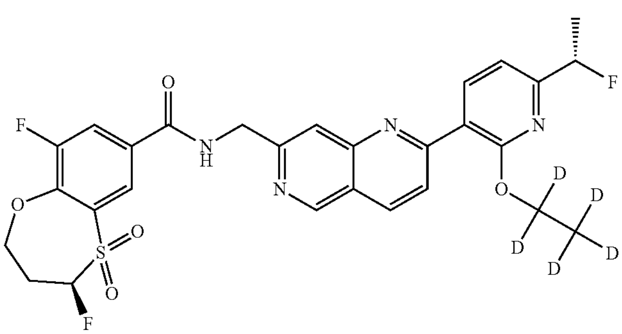 [SMILES: [2H]C([2H])([2H])C([2H])([2H])Oc1nc([C@H](C)F)ccc1-c1ccc2cnc(CNC(=O)c3cc(F)c4c(c3)S(=O)(=O)[C@@H](F)CCO4)cc2n1] |
| 422 | 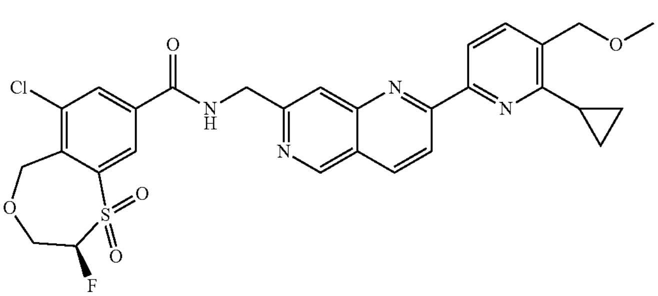 [SMILES: COCc1ccc(-c2ccc3cnc(CNC(=O)c4cc(Cl)c5c(c4)S(=O)(=O)[C@@H](F)COC5)cc3n2)nc1C1CC1] |

TABLE 1-continued
Compounds of the invention
| # | Structure |
|---|---|
| 423 | 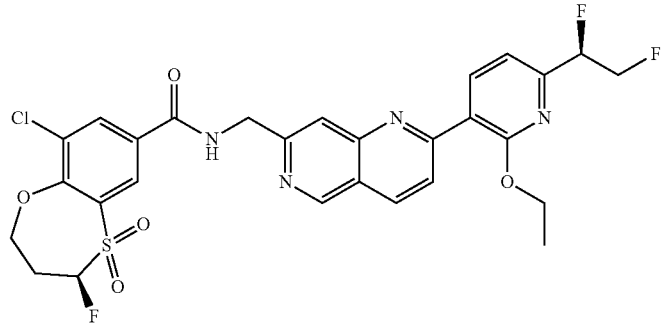 [SMILES: CCOc1nc([C@@H](F)CF)ccc1-c1ccc2cnc(CNC(=O)c3cc(Cl)c4c(c3)S(=O)(=O)[C@@H](F)CCO4)cc2n1] |
| 424 | 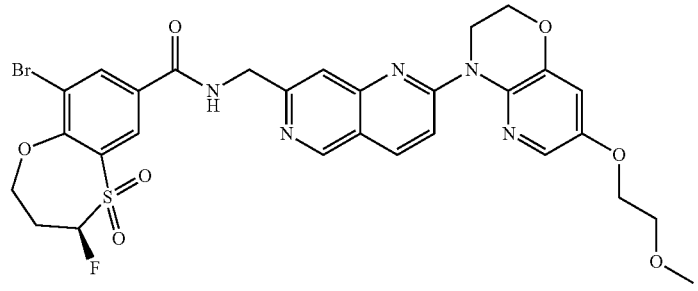 |
| 425 | 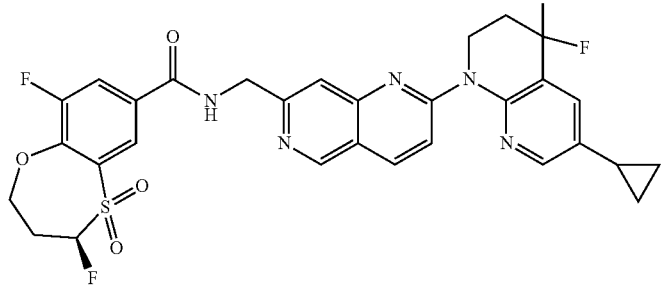 |
| 426 | 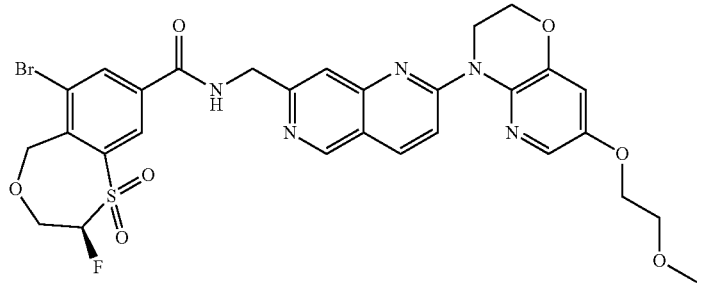 |
| 427 | 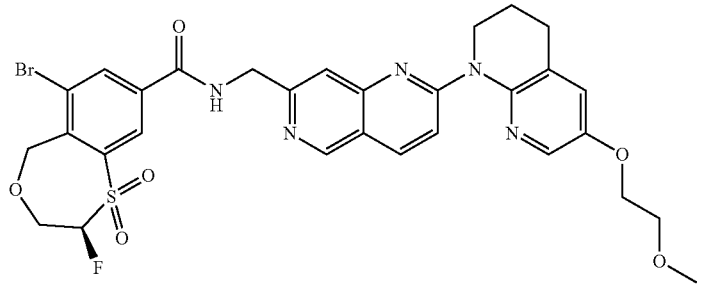 [SMILES: COCCOc1cnc2c(c1)OCCN2c1ccc2cnc(CNC(=O)c3cc(Br)c4c(c3)S(=O)(=O)[C@@H](F)COC4)cc2n1] |

TABLE 1-continued

Compounds of the invention

| # | Structure |
|---|---|
| 428 | 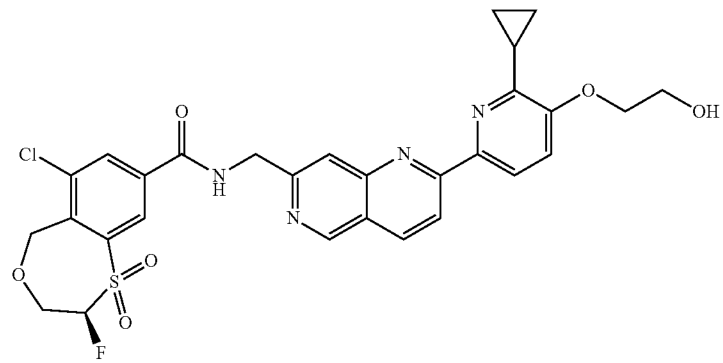 [SMILES: O=C(NCc1cc2nc(-c3ccc(OCCO)c(C4CC4)n3)ccc2cn1)c1cc(Cl)c2c(c1)S(=O)(=O)[C@@H](F)COC2] |
| 429 | 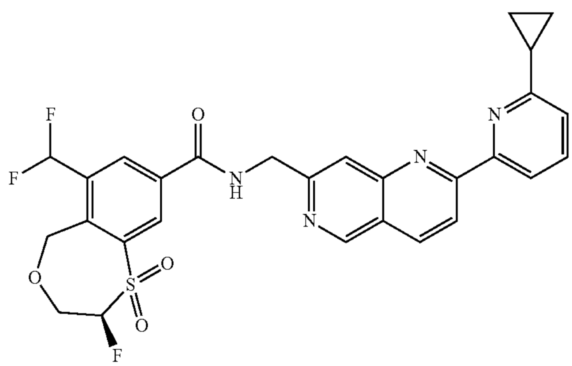 [SMILES: O=C(NCc1cc2nc(-c3cccc(C4CC4)n3)ccc2cn1)c1cc(C(F)F)c2c(c1)S(=O)(=O)[C@@H](F)COC2] |
| 430 | 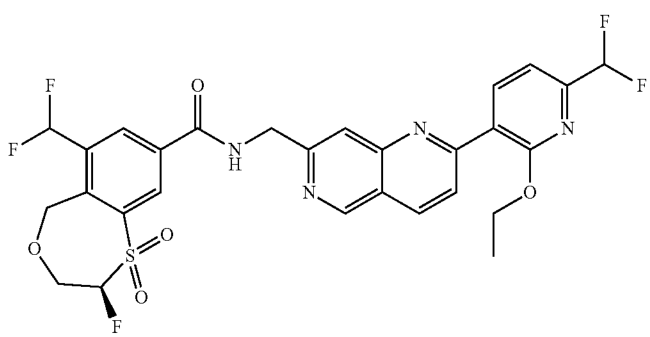 [SMILES: CCOc1nc(C(F)F)ccc1-c1ccc2cnc(CNC(=O)c3cc(C(F)F)c4c(c3)S(=O)(=O)[C@@H](F)COC4)cc2n1] |
| 431 | 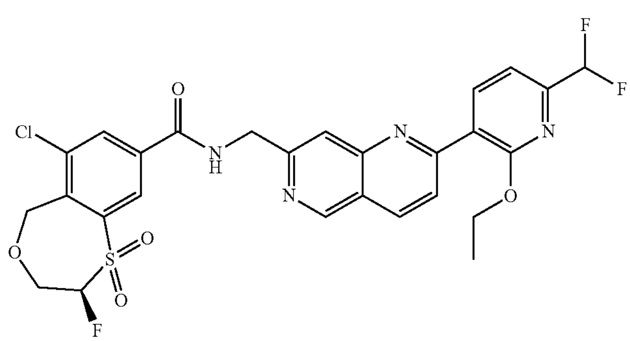 [SMILES: CCOc1nc(C(F)F)ccc1-c1ccc2cnc(CNC(=O)c3cc(Cl)c4c(c3)S(=O)(=O)[C@@H](F)COC4)cc2n1] |

TABLE 1-continued
Compounds of the invention
| # | Structure |
|---|---|
| 432 | 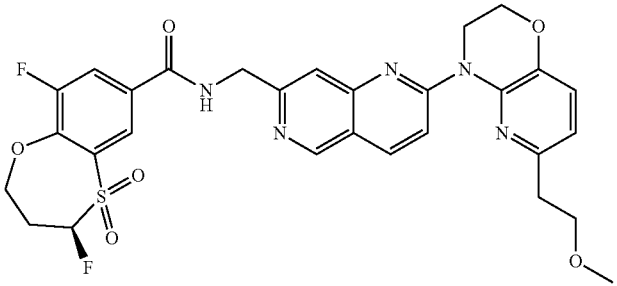 [SMILES: COCCc1ccc2c(n1)N(c1ccc3cnc(CNC(=O)c4cc(F)c5c(c4)S(=O)(=O)[C@@H](F)CCO5)cc3n1)CCO2] |
| 433 | 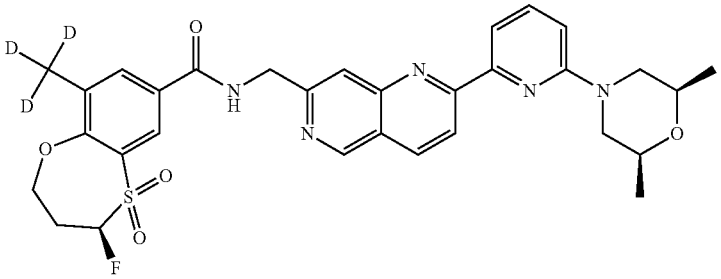 [SMILES: [2H]C([2H])([2H])c1cc(C(=O)NCc2cc3nc(-c4cccc(N5C[C@@H](C)O[C@@H](C)C5)n4)ccc3cn2)cc2c1OCC[C@H](F)S2(=O)=O] |
| 434 | 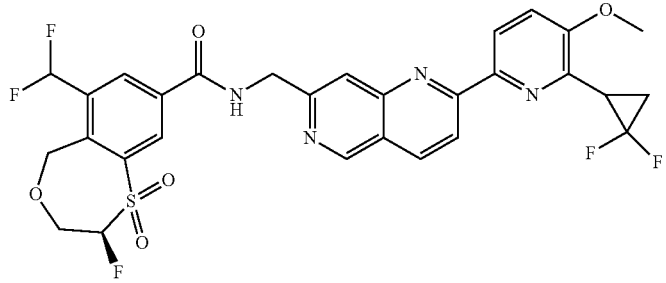 [SMILES: COc1ccc(-c2ccc3cnc(CNC(=O)c4cc(C(F)F)c5c(c4)S(=O)(=O)[C@@H](F)COC5)cc3n2)nc1C1CC1(F)F] |
| 435 | 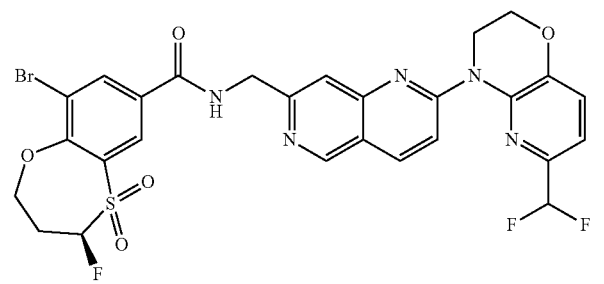 [SMILES: O=C(NCc1cc2nc(N3CCOc4ccc(C(F)F)nc43)ccc2cn1)c1cc(Br)c2c(c1)S(=O)(=O)[C@@H](F)CCO2] |
| 436 | 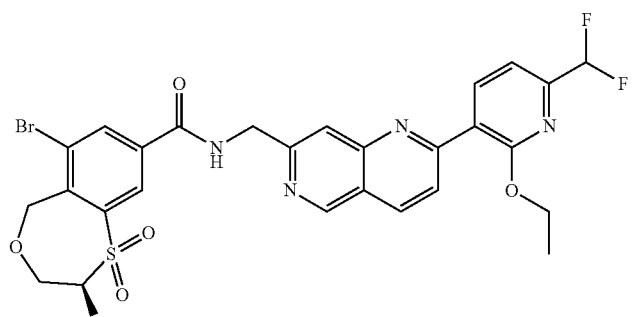 |

TABLE 1-continued
Compounds of the invention
| # | Structure |
|---|---|
| 437 | 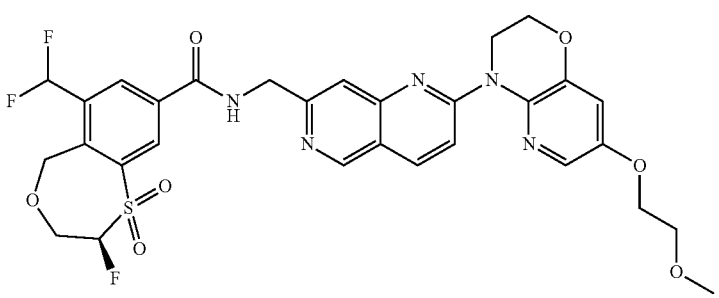 [SMILES: COCCOc1cnc2c(c1)OCCN2c1ccc2cnc(CNC(=O)c3cc(C(F)F)c4c(c3)S(=O)(=O)[C@@H](F)COC4)cc2n1] |
| 439 | 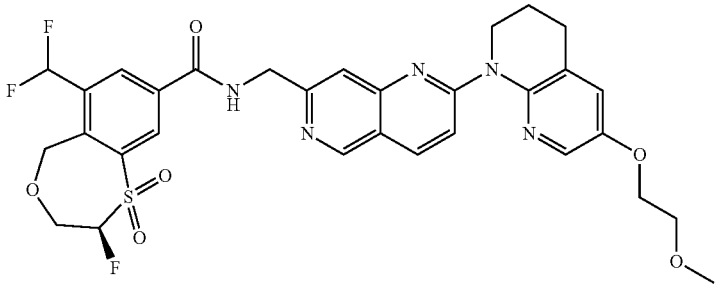 [SMILES: COCCOc1cnc2c(c1)CCCN2c1ccc2cnc(CNC(=O)c3cc(C(F)F)c4c(c3)S(=O)(=O)[C@@H](F)COC4)cc2n1] |
| 440 | 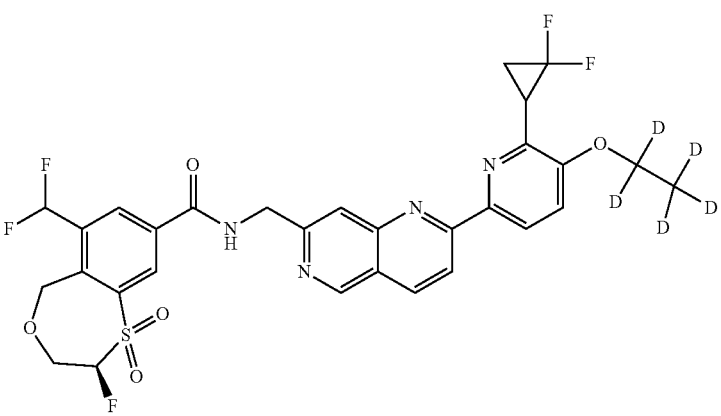 [SMILES: [2H]C([2H])([2H])C([2H])([2H])Oc1ccc(-c2ccc3cnc(CNC(=O)c4cc(C(F)F)c5c(c4)S(=O)(=O)[C@@H](F)COC5)cc3n2)nc1C1CC1(F)F] |
| 441 | 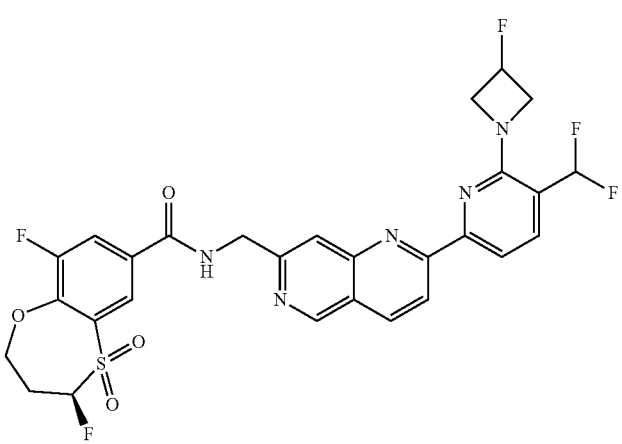 [SMILES: O=C(NCc1cc2nc(-c3ccc(C(F)F)c(N4CC(F)C4)n3)ccc2cn1)c1cc(F)c2c(c1)S(=O)(=O)[C@@H](F)CCO2] |

TABLE 1-continued

Compounds of the invention

| # | Structure |
|---|---|
| 442 | 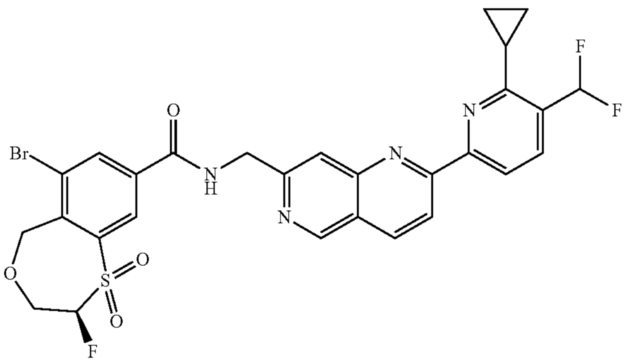 [SMILES: O=C(NCc1cc2nc(-c3ccc(C(F)F)c(C4CC4)n3)ccc2cn1)c1cc(Br)c2c(c1)S(=O)(=O)[C@@H](F)COC2] |
| 443 | 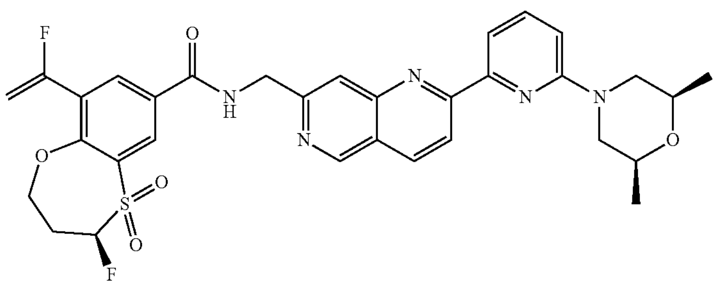 [SMILES: C=C(F)c1cc(C(=O)NCc2cc3nc(-c4cccc(N5C[C@@H](C)O[C@@H](C)C5)n4)ccc3cn2)cc2c1OCC[C@H](F)S2(=O)=O] |
| 444 | 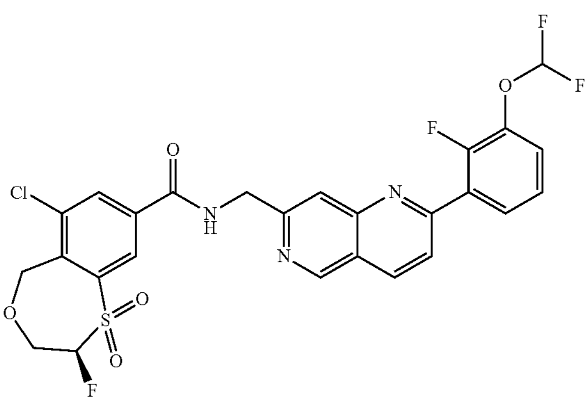 [SMILES: O=C(NCc1cc2nc(-c3cccc(OC(F)F)c3F)ccc2cn1)c1cc(Cl)c2c(c1)S(=O)(=O)[C@@H](F)COC2] |
| 445 | 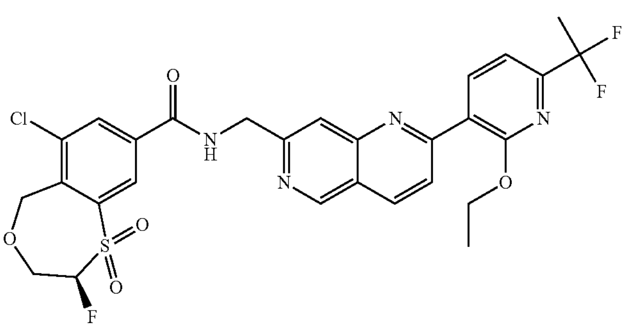 [SMILES: CCOc1nc(C(C)(F)F)ccc1-c1ccc2cnc(CNC(=O)c3cc(Cl)c4c(c3)S(=O)(=O)[C@@H](F)COC4)cc2n1] |

TABLE 1-continued

Compounds of the invention

| # | Structure |
|---|---|
| 446 | 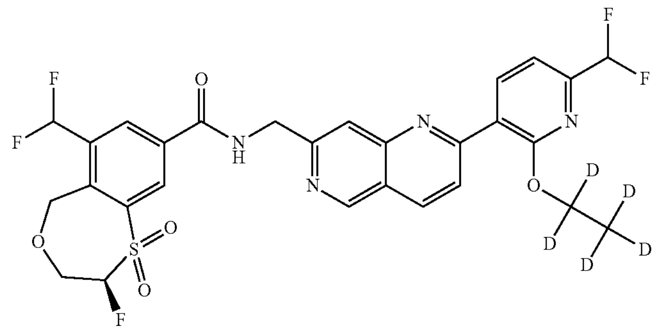 [SMILES: [2H]C([2H])([2H])C([2H])([2H])Oc1nc(C(F)F)ccc1-c1ccc2cnc(CNC(=O)c3cc(C(F)F)c4c(c3)S(=O)(=O)[C@@H](F)COC4)cc2n1] |
| 447 | 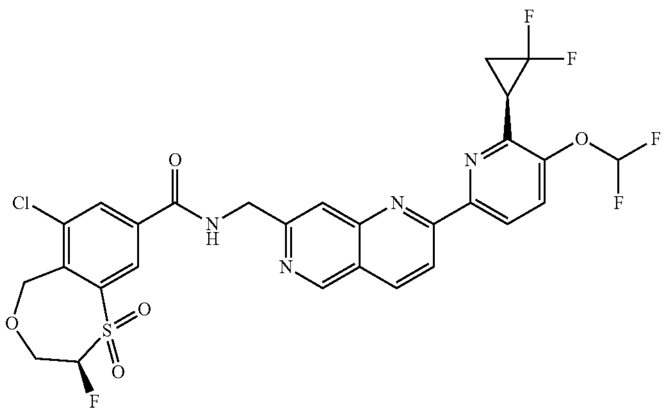 [SMILES: O=C(NCc1cc2nc(-c3ccc(OC(F)F)c([C@H]4CC4(F)F)n3)ccc2cn1)c1cc(Cl)c2c(c1)S(=O)(=O)[C@@H](F)COC2] |
| 448 | 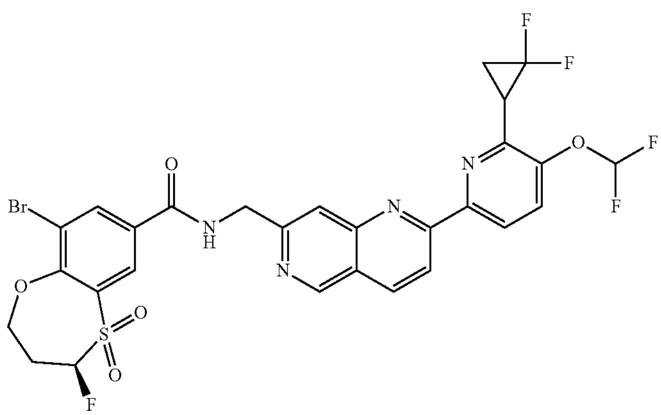 [SMILES: O=C(NCc1cc2nc(-c3ccc(OC(F)F)c(C4CC4(F)F)n3)ccc2cn1)c1cc(Br)c2c(c1)S(=O)(=O)[C@@H](F)CCO2] |
| 449 | 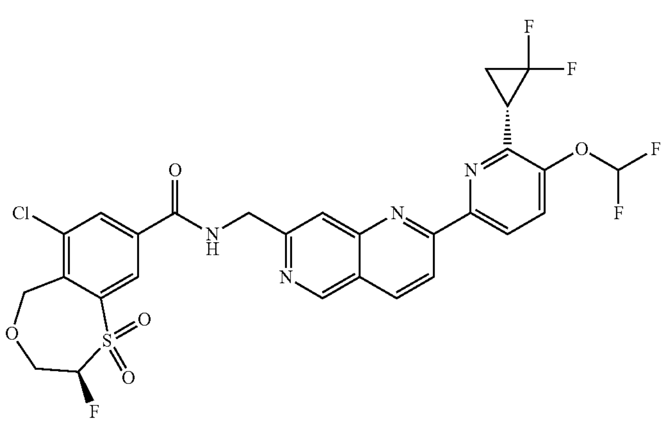 [SMILES: O=C(NCc1cc2nc(-c3ccc(OC(F)F)c([C@@H]4CC4(F)F)n3)ccc2cn1)c1cc(Cl)c2c(c1)S(=O)(=O)[C@@H](F)COC2] |

TABLE 1-continued
Compounds of the invention
| # | Structure |
|---|---|
| 450 | 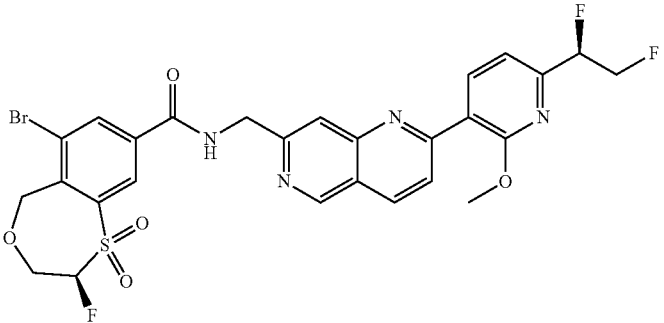 [SMILES: COc1nc([C@@H](F)CF)ccc1-c1ccc2cnc(CNC(=O)c3cc(Br)c4c(c3)S(=O)(=O)[C@@H](F)COC4)cc2n1] |
| 451 | 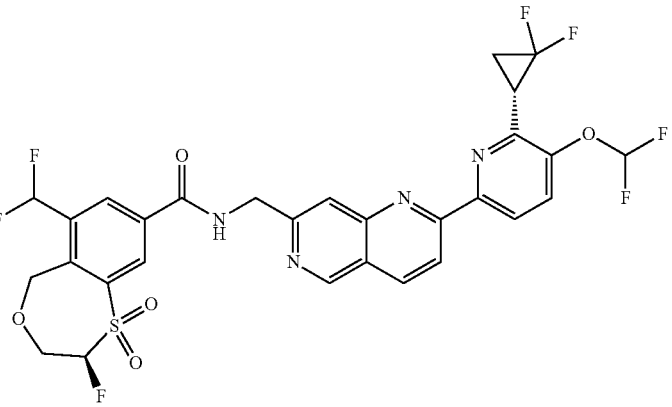 |
| 452 | 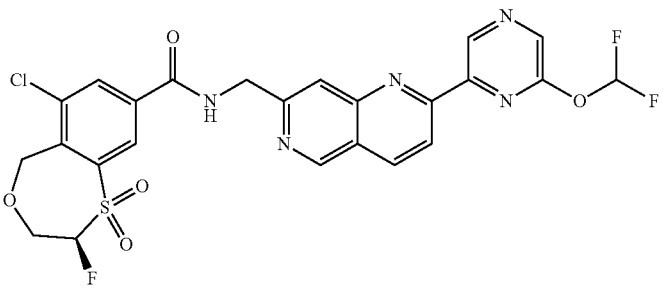 [SMILES: O=C(NCc1cc2nc(-c3cncc(OC(F)F)n3)ccc2cn1)c1cc(Cl)c2c(c1)S(=O)(=O)[C@@H](F)COC2] |
| 453 | 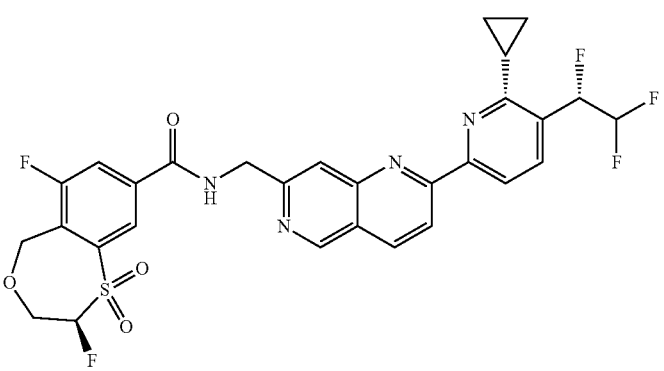 |

193 194
TABLE 1-continued
Compounds of the invention
| # | Structure |
|---|---|
| 454 | 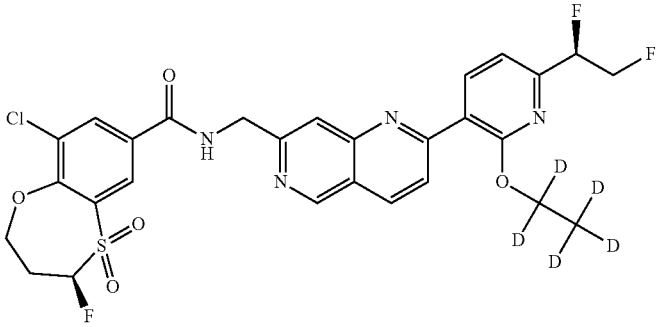 [SMILES: [2H]C([2H])([2H])C([2H])([2H])Oc1nc([C@@H](F)CF)ccc1-c1ccc2cnc(CNC(=O)c3cc(Cl)c4c(c3)S(=O)(=O)[C@@H](F)CCO4)cc2n1] |
| 455 | 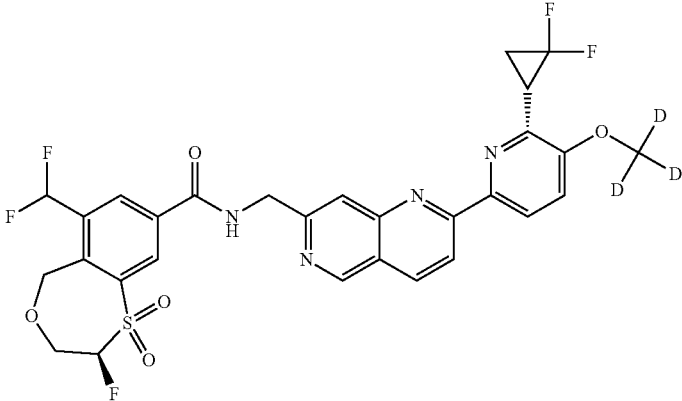 |
| 456 | 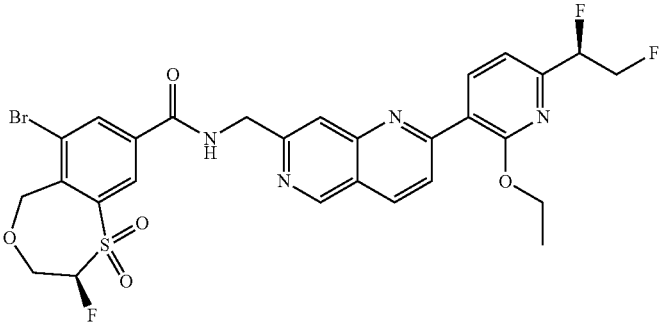 [SMILES: CCOc1nc([C@@H](F)CF)ccc1-c1ccc2cnc(CNC(=O)c3cc(Br)c4c(c3)S(=O)(=O)[C@@H](F)COC4)cc2n1] |
| 457 | 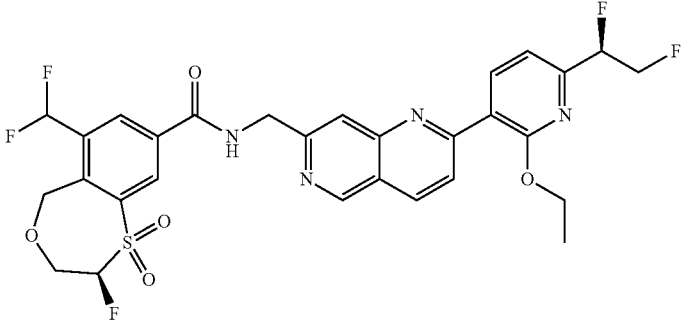 [SMILES: CCOc1nc([C@@H](F)CF)ccc1-c1ccc2cnc(CNC(=O)c3cc(C(F)F)c4c(c3)S(=O)(=O)[C@@H](F)COC4)cc2n1] |

TABLE 1-continued

Compounds of the invention

| # | Structure |
|---|---|
| 458 | 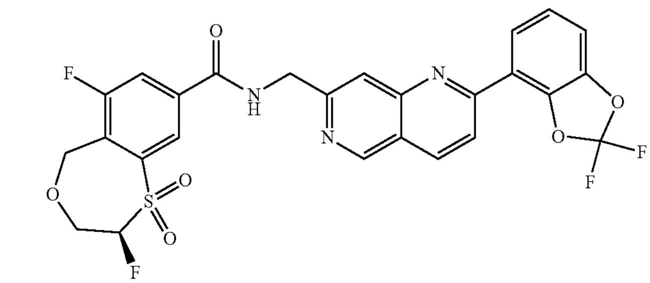 [SMILES: O=C(NCc1cc2nc(-c3cccc4c3OC(F)(F)O4)ccc2cn1)c1cc(F)c2c(c1)S(=O)(=O)[C@@H](F)COC2] |
| 459 | 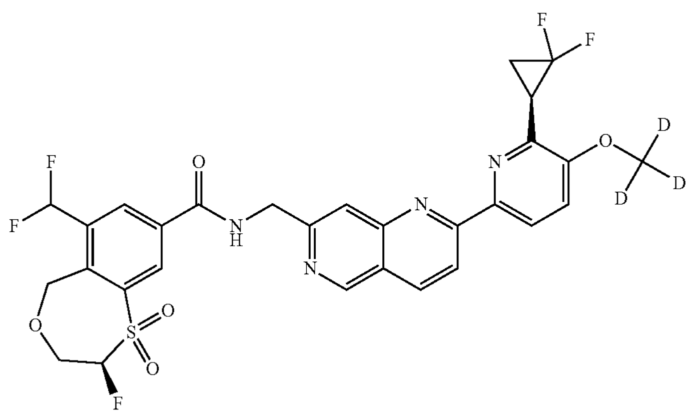 [SMILES: [2H]C([2H])([2H])Oc1ccc(-c2ccc3cnc(CNC(=O)c4cc(C(F)F)c5c(c4)S(=O)(=O)[C@@H](F)COC5)cc3n2)nc1[C@H]1CC1(F)F] |
| 460 | 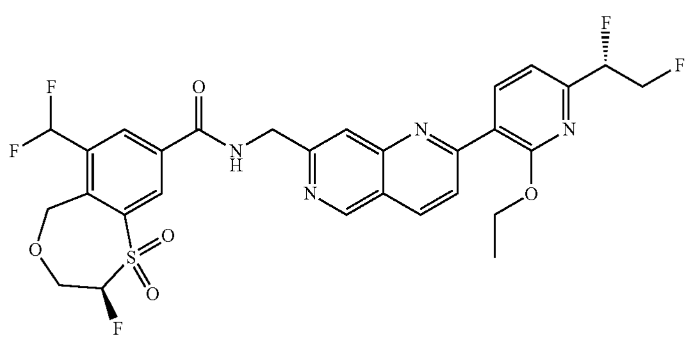 [SMILES: CCOc1nc([C@H](F)CF)ccc1-c1ccc2cnc(CNC(=O)c3cc(C(F)F)c4c(c3)S(=O)(=O)[C@@H](F)COC4)cc2n1] |
| 461 | 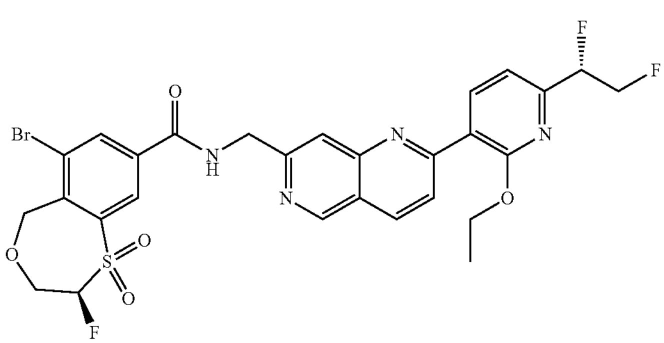 [SMILES: CCOc1nc([C@H](F)CF)ccc1-c1ccc2cnc(CNC(=O)c3cc(Br)c4c(c3)S(=O)(=O)[C@@H](F)COC4)cc2n1] |

TABLE 1-continued
Compounds of the invention
| # | Structure |
|---|---|
| 462 | 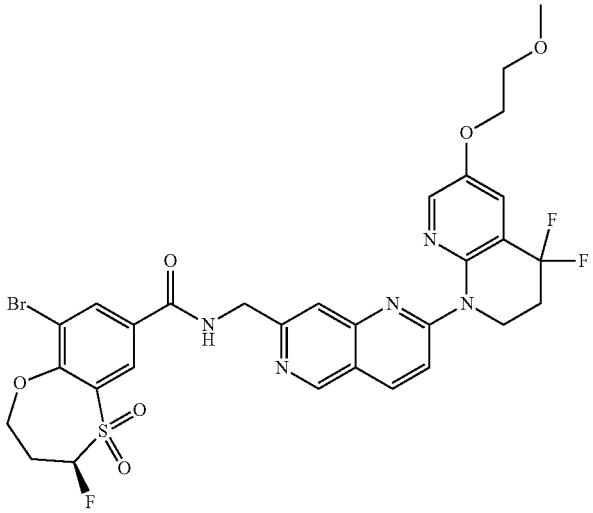 [SMILES: COCCOc1cnc2c(c1)C(F)(F)CCN2c1ccc2cnc(CNC(=O)c3cc(Br)c4c(c3)S(=O)(=O)[C@@H](F)CCO4)cc2n1] |
| 463 | 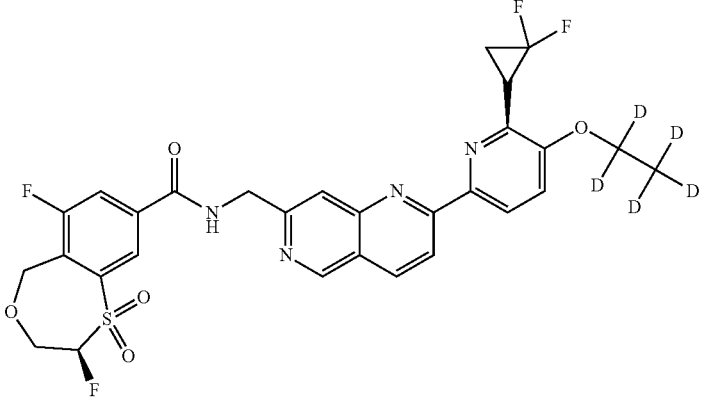 |
| 464 | 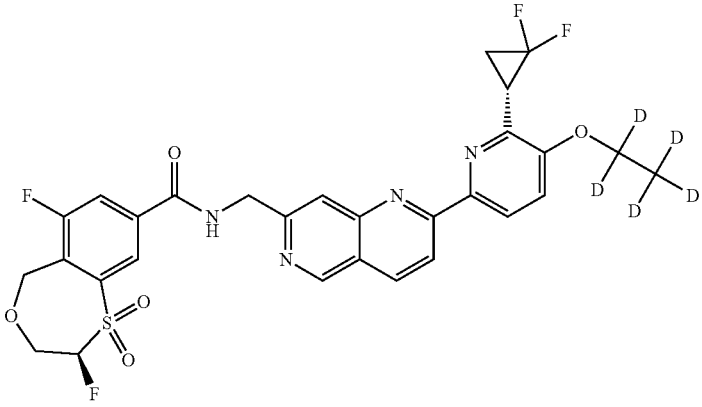 [SMILES: [2H]C([2H])([2H])C([2H])([2H])Oc1ccc(-c2ccc3cnc(CNC(=O)c4cc(F)c5c(c4)S(=O)(=O)[C@@H](F)COC5)cc3n2)nc1[C@@H]1CC1(F)F] |

TABLE 1-continued

Compounds of the invention

| # | Structure |
|---|-----------|
| 465 | 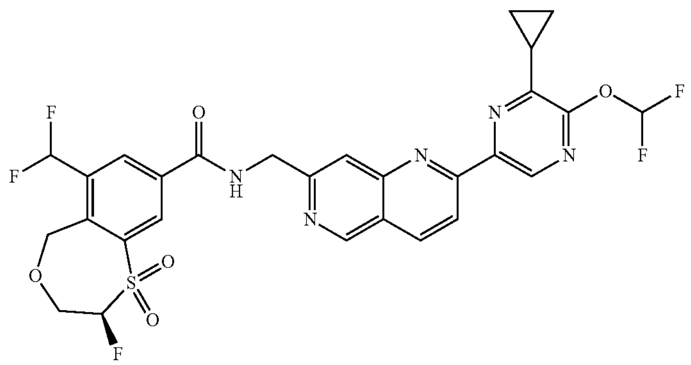 [SMILES: O=C(NCc1cc2nc(-c3cnc(OC(F)F)c(C4CC4)n3)ccc2cn1)c1cc(C(F)F)c2c(c1)S(=O)(=O)[C@@H](F)COC2] |
| 466 | 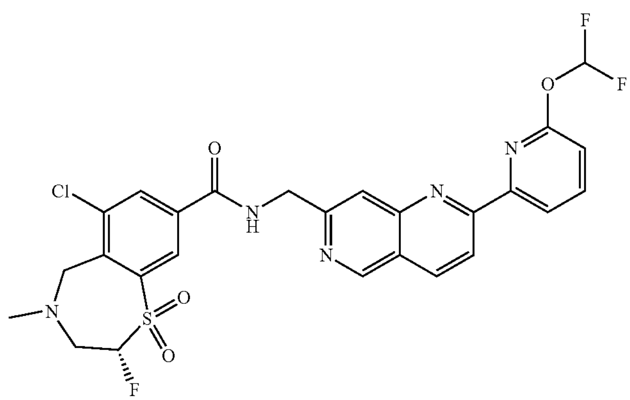 [SMILES: CN1Cc2c(Cl)cc(C(=O)NCc3cc4nc(-c5cccc(OC(F)F)n5)ccc4cn3)cc2S(=O)(=O)[C@H](F)C1] |
| 467 | 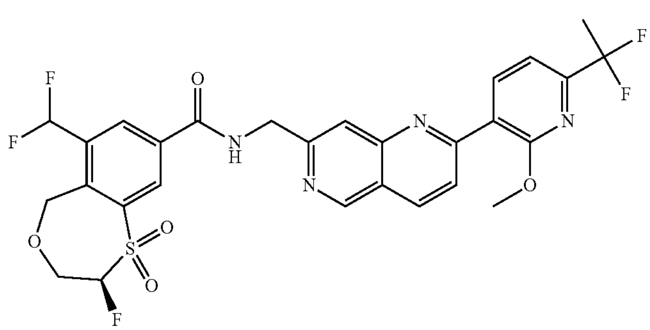 [SMILES: COc1nc(C(C)(F)F)ccc1-c1ccc2cnc(CNC(=O)c3cc(C(F)F)c4c(c3)S(=O)(=O)[C@@H](F)COC4)cc2n1] |
| 468 | 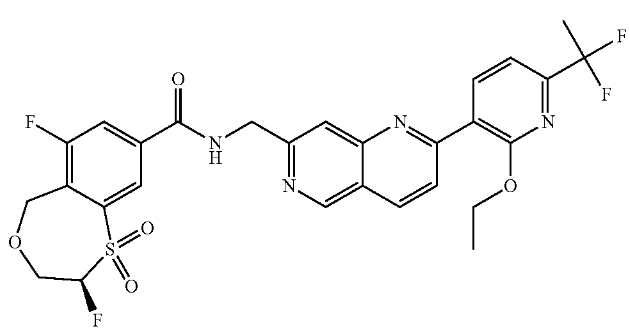 [SMILES: CCOc1nc(C(C)(F)F)ccc1-c1ccc2cnc(CNC(=O)c3cc(F)c4c(c3)S(=O)(=O)[C@@H](F)COC4)cc2n1] |

TABLE 1-continued
Compounds of the invention
| # | Structure |
|---|---|
| 469 | 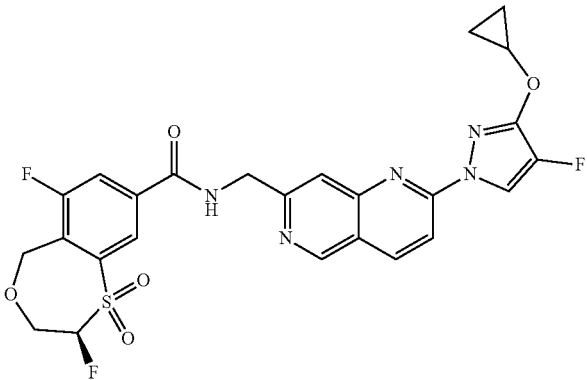 [SMILES: O=C(NCc1cc2nc(-n3cc(F)c(OC4CC4)n3)ccc2cn1)c1cc(F)c2c(c1)S(=O)(=O)[C@@H](F)COC2] |
| 470 | 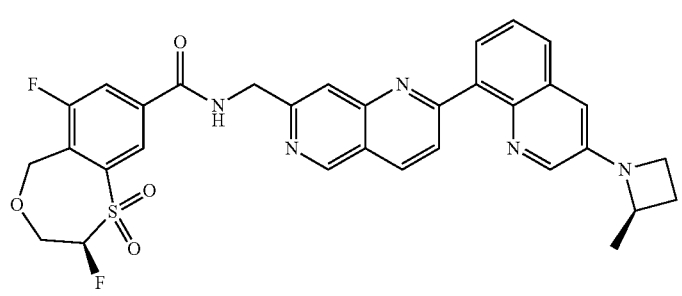 [SMILES: C[C@@H]1CCN1c1cnc2c(-c3ccc4cnc(CNC(=O)c5cc(F)c6c(c5)S(=O)(=O)[C@@H](F)COC6)cc4n3)cccc2c1] |
| 471 | 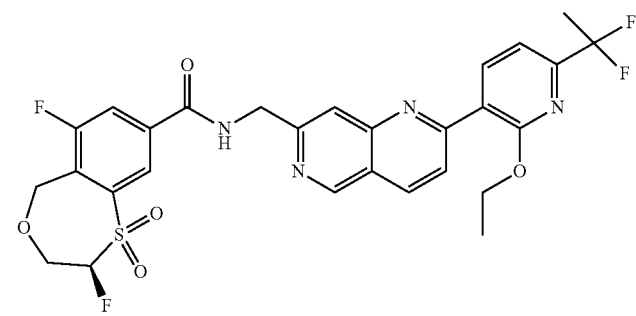 [SMILES: CCOc1nc(C(C)(F)F)ccc1-c1ccc2cnc(CNC(=O)c3cc(F)c4c(c3)S(=O)(=O)[C@@H](F)COC4)cc2n1] |
| 472 | 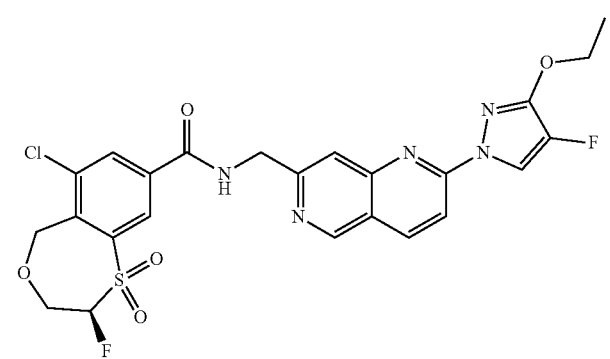 [SMILES: CCOc1nn(-c2ccc3cnc(CNC(=O)c4cc(Cl)c5c(c4)S(=O)(=O)[C@@H](F)COC5)cc3n2)cc1F] |

TABLE 1-continued
Compounds of the invention
| # | Structure |
|---|---|
| 473 | 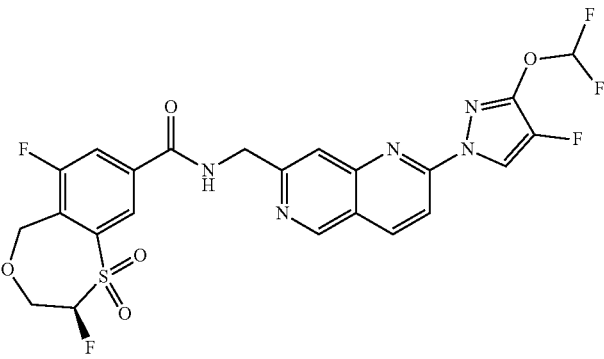 [SMILES: O=C(NCc1cc2nc(-n3cc(F)c(OC(F)F)n3)ccc2cn1)c1cc(F)c2c(c1)S(=O)(=O)[C@@H](F)COC2] |
| 474 | 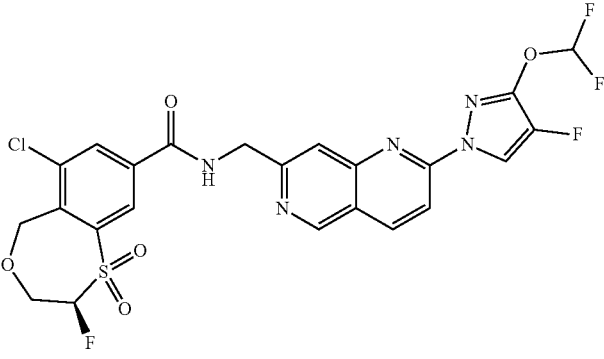 [SMILES: O=C(NCc1cc2nc(-n3cc(F)c(OC(F)F)n3)ccc2cn1)c1cc(Cl)c2c(c1)S(=O)(=O)[C@@H](F)COC2] |
| 475 | 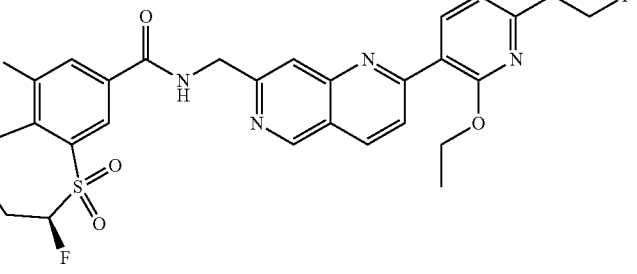 |
| 476 | 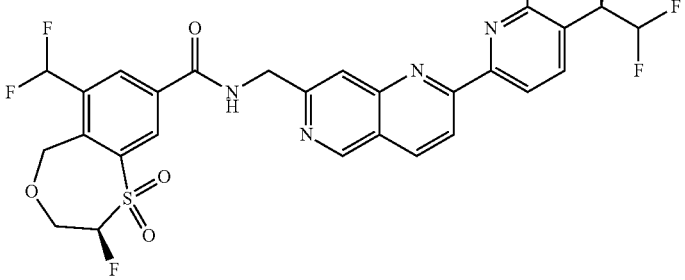 |

TABLE 1-continued

Compounds of the invention

| # | Structure |
|---|---|
| 477 | 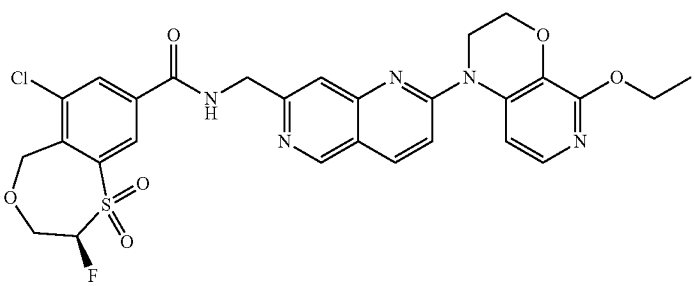 [SMILES: CCOc1nccc2c1OCCN2c1ccc2cnc(CNC(=O)c3cc(Cl)c4c(c3)S(=O)(=O)[C@@H](F)COC4)cc2n1] |
| 478 | 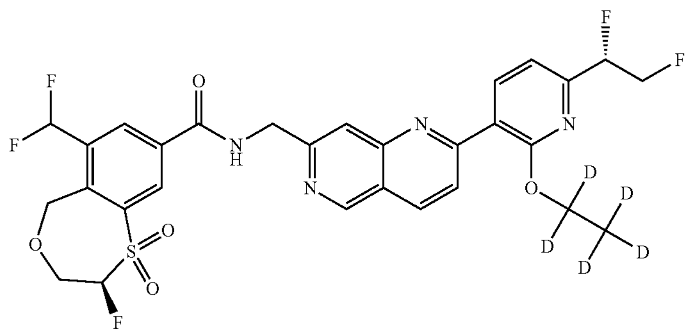 [SMILES: [2H]C([2H])([2H])C([2H])([2H])Oc1nc([C@H](F)CF)ccc1-c1ccc2cnc(CNC(=O)c3cc(C(F)F)c4c(c3)S(=O)(=O)[C@@H](F)COC4)cc2n1] |
| 479 | 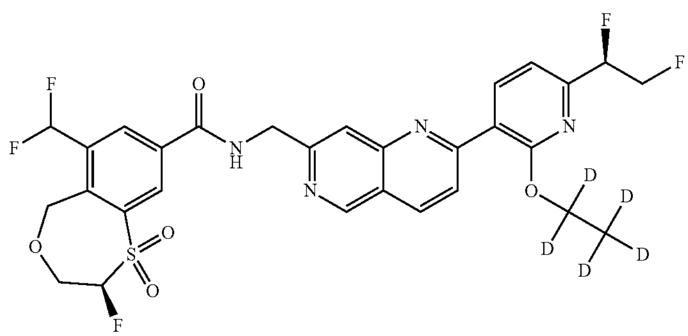 [SMILES: [2H]C([2H])([2H])C([2H])([2H])Oc1nc([C@@H](F)CF)ccc1-c1ccc2cnc(CNC(=O)c3cc(C(F)F)c4c(c3)S(=O)(=O)[C@@H](F)COC4)cc2n1] |
| 480 | 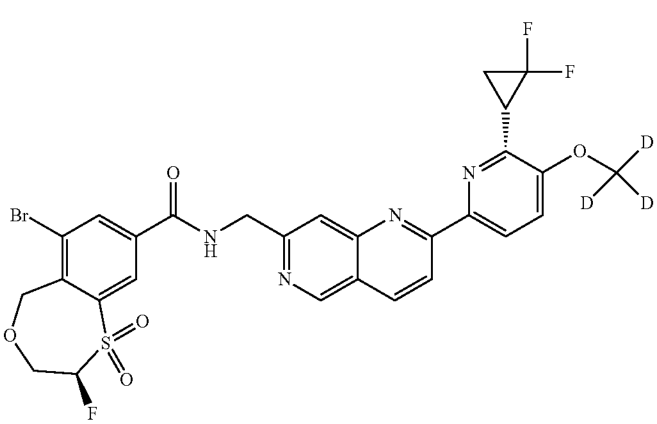 |

TABLE 1-continued
Compounds of the invention
| # | Structure |
|---|---|
| 481 | 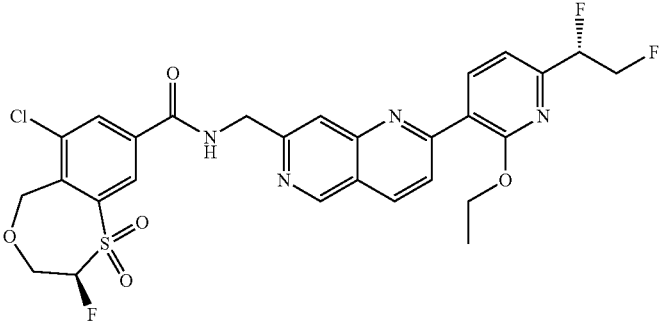 |
| 482 | 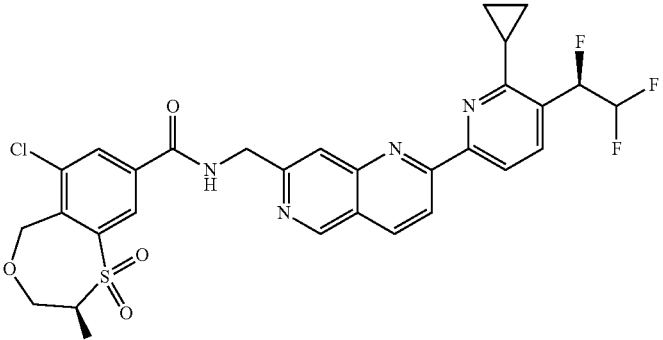 |
| 483 | 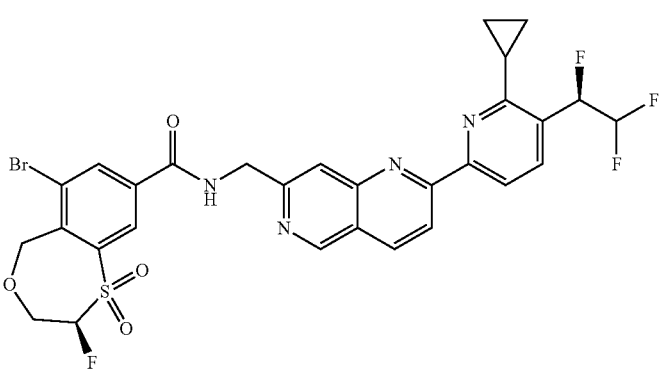 [SMILES: O=C(NCc1cc2nc(-c3ccc([C@@H](F)C(F)F)c(C4CC4)n3)ccc2cn1)c1cc(Br)c2c(c1)S(=O)(=O)[C@@H](F)COC2] |
| 484 | 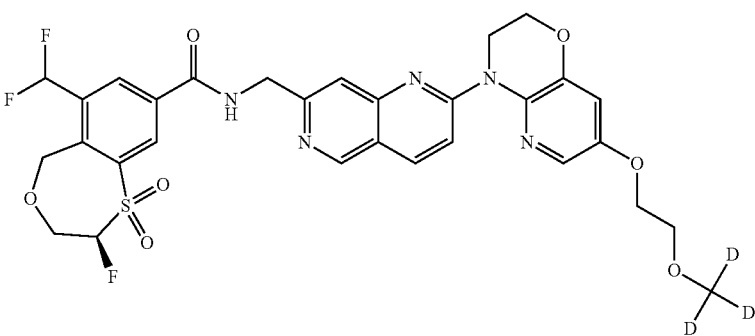 [SMILES: [2H]C([2H])([2H])OCCOc1cnc2c(c1)OCCN2c1ccc2cnc(CNC(=O)c3cc(C(F)F)c4c(c3)S(=O)(=O)[C@@H](F)COC4)cc2n1] |

TABLE 1-continued

Compounds of the invention

| # | Structure |
|---|-----------|
| 485 | 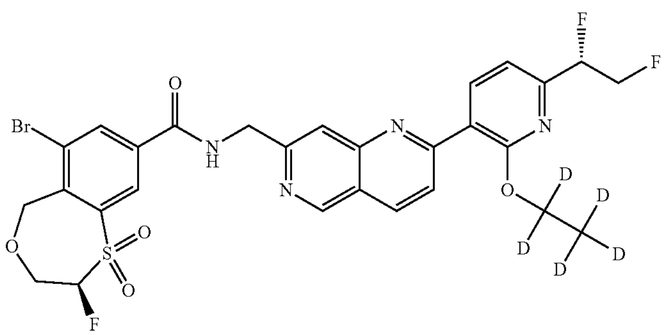 [SMILES: [2H]C([2H])([2H])C([2H])([2H])Oc1nc([C@H](F)CF)ccc1-c1ccc2cnc(CNC(=O)c3cc(Br)c4c(c3)S(=O)(=O)[C@@H](F)COC4)cc2n1] |
| 486 | 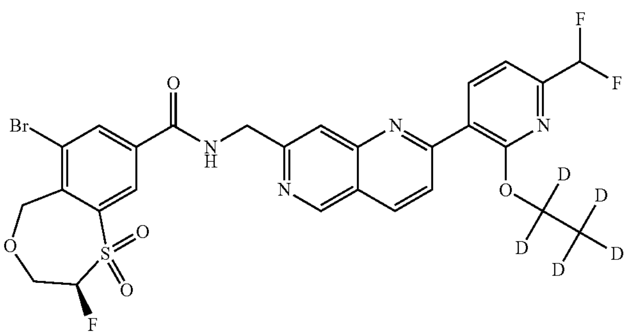 |
| 487 | 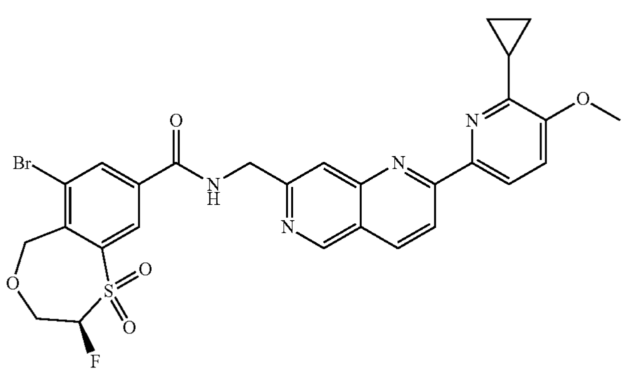 [SMILES: COc1ccc(-c2ccc3cnc(CNC(=O)c4cc(Br)c5c(c4)S(=O)(=O)[C@@H](F)COC5)cc3n2)nc1C1CC1] |
| 488 | 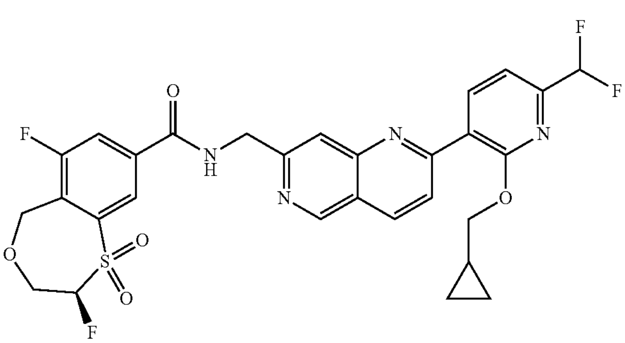 [SMILES: O=C(NCc1cc2nc(-c3ccc(C(F)F)nc3OCC3CC3)ccc2cn1)c1cc(F)c2c(c1)S(=O)(=O)[C@@H](F)COC2] |

TABLE 1-continued

Compounds of the invention

| # | Structure |
|---|---|
| 489 | 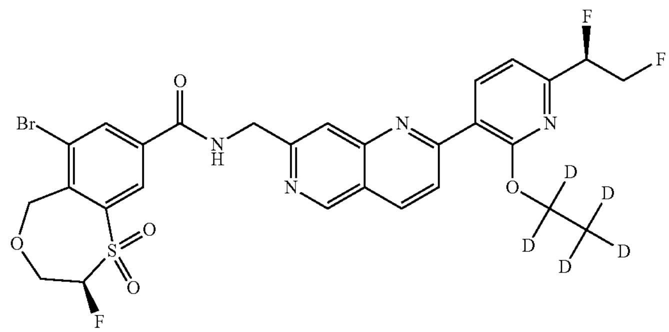 [SMILES: [2H]C([2H])([2H])C([2H])([2H])Oc1nc([C@@H](F)CF)ccc1-c1ccc2cnc(CNC(=O)c3cc(Br)c4c(c3)S(=O)(=O)[C@@H](F)COC4)cc2n1] |
| 490 | 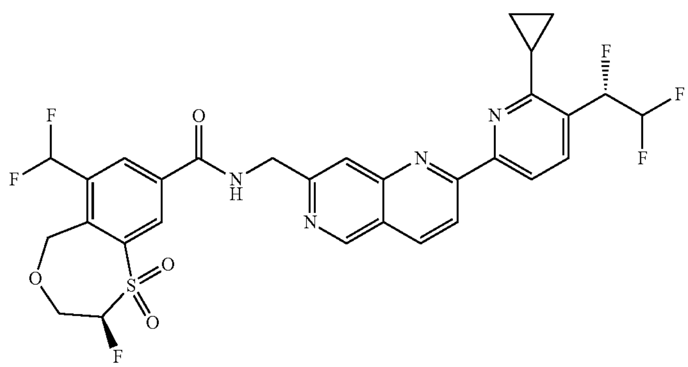 [SMILES: O=C(NCc1cc2nc(-c3ccc([C@H](F)C(F)F)c(C4CC4)n3)ccc2cn1)c1cc(C(F)F)c2c(c1)S(=O)(=O)[C@@H](F)COC2] |
| 491 | 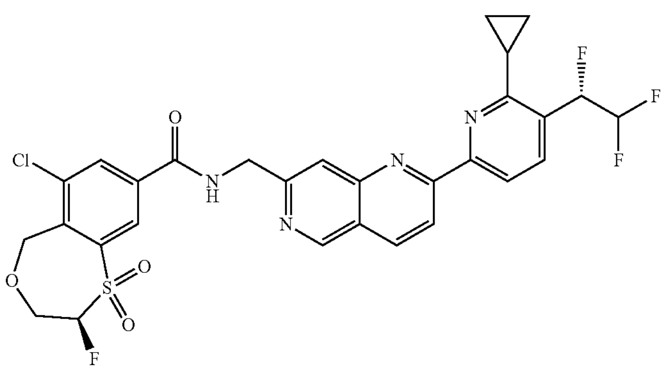 [SMILES: O=C(NCc1cc2nc(-c3ccc([C@H](F)C(F)F)c(C4CC4)n3)ccc2cn1)c1cc(Cl)c2c(c1)S(=O)(=O)[C@@H](F)COC2] |
| 492 | 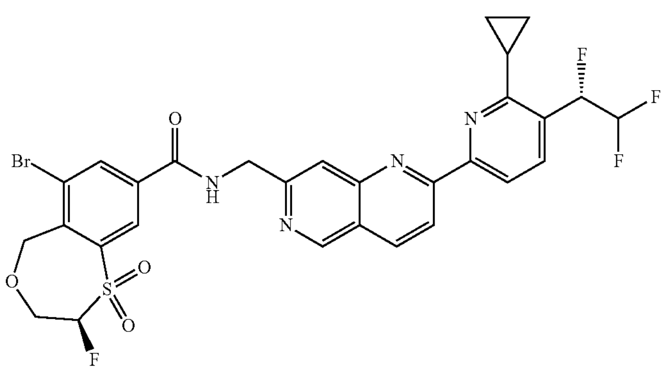 [SMILES: O=C(NCc1cc2nc(-c3ccc([C@H](F)C(F)F)c(C4CC4)n3)ccc2cn1)c1cc(Br)c2c(c1)S(=O)(=O)[C@@H](F)COC2] |

TABLE 1-continued

Compounds of the invention

| # | Structure |
|---|---|
| 493 | 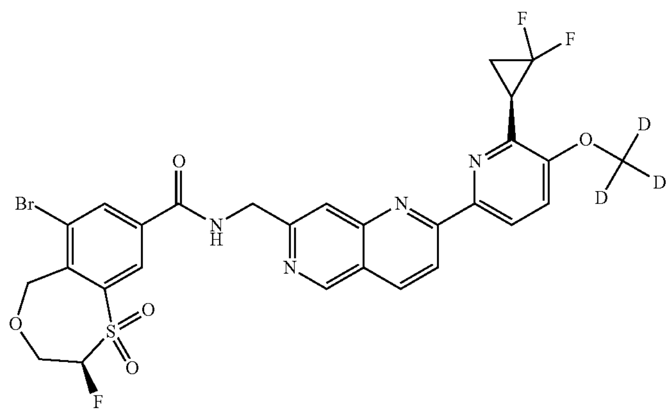 [SMILES: [2H]C([2H])([2H])Oc1ccc(-c2ccc3cnc(CNC(=O)c4cc(Br)c5c(c4)S(=O)(=O)[C@@H](F)COC5)cc3n2)nc1[C@H]1CC1(F)F] |
| 494 | 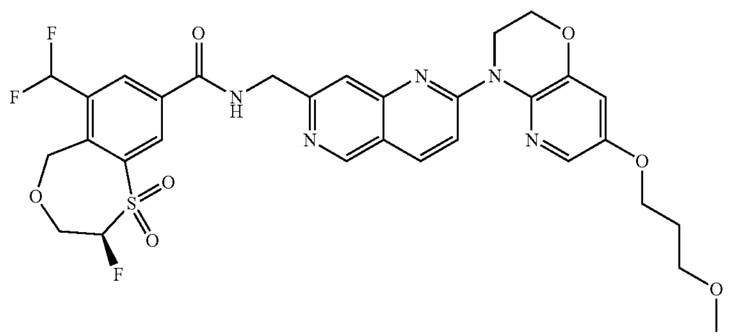 [SMILES: COCCCOc1cnc2c(c1)OCCN2c1ccc2cnc(CNC(=O)c3cc(C(F)F)c4c(c3)S(=O)(=O)[C@@H](F)COC4)cc2n1] |
| 495 | 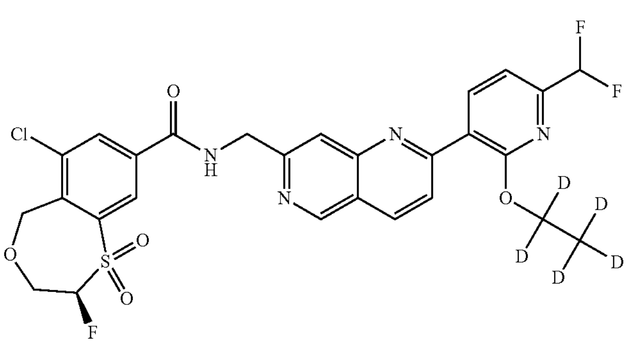 [SMILES: [2H]C([2H])([2H])C([2H])([2H])Oc1nc(C(F)F)ccc1-c1ccc2cnc(CNC(=O)c3cc(Cl)c4c(c3)S(=O)(=O)[C@@H](F)COC4)cc2n1] |
| 496 | 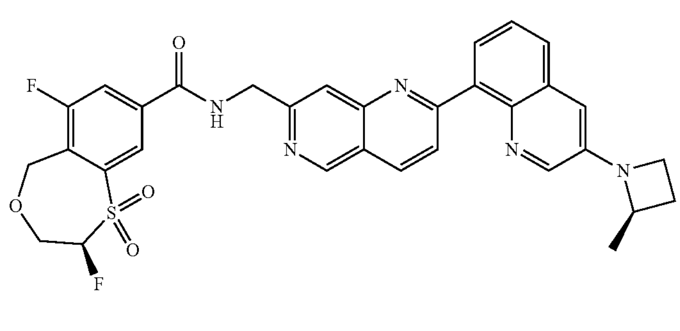 [SMILES: C[C@@H]1CCN1c1cnc2c(-c3ccc4cnc(CNC(=O)c5cc(F)c6c(c5)S(=O)(=O)[C@@H](F)COC6)cc4n3)cccc2c1] |

TABLE 1-continued

Compounds of the invention

| # | Structure |
|---|---|
| 497 | 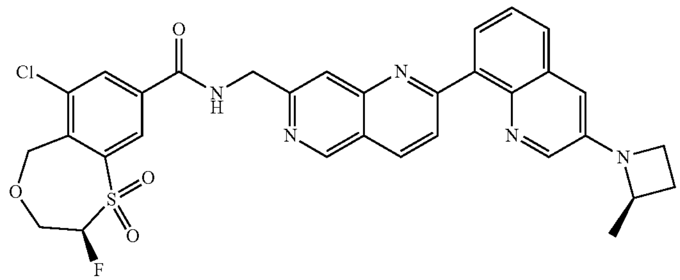 [SMILES: C[C@@H]1CCN1c1cnc2c(-c3ccc4cnc(CNC(=O)c5cc(Cl)c6c(c5)S(=O)(=O)[C@@H](F)COC6)cc4n3)cccc2c1] |
| 498 | 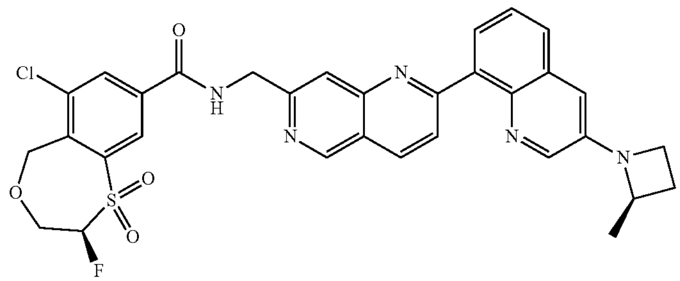 [SMILES: C[C@@H]1CCN1c1cnc2c(-c3ccc4cnc(CNC(=O)c5cc(Cl)c6c(c5)S(=O)(=O)[C@@H](F)COC6)cc4n3)cccc2c1] |
| 499 | 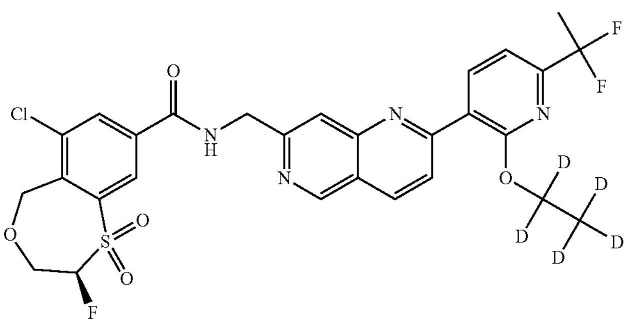 [SMILES: [2H]C([2H])([2H])C([2H])([2H])Oc1nc(C(C)(F)F)ccc1-c1ccc2cnc(CNC(=O)c3cc(Cl)c4c(c3)S(=O)(=O)[C@@H](F)COC4)cc2n1] |
| 500 | 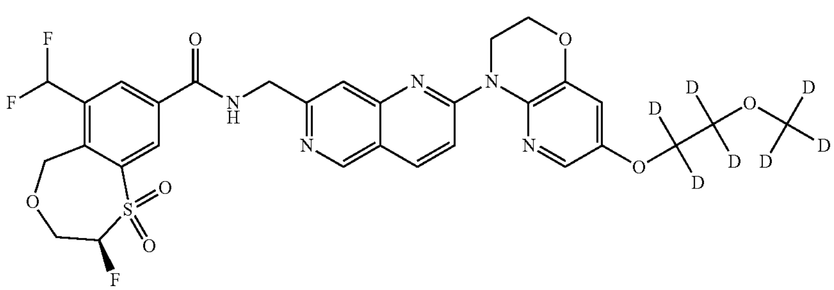 [SMILES: [2H]C([2H])([2H])OC([2H])([2H])C([2H])([2H])Oc1cnc2c(c1)OCCN2c1ccc2cnc(CNC(=O)c3cc(C(F)F)c4c(c3)S(=O)(=O)[C@@H](F)COC4)cc2n1] |
| 501 | 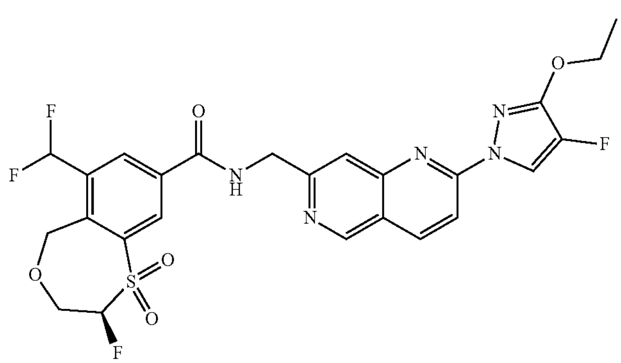 [SMILES: CCOc1nn(-c2ccc3cnc(CNC(=O)c4cc(C(F)F)c5c(c4)S(=O)(=O)[C@@H](F)COC5)cc3n2)cc1F] |

TABLE 1-continued

Compounds of the invention

| # | Structure |
|---|---|
| 502 | 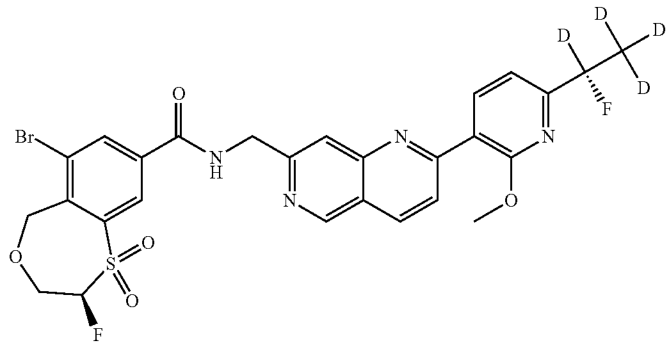 [SMILES: [2H]C([2H])([2H])[C@@]([2H])(F)c1ccc(-c2ccc3cnc(CNC(=O)c4cc(Br)c5c(c4)S(=O)(=O)[C@@H](F)COC5)cc3n2)c(OC)n1] |
| 503 | 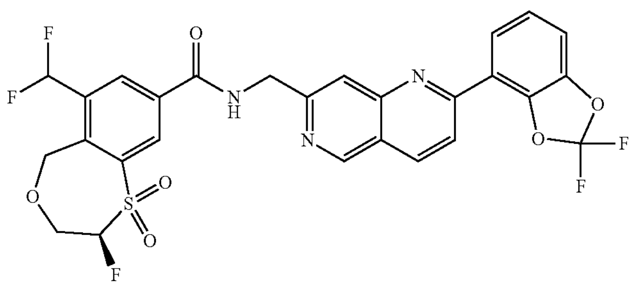 [SMILES: O=C(NCc1cc2nc(-c3cccc4c3OC(F)(F)O4)ccc2cn1)c1cc(C(F)F)c2c(c1)S(=O)(=O)[C@@H](F)COC2] |
| 504 | 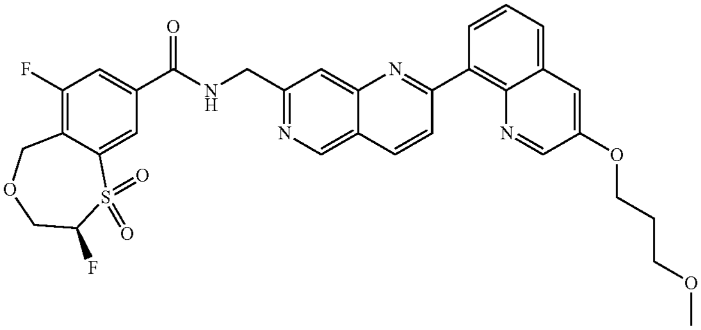 [SMILES: COCCCOc1cnc2c(-c3ccc4cnc(CNC(=O)c5cc(F)c6c(c5)S(=O)(=O)[C@@H](F)COC6)cc4n3)cccc2c1] |
| 505 | 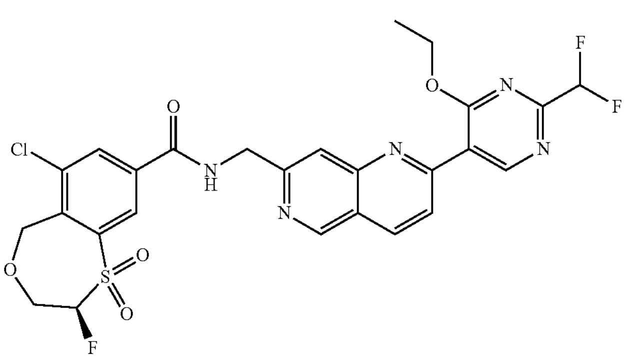 [SMILES: CCOc1nc(C(F)F)ncc1-c1ccc2cnc(CNC(=O)c3cc(Cl)c4c(c3)S(=O)(=O)[C@@H](F)COC4)cc2n1] |

TABLE 1-continued
Compounds of the invention
| # | Structure |
|---|---|
| 506 | 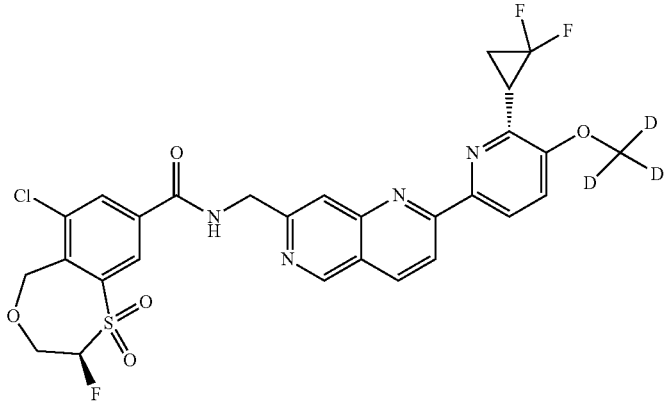 |
| 507 | 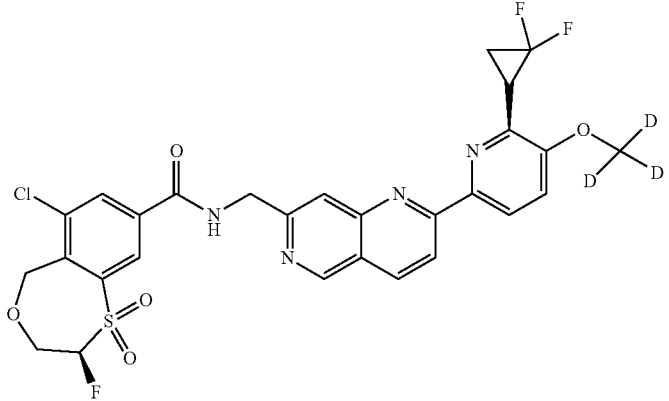 |
| 508 | 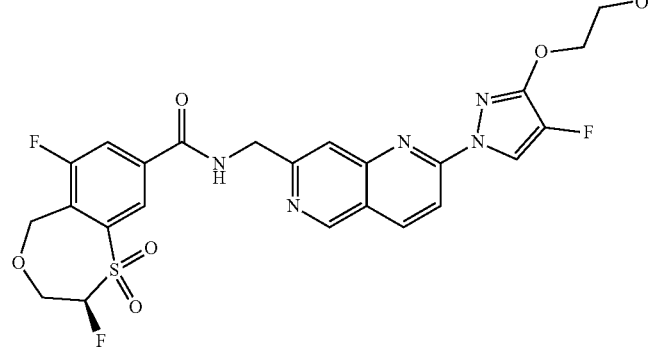 |
| 509 | 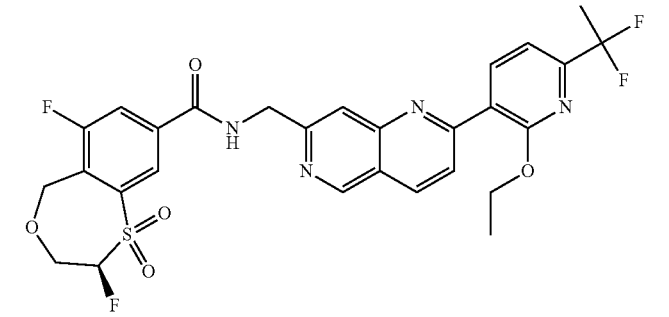 [SMILES: CCOc1nc(C(C)(F)F)ccc1-c1ccc2cnc(CNC(=O)c3cc(F)c4c(c3)S(=O)(=O)[C@@H](F)COC4)cc2n1] |

US 12,139,487 B2
221                                                                                           222
TABLE 1-continued
Compounds of the invention
| # | Structure |
|---|-----------|
| 510 | 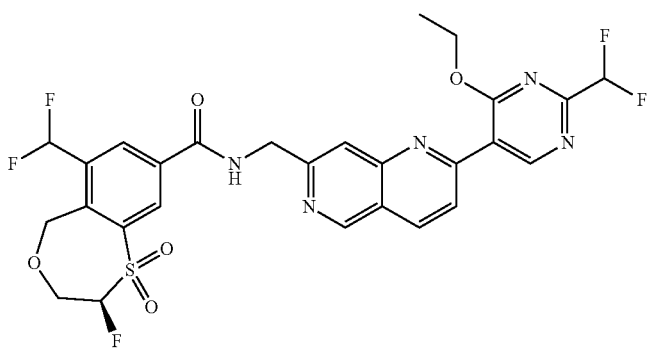 [SMILES: CCOc1nc(C(F)F)ncc1-c1ccc2cnc(CNC(=O)c3cc(C(F)F)c4c(c3)S(=O)(=O)[C@@H](F)COC4)cc2n1] |
| 511 | 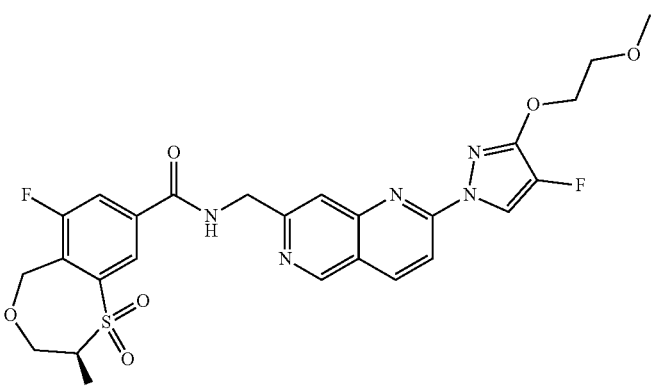 |
| 512 | 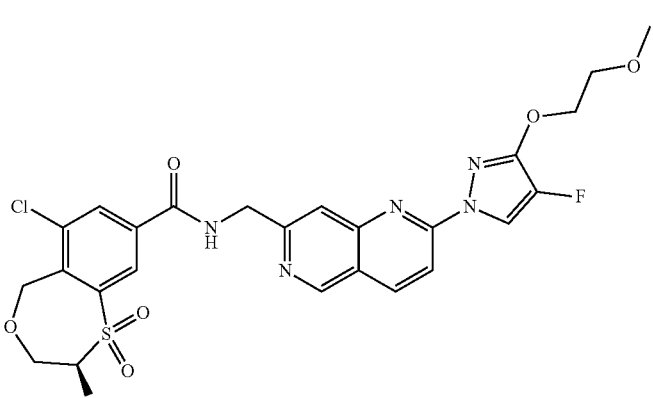 |
| 513 | 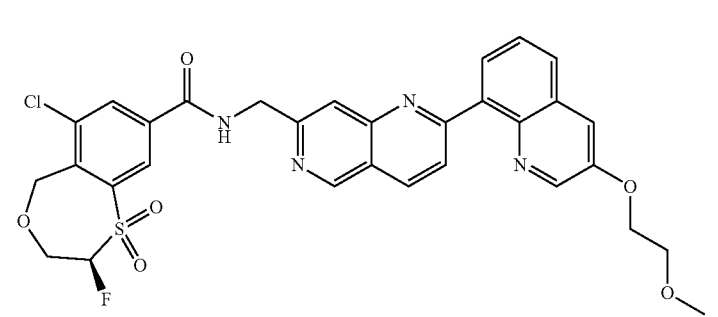 [SMILES: COCCOc1cnc2c(-c3ccc4cnc(CNC(=O)c5cc(Cl)c6c(c5)S(=O)(=O)[C@@H](F)COC6)cc4n3)cccc2c1] |

TABLE 1-continued
Compounds of the invention
| # | Structure |
|---|---|
| 514 | 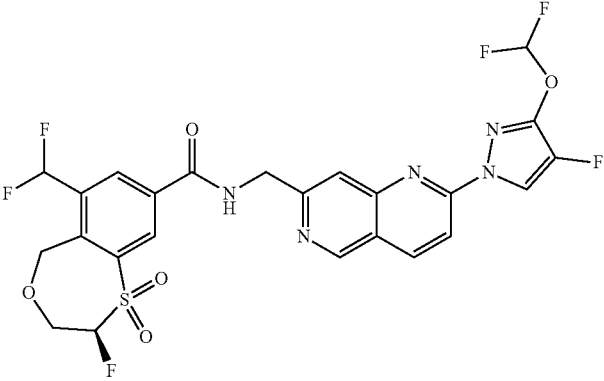 [SMILES: O=C(NCc1cc2nc(-n3cc(F)c(OC(F)F)n3)ccc2cn1)c1cc(C(F)F)c2c(c1)S(=O)(=O)[C@@H](F)COC2] |
| 515 | 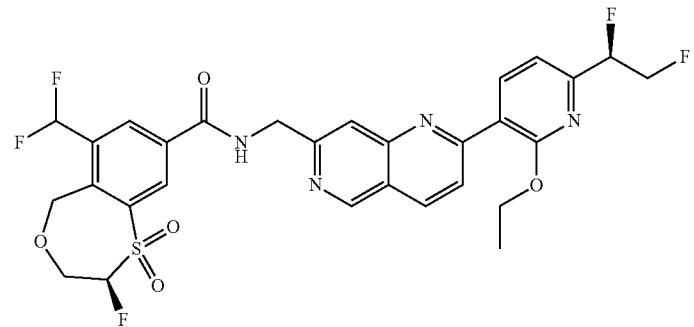 |
| 516 | 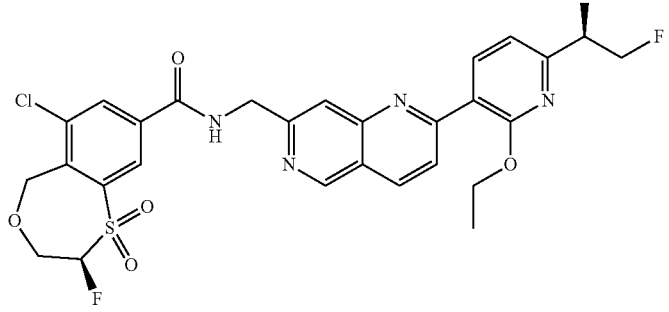 |
| 517 | 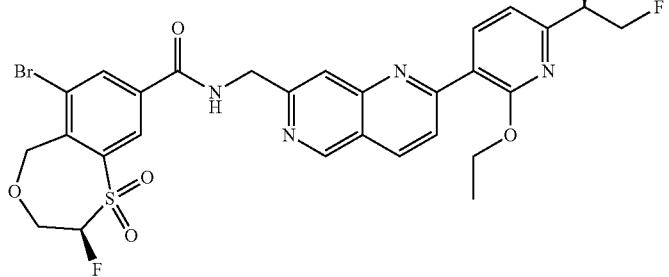 |

TABLE 1-continued
Compounds of the invention
| # | Structure |
|---|---|
| 518 | 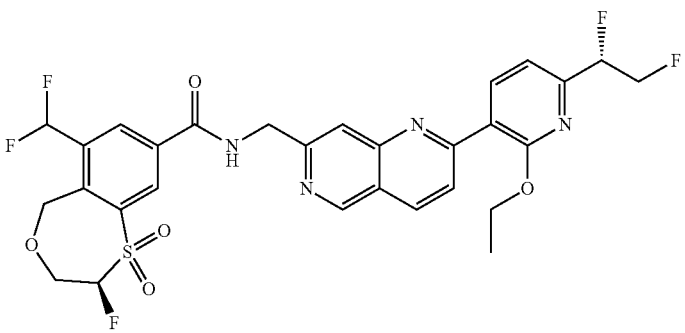 [SMILES: CCOc1nc([C@H](F)CF)ccc1-c1ccc2cnc(CNC(=O)c3cc(C(F)F)c4c(c3)S(=O)(=O)[C@@H](F)COC4)cc2n1] |
| 519 | 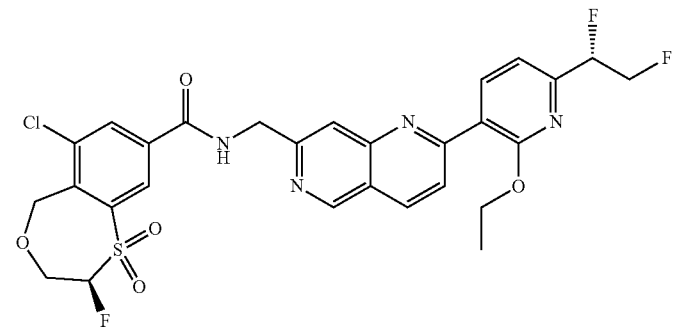 |
| 520 | 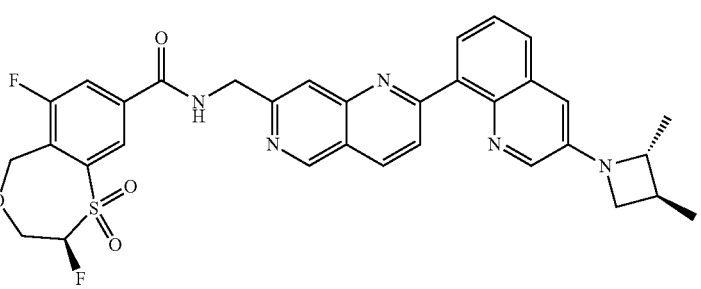 |
| 521 | 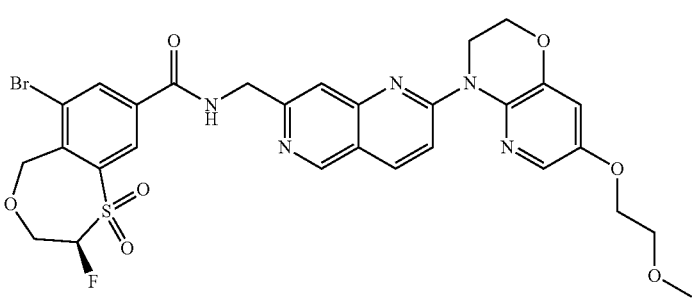 [SMILES: COCCOc1cnc2c(c1)OCCN2c1ccc2cnc(CNC(=O)c3cc(Br)c4c(c3)S(=O)(=O)[C@@H](F)COC4)cc2n1] |

TABLE 1-continued

Compounds of the invention

| # | Structure |
|---|---|
| 522 | 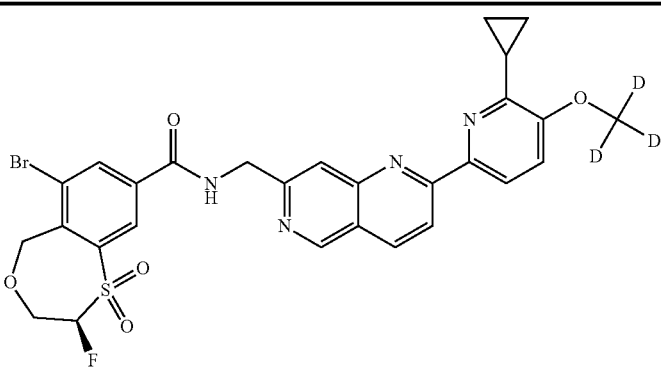 |
| 523 | 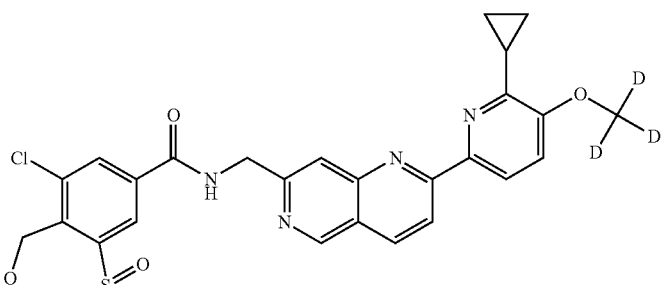 |

In some embodiments, the compound has a ratio of BRG1 $IC_{50}$ to BRM $IC_{50}$ of at least 5. In some embodiments, the compound has a ratio of BRG1 $IC_{50}$ to BRM $IC_{50}$ of at least 7. In some embodiments, the compound has a ratio of BRG1 $IC_{50}$ to BRM $IC_{50}$ of at least 10. In some embodiments, the compound has a ratio of BRG1 $IC_{50}$ to BRM $IC_{50}$ of at least 15. In some embodiments, the compound has a ratio of BRG1 $IC_{50}$ to BRM $IC_{50}$ of at least 20. In some embodiments, the compound has a ratio of BRG1 $IC_{50}$ to BRM $IC_{50}$ of at least 25. In some embodiments, the compound has a ratio of BRG1 $IC_{50}$ to BRM $IC_{50}$ of at least 30.

In another aspect, the invention features a pharmaceutical composition including any one of the above compounds and a pharmaceutically acceptable excipient.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds or a pharmaceutical composition thereof.

In some embodiments, the BAF complex-related disorder is cancer.

In a further aspect, the invention features a method of inhibiting BRM, the method involving contacting a cell with an effective amount of any of the foregoing compounds or a pharmaceutical composition thereof. In some embodiments, the cell is a cancer cell.

In another aspect, the invention features a method of inhibiting BRG1, the method involving contacting the cell with an effective amount of any of the foregoing compounds or a pharmaceutical composition thereof. In some embodiments, the cell is a cancer cell.

In a further aspect, the invention features a method of inhibiting BRM and BRG1, the method involving contacting the cell with an effective amount of any of the foregoing compounds or a pharmaceutical composition thereof. In some embodiments, the cell is a cancer cell.

In another aspect, the invention features a method of treating a disorder related to a BRG1 loss of function mutation in a subject in need thereof, the method involving administering to the subject an effective amount of any of the foregoing compounds or a pharmaceutical composition thereof.

In some embodiments, the disorder related to a BRG1 loss of function mutation is cancer.

In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds or a pharmaceutical composition thereof. In some embodiments, the cell is a cancer cell.

In a further aspect, the invention features a method of treating cancer in a subject in need thereof, the method including administering to the subject an effective amount of any of the foregoing compounds or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inhibitors, alimta, abraxane, Adriamycin®, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In some embodiments of any of the foregoing methods, the cancer has or has been determined to have BRG1 mutations. In some embodiments of any of the foregoing methods, the BRG1 mutations are homozygous. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation. In some embodiments of any of the foregoing methods, the BRG1 mutation is in the ATPase catalytic domain of the protein. In some embodiments of any of the foregoing methods, the BRG1 mutation is a deletion at the C-terminus of BRG1.

In another aspect, the disclosure provides a method treating a disorder related to BAF (e.g., cancer or viral infections) in a subject in need thereof. This method includes contacting a cell with an effective amount of any of the foregoing compounds, or pharmaceutically acceptable salts thereof, or any of the foregoing pharmaceutical compositions. In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae fam-ily (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference. In some embodiments, the effective amount of the compound that reduces the level and/or activity of BRM by at least 90% (e.g., 91%, 92%, 93%, 94%, 95%, 96%, 97%, 98%, or 99%).

In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of a compound of the invention is an amount effective to inhibit metastatic colonization of the cancer to the liver.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a MITF translocation. In some embodiments the cancer harbors an EZH2 mutation. In some embodiments the cancer harbors a SUZ12 mutation. In some embodiments the cancer harbors an EED mutation.

In some embodiments of any of the foregoing methods, the method further includes administering to the subject or contacting the cell with an anticancer therapy, e.g., a chemotherapeutic or cytotoxic agent, immunotherapy, surgery, radiotherapy, thermotherapy, or photocoagulation, or a combination thereof. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor, or a combination thereof.

In some embodiments of any of the foregoing methods, the compound of the invention is used in combination with another anti-cancer therapy used for the treatment of uveal melanoma such as surgery, a MEK inhibitor, and/or a PKC inhibitor. For example, in some embodiments, the method further includes performing surgery prior to, subsequent to, or at the same time as administration of the compound of the invention. In some embodiments, the method further includes administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

In an aspect, the invention provides a compound disclosed herein, or a pharmaceutically acceptable salt thereof, or a pharmaceutical composition disclosed herein, for use in therapy.

In an aspect, the invention provides a compound disclosed herein, or a pharmaceutically acceptable salt thereof, or a pharmaceutical composition disclosed herein, for use in decreasing the activity of a BAF complex in a cell.

In some embodiments, the BAF complex is in a cancer cell.

In an aspect, the invention provides a compound disclosed herein, or a pharmaceutically acceptable salt thereof, or a pharmaceutical composition disclosed herein, for use in treating a BAF complex-related disorder.

In some embodiments, the BAF complex-related disorder is cancer or a viral infection.

In an aspect, the invention provides a compound disclosed herein, or a pharmaceutically acceptable salt thereof, or a pharmaceutical composition disclosed herein, for use in inhibiting BRM in a cell.

In some embodiments, the cell is a cancer cell.

In an aspect, the invention provides a compound disclosed herein, or a pharmaceutically acceptable salt thereof, or a pharmaceutical composition disclosed herein, for use in treating a disorder related to a BRG1 loss of function mutation.

In some embodiments, the disorder related to a BRG1 loss of function mutation is cancer.

In an aspect, the invention provides a compound disclosed herein, or a pharmaceutically acceptable salt thereof, or a pharmaceutical composition disclosed herein, for use in inducing apoptosis in a cell.

In some embodiments, the cell is a cancer cell.

In an aspect, the invention provides a compound disclosed herein, or a pharmaceutically acceptable salt thereof, or a pharmaceutical composition disclosed herein, for use in treating cancer.

In some embodiments, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments, the cancer is non-small cell lung cancer. In some embodiments, the cancer is soft tissue sarcoma.

In an aspect, the invention provides a compound disclosed herein, or a pharmaceutically acceptable salt thereof, or a pharmaceutical composition disclosed herein, for use in treating a cancer selected from the group consisting of melanoma, prostate cancer, breast cancer, bone cancer, renal cell carcinoma, and a hematologic cancer.

In an aspect, the invention provides a compound disclosed herein, or a pharmaceutically acceptable salt thereof, or a pharmaceutical composition disclosed herein, for use in reducing tumor growth of a cancer selected from the group consisting of melanoma, prostate cancer, breast cancer, bone cancer, renal cell carcinoma, and a hematologic cancer.

In an aspect, the invention provides a compound disclosed herein, or a pharmaceutically acceptable salt thereof, or a pharmaceutical composition disclosed herein, for use in suppressing metastatic progression of a cancer selected from the group consisting of melanoma, prostate cancer, breast cancer, bone cancer, renal cell carcinoma, and a hematologic cancer.

In an aspect, the invention provides a compound disclosed herein, or a pharmaceutically acceptable salt thereof, or a pharmaceutical composition disclosed herein, for use in suppressing metastatic colonization of a cancer selected from the group consisting of melanoma, prostate cancer, breast cancer, bone cancer, renal cell carcinoma, and a hematologic cancer.

In an aspect, the invention provides a compound disclosed herein, or a pharmaceutically acceptable salt thereof, or a pharmaceutical composition disclosed herein, for use in reducing the level and/or activity of BRM in a cancer cell selected from the group consisting of melanoma, prostate cancer, breast cancer, bone cancer, renal cell carcinoma, and hematologic cancer.

In some embodiments, the cell is in a subject.

In some embodiments, the cancer is metastatic.

In some embodiments, the use further includes an anticancer therapy.

In some embodiments, the anticancer therapy is a chemotherapeutic or cytotoxic agent, immunotherapy, surgery, radiotherapy, thermotherapy, or photocoagulation.

In some embodiments, the anticancer therapy is surgery.

In some embodiments, the anticancer therapy is a chemotherapeutic or cytotoxic agent.

In some embodiments, the chemotherapeutic or cytotoxic agent is an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor.

In some embodiments, the one or more chemotherapeutic or cytotoxic agent is dacarbazine, temozolomide, cisplatin, treosulfan, fotemustine, IMCgp100, a CTLA-4 inhibitor, a PD-1 inhibitor, a PD-L1 inhibitor, a mitogen-activated protein kinase inhibitor, and/or a protein kinase C inhibitor.

In some embodiments, the anticancer therapy and the compound of any one of claims 1 to 93 or a pharmaceutical composition of claim 94 are administered within 28 days of each other and each in an amount that together are effective to treat the subject.

In some embodiments, the subject or cancer has and/or has been identified as having a BRG1 loss of function mutation.

In some embodiments, the cancer has failed to respond to or progressed after administration of one or more chemotherapeutic or cytotoxic agents.

In some embodiments, the cancer is resistant to, or predicted to be resistant to one or more chemotherapeutic agents.

In some embodiments, the one or more chemotherapeutic or cytotoxic agents is dacarbazine, temozolomide, cisplatin, treosulfan, fotemustine, IMCgp100, a CTLA-4 inhibitor, a PD-1 inhibitor, a PD-L1 inhibitor, a mitogen-activated protein kinase inhibitor, and/or a protein kinase C inhibitor.

In some embodiments, the cancer is melanoma. In some embodiments, the melanoma is uveal melanoma. In some embodiments, the melanoma is mucosal melanoma. In some embodiments, the melanoma is cutaneous melanoma. In some embodiments, the cancer is a hematologic cancer. In some embodiments, the hematologic cancer is multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia, diffuse large cell lymphoma, or non-Hodgkin's lymphoma. In some embodiments, the cancer is prostate cancer. In some embodiments, the cancer is breast cancer. In some embodiments, the breast cancer is an ER positive breast cancer, an ER negative breast cancer, triple positive breast cancer, or triple negative breast cancer. In some embodiments, the cancer is bone cancer. In some embodiments, the bone cancer is Ewing's sarcoma. In some embodiments, the cancer is renal cell carcinoma. In some embodiments, the renal cell carcinoma is Microphthalmia Transcription Factor (MITF) family translocation renal cell carcinoma.

In an aspect, the invention provides a compound disclosed herein, or a pharmaceutically acceptable salt thereof, or a pharmaceutical composition disclosed herein, for use in treating a viral infection.

In some embodiments, the viral infection is an infection with a virus of the Retroviridae family, Hepadnaviridae family, Flaviviridae family, Adenoviridae family, Herpesviridae family, Papillomaviridae family, Parvoviridae family, Polyomaviridae family, Paramyxoviridae family, or Togaviridae family.

In an aspect, the invention provides the use of any of the foregoing compounds (e.g., a BRM/BRG1 dual inhibitor compound or a BRM-selective compound), or pharmaceutically acceptable salts thereof, or any of the foregoing pharmaceutical compositions in the manufacture of a medicament. In some embodiments, the use is as described for the methods described herein.

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups.

A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms).

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$).

The term "aryl," as used herein, refers to an aromatic mono- or polycarbocyclic radical of 6 to 12 carbon atoms having at least one aromatic ring. When polycyclic, the aryl group contains 2 or 3 rings. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Unsubstituted arylalkyl groups contain from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each are further substituted with 1, 2, 3, or 4 substituent groups, valency permitting, as defined herein for the respective groups.

The term "azido," as used herein, represents a —$N_3$ group.

The term "bridged polycycloalkyl," as used herein, refers to a bridged polycyclic group of 5 to 20 carbons, containing from 1 to 3 bridges. A bridged polycycloalkyl group may be unsubstituted or substituted as defined herein for cycloalkyl.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, and monovalent mono- di-, or tricyclic radical of 3 to 10, preferably 3 to 6 carbon atoms. The cycloalkyl group may be fully saturated or contain 1 or more double or triple bonds, provided that no ring is aromatic. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group is further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group is further substituted with 1, 2, 3, or 4 substituent groups, valency permitting, as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group is further substituted with 1, 2, 3, or 4 substituent groups, valency permitting, as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to a monocyclic, bicyclic, or tricyclic radical of 5 to 12 atoms having at least one aromatic ring and containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxazolyl, and thiazolyl.

The term "heteroarylalkyl," as used herein, represents an alkyl group substituted with a heteroaryl group. Unsubstituted heteroarylalkyl groups contain from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each are further substituted with 1, 2, 3, or 4 substituent groups, valency permitting, as defined herein for the respective groups.

The term "heteroarylcycloalkyl," as used herein, represents a cycloalkyl group substituted with a heteroaryl group. Exemplary unsubstituted heteroarylcycloalkyl groups are from 5 to 30 carbons (e.g., from 5 to 17 carbons, such as $C_2$-$C_9$ heteroaryl $C_3$-$C_8$ cycloalkyl). In some embodiments, the cycloalkyl and the heteroaryl each can be further substituted with 1, 2, 3, or 4 substituent groups as defined herein for the respective groups.

The term "heteroarylethynyl," a used herein, represents a group of formula —$R^A$—$R^B$—, where $R^A$ is heteroaryl, and $R^B$ is ethynyl. An optionally substituted heteroarylethynyl is a heteroarylethynyl, in which the heteroaryl portion is optionally substituted as defined herein for heteroaryl.

The term "heteroarylvinyl," a used herein, represents a group of formula —$R^A$—$R^B$—, where $R^A$ is heteroaryl, and $R^B$ is vinyl. An optionally substituted heteroarylvinyl is a heteroarylvinyl, in which the heteroaryl portion is optionally substituted as defined herein for heteroaryl.

The term "heterocyclyl," as used herein, refers a monocyclic, bicyclic, or tricyclic radical having 3 to 12 atoms having at least one ring containing 1, 2, 3, or 4 ring atoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Unsubstituted heterocyclylalkyl groups contain from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each are further substituted with 1, 2, 3, or 4 substituent groups as defined herein for the respective groups.

The term "hydroxyalkyl," as used herein, represents an alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "oxo," as used herein, represents a divalent oxygen atom (e.g., the structure of oxo may be shown as =O). For example, a carbonyl group is a carbon (e.g., alkyl carbon, alkenyl carbon, alkynyl carbon, heteroalkyl carbon, heteroalkenyl carbon, heteroalkynyl carbon, carbocyclyl carbon, etc.) substituted with oxo. Alternatively, sulfur may be substituted with one or two oxo groups (e.g., —SO— or —SO$_2$— within a substituted heteroalkyl, heteroalkenyl, heteroalkynyl, or heterocyclyl group).

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will be 1, 2, 3, 4, or 5 substituents present, valency permitting, unless otherwise specified. The 1 to 5 substituents are each, independently, selected from the group consisting of acyl, alkyl (e.g., unsubstituted and substituted, where the substituents include any group described herein, e.g., aryl, halo, hydroxy), alkenyl, alkynyl, aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroalkenyl, heteroalkynyl, heteroaryl, heterocyclyl, amino (e.g., NH$_2$ or mono- or dialkyl amino), azido, cyano, nitro, thiol, and oxo. Each of the substituents is unsubstituted or substituted with unsubstituted substituent(s) as defined herein for each respective group. In some embodiments, alkyl, alkenyl, alkynyl, heteroalkyl, heteroalkenyl, and heteroalkynyl are optionally substituted with 1, 2, 3, 4, or 5 substituents independently selected from the group consisting of aryl (e.g., substituted and unsubstituted phenyl), carbocyclyl (e.g., substituted and unsubstituted cycloalkyl), halo (e.g., fluoro), hydroxyl, heteroaryl, heterocyclyl, amino (e.g., NH$_2$ or mono- or dialkyl amino), azido, cyano, nitro, thiol, and oxo. Each of the substituents is unsubstituted or substituted with unsubstituted substituent(s) as defined herein for each respective group. In some embodiments, the substituents are themselves unsubstituted.

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, where such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "including" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HBRM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, µg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "inhibiting BRM" refers to blocking or reducing the level or activity of the ATPase catalytic binding domain or the bromodomain of the protein. BRM inhibition may be determined using methods known in the art, e.g., a BRM ATPase assay, a Nano DSF assay, or a BRM Luciferase cell assay.

As used herein, the term "LXS196," also known as IDE196, refers to the PKC inhibitor having the structure:

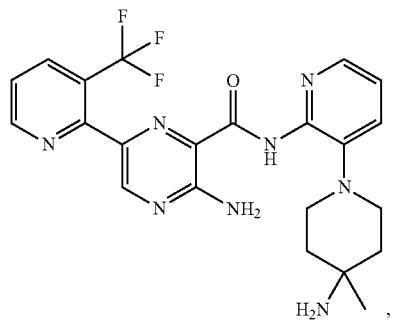 [SMILES: CC1(N)CCN(c2cccnc2NC(=O)c2nc(-c3ncccc3C(F)(F)F)cnc2N)CC1]

or a pharmaceutically acceptable salt thereof.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

As used herein, the term "pharmaceutically acceptable salt" means any pharmaceutically acceptable salt of a compound, for example, any compound of Formula I. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment and any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
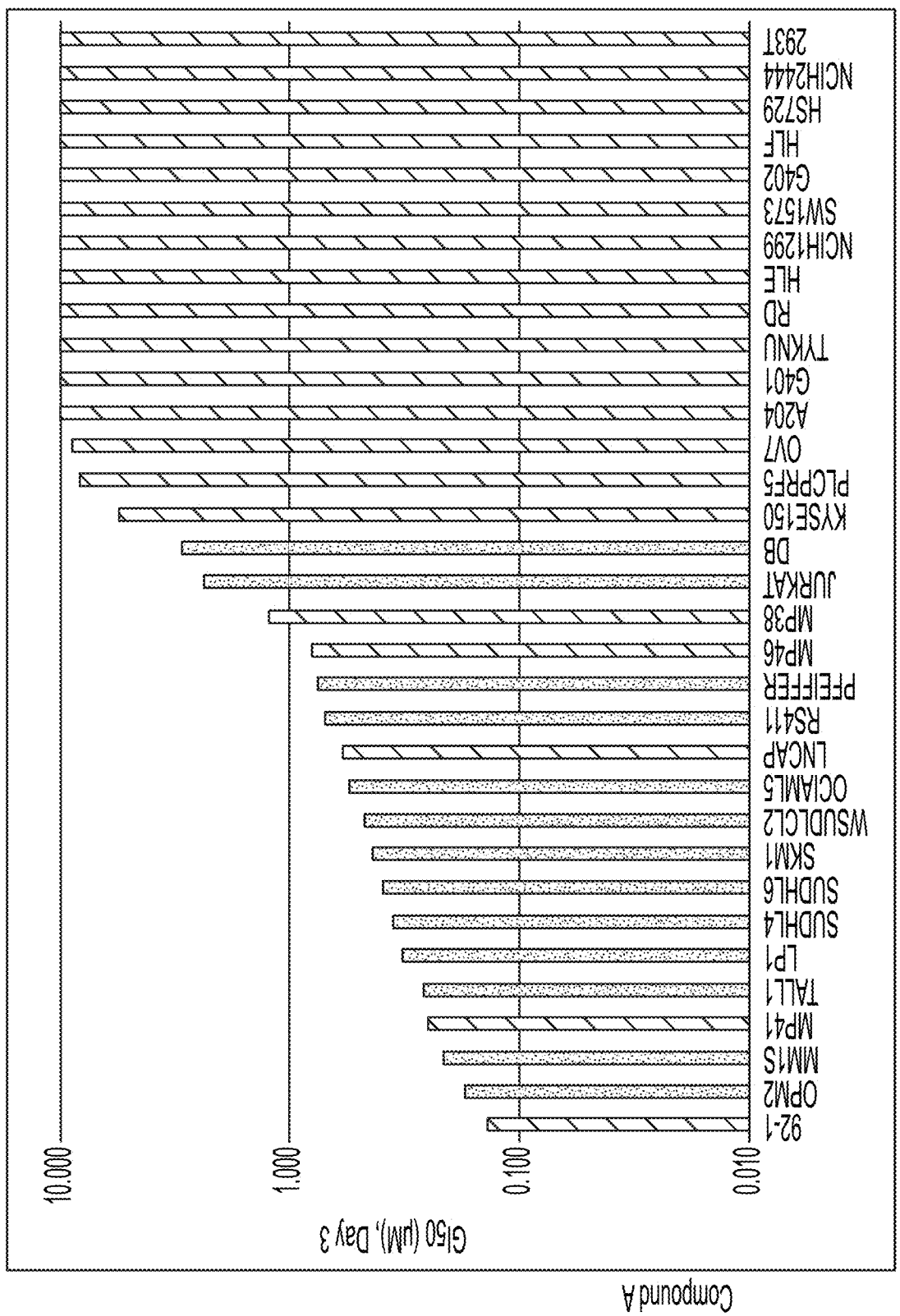
FIG. 1 is a graph illustrating inhibition of cell proliferation of several cancer cell lines by a BRG1/BRM inhibitor (Compound A).

The present disclosure features compounds useful for the inhibition of BRM and optionally BRG1. These compounds may be used to modulate the activity of a BAF complex, for example, for the treatment of a BAF-related disorder, such as cancer (e.g., BRG1-loss of function disorders). Exemplary compounds described herein include compounds having a structure according to Formula I:

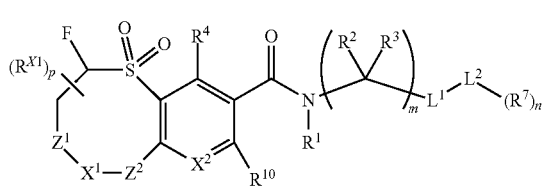

Formula I wherein
m is 0, 1, 2, or 3;
n is 0, 1, 2, 3, or 4;
p is 0, 1, 2, or 3;
$X^1$ is O, $NR^5$, or $(C(R^5)(R^6))$, and each of $Z^1$ and $Z^2$ is independently absent or $(C(R^9)_2)$ or O, provided that, if $X^1$ is O, then each of $Z^1$ and $Z^2$ is independently absent or $(C(R^9)_2)$;
$X^2$ is N or $CR^8$;
each $R^{X1}$ is independently deuterium, optionally substituted $C_1$-$C_6$ alkyl, or halo, or two geminal $R^{X1}$ groups, together with the atom to which they are attached, combine to form a carbonyl;
$L^1$ is optionally substituted 9- or 10-membered bicyclic heterocyclyl, optionally substituted 9- or 10-membered bicyclic heteroaryl, optionally substituted monocyclic 6-membered heteroarylvinyl, optionally substituted monocyclic 6-membered heteroaryl-$C_3$-$C_8$-cycloalkyl, or optionally substituted monocyclic 6-membered heteroarylethynyl;
$L^2$ is absent, optionally substituted $C_3$-$C_{10}$ cycloalkyl, optionally substituted $C_6$-$C_{10}$ aryl, optionally substituted 5- to 10-membered heteroaryl, or optionally substituted 4- to 10-membered heterocyclyl;
$R^1$ is hydrogen or optionally substituted $C_1$-$C_6$ alkyl;
each $R^2$ and each $R^3$ are independently hydrogen, optionally substituted $C_1$-$C_6$ alkyl, or optionally substituted $C_1$-$C_6$ heteroalkyl;
$R^4$ is hydrogen, halo, optionally substituted $C_1$-$C_6$ alkyl, or optionally substituted $C_3$-$C_{10}$ cycloalkyl;
$R^5$ is hydrogen, deuterium, or optionally substituted $C_1$-$C_6$ alkyl;
$R^6$ is hydrogen, deuterium, optionally substituted $C_1$-$C_6$ alkyl, or halo, and each $R^9$ is independently hydrogen, deuterium, optionally substituted $C_1$-$C_6$ alkyl, or halo; or $R^6$ and one vicinal $R^9$, together with the atoms to which they are attached combine to form optionally substituted $C_3$-$C_8$ cycloalkyl, and the remaining $R^9$ groups, if present, are independently deuterium, optionally substituted $C_1$-$C_6$ alkyl, or halo;
each $R^7$ is independently optionally substituted $C_1$-$C_6$ alkyl, optionally substituted $C_1$-$C_6$ heteroalkyl, halo, optionally substituted $C_3$-$C_{10}$ cycloalkyl, optionally substituted 5- to 10-membered heteroaryl, optionally substituted 4- to 10-membered heterocyclyl, $-N(R^{7A})_2$, or $-OR^{7A}$, wherein each $R^{7A}$ is independently H, optionally substituted $C_1$-$C_6$ alkyl, optionally substituted $C_1$-$C_6$ heteroalkyl, optionally substituted $C_3$-$C_{10}$ cycloalkyl, optionally substituted $C_6$-$C_{10}$ aryl, optionally substituted 5- to 10-membered heteroaryl, or optionally substituted 4- to 10-membered heterocyclyl, or two geminal $R^{7A}$ groups, together with the atom to which they are attached, combine to form optionally substituted 5- to 10-membered heteroaryl or optionally substituted 4- to 10-membered heterocyclyl;
$R^8$ is hydrogen, halo, cyano, optionally substituted $C_1$-$C_6$ alkyl, optionally substituted $C_2$-$C_6$ alkynyl, optionally substituted $C_1$-$C_6$ heteroalkyl, or optionally substituted $C_3$-$C_{10}$ cycloalkyl; and
$R^{10}$ is hydrogen or halo;
or a pharmaceutically acceptable salt thereof.

In some embodiments, the compound, or pharmaceutically acceptable salt thereof, has the structure of any one of compounds 1-330 in Table 1.

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine;

androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chlorambucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-I-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK1, CHK2, A2aR, B-7 family ligands, or a combination thereof.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers. A compound of the invention may also be administered parenterally. Solutions of a compound of the invention can be prepared in water suitably mixed with a surfactant. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant. The aerosol dosage forms can also take the form of a pump-atomizer. Compositions suitable for buccal or sublingual administration include tablets, lozenges, and pastilles, where the active ingredient is formulated with a carrier. Compositions for rectal administration are conveniently in the form of suppositories containing a conventional suppository base. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg. Dose ranges include, for example, between 10-1000 mg.

Alternatively, the dosage amount can be calculated using the body weight of the patient. For example, the dose of a compound, or pharmaceutical composition thereof, administered to a patient may range from 0.1-100 mg/kg.

EXAMPLES

Definitions Used in the Following Schemes and Elsewhere Herein are:
MeCN or ACN acetonitrile
AIBN azobisisobutyronitrile
Boc tert-butoxycarbonyl
t-BuOK potassium tert-butoxide
DAST diethylaminosulfur trifluoride
DCE dichloroethane
DCM dichloromethane
DCPP-2HBF$_4$ 1,3-bis(dicyclohexylphosphino)propane bis(tetrafluoroborate)
DEA N,N-diethylamine
DMP Dess-Martin periodinane
DIAD diisopropyl azodicarboxylate
DIBAL-H diisobutylaluminum hydride
DIEA or DIPEA N,N-diisopropylethylamine
DMA dimethylacetamide
DMAP 4-(dimethylamino)pyridine
DME 1,2-dimethoxyethane
DMF N,N-dimethylformamide
DMSO dimethylsulfoxide
dppf bis(diphenylphosphino)ferrocene
EDCl 1-ethyl-(3-dimethylaminopropyl)carbodiimide hydrochloride
ESI electrospray ionization
Et$_3$N or TEA triethylamine
EA ethyl acetate
EtOH ethyl alcohol
FA formic acid
FCC flash column chromatography
g grams
HATU 2-(3H-[1,2,3]triazolo[4,5-b]pyridin-3-yl)-1,1,3,3-tetramethylisouronium
HCl hydrochloric acid
HOAc acetic acid
HOBt hydroxybenzotriazole
HPLC high performance liquid chromatography
IPA isopropyl alcohol
L liter
LCMS liquid chromatography/mass spectrometry
m-CPBA 3-chloroperoxybenzoic acid
MeCN acetonitrile
MeI methyl iodide
MeOH methyl alcohol
mL milliliter
mmol millimole
mg milligrams
MHz megahertz
MS mass spectrometry
MTBE methyl tert-butyl ether
m/z mass/charge ratio
NBS N-bromosuccinimide
NIS N-iodosuccinimide
nm nanometer
NMR nuclear magnetic resonance
PE petroleum ether
PhMe toluene
ppm parts per million
rt room temperature
RT retention time
SFC supercritical fluid chromatography
SPhos Pd G3 (2-dicyclohexylphosphino-2',6'-dimethoxybiphenyl) [2-(2'-amino-1,1'-biphenyl)]palladium (II) methanesulfonate
TBS tert-butyldimethylsilyl
TBSCl tert-butyldimethylsilyl chloride
TBDMS tert-butyldimethylsilyl chloride
TFA trifluoroacetic acid
TFAA trifluoroacetic anhydride
THF tetrahydrofuran
TMSCN trimethylsilyl cyanide
TosMIC toluenesulfonylmethyl isocyanide
Ziram zinc dimethyldithiocarbamate Table 1 lists compounds of the invention prepared using methods described herein.

Materials

Unless otherwise noted, all materials were obtained from commercial suppliers and were used without further purification. All reactions involving air- or moisture-sensitive reagents were performed under a nitrogen atmosphere.

Example 1. Preparation of Compounds (2R)-2,6-difluoro-1,1-dioxo-3,5-dihydro-2H-4,1λ6-benzoxathiepine-8-carboxylic Acid

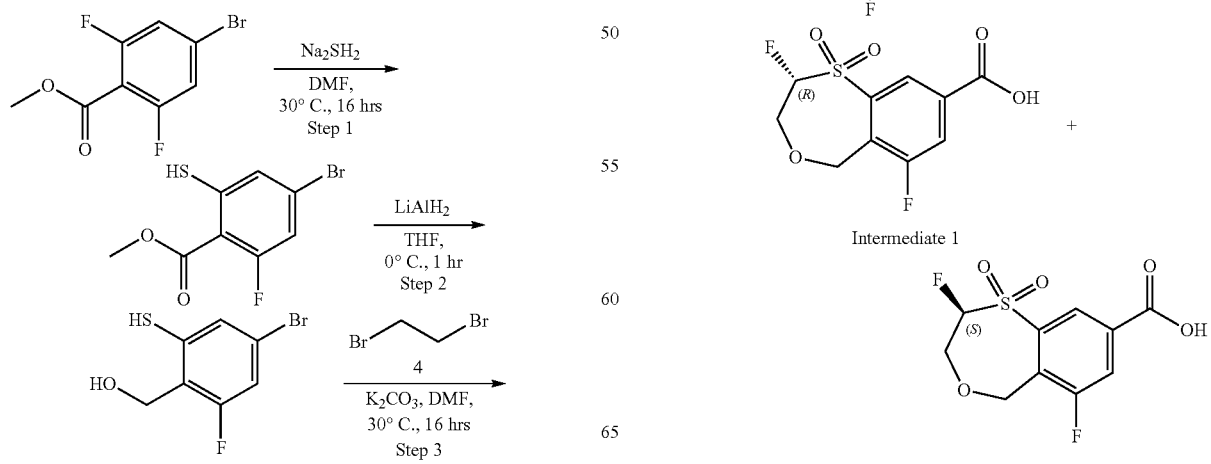

Step 1: Preparation of 2-methyl 4-bromo-2-fluoro-6-sulfanyl-benzoate

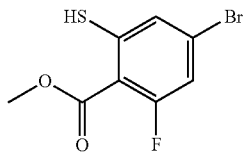

To a solution of methyl 4-bromo-2,6-difluoro-benzoate (100 g, 398.37 mmol) in DMF (1000 mL) was added Na$_2$S (34.54 g, 398.37 mmol, 90% purity), the mixture was stirred at 30° C. for 16 hrs. The reaction mixture was poured into water (1500 mL) and extracted with MTBE (1500 mL*2). The aqueous phase was adjusted to pH=2 with 1 N HCl and extracted with MTBE (1500 mL*3). The combined organic layer was washed with water (2000 mL*2) and brine (5000 mL), dried over Na$_2$SO$_4$, filtered, and concentrated to give 2-methyl 4-bromo-2-fluoro-6-sulfanyl-benzoate (105 g, crude) as yellow oil. LCMS (ESI) m/z: [Br$^{79}$M+H]$^+$=232.9

Step 2: Preparation of 3-(4-bromo-2-fluoro-6-sulfanyl-phenyl)methanol

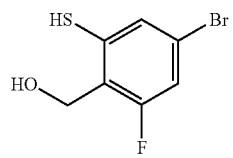

To a solution of 2-methyl 4-bromo-2-fluoro-6-sulfanyl-benzoate (105 g, 396.08 mmol) in THF (1000 mL) was added LiAlH$_4$ (15.03 g, 396.08 mmol) at 0° C. under N$_2$, the mixture was stirred at 0° C. for 1 hr. The mixture was poured into 1 N HCl (1000 mL) and extracted with EtOAc (1000 mL*2). The combined organic phase was washed with brine (2000 mL), dried over anhydrous Na$_2$SO$_4$, filtered, and concentrated under vacuum to give 3-(4-bromo-2-fluoro-6-sulfanyl-phenyl)methanol (93 g, crude) as yellow oil.

Step 3: Preparation of 5-(4-bromo-2-fluoro-6-vinylsulfanyl-phenyl)methanol

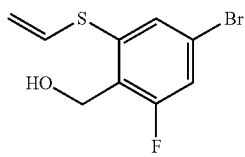

To a solution of 2-methyl 4-bromo-2-fluoro-6-sulfanyl-benzoate (93 g, 392.26 mmol) in DMF (1800 mL) was added K$_2$CO$_3$ (162.64 g, 1.18 mol) and 1,2-dibromoethane (221.07 g, 1.18 mol, 88.78 mL), the mixture was stirred at 30° C. for 16 hrs. The reaction was quenched by water (2000 mL). The mixture was extracted with ethyl acetate (2000 mL*3). The combined organic layers were dried over Na$_2$SO$_4$ and concentrated to give a residue. The residue was purified by column chromatography (SiO$_2$, Petroleum ether/Ethyl acetate=10:1-1:1), the solution was concentrated to give 5-(4-bromo-2-fluoro-6-vinylsulfanyl-phenyl)methanol (56 g, 212.83 mmol) as yellow oil. $^1$H NMR (400 MHz, CDCl$_3$) δ=7.33 (s, 1H), 7.19-7.17 (m, 1H), 6.50-6.44 (m, 1H), 5.54-5.42 (m, 2H), 4.78 (d, J=1.2 Hz, 2H), 2.13 (s, 1H) ppm

Step 4: Preparation of 4-bromo-2-fluoro-6-vinylsulfinyl-phenyl)methanol

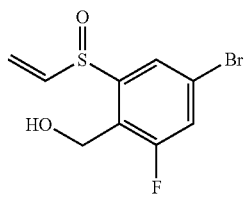

To a solution of 5-(4-bromo-2-fluoro-6-vinylsulfanyl-phenyl) methanol (10 g, 38.00 mmol) in MeOH (100 mL) and H$_2$O (100 ml) was added Oxone (11.68 g, 19.00 mmol), the mixture was stirred at 30° C. for 16 hrs. The reaction mixture was poured into water (1 L), the solution was extracted with EA (1 L*3), the combined organic layer was washed with sat·Na$_2$SO$_3$ (1 L) and brine (1 L), dried over Na$_2$SO$_4$, filtered, and concentrated to give 6-(4-bromo-2-fluoro-6-vinylsulfinyl-phenyl)methanol (10.61 g, crude) as yellow oil. LCMS (ESI) m/z: [Br$^{79}$M+H]$^+$=263.0

Step 5: Preparation of 8-bromo-6-fluoro-3,5-dihydro-2H-4,1λ4-benzoxathiepine 1-oxide

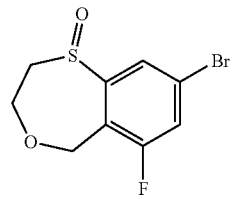 [SMILES: O=S1CCOCc2c(F)cc(Br)cc21]

To a solution of 6-(4-bromo-2-fluoro-6-vinylsulfinyl-phenyl) methanol (10.6 g, 37.98 mmol) in THF (110 mL) was added NaH (3.04 g, 75.95 mmol, 60% purity) at 0° C., then the mixture was stirred at 20° C. for 1 hr. The reaction mixture was poured into NH$_4$Cl (500 mL), the solution was extracted with EA (500 mL*3), the combined organic layer was washed with brine (1000 mL), dried over Na$_2$SO$_4$, filtered, and concentrated to give a tan residue. The residue was purified by column chromatography (SiO$_2$, Petroleum ether/Ethyl acetate=10:1-1:1), the solution was concentrated to give 8-bromo-6-fluoro-3,5-dihydro-2H-4,1λ4-benzoxathiepine 1-oxide (5.5 g, 19.70 mmol, 51.89% yield) as a white solid. $^1$H NMR (400 MHz, DMSO-d$_6$) δ=7.78-7.75 (m, 1H), 7.62 (s, 1H), 4.96 (d, J=15.2 Hz, 1H), 4.54-4.50 (m, 1H), 4.33-4.24 (m, 2H), 3.41-3.39 (m, 2H) ppm Step 6: Preparation of 8-bromo-6-fluoro-3,5-dihydro-2H-4,1λ4-benzoxathiepine 1-oxide & 8-bromo-2,6-difluoro-3,5-dihydro-2H-4,1-benzoxathiepine

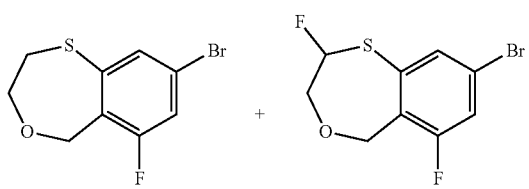 [SMILES: Fc1cc(Br)cc2c1COCCS2 ; Fc1cc(Br)cc2c1COCC(F)S2]

To a solution of 8-bromo-6-fluoro-3,5-dihydro-2H-4,1λ4-benzoxathiepine 1-oxide 1.9 g, 6.81 mmol) in DCM (40 mL) was added SbCl$_3$ (46.58 mg, 204.21 umol) and then DAST (2.19 g, 13.61 mmol, 1.80 mL) was added. The mixture was stirred at 20° C. for 16 hrs. Then DAST (5.49 g, 34.03 mmol, 4.50 mL) was added, the mixture was stirred at 20° C. for 16 hrs. SbCl$_3$ (1.55 g, 6.81 mmol) and DAST (10.97 g, 68.07 mmol, 8.99 mL) was added, the mixture was stirred at 20° C. for 16 hrs. The reaction mixture was poured into NaHCO$_3$ solution (200 mL), the solution was extracted with EA (200 mL*3), the combined organic layer was washed with brine (500 mL), dried over Na$_2$SO$_4$, filtered, and concentrated to give a residue. The residue was purified by column chromatography (SiO$_2$, Petroleum ether/Ethyl acetate=20:1-5:1), the peak 1 eluent was concentrated to give 8-bromo-6-fluoro-3,5-dihydro-2H-4,1λ4-benzoxathiepine 1-oxide (1.2 g, 4.56 mmol, 67.00% yield) as yellow oil. $^1$H NMR (400 MHz, CDCl$_3$) δ=7.54-7.51 (m, 1H), 7.18-7.15 (m, 1H), 4.91-4.89 (m, 2H), 4.17-4.14 (m, 2H), 2.89-2.86 (m, 2H) ppm The peak 2 eluent was concentrated to give 8-bromo-2,6-difluoro-3,5-dihydro-2H-4,1-benzoxathiepine (600 mg, 2.13 mmol, 31.36% yield) as a yellow solid. $^1$H NMR (400 MHz, CDCl$_3$) δ=7.55-7.54 (m, 1H), 7.27-7.24 (m, 1H), 5.63-5.51 (m, 1H), 5.25 (d, J=13.6 Hz, 1H), 4.69-4.65 (m, 1H), 4.43-4.41 (m, 1H), 4.13-4.05 (m, 1H) ppm Step 7: Preparation of 8-bromo-2,6-difluoro-3,5-dihydro-2H-4,1-benzoxathiepine

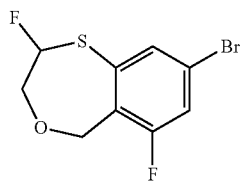

To a solution of 8-bromo-6-fluoro-3,5-dihydro-2H-4,1λ4-benzoxathiepine 1-oxide (peak 1 above) (1.2 g, 4.56 mmol) in MeCN (25 mL) was added Select F (2.02 g, 5.70 mmol) and then DAST (147.02 mg, 912.11 umol, 120.51 uL) was added under ice-bath. The solution was stirred at 20° C. for 1 hr. Then to the mixture was added DIEA (884.11 mg, 6.84 mmol, 1.19 mL) at 0° C., then the mixture was stirred at 20° C. for 1 hrs. The reaction mixture was poured into NaHCO$_3$ solution (200 mL) and extracted with EA (200 mL*3). The combined organic layer was washed with brine (500 mL), dried over Na$_2$SO$_4$, filtered, and concentrated to give a residue. The residue was purified by column chromatography (SiO$_2$, Petroleum ether/Ethyl acetate=20:1-5:1), the solution was concentrated to give 8-bromo-2,6-difluoro-3,5-dihydro-2H-4,1-benzoxathiepine (500 mg, 1.78 mmol, 39.00% yield) as a yellow solid. $^1$H NMR (400 MHz, CDCl$_3$) δ=7.54 (m, 1H), 7.27-7.24 (m, 1H), 5.63-5.51 (m, 1H), 5.25 (d, J=13.6 Hz, 1H), 4.70-4.66 (m, 1H), 4.43-4.42 (m, 1H), 4.13-4.05 (m, 1H) ppm Step 8: Preparation of 2,6-difluoro-3,5-dihydro-2H-4,1-benzoxathiepine-8-carboxylic Acid

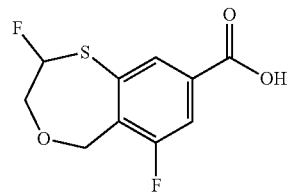

To a solution of 8-bromo-2,6-difluoro-3,5-dihydro-2H-4,1-benzoxathiepine (1.3 g, 4.62 mmol) in DMSO (20 mL) and H$_2$O (4 mL) was added K$_2$CO$_3$ (958.71 mg, 6.94 mmol), dicyclohexyl(3-dicyclohexylphosphaniumylpropyl)phosphonium; ditetrafluoroborate (283.13 mg, 462.44 umol) and Pd(OAc)$_2$ (103.82 mg, 462.44 umol). The suspension was degassed under vacuum and purged with CO several times. The mixture was stirred under CO (15 psi) at 100° C. for 2 hrs. The reaction mixture was poured into NaHCO$_3$ solution (100 mL) and extracted with EA (100 mL*2). The aqueous phase was adjusted to pH=1 with 1 N HCl and extracted with EA (50 mL*2), the combined organic layer was dried over Na$_2$SO$_4$, filtered, and concentrated to give 2,6-difluoro-3,5-dihydro-2H-4,1-benzoxathiepine-8-carboxylic acid (1.1 g, crude) as a yellow solid that was used without purification.

Step 9: Preparation of 2,6-difluoro-1,1-dioxo-3,5-dihydro-2H-4,1λ$^6$-benzoxathiepine-8-carboxylic Acid

To a solution of 2,6-difluoro-3,5-dihydro-2H-4,1-benzoxathiepine-8-carboxylic acid (1.1 g, 4.47 mmol) in MeOH (12 mL) and H$_2$O (12 mL) was added Oxone (5.49 g, 8.93 mmol), the mixture was stirred at 20° C. for 16 hrs. The reaction mixture was poured into water (100 mL), the solution was extracted with EA (100 mL*3), the combined organic layer was washed with brine (200 mL), dried over Na$_2$SO$_4$, filtered and concentrated to give 2,6-difluoro-1,1-dioxo-3,5-dihydro-2H-4,1λ$^6$-benzoxathiepine-8-carboxylic acid (1.1 g, 3.95 mmol, 88.50% yield) as a white solid. $^1$H NMR (400 MHz, DMSO-d$_6$) δ=14.03-13.95 (m, 1H), 8.34 (d, J=1.2 Hz, 1H), 8.13-8.11 (m, 1H), 6.27-6.16 (m, 1H), 5.25-5.21 (m, 1H), 4.91-4.86 (m, 1H), 4.47-4.38 (m, 2H) ppm.

Step 10: Preparation of (2R)-2,6-difluoro-1,1-dioxo-3,5-dihydro-2H-4,1λ⁶-benzoxathiepine-8-carboxylic Acid (Intermediate 1) and (2S)-2,6-difluoro-1,1-dioxo-3,5-dihydro-2H-4,1λ⁶-benzoxathiepine-8-carboxylic Acid Preparation of (R)-2,6-difluoro-N-((2-(7-methyl-2,3-dihydro-4H-pyrido[3,2-b][1,4]oxazin-4-yl)-1,6-naphthyridin-7-yl)methyl)-2,3-dihydro-5H-benzo[e][1,4]oxathiepine-8-carboxamide 1,1-di oxide (Compound 6)

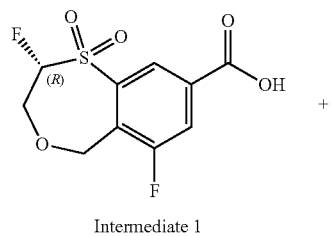

Intermediate 1

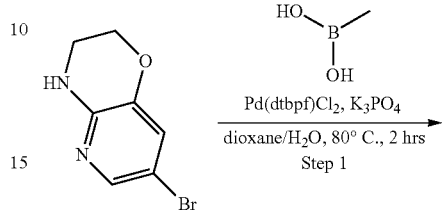

Step 1

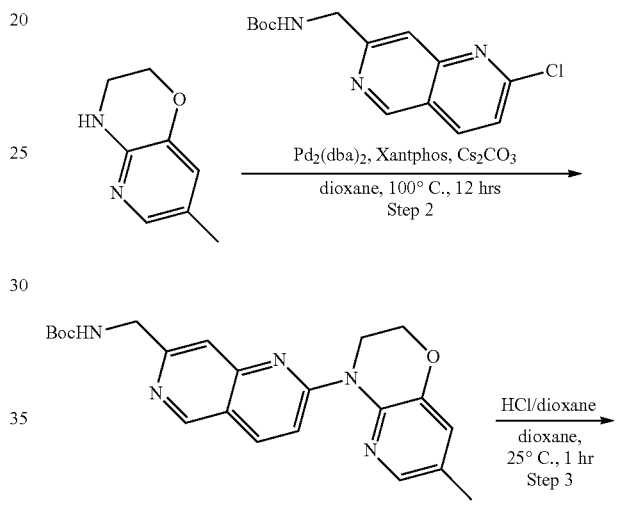

Step 2, Step 3

2,6-difluoro-1,1-dioxo-3,5-dihydro-2H-4,1λ⁶-benzoxathiepine-8-carboxylic acid (1.1 g, 3.95 mmol) was separated by chiral SFC (column: Daicel ChiralPak IG (250*30 mm, 10 um); mobile phase: [0.1% NH₃H₂O MEOH]; B %: 20%-20%, 4.75; 310 min) give two peaks. The peak 1 eluent was concentrated to give a colorless residue, the residue was diluted with water (100 mL) and adjusted to pH=2 with 4 N HCl solution, the solution was extracted with EA (100 mL*2), the combined organic layer was dried over Na₂SO₄, filtered, and concentrated to get (2R)-2,6-difluoro-1,1-dioxo-3,5-dihydro-2H-4,1λ⁶-benzoxathiepine-8-carboxylic acid (Intermediate 1) (350 mg, 1.25 mmol, 31.69% yield) as a white solid. $^1$H NMR (400 MHz, DMSO-d₆) δ=14.17-13.92 (m, 1H), 8.33 (s, 1H), 8.13-8.11 (m, 1H), 6.27-6.17 (m, 1H), 5.25-5.21 (m, 1H), 4.91-4.86 (m, 1H), 4.47-4.35 (m, 2H) ppm Chiral SFC: IG-3_5CM_MEOH(DEA)_5_40_3ML_T35.M; Rt=1.408 mins, ee %=98.14%.

The peak 2 eluent was concentrated to give a residue, the residue was diluted with water (100 mL) and adjusted to pH=2 with 4 N HCl solution, the solution was extracted with EA (100 mL*2), the combined organic layer was dried over Na₂SO₄, filtered and concentrated to get (2S)-2,6-difluoro-1,1-dioxo-3,5-dihydro-2H-4,1λ⁶-benzoxathiepine-8-carboxylic acid (500 mg, 1.66 mmol, 41.94% yield) as a white solid. $^1$H NMR (400 MHz, DMSO-d₆) δ=14.27-13.55 (m, 1H), 8.34 (d, J=1.2 Hz, 1H), 8.13-8.10 (m, 1H), 6.27-6.16 (m, 1H), 5.26-5.21 (m, 1H), 4.91-4.86 (m, 1H), 4.47-4.38 (m, 2H) ppm. Chiral SFC: IG-3_5CM_MEOH(DEA)_5_40_3ML

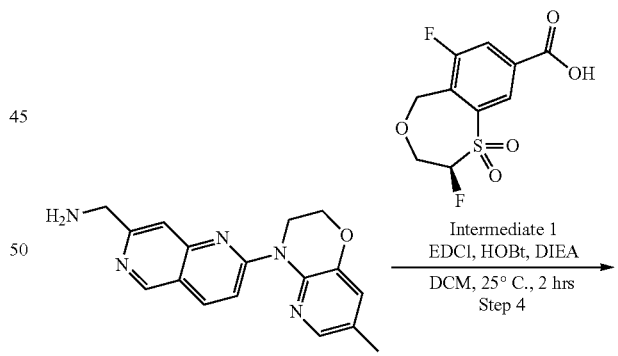

Step 4

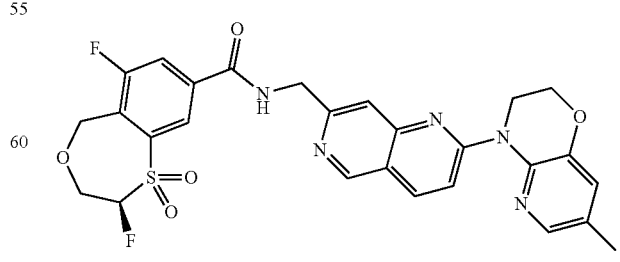

Example 1

Step 1: Preparation of 7-methyl-3,4-dihydro-2H-pyrido[3,2-b][1,4]oxazine

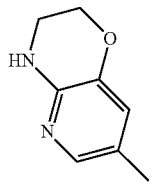

To a solution of 7-bromo-3,4-dihydro-2H-pyrido[3,2-b][1,4]oxazine (350 mg, 1.63 mmol) and methylboronic acid (292.28 mg, 4.88 mmol) in dioxane (5.6 mL) and H$_2$O (1.4 mL) was added ditertbutyl(cyclopentyl)phosphane; dichloropalladium; iron (106.07 mg, 162.76 umol) and K$_3$PO$_4$ (1.04 g, 4.88 mmol). The reaction was stirred at 80° C. for 2 hrs. The reaction mixture was poured into H$_2$O (5 mL), the solution was extracted with EA (5 mL*2), the combined organic layer was washed with brine (6 mL), dried over Na$_2$SO$_4$, filtered, and concentrated to give a residue.

The residue was purified by flash silica gel chromatography using a gradient of 0 to 80% ethyl acetate/petroleum. The desired eluent was concentrated in vacuum to give 7-methyl-3,4-dihydro-2H-pyrido[3,2-b][1,4]oxazine (200 mg, 1.33 mmol, 81.83% yield) as yellow oil. LCMS (ESI) m/z: [M+H]$^+$=151.1.

Step 2: Preparation of tert-butyl ((2-(7-methyl-2,3-dihydro-4H-pyrido[3,2-b][1,4]oxazin-4-yl)-1,6-naphthyridin-7-yl)methyl)carbamate

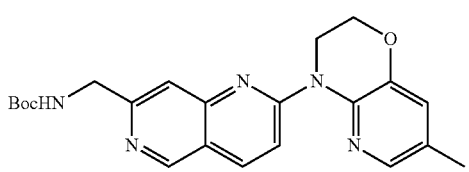 [SMILES: Cc1cnc2c(c1)OCCN2c1ccc2cnc(CNC(=O)OC(C)(C)C)cc2n1]

To a solution of tert-butyl N-[(2-chloro-1,6-naphthyridin-7-yl)methyl]carbamate (200 mg, 680.86 umol) and 7-methyl-3,4-dihydro-2H-pyrido[3,2-b][1,4]oxazine (122.70 mg, 817.03 umol) in dioxane (4 mL) was added Cs$_2$CO$_3$ (1.11 g, 3.40 mmol) and Xantphos (78.79 mg, 136.17 umol) and Pd$_2$(dba)$_3$ (62.35 mg, 68.09 umol, 0.1 eq). The reaction was stirred at 100° C. for 12 hrs. The reaction mixture was filtered. The filtrate was concentrated in vacuum to give the crude. The residue was purified by flash silica gel chromatography (ISCO®; 12 g SepaFlash® Silica Flash Column, Eluent of 0-100% Ethyl acetate/Petroleum ether gradient @ 36 mL/min). The eluent was concentrated in vacuum to give tert-butyl ((2-(7-methyl-2,3-dihydro-4H-pyrido[3,2-b][1,4]oxazin-4-yl)-1,6-naphthyridin-7-yl)methyl)carbamate (250 mg, 531.33 umol, 78.04% yield) as a yellow solid. LCMS (ESI) m/z: [M+H]$^+$=408.1.

Step 3: Preparation of (2-(7-methyl-2,3-dihydro-4H-pyrido[3,2-b][1,4]oxazin-4-yl)-1,6-naphthyridin-7-yl)methanamine

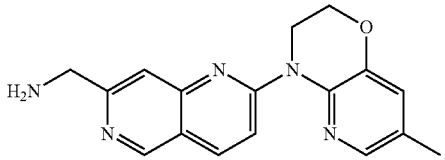 [SMILES: Cc1cnc2c(c1)OCCN2c1ccc2cnc(CN)cc2n1]

To a solution of tert-butyl ((2-(7-methyl-2,3-dihydro-4H-pyrido[3,2-b][1,4]oxazin-4-yl)-1,6-naphthyridin-7-yl)methyl)carbamate (250 mg, 613.55 umol) in dioxane (1 mL) was added HCl/dioxane (4 M, 4 mL). The reaction was stirred at 25° C. for 1 hr. The reaction mixture was concentrated in vacuum to give (2-(7-methyl-2,3-dihydro-4H-pyrido[3,2-b][1,4]oxazin-4-yl)-1,6-naphthyridin-7-yl)methanamine (150 mg, crude, HCl) as a yellow solid, which was used for next step directly without further purification. LCMS (ESI) m/z: [M+H]$^+$=308.1.

Step 4: Preparation of (R)-2,6-difluoro-N-((2-(7-methyl-2,3-dihydro-4H-pyrido[3,2-b][1,4]oxazin-4-yl)-1,6-naphthyridin-7-yl)methyl)-2,3-dihydro-5H-benzo[e][1,4]oxathiepine-8-carboxamide 1,1-dioxide (Compound 6)

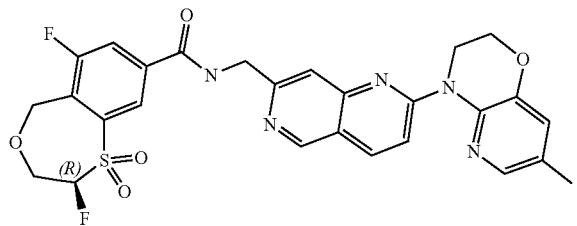

To a solution of (2R)-2,6-difluoro-1,1-dioxo-3,5-dihydro-2H-4,1λ6-benzoxathiepine-8-carboxylic acid (Intermediate 1, described above) (40.46 mg, 145.43 umol) in DCM (1 mL) was added (2-(7-methyl-2,3-dihydro-4H-pyrido[3,2-b][1,4]oxazin-4-yl)-1,6-naphthyridin-7-yl)methanamine (50 mg, 145.43 umol), DIEA (187.95 mg, 1.45 mmol, 253.31 uL) and EDCI (55.76 mg, 290.86 umol), HOBt (39.30 mg, 290.86 umol). The reaction was stirred at 25° C. for 2 hrs. The reaction mixture was poured into water (5 mL) and the mixture was extracted with EtOAc (5 mL*3). The combined organic layer was washed with brine (10 mL), dried over Na$_2$SO$_4$, filtered and concentrated in vacuum to give a residue. The residue was purified by prep-HPLC (FA condition; column: Phenomenex Synergi C18 150*25 mm*10 um; mobile phase: [water(FA)-ACN]; B %: 17%-50%, 11 min). The desired fraction was lyophilized to give (R)-2,6-difluoro-N-((2-(7-methyl-2,3-dihydro-4H-pyrido[3,2-b][1,4]oxazin-4-yl)-1,6-naphthyridin-7-yl)methyl)-2,3-dihydro-5H-benzo[e][1,4]oxathiepine-8-carboxamide 1,1-dioxide (34.84 mg, 56.78 umol, 39.04% yield, FA) as a yellow solid. LCMS (ESI) m/z: [M+H]$^+$=568.2. $^1$H NMR (400 MHz, DMSO-d$_6$) δ=9.71-9.68 (m, 1H), 9.08 (s, 1H), 8.47 (d, J=1.2 Hz, 1H), 8.39-8.22 (m, 4H), 7.77-7.76 (m, 1H), 7.53 (s, 1H), 7.20-7.20 (m, 1H), 6.31-6.15 (m, 1H), 5.24 (d, J=14.8 Hz, 1H), 4.91-4.87 (m, 1H), 4.74 (d, J=6.0 Hz, 2H), 4.48-4.35 (m, 2H), 4.33 (s, 4H), 2.25 (s, 3H) ppm.

The following examples in Table 2 were prepared using standard chemical manipulations and procedures similar to those used for the preparation of Compound 6.

TABLE 2

Compounds of the Invention

| # | LCMS (ESI/ M + H) | ¹HNMR |
|---|---|---|
| 326 | 596.2 | 1H NMR (400 MHz, DMSO-d6) δ = 9.74-9.73 (m, 1H), 9.39 (s, 1H), 8.84 (d, J = 5.2 Hz, 1H), 8.68-8.59 (m, 2H), 8.12 (s, 1H), 7.97-7.95 (m, 1H), 7.84-7.82 (m, 2H), 7.71-7.69 (m, 1H), 7.04 (d, J = 8.8 Hz, 1H), 6.59-6.45 (m, 1H), 4.83 (d, J = 6.0 Hz, 2H), 4.64-4.59 (m, 1H), 3.94 (br d, J = 2.8 Hz, 1H), 3.82-3.80 (m, 1H), 3.74-3.70 (m, 2H), 3.61-3.57 (m, 1H), 3.33 (br s, 3H), 1.82-1.75 (m, 4H), 1.65-1.62 (m, 1H) ppm |
| 3 | 599.2 | 1H NMR (400 MHz, DMSO-d6) δ = 9.82-9.61 (m, 1H), 9.08 (s, 1H), 8.46 (s, 1H), 8.32-8.21 (m, 2H), 7.79 (d, J = 1.6 Hz, 1H), 7.52 (s, 1H), 6.99 (d, J = 2.0 Hz, 1H), 6.61-5.80 (m, 1H), 4.73 (d, J = 6.0 Hz, 2H), 4.32 (s, 4H), 1.96-1.89 (m, 1H), 0.99-0.92 (m, 2H), 0.74-0.67 (m, 2H) ppm |
| 8 | 594.2 | 1H NMR (400 MHz, DMSO-d6) δ = 9.69 (s, 1H), 9.08 (s, 1H), 8.47 (d, J = 1.2 Hz, 1H), 8.32-8.22 (m, 3H), 7.79 (d, J = 2.0 Hz, 1H), 7.52 (s, 1H), 6.99 (d, J = 2.0 Hz, 1H), 6.30-6.13 (m, 1H), 5.24 (d, J = 14.4 Hz, 1H), 4.90 (d, J = 2.0 Hz, 1H), 4.73 (d, J = 5.6 Hz, 2H), 4.48 (s, 1H), 4.46-4.35 (m, 1H), 4.32 (s, 4H), 1.98-1.86 (m, 1H), 1.01-0.89 (m, 2H), 0.78-0.64 (m, 2H) ppm |
| 9 | 593.2 | 1H NMR (400 MHz, DMSO-d6) δ = 9.70-9.67 (m, 1H), 9.13 (s, 1H), 8.47 (d, J = 1.2 Hz, 1H), 8.37-8.34(m, 1H), 8.27-8.24 (m, 1H), 7.98-7.94 (m, 1H), 7.88-7.85 (m, 1H), 7.65-7.59 (m, 3H), 6.86 (d, J = 2.0 Hz, 1H), 6.27-6.16 (m, 1H), 5.24 (d, J = 14.6 Hz, 1H), 4.91-4.87 (m, 1H), 4.74-4.71 (m, 2H), 4.47-4.30 (m, 2H), 4.33-4.30 (m, 2H), 4.00-3.93 (m, 2H), 1.86-1.80 (m, 1H), 0.91-0.86 (m, 2H), 0.65-0.61 (m, 2H) ppm |
| 11 | 598.2 | 1H NMR (400 MHz, DMSO-d6) δ = 9.71-9.68 (m, 1H), 9.08 (s, 1H), 8.47 (s, 1H), 8.27-8.25 (m, 3H), 7.82 (d, J = 5.6 Hz, 1H), 7.53 (s, 1H), 6.88 (d, J = 5.2 Hz, 1H), 6.28-6.17 (m, 1H), 5.24 (d, J = 14.8 Hz, 1H), 4.91-4.88 (m, 1H), 4.74-4.73 (m, 2H), 4.47-4.31 (m, 6H), 4.16-4.11 (m, 2H), 1.37-1.34 (m, 3H) ppm |
| 13 | 608.3 | 1H NMR (400 MHz, DMSO-d6) δ = 9.63-9.60 (m, 1H), 9.09 (s, 1H), 8.40-8.25 (m, 3H), 8.23-8.15 (m, 1H), 7.50 (s, 1H), 7.19 (d, J = 8.0 Hz, 1H), 6.95 (d, J = 8.0 Hz, 1H), 6.39-6.13 (m, 1H), 4.72 (d, J = 5.6 Hz, 2H), 4.63-4.58 (m, 1H), 4.34-4.23 (m, 4H), 4.19-4.13 (m, 1H), 2.92-2.70 (m, 1H), 2.61 (d, J = 3.2 Hz, 1H), 1.77-1.63 (m, 1H), 1.20-1.08 (m, 4H), 1.03-0.92 (m, 1H), 0.73-0.60 (m, 1H) ppm. |
| 17 | 625.3 | 1H NMR (400 MHz, DMSO-d6) δ = 9.68-9.66 (m, 1H), 9.00 (s, 1H), 8.46 (d, J = 1.2 Hz, 1H), 8.38-8.32 (m, 1H), 8.29-8.15 (m, 3H), 7.54-7.40 (m, 2H), 6.67 (d, J = 2.8 Hz, 1H), 6.31-6.10 (m, 1H), 5.25 (d, J = 14.6 Hz, 1H), 4.92-4.88 (m, 1H), 4.71 (br d, J = 5.6 Hz, 2H), 4.51-4.26 (m, 6H), 3.32 (br s, 4H), 1.10-1.07 (m, 6H) ppm |
| 25 | 644.2 | 1H NMR (400 MHz, DMSO-d6) δ = 9.76-9.73 (m, 1H), 9.20 (s, 1H), 8.47 (d, J = 1.2 Hz, 1H), 8.36 (d, J = 1.6 Hz, 2H), 8.26-8.24 (m, 1H), 7.93 (d, J = 2.2 Hz, 1H), 7.65 (s, 1H), 7.33 (d, J = 2.2 Hz, 1H), 6.36-6.10 (m, 1H), 6.05-5.65 (m, 1H), 5.25 (d, J = 14.6 Hz, 1H), 4.90-4.88 (mz, 1H), 4.78 (d, J = 5.6 Hz, 2H), 4.52-4.34 (m, 6H), 1.19-1.11 (m, 2H), 1.03 (br s, 2H) ppm |
| 26 | 644.2 | 1H NMR (400 MHz, DMSO-d6) δ = 9.76-9.69 (m, 1H), 9.15-9.12 (m, 1H), 8.47 (s, 1H), 8.34 (s, 1H), 8.32 (s, 1H), 8.28 (d, J = 3.2 Hz, 1H), 8.15 (d, J = 9.2 Hz, 1H), 7.54 (s, 1H), 7.25 (d, J = 8.0 Hz, 1H), 7.07 (d, J = 8.0 Hz, 1H), 6.34-5.73 (m, 2H), 5.24 (d, J = 14.4 Hz, 1H), 4.90 (d, J = 16.4 Hz, 1H), 4.74 (s, 2H), 4.48 (s, 2H), 4.38-4.29 (m, 4H), 3.13-3.03 (m, 1H), 1.82-1.75 (m, 1H), 1.16-1.13 (m, 2H) ppm |
| 27 | 614.2 | 1H NMR (400 MHz, DMSO-d6) δ = 9.73-9.70 (m, 1H), 9.08 (s, 1H), 8.56-8.49 (m, 2H), 8.35 (br s, 1H), 8.25 (s, 2H), 7.82 (d, J = 5.6 Hz, 1H), 7.53 (s, 1H), 6.88 (d, J = 5.6 Hz, 1H), 6.28-6.18 (m, 1H), 5.41 (d, J = 14.8 Hz, 1H), 5.09 (d, J = 14.8 Hz, 1H), 4.74 (br d, J = 5.2 Hz, 2H), 4.49-4.32 (m, 6H), 4.16-4.13 (m, 2H), 1.37-1.34 (m, 3H) ppm |
| 28 | 619.3 | 1H NMR (400 MHz, DMSO-d6) δ = 9.57-9.54 (m, 1H), 9.02 (s, 1H), 8.45 (d, J = 1.2 Hz, 1H), 8.32-8.09 (m, 3H), 7.43 (s, 1H), 7.30 (d, J = 2.4 Hz, 1H), 6.49 (d, J = 2.4 Hz, 1H), 6.26-5.98 (m, 1H), 5.20 (d, J = 14.8 Hz, 1H), 4.98 (d, J = 14.8 Hz, 1H), 4.70 (d, J = 5.6 Hz, 2H), 4.49-4.24 (m, 6H), 4.16-4.03 (m, 1H), 3.94-3.79 (m, 1H), 3.55-3.49 (m, 1H), 2.52 (s, 3H), 2.41-2.36 (m, 1H), 2.08-1.97 (m, 1H), 1.40 (d, J = 6.0 Hz, 3H) ppm |
| 30 | 627.3 | 1H NMR (400 MHz, DMSO-d6) δ = 9.69-9.66 (m, 1H), 9.03 (s, 1H), 8.47 (s, 1H), 8.27-8.16 (m, 3H), 7.47 (s, 1H), 7.30 (d, J = 2.8 Hz, 1H), 6.59 (d, J = 2.4 Hz, 1H), 6.27-6.17 (m, 1H), 5.55-5.42 (m, 1H), 5.26 (d, J = 14.4 Hz, 1H), 4.91 (d, J =1.6 Hz, 1H), 4.72 (d, J = 5.6 Hz, 2H), 4.47 (s, 2H), 4.34-4.29 (m, 4H), 4.20-3.89 (m, 2H) ppm |
| 32 | 604.2 | 1H NMR (400 MHz, DMSO-d6) δ = 9.72-9.69 (m, 1H), 9.16 (s, 1H), 8.47 (d, J = 1.2 Hz, 1H), 8.39-8.23 (m, 3H), 8.10 (d, J = 1.6 Hz, 1H), 7.59 (s, 1H), 7.50 (d, J = 1.6 Hz, 1H), 7.23-6.90 (m, 1H), 6.31-6.15 (m, 1H), 5.25 (d, J = 14.4 Hz, 1H), 4.91-4.87 (m, 1H), 4.76 (d, J = 5.6 Hz, 2H), 4.50-4.33 (m, 6H) ppm. |
| 33 | 597.2 | 1H NMR (400 MHz, DMSO-d6) δ = 9.71-9.67 (m, 1H), 9.02 (s, 1H), 8.47 (d, J = 1.2 Hz, 1H), 8.29-8.24 (m, 1H), 8.21 (s, 2H), 7.59-7.44 (m, 2H), 6.77 (d, J = 2.8 Hz, 1H), 6.32-6.14 (m, 1H), 5.24 (d, J = 14.8 Hz, 1H), 4.94-4.86 (m, 1H), 4.72 (d, J = 5.6 Hz, 2H), |

TABLE 2-continued

Compounds of the Invention

| # | LCMS (ESI/ M + H) | ¹HNMR |
|---|---|---|
| 39 | 576.2 | 4.51-4.46 (m, 1H), 4.46-4.26 (m, 5H), 2.89 (s, 6H) ppm 1H NMR (400 MHz, DMSO-d6) δ = 9.64-9.61 (m, 1H), 9.10 (s, 1H), 8.59 (d, J = 1.6 Hz, 1H), 8.34-8.28 (m, 2H), 8.21-8.19 (m, 1H), 7.82-7.80 (m, 1H), 7.51 (s, 1H), 7.21(d, J = 8.0 Hz, 1H), 6.98 (d, J = 8.0 Hz, 1H), 6.18-6.07 (m, 1H), 5.08-4.97 (m, 2H), 4.74 (d, J = 5.6 Hz, 2H), 4.45-4.37 (m, 2H), 4.28 (s, 4H), 2.02-1.98 (m, 1H), 0.87-0.85 (m, 2H), 0.79-0.77(m, 2H) ppm. |
| 41 | 608.3 | 1H NMR (400 MHz, DMSO-d6 ) δ = 9.71-9.68 (m, 1H), 9.10 (s, 1H), 8.47 (d, J = 1.2 Hz, 1H), 8.35-8.14 (m, 3H), 7.53 (s, 1H), 7.19 (d, J = 8.0 Hz, 1H), 6.95 (d, J = 8.0 Hz, 1H), 6.39-6.09 (m, 1H), 5.24 (d, J = 14.4 Hz, 1H), 4.91-4.87 (m, 1H), 4.74 (d, J = 5.6 Hz, 2H), 4.48 (s, 1H), 4.44-4.33 (m, 1H), 4.29 (s, 4H), 1.79-1.66 (m, 1H), 1.21-1.07 (m, 4H), 0.99-0.97 (m, 1H), 0.68-0.66 (m, 1H) ppm |
| 48 | 609.3 | 1H NMR (400 MHz, DMSO-d6) δ = 9.70-9.67 (m, 1H), 9.02 (s, 1H), 8.47 (s, 1H), 8.27-8.21 (m, 1H), 8.19-8.14 (m, 2H), 7.46 (s, 1H), 7.24 (d, J = 2.68Hz, 1H), 6.47 (d, J = 2.4 Hz, 1H), 6.29-6.15 (m, 1H), 5.24 (d, J = 14.8 Hz, 1H), 4.90-4.87 (m, 1H), 4.72 (d, J = 5.2 Hz, 2H), 4.50-4.39 (m, 2H), 4.35-4.31 (m, 2H), 4.30-4.25 (m, 2H), 3.84-3.81 (m, 4H), 2.36-2.30 (m, 2H) ppm. |
| 50 | 659.00 | 1H NMR (400 MHz, METHANOL-d4) δ = 8.95 (s, 1H), 8.53 (d, J = 1.0 Hz, 1H), 8.15-8.05 (m, 3H), 7.59 (s, 1H), 7.41 (d, J = 2.6 Hz, 1H), 6.69 (d, J = 2.6 Hz, 1H), 5.78-5.66 (m, 1H), 5.44-5.27 (m, 3H), 5.01-5.00 (m, J = 2.2, 14.3 Hz, 1H), 4.82 (s, 2H), 4.52-4.47 (m, 1H), 4.45-4.44 (m, 1H), 4.41-4.39 (m, 2H), 4.34-4.29 (m, 2H), 3.81-3.73 (m, 1H), 3.69-3.55 (m, 3H) ppm |
| 56 | 632.2 | 1H NMR (400 MHz, DMSO-d6) δ = 9.69-9.66 (m, 1H), 9.03 (s, 1H), 8.47 (s, 1H), 8.29-8.15 (m, 3H), 7.47 (s, 1H), 7.30 (d, J = 2.4 Hz, 1H), 6.59 (d, J = 2.4 Hz, 1H), 6.28-6.12 (m, 1H), 5.59-5.37 (m, 1H), 4.72 (d, J = 5.2 Hz, 2H), 4.33-4.29 (m, 4H), 4.25-4.13 (m, 2H), 3.99-3.84 (m, 2H) ppm |
| 58 | 604.2 | 1H NMR (400 MHz, DMSO-d6) δ = 9.73-9.70 (m, 1H), 9.14 (s, 1H), 8.47 (s, 1H), 8.37-8.33 (m, 2H), 8.27-8.24 (m, 1H), 7.57 (s, 1H), 7.48 (d, J = 8.0 Hz, 1H), 7.34 (d, J = 8.0 Hz, 1H), 7.05-6.79 (m, 1H), 6.27-6.16 (m, 1H), 5.26-5.22 (m, 1H), 4.91-4.87 (m, 1H), 4.76 (d, J = 5.6 Hz, 2H), 4.47-4.39 (m, 6H) ppm |
| 59 | 599.2 | 1H NMR (400 MHz, DMSO-d6) δ = 9.77-9.76 (m, 1H), 9.29-9.27 (m, 1H), 8.45-8.38 (m, 2H), 8.32-8.25 (m, 2H), 7.74 (d, J = 6.8 Hz, 1H), 7.26 (d, J = 8.0 Hz, 1H), 7.05 (br d, J = 8.0 Hz, 1H), 6.33-6.16 (m, 1H), 4.81 (d, J = 4.8 Hz, 2H), 4.34 (s, 4H), 2.07-2.02 (m, 1H), 0.90-0.79 (m, 4H) ppm |
| 61 | 610.3 | 1H NMR (400 MHz, DMSO-d6) δ = 9.72-9.69 (m, 1H), 9.08 (s, 1H), 8.57 (d, J = 1.6 Hz, 1H), 8.49 (d, J = 1.6 Hz, 1H), 8.42-8.39 (m, 1H), 8.28 (d, J = 2.8 Hz, 2H), 7.79 (d, J = 2.0 Hz, 1H), 7.53 (s, 1H), 6.99 (d, J = 2.0 Hz, 1H), 6.37-6.09 (m, 1H), 5.41 (d, J = 14.8 Hz, 1H), 5.09 (d, J = 14.8 Hz, 1H), 4.73 (d, J = 5.6 Hz, 2H), 4.49 (d, J = 2.8 Hz, 1H), 4.46-4.41 (m, 1H), 4.35-4.29 (m, 4H), 2.00-1.85 (m, 1H), 1.02-0.89 (m, 2H), 0.77-0.60 (m, 2H) ppm |
| 62 | 618.2 | 1H NMR (400 MHz, DMSO-d6) δ = 9.75-9.71 (m, 1H), 9.14 (s, 1H), 8.48 (d, J = 1.2 Hz, 2H), 8.36-8.34 (m, 1H), 8.27 (d, J = 9.2 Hz, 2H), 7.57 (s, 1H), 7.44-7.41 (m, 1H), 7.21 (d, J = 8.4 Hz, 1H), 6.28-6.17 (m, 1H), 5.74-5.70 (m, 1H), 5.25 (d, J = 14.8 Hz, 1H), 4.95-4.88 (m, 2H), 4.82-4.75 (m, 3H), 4.48-4.40 (m, 1H), 4.39-4.36 (m, 4H) ppm. |
| 63 | 627.2 | 1H NMR (400 MHz, DMSO-d6) δ = 9.71-9.68 (m, 1H), 9.09 (s, 1H), 8.47-8.42 (m, 2H), 8.29-8.24 (m, 2H), 7.53 (s, 1H), 7.22 (d, J = 8.4 Hz, 1H), 6.27-6.16 (m, 2H), 5.54-5.35 (m, 1H), 5.24 (br d, J = 14.4 Hz, 1H), 4.90 (br d, J = 14.8 Hz, 1H), 4.74 (br d, J = 5.2 Hz, 2H), 4.48-4.38 (m, 2H), 4.26-4.16 (m, 6H), 3.96-3.90 (m, 2H) ppm |
| 72 | 594.1 | 1H NMR (400 MHz, DMSO-d6) δ = 9.75-9.68 (m, 1H), 9.11 (s, 1H), 8.48 (d, J = 1.2 Hz, 1H), 8.32-8.20 (m, 3H), 7.54 (s, 1H), 7.22 (d, J = 8.0 Hz, 1H), 6.99 (d, J = 8.0 Hz, 1H), 6.28-6.17 (m, 1H), 5.25 (d, J = 14.4 Hz, 1H), 4.92-4.88 (m, 1H), 4.75 (d, J = 5.6 Hz, 2H), 4.48-4.30 (m, 6H), 2.05-1.99 (m, 1H), 0.88-0.86 (m, 2H), 0.80-0.76 (m, 2H) ppm |
| 74 | 630.2 | 1H NMR (400 MHz, DMSO-d6) δ = 9.72-9.69 (m, 1H), 9.11 (s, 1H), 8.47 (s, 1H), 8.45 (s, 1H), 8.34-8.22 (m, 3H), 7.89 (d, J = 1.6 Hz, 1H), 7.54 (s, 1H), 7.25 (d, J = 1.6 Hz, 1H), 6.34-6.10 (m, 1H), 5.24 (d, J = 14.4 Hz, 1H), 4.96-4.83 (m, 1H), 4.74 (d, J = 5.6 Hz, 2H), 4.48 (s, 1H), 4.46-4.38 (m, 1H), 4.35 (s, 4H), 3.05-2.97 (m, 1H), 2.11-1.94 (m, 2H) ppm |
| 76 | 608.3 | 1H NMR (400 MHz, DMSO-d6) δ = 9.63-9.60 (m, 1H), 9.11 (s, 1H), 8.41 (s, 1H), 8.35-8.26 (m, 3H), 7.85 (d, J = 5.6 Hz, 1H), 7.53 (s, 1H), 6.96 (d, J = 6.0 Hz, 1H), 6.37-6.17 (m, 1H), 4.71 (d, J = 5.6 Hz, 2H), 4.62-4.57 (m, 1H), 4.31-4.26 (m, 1H), 4.18-4.12 (m, 1H), 4.05-3.95 (m, 1H), 2.88-2.70 (m, 1H), 2.61-2.58 (m, 1H), 2.54 (s, 2H), 1.96-1.86 (m, 2H), 0.78-0.71 (m, 2H), 0.71-0.62 (m, 2H) ppm |
| 78 | 599.3 | 1H NMR (400 MHz, MeOD) δ = 9.01 (s, 1H), 8.39 (d, J = 1.6 Hz, 1H), 8.29-8.27 (m, 1H), 8.21-8.16 (m, 1H), 8.16-8.14 (m, 1H), 7.63 (s, 1H), 7.16 (d, J = 8.0 Hz, 1H), 6.93 (d, J = 8.0 Hz, 1H), 4.82 (s, 2H), 4.36-4.30 (m, 4H), 2.00-1.95 (m, 1H), 0.89-0.84 (m, 4H) ppm. |
| 88 | 612.2 | 1H NMR (400 MHz, DMSO-d6) δ = 9.71-93.68 (m, 1H), 9.10 (s, 1H), 8.47 (d, J = 0.8 Hz, 1H), 8.34 (s, 1H), 8.31-8.25 (m, 3H), 7.54 (s, 1H), 7.28 (d, J = 8.4 Hz, 1H), 7.07 (d, J = 8.0 Hz, 1H), 6.27-6.16 (m, 1H), 5.25 (d, J = 14.4 Hz, 1H), 5.00-4.83 (m, 2H), 4.75-4.73 |

TABLE 2-continued

Compounds of the Invention

| # | LCMS (ESI/ M + H) | ¹HNMR |
|---|---|---|
| | | (m, 2H), 4.58-4.53 (m, 1H), 4.45-4.44 (m, 3H), 4.31-4.26 (m, 1H), 4.13-4.07 (m, 1H), 2.29-2.27 (m, 1H), 1.71-1.61 (m, 1H), 1.19-1.12 (m, 1H) ppm |
| 102 | 572.2 | 1H NMR (400 MHz, DMSO-d6) δ = 9.72-9.68 (m, 1H), 9.11 (s, 1H), 8.47 (d, J = 1.2 Hz, 1H), 8.37-8.15 (m, 3H), 7.98-7.93 (m, 1H), 7.54 (s, 1H), 7.47-7.43 (m, 1H), 6.32-6.14 (m, 1H), 5.24 (d, J = 14.4 Hz, 1H), 4.94-4.86 (m, 1H), 4.74 (d, J = 5.6 Hz, 2H), 4.48 (s, 1H), 4.40-4.33 (m, 4H), 3.44 (s, 1H) ppm |
| 112 | 689.2 | 1H NMR (400 MHz, DMSO-d6) δ = 9.71-9.68 (m, 1H), 9.04 (s, 1H), 8.56 (d, J = 1.6 Hz, 1H), 8.49 (d, J = 1.6 Hz, 1H), 8.23 (s, 2H), 7.75 (d, J = 2.8 Hz, 1H), 7.49 (s, 1H), 7.07 (d, J = 2.7 Hz, 1H), 6.32-6.14 (m, 1H), 5.41 (d, J = 14.8 Hz, 1H), 5.09 (d, J = 14.8 Hz, 1H), 5.05-4.96 (m, 1H), 4.94-4.84 (m, 1H), 4.72 (d, J = 4.8 Hz, 2H), 4.50-4.40 (m, 2H), 4.33-4.30 (m, 4H), 3.65-3.54 (m, 1H), 3.42-3.36 (m, 2H), 3.19-3.09 (m, 1H), 2.06-1.89 (m, 2H) ppm |
| 116 | 630.2 | 1H NMR (400MHz, DMSO-d6) δ = 9.72-9.69 (m, 1H), 9.10 (s, 1H), 8.47 (d, J = 1.2 Hz, 1H), 8.45-8.38 (m, 1H), 8.29-8.24 (m, 3H), 7.88 (d, J = 2.0 Hz, 1H), 7.54 (s, 1H), 7.25 (d, J = 2.0 Hz, 1H), 6.27-6.16 (m, 1H), 5.24 (d, J = 14.4 Hz, 1H), 4.91-4.87 (m, 1H), 4.74 (d, J = 5.6 Hz, 2H), 4.47-4.34 (m, 6H), 3.05-2.96 (m, 1H), 2.07-1.97 (m, 2H) ppm |
| 121 | 675.00 | 1H NMR (400 MHz, METHANOL-d4) δ = 8.96 (s, 1H), 8.64 (d, J = 1.6 Hz, 1H), 8.39 (d, J = 1.6 Hz, 1H), 8.14 (d, J = 3.2 Hz, 2H), 7.60 (s, 1H), 7.42 (d, J = 2.8 Hz, 1H), 6.70 (d, J = 2.8 Hz, 1H), 5.81-5.67 (m, 1H), 5.57 (d, J = 14.4 Hz, 1H), 5.44-5.28 (m, 2H), 5.18 (d, J = 14.4 Hz, 1H), 4.82 (s, 2H), 4.58-4.48 (m, 1H), 4.46-4.40 (m, 3H), 4.35-4.31 (m, 2H), 3.81-3.75 (m, 1H), 3.70-3.63 (m, 2H), 3.61-3.56 (m, 1H) ppm |
| 132 | 612.1 | 1H NMR (400 MHz, DMSO-d6) δ = 9.71-9.68 (m, 1H), 9.11 (s, 1H), 8.46 (s, 1H), 8.43-8.41 (m, 1H), 8.33(d, J = 9.2 Hz, 1H), 8.26-8.24 (m, 1H), 8.13 (d, J = 9.2 Hz, 1H), 7.53 (s, 1H), 7.26 (d, J = 8.0 Hz, 1H), 7.07 (d, J = 8.0 Hz, 1H), 6.26-6.16 (m, 1H), 5.25 (d, J = 14.4 Hz, 1H), 4.92-4.73 (m, 4H), 4.47-4.38 (m, 2H), 4.31-4.26 (m, 4H), 2.59-2.55 (m, 1H), 1.49-1.43 (m, 1H), 1.22-1.15 (m, 1H) ppm |
| 140 | 606.2 | 1H NMR (400 MHz, DMSO-d6) δ = 9.77-9.63 (m, 1H), 9.18-9.13 (m, 1H), 8.50-8.46 (m, 1H), 8.36 (s, 2H), 8.28-8.24 (m, 1H), 7.58 (s, 1H), 7.47 (d, J = 8.4 Hz, 1H), 7.34 (d, J = 8.0 Hz, 1H), 7.05-6.68 (m, 1H), 6.33-6.09 (m, 1H), 4.80-4.72 (m, 2H), 4.49-4.37 (m, 6H) ppm |
| 146 | 620.3 | 1H NMR (400 MHz, MeOD) δ = 9.02 (s, 1H), 8.53 (s, 1H), 8.26-8.21 (m, 2H), 8.12-8.09 (m, 1H), 7.74 (d, J = 2.0 Hz, 1H), 7.65 (s, 1H), 7.14 (d, J = 1.6 Hz, 1H), 5.77-6.67 (m, 1H), 5.37(d, J = 14.0 Hz, 1H), 5.01-4.96 (m, 1H), 4.84 (br s, 2H), 4.53-4.31 (m, 6H), 2.56 (s, 1H), 2.12 (s, 6H) ppm |
| 163 | 609.2 | 1H NMR (400 MHz, DMSO-d6) δ = 9.72-9.70 (m, 1H), 9.14 (s, 1H), 8.47 (d, J = 1.2 Hz, 1H), 8.35 (s, 2H), 8.27-8.25 (m, 1H), 7.58 (s, 1H), 7.47 (d, J = 8.4 Hz, 1H), 7.34 (d, J = 8.0 Hz, 1H), 6.99-6.72 (m, 1H), 6.26-6.16 (m, 1H), 4.76 (d, J = 5.6 Hz, 2H), 4.41-4.39 (m, 4H)ppm |
| 175 | 655.2 | 1H NMR (400 MHz, DMSO-d6) δ = 9.81-9.78 (m, 1H), 9.02 (s, 1H), 8.77 (s, 1H), 8.58 (s, 1H), 8.21-8.15 (m, 3H), 7.66-7.39 (m, 2H), 7.30 (d, J = 2.8 Hz, 1H), 6.50-6.46 (m, 1H), 6.29-6.18 (m, 1H), 5.31-5.22 (m, 1H), 5.10-5.05 (m, 1H), 4.72 (d, J = 4.8 Hz, 2H), 4.51-4.43 (m, 2H), 4.34-4.29 (m, 2H), 4.28 (s, 2H), 4.11-4.06 (m, 1H), 3.88-3.83 (m, 1H), 3.55-3.49 (m, 1H), 2.39-2.36 (m, 1H), 2.02-1.99 (m, 1H), 1.40 (d, J = 6.4Hz, 3H) ppm |
| 199 | 607.2 | 1H NMR (400 MHz, DMSO-d6) δ = 9.74-9.71 (m, 1H), 9.15 (s, 1H), 8.47 (d, J = 1.2 Hz, 1H), 8.36 (s, 2H), 8.29-8.26 (m, 1H), 7.58 (s, 1H), 7.47 (d, J = 8.2 Hz, 1H), 7.34 (d, J = 8.2 Hz, 1H), 7.04-6.68 (m, 1H), 6.34-6.09 (m, 1H), 5.24 (d, J = 14.8 Hz, 1H), 4.92-4.88 (m, 1H), 4.76 (d, J = 5.6 Hz, 2H), 4.48-4.33 (m, 4H) ppm |
| 207 | 612.3 | 1H NMR (400 MHz, DMSO-d6) δ = 9.72-9.69 (m, 1H), 9.12 (s, 1H), 8.47 (d, J = 1.0 Hz, 1H), 8.33 (d, J = 9.2 Hz, 1H), 8.27-8.24 (m, 1H), 8.12 (d, J = 9.2 Hz, 1H), 7.54 (s, 1H), 7.25 (d, J = 8.0 Hz, 1H), 7.07 (d, J = 8.4 Hz, 1H), 6.27-6.16 (m, 1H), 5.24 (d, J = 14.4 Hz, 1H), 4.91-4.73 (m, 4H), 4.47-4.39 (m, 2H), 4.31-4.27 (m, 4H), 2.60-2.55 (m, 1H), 1.49-1.44 (m, 1H), 1.23-1.17 (m, 1H) ppm |
| 208 | 620.2 | 1H NMR (400 MHz, DMSO-d6) δ = 9.74-9.72 (m, 1H), 9.15 (s, 1H), 8.57 (d, J = 1.2 Hz, 1H), 8.50 (s, 1H), 8.36 (s, 2H), 7.59 (s, 1H), 7.48 (d, J = 8.0 Hz, 1H), 7.34 (d, J = 8.4 Hz, 1H), 7.03-6.70 (m, 1H), 6.33-6.14 (m, 1H), 5.41 (d, J = 14.8 Hz, 1H), 5.09 (d, J = 14.8 Hz, 1H), 4.76 (br d, J = 5.6 Hz, 2H), 4.50-4.38 (m, 6H) ppm |
| 209 | 612.2 | 1H NMR (400 MHz, DMSO-d6) δ = 9.72-9.69 (m, 1H), 9.10 (s, 1H), 8.47 (d, J = 1.2 Hz, 1H), 8.37-8.18 (m, 4H), 7.54 (s, 1H), 7.28 (d, J = 8.0 Hz, 1H), 7.07 (d, J = 8.0 Hz, 1H), 6.44-6.03 (m, 1H), 5.24 (d, J = 14.4 Hz, 1H), 5.05-4.80 (m, 2H), 4.74 (br d, J = 5.6 Hz, 2H), 4.60-4.47 (m, 2H), 4.46-4.34 (m, 2H), 4.33-4.23 (m, 1H), 4.13-4.06 (m, 1H), 2.31-2.18 (m, 1H), 1.73-1.55 (m, 1H), 1.19-1.10 (m, 1H) ppm |
| 237 | 600.2 | 1H NMR (400 MHz, DMSO-d6) δ = 9.60-9057 (m, 1H), 9.15 (s, 1H), 8.46 (d, J = 0.8 Hz, 1H), 8.35 (s, 2H), 8.24 (s, 1H), 7.54 (s, 1H), 7.47 (d, J = 8.0 Hz, 1H), 7.33 (d, J = 8.0 Hz, 1H), 7.03-6.70 (m, 1H), 6.19-6.03 (m, 1H), 5.21 (d, J = 14.8 Hz, 1H), 4.98 (d, J = 14.8 Hz, 1H), 4.75 (d, J = 6.0 Hz, 2H), 4.47-4.36 (m, 6H), 2.52-2.51 (m, 3H) ppm |
| 239 | 592.00 | 1H NMR (400 MHz, DMSO-d6) δ = 9.70-9.68 (m, 1H), 9.13 (s, 1H), 8.47 (s, 1H), 8.36-8.29 (m, 1H), 8.29-8.22 (m, 2H), 7.93 (d, J = 1.8 Hz, 1H), 7.56 (s, 1H), 7.33 (d, J = 1.8 Hz, 1H), 6.39-6.11 |

TABLE 2-continued

Compounds of the Invention

| # | LCMS (ESI/ M + H) | ¹HNMR |
|---|---|---|
| | | (m, 1H), 5.24 (d, J = 14.4 Hz, 1H), 4.90 (br d, J = 14.8 Hz, 1H), 4.75 (br d, J = 5.6 Hz, 2H), 4.53-4.42 (m, 2H), 4.41-4.31 (m, 4H), 2.06 (s, 3H) ppm |
| 260 | 618.1 | 1H NMR (400 MHz, DMSO-d6) δ = 9.47 (d, J = 7.6 Hz, 1H), 9.15 (s, 1H), 8.46 (s, 1H), 8.39-8.32 (m, 2H), 8.32-8.27 (m, 1H), 7.65 (s, 1H), 7.48 (d, J = 8.4 Hz, 1H), 7.34 (br d, J = 8.4 Hz, 1H), 6.99-6.72 (m, 1H), 6.27-6.13 (m, 1H), 5.37-5.33 (m, 1H), 5.24 (d, J = 14.8 Hz, 1H), 4.89 (br d, J = 14.8 Hz, 1H), 4.48-4.34 (m, 6H), 1.63 (br d, J = 7.2 Hz, 3H) ppm |
| 272 | 620.00 | 1H NMR (400 MHz, DMSO-d6) δ = 9.65-9.62 (m, 1H), 9.13 (s, 1H), 8.52 (d, J = 2.0 Hz, 1H), 8.44 (d, J = 2.4 Hz, 1H), 8.34 (s, 2H), 7.55 (s, 1H), 7.46 (s, 1H), 7.33 (d, J = 8.2 Hz, 1H), 7.02-6.69 (m, 1H), 6.34-6.17 (m, 1H), 4.73 (d, J = 5.8 Hz, 2H), 4.62-4.58 (m, 1H), 4.44-4.34 (m, 4H), 4.09 (d, J = 11.6 Hz, 1H), 2.95-2.71 (m, 1H), 2.63-2.53 (m, 1H) ppm |
| 278 | 608.0 | 1HNMR (400 MHz, DMSO-d6) δ = 9.45 (d, J = 7.6 Hz, 1H), 9.09 (s, 1H), 8.45 (d, J = 0.8 Hz, 1H), 8.31-8.25 (m, 3H), 7.79 (d, J = 2.0 Hz, 1H), 7.59 (s, 1H), 6.99 (d, J = 2.4 Hz, 1H), 6.38-5.96 (m, 1H), 5.33-5.31 (m, 1H), 5.24 (d, J = 14.8 Hz, 1H), 4.90-4.86 (m, 1H), 4.49-4.26 (m, 6H), 1.96- 1.86 (m, 1H), 1.62 (d, J = 6.8 Hz, 3H), 1.01-0.89 (m, 2H), 0.76-0.65 (m, 2H) ppm |
| 289 | 639.1 | 1H NMR (400 MHz, DMSO-d6) δ = 9.70 (s, 1H), 9.02 (s, 1H), 8.56 (d, J = 1.6 Hz, 1H), 8.49 (d, J = 0.8 Hz, 1H), 8.23-8.15 (m, 2H), 7.47 (s, 1H), 7.30 (d, J = 2.4 Hz, 1H), 6.49 (d, J = 2.4 Hz, 1H), 6.30-6.16 (m, 1H), 5.41 (d, J = 14.8 Hz, 1H), 5.09 (d, J = 14.8 Hz, 1H), 4.71 (br d, J = 5.2 Hz, 2H), 4.50-4.41 (m, 2H), 4.36-4.24 (m, 4H), 4.13-4.06 (m, 1H), 3.88-3.82 (m, 1H), 3.53 (d, J = 7.6 Hz, 1H), 2.39-2.36 (m, 1H), 2.05-1.96 (m, 1H), 1.40 (d, J = 6.0 Hz, 3H) ppm |
| 309 | 617.90 | 1H NMR (400 MHz, DMSO-d6) δ = 9.71 (m, 1H), 9.13 (s, 1H), 8.48 (s, 1H), 8.36 (br s, 1H), 8.35-8.31 (m, 1H), 8.26 (d, J = 9.2 Hz, 2H), 7.91 (d, J = 2.0 Hz, 1H), 7.57 (s, 1H), 7.31 (d, J = 2.0 Hz, 1H), 6.30-6.15 (m, 1H), 5.25 (d, J = 14.8 Hz, 1H), 4.94-4.87 (m, 1H), 4.75 (d, J = 6.0 Hz, 2H), 4.50-4.33 (m, 6H), 1.61-1.53 (m, 1H), 0.94-0.87 (m, 2H), 0.78-0.73 (m, 2H) ppm |

Preparation of (2R)—N-[[2-[3-(difluoromethoxy)phenyl]-1,6-naphthyridin-7-yl]methyl]-2,6-difluoro-1,1-dioxo-3,5-dihydro-2H-4,1λ6-benzoxathiepine-8-carboxamide (Compound 297)

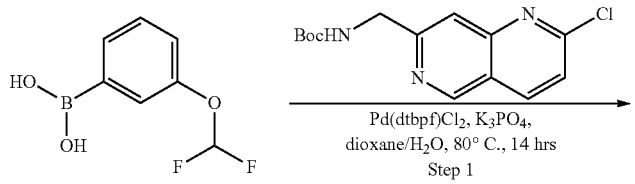

Pd(dtbpf)Cl₂, K₃PO₄, dioxane/H₂O, 80° C., 14 hrs
Step 1

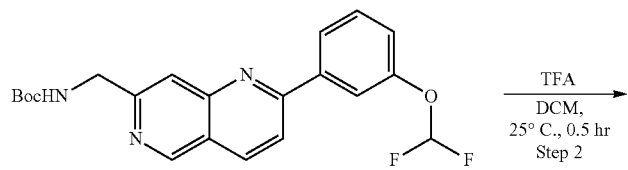

TFA
DCM, 25° C., 0.5 hr
Step 2

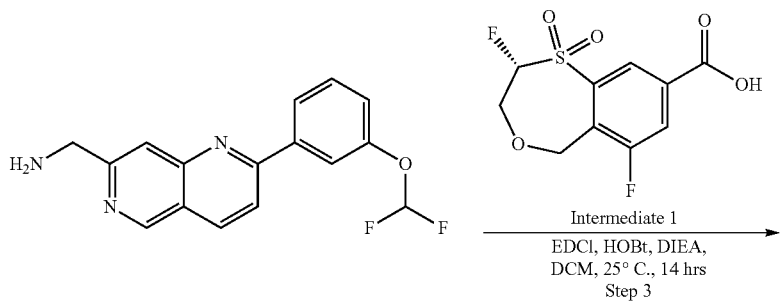

Intermediate 1
EDCl, HOBt, DIEA, DCM, 25° C., 14 hrs
Step 3

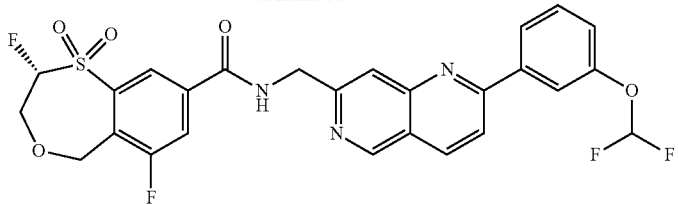

Step 1: Preparation of tert-butyl ((2-(3-(difluoromethoxy)phenyl)-1,6-naphthyridin-7-yl)methyl)carbamate

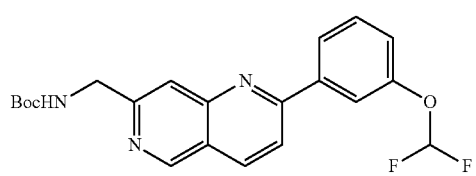 [SMILES: CC(C)(C)OC(=O)NCc1cc2nc(-c3cccc(OC(F)F)c3)ccc2cn1]

A mixture of tert-butyl N-[(2-chloro-1,6-naphthyridin-7-yl)methyl]carbamate (208.40 mg, 709.46 umol), [3-(difluoromethoxy)phenyl]boronic acid (200 mg, 1.06 mmol), ditert-butyl(cyclopentyl)phosphane; dichloropalladium; iron (46.24 mg, 70.95 umol) and K₃PO₄ (451.78 mg, 2.13 mmol) in dioxane (3 mL) and H₂O (1 mL) was degassed and purged with N₂ for 3 times, and then the mixture was stirred at 80° C. for 14 hrs under N₂ atmosphere. The reaction mixture diluted with H₂O (15 mL) and extracted with EA (15 mL*3). The combined organic layers was dried over anhydrous Na₂SO₄, filtered and concentrated under reduced pressure to give a residue. The residue was purified by flash silica gel chromatography (SiO₂, Petroleum ether/Ethyl acetate=1/0 to 1/2), the fraction was concentrated under reduced pressure to get tert-butyl ((2-(3-(difluoromethoxy)phenyl)-1,6-naphthyridin-7-yl)methyl)carbamate (255 mg, 635.27 umol, 89.54% yield) was brown oil. LCMS (ESI) m/z: [M+H]⁺=402.1. ¹H NMR (400 MHz, DMSO-d₆) δ=9.36 (s, 1H), 8.68 (d, J=8.4 Hz, 1H), 8.32 (d, J=8.4 Hz, 1H), 8.19 (d, J=8.0 Hz, 1H), 8.11 (d, J=2.0 Hz, 1H), 7.77 (s, 1H), 7.67-7.59 (m, 2H), 7.58-7.21 (m, 2H), 4.45 (d, J=6.0 Hz, 2H), 1.44 (s, 9H) ppm.

Step 2: Preparation of (2-(3-(difluoromethoxy)phenyl)-1,6-naphthyridin-7-yl)methanamine

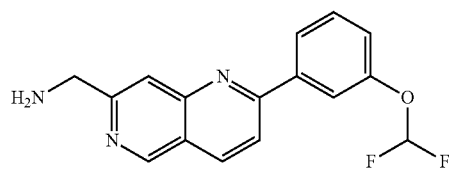 [SMILES: NCc1cc2nc(-c3cccc(OC(F)F)c3)ccc2cn1]

To a solution of tert-butyl ((2-(3-(difluoromethoxy)phenyl)-1,6-naphthyridin-7-yl)methyl)carbamate (250 mg, 622.81 umol) in TFA (1 mL) and DCM (3 mL). The mixture was stirred at 25° C. for 0.5 hr. The mixture was poured into aq·NaHCO₃ (10 mL), then extracted with EA (10 mL*3), the combined organic layers was dried over Na₂SO₄, filtered, and concentrated under reduced pressure to get (2-(3-(difluoromethoxy)phenyl)-1,6-naphthyridin-7-yl)methanamine (185 mg, 614.03 umol, 98.59% yield) as brown solid. LCMS (ESI) m/z: [M+H]⁺=302.1.

Step 3: Preparation of (2R)—N-[[2-[3-(difluoromethoxy)phenyl]-1,6-naphthyridin-7-yl]methyl]-2,6-difluoro-1,1-dioxo-3,5-dihydro-2H-4,1λ6-benzoxathiepine-8-carboxamide

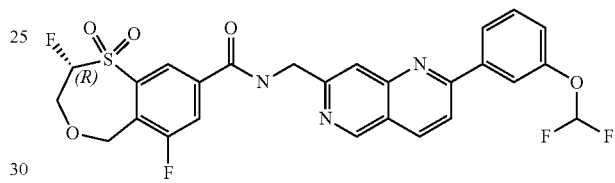

To a solution of (2-(3-(difluoromethoxy)phenyl)-1,6-naphthyridin-7-yl)methanamine (50 mg, 165.95 umol) in DCM (1 mL) was added (2R)-2,6-difluoro-1,1-dioxo-3,5-dihydro-2H-4,1λ6-benzoxathiepine-8-carboxylic (46.17 mg, 165.95 umol), EDCl (47.72 mg, 248.93 umol), HOBt (33.64 mg, 248.93 umol) and DIEA (107.24 mg, 829.76 umol). The mixture was stirred at 25° C. for 14 hrs. The reaction mixture was diluted with H₂O (5 mL) extracted with DCM (5 mL*3). The combined organic layer was dried over anhydrous Na₂SO₄, filtered and concentrated under reduced pressure to get the residue. The residue was purified by reversed-phase HPLC (acetonitrile and water with 0.1% FA condition). Then the solution was concentrated under reduced pressure and then lyophilized to give (2R)—N-[[2-[3-(difluoromethoxy)phenyl]-1,6-naphthyridin-7-yl]methyl]-2,6-difluoro-1,1-dioxo-3,5-dihydro-2H-4,1λ6-benzoxathiepine-8-carboxamide (20.83 mg, 37.10 umol, 22.35% yield) as off-white solid. LCMS (ESI) m/z: [M+H]⁺= 562.2. ¹H NMR (400 MHz, DMSO-d₆) δ=9.76-9.73 (m, 1H), 9.41 (s, 1H), 8.69 (d, J=8.8 Hz, 1H), 8.47 (s, 1H), 8.33 (d, J=8.4 Hz, 1H), 8.26 (d, J=10.4 Hz, 1H), 8.19 (d, J=7.6 Hz, 1H), 8.10 (s, 1H), 7.92-7.82 (m, 1H), 7.65-7.61 (m, 1H), 7.57-7.17 (m, 2H), 6.33-6.10 (m, 1H), 5.25 (d, J=14.4 Hz, 1H), 4.95-4.68 (m, 3H), 4.53-4.32 (m, 2H) ppm. Chiral SFC: OJ-3-MeOH(DEA)-5-40-3 mL-35T.lcm; Rt=2.427 mins, ee %=100.00%.

The following examples in Table 3 were prepared using standard chemical manipulations and procedures similar to those used for the preparation of Compound 297.

TABLE 3

Compounds of the Invention

| # | LCMS (ESI/ M + H) | ¹HNMR |
|---|---|---|
| 327 | 550.6 | 1H NMR (400 MHz, DMSO-d6) δ = 9.77-9.74 (m, 1H), 9.42 (s, 1H), 8.68-8.61 (m, 2H), 8.51 (d, J = 1.2 Hz, 1H), 8.35-8.33 (m, 2H), 7.88-7.83 (m, 2H), 7.48-7.46 (m, 1H), 6.14-6.02 (m, 1H), 5.11-4.98 (m, 2H), 4.84-4.83 (m, 2H), 3.76-3.71 (m, 1H), 3.43-3.42 (m, 1H), 2.52 (d, J = 1.6 Hz, 2H), 2.25-2.21 (m, 1H), 1.12-1.05 (m, 5H) ppm |
| 12 | 610.1 | 1H NMR (400 MHz, DMSO-d6) δ = 9.75-9.72 (m, 1H), 9.42 (s, 1H), 8.68 (s, 2H), 8.48 (d, J = 1.2 Hz, 1H), 8.27-8.25 (m, 1H), 7.90 (s, 1H), 7.83 (d, J = 7.2 Hz, 1H), 7.72-7.68 (m, 1H), 6.65 (d, J = 8.4 Hz, 1H), 6.31-6.12 (m, 1H), 5.25 (d, J = 14.4 Hz, 1H), 4.95-4.80 (m, 3H), 4.51-4.34 (m, 2H), 4.26-4.20 (m, 1H), 3.58-3.43 (m, 6H), 2.18-2.03 (m, 2H), 1.14-1.10 (m, 3H) ppm |
| 21 | 606.3 | 1HNMR (400 MHz, DMSO-d6) δ = 9.63-9.60 (m, 1H), 9.40 (s, 1H), 8.68-8.61 (m, 2H), 8.46 (s, 1H), 8.24 (s, 1H), 7.92 (d, J = 7.2 Hz, 1H), 7.83 (s, 1H), 7.76-7.72 (m, 1H), 7.03 (d, J = 8.8 Hz, 1H), 6.15-6.05 (m, 1H), 5.21 (d, J = 14.8 Hz, 1H), 4.99 (d, J = 14.8 Hz, 1H), 4.81 (d, J = 6 Hz, 2H), 4.45-4.38 (m, 2H), 4.32-4.30 (m, 2H), 3.70-3.64 (m, 2H), 2.52 (s, 3H), 2.47 (s, 2H), 1.21 (d, J = 4 Hz, 6H) ppm. |
| 23 | 582.3 | 1H NMR (400 MHz, METHANOL-d4) δ = 9.33 (s, 1H), 8.63-8.48 (m, 2H), 8.41 (d, J = 7.6 Hz, 1H), 8.20 (d, J = 8.6 Hz, 1H), 8.10 (br d, J = 9.4 Hz, 1H), 7.95 (s, 1H), 7.43 (d, J = 7.8 Hz, 1H), 6.93-6.48 (m, 1H), 5.88-5.54 (m, 1H), 4.92 (s, 2H), 4.07 (s, 3H) ppm |
| 29 | 591.2 | 1H NMR (400 MHz, DMSO-d6) δ = 9.85-9.65 (m, 1H), 9.53-9.28 (m, 1H), 8.72-8.58 (m, 1H), 8.47 (d, J = 6.4 Hz, 2H), 8.29-8.20 (m, 2H), 7.88 (s, 1H), 7.59-7.38 (m, 1H), 7.16-6.77 (m, 1H), 6.45-6.01 (m, 1H), 5.41-5.12 (m, 1H), 4.90 (d, J = 15.2 Hz, 1H), 4.83 (s, 2H), 4.52-4.40 (m, 4H), 1.40-1.34 (m, 3H) ppm |
| 43 | 618.6 | 1H NMR (400 MHz, DMSO-d6) δ = 9.68-9.65 (m, 1H), 9.42 (s, 1H), 8.71-8.57 (m, 2H), 8.49-8.33 (m, 2H), 8.21 (d, J = 8.8 Hz, 1H), 7.89-7.73 (m, 2H), 7.39-7.37 (m, 1H), 6.84-6.40 (m, 1H), 6.17-5.83 (m, 1H), 5.13 (d, J = 13.6 Hz, 1H), 4.93-4.76 (m, 3H), 4.01 (s, 3H), 3.74-3.69 (m, 1H), 3.48-3.36 (m, 1H), 2.44-2.38 (m, 2H), 1.85-1.75 (m, 3H) ppm |
| 44 | 591.3 | 1H NMR (400 MHz, DMSO-d6) δ = 9.80-9.72 (m, 1H), 9.41 (s, 1H), 8.63 (d, J = 8.8 Hz, 1H), 8.48-8.45 (m, 1H), 8.41 (d, J = 8.0 Hz, 1H), 8.27-8.24 (m, 1H), 8.20 (d, J = 8.8 Hz, 1H), 7.86 (s, 1H), 7.33 (d, J = 7.6 Hz, 1H), 6.31-6.12 (m, 1H), 6.06-5.80 (m, 1H), 5.24 (d, J = 14.4 Hz, 1H), 5.09-4.86 (m, 3H), 4.82 (d, J = 5.6 Hz, 2H), 4.51-4.32 (m, 2H), 4.00 (s, 3H) ppm |
| 46 | 591.2 | 1H NMR (400 MHz, DMSO-d6) δ = 9.83-9.74 (m, 1H), 9.41 (s, 1H), 8.63 (d, J = 8.8 Hz, 1H), 8.47 (s, 1H), 8.42 (d, J = 7.6 Hz, 1H), 8.27 (d, J = 9.6 Hz, 1H), 8.21 (d, J = 8.8 Hz, 1H), 7.86 (s, 1H), 7.33 (d, J = 7.6 Hz, 1H), 6.34-6.13 (m, 1H), 6.07-5.77 (m, 1H), 5.24 (d, J = 14.4 Hz, 1H), 5.10-4.86 (m, 3H), 4.82 (d, J = 5.6 Hz, 2H), 4.53-4.32 (m, 2H), 4.00 (s, 3H) ppm |
| 53 | 577.2 | 1H NMR (400 MHz, DMSO-d6) δ = 9.76-9.73 (m, 1H), 9.42 (s, 1H), 8.65 (d, J = 8.8 Hz, 1H), 8.46-8.45 (m, 2H), 8.27-8.20 (m, 2H), 7.87 (s, 1H), 7.48 (d, J = 7.6 Hz, 1H), 7.12-6.84 (m, 1H), 6.21-6.15 (m, 1H), 5.24 (d, J = 14.4 Hz, 1H), 4.91-4.82 (m, 3H), 4.47-4.39 (m, 2H), 4.01 (s, 3H) ppm |
| 54 | 614.1 | 1H NMR (400 MHz, DMSO-d6) δ = 9.74-9.72 (m, 1H), 9.39 (s, 1H), 8.73-8.63 (m, 2H), 8.48 (d, J = 1.2 Hz, 1H), 8.28-8.25 (m, 1H), 7.91-7.84 (m, 2H), 7.74-7.70 (m, 1H), 6.70 (d, J = 8.0 Hz, 1H), 6.31-6.14 (m, 1H), 5.48-5.30 (m, 1H), 5.25 (d, J = 14.8 Hz, 1H), 5.22-4.87 (m, 1H), 4.82 (d, J = 5.6 Hz, 2H), 4.48 (s, 1H), 4.45-4.34 (m,1H), 4.23-4.15 (m, 1H), 3.93-3.84 (m, 1H), 3.94-3.77 (m, 1H), 3.84-3.76 (m, 1H), 3.75-3.70 (m, 2H), 3.40 (s, 3H), 2.68-2.64 (m, 2H), 2.35-2.30 (m, 2H) ppm. |
| 64 | 642.2 | 1H NMR (400 MHz, DMSO-d6) δ = 9.86-9.85 (m, 1H), 9.40 (s, 1H), 8.78 (s, 1H), 8.68-8.59 (m, 3H), 7.93-7.87 (m, 2H), 7.76-7.72(m, 1H), 7.66-7.39 (m, 1H), 7.03 (d, J = 8.4 Hz, 1H), 6.28-6.17 (m, 1H), 5.30-5.07 (m, 2H), 4.84 (d, J = 5.6 Hz, 2H), 4.51-4.44 (m, 2H), 4.31 (d, J = 11.6 Hz, 2H), 3.71-3.64 (m, 2H), 2.52 (s, 2H), 1.21 (d, J = 6.0Hz, 6H) ppm |
| 73 | 577.2 | 1H NMR (400 MHz, DMSO-d6) δ = 9.77-9.74 (m, 1H), 9.42 (s, 1H), 8.68 (d, J = 8.8 Hz, 1H), 8.47 (s, 1H), 8.35 (d, J = 7.6 Hz, 1H), 8.29-8.24 (m, 1H), 8.07 (d, J = 8.8 Hz, 1H), 8.02-7.61 (m, 2H), 7.33 (d, J = 7.6 Hz, 1H), 6.44-6.07 (m, 1H), 5.24 (d, J = 14.8 Hz, 1H), 4.96-4.77 (m, 3H), 4.54-4.31 (m, 2H), 2.53 (s, 3H) ppm |
| 75 | 591.2 | 1H NMR (400 MHz, DMSO-d6) δ = 9.77-9.75 (m, 1H), 9.44-9.43 (m, 1H), 8.65 (d, J = 8.8 Hz, 1H), 8.46 (d, J = 8.4 Hz, 2H),8.28-8.21 (m, 2H), 7.87 (s, 1H), 7.48 (d, J = 7.6 Hz, 1H), 6.27-6.16 (m, 1H), 5.25 (d, J = 14.4 Hz, 1H), 4.92-4.82 (m, 3H), 4.48-4.39 (m, 2H), 4.02 (s, 3H), 2.01-2.00 (m, 3H) ppm |
| 77 | 537.2 | 1HNMR (400 MHz, DMSO-d6) δ = 9.75-9.72 (m, 1H), 9.36 (s, 1H), 9.16 (s, 1H), 8.72 (s, 1H), 8.66 (s, 1H), 8.49 (d, J = 1.2 Hz, 1H), 8.41 (d, J = 1.2 Hz, 1H), 8.39-8.32 (m, 1H), 8.31-8.22 (m, 1H), 7.90 (s, 1H), 6.35-6.08 (m, 1H), 5.26 (d, J =14.8 Hz, |

TABLE 3-continued

Compounds of the Invention

| # | LCMS (ESI/ M + H) | ¹HNMR |
|---|---|---|
| | | 1H), 4.92-4.88 (m, 1H), 4.80 (d, J = 5.6 Hz, 2H), 4.48-4.36 (m, 2H), 2.32-2.25 (m, 1H), 1.17-1.09 (m, 4H) ppm |
| 79 | 626.2 | 1H NMR (400 MHz, DMSO-d6) δ = 9.77-9.74 (m, 1H), 9.40 (s, 1H), 8.68-8.61 (m, 2H), 8.57-8.49 (m, 2H), 7.93-7.87 (m, 2H), 7.77-7.73 (m, 1H), 7.03 (d, J = 8.4 Hz, 1H), 6.29-6.17 (m, 1H), 5.41 (d, J = 14.4 Hz, 1H), 5.09 (d, J = 14.4 Hz, 1H), 4.82 (d, J = 6 Hz, 2H), 4.49-4.42 (m, 2H), 4.32 (d, J = 11.2 Hz, 2H), 3.70-3.65 (m, 2H), 2.54-2.53 (m, 2H), 1.22 (d, J = 4.0 Hz, 6H) ppm |
| 85 | 603.2 | 1H NMR (400 MHz, CHLOROFORM-d) δ = 9.31 (s, 1H), 8.71 (d, J = 8.8 Hz, 1H), 8.50 (d, J = 8.4 Hz, 1H), 8.46-8.40 (m, 2H), 8.12-8.05 (m, 2H), 8.04-7.96 (m, 1H), 7.59 (d, J = 8.4 Hz, 1H), 6.84-6.48 (m, 1H), 5.39 (d, J = 14.0 Hz, 2H), 5.04 (d, J = 5.2 Hz, 2H), 4.98-4.94 (m, 1H), 4.53-4.44 (m, 2H), 2.56-2.50 (m, 1H), 1.29 (br s, 2H), 1.14-1.11 (m, 2H) ppm |
| 95 | 608.3 | 1H NMR (400 MHz, DMSO-d6) δ = 9.80-9.77 (m, 1H), 9.42 (s, 1H), 8.69 (d, J = 8.8 Hz, 1H), 8.56 (d, J = 8.8 Hz, 1H), 8.50-8.45 (m, 2H), 8.42 (d, J = 8.8 Hz, 1H), 8.29-8.27 (m, 1H), 7.88 (s, 1H), 7.76 (d, J = 8.8 Hz, 1H), 7.66-7.19 (m, 1H), 6.29-6.17 (m, 1H), 4.87-4.79 (m, 2H), 2.41-2.38 (m, 1H), 1.24-1.16 (m, 2H), 1.15-1.07 (m, 2H) ppm |
| 103 | 580.0 | 1H NMR (400 MHz, DMSO-d6) δ = 9.77-9.74 (m, 1H), 9.43 (s, 1H), 8.65 (d, J = 8.4 Hz, 1H), 8.47-8.44 (m, 2H), 8.27-8.20 (m, 2H), 7.87 (s, 1H), 7.48 (d, J = 7.6 Hz, 1H), 7.12-6.84 (m, 1H), 6.27-6.16 (m, 1H), 5.26 (d, J = 14.8 Hz, 1H), 4.91-4.82 (m, 3H), 4.47-4.39 (m, 2H) ppm |
| 111 | 552.2 | 1H NMR (400 MHz, DMSO-d6) δ = 9.75-9.73 (m, 1H), 9.39 (d, J = 0.4 Hz, 1H), 8.69-8.57 (m, 2H), 8.48 (d, J = 1.6 Hz, 1H), 8.28-8.25 (m, 1H), 7.91-7.84 (m, 2H), 7.72-7.68 (m, 1H), 6.58-6.50 (m, 1H), 6.30-6.13 (m, 1H), 5.25 (d, J = 14.4 Hz, 1H), 4.92-4.88 (m, 1H), 4.82 (d, J = 5.6 Hz, 2H), 4.49-4.35 (m, 2H), 4.08-4.04 (m, 4H), 2.41-2.36 (m, 2H) ppm |
| 114 | 537.2 | 1H NMR (400 MHz, DMSO-d6) δ = 9.76-9.73 (m, 1H), 9.41 (s, 1H), 8.72-8.66 (m, 1H), 8.64-8.59 (m, 1H), 8.48 (s, 1H), 8.35 (d, J = 8.0 Hz, 1H), 8.27 (d, J = 9.2 Hz, 1H), 7.91-7.81 (m, 2H), 7.47 (d, J = 7.6 Hz, 1H), 6.32-6.10 (m, 1H), 5.25 (d, J = 14.4 Hz, 1H), 4.92-4.88 (m, 1H), 4.83 (d, J = 5.6 Hz, 2H), 4.48 (s, 1H), 4.46-4.35 (m, 1H), 2.27-2.21 (m, 1H), 1.13-1.02 (m, 4H) ppm |
| 118 | 536.3 | 1H NMR (400 MHz, DMSO-d6) δ = 9.72-9.69 (m, 1H), 9.32 (s, 1H), 8.62 (s, 1H), 8.48 (d, J = 1.2 Hz, 1H), 8.41 (s, 1H), 8.38-8.32 (m, 1H), 8.30-8.24 (m, 1H), 8.20 (d, J = 8.8 Hz, 1H), 7.92-7.85 (m, 2H), 7.81-7.79 (m, 1H), 7.33 (d, J = 7.6 Hz, 1H), 6.29-6.14 (m, 1H), 5.26-5.23 (m, 1H), 4.90 (d, J = 15.6 Hz, 1H), 4.78 (d, J = 6.0 Hz, 2H), 4.48 (S, 1H), 4.45-4.34 (m, 1H), 2.23-2.15 (m, 1H), 1.09-1.06 (m, 2H), 1.04-0.98 (m, 2H) ppm |
| 127 | 595.1 | 1H NMR (400 MHz, DMSO-d6) δ = 9.80-9.72 (m, 1H), 9.45 (s, 1H), 8.68 (d, J = 8.8 Hz, 1H), 8.54-8.45 (m, 2H), 8.30-8.19 (m, 2H), 7.89 (s, 1H), 7.68 (d, J = 7.6 Hz, 1H), 6.31-6.13 (m, 1H), 5.24 (d, J = 14.4 Hz, 1H), 4.95-4.80 (m, 3H), 4.52-4.31 (m, 2H), 4.03 (s, 3H) ppm |
| 128 | 573.2 | 1H NMR (400 MHz, DMSO-d6) δ = 9.78-9.75 (m, 1H), 9.44 (s, 1H), 8.75-8.66 (m, 2H), 8.55-8.46 (m, 2H), 8.32-8.25 (m, 1H), 8.02-7.98 (m, 1H), 7.91 (s, 1H), 7.65 (d, J = 8.0 Hz, 1H), 6.29-6.17 (m, 1H), 5.26 (d, J = 14.8 Hz, 1H), 4.94-4.89 (m, 1H), 4.85 (d, J = 5.6 Hz, 2H), 4.50-4.37 (m, 2H), 3.42-3.40 (m, 1H), 2.64-2.57 (m, 1H), 2.17-2.08 (m, 1H) ppm |
| 131 | 573.2 | 1H NMR (400 MHz, DMSO-d6) δ = 9.66-9.63 (m, 1H), 9.43 (s, 1H), 8.65 (d, J = 8.8 Hz, 1H), 8.46-8.45 (m, 2H), 8.24-8.20 (m, 2H), 7.83 (s, 1H), 7.47 (d, J = 8.0 Hz, 1H), 7.12-6.85 (m, 1H), 6.16-6.06 (m, 1H), 5.22-4.95 (m, 2H), 4.82 (br d, J = 5.6 Hz, 2H), 4.45-4.37 (m, 2H), 4.01 (s, 3H), 2.51 (br s, 3H) ppm |
| 137 | 576.2 | 1H NMR (400 MHz, DMSO-d6) δ = 9.72-9.69 (m, 1H), 9.33 (s, 1H), 8.46 (d, J = 1.2 Hz, 1H), 8.27 (s, 1H), 8.19-8.17 (m, 2H), 8.07 (d, J = 7.6 Hz, 1H), 7.87-7.82 (m, 2H), 7.44 (d, J = 7.6 Hz, 1H), 7.09-6.81 (m, 1H), 6.26-6.15 (m, 1H), 5.26 (d, J = 14.8 Hz, 1H), 4.91-4.87 (m, 1H), 4.78 (br d, J = 5.6 Hz, 2H), 4.47-4.38 (m, 2H), 3.94 (s, 3H) ppm. |
| 144 | 603.2 | 1H NMR (400 MHz, DMSO-d6) δ = 9.83-9.68 (m, 1H), 9.38 (s, 1H), 8.71-8.45 (m, 4H), 8.27 (d, J = 10.4 Hz, 1H), 7.86 (s, 1H), 7.70-7.59 (m, 1H), 6.33-6.12 (m, 1H), 5.25 (d, J = 14.4 Hz, 1H), 4.97-4.76 (m, 3H), 4.55-4.33 (m, 2H), 3.98 (s, 3H), 3.38-3.33 (m, 1H), 2.39-2.36 (m, 1H), 2.10-2.04 (m, 1H) ppm |
| 158 | 544.2 | 1H NMR (400 MHz, DMSO-d6) δ = 9.75-9.73 (m, 1H), 9.37 (s, 1H), 8.55 (d, J = 8.0 Hz, 1H), 8.47 (d, J = 1.2 Hz, 1H), 8.27-8.24 (m, 1H), 8.06 (d, J = 8.4 Hz, 1H), 7.93-7.80 (m, 2H), 7.14-7.12 (m, 1H), 6.94-6.93 (m, 1H), 6.32-6.11 (m, 1H), 5.24 (d, J = 14.4 Hz, 1H), 4.87 (d, J = 2.0 Hz, 1H), 4.81 (d, J = 6.0 Hz, 2H), 4.51-4.35 (m, 2H), 3.89 (s, 3H) ppm. |
| 167 | 595.2 | 1H NMR (400 MHz, DMSO-d6) δ = 9.68-9.65 (m, 1H), 9.28 (s, 1H), 8.73-8.71 (m, 1H), 8.50 (d, J = 7.6 Hz, 1H), 8.41 (s, 1H), 8.33 (d, J = 8.8 Hz, 1H), 8.18 (d, J = 9.6 Hz, 1H), 7.54 (d, J = 7.6 Hz, 1H), 7.18-6.81 (m, 1H), 6.27-6.13 (m, 1H), 5.25-5.19 (m, 1H), 4.90-4.83 (m, 3H), 4.46 (br s, 1H), 4.44-4.32 (m, 1H), 4.04 (s, 3H) ppm |

TABLE 3-continued

Compounds of the Invention

| # | LCMS (ESI/ M + H) | ¹HNMR |
|---|---|---|
| 170 | 541.1 | 1H NMR (400 MHz, DMSO-d6) δ = 9.78-9.76 (m, 1H), 9.42 (s, 1H), 8.75-8.68 (m, 1H), 8.67-8.60 (m, 1H), 8.48 (s, 1H), 8.29-8.26 (m, 1H), 8.21 (d, J = 7.6 Hz, 1H), 7.95-7.84 (m, 2H), 6.98 (d, J = 8.0 Hz, 1H), 6.34-6.07 (m, 1H), 5.25 (d, J = 14.4 Hz, 1H), 4.95-4.87 (m, 1H), 4.83 (d, J = 4.8 Hz, 2H), 4.56-4.47 (m, 3H), 4.46-4.35 (m, 1H), 1.43-1.39 (m, 3H) ppm |
| 174 | 589.2 | 1H NMR (400 MHz, DMSO-d6) δ = 9.77 (br t, J = 5.7 Hz, 1H), 9.40 (s, 1H), 8.66-8.54 (m, 2H), 8.49 (d, J = 1.6 Hz, 1H), 8.39 (d, J = 7.6 Hz, 1H), 8.21 (d, J = 8.7 Hz, 1H), 7.87 (s, 1H), 7.27 (d, J = 7.6 Hz, 1H), 6.36-6.08 (m, 1H), 5.84-5.59 (m, 1H), 5.41 (d, J = 14.8 Hz, 1H), 5.09 (d, J = 14.7 Hz, 1H), 4.82 (br d, J = 5.6 Hz, 2H), 4.57-4.32 (m, 2H), 4.00 (s, 3H), 1.72-1.62 (m, 3H) ppm |
| 193 | 541.2 | 1H NMR (400 MHz, DMSO-d6) δ = 9.76-9.73 (m, 1H), 9.37 (s, 1H), 8.58 (d, J = 8.8 Hz, 1H), 8.47 (s, 1H), 8.29-8.23 (m, 2H), 8.20 (d, J = 8.8 Hz, 1H), 7.84 (s, 1H), 7.05 (d, J = 7.6 Hz, 1H), 6.31-6.13 (m, 1H), 5.24 (d, J = 14.8 Hz, 1H), 4.89 (d, J = 15.2 Hz, 1H), 4.81 (d, J = 5.6 Hz, 2H), 4.49-4.33 (m, 2H), 3.98 (s, 3H), 2.53 (s, 3H) ppm |
| 195 | 574.2 | 1H NMR (400 MHz, DMSO-d6) δ = 9.79-9.76 (m, 1H), 9.51 (s, 1H), 9.01 (d, J = 5.2 Hz, 1H), 8.82 (d, J = 8.8 Hz, 1H), 8.71 (d, J = 8.8 Hz, 1H), 8.48-8.45 (m, 2H), 8.41-8.39 (m, 1H), 8.26 (s, 1H), 7.96 (s, 1H), 6.28-6.17 (m, 1H), 5.25 (d, J = 14.8 Hz, 1H), 4.92-4.84 (m, 3H), 4.48-4.39 (m, 2H), 3.42-3.39 (m, 1H), 2.25-2.17 (m, 1H) ppm |
| 205 | 563.2 | 1H NMR (400 MHz, DMSO-d6) δ = 9.78-9.75 (m, 1H), 9.45 (s, 1H), 8.85-8.72 (m, 1H), 8.66 (d, J = 8.8 Hz, 1H), 8.52-8.42 (m, 2H), 8.32-7.85 (m, 4H), 7.27 (d, J = 8.0 Hz, 1H), 6.32-6.16 (m, 1H), 5.25 (d, J = 14.8 Hz, 1H), 4.95-4.80 (m, 3H), 4.53-4.34 (m, 2H) ppm |
| 221 | 593.2 | 1H NMR (400 MHz, DMSO-d6) δ = 9.79-9.76 (m, 1H), 9.42 (s, 1H), 8.65 (d, J = 8.4 Hz, 1H), 8.56 (d, J = 1.2 Hz, 1H), 8.49 (d, J = 1.6 Hz, 1H), 8.46 (d, J = 7.6 Hz, 1H), 8.21 (d, J = 8.8 Hz, 1H), 7.88 (s, 1H), 7.48 (d, J = 7.6 Hz, 1H), 7.11-6.84 (m, 1H), 6.27-6.17 (m, 1H), 5.42 (d, J = 14.8 Hz, 1H), 5.10 (d, J = 14.4 Hz, 1H), 4.83 (d, J = 5.6 Hz, 2H), 4.48 (br d, J = 2.8 Hz, 1H), 4.44-4.37 (m, 1H), 4.01 (s, 3H) ppm |
| 225 | 579.1 | 1H NMR (400 MHz, DMSO-d6) δ = 9.80-9.77 (m, 1H), 9.45 (s, 1H), 8.81-8.72 (m, 1H), 8.67 (d, J = 8.8 Hz, 1H), 8.58 (d, J = 1.6 Hz, 1H), 8.51 (d, J = 1.6 Hz, 1H), 8.49-8.45 (m, 1H), 8.27-7.89 (m, 3H), 7.27 (d, J = 7.6 Hz, 1H), 6.34-6.10 (m, 1H), 5.41 (d, J = 14.8 Hz, 1H), 5.09 (d, J = 14.8 Hz, 1H), 4.84 (d, J = 5.6 Hz, 2H), 4.55-4.38 (m, 2H) ppm. |
| 228 | 553.2 | 1H NMR (400 MHz, DMSO-d6) δ = 9.76-9.73 (m, 1H), 9.46 (s, 1H), 8.75 (d, J = 8.8 Hz, 1H), 8.63-8.52 (m, 2H), 8.48 (s, 1H), 8.28-8.25 (m, 1H), 7.92 (s, 1H), 7.72 (d, J = 5.2 Hz, 1H), 6.30-6.15 (m, 1H), 5.25 (d, J = 14.4 Hz, 1H), 4.95-4.87 (m, 1H), 4.84 (d, J = 5.6 Hz, 2H), 4.50-4.34 (m, 2H), 4.18-4.14 (m, 4H), 2.42-2.34 (m, 2H) ppm |
| 234 | 609.1 | 1H NMR (400 MHz, DMSO-d6) δ = 9.90-9.86 (m, 1H), 9.43 (s, 1H), 8.78 (s, 1H), 8.66-8.59 (m, 2H), 8.46 (d, J = 7.6 Hz, 1H), 8.21 (d, J = 8.4 Hz, 1H), 7.87 (s, 1H), 7.66-7.39 (m, 2H), 7.12-6.84 (m, 1H), 6.28-6.17 (m, 1H), 5.29-5.07 (m, 2H), 4.84 (d, J = 5.6 Hz, 2H), 4.51-4.36 (m, 2H), 4.01 (s, 3H) ppm |
| 238 | 538.2 | 1H NMR (400 MHz, DMSO-d6) δ = 9.78-9.76 (m, 1H), 9.47 (d, J = 3.6 Hz, 2H), 8.79-8.76 (m, 2H), 8.57-8.48 (m, 2H), 8.29-8.26 (m, 1H), 7.94 (s, 1H), 6.28-6.17 (m, 1H), 5.25 (d, J = 14.4 Hz, 1H), 4.92-4.83 (m, 3H), 4.48-4.40 (m, 2H), 2.38-2.34 (m, 1H), 1.16-1.14 (m, 4H) ppm |
| 242 | 589.2 | 1H NMR (400 MHz, DMSO-d6) δ = 9.78-7.75 (m, 1H), 9.40 (s, 1H), 8.61 (d, J = 8.7 Hz, 1H), 8.56 (d, J = 1.6 Hz, 1H), 8.49 (d, J = 1.6 Hz, 1H), 8.39 (d, J = 7.6 Hz, 1H), 8.21 (d, J = 8.8 Hz, 1H), 7.86 (s, 1H), 7.27 (d, J = 7.6 Hz, 1H), 6.34-6.07 (m, 1H), 5.87-5.59 (m, 1H), 5.41 (d, J = 14.8 Hz, 1H), 5.08 (d, J = 14.8 Hz, 1H), 4.82 (d, J = 5.8 Hz, 2H), 4.53-4.38 (m, 2H), 4.00 (s, 3H), 1.76-1.58 (m, 3H) ppm |
| 251 | 623.00 | 1H NMR (400 MHz, METHANOL-d4) δ = 9.34 (s, 1H), 8.58-8.52 (m, 2H), 8.38 (d, J = 7.8 Hz, 1H), 8.21 (d, J = 8.6 Hz, 1H), 8.12-8.09 (m, 1H), 7.95 (s, 1H), 7.40-7.38 (m, 1H), 6.52-6.11 (m, 1H), 5.79-5.65 (m, 1H), 5.35 (d, J = 14.4 Hz, 1H), 5.00-4.96 (m, 1H), 4.92 (s, 2H), 4.51-4.47 (m, 1H), 4.44-4.43 (m, 1H), 4.05 (s, 3H), 1.86-1.77 (m, 3H) ppm |
| 253 | 573.2 | 1H NMR (400 MHz, DMSO-d6) δ = 9.79-9.76 (m, 1H), 9.44 (s, 1H), 8.83-8.60 (m, 2H), 8.57-8.46 (m, 2H), 8.30-8.27 (m, 1H), 8.02-7.98 (m, 1H), 7.92 (s, 1H), 7.65 (d, J = 8.0 Hz, 1H), 6.34-6.11 (m, 1H), 5.26 (d, J = 14.8 Hz, 1H), 4.97-4.80 (m, 3H), 4.55-4.33 (m, 2H), 3.40-3.36 (m, 1H), 2.57-2.53 (m, 1H), 2.21-2.03 (m, 1H) ppm |
| 270 | 527.1 | 1HNMR (400 MHz, DMSO-d6) δ = 9.76-9.74 (m, 1H), 9.42 (s, 1H), 8.75-8.64 (m, 2H), 8.48 (d, J = 1.2 Hz, 1H), 8.26-8.21 (m, 1H), 8.23 (d, J = 7.2 Hz, 1H), 7.96-7.86 (m, 2H), 7.01 (d, J = 8.4 Hz, 1H), 6.37-6.06 (m, 1H), 5.25 (d, J = 14.6 Hz, 1H), 4.92-4.91 (m, 1H), 4.83 (d, J = 6.0 Hz, 2H), 4.51-4.34 (m, 2H), 4.04 (s, 3H) ppm |
| 280 | 603.2 | 1H NMR (400 MHz, DMSO-d6) δ = 9.81-9.65 (m, 1H), 9.38 (s, 1H), 8.67-8.61 (m, 2H), 8.55 (d, J = 8.8 Hz, 1H), 8.48 (s, 1H), 8.30-8.25 |

TABLE 3-continued

Compounds of the Invention

| # | LCMS (ESI/ M + H) | ¹HNMR |
|---|---|---|
|  |  | (m, 1H), 7.86 (s, 1H), 7.66 (d, J = 8.8 Hz, 1H), 6.30-6.14 (m, 1H), 5.25 (d, J = 14.4 Hz, 1H), 4.92-4.88 (m, 1H), 4.83 (d, J = 4.0 Hz, 2H), 4.48 (s, 1H), 4.46-4.35 (m, 1H), 3.98 (s, 3H), 3.38-3.34 (m, 1H), 2.38-2.36 (m, 1H), 2.10-2.04 (m, 1H) ppm |
| 290 | 564.2 | 1H NMR (400 MHz, DMSO-d6) δ = 9.81-9.79 (m, 1H), 9.50 (s, 1H), 8.97 (d, J = 5.2 Hz, 1H), 8.83 (d, J = 8.4 Hz, 1H), 8.70 (d, J = 8.4 Hz, 1H), 8.48 (s, 1H), 8.45 (br s, 1H), 8.40 (d, J = 5.2 Hz, 1H), 8.29-8.26 (m, 1H), 7.94 (s, 1H), 6.28-6.17 (m, 1H), 5.27 (d, J = 14.8 Hz, 1H), 4.91-4.88 (m, 1H), 4.85 (d, J = 5.6 Hz, 2H), 4.48-4.36(m, 2H), 2.60 (s, 1H), 2.26 (s, 6H) ppm |
| 294 | 619.2 | 1H NMR (400 MHz, DMSO-d6) δ = 9.77-9.38 (m, 1H), 9.39 (s, 1H), 8.68-8.61 (m, 2H), 8.60-8.54 (m, 2H), 8.51 (d, J = 1.6 Hz, 1H), 7.88 (s, 1H), 7.67 (d, J = 8.8 Hz, 1H), 6.34-6.16 (m, 1H), 5.42 (d, J = 14.4 Hz, 1H), 5.10 (d, J = 14.4 Hz, 1H), 4.83 (d, J = 5.6 Hz, 2H), 4.52-4.42 (m, 2H), 3.99 (s, 3H), 3.40-3.34 (m, 1H), 2.66-2.58 (m, 1H), 2.13-2.03 (m, 1H) ppm |
| 297 | 562.2 | 1H NMR (400 MHz, DMSO-d6) δ = 9.76-9.73 (m, 1H), 9.41 (s, 1H), 8.69 (d, J = 8.8 Hz, 1H), 8.47 (s, 1H), 8.33 (d, J = 8.4 Hz, 1H), 8.26 (d, J = 10.4 Hz, 1H), 8.19 (d, J = 7.6 Hz, 1H), 8.10 (s, 1H), 7.92-7.82 (m, 1H), 7.65-7.61 (m, 1H), 7.57-7.17 (m, 2H), 6.33-6.10 (m, 1H), 5.25 (d, J = 14.4 Hz, 1H), 4.95-4.68 (m, 3H), 4.53-4.32 (m, 2H) ppm |
| 301 | 593.2 | 1H NMR (400 MHz, DMSO-d6) δ = 9.80-9.77 (m, 1H), 9.45 (s, 1H), 8.77-8.67 (m, 2H), 8.58-8.51 (m, 2H), 8.34 (br d, J = 7.6 Hz, 1H), 8.15 (br d, J = 7.6 Hz, 1H), 7.92 (s, 1H), 7.29-7.02 (m, 1H), 6.28-6.18 (m, 1H), 5.43 (br d, J = 14.8 Hz, 1H), 5.07 (br d, J = 14.4 Hz, 1H), 4.84 (br d, J = 4.8 Hz, 2H), 4.49-4.38 (m, 2H), 4.14 (s, 3H) ppm |
| 302 | 553.1 | 1H NMR (400 MHz, DMSO-d6) δ = 9.79-9.73 (m, 1H), 9.41 (s, 1H), 8.72-8.66 (m, 1H), 8.64-8.60 (m, 1H), 8.58 (d, J =1.2 Hz, 1H), 8.50 (d, J = 1.2 Hz, 1H), 8.35 (d, J = 7.6 Hz, 1H), 7.91-7.82 (m, 2H), 7.47 (d, J = 7.6 Hz, 1H), 6.30-6.15 (m, 1H), 5.41 (d, J = 14.8 Hz, 1H), 5.09 (d, J = 14.8 Hz, 1H), 4.83-4.82 (m, 2H), 4.51-4.39 (m, 2H), 2.27-2.20 (m, 1H), 1.12-1.03 (m, 4H) ppm |
| 307 | 581.2 | 1H NMR (400 MHz, DMSO-d6) δ = 9.80-9.77 (m, 1H), 9.46 (s, 1H), 8.78 (d, J = 8.4 Hz, 1H), 8.62 (d, J = 7.6 Hz, 1H), 8.51-8.49 (m, 2H), 8.29-8.22 (m, 1H), 7.92 (s, 1H), 7.49 (d, J = 8.0 Hz, 1H), 6.28-6.18 (m, 1H), 5.25 (d, J = 14.4 Hz, 1H), 4.92-4.84 (m, 3H), 4.48-4.39 (m, 2H) ppm |

Preparation of Intermediate 2 (4R)-4,9-difluoro-5,5-dioxo-3,4-dihydro-2H-1,5λ6-benzoxathiepine-7-carboxylic Acid

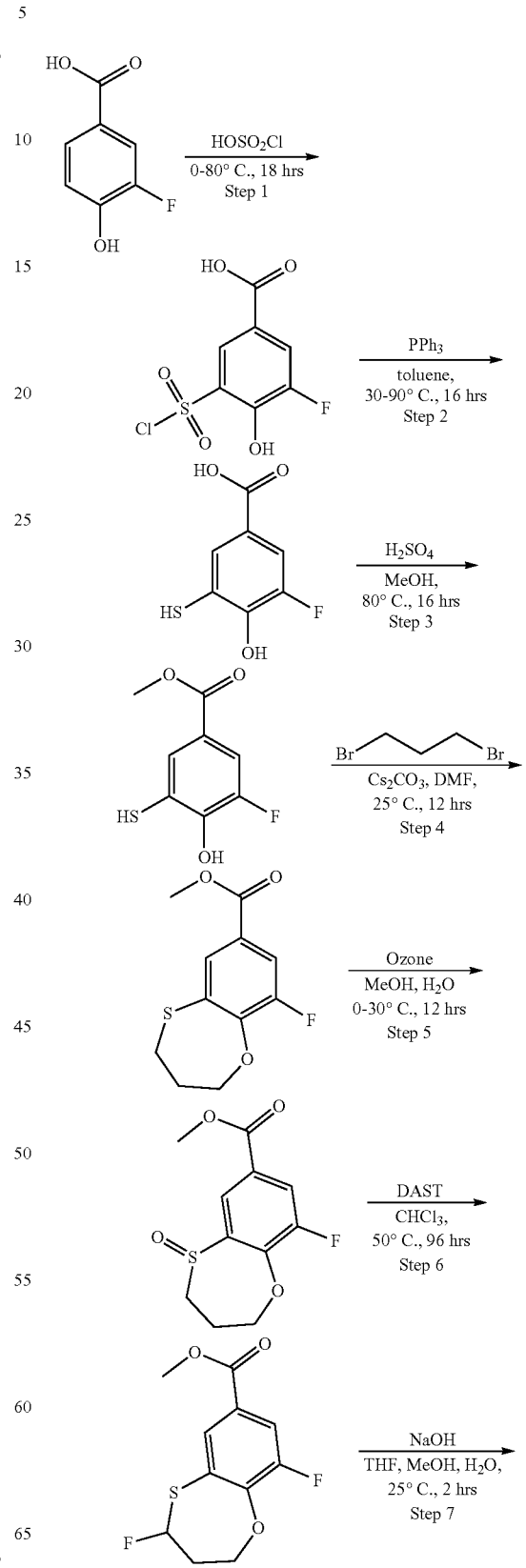

-continued

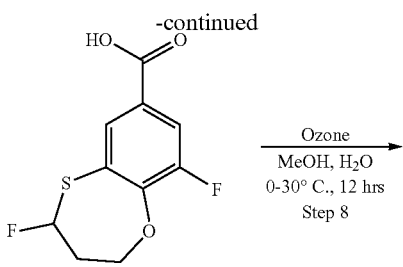

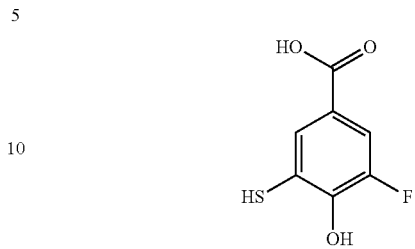

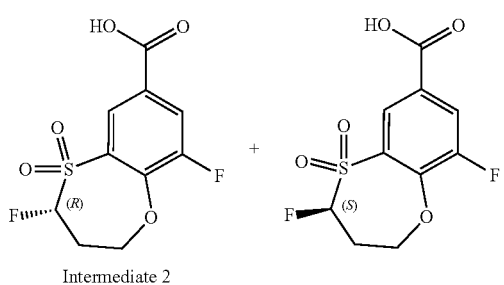

Intermediate 2

Step 1: Preparation of 3-chlorosulfonyl-5-fluoro-4-hydroxy-benzoic Acid

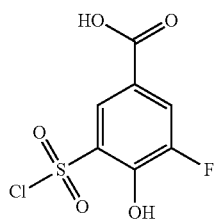 [SMILES: O=C(O)c1cc(F)c(O)c(S(=O)(=O)Cl)c1]

To the solution of HOSO$_2$Cl (175.00 g, 1.50 mol, 100 mL) was added 3-fluoro-4-hydroxy-benzoic acid (12 g, 76.87 mmol) in 10 portions at 0° C. The mixture was stirred at 30° C. for 16 hrs and then stirred at 80° C. for 2 hrs. The reaction solution was added to ice water (100 mL) dropwise. The mixture was filtrated, the filter cake was washed with water (3*10 mL) and dried in vacuo to give 3-chlorosulfonyl-5-fluoro-4-hydroxy-benzoic acid (15 g, 55.97 mmol, 72.81% yield) as a yellow solid. 1H NMR (400 MHz, DMSO-d$_6$) δ=11.52-11.09 (m, 1H), 7.90-7.85 (m, 1H), 7.65-7.62 (m, 1H) ppm.

Step 2: Preparation of 3-fluoro-4-hydroxy-5-sulfanyl-benzoic Acid

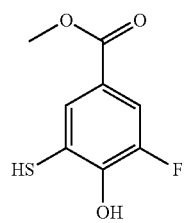

To a solution of 3-chlorosulfonyl-5-fluoro-4-hydroxy-benzoic acid (15 g, 58.91 mmol) in Toluene (300 mL) was added PPh$_3$ (54.08 g, 206.19 mmol) at 30° C., the mixture was stirred at 90° C. for 16 hrs. The reaction mixture was quenched by addition sat·NaHCO$_3$ (100 mL) and extracted with MTBE (100 mL*3). The aqueous layer was adjusted by 12N HCl to pH=3 and extracted with EA (100 mL*3). The EA layers were dried over Na$_2$SO$_4$, filtered and concentrated under reduced pressure to give 3-fluoro-4-hydroxy-5-sulfanyl-benzoic acid (8.5 g, 45.17 mmol, 76.68% yield) as a white solid. $^1$H NMR (400 MHz, DMSO-d$_6$) δ=12.96-12.89 (m, 1H), 11.57-11.51 (m, 1H), 7.82-7.74 (m, 1H), 7.61-7.42 (m, 1H) ppm.

Step 3: Preparation of methyl 3-fluoro-4-hydroxy-5-sulfanyl-benzoate

To a solution of 3-fluoro-4-hydroxy-5-sulfanyl-benzoic acid (8 g, 42.51 mmol) in MeOH (80 mL) was added H$_2$SO$_4$ (14.72 g, 150.08 mmol, 8 mL). The mixture was stirred at 80° C. for 16 hrs. The reaction mixture was concentrated under reduced pressure to remove MeOH. The residue was diluted with H$_2$O (100 mL). Adjusted the pH to 3 with a.q NaHCO$_3$ and extracted with EA (100 mL*3). The combined organic layers were dried over Na$_2$SO$_4$, filtered, and concentrated under reduced pressure to give a residue. The residue was purified by flash silica gel chromatography (ISCO®; 80 g SepaFlash® Silica Flash Column, Eluent of. 0~100% Ethylacetate/Petroleum ether gradient @ 100 mL/min), the eluent was concentrated under to reduced pressure give 3-fluoro-4-hydroxy-5-sulfanyl-benzoate (8 g, 19.78 mmol, 93.06% yield) as a white solid. LCMS (ESI) m/z: [M+H]$^+$=202.9. $^1$H NMR (400 MHz, DMSO-d$_6$) δ=12.27-11.29 (m, 1H), 7.86-7.78 (m, 1H), 7.65-7.43 (m, 1H), 3.81 (d, J=8.4 Hz, 3H) ppm.

Step 4: Preparation of methyl 9-fluoro-3,4-dihydro-2H-1,5-benzoxathiepine-7-carboxylate

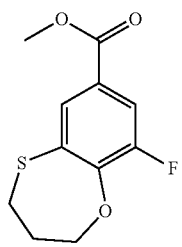 [SMILES: COC(=O)c1cc(F)c2c(c1)SCCCO2]

To a solution of methyl 3-fluoro-4-hydroxy-5-sulfanyl-benzoate (7 g, 34.62 mmol) and 1,3-dibromopropane (6.99 g, 34.62 mmol, 3.53 mL) in DMF (350 mL) was added $Cs_2CO_3$ (56.40 g, 173.09 mmol). The mixture was stirred at 25° C. for 12 hrs. The mixture was diluted with $H_2O$ (200 mL) and extracted with MTBE (200 mL*2). The combined organic layers were dried over anhydrous $Na_2SO_4$, filtered, and concentrated to afford the residue. The residue was purified by column chromatography ($SiO_2$, Petroleum ether/Ethyl acetate=1/0 to 5/1). The eluent was concentrated to afford methyl 9-fluoro-3,4-dihydro-2H-1,5-benzoxathiepine-7-carboxylate (7.5 g, 30.96 mmol, 89.42% yield) as yellow oil. LCMS (ESI) m/z: $[M+H]^+$=242.9. $^1H$ NMR (400 MHz, $CDCl_3$) δ=7.81 (s, 1H), 7.60-7.57 (m, 1H), 4.45-4.43 (m, 2H), 3.89 (s, 3H), 3.08-3.05 (m, 2H), 2.34-2.29 (m, 2H) ppm.

Step 5: Preparation of methyl 9-fluoro-5-oxo-3,4-dihydro-2H-1,5λ4-benzoxathiepine-7-carboxylate

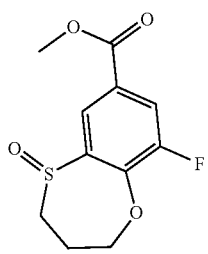 [SMILES: COC(=O)c1cc(F)c2c(c1)S(=O)CCCO2]

To a solution of methyl 9-fluoro-3,4-dihydro-2H-1,5-benzoxathiepine-7-carboxylate (7 g, 28.89 mmol) in MeOH (140 mL) and $H_2O$ (70 mL) was added Oxone (9.77 g, 15.89 mmol) at 0° C. The mixture was stirred at 30° C. for 12 hrs. The mixture was diluted with $H_2O$ (300 mL) and extracted with EA (300 mL*2). The combined organic layers were washed with sat·$Na_2SO_3$ (300 mL), dried over anhydrous $Na_2SO_4$, filtered and concentrated to afford the residue. The residue was purified by column chromatography ($SiO_2$, Petroleum ether/Ethyl acetate=1/0 to 0/1). The eluent was concentrated to afford methyl 9-fluoro-5-oxo-3,4-dihydro-2H-1,5λ4-benzoxathiepine-7-carboxylate (7 g, 27.10 mmol, 93.81% yield) as a white solid. LCMS (ESI) m/z: $[M+H]^+$=258.9. $^1H$ NMR (400 MHz, CDCl3) δ=8.19-8.18 (m, 1H), 7.90-7.87 (m, 1H), 4.57-4.53 (m, 1H), 3.93 (s, 3H), 3.91-3.89 (m, 1H), 3.32-3.29 (m, 1H), 3.23-3.19 (m, 1H), 2.70-2.66 (m, 1H), 2.40-2.39 (m, 1H) ppm.

Step 6: Preparation of methyl 4,9-difluoro-3,4-dihydro-2H-1,5-benzoxathiepine-7-carboxylate

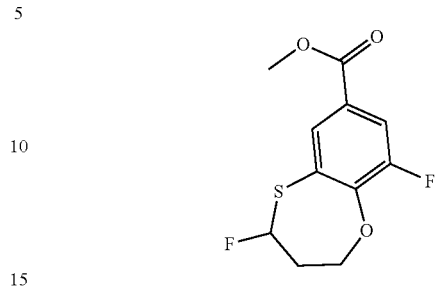

To a solution of methyl 9-fluoro-5-oxo-3,4-dihydro-2H-1,5λ4-benzoxathiepine-7-carboxylate (500 mg, 1.94 mmol) in $CHCl_3$ (5 mL) was added DAST (6.10 g, 37.84 mmol, 5.00 mL). The mixture was stirred at 50° C. for 96 hrs. The reaction mixture was combined with another four batches for workup. The reaction mixture was added to sat·$NaHCO_3$ (200 mL) at 0° C. and extracted with DCM (200 mL*2). The combined organic layers were dried over anhydrous $Na_2SO_4$, filtered and concentrated to afford the residue. The residue was purified by column chromatography ($SiO_2$, Petroleum ether/Ethyl acetate=1/0 to 10/1). The eluent was concentrated to afford methyl 4,9-difluoro-3,4-dihydro-2H-1,5-benzoxathiepine-7-carboxylate (1.3 g, 5.00 mmol, 51.60% yield) as a yellow solid.

$^1H$ NMR (400 MHz, $CDCl_3$) δ=7.94-7.93 (m, 1H), 7.76-7.73 (m, 1H), 5.96-5.83 (m, 1H), 4.63-4.58 (m, 1H), 4.16-4.10 (m, 1H), 3.91 (s, 3H), 2.64-2.57 (m, 2H) ppm.

Step 7: Preparation of 4,9-difluoro-3,4-dihydro-2H-1,5-benzoxathiepine-7-carboxylic Acid

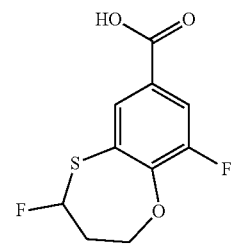 [SMILES: O=C(O)c1cc(F)c2c(c1)SC(F)CCO2]

To a mixture of methyl 4,9-difluoro-3,4-dihydro-2H-1,5-benzoxathiepine-7-carboxylate (1.95 g, 7.49 mmol) in THF (10 mL), MeOH (5 mL) and $H_2O$ (5 mL) was added NaOH (599.41 mg, 14.99 mmol). The mixture was stirred at 25° C. for 2 hrs. The mixture was diluted with $H_2O$ (50 mL) and added 1 N HCl to adjust the pH=3, then extracted with EA (50 mL*2). The combined organic layers were dried over anhydrous $Na_2SO_4$, filtered and concentrated to afford 4,9-difluoro-3,4-dihydro-2H-1,5-benzoxathiepine-7-carboxylic acid (1.8 g, 7.31 mmol, 97.57% yield) as a white solid which was used directly in the next step.

Step 8: Preparation of 4,9-difluoro-5,5-dioxo-3,4-dihydro-2H-1,5λ6-benzoxathiepine-7-carboxylic Acid

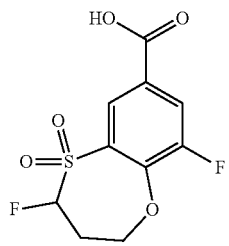 [SMILES: O=C(O)c1cc(F)c2c(c1)S(=O)(=O)C(F)CCO2]

To a solution of 4,9-difluoro-3,4-dihydro-2H-1,5-benzoxathiepine-7-carboxylic acid (1.8 g, 7.31 mmol) in MeOH (40 mL) and H$_2$O (20 mL) was added Oxone (13.48 g, 21.93 mmol) at 0° C. The mixture was stirred at 30° C. for 12 hrs. The mixture was diluted with H$_2$O (100 mL) and extracted with DCM (100 mL*2). The combined organic layers were washed with aq·Na$_2$SO$_3$ (100 mL) and dried over anhydrous Na$_2$SO$_4$, filtered, and concentrated to afford 4,9-difluoro-5,5-dioxo-3,4-dihydro-2H-1,5λ6-benzoxathiepine-7-carboxylic acid (1.9 g, 6.83 mmol, 93.42% yield) as a white solid. $^1$H NMR (400 MHz, DMSO-d$_6$) δ=8.33-8.25 (m, 1H), 8.19-8.15 (m, 1H), 6.33-6.20 (m, 1H), 4.63-4.59 (m, 1H), 4.19-4.13 (m, 1H), 2.84-2.74 (m, 1H), 2.61-2.57 (m, 1H) ppm.

Step 9: Preparation of Intermediate 2 (4R)-4,9-difluoro-5,5-dioxo-3,4-dihydro-2H-1,5, λ6-benzoxathiepine-7-carboxylic acid & (4S)-4,9-difluoro-5,5-dioxo-3,4-dihydro-2H-1,5λ6-benzoxathiepine-7-carboxylic Acid

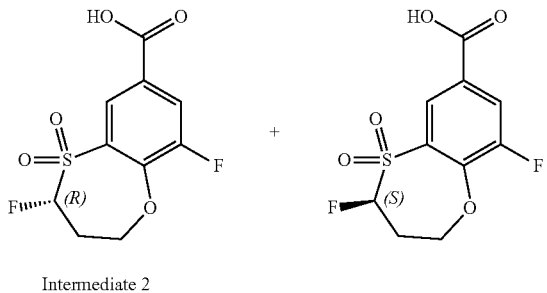

Intermediate 2

4,9-difluoro-5,5-dioxo-3,4-dihydro-2H-1,5λ6-benzoxathiepine-7-carboxylic acid (1.88 g, 6.76 mmol) was separated by Chiral SFC (column: DAICEL CHIRALPAK AD-H (250 mm*30 mm, 5 um); mobile phase: [0.1% NH$_3$H$_2$O MEOH]; B %: 15%-15%, 8.5 min; 750 min).

Intermediate 2: (4R)-4,9-difluoro-5,5-dioxo-3,4-dihydro-2H-1,5λ6-benzoxathiepine-7-carboxylic acid The eluent of peak 1 was concentrated to afford the residue. The residue was diluted with H$_2$O (50 mL) and added 1 N HCl to adjust the pH=2, then extracted with DCM (50 mL*2), the combined organic layers were dried over anhydrous Na$_2$SO$_4$, filtered and concentrated to afford (4R)-4,9-difluoro-5,5-dioxo-3,4-dihydro-2H-1,5λ6-benzoxathiepine-7-carboxylic acid (Intermediate 2) (850 mg, 2.99 mmol, 44.22% yield) as a white solid. $^1$H NMR (400 MHz, DMSO-d$_6$) δ=13.84-13.73 (m, 1H), 8.20-8.15 (m, 2H), 6.34-6.21 (m, 1H), 4.63-4.58 (m, 1H), 4.19-4.13 (m, 1H), 2.75-2.71 (m, 1H), 2.61-2.56 (m, 1H) ppm. Chiral SFC: AD-3-MeOH(DEA)-5-40-3ML-35T.lcm. Rt=1.304 mins, ee %=96.54%. The eluent of peak 2 was concentrated to afford a residue. The residue was diluted with H$_2$O (50 mL) and added 1 N HCl to adjust the pH=2, then extracted with DCM (50 mL*2), the combined organic layers were dried over anhydrous Na$_2$SO$_4$, filtered and concentrated to afford (4S)-4,9-difluoro-5,5-dioxo-3,4-dihydro-2H-1,5λ6-benzoxathiepine-7-carboxylic acid. (800 mg, 2.81 mmol, 41.65% yield) as a white solid. $^1$H NMR (400 MHz, DMSO-d$_6$) δ=13.80-13.73 (m, 1H), 8.19-8.15 (m, 2H), 6.34-6.21 (m, 1H), 4.63-4.58 (m, 1H), 4.19-4.13 (m, 1H), 2.85-2.75 (m, 1H), 2.61-2.56 (m, 1H) ppm. Chiral SFC: AD-3-MeOH(DEA)-5-40-3ML-35T.lcm. Rt=1.410 mins, ee %=99.25%.

Preparation of (4R)—N-[[6-[6-[(2S,6R)-2,6-dimethylmorpholin-4-yl]pyrazin-2-yl]-3-isoquinolyl]methyl]-4,9-difluoro-5,5-dioxo-3,4-dihydro-2H-1,5λ6-benzoxathiepine-7-carboxamide (Compound 19)

Step 1: Preparation of (2S,6R)-4-(6-chloropyrazin-2-yl)-2,6-dimethyl-morpholine

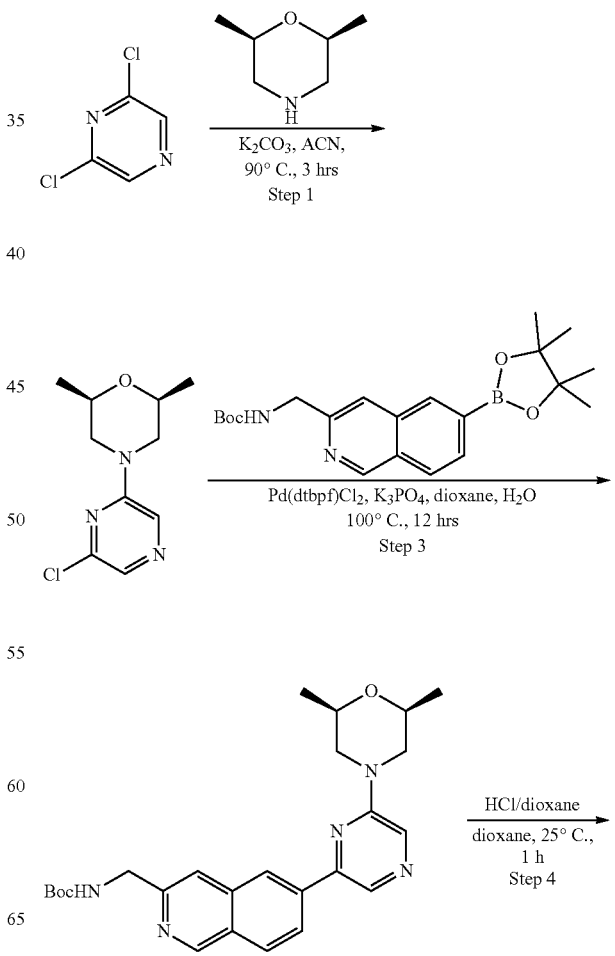

-continued

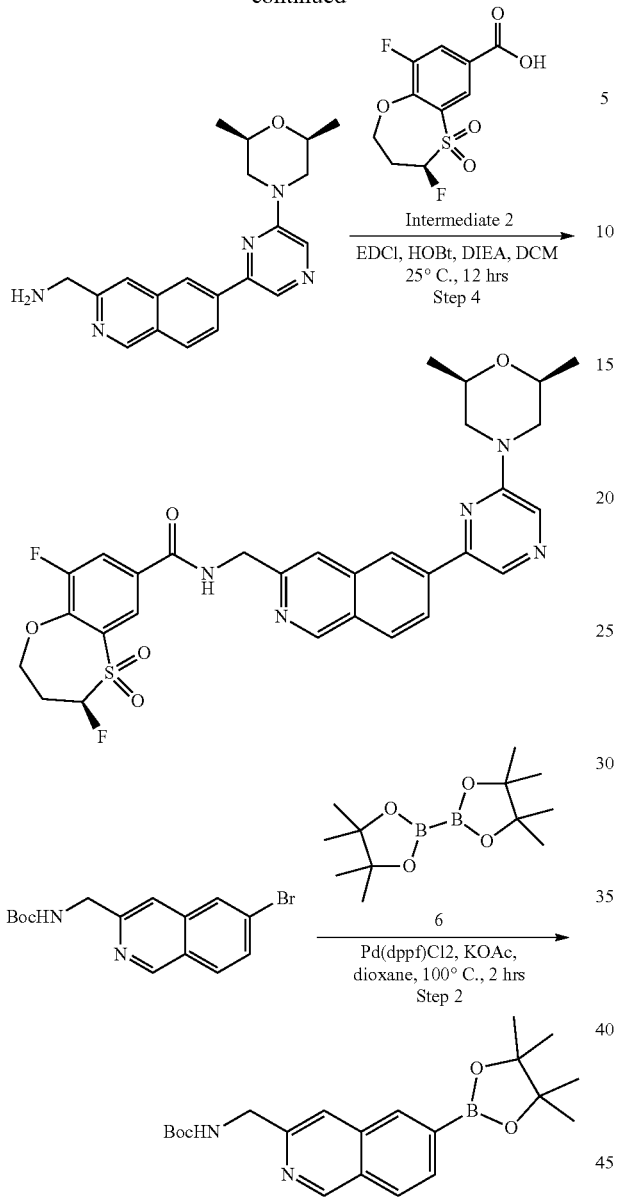

To a solution of 2,6-dichloropyrazine (1 g, 6.71 mmol) in ACN (50 mL) was added K₂CO₃ (2.78 g, 20.14 mmol) and (2S,6R)-2,6-dimethylmorpholine (850.40 mg, 7.38 mmol). The mixture was stirred at 90° C. for 3 hrs. The reaction mixture was poured into water (100 mL) and extracted with EA (100 mL*3). The combined organic layer was washed with brine (200 mL), dried over Na₂SO₄, filtered, and concentrated to dryness. The residue was purified by column chromatography (SiO₂, PE:EA=20:1-1:1), the fraction was concentrated under reduced pressure to get (2S,6R)-4-(6-chloropyrazin-2-yl)-2,6-dimethyl-morpholine (1.2 g, 5.27 mmol, 78.52% yield) as a white solid. LCMS (ESI) m/z: [M+H]⁺=228.1. ¹H NMR (400 MHz, DMSO-d6) δ=8.40-8.23 (m, 1H), 7.91-7.78 (m, 1H), 4.21-4.10 (m, 2H), 3.67-3.52 (m, 2H), 3.31 (s, 1H), 2.53 (d, J=2.4 Hz, 1H), 1.17-1.14 (m, 6H) ppm.

Step 2: Preparation of tert-butyl N-[[6-(4,4,5,5-tetramethyl-1,3,2-dioxaborolan-2-yl)-3-isoquinolyl]methyl]carbamate

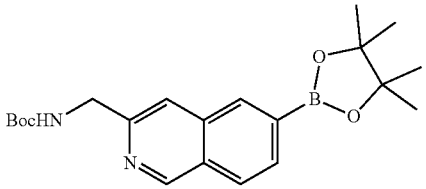 [SMILES: CC(C)(C)OC(=O)NCc1cc2cc(B3OC(C)(C)C(C)(C)O3)ccc2cn1]

A mixture of tert-butyl N-[(6-bromo-3-isoquinolyl)methyl]carbamate (200 mg, 593.10 umol, 4,4,5,5-tetramethyl-2-(4,4,5,5-tetramethyl-1,3,2-dioxaborolan-2-yl)-1,3,2-dioxaborolane (180.73 mg, 711.72 umol), Pd(dppf)Cl₂ (43.40 mg, 59.31 umol) and KOAc (174.62 mg, 1.78 mmol) in dioxane (5 mL) was degassed and purged with N₂ for 3 times, and then the mixture was stirred at 100° C. for 2 hrs under N₂ atmosphere. The mixture was diluted with H₂O (30 mL) and extracted with EA (30 mL*2). The combined organic layers were dried over anhydrous Na₂SO₄, filtered and concentrated to afford tert-butyl N-[[6-(4,4,5,5-tetramethyl-1,3,2-dioxaborolan-2-yl)-3-isoquinolyl]methyl]carbamate (220 mg, crude) as brown oil, which it was used directly in the next step.

Step 3: Preparation of tert-butyl N-[[6-[6-[(2S,6R)-2,6-dimethylmorpholin-4-yl]pyrazin-2-yl]-3-isoquinolyl]methyl]carbamate

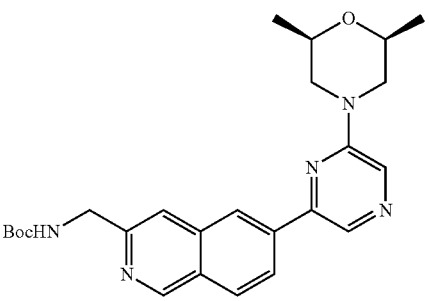 [SMILES: C[C@@H]1CN(c2cncc(-c3ccc4cnc(CNC(=O)OC(C)(C)C)cc4c3)n2)C[C@H](C)O1]

A mixture of (2S,6R)-4-(6-chloropyrazin-2-yl)-2,6-dimethyl-morpholine (from step 1) (100 mg, 439.19 umol), N-[[6-(4,4,5,5-tetramethyl-1,3,2-dioxaborolan-2-yl)-3-isoquinolyl]methyl]carbamate (202.53 mg, 527.03 umol), K₃PO₄ (279.68 mg, 1.32 mmol) and ditert-butyl(cyclopentyl)phosphane; dichloropalladium; iron (28.62 mg, 43.92 umol) in dioxane (2.5 mL) and H₂O (0.5 mL) was degassed and purged with N₂ for 3 times, and then the mixture was stirred at 100° C. for 12 hrs. The reaction mixture was poured into H₂O (30 mL) and extracted with EA (30 mL*3). The combined organic layer was washed with brine (60 mL), dried over Na₂SO₄, filtered and concentrated. The residue was purified by column chromatography (SiO₂, PE:EA=20:1-1:1), the fraction was concentrated under reduced pressure to get tert-butyl N-[[6-[6-[(2S,6R)-2,6-dimethylmorpholin-4-yl]pyrazin-2-yl]-3-isoquinolyl]methyl]carbamate (150 mg, 333.67 umol, 75.97% yield) as a yellow solid. LCMS (ESI) m/z: [M+H]⁺=450.1.

Step 4: Preparation of [6-[6-[(2S,6R)-2,6-dimethyl-morpholin-4-yl]pyrazin-2-yl]-3-isoquinolyl]methanamine

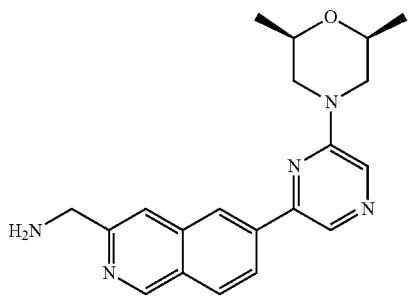 [SMILES: C[C@@H]1CN(c2cncc(-c3ccc4cnc(CN)cc4c3)n2)C[C@H](C)O1]

To a solution of tert-butyl N-[[6-[6-[(2S,6R)-2,6-dimethylmorpholin-4-yl]pyrazin-2-yl]-3-isoquinolyl]methyl]carbamate (150 mg, 333.67 umol) in dioxane (2 mL) was added HCl/dioxane (4 M, 4 mL). The mixture was stirred at 25° C. for 1 h. The reaction mixture was concentrated to get [6-[6-[(2S,6R)-2,6-dimethylmorpholin-4-yl]pyrazin-2-yl]-3-isoquinolyl]methanamine (120 mg, crude, HCl·salt) as a light yellow solid, which it's used next step without further purification. LCMS (ESI) m/z: [M+H]$^+$=350.2

Step 5: Preparation of (4R)—N-[[6-[6-[(2S,6R)-2,6-dimethylmorpholin-4-yl]pyrazin-2-yl]-3-isoquinolyl]methyl]-4,9-difluoro-5,5-dioxo-3,4-dihydro-2H-1,5λ6-benzoxathiepine-7-carboxamide (Compound 19)

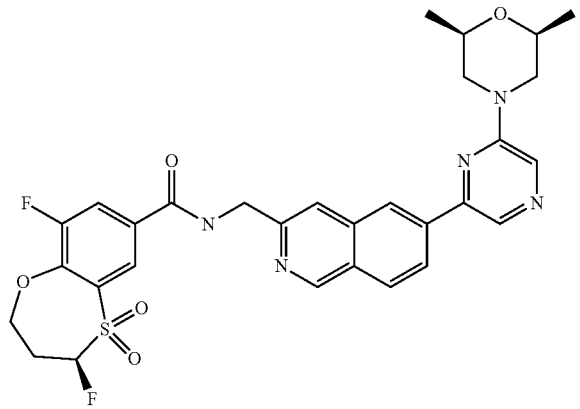 [SMILES: C[C@@H]1CN(c2cncc(-c3ccc4cnc(CNC(=O)c5cc(F)c6c(c5)S(=O)(=O)[C@@H](F)CCO6)cc4c3)n2)C[C@H](C)O1]

To a solution of [6-[6-[(2S,6R)-2,6-dimethylmorpholin-4-yl]pyrazin-2-yl]-3-isoquinolyl]methanamine hydrochloride (70 mg, 200.33 umol) in DCM (2 mL) was added (4R)-4,9-difluoro-5,5-dioxo-3,4-dihydro-2H-1,5λ6-benzoxathiepine-7-carboxylic acid (Intermediate 2) (55.74 mg, 200.33 umol), EDCl (76.81 mg, 400.65 umol), HOBt (54.14 mg, 400.65 umol) and DIEA (155.35 mg, 1.20 mmol, 209.36 uL). The mixture was stirred at 25° C. for 2 hrs. The reaction mixture was poured into water (15 mL) and extracted with EA (15 mL*3). The combined organic layer was washed with brine (20 mL), dried over Na$_2$SO$_4$, filtered and concentrated. The residue was purified by Prep-HPLC (column: Phenomenex C18 75*30 mm*3 um; mobile phase: [water (FA)-ACN]; B %: 55%-8%, 5 min). The fraction was concentrated in vacuo to removed MeCN and lyophilized to give (4R)—N-[[6-[6-[(2S,6R)-2,6-dimethylmorpholin-4-yl]pyrazin-2-yl]-3-isoquinolyl]methyl]-4,9-difluoro-5,5-dioxo-3,4-dihydro-2H-1,5λ6-benzoxathiepine-7-carboxamide (39.15 mg, 63.38 umol, 31.64% yield) as a yellow solid. LCMS (ESI) m/z: [M+H]$^+$=610.3. $^1$H NMR (400 MHz, DMSO-d$_6$) δ=9.66-9.58 (m, 1H), 9.36-9.31 (m, 1H), 8.71-8.62 (m, 2H), 8.39-8.19 (m, 5H), 7.87 (s, 1H), 6.41-6.12 (m, 1H), 4.80-4.73 (m, 2H), 4.65-4.57 (m, 1H), 4.44-4.33 (m, 2H), 4.13-4.15 (m, 1H), 3.71-3.62 (m, 2H), 2.90-2.72 (m, 1H), 2.61-2.55 (m, 3H), 1.20 (d, J=6.4 Hz, 6H) ppm. Chiral SFC: OD-MeOH+CAN (DEA)-40-3 mL-35T.lcm, T=0.904, ee %=100%.

Preparation of (2R)-6-chloro-N-[[6-[6-(difluoromethoxy)-2-pyridyl]-3-isoquinolyl]methyl]-2-fluoro-1,1-dioxo-3,5-dihydro-2H-4,1λ6-benzoxathiepine-8-carboxamide (Compound 235)

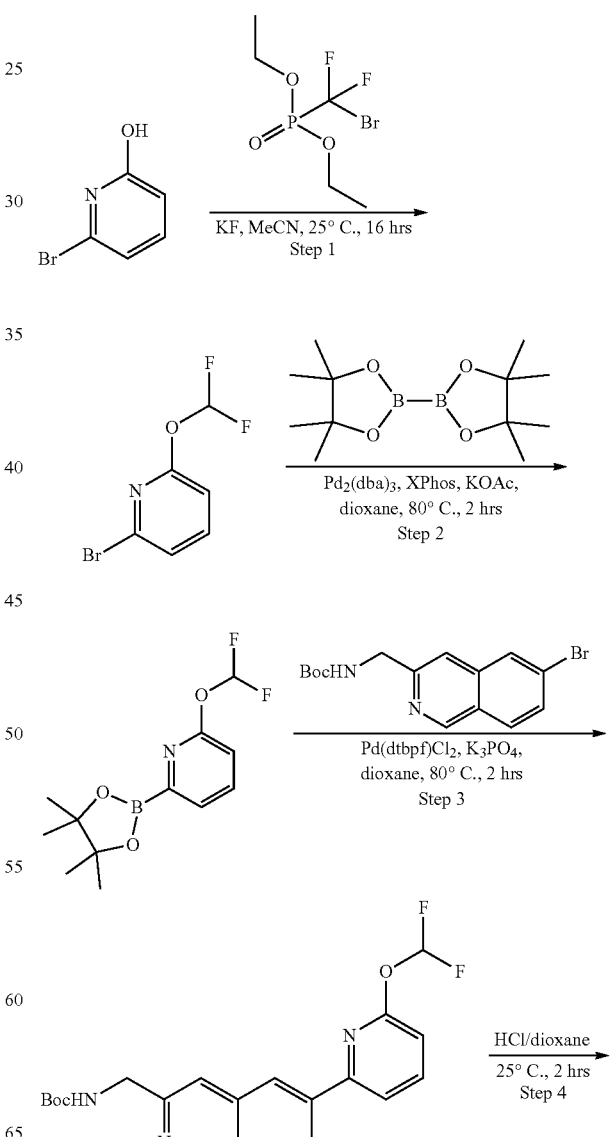

Step 2: Preparation of 2-(difluoromethoxy)-6-(4,4,5,5-tetramethyl-1,3,2-dioxaborolan-2-yl)pyridine

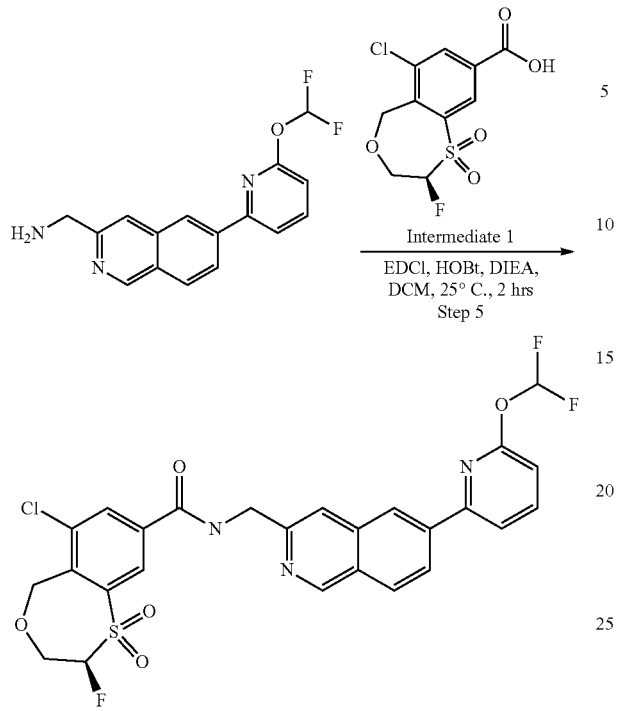

To a solution of XPhos (106.41 mg, 223.21 umol) in dioxane (5 mL) was added Pd₂(dba)₃ (81.76 mg, 89.28 umol), then the mixture was degassed and purged with N₂ for 3 times, and then the mixture was stirred at 25° C. for 30 min under N₂ atmosphere. Then 2-bromo-6-(difluoromethoxy)pyridine (200 mg, 892.85 umol), 4,4,5,5-tetramethyl-2-(4,4,5,5-tetramethyl-1,3,2-dioxaborolan-2-yl)-1,3,2-dioxaborolane (272.07 mg, 1.07 mmol) and KOAc (262.88 mg, 2.68 mmol) was added the mixture. The resulting mixture was stirred at 80° C. for 2 hrs. The reaction mixture was filtered and the filter cake was washed with EA (20 mL*3). The combined filtrate were concentrated under reduced pressure to give 2-(difluoromethoxy)-6-(4,4,5,5-tetramethyl-1,3,2-dioxaborolan-2-yl)pyridine (240 mg, 885.39 umol, 99.16% yield) as brown oil, which was used for next step directly and without further purification.

Step 3: Preparation of tert-butyl N-[[6-[6-(difluoromethoxy)-2-pyridyl]-3-isoquinolyl]methyl]carbamate To a solution of 2-(difluoromethoxy)-6-(4,4,5,5-tetramethyl-1,3,2-dioxaborolan-2-yl)pyridine (240 mg, 885.39 umol) in dioxane (2 mL) and H₂O (0.2 mL) was added tert-butyl N-[(6-bromo-3-isoquinolyl)methyl]carbamate (149.28 mg, 442.69 umol), ditert-butyl(cyclopentyl)phosphane; dichloropalladium; iron (28.85 mg, 44.27 umol) and K₃PO₄ (281.91 mg, 1.33 mmol). The mixture was degassed and purged with N₂ for 3 times, and then the mixture was stirred at 80° C. for 16 hrs under N₂ atmosphere. The mixture was diluted with H₂O (30 mL) and extracted with EA (50 mL*3). The combined organic phase was washed with brine (50 mL*2), dried over anhydrous Na₂SO₄, filtered and concentrated under vacuum to give a residue, which was purified by column chromatography (SiO₂,

Step 1: Preparation of 2-bromo-6-(difluoromethoxy)pyridine

To a solution of 1-[[bromo(difluoro)methyl]-ethoxyphosphoryl]oxyethane (3.38 g, 12.64 mmol) in MeCN (20 mL) was added 6-bromopyridin-2-ol (2.00 g, 11.49 mmol) and KF (1.34 g, 22.99 mmol). The mixture was stirred at 25° C. for 16 hrs. The reaction mixture was concentrated under reduced pressure to give a residue, then the residue was diluted with H₂O (100 mL*3), dried over Na₂SO₄, filtered and concentrated under reduced pressure to give a residue, which was purified by column chromatography (SiO₂, PE/EA=50/1 to 5/1). The eluent was concentrated under reduced pressure to give 2-bromo-6-(difluoromethoxy)pyridine (1.2 g, 5.36 mmol, 46.61% yield) as colorless oil. LCMS (ESI) m/z: [81 BrM+H]⁺=226.2. ¹H NMR (400 MHz, CDCl₃) δ=7.66-7.43 (m, 2H), 7.32-7.30 (m, 1H), 6.87 (d, J=8.0 Hz, 1H) ppm.

PE/EA=10/1 to 1/3). The eluent was concentrated under reduced pressure to give tert-butyl N-[[6-[6-(difluoromethoxy)-2-pyridyl]-3-isoquinolyl]methyl]carbamate (160 mg, 398.60 umol, 90.04% yield) as a yellow solid. LCMS (ESI) m/z: [M+H]$^+$=402.2. $^1$H NMR (400 MHz, CDCl$_3$) δ=9.25 (s, 1H), 8.39 (s, 1H), 8.20 (d, J=8.8 Hz, 1H), 8.06 (d, J=8.8 Hz, 1H), 7.91-7.85 (m, 1H), 7.78-7.49 (m, 3H), 6.95 (d, J=8.0 Hz, 1H), 5.53 (s, 1H), 4.62 (d, J=5.6 Hz, 2H), 1.49 (s, 9H) ppm.

Step 4: Preparation of [6-[6-(difluoromethoxy)-2-pyridyl]-3-isoquinolyl]methanamine

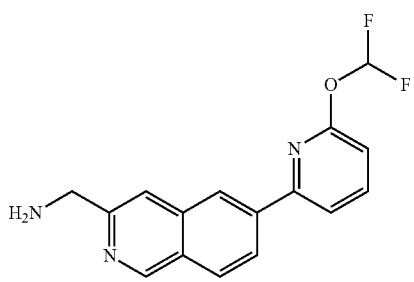 [SMILES: NCc1cc2cc(-c3cccc(OC(F)F)n3)ccc2cn1]

A mixture of tert-butyl N-[[6-[6-(difluoromethoxy)-2-pyridyl]-3-isoquinolyl]methyl]carbamate (160 mg, 398.60 umol) in HCl/dioxane (4 M) was stirred at 25° C. for 2 hrs. The reaction mixture was concentrated under reduced pressure to give [6-[6-(difluoromethoxy)-2-pyridyl]-3-isoquinolyl]methanamine (130 mg, 384.90 umol, 96.56% yield, HCl) as a gray solid, which was used for next step directly and without further purification. LCMS (ESI) m/z: [M+H]$^+$= 302.1.

Step 5: Preparation of (2R)-6-chloro-N-[[6-[6-(difluoromethoxy)-2-pyridyl]-3-isoquinolyl]methyl]-2-fluoro-1,1-dioxo-3,5-dihydro-2H-4,1λ6-benzoxathiepine-8-carboxamide

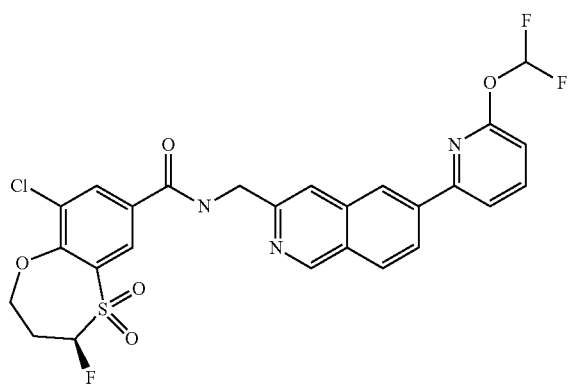 [SMILES: O=C(NCc1cc2cc(-c3cccc(OC(F)F)n3)ccc2cn1)c1cc(Cl)c2c(c1)S(=O)(=O)[C@@H](F)CCO2]

To a mixture of [6-[6-(difluoromethoxy)-2-pyridyl]-3-isoquinolyl] methanamine (30 mg, 88.82 umol) and (2R)-6-chloro-2-fluoro-1,1-dioxo-3,5-dihydro-2H-4,1λ6-benzoxathiepine-8-carboxylic acid (Intermediate 1) (31.41 mg, 106.59 umol) in DCM (1 mL) was added EDCI (22.14 mg, 115.47 umol), HOBt (15.60 mg, 115.47 umol) and DIEA (68.88 mg, 532.94 umol). The mixture was stirred at 25° C. for 2 hrs. The reaction mixture was poured into H$_2$O (10 mL) and extracted with DCM (20 mL*3). The combined organic layers were washed with brine (30 mL), dried over Na$_2$SO$_4$, filtered and concentrated under reduced pressure to give a residue, which was purified by reversed phase flash (0.1% FA condition). The eluent was concentrated under reduced pressure to remove MeCN and the residue was lyophilized to give (2R)-6-chloro-N-[[6-[6-(difluoromethoxy)-2-pyridyl]-3-isoquinolyl]methyl]-2-fluoro-1,1-dioxo-3,5-dihydro-2H-4,1λ6-benzoxathiepine-8-carboxamide (19.12 mg, 33.08 umol, 37.24% yield) as a white solid. LCMS (ESI) m/z: [M+H]$^+$=578.1 $^1$H NMR (400 MHz, DMSO-d$_6$) δ=9.76-9.73 (m, 1H), 9.35 (s, 1H), 8.73 (s, 1H), 8.58 (d, J=1.6 Hz, 1H), 8.50 (d, J=1.6 Hz, 1H), 8.39-8.37 (m, 1H), 8.27-7.83 (m, 5H), 7.13-7.11 (m, 1H), 6.36-6.10 (m, 1H), 5.41 (d, J=14.8 Hz, 1H), 5.09 (d, J=14.8 Hz, 1H), 4.78 (d, J=5.2 Hz, 2H), 4.52-4.36 (m, 2H) ppm. Chiral SFC: OD-3-MeOH+ACN(DEA)-40-3ML-35T.lcm, Rt=0.853 min, ee %=97.36%.

The following examples in Table 4 were prepared using standard chemical manipulations and procedures similar to those used for the preparation of Compound 235.

TABLE 4

| # | LCMS (ESI/M + H) | $^1$HNMR |
|---|---|---|
| | | Compounds of the Invention |
| 16 | 610.2 | 1H NMR (400 MHz, DMSO-d6) δ = 9.64-9.62 (m, 1H), 9.36 (s, 1H), 8.75 (s, 1H), 8.52 (d, J = 4.8 Hz, 1H), 8.37-8.32 (m, 3H), 8.24 (d, J = 8.4 Hz, 1H), 7.90 (s, 1H), 7.41 (d, J = 5.2 Hz, 1H), 6.33-6.21 (m, 1H), 4.77 (d, J = 5.6 Hz, 2H), 4.68-4.60 (m, 3H), 3.62-3.58 (m, 2H), 2.75-2.62 (m, 1H), 2.59-2.56 (m, 3H), 1.19 (d, J = 6.0 Hz, 6H) ppm |
| 19 | 610.3 | 1H NMR (400 MHz, DMSO-d6) δ = 9.66-9.58 (m, 1H), 9.36-9.31 (m, 1H), 8.71-8.62 (m, 2H), 8.39-8.19 (m, 5H), 7.87 (s, 1H), 6.41-6.12 (m, 1H), 4.80-4.73 (m, 2H), 4.65-4.57 (m, 1H), 4.44-4.33 (m, 2H), 4.13-4.15 (m, 1H), 3.71-3.62 (m, 2H), 2.90-2.72 (m, 1H), 2.61-2.55 (m, 3H), 1.20 (d, J = 6.4 Hz, 6H) |
| 196 | 579.2 | 1H NMR (400 MHz, DMSO-d6) δ = 9.91 (t, J = 5.8 Hz, 1H), 8.86 (d, J = 1.7 Hz, 1H), 8.71-8.64 (m, 1H), 8.62-8.55 (m, 2H), 8.49 (d, J = 1.6 Hz, 1H), 8.28-7.87 (m, 4H), 7.28-7.09 (m, 1H), 6.40-6.10 (m, 1H), 5.41 (d, J = 14.8 Hz, 1H), 5.18-5.02 (m, 3H), 4.51-4.36 (m, 2H) ppm |
| 231 | 626.1 | 1H NMR (400 MHz, DMSO-d6) δ = 9.78 (t, J = 5.6 Hz, 1H), 8.73 (d, J = 1.6 Hz, 1H), 8.65-8.60 (m, 1H), 8.56-8.50 (m, 2H), 8.44 (d, J = 2.4 Hz, 1H), 8.24 (s, 1H), 7.81-7.65 (m, 1H), 7.49 (d, J = 7.6 Hz, 1H), 6.94 (d, J = 8.8 Hz, 1H), 6.40-6.15 (m, 1H), 5.06 (br d, J = 5.2 Hz, 2H), 4.62 (m, 1H), 4.32 (br d, J = 11.4 Hz, 2H), 4.06 (br t, J = 11.8 Hz, 1H), 3.74-3.59 (m, 2H), 2.95-2.73 (m, 1H), 2.59 (br d, J = 7.8 Hz, 3H), 1.21 (d, J = 6.2 Hz, 6H) ppm |
| 231 | 626.1 | 1H NMR (400 MHz, DMSO-d6) δ = 9.78 (t, J = 5.6 Hz, 1H), 8.73 (d, J = 1.6 Hz, 1H), 8.65-8.60 (m, 1H), 8.56-8.50 (m, 2H), 8.44 (d, J = 2.4 Hz, 1H), 8.24 (s, 1H), 7.81-7.65 (m, 1H), 7.49 (d, J = 7.6 Hz, 1H), 6.94 (d, J = 8.8 Hz, 1H), 6.40-6.15 (m, 1H), 5.06 (br d, J = 5.2 Hz, 2H), 4.62 (m, 1H), 4.32 |

TABLE 4-continued

Compounds of the Invention

| # | LCMS (ESI/M + H) | ¹HNMR |
|---|---|---|
| | | (br d, J = 11.4 Hz, 2H), 4.06 (br t, J = 11.8 Hz, 1H), 3.74-3.59 (m, 2H), 2.95-2.73 (m, 1H), 2.59 (br d, J = 7.8 Hz, 3H), 1.21 (d, J = 6.2 Hz, 6H) ppm |
| 232 | 546.1 | 1H NMR (400 MHz, DMSO-d6) δ = 9.73-9.71 (m, 1H), 9.36 (s, 1H), 8.72 (s, 1H), 8.47 (s, 1H), 8.38-8.34 (m, 2H), 8.27-8.25 (m, 2H), 8.16 (s, 1H), 7.90 (s, 1H), 7.74 (d, J = 7.6 Hz, 1H), 7.20-6.92 (m, 1H), 6.27-6.16 (m, 1H), 5.25 (d, J = 14.8 Hz, 1H), 4.91-4.87 (m, 1H), 4.79 (d, J = 5.2 Hz, 2H), 4.47-4.35 (m, 2H) ppm |
| 235 | 578.1 | 1H NMR (400 MHz, DMSO-d6) δ = 9.76-9.73 (m, 1H), 9.35 (s, 1H), 8.73 (s, 1H), 8.58 (d, J = 1.6 Hz, 1H), 8.50 (d, J = 1.6 Hz, 1H), 8.39-8.37 (m, 1H), 8.27-7.83 (m, 5H), 7.13-7.11 (m, 1H), 6.36-6.10 (m, 1H), 5.41 (d, J = 14.8 Hz, 1H), 5.09 (d, J = 14.8 Hz, 1H), 4.78 (d, J = 5.2 Hz, 2H), 4.52-4.36 (m, 2H) ppm |
| 268 | 572.1 | 1H NMR (400 MHz, DMSO-d6) δ = 9.63-9.60 (m, 1H), 9.34 (s, 1H), 8.67 (s, 1H), 8.40-8.30 (m, 3H), 8.22 (d, J = 8.8 Hz, 1H), 8.09 (d, J = 7.6 Hz, 1H), 7.95-7.91 (m, 1H), 7.89-7.85 (m, 1H), 7.58-7.47 (m, 1H), 6.36-6.18 (m, 1H), 4.77 (br d, J = 5.6 Hz, 2H), 4.65-4.58 (m, 1H), 4.17-4.11 (m, 1H), 3.26 (br s, 1H), 2.91-2.82 (m, 1H), 2.61 (br s, 2H), 2.13-2.00 (m, 1H) ppm |

Preparation of (R)—N-((4-((E)-2-(6-((2S,6R)-2,6-dimethylmorpholino)pyridin-2-yl)vinyl)pyridin-2-yl)methyl)-4,9-difluoro-3,4-dihydro-2H-benzo[b][1,4]oxathiepine-7-carboxamide 5,5-dioxide (Compound 52)

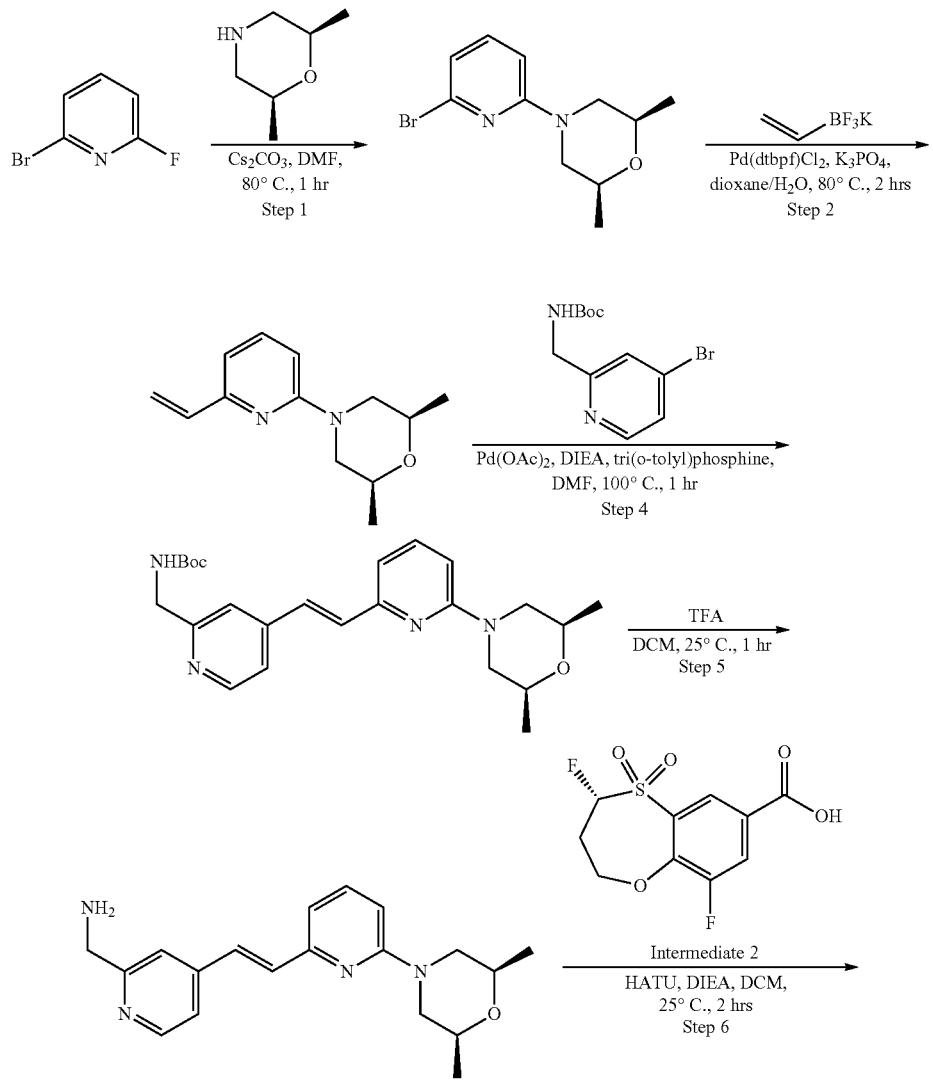

-continued

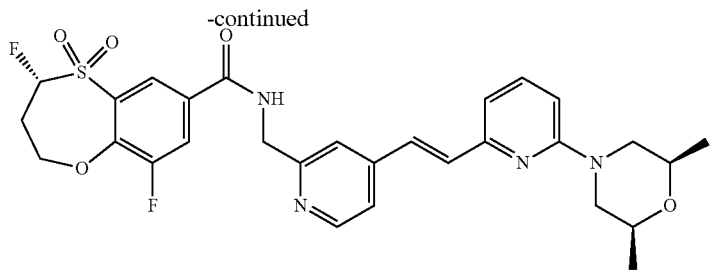

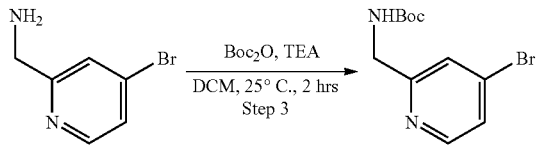

Step 1: Preparation of (2S,6R)-4-(6-bromopyridin-2-yl)-2,6-dimethylmorpholine

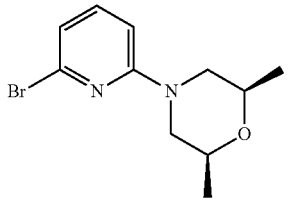

To a solution of 2-bromo-6-fluoro-pyridine (2 g, 11.36 mmol) in DMF (20 mL) was added (2S,6R)-2,6-dimethylmorpholine (1.96 g, 17.05 mmol) and $Cs_2CO_3$ (7.41 g, 22.73 mmol). The mixture was stirred at 80° C. for 1 hr. The reaction mixture was poured into water (200 mL) and extracted with EA (50 mL*3). The combined organic layer was washed by brine (50 mL), dried over anhydrous $Na_2SO_4$, filtered and concentrated under vacuum. The residue was purified by normal phase flash (column: $SiO_2$, 40 g; PE:EA=1:0-0:1, RF=0.3). The eluent was concentrated under vacuum to give (2S,6R)-4-(6-bromopyridin-2-yl)-2,6-dimethylmorpholine (2.9 g, 10.30 mmol, 90.63% yield) as white solid. LCMS (ESI) m/z: [M+H]$^+$=270.8 $^1$H NMR (400 MHz, CHLOROFORM-d) δ=7.31-7.27 (m, 1H), 6.77 (d, J=7.6 Hz, 1H), 6.50 (d, J=8.4 Hz, 1H), 4.03-4.00 (m, 2H), 3.76-3.62 (m, 2H), 2.55-2.49 (m, 2H), 1.27 (d, J=6.2 Hz, 6H) ppm.

Step 2: Preparation of (2S,6R)-2,6-dimethyl-4-(6-vinylpyridin-2-yl)morpholine

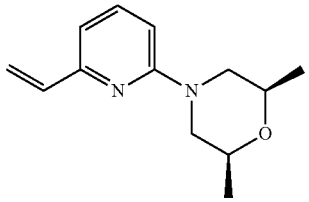 [SMILES: C=Cc1cccc(N2C[C@@H](C)O[C@@H](C)C2)n1]

To a solution of (2S,6R)-4-(6-bromopyridin-2-yl)-2,6-dimethylmorpholine (1 g, 3.69 mmol) in Dioxane (10 mL) was added potassium hydride; trifluoro(vinyl)boron (988.00 mg, 7.38 mmol), Pd(dtbpf)Cl$_2$ (240.36 mg, 368.80 umol), $K_3PO_4$ (2.35 g, 11.06 mmol) and $H_2O$ (2 mL). The mixture was degassed and purged with $N_2$ for three times and stirred at 80° C. for 2 hrs. The mixture was poured into water (100 mL) and extracted with EA (30 mL*3). The combined organic layer was washed by brine (30 mL), dried over anhydrous $Na_2SO_4$, filtered and concentrated under vacuum. The residue was purified by normal phase flash (column: $SiO_2$, 40 g, PE:EA=1:0-0:1, Rf=0.4). The eluent was concentrated under vacuum to give (2S,6R)-2,6-dimethyl-4-(6-vinylpyridin-2-yl)morpholine (850 mg, 3.64 mmol, 98.81% yield) as brown oil. LCMS (ESI) m/z: [M+H]$^+$=218.9. $^1$H NMR (400 MHz, CHLOROFORM-d) δ=7.47-7.43 (m, 1H), 6.73-6.63 (m, 2H), 6.54 (d, J=8.4 Hz, 1H), 6.23 (d, J=1.8 Hz, 1H), 6.19 (d, J=1.8 Hz, 1H), 5.39-5.36 (m, 1H), 4.15-4.12 (m, 2H), 3.75-3.72 (m, 2H), 2.55-2.49 (m, 2H), 1.28 (d, J=6.2 Hz, 6H) ppm.

Step 3: Preparation of tert-butyl ((4-bromopyridin-2-yl)methyl)carbamate

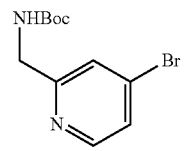 [SMILES: CC(C)(C)OC(=O)NCc1cc(Br)ccn1]

To a solution of (4-bromo-2-pyridyl)methanamine (2 g, 10.69 mmol) in DCM (20 mL) was added tert-butoxycarbonyl tert-butyl carbonate (4.20 g, 19.25 mmol, 4.42 mL), TEA (2.16 g, 21.39 mmol, 2.98 mL). The mixture was stirred at 25° C. for 2 hrs. The mixture was poured into water (50 mL) and extracted with DCM (50 mL*3). The combined organic layer was washed by brine (50 mL), dried over anhydrous $Na_2SO_4$, filtered and concentrated under vacuum. The residue was purified by normal phase flash (column: $SiO_2$, 80 g, PE:EA=1:0-1:1, RF=0.4). The eluent was concentrated to give tert-butyl ((4-bromopyridin-2-yl)methyl)carbamate (3 g, 10.19 mmol, 95.28% yield) as colorless oil. LCMS (ESI) m/z: [M+H-56]$^+$=230.8. $^1$H NMR (400 MHz, CHLOROFORM-d) δ=8.34 (d, J=5.4 Hz, 1H), 7.46 (d, J=1.2 Hz, 1H), 7.35-7.27 (m, 1H), 5.51 (br s, 1H), 4.42 (br d, J=5.2 Hz, 2H), 1.46 (s, 9H) ppm.

Step 4: Preparation of tert-butyl ((4-((E)-2-(6-((2S, 6R)-2,6-dimethylmorpholino)pyridin-2-yl)vinyl)pyridin-2-yl)methyl)carbamate

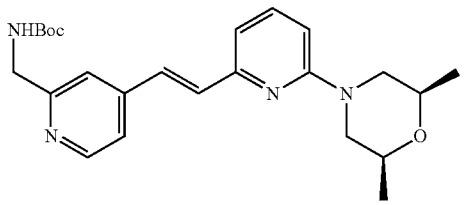 [SMILES: C[C@@H]1CN(c2cccc(/C=C/c3ccnc(CNC(=O)OC(C)(C)C)c3)n2)C[C@H](C)O1]

To a solution of (2S,6R)-2,6-dimethyl-4-(6-vinylpyridin-2-yl)morpholine (100 mg, 458.10 umol) in DMF (2 mL) was added tert-butyl ((4-bromopyridin-2-yl)methyl)carbamate (197.32 mg, 687.15 umol), Pd(OAc)$_2$ (10.28 mg, 45.81 umol), tris-o-tolylphosphane (34.86 mg, 114.52 umol) and DIEA (177.61 mg, 1.37 mmol, 239.37 uL). The mixture was degassed and purged with N$_2$ and stirred at 100° C. for 1 hr. The reaction mixture was poured into water (15 mL) and extracted with EA (10 mL*3). The combined organic layer was washed by brine (10 mL), dried over anhydrous Na$_2$SO$_4$, filtered and concentrated under vacuum. The residue was purified by normal phase flash (column: SiO$_2$, 12 g, PE:EA=1:0-0:1, Rf=0.4). The eluent was concentrated to give tert-butyl ((4-((E)-2-(6-((2S,6R)-2,6-dimethylmorpholino)pyridin-2-yl)vinyl)pyridin-2-yl)methyl)carbamate (190 mg, 399.62 umol, 87.23% yield) as white solid. LCMS (ESI) m/z: [M+H]$^+$=425.1. $^1$H NMR (400 MHz, CHLOROFORM-d) δ=8.51 (br d, J=5.4 Hz, 1H), 7.59-7.39 (m, 4H), 7.28 (br s, 1H), 7.24 (br s, 1H), 6.76 (d, J=7.2 Hz, 1H), 6.63 (d, J=8.4 Hz, 1H), 5.85-5.70 (m, 1H), 4.52 (br d, J=4.8 Hz, 2H), 4.17 (br d, J=12.6 Hz, 2H), 3.82-3.73 (m, 2H), 2.61-2.55 (m, 2H), 1.47 (s, 9H), 1.32 (d, J=6.2 Hz, 6H) ppm.

Step 5: Preparation of (4-((E)-2-(6-((2S,6R)-2,6-dimethylmorpholino)pyridin-2-yl)vinyl)pyridin-2-yl)methanamine

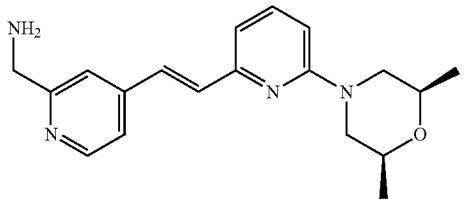 [SMILES: C[C@@H]1CN(c2cccc(/C=C/c3ccnc(CN)c3)n2)C[C@H](C)O1]

To a mixture of tert-butyl ((4-((E)-2-(6-((2S,6R)-2,6-dimethylmorpholino)pyridin-2-yl)vinyl)pyridin-2-yl)methyl)carbamate (100 mg, 235.55 umol) in DCM (1 mL) was added TFA (0.3 mL). The mixture was stirred at 25° C. for 1 hr. The mixture was poured into sat. NaHCO$_3$ (5 mL) and extracted with DCM (5 mL*3). The combined organic layer was washed by brine (5 mL), dried over anhydrous Na$_2$SO$_4$, filtered and concentrated under vacuum to give (4-((E)-2-(6-((2S,6R)-2,6-dimethylmorpholino)pyridin-2-yl)vinyl)pyridin-2-yl)methanamine (75 mg, crude) as yellow oil. LCMS (ESI) m/z: [M+H]$^+$=325.0

Step 6: Preparation of (R)—N-((4-((E)-2-(6-((2S, 6R)-2,6-dimethylmorpholino)pyridin-2-yl)vinyl)pyridin-2-yl)methyl)-4,9-difluoro-3,4-dihydro-2H-benzo[b][1,4]oxathiepine-7-carboxamide 5,5-dioxide (Compound 52)

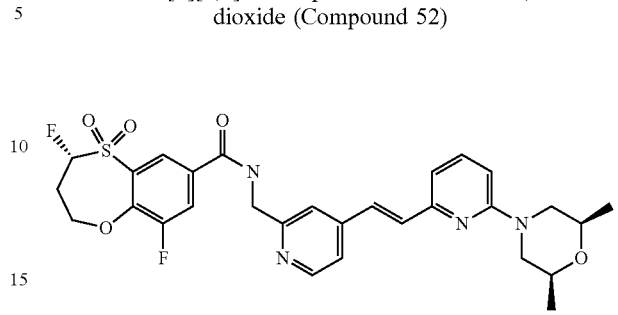

To a solution of (4R)-4,9-difluoro-5,5-dioxo-3,4-dihydro-2H-1,5λ6-benzoxathiepine-7-carboxylic acid (Intermediate 2) (64.32 mg, 231.18 umol) in DCM (2 mL) was added HATU (131.85 mg, 346.77 umol) and DIEA (89.64 mg, 693.55 umol, 120.80 uL). Then (4-((E)-2-(6-((2S,6R)-2,6-dimethylmorpholino)pyridin-2-yl)vinyl)pyridin-2-yl)methanamine (75 mg, 231.18 umol) was added. The mixture was stirred at 25° C. for 2 hrs. The mixture was poured into water (20 mL) and extracted with EA (10 mL*3). The combined organic layer was washed by brine (10 mL), dried over anhydrous Na$_2$SO$_4$, filter and concentrated under vacuum. The residue was purified by prep-HPLC (column: Phenomenex luna C18 150*25 mm*10 um; mobile phase: [water (FA)-ACN]; B %: 30%-60%, 10 min). Then the eluent was concentrated and lyophilized to give (R)—N-((4-((E)-2-(6-((2S,6R)-2,6-dimethylmorpholino)pyridin-2-yl)vinyl)pyridin-2-yl)methyl)-4,9-difluoro-3,4-dihydro-2H-benzo[b][1,4]oxathiepine-7-carboxamide 5,5-dioxide (28.28 mg, 43.20 umol, 18.69% yield, FA) as yellow solid. LCMS (ESI) m/z: [M+H]$^+$=585.1. $^1$H NMR (400 MHz, CHLOROFORM-d) δ=8.53 (d, J=5.4 Hz, 1H), 8.30-8.26 (m, 1H), 8.15 (s, 1H), 8.08-8.05 (m, 2H), 7.56-7.50 (m, 3H), 7.46-7.44 (m, 1H), 7.30 (s, 1H), 7.26 (br s, 1H), 6.78 (d, J=7.2 Hz, 1H), 6.63 (d, J=8.4 Hz, 1H), 5.76-5.38 (m, 1H), 4.80 (d, J=5.2 Hz, 2H), 4.67-4.65 (m, 1H), 4.19-4.16 (m, 2H), 4.11-4.09 (m, 1H), 3.85-3.68 (m, 2H), 3.21-2.96 (m, 1H), 2.59-5.28 (m, 2H), 2.52-2.42 (m, 1H), 1.32 (d, J=6.4 Hz, 7H) ppm. Chiral SFC: OJ-3-EtOH (DEA)-5-40-3ML-35T.lcm, Rt=1.847 mins, ee %=100%.

Preparation of Intermediate 4 (2R)-2,6-difluoro-1,1-dioxo-3,5-dihydro-2H-4,1λ6-benzoxathiepine-8-carboxylic Acid

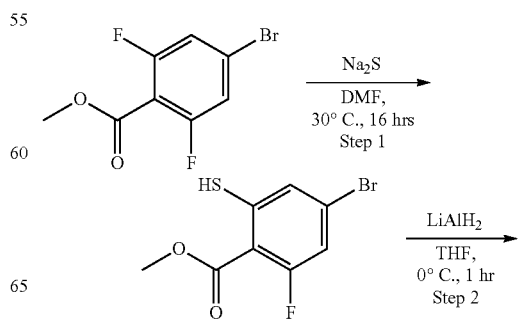

-continued

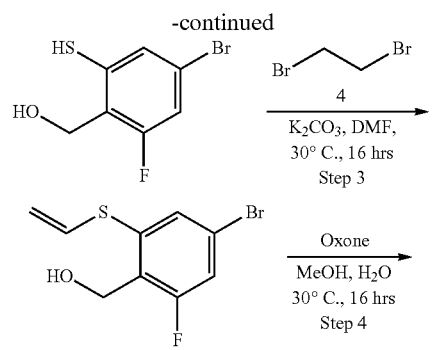

K₂CO₃, DMF,
30° C., 16 hrs
Step 3

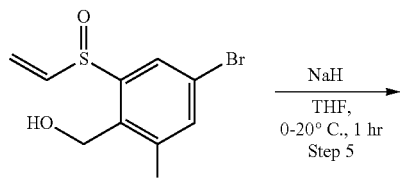

Oxone
MeOH, H₂O
30° C., 16 hrs
Step 4

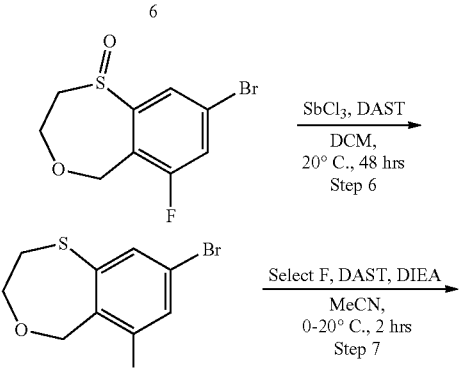

NaH
THF,
0-20° C., 1 hr
Step 5

6

SbCl₃, DAST
DCM,
20° C., 48 hrs
Step 6

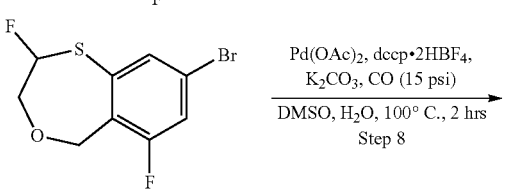

Select F, DAST, DIEA
MeCN,
0-20° C., 2 hrs
Step 7

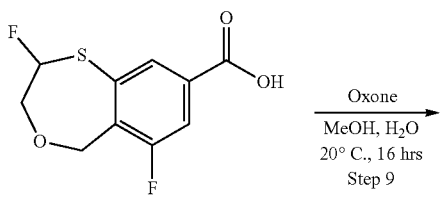

Pd(OAc)₂, dccp·2HBF₄,
K₂CO₃, CO (15 psi)
DMSO, H₂O, 100° C., 2 hrs
Step 8

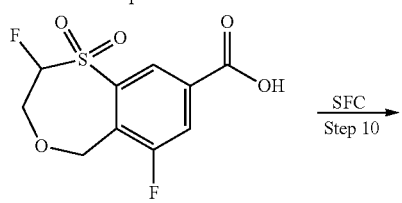

Oxone
MeOH, H₂O
20° C., 16 hrs
Step 9

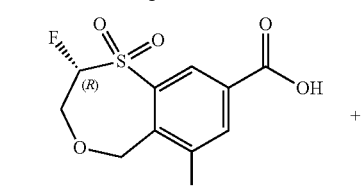

SFC
Step 10

Intermediate 4

-continued

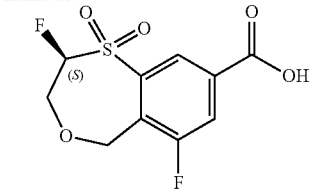

Step 1: Preparation of methyl
4-bromo-2-fluoro-6-sulfanyl-benzoate

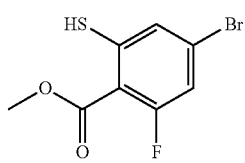

To a solution of methyl 4-bromo-2,6-difluoro-benzoate (100 g, 398.37 mmol) in DMF (1000 mL) was added Na₂S (34.54 g, 398.37 mmol, 90% purity), the mixture was stirred at 30° C. for 16 hrs. The reaction mixture was poured into water (1500 mL) and extracted with MTBE (1500 mL*2). The aqueous phase was adjusted to pH=2 with 1 N HCl and extracted with MTBE (1500 mL*3). The combined organic layer was washed with water (2000 mL*2) and brine (5000 mL), dried over Na₂SO₄, filtered and concentrated to give methyl 4-bromo-2-fluoro-6-sulfanyl-benzoate (105 g, crude) as yellow oil. LCMS (ESI) m/z: [Br⁷⁹M+H]⁺=232.9

Step 2: Preparation of
(4-bromo-2-fluoro-6-sulfanyl-phenyl)methanol

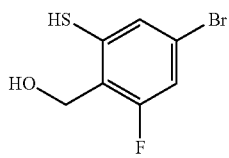

To a solution of methyl 4-bromo-2-fluoro-6-sulfanyl-benzoate (105 g, 396.08 mmol) in THF (1000 mL) was added LiAlH₄ (15.03 g, 396.08 mmol) at 0° C. under N₂, the mixture was stirred at 0° C. for 1 hr. The mixture was poured into 1 N HCl (1000 mL) and extracted with EtOAc (1000 mL*2). The combined organic phase was washed with brine (2000 mL), dried over anhydrous Na₂SO₄, filtered and concentrated under vacuum to give (4-bromo-2-fluoro-6-sulfanyl-phenyl)methanol (93 g, crude) as yellow oil and used directly in the next step.

Step 3: Preparation of
(4-bromo-2-fluoro-6-vinylsulfanyl-phenyl)methanol

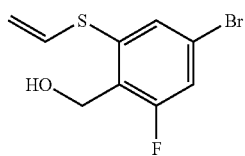

To a solution of (4-bromo-2-fluoro-6-sulfanyl-phenyl)methanol (93 g, 392.26 mmol) in DMF (1800 mL) was added K$_2$CO$_3$ (162.64 g, 1.18 mol) and 1,2-dibromoethane (221.07 g, 1.18 mol, 88.78 mL), the mixture was stirred at 30° C. for 16 hrs. The reaction was quenched by water (2000 mL). The mixture was extracted with ethyl acetate (2000 mL*3). The combined organic layers were dried over Na$_2$SO$_4$ and concentrated to give a residue. The residue was purified by column chromatography (SiO$_2$, Petroleum ether/Ethyl acetate=10:1-1:1), the solution was concentrated to give (4-bromo-2-fluoro-6-vinylsulfanyl-phenyl)methanol (56 g, 212.83 mmol) as yellow oil. $^1$H NMR (400 MHz, CDCl$_3$) δ=7.33 (s, 1H), 7.19-7.17 (m, 1H), 6.50-6.44 (m, 1H), 5.54-5.42 (m, 2H), 4.78 (d, J=1.2 Hz, 2H), 2.13 (s, 1H) ppm Step 4: Preparation of (4-bromo-2-fluoro-6-vinylsulfinyl-phenyl)methanol

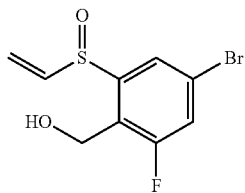

To a solution of (4-bromo-2-fluoro-6-vinylsulfanyl-phenyl)methanol (10 g, 38.00 mmol) in MeOH (100 mL) and H$_2$O (100 ml) was added Oxone (11.68 g, 19.00 mmol), the mixture was stirred at 30° C. for 16 hrs. The reaction mixture was poured into water (1 L), the solution was extracted with EA (1 L*3), the combined organic layer was washed with sat·Na$_2$SO$_3$ (1 L) and brine (1 L), dried over Na$_2$SO$_4$, filtered and concentrated to give (4-bromo-2-fluoro-6-vinylsulfinyl-phenyl)methanol (10.61 g, crude) as yellow oil. LCMS (ESI) m/z: [Br$^{79}$M+H]$^+$=263.0

Step 5: Preparation of 8-bromo-6-fluoro-3,5-dihydro-2H-4,1λ4-benzoxathiepine 1-oxide

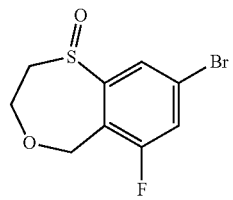 [SMILES: O=S1CCOCc2c(F)cc(Br)cc21]

To a solution of (4-bromo-2-fluoro-6-vinylsulfinyl-phenyl)methanol (10.6 g, 37.98 mmol) in THF (110 mL) was added NaH (3.04 g, 75.95 mmol, 60% purity) at 0° C., then the mixture was stirred at 20° C. for 1 hr. The reaction mixture was poured into NH$_4$Cl (500 mL), the solution was extracted with EA (500 mL*3), the combined organic layer was washed with brine (1000 mL), dried over Na$_2$SO$_4$, filtered and concentrated to give a residue. The residue was purified by column chromatography (SiO$_2$, Petroleum ether/Ethyl acetate=10:1-1:1), the solution was concentrated to give 8-bromo-6-fluoro-3,5-dihydro-2H-4,1λ4-benzoxathiepine 1-oxide (5.5 g, 19.70 mmol, 51.89% yield) as a white solid. $^1$H NMR (400 MHz, DMSO-d$_6$) δ=7.78-7.75 (m, 1H), 7.62 (s, 1H), 4.96 (d, J=15.2 Hz, 1H), 4.54-4.50 (m, 1H), 4.33-4.24 (m, 2H), 3.41-3.39 (m, 2H) ppm Step 6: Preparation of 8-bromo-6-fluoro-3,5-dihydro-2H-4,1λ4-benzoxathiepine 1-oxide & 8-bromo-2,6-difluoro-3,5-dihydro-2H-4,1-benzoxathiepine

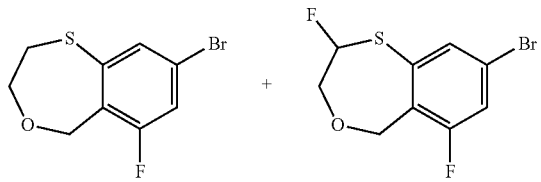 [SMILES: Fc1cc(Br)cc2c1COCCS2 ; Fc1cc(Br)cc2c1COCC(F)S2]

To a solution of 8-bromo-6-fluoro-3,5-dihydro-2H-4,1λ4-benzoxathiepine 1-oxide (1.9 g, 6.81 mmol) in DCM (40 mL) was added SbCl$_3$ (46.58 mg, 204.21 umol) and then DAST (2.19 g, 13.61 mmol, 1.80 mL) was added. The mixture was stirred at 20° C. for 16 hrs. Then DAST (5.49 g, 34.03 mmol, 4.50 mL) was added, the mixture was stirred at 20° C. for 16 hrs. SbCl$_3$ (1.55 g, 6.81 mmol) and DAST (10.97 g, 68.07 mmol, 8.99 mL) was added, the mixture was stirred at 20° C. for 16 hrs. The reaction mixture was poured into NaHCO$_3$ solution (200 mL), the solution was extracted with EA (200 mL*3), the combined organic layer was washed with brine (500 mL), dried over Na$_2$SO$_4$, filtered and concentrated to give a residue. The residue was purified by column chromatography (SiO$_2$, Petroleum ether/Ethyl acetate=20:1-5:1), the peak 1 eluent was concentrated to give 8-bromo-6-fluoro-3,5-dihydro-2H-4,1λ4-benzoxathiepine 1-oxide (1.2 g, 4.56 mmol, 67.00% yield) as yellow oil. $^1$H NMR (400 MHz, CDCl$_3$) δ=7.54-7.51 (m, 1H), 7.18-7.15 (m, 1H), 4.91-4.89 (m, 2H), 4.17-4.14 (m, 2H), 2.89-2.86 (m, 2H) ppm. The peak 2 eluent was concentrated to give 8-bromo-2,6-difluoro-3,5-dihydro-2H-4,1-benzoxathiepine (600 mg, 2.13 mmol, 31.36% yield) as a yellow solid. $^1$H NMR (400 MHz, CDCl$_3$) δ=7.55-7.54 (m, 1H), 7.27-7.24 (m, 1H), 5.63-5.51 (m, 1H), 5.25 (d, J=13.6 Hz, 1H), 4.69-4.65 (m, 1H), 4.43-4.41 (m, 1H), 4.13-4.05 (m, 1H) ppm Step 7: Preparation of 8-bromo-2,6-difluoro-3,5-dihydro-2H-4,1-benzoxathiepine

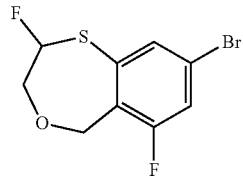 [SMILES: Fc1cc(Br)cc2c1COCC(F)S2]

To a solution of 8-bromo-6-fluoro-3,5-dihydro-2H-4,1λ4-benzoxathiepine 1-oxide (1.2 g, 4.56 mmol) in MeCN (25 mL) was added Select F (2.02 g, 5.70 mmol) and then DAST (147.02 mg, 912.11 umol, 120.51 uL) was added under ice-bath. The solution was stirred at 20° C. for 1 hr. Then to the mixture was added DIEA (884.11 mg, 6.84 mmol, 1.19 mL) at 0° C., then the mixture was stirred at 20° C. for 1 hr. The reaction mixture was poured into NaHCO$_3$ solution (200 mL) and extracted with EA (200 mL*3). The combined organic layer was washed with brine (500 mL), dried over Na$_2$SO$_4$, filtered, and concentrated to give a residue. The residue was purified by column chromatography (SiO$_2$, Petroleum ether/Ethyl acetate=20:1-5:1), the solution was concentrated to give 8-bromo-2,6-difluoro-3,5-dihydro-2H-4,1-benzoxathiepine (500 mg, 1.78 mmol, 39.00% yield) as a yellow solid. $^1$H NMR (400 MHz, CDCl$_3$) δ=7.54 (m, 1H), 7.27-7.24 (m, 1H), 5.63-5.51 (m, 1H), 5.25 (d, J=13.6 Hz, 1H), 4.70-4.66 (m, 1H), 4.43-4.42 (m, 1H), 4.13-4.05 (m, 1H) ppm Step 8: Preparation of 2,6-difluoro-3,5-dihydro-2H-4,1-benzoxathiepine-8-carboxylic Acid

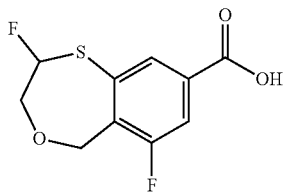 [SMILES: O=C(O)c1cc(F)c2c(c1)SC(F)COC2]

To a solution of 8-bromo-2,6-difluoro-3,5-dihydro-2H-4,1-benzoxathiepine (1.3 g, 4.62 mmol) in DMSO (20 mL) and H$_2$O (4 mL) was added K$_2$CO$_3$ (958.71 mg, 6.94 mmol), dicyclohexyl(3-dicyclohexylphosphaniumylpropyl)phosphonium; ditetrafluoroborate (283.13 mg, 462.44 umol) and Pd(OAc)$_2$ (103.82 mg, 462.44 umol). The suspension was degassed under vacuum and purged with CO several times. The mixture was stirred under CO (15 psi) at 100° C. for 2 hrs. The reaction mixture was poured into NaHCO$_3$ solution (100 mL) and extracted with EA (100 mL*2). The aqueous phase was adjusted to pH=1 with 1 N HCl and extracted with EA (50 mL*2), the combined organic layer was dried over Na$_2$SO$_4$, filtered and concentrated to give 2,6-difluoro-3,5-dihydro-2H-4,1-benzoxathiepine-8-carboxylic acid (1.1 g, crude) as a yellow solid that was used without purification.

Step 9: Preparation of 2,6-difluoro-1,1-dioxo-3,5-dihydro-2H-4,1λ$^6$-benzoxathiepine-8-carboxylic Acid

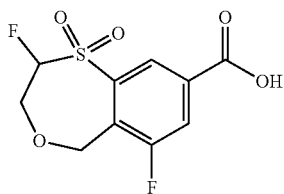 [SMILES: O=C(O)c1cc(F)c2c(c1)S(=O)(=O)C(F)COC2]

To a solution of 2,6-difluoro-3,5-dihydro-2H-4,1-benzoxathiepine-8-carboxylic acid (1.1 g, 4.47 mmol) in MeOH (12 mL) and H$_2$O (12 mL) was added Oxone (5.49 g, 8.93 mmol), the mixture was stirred at 20° C. for 16 hrs. The reaction mixture was poured into water (100 mL), the solution was extracted with EA (100 mL*3), the combined organic layer was washed with brine (200 mL), dried over Na$_2$SO$_4$, filtered and concentrated to give 2,6-difluoro-1,1-dioxo-3,5-dihydro-2H-4,1λ6-benzoxathiepine-8-carboxylic acid (1.1 g, 3.95 mmol, 88.50% yield) as a white solid. $^1$H NMR (400 MHz, DMSO-d$_6$) δ=14.03-13.95 (m, 1H), 8.34 (d, J=1.2 Hz, 1H), 8.13-8.11 (m, 1H), 6.27-6.16 (m, 1H), 5.25-5.21 (m, 1H), 4.91-4.86 (m, 1H), 4.47-4.38 (m, 2H) ppm.

Step 10: Preparation of (2R)-2,6-difluoro-1,1-dioxo-3,5-dihydro-2H-4,1λ$^6$-benzoxathiepine-8-carboxylic acid (Intermediate 4) and (2S)-2,6-difluoro-1,1-dioxo-3,5-dihydro-2H-4,1λ$^6$-benzoxathiepine-8-carboxylic Acid

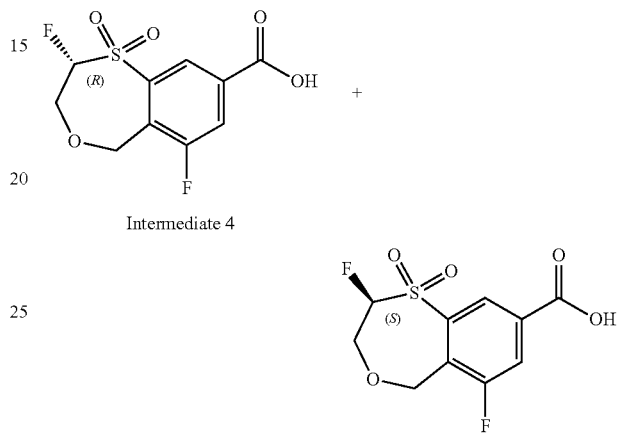

Intermediate 4

2,6-difluoro-1,1-dioxo-3,5-dihydro-2H-4,1λ6-benzoxathiepine-8-carboxylic acid (1.1 g, 3.95 mmol) was separated by chiral SFC (column: Daicel ChiralPak IG (250*30 mm, 10 um); mobile phase: [0.1% NH$_3$H$_2$O MEOH]; B %: 20%-20%, 4.75; 310 min) give two peaks. The peak 1 eluent was concentrated to give a residue, the residue was diluted with water (100 mL) and adjusted to pH=2 with 4 N HCl solution, the solution was extracted with EA (100 mL*2), the combined organic layer was dried over Na$_2$SO$_4$, filtered and concentrated to get (2R)-2,6-difluoro-1,1-dioxo-3,5-dihydro-2H-4,1λ6-benzoxathiepine-8-carboxylic acid (Intermediate 4) (350 mg, 1.25 mmol, 31.69% yield) as a white solid. $^1$H NMR (400 MHz, DMSO-d$_6$) δ=14.17-13.92 (m, 1H), 8.33 (s, 1H), 8.13-8.11 (m, 1H), 6.27-6.17 (m, 1H), 5.25-5.21 (m, 1H), 4.91-4.86 (m, 1H), 4.47-4.35 (m, 2H) ppm Chiral SFC: IG-3_5CM_MEOH(DEA)_5_40_3ML_T35.M; Rt=1.408 mins, ee %=98.14%. The peak 2 eluent was concentrated to give a residue, the residue was diluted with water (100 mL) and adjusted to pH=2 with 4 N HCl solution, the solution was extracted with EA (100 mL*2), the combined organic layer was dried over Na$_2$SO$_4$, filtered and concentrated to get (2S)-2,6-difluoro-1,1-dioxo-3,5-dihydro-2H-4,1λ6-benzoxathiepine-8-carboxylic acid (500 mg, 1.66 mmol, 41.94% yield) as a white solid. $^1$H NMR (400 MHz, DMSO-d$_6$) δ=14.27-13.55 (m, 1H), 8.34 (d, J=1.2 Hz, 1H), 8.13-8.10 (m, 1H), 6.27-6.16 (m, 1H), 5.26-5.21 (m, 1H), 4.91-4.86 (m, 1H), 4.47-4.38 (m, 2H) ppm. Chiral SFC: IG-3_5CM_MEOH(DEA)_5_40_3ML_T35.M; Rt=1.624 mins, ee %=98.96%

309

Preparation of (R)—N-((4-((6-(difluoromethoxy) pyridin-2-yl) ethynyl) pyridin-2-yl) methyl)-2,6-difluoro-3,5-dihydro-2H-benzo[e] [1,4] oxathiepine-8-carboxamide 1,1-dioxide (Compound 184)

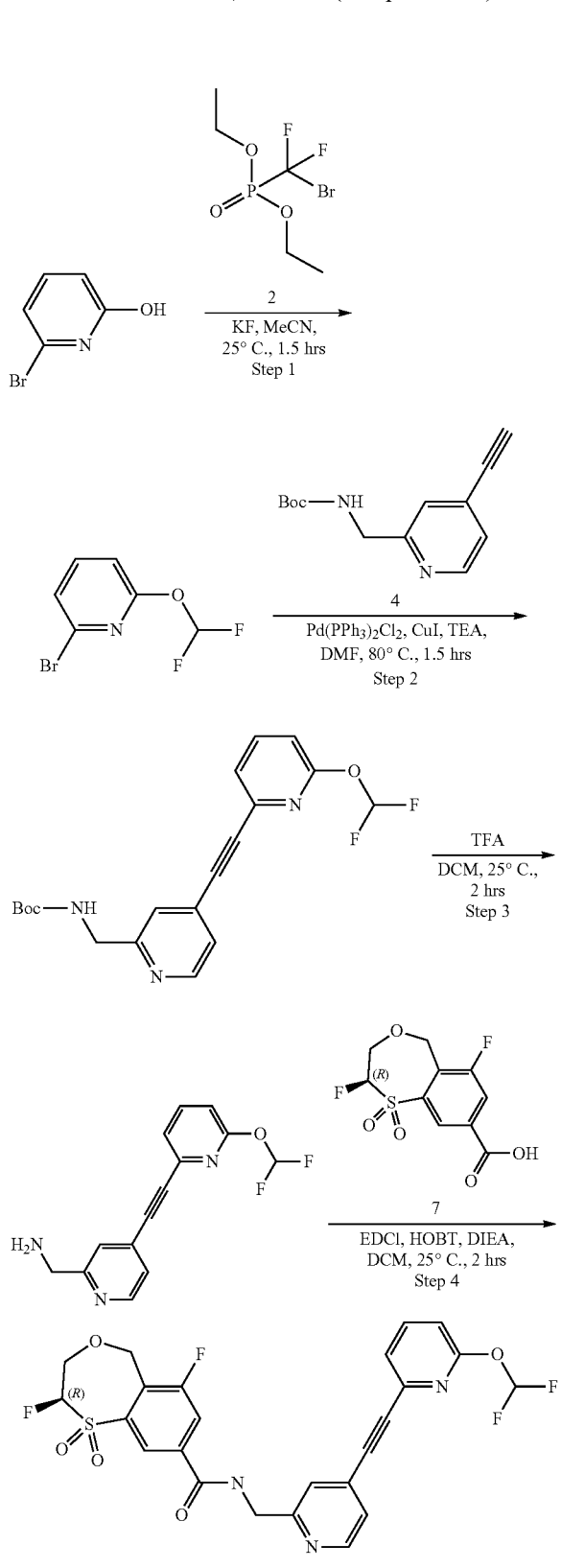

310

Step 1: Preparation of 2-bromo-6-(difluoromethoxy) pyridine

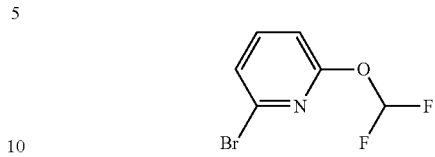

To a solution of 6-bromopyridin-2-ol (2 g, 11.49 mmol) in MeCN (20 mL) was added KF (1.34 g, 22.99 mmol, 538.55 uL) and 1-[[bromo (difluoro)methyl]-ethoxy-phosphoryl] oxyethane (3.38 g, 12.64 mmol). The mixture was stirred at 25° C. for 1.5 hrs. The reaction mixture was poured into water (100 mL) and extracted with DCM (100 mL*3). The organic layer was dried over anhydrous $Na_2SO_4$, filtered and concentrated in vacuum. The residue was purified by flash silica gel chromatography (column: $SiO_2$, 80 g; PE/EA=1/0-0/1, 40 mL/min, Rf=0.80). The eluent was concentrated in vacuum to give 2-bromo-6-(difluoromethoxy) pyridine (2.23 g, 9.59 mmol, 83.47% yield) as a yellow oil. LCMS (ESI) m/z: $[M+H]^+$=225.7 $^1$H NMR (400 MHz, DMSO-$d_6$) δ=7.91-7.80 (m, 1H), 7.66-7.54 (m, 1H), 7.50 (d, J=28.8 Hz, 1H), 7.15 (d, J=8.0 Hz, 1H) ppm.

Step 2: Preparation of tert-butyl ((4-((6-(difluoromethoxy) pyridin-2-yl) ethynyl) pyridin-2-yl) methyl) carbamate

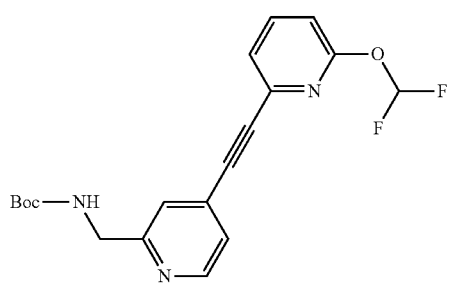 [SMILES: CC(C)(C)OC(=O)NCc1cc(C#Cc2cccc(OC(F)F)n2)ccn1]

To a solution of 2-bromo-6-(difluoromethoxy) pyridine (100 mg, 446.42 umol) and tert-butyl N-[(4-ethynyl-2-pyridyl)methyl]carbamate (103.69 mg, 446.42 umol) in DMF (1 mL) was added TEA (451.73 mg, 4.46 mmol, 621.36 uL), Pd(PPh$_3$)$_2$Cl$_2$ (31.33 mg, 44.64 umol) and CuI (8.50 mg, 44.64 umol). The mixture was degassed and purged with N$_2$ and stirred at 80° C. for 1.5 hrs. The reaction mixture was poured into water (5 mL) and extracted with EA (5 mL*3). The combined organic layer was washed with brine (5 mL), dried over Na$_2$SO$_4$, filtered and concentrated in vacuum. The residue was purified by flash silica gel chromatography (column: SiO$_2$, 20 g; PE/EA=1/0~1/0, 40 mL/min, Rf=0.30). The eluent was concentrated in vacuum to give tert-butyl ((4-((6-(difluoromethoxy) pyridin-2-yl) ethynyl) pyridin-2-yl) methyl) carbamate (116 mg, 289.24 umol, 64.79% yield) as a yellow oil.

LCMS (ESI) m/z: $[M+H]^+$=375.9. $^1$H NMR (400 MHz, CHLOROFORM-d) δ=8.77-8.39 (m, 1H), 7.79-7.73 (m, 1H), 7.55 (s, 1H), 7.48-7.47 (m, 1H), 7.37 (d, J=6.8 Hz, 1H), 6.93 (d, J=8.4 Hz, 1H), 5.53 (br s, 1H), 4.47 (br s, 2H), 1.48 (s, 9H) ppm.

Step 3: Preparation of (4-((6-(difluoromethoxy) pyridin-2-yl) ethynyl) pyridin-2-yl)methanamine

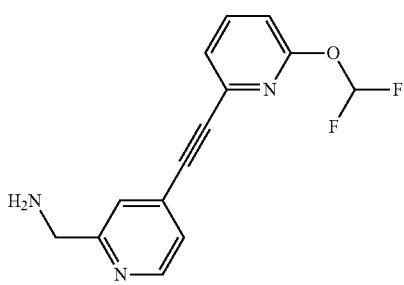 [SMILES: NCc1cc(C#Cc2cccc(OC(F)F)n2)ccn1]

To a solution of tert-butyl ((4-((6-(difluoromethoxy) pyridin-2-yl) ethynyl) pyridin-2-yl) methyl) carbamate (110 mg, 293.05 umol) in DCM (1 mL) was added TFA (0.3 mL). The mixture was stirred at 25° C. for 2 hrs. The reaction mixture was poured into aq·NaHCO₃ (10 mL) and extracted EA (10 mL*3). The combined organic layer was dried over with Na₂SO₄, filtered and concentrated to dryness to give (4-((6-(difluoromethoxy) pyridin-2-yl) ethynyl) pyridin-2-yl)methanamine (80 mg, 257.81 umol, 87.98% yield) as a yellow solid.

LCMS (ESI) m/z: [M+H]$^+$=275.8

Step 4: Preparation of (R)—N-((4-((6-(difluoromethoxy) pyridin-2-yl)ethynyl)pyridin-2-yl) methyl)-2,6-difluoro-3,5-dihydro-2H-benzo[e][1,4]oxathiepine-8-carboxamide 1,1-dioxide (Compound 184)

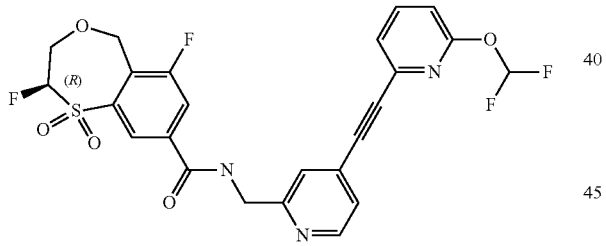

To a solution of (2R)-2,6-difluoro-1,1-dioxo-3,5-dihydro-2H-4, 1λ⁶-benzoxathiepine-8-carboxylic acid (Intermediate 4) (80.86 mg, 290.64 umol) in DCM (1 mL) was added EDCI (83.57 mg, 435.96 umol), HOBt (58.91 mg, 435.96 umol) and DIEA (112.69 mg, 871.93 umol, 151.87 uL). Then (4-((6-(difluoromethoxy) pyridin-2-yl) ethynyl) pyridin-2-yl)methanamine (80 mg, 290.64 umol) was added. The mixture was stirred at 25° C. for 2 hrs. The reaction mixture was poured into water (10 mL) and extracted EA (10 mL*3). The combined organic layer was dried over with Na₂SO₄, filtered and concentrated in vacuum. The residue was purified by prep-HPLC (column: Phenomenex luna C18 150*25 mm*10 um; mobile phase: [water (FA)-ACN]; B %: 42%-72%, 10 min). The eluent was concentrated and lyophilized to give (R)—N-((4-((6-(difluoromethoxy) pyridin-2-yl)ethynyl)pyridin-2-yl)methyl)-2,6-difluoro-3,5-dihydro-2H-benzo[e][1,4]oxathiepine-8-carboxamide 1,1-dioxide (13.44 mg, 25.10 umol, 8.64% yield) as a yellow solid.

LCMS (ESI) m/z: [M+H]$^+$=536.0. ¹H NMR (400 MHz, CHLOROFORM-d) δ=8.63 (d, J=5.2 Hz, 1H), 8.41 (s, 1H), 8.05-8.00 (m, 1H), 7.86 (br s, 1H), 7.77-7.75 (m, 1H), 7.56 (s, 1H), 7.45 (d, J=5.2 Hz, 1H), 7.41-7.37 (m, 1H), 6.96 (d, J=8.4 Hz, 1H), 5.44-5.29 (m, 2H), 4.99-4.95 (m, 1H), 4.83 (d, J=4.8 Hz, 2H), 4.54-4.49 (m, 1H), 4.48-4.44 (m, 1H) ppm. Chiral SFC: OJ-3-MeOH (DEA)-5-40-3ML-35T.lcm, Rt=1.676 mins, ee %=100%.

Preparation of Intermediate 3 (R)-9-chloro-4-fluoro-3,4-dihydro-2H-benzo[b][1,4]oxathiepine-7-carboxylic acid 5,5-dioxide

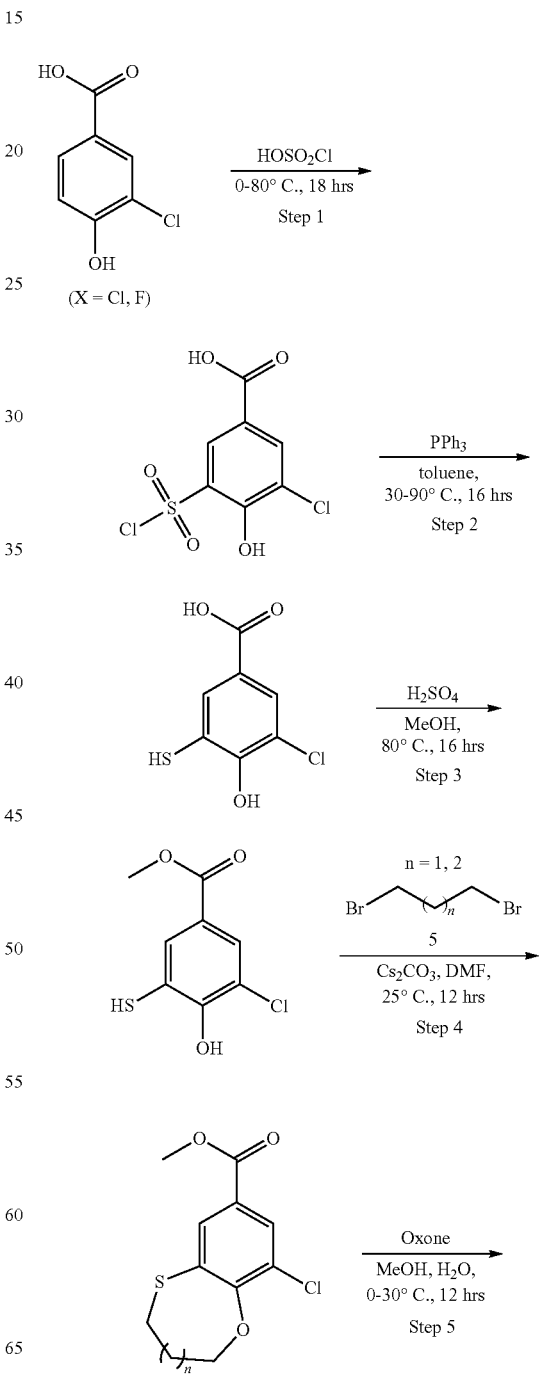

-continued

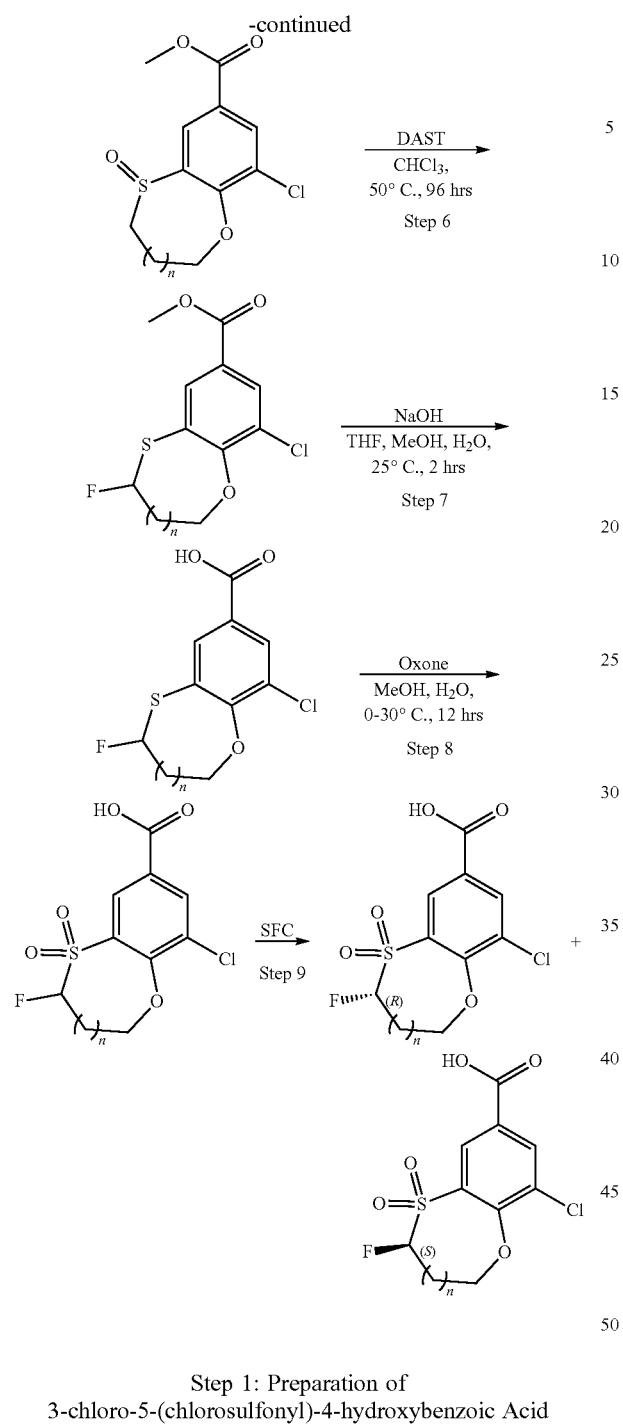

Step 1: Preparation of
3-chloro-5-(chlorosulfonyl)-4-hydroxybenzoic Acid

To HSO₃Cl (525.00 g, 4.51 mol, 300.00 mL) was added 3-chloro-4-hydroxy-benzoic acid (60 g, 347.69 mmol) at 20° C. The mixture was stirred at 80° C. for 16 h. The reaction mixture was poured into ice water (2000 mL) slowly and a lot of solid was formed. Then the solid was collected by filtered, washed with water (1000 mL) and the filter cake was diluted EA (3000 mL), washed with water (1000 mL). The organic layer was dried over Na$_2$SO$_4$, filtered and concentrated to give 3-chloro-5-(chlorosulfonyl)-4-hydroxybenzoic acid (78 g, 244.58 mmol, 70.34% yield, 85% purity) as white solid. $^1$H NMR (400 MHz, DMSO-d$_6$) δ=12.29-11.14 (m, 1H), 8.01 (d, J=2.0 Hz, 1H), 7.86 (d, J=2.0 Hz, 1H) ppm.

Step 2: Preparation of
3-chloro-4-hydroxy-5-mercaptobenzoic Acid

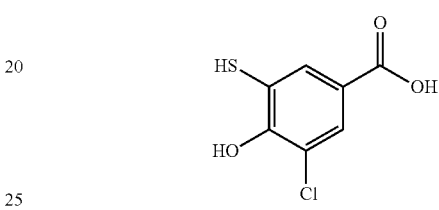

To a solution of 3-chloro-5-(chlorosulfonyl)-4-hydroxybenzoic acid (78 g, 287.74 mmol) in toluene (1600 mL) was added PPh$_3$ (264.15 g, 1.01 mol, 3.5 eq). The mixture was stirred at 90° C. for 2 h. The reaction mixture was quenched by addition 10% NaOH (aq) until pH=9, then extracted with DCM (1000 mL). The organic layer was discarded and the aqueous layer was adjusted to pH=3 with 1 N HCl, and then diluted with H$_2$O (8000 mL) and extracted with EtOAc (1000 mL*2). The combined organic layers were washed with brine (500 mL), dried over Na2SO4, filtered and concentrated under reduced pressure to give 3-chloro-5-(chlorosulfonyl)-4-hydroxybenzoic acid (70 g, crude) as white solid, which was used for the next step directly.

Step 3: Preparation of methyl
3-chloro-4-hydroxy-5-mercaptobenzoate

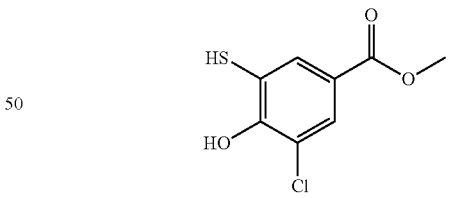

To a solution of 3-chloro-5-(chlorosulfonyl)-4-hydroxybenzoic acid (70 g, 342.08 mmol, 1 eq) in MeOH (700 mL) was added H$_2$SO$_4$ (33.55 g, 342.08 mmol, 18.23 mL, 1 eq). The mixture was stirred at 70° C. for 16 hrs. The reaction mixture was diluted with H$_2$O (2000 mL) and extracted with EtOAc (1000 mL*3). The combined organic layers were washed with brine (1000 mL), dried over Na$_2$SO$_4$, filtered and concentrated under reduced pressure to give methyl 3-chloro-4-hydroxy-5-mercaptobenzoate (61.4 g, 280.80 mmol, 82.09% yield) as white solid, which was used for the next step directly. $^1$H NMR (400 MHz, DMSO-d$_6$) δ=8.00-7.69 (m, 2H), 3.78 (s, 3H) ppm.

Step 4: Preparation of methyl 9-chloro-3,4-dihydro-2H-benzo[b][1,4]oxathiepine-7-carboxylate

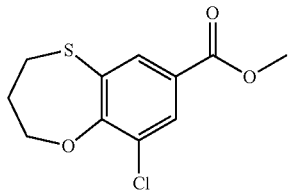 [SMILES: COC(=O)c1cc(Cl)c2c(c1)SCCCO2]

To a mixture of methyl 3-chloro-4-hydroxy-5-mercaptobenzoate (30 g, 137.20 mmol, 1 eq) and $Cs_2CO_3$ (223.51 g, 686.01 mmol, 5 eq) in DMF (1200 mL) was added 1,3-dibromopropane (30.47 g, 150.92 mmol, 15.39 mL, 1.1 eq). The mixture was stirred at 25° C. for 16 hrs. The mixture was diluted with water (1500 mL) and extracted with MTBE (methyl tert-butyl ether) (1500 mL×2). The organic layer was dried over $Na_2SO_4$ (1000 mL), filtered and concentrated. The material was purified by silica gel chromatography with Petroleum ether/Ethyl acetate (gradient: 0-50% of Ethyl acetate) and the eluent was concentrated in vacuum to give 9-chloro-3,4-dihydro-2H-benzo[b][1,4]oxathiepine-7-carboxylate (43 g, 56% of yield) as yellow solid. $^1$H NMR (400 MHz, DMSO-$d_6$) δ=7.90-7.76 (m, 2H), 4.38-4.22 (m, 2H), 3.83 (s, 3H), 3.12-2.97 (m, 2H), 2.26-2.15 (m, 2H) ppm.

Step 5: Preparation of methyl 9-chloro-4-fluoro-3,4-dihydro-2H-benzo[b][1,4]oxathiepine-7-carboxylate

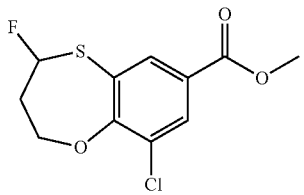 [SMILES: COC(=O)c1cc(Cl)c2c(c1)SC(F)CCO2]

To a solution of 9-chloro-3,4-dihydro-2H-benzo[b][1,4]oxathiepine-7-carboxylate (43 g, 166.20 mmol, 1 eq) in MeCN (800 mL) was added DAST (5.36 g, 33.24 mmol, 4.39 mL, 0.2 eq), then Select F (73.60 g, 207.75 mmol, 1.25 eq) was added at 0° C. The mixture was stirred at 0° C. for 1 hr. The reaction mixture was poured into $NaHCO_3$ (1000 mL), and extracted with EA (1000 mL*2). The combined organic layers were washed with brine (300 mL), dried over $Na_2SO_4$, filtered and concentrated under reduced pressure. The residue was purified by silica gel chromatography with Petroleum ether/Ethyl acetate (gradient: 0-50% of ethyl acetate) to give methyl 9-chloro-4-fluoro-3,4-dihydro-2H-benzo[b][1,4]oxathiepine-7-carboxylate (27 g, 97.57 mmol, 58.71% yield) as white solid. $^1$H NMR (400 MHz, DMSO-$d_6$) δ=7.98 (d, J=2.0 Hz, 1H), 7.90 (d, J=2.0 Hz, 1H), 6.37-6.20 (m, 1H), 4.63-4.58 (m, 1H), 4.07-3.98 (m, 1H), 3.85 (s, 3H), 2.61-2.52 (m, 1H), 2.49-2.46 (m, 1H) ppm.

Step 6: Preparation of 9-chloro-4-fluoro-3,4-dihydro-2H-benzo[b][1,4]oxathiepine-7-carboxylic Acid

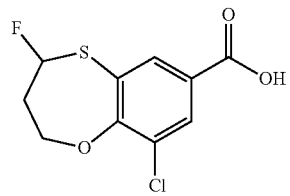 [SMILES: O=C(O)c1cc(Cl)c2c(c1)SC(F)CCO2]

To a solution of methyl 9-chloro-4-fluoro-3,4-dihydro-2H-benzo[b][1,4]oxathiepine-7-carboxylate (27 g, 97.57 mmol, 1 eq) in THF (280 mL), MeOH (140 mL) and Water (70 mL) was added LiOH·H2O (8.19 g, 195.15 mmol, 2 eq). The mixture was stirred at 25° C. for 1 hr. The reaction mixture was poured into ice cold $NaHCO_3$ (900 mL) and extracted with EA (300 mL*2). The combined organic layers were washed with brine (100 mL), dried over Na2SO4, filtered and concentrated under reduced pressure. The residue was purified by silica gel chromatography with Petroleum ether/Ethyl acetate (gradient: 0-50% of Ethyl acetate) to give 9-chloro-4-fluoro-3,4-dihydro-2H-benzo[b][1,4]oxathiepine-7-carboxylic acid (25.6 g, 97.46 mmol, 99.88% yield) as white solid. $^1$H NMR (400 MHz, DMSO-$d_6$) δ=13.38 (br s, 1H), 7.95 (d, J=2.0 Hz, 1H), 7.88 (d, J=2.0 Hz, 1H), 6.43-6.12 (m, 1H), 4.61-4.57 (m, 1H), 4.09-3.92 (m, 1H), 2.61-2.53 (m, 1H), 2.48-2.44 (m, 1H) ppm.

Step 7: Preparation of 9-chloro-4-fluoro-3,4-dihydro-2H-benzo[b][1,4]oxathiepine-7-carboxylic Acid 5,5-dioxide

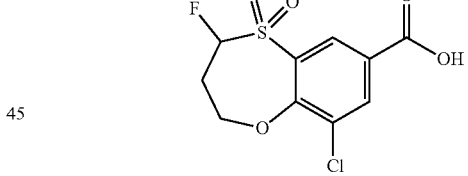

To a solution of 9-chloro-4-fluoro-3,4-dihydro-2H-benzo[b][1,4]oxathiepine-7-carboxylic acid (25.6 g, 97.46 mmol, 1 eq) in MeOH (500 mL) and Water (200 mL) was added Oxone (119.82 g, 194.91 mmol, 2 eq). The mixture was stirred at 40° C. for 48 hrs. The mixture was diluted with water (1000 mL) and extracted with EA (1000 mL×2). The organic layer was washed with mixed solution of 1 M, HCl (250 mL) and sat·$Na_2SO_3$ (250 mL), dried over $Na_2SO_4$, filtered and concentrated. The residue was purified by silica gel chromatography with Petroleum ether/Ethyl acetate (gradient: 0-80% of ethyl acetate) to give 9-chloro-4-fluoro-3,4-dihydro-2H-benzo[b][1,4]oxathiepine-7-carboxylic acid 5,5-dioxide (16 g, 54.30 mmol, 55.71% yield) as white solid. $^1$H NMR (400 MHz, DMSO-$d_6$) δ=14.40-13.23 (m, 1H), 8.34 (d, J=2.0 Hz, 1H), 8.30 (d, J=2.0 Hz, 1H), 6.44-6.10 (m, 1H), 4.64-4.58 (m, 1H), 4.16-4.04 (m, 1H), 2.93-2.60 (m, 2H). Chiral SFC: AD-3-MeOH(DEA)-5-40-3ML-35T.lcm, Rt=1.411 mins, 1.640 mins.

Step 8: Preparation of (R)-9-chloro-4-fluoro-3,4-dihydro-2H-benzo[b][1,4]oxathiepine-7-carboxylic Acid 5,5-dioxide (Intermediate 3) & (S)-9-chloro-4-fluoro-3,4-dihydro-2H-benzo[b][1,4]oxathiepine-7-carboxylic acid 5,5-dioxide

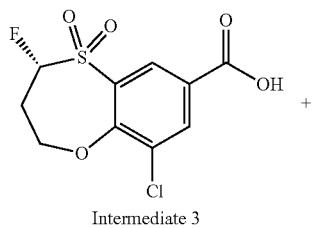

Intermediate 3

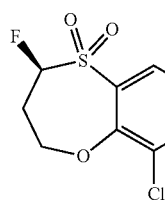

9-chloro-4-fluoro-3,4-dihydro-2H-benzo[b][1,4]oxathiepine-7-carboxylic acid 5,5-dioxide (1 g, 3.39 mmol) was separated by SFC separation: (column: DAICEL CHIRAL-PAK AD-H (250 mm*30 mm, 5 um); mobile phase: [0.1% NH₃H₂O MEOH]; B %: 35%-35%, 2.4; 80 min) to give Peak 1 and Peak 2. The eluent of Peak 1 was concentrated under reduced pressure to remove MeOH. The residue was diluted with water (30 mL) and adjusted pH=4 with 1 M a.q HCl and extracted with EA (20 mL*3). The combined organic layers were washed with brine (50 mL), dried over Na₂SO₄, filtered and concentrated under reduced pressure to give (R)-9-chloro-4-fluoro-3,4-dihydro-2H-benzo[b][1,4]oxathiepine-7-carboxylic acid 5,5-dioxide (Intermediate 3) (400 mg, 1.35 mmol, 39.64% yield) as white solid. ¹H NMR (400 MHz, DMSO-d₆) δ=8.34 (d, J=2.0 Hz, 1H), 8.29 (d, J=2.0 Hz, 1H), 6.37-6.16 (m, 1H), 4.64-4.58 (m, 1H), 4.16-4.04 (m, 1H), 2.94-2.72 (m, 2H), 2.64-2.53 (m, 1H) Chiral SFC: AD-3-MeOH(DEA)-5-40-3ML-35T.lcm, Rt=1.401 mins, ee %=100%. The eluent of Peak 2 was concentrated under reduced pressure to remove MeOH. The residue was diluted with water (30 mL) and adjusted pH=4 with 1 M a.q HCl and extracted with EA (20 mL*3). The combined organic layers were washed with brine (50 mL), dried over Na₂SO₄, filtered and concentrated under reduced pressure to give (S)-9-chloro-4-fluoro-3,4-dihydro-2H-benzo[b][1,4]oxathiepine-7-carboxylic acid 5,5-dioxide ¹H NMR (400 MHz, DMSO-d₆) δ=8.35 (d, J=2.0 Hz, 1H), 8.30 (d, J=2.0 Hz, 1H), 6.40-6.15 (m, 1H), 4.64-4.58 (m, 1H), 4.16-4.04 (m, 1H), 2.92-2.73 (m, 1H), 2.66-2.54 (m, 1H). Chiral SFC: AD-3-MeOH(DEA)-5-40-3ML-35T.lcm, Rt=1.626 mins, ee %=99%.

Preparation of (R)-9-chloro-N-((2-(7-((3R,4R)-3,4-difluoropyrrolidin-1-yl)-2,3-dihydro-4H-pyrido[3,2-b][1,4]oxazin-4-yl)-1,6-naphthyridin-7-yl)methyl)-4-fluoro-3,4-dihydro-2H-benzo[b][1,4]oxathiepine-7-carboxamide 5,5-dioxide (Compound 258)

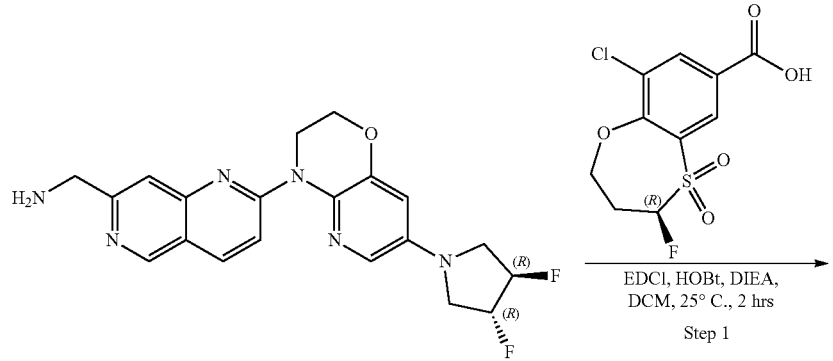

Step 1

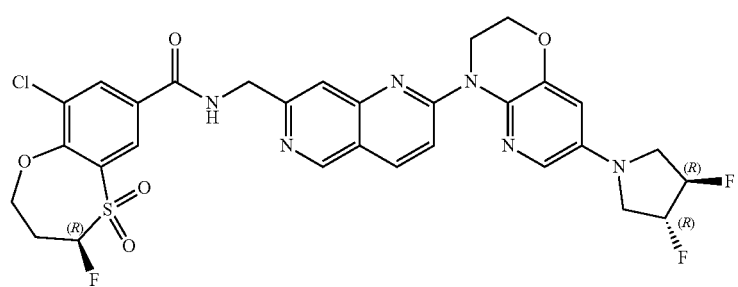

Step 1: Preparation of (R)-9-chloro-N-((2-(7-((3R, 4R)-3,4-difluoropyrrolidin-1-yl)-2,3-dihydro-4H-pyrido[3,2-b][1,4]oxazin-4-yl)-1,6-naphthyridin-7-yl)methyl)-4-fluoro-3,4-dihydro-2H-benzo[b][1,4]oxathiepine-7-carboxamide 5,5-dioxide

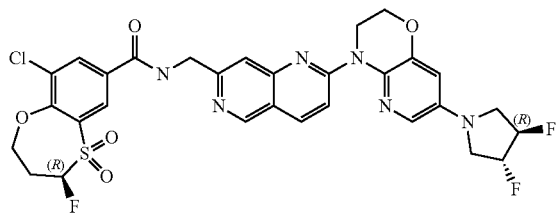

To a solution of (4R)-9-chloro-4-fluoro-5,5-dioxo-3,4-dihydro-2H-1,5λ6-benzoxathiepine-7-carboxylic acid (Intermediate 2, described above) (24.41 mg, 82.83 umol) in DCM (1 mL) was added EDCl (21.65 mg, 112.95 umol), HOBt (15.26 mg, 112.95 umol) and DIEA (29.20 mg, 225.90 umol, 39.35 uL). Then [2-[7-[(3R,4R)-3,4-difluoropyrrolidin-1-yl]-2,3-dihydropyrido[3,2-b][1,4]oxazin-4-yl]-1,6-naphthyridin-7-yl]methanamine (Prepared in a manner similar to that described for Example 1) (30 mg, 75.30 umol) was added. The mixture was stirred at 25° C. for 2 hrs. The mixture was poured into water (10 mL) and extracted with EA (5 mL*3). The combined organic layer was washed by brine (5 mL), dried over anhydrous $Na_2SO_4$, filtered and concentrated under vacuum. The residue was purified by prep-HPLC (column: Phenomenex C18 150*25 mm*10 um; mobile phase: [water ($NH_4HCO_3$)-ACN]; B %: 33%-63%, 8 mins). Then the eluent was concentrated and lyophilized to give (R)-9-chloro-N-((2-(7-((3R,4R)-3,4-difluoropyrrolidin-1-yl)-2,3-dihydro-4H-pyrido[3,2-b][1,4]oxazin-4-yl)-1,6-naphthyridin-7-yl)methyl)-4-fluoro-3,4-dihydro-2H-benzo[b][1,4]oxathiepine-7-carboxamide 5,5-dioxide (4.73 mg, 6.48 umol, 8.61% yield) as yellow solid. LCMS (ESI) m/z: [M+H]⁺=675.0. ¹H NMR (400 MHz, DMSO-d6) δ=9.62-9.59 (m, 1H), 9.02 (s, 1H), 8.53 (d, J=2.0 Hz, 1H), 8.45 (d, J=2.0 Hz, 1H), 8.24-8.18 (m, 2H), 7.49-7.44 (m, 2H), 6.73 (d, J=2.4 Hz, 1H), 6.37-6.17 (m, 1H), 5.58-5.42 (m, 2H), 4.71 (d, J=5.8 Hz, 2H), 4.65-4.59 (m, 1H), 4.37-4.29 (m, 4H), 4.14-4.08 (m, 1H), 3.77-3.70 (m, 1H), 3.68-3.57 (m, 3H), 2.94-2.75 (m, 1H), 2.61-2.58 (m, 1H) ppm. Chiral SFC: AS-3-MeOH+ACN (DEA)-50-3 mL-35T.lcm, Rt=0.805 min, ee %=100%.

The following examples in Table 5 were prepared using standard chemical manipulations and procedures similar to those used for the preparation of Compound 258.

TABLE 5

Compounds of the Invention

| # | LCMS (ESI/M + H) | 1HNMR |
|---|---|---|
| 4 | 596.30 | 1H NMR (400 MHz, DMSO-d6) δ = 9.60 (m 1H), 9.05 (s, 1H), 8.35 (s, 1H), 8.31 (m, 1H), 8.18-8.14 (m, 1H), 8.05 (d, J = 5.6 Hz, 1H), 7.91 (d, J = 9.2 Hz, 1H), 7.49 (s, 1H), 6.80 (d, J = 5.6 Hz, 1H), 6.35-6.21 (m, 1H), 4.72 (d, J = 5.6 Hz, 2H), 4.61 (m, 1H), 4.21-4.12 (m, 5H), 2.91-2.72 (m, 1H), 2.68 (m, 2H), 2.63-2.59 (m, 1H), 1.97-1.89 (m, 2H), 1.38 (m, 3H) ppm |
| 5 | 624.3 | 1H NMR (400 MHz, DMSO-d6) δ = 9.68-9.65 (m, 1H), 9.39 (s, 1H), 8.67-9.61 (m, 2H), 8.39-8.36 (m, 2H), 7.91 (d, J = 7.2 Hz, 1H), 7.84 (s, 1H), 7.77-7.73 (m, 1H), 7.03 (d, J = 8.8 Hz, 1H), 6.06-5.94 (m, 1H), 4.81 (br d, J = 5.6 Hz, 2H), 4.42-4.29 (m, 4H), 3.69-3.65 (m, 2H), 2.58-2.56 (m, 2H), 2.46-2.35 (m, 2H), 1.75-1.61 (m, 2H), 1.24 (d, J = 6.4 Hz, 6H) ppm. |
| 10 | 649.2 | 1H NMR (400 MHz, METHANOL-d4) δ = 9.02 (s, 1H), 8.53-8.48 (m, 2H), 8.38 (s, 1H), 8.28 (d, J = 9.2 Hz, 1H), 8.15-8.12 (m, 1H), 7.59 (s, 1H), 7.20-7.09 (m, 1H), 6.97 (s, 1H), 5.99-5.75 (m, 1H), 4.81 (s, 2H), 4.66-4.57 (m, 1H), 4.53 (s, 2H), 4.38-4.27 (m, 4H), 4.20-4.10 (m, 1H), 3.47-3.45 (m, 3H), 3.03-2.86 (m, 1H), 2.66-2.48 (m, 1H) ppm |
| 15 | 626.2 | 1H NMR (400 MHz, DMSO-d6) δ = 9.60-9.58 (m, 1H), 9.05 (s, 1H), 8.36-8.26 (m, 2H), 8.21-8.12 (m, 2H), 7.84 (d, J = 9.2 Hz, 1H), 7.49 (s, 1H), 6.36-6.15 (m, 1H), 4.72 (d, J = 4.8 Hz, 2H), 4.60 (d, J = 13.2 Hz, 1H), 4.43 (d, J = 3.2 Hz, 1H), 4.23-4.05 (m, 3H), 2.92-2.74 (m, 1H), 2.67 (d, J = 5.6 Hz, 2H), 2.62-2.57 (m, 1H), 1.94-1.85 (m, 2H), 0.80-0.74 (m, 2H), 0.75-0.67 (m, 2H) ppm |
| 20 | 608.3 | 1H NMR (400 MHz, DMSO-d6) δ = 9.63-9.60 (m, 1H), 9.09 (s, 1H), 8.40-8.25 (m, 3H), 8.23-8.15 (m, 1H), 7.50 (s, 1H), 7.19 (d, J = 8.0 Hz, 1H), 6.95 (d, J = 8.0 Hz, 1H), 6.39-6.13 (m, 1H), 4.72 (d, J = 5.6 Hz, 2H), 4.63-4.58 (m, 1H), 4.34-4.23 (m, 4H), 4.19-4.13 (m, 1H), 2.92-2.70 (m, 1H), 2.61 (d, J = 3.2 Hz, 1H), 1.77-1.63 (m, 1H), 1.20-1.08 (m, 4H), 1.03-0.92 (m, 1H), 0.73-0.60 (m, 1H) ppm |
| 24 | 641.10 | 1H NMR (400 MHz, DMSO-d6) δ = 9.62-9.59 (m, 1H), 9.10 (s, 1H), 8.36-8.26 (m, 3H), 8.13 (s, 1H), 7.64 (d, J = 9.0 Hz, 1H), 7.48 (s, 1H), 7.09 (d, J = 2.8 Hz, 1H), 6.88 (d, J = 9.0 Hz, 1H), 6.70-6.67 (m, 1H), 6.35-6.19 (m, 1H), 4.72 (d, J = 5.6 Hz, 2H), 4.63-4.60 (m, 1H), 4.24 (br d, J = 1.6 Hz, 2H), 4.22-4.17 (m, 2H), 4.16-4.11 (m, 1H), 3.85-3.83 (m, 2H), 3.66-3.55 (m, 1H), 3.27 (s, 3H), 2.94-2.69 (m, 1H), 2.65-2.56 (m, 1H), 1.11 (d, J = 6.4 Hz, 3H) ppm |
| 31 | 641.3 | 1H NMR (400 MHz, DMSO-d6) δ = 9.60-9.57 (m, 1H), 9.02 (s, 1H), 8.34-8.29 (m, 2H), 8.20-8.16 (m, 2H), 7.44 (s, 1H), 7.36 (d, J = 2.8 Hz, 1H), 6.60 (d, J = 2.4 Hz, 1H), 6.33-6.20 (m, 1H), 4.70-4.61 (m, 5H), 4.33-4.28 (m, 5H), 3.89-3.60 (m, 1H), 2.63-2.61 (m, 1H), 2.52-2.51 (m, 1H), 2.30-2.23 (m, 2H) ppm |
| 35 | 627.10 | 1H NMR (400 MHz, METHANOL-d4) δ = 8.99 (s, 1H), 8.39-8.36 (m, 1H), 8.22 (d, J = 9.4 Hz, 1H), 8.14 (m, 1H), 7.68 (d, J = 9.4 Hz, 1H), 7.61 (s, 1H), 7.05 (d, J = 2.8 Hz, 1H), 6.87 (d, J = 9.2 Hz, 1H), 6.71 (m, 1H), 5.95-5.80 (m, 1H), 4.81 (s, 2H), 4.63 (m, 1H), 4.28 (s, 4H), 4.16 (m, 1H), 4.06-4.03 (m, 2H), 3.71-3.68 (m, 2H), 3.41-3.38 (m, 3H), 3.05-2.87 (m, 2H), 2.62-2.53 (m, 1H) ppm |

TABLE 5-continued

Compounds of the Invention

| # | LCMS (ESI/M + H) | 1HNMR |
|---|---|---|
| 36 | 608.3 | 1H NMR (400 MHz, DMSO-d6) δ = 9.63-9.61 (m, 1H), 9.09 (s, 1H), 8.37-8.27 (m, 3H), 8.20 (d, J = 9.2 Hz, 1H), 7.50 (s, 1H), 7.19 (d, J = 8.0 Hz, 1H), 6.95 (d, J = 8.0 Hz, 1H), 6.37-6.16 (m, 1H), 4.72 (d, J = 5.6 Hz, 2H), 4.67-4.54 (m, 1H), 4.34-4.23 (m, 4H), 4.18-4.16 (m, 1H), 2.95-2.70 (m, 1H), 2.60-2.55 (m, 1H), 1.77-1.67 (m, 1H), 1.21-1.07 (m, 4H), 0.98-0.96 (m, 1H), 0.68-0.66 (m, 1H) ppm |
| 37 | 592.2 | 1H NMR (400 MHz, DMSO-d6) δ = 9.63-9.60 (m, 1H), 9.12 (s, 1H), 8.37-8.28 (m, 3H), 8.25 (d, J = 9.2 Hz, 1H), 7.53 (s, 1H), 7.29 (d, J = 8.0 Hz, 1H), 7.13 (d, J = 8.0 Hz, 1H), 6.36-6.18 (m, 1H), 4.74 (d, J = 5.6 Hz, 2H), 4.63-4.68 (m, 1H), 4.36-4.33 (m, 4H), 4.19-4.13 (m, 1H), 2.90-2.72 (m, 1H), 2.63-2.56 (m, 1H), 2.03 (s, 3H) ppm |
| 38 | 576.3 | 1H NMR (400 MHz, DMSO-d6) δ = 9.57-9.54 (m, 1H), 9.07 (s, 1H), 8.50 (d, J = 2.0 Hz, 1H), 8.35-8.33 (m, 1H), 8.31-8.2 (m, 2H), 7.78 (d, J = 2.0 Hz, 1H), 7.48-7.46 (m, 2H), 6.98 (d, J = 2.0 Hz, 1H), 6.38-6.02 (m, 1H), 4.71 (d, J = 5.6 Hz, 2H), 4.58-4.45 (m, 1H), 4.31 (s, 4H), 4.06-4.00 (m, 1H), 2.89-2.69 (m, 1H), 2.59-2.55 (m, 1H), 1.99-1.86 (m, 1H), 1.01-0.91 (m, 2H), 0.75-0.66 (m, 2H) ppm |
| 40 | 594.2 | 1H NMR (400 MHz, DMSO-d6) δ = 9.63-9.59 (m, 1H), 9.07 (s, 1H), 8.36-8.19 (m, 4H), 7.78 (d, J = 2.0 Hz, 1H), 7.48 (s, 1H), 6.98 (d, J = 2.0 Hz, 1H), 6.40-6.15 (m, 1H), 4.71 (d, J = 5.6 Hz, 2H), 4.63-4.59 (m, 1H), 4.31 (s, 4H), 4.18-4.12 (m, 1H), 2.90-2.72 (m, 1H), 2.63-2.57 (m, 1H), 1.98-1.83 (m, 1H), 1.00-0.89 (m, 2H), 0.76-0.65 (m, 2H)ppm |
| 45 | 624.3 | 1H NMR (400 MHz, DMSO-d6) δ = 9.62-9.59 (m, 1H), 9.07 (s, 1H), 8.36 (d, J = 2.8 Hz, 1H), 8.35-8.35 (m, 1H), 8.35-8.24 (m, 4H), 7.86 (d, J = 1.6 Hz, 1H), 7.49 (s, 1H), 7.12 (d, J = 2.0 Hz, 1H), 6.38-6.13 (m, 1H), 4.72-4.71 (m, 2H), 4.62-4.59 (m, 1H), 4.39-4.29 (m, 4H), 4.19-4.16 (m, 1H), 3.49-3.46 (m, 1H), 3.10 (s, 3H), 2.91-2.71 (m, 1H), 2.63-2.57 (m, 1H), 2.04-2.00 (m, 1H), 1.16-1.00 (m, 2H) ppm |
| 47 | 623.3 | 1H NMR (400 MHz, DMSO-d6) δ = 9.73-9.45 (m, 1H), 9.01 (s, 1H), 8.39-8.26 (m, 2H), 8.23-8.13 (m, 2H), 7.44 (s, 1H), 7.29 (d, J = 2.4 Hz, 1H), 6.49 (d, J = 2.4 Hz, 1H), 6.39-6.15 (m, 1H), 4.70 (d, J = 5.6 Hz, 2H), 4.67-4.56 (m, 1H), 4.42-4.25 (m, 4H), 4.22-4.02 (m, 2H), 3.88-3.83 (m, 1H), 3.55-3.49 (m, 1H), 2.94-2.70 (m, 1H), 2.64-2.58 (m, 1H), 2.40-2.31 (m, 1H), 2.07-1.96 (m, 1H), 1.40 (d, J = 6.0 Hz, 3H) ppm |
| 51 | 568.3 | 1H NMR (400 MHz, DMSO-d6) δ = 9.61-9.59 (m, 1H), 9.08 (s, 1H), 8.36-8.24 (m, 4H), 7.77-7.76 (m, 1H), 7.50 (s, 1H), 7.22-7.18 (m, 1H), 6.37-6.19 (m, 1H), 4.72 (d, J = 6.0 Hz, 2H), 4.63-4.59 (m, 1H), 4.33 (s, 4H), 4.19-4.13 (m, 1H), 2.87-2.72 (m, 1H), 2.61-2.56 (m, 1H), 2.25 (s, 3H) ppm |
| 55 | 594.2 | 1H NMR (400 MHz, DMSO-d6) δ = 9.63-9.60 (m, 1H), 9.09 (s, 1H), 8.40 (s, 1H), 8.34 (s, 1H), 8.32-8.28 (m, 2H), 8.21-8.18 (m, 1H), 7.50 (s, 1H), 7.21 (d, J = 8.4 Hz, 1H), 6.98 (d, J = 8.0 Hz, 1H), 6.33-6.21 (m, 1H), 4.73 (br d, J = 5.6 Hz, 2H), 4.62-4.59 (m, 1H), 4.29 (s, 4H), 4.19-4.13 (m, 1H), 2.85-2.59 (m, 2H), 2.03-1.98 (m, 1H), 0.87-0.85 (m, 2H), 0.79-0.77 (m, 2H) ppm |
| 57 | 641.3 | 1H NMR (400 MHz, DMSO-d6) δ = 9.62-9.59 (m, 1H), 9.08 (s, 1H), 8.48 (d, J = 9.2 Hz, 1H), 8.34-8.27 (m, 3H), 7.49 (s, 1H), 7.22-7.19 (m, 1H), 6.22-6.19 (m, 2H), 5.58-5.35 (m, 1H), 4.72 (d, J = 5.6 Hz, 2H), 4.63-4.59 (m, 1H), 4.25 (s, 4H), 4.19-4.16 (m, 1H), 3.62-3.41 (m, 4H), 2.89-2.75 (m, 1H), 2.66-2.63 (m, 1H), 2.25-2.20 (m, 2H) ppm |
| 65 | 609.3 | 1H NMR (400 MHz, DMSO-d6) δ = 9.61 (s, 1H), 9.04 (s, 1H), 8.34-8.19 (m, 4H), 7.62 (d, J = 5.4 Hz, 1H), 7.46 (s, 1H), 6.34-6.32 (m, 1H), 6.23-6.15 (m, 1H), 4.71-4.70 (m, 2H), 4.63-4.59 (m, 1H), 4.27-4.24 (m, 4H), 4.19-4.12 (m, 1H), 4.04-4.01 (m, 4H), 2.85-2.81 (m, 1H), 2.71 (s, 1H), 2.29-2.24 (m, 2H) ppm |
| 66 | 659.10 | 1H NMR (400 MHz, DMSO-d6) δ = 9.60-9.57 (m, 1H), 9.02 (s, 1H), 8.35 (d, J = 2.0 Hz, 1H), 8.34-8.28 (m, 1H), 8.25-8.15 (m, 2H), 7.46 (d, J = 2.6 Hz, 1H), 7.44 (s, 1H), 6.72 (d, J = 2.6 Hz, 1H), 6.38-6.19 (m, 1H), 5.63-5.35 (m, 2H), 4.70 (d, J = 5.8 Hz, 2H), 4.63-4.58 (m, 1H), 4.39-4.27 (m, 4H), 4.19-4.13 (m, 1H), 3.76-3.56 (m, 4H), 2.91-2.79 (m, 2H) ppm |
| 69 | 641.2 | 1H NMR (400 MHz, METHANOL-d4) δ = 8.96 (br s, 1H), 8.39 (br d, J = 1.6 Hz, 1H), 8.19-8.09 (m, 3H), 7.58 (s, 1H), 7.29 (br s, 1H), 6.57 (d, J = 2.4 Hz, 1H), 5.98-5.80 (m, 1H), 5.38-5.20 (m, 1H), 4.80 (s, 2H), 4.68-4.61 (m, 1H), 4.43-4.29 (m, 5H), 4.17-4.16 (m, 1H), 4.10-3.89 (m, 2H), 2.92 (s, 1H), 2.63-2.53 (m, 1H), 1.46-1.44 (m, 3H) ppm |
| 70 | 644.1 | 1H NMR (400 MHz, DMSO-d6) δ = 9.68-9.64 (m, 1H), 9.23 (s, 1H), 8.44-8.25 (m, 4H), 7.94 (d, J = 2.0 Hz, 1H), 7.65 (s, 1H), 7.34 (d, J = 2.0 Hz, 1H), 6.44-6.16 (m, 1H), 6.06-5.68 (m, 1H), 4.77 (br d, J = 5.6 Hz, 2H), 4.63-4.61 (m, 1H), 4.38 (s, 4H), 4.18-4.14 (m, 1H), 2.89-2.75 (m, 1H), 2.64-2.59 (m, 1H), 1.17-1.11 (m, 2H), 1.03 (br s, 2H) ppm |
| 71 | 583.9 | 1H NMR (400 MHz, DMSO-d6) δ = 9.65-9.54 (m, 1H), 9.05 (s, 1H), 8.37-8.14 (m, 4H), 7.75-7.67 (m, 1H), 7.47 (s, 1H), 7.08 (d, J = 3.2 Hz, 1H), 6.36-6.15 (m, 1H), 4.71 (d, J = 5.6 Hz, 2H), 4.63-4.57 (m, 1H), 4.36-4.34 (m, 4H), 4.21-4.12 (m, 1H), 3.81 (s, 3H), 2.86-2.79 (m, 1H), 2.60 (s, 1H) ppm. |
| 80 | 641.3 | 1H NMR (400 MHz, DMSO-d6) δ = 9.61-9.58 (m, 1H), 9.02 (s, 1H), 8.34-8.28 (m, 2H), 8.25-8.15 (m, 2H), 7.45 (s, 1H), 7.38 (d, J = 2.4 Hz, 1H), 6.63 (d, J = 2.4 Hz, 1H), 6.37-6.14 (m, 1H), 5.21-4.96 (m, 1H), 4.70 (d, J = |

TABLE 5-continued

Compounds of the Invention

| # | LCMS (ESI/M + H) | 1HNMR |
|---|---|---|
| | | 5.6 Hz, 2H), 4.62-4.59 (m, 1H), 4.39-4.24 (m, 5H), 4.20-4.03 (m, 2H), 3.63-3.53 (m, 1H), 2.89-2.77 (m, 1H), 2.62-2.59 (m, 1H), 1.45 (d, J = 6.4 Hz, 3H) ppm |
| 81 | 634.2 | 1H NMR (400 MHz, DMSO-d6) δ = 9.61 (br t, J = 5.7 Hz, 1H), 9.08 (s, 1H), 8.41-8.19 (m, 4H), 7.50 (s, 1H), 7.34 (s, 1H), 7.15-6.78 (m, 1H), 6.47-6.16 (m, 1H), 4.72 (br d, J = 5.0 Hz, 2H), 4.61 (br d, J = 13.6 Hz, 1H), 4.40 (s, 4H), 4.16 (br t, J = 12.5 Hz, 1H), 3.87 (s, 3H), 2.93-2.71 (m, 1H), 2.67 (br s, 1H) ppm |
| 82 | 582.3 | 1H NMR (400 MHz, DMSO-d6) δ = 9.66-9.57 (m, 1H), 9.00 (s, 1H), 8.49-8.43 (m, 1H), 8.37-8.28 (m, 2H), 8.12 (d, J = 9.2 Hz, 1H), 7.91 (d, J = 3.2 Hz, 1H), 7.83 (d, J = 9.2 Hz, 1H), 7.45 (s, 1H), 7.34 (d, J = 2.8 Hz, 1H), 6.37-6.19 (m, 1H), 4.70 (d, J = 6.0 Hz, 2H), 4.65-4.56 (m, 1H), 4.20-4.08 (m, 5H), 3.70-3.63 (m, 2H), 3.31 (s, 3H), 2.92-2.68 (m, 4H), 1.96-1.91 (m, 2H) ppm. |
| 83 | 550.2 | 1H NMR (400 MHz, DMSO-d6) δ = 9.58-9.55 (m, 1H), 9.08 (s, 1H), 8.51 (d, J = 2.0 Hz, 1H), 8.46-8.41 (m, 1H), 8.38-8.24 (m, 3H), 7.77 (d, J = 1.2 Hz, 1H), 7.51-7.42 (m, 2H), 7.20 (d, J = 1.6 Hz, 1H), 6.31-6.09 (m, 1H), 4.72 (d, J = 5.6 Hz, 2H), 4.56-4.48 (m, 1H), 4.32 (s, 4H), 4.06-4.00 (m, 1H), 2.86-2.68 (m, 1H), 2.59-2.54 (m, 1H), 2.25 (s, 3H) ppm |
| 86 | 641.2 | 1H NMR (400 MHz, DMSO-d6) δ = 9.63-9.60 (m, 1H), 9.08 (s, 1H), 8.48 (d, J = 8.8 Hz, 1H), 8.37-8.23 (m, 3H), 7.49 (s, 1H), 7.21 (d, J = 8.8 Hz, 1H), 6.36-6.14 (m, 2H), 5.68-5.22 (m, 1H), 4.84-4.51 (m, 1H), 4.32-4.23 (m, 4H), 4.19-4.13 (m, 1H), 3.65-3.39 (m, 4H), 2.91-2.70 (m, 1H), 2.64-2.59 (m, 1H), 2.30-2.13 (m, 2H) ppm |
| 87 | 630.3 | 1H NMR (400 MHz, DMSO-d6) δ = 9.62 (s, 1H), 9.11 (s, 1H), 8.42 (d, J = 2.0 Hz, 1H), 8.38-8.27 (m, 4H), 7.89 (d, J = 2.0 Hz, 1H), 7.52 (s, 1H), 7.26 (d, J = 1.6 Hz, 1H), 6.39-6.16 (m, 1H), 4.73 (d, J = 5.6 Hz, 2H), 4.65-4.57 (m, 1H), 4.35 (s, 4H), 4.21-4.12 (m, 1H), 3.02-3.00 (m, 1H), 2.91-2.68 (m, 1H), 2.67-2.55 (m, 1H), 2.08-1.98 (m, 2H) ppm |
| 90 | 599.3 | 1H NMR (400 MHz, DMSO-d6) δ = 9.62-9.60 (m, 1H), 9.08 (s, 1H), 8.35 (d, J = 2.2 Hz, 1H), 8.34-8.27 (m, 3H), 7.80 (d, J = 2.2 Hz, 1H), 7.50 (s, 1H), 7.00 (d, J = 2.2 Hz, 1H), 4.73 (d, J = 5.8 Hz, 2H), 4.33 (s, 4H), 1.98-1.89 (m, 1H), 1.00-0.92 (m, 2H), 0.75-0.69 (m, 2H) ppm |
| 91 | 648.2 | 1H NMR (400 MHz, DMSO-d6) δ = 9.63-9.60 (m, 1H), 9.12 (s, 1H), 8.54-8.09 (m, 4H), 7.53 (s, 1H), 7.14 (s, 1H), 6.98-6.56 (m, 1H), 6.39-6.12 (m, 1H), 4.80-4.70 (m, 2H), 4.63-4.58 (m, 1H), 4.42-4.30 (m, 4H), 4.26-4.10 (m, 3H), 2.92-2.71 (m, 1H), 2.64-2.59 (m, 1H), 1.39-1.35 (m, 3H) ppm |
| 93 | 627.20 | 1H NMR (400 MHz, DMSO-d6) δ = 9.58-9.55 (m, 1H), 9.00 (s, 1H), 8.35-8.26 (m, 2H), 8.22 (d, J = 9.2 Hz, 1H), 8.15 (s, 1H), 7.46 (d, J = 9.2 Hz, 1H), 7.41-7.34 (m, 2H), 6.57-6.52 (m, 2H), 6.35-6.20 (m, 1H), 4.69 (br d, J = 5.6 Hz, 2H), 4.65-4.56 (m, 1H), 4.29-4.20 (m, 4H), 4.19-4.13 (m, 1H), 4.09-4.04 (m, 2H), 3.68-3.60 (m, 2H), 3.29 (s, 3H), 2.92-2.70 (m, 1H), 2.64-2.56 (m, 1H) ppm |
| 94 | 614.2 | 1H NMR (400 MHz, DMSO-d6) δ = 9.64-9.61 (m, 1H), 9.08 (s, 1H), 8.52-8.43 (m, 2H), 8.25 (d, J = 1.2 Hz, 2H), 7.82 (d, J = 5.6 Hz, 1H), 7.50 (s, 1H), 6.88 (d, J = 5.2 Hz, 1H), 6.37-6.16 (m, 1H), 4.72 (br d, J = 5.2 Hz, 2H), 4.61-4.59 (m, 1H), 4.31 (s, 4H), 4.16-4.09 (m, 3H), 2.88-2.81 (m, 1H), 2.62-2.61 (m, 1H), 1.37-1.34 (m, 3H) ppm |
| 96 | 576.3 | 1H NMR (400 MHz, DMSO-d6) δ = 9.58-9.55 (m, 1H), 9.09 (s, 1H), 8.50 (d, J = 2.4 Hz, 1H), 8.35-8.28 (m, 2H), 8.20 (d, J = 9.2 Hz, 1H), 7.48-7.46 (m, 2H), 7.21 (d, J = 8.0 Hz, 1H), 6.98 (d, J = 8.4 Hz, 1H), 6.26-6.14 (m, 1H), 4.72 (br d, J = 6.0 Hz, 2H), 4.53-4.50 (m, 1H), 4.28 (s, 4H), 4.06-4.00 (m, 1H), 2.81-2.71 (m, 1H), 2.02-1.98 (m, 1H), 0.87-0.77 (m, 4H) ppm |
| 99 | 625.3 | 1H NMR (400 MHz, DMSO-d6) δ = 9.60-9.57 (m, 1H), 8.99 (s, 1H), 8.38-8.28 (m, 3H), 8.22-8.16 (m, 2H), 7.49-7.42 (m, 2H), 6.67 (d, J = 2.8 Hz, 1H), 6.33-6.32 (m, 1H), 4.70-4.59 (m, 3H), 4.33-4.26 (m, 4H), 4.26-4.16 (m, 1H), 3.42-3.39 (m, 4H), 2.85-2.76 (m, 1H), 2.63 (s, 1H), 1.10-1.06 (m, 6H) ppm |
| 105 | 647.2 | 1H NMR (400 MHz, DMSO-d6) δ = 9.59-9.57 (m, 1H), 9.02 (s, 1H), 8.34 (s, 1H), 8.34-8.28 (m, 1H), 8.21 (s, 2H), 7.60 (d, J = 2.8 Hz, 1H), 7.44 (s, 1H), 6.87 (d, J = 2.8 Hz, 1H), 6.39-6.30 (m, 1H), 6.22 (br d, J = 3.6 Hz, 1H), 4.70 (br d, J = 5.6 Hz, 2H), 4.63-4.60 (m, 1H), 4.35-4.30 (m, 4H), 4.16 (d, J = 11.8 Hz, 1H), 3.78-3.68 (m, 2H), 2.99 (s, 3H), 2.89-2.60 (m, 2H) ppm |
| 108 | 612.2 | 1H NMR (400 MHz, DMSO-d6) δ = 9.63-9.60 (m, 1H), 9.10 (s, 1H), 8.37-8.26 (m, 4H), 7.90 (d, J = 4.8 Hz, 1H), 7.51 (s, 1H), 7.11 (d, J = 4.8 Hz, 1H), 6.43-6.15 (m, 1H), 4.73 (d, J = 5.6 Hz, 2H), 4.65-4.57 (m, 1H), 4.51 (s, 2H), 4.38-4.34 (m, 4H), 4.16 (d, J = 12.0 Hz, 1H), 3.59-3.54 (m, 2H), 2.85-2.82 (m, 1H), 2.61 (s, 1H), 1.22-1.18 (m, 3H) ppm |
| 109 | 673.3 | 1H NMR (400 MHz, DMSO-d6) δ = 9.65-9.54 (m, 1H), 9.04 (s, 1H), 8.34 (d, J = 1.6 Hz, 1H), 8.31-8.28 (m, 1H), 8.23 (s, 2H), 7.75 (d, J = 2.8 Hz, 1H), 7.46 (s, 1H), 7.07 (d, J = 2.4 Hz, 1H), 6.36-6.18 (m, 1H), 5.04-4.89 (m, 2H), 4.71 (d, J = 5.6 Hz, 2H), 4.64-4.57 (m, 1H), 4.35-4.30 (m, 4H), 4.21-4.12 (m, 1H), 3.62-3.56 (m, 1H), 3.43-3.39 (m, 2H), 3.20-3.13 (m, 1H), 2.89-2.79 (m, 1H), 2.63-2.61 (m, 1H), 2.09-1.91 (m, 2H) ppm |
| 110 | 578.2 | 1H NMR (400 MHz, DMSO-d6) δ = 9.66-9.64 (m, 1H), 9.12 (s, 1H), 8.38-8.30 (m, 3H), 8.26 (d, J = 9.2 Hz, 1H), 7.54 (s, 1H), 7.33 (d, J = 8.0 Hz, 1H), 7.24 (d, J = 8.4 Hz, 1H), 6.38-6.19 (m, 1H), 4.74 (d, J = 5.2 Hz, 2H), |

TABLE 5-continued

Compounds of the Invention

| # | LCMS (ESI/M + H) | 1HNMR |
|---|---|---|
| 113 | 624.2 | 4.65-4.55 (m, 1H), 4.38-4.33 (m, 4H), 4.23-4.10 (m, 2H), 2.90-2.71 (m, 1H), 2.64-2.55 (m, 1H) ppm 1H NMR (400 MHz, DMSO-d6) δ = 9.63 (br t, J = 5.6 Hz, 1H), 9.08 (s, 1H), 8.37-8.28 (m, 2H), 8.28-8.21 (m, 2H), 7.80 (d, J = 5.5 Hz, 1H), 7.50 (s, 1H), 6.85 (d, J = 5.6 Hz, 1H), 6.41-6.16 (m, 1H), 4.72 (br d, J = 5.6 Hz, 2H), 4.66-4.52 (m, 1H), 4.32 (br s, 4H), 4.25-4.08 (m, 1H), 3.92 (d, J = 7.1 Hz, 2H), 2.91-2.73 (m, 1H), 2.60 (br s, 1H), 1.33-1.17 (m, 1H), 0.70-0.54 (m, 2H), 0.34 (q, J = 4.7 Hz, 2H) ppm |
| 119 | 659.2 | 1H NMR (400 MHz, DMSO-d6) δ = 9.61-9.56(m, 1H), 9.09 (s, 1H), 8.45-8.37 (m, 1H), 8.36-8.26 (m, 3H), 7.50 (s, 1H), 7.24 (d, J = 8.4 Hz, 1H), 6.34-6.21 (m, 2H), 4.72 (d, J = 4.8 Hz, 2H), 4.61 (d, J = 13.2 Hz, 1H), 4.26 (s, 4H), 4.19-4.13 (m, 1H), 3.78-3.71 (m, 2H), 3.56-3.53 (m, 2H), 2.89-2.72 (m, 1H), 2.64-2.58 (m, 1H), 2.57-2.53 (m, 2H) ppm |
| 123 | 644.2 | 1H NMR (400 MHz, DMSO-d6) δ = 9.64-9.61 (m, 1H), 9.12 (s, 1H), 8.42-8.37 (m, 1H), 8.36-8.28 (m, 3H), 8.14 (d, J = 9.2 Hz, 1H), 7.51 (s, 1H), 7.25 (d, J = 8.0 Hz, 1H), 7.07 (d, J = 8.0 Hz, 1H), 6.46-6.17 (m, 1H), 6.12-5.68 (m, 1H), 4.73 (d, J = 5.6 Hz, 2H), 4.66-4.54 (m, 1H), 4.33-4.13 (m, 5H), 2.80-2.71 (m, 1H), 2.61-2.60 (m, 1H), 2.31-2.27 (m, 1H), 1.82-1.74 (m, 1H), 1.17-1.12 (m, 2H) ppm |
| 124 | 659.20 | 1H NMR (400 MHz, DMSO-d6) δ = 9.60-9.57 (m, 1H), 9.02 (s, 1H), 8.37-8.27 (m, 2H), 8.24-8.16 (m, 2H), 7.43 (br d, J = 12.8 Hz, 2H), 6.68 (d, J = 2.0 Hz, 1H), 6.35-6.19 (m, 1H), 5.54-5.32 (m, 1H), 4.70 (br d, J = 5.2 Hz, 2H), 4.61 (br d, J = 13.2 Hz, 1H), 4.38-4.27 (m, 4H), 4.18-4.13 (m, 1H), 3.70-3.69 (m, 2H), 3.55-3.43 (m, 2H), 2.93-2.70 (m, 1H), 2.61 (br s, 1H) ppm |
| 125 | 644.2 | 1H NMR (400 MHz, DMSO-d6) δ = 9.62-6.59 (m, 1H), 9.12 (s, 1H), 8.38 (s, 1H), 8.35-8.29 (m, 3H), 8.15-8.13 (m, 1H), 7.51 (s, 1H), 7.25 (d, J = 8.0 Hz, 1H), 7.06 (d, J = 8.0 Hz, 1H), 6.35-6.19 (m, 1H), 6.08-5.76 (m, 1H), 4.72 (s, 2H), 4.63-4.58 (m, 1H), 4.13 (s, 5H), 2.91-2.80 (m, 1H), 2.61-2.60 (m, 1H), 2.30-2.29 (m, 1H), 1.83-1.73 (m, 1H), 1.16-1.12 (m, 2H) ppm |
| 126 | 620.2 | 1H NMR (400 MHz, DMSO-d6) δ = 9.64-9.62 (m, 1H), 9.16 (s, 1H), 8.37-8.23 (m, 4H), 7.64-7.28 (m, 3H), 6.71-6.69 (m, 1H), 6.34-6.21 (m, 1H), 4.74 (br d, J = 4.4 Hz, 2H), 4.60-4.58 (m, 1H), 4.35-4.34 (m, 4H), 4.30-4.15 (m, 1H), 2.79-2.61 (m, 2H) ppm |
| 129 | 598.3 | 1H NMR (400 MHz, DMSO-d6) δ = 9.61-9.58 (m, 1H), 9.07 (s, 1H), 8.33-8.14 (m, 4H), 8.17 (s, 1H), 7.81 (d, J = 5.6 Hz, 1H), 7.49 (s, 1H), 6.87 (d, J = 5.6 Hz, 1H), 6.32-6.20 (m, 1H), 4.72-4.70(m, 2H), 4.61-4.57 (m, 1H), 4.31 (s, 4H), 4.16-4.12 (m, 3H), 2.84-2.75 (m, 1H), 2.61-2.60 (m, 1H), 1.37-1.33 (m, 3H) ppm |
| 130 | 620.3 | 1H NMR (400 MHz, MeOD) δ = 9.01 (s, 1H), 8.51-8.41 (m, 1H), 8.38(s, 1H), 8.23-8.21 (m, 2H), 8.16-8.13 (m, 1H), 7.74 (d, J = 2.0 Hz, 1H), 7.63 (s, 1H), 7.14 (d, J = 2.0 Hz, 1H), 5.93-5.81 (m, 1H), 4.81 (s, 2H), 4.64-4.61 (m, 1H), 4.40-4.34 (m, 4H), 4.16-4.14 (m, 1H), 3.01-2.91 (m, 1H), 2.60-2.55 (m, 1H), 2.55 (s, 1H), 2.12 (s, 6H) ppm |
| 133 | 582.0 | 1H NMR (400 MHz, DMSO-d6) δ = 9.61-9.58 (m, 1H), 9.00 (s, 1H), 8.37-8.28 (m, 2H), 8.25 (s, 1H), 8.11 (d, J = 9.6 Hz, 1H), 7.91 (d, J = 2.8 Hz, 1H), 7.82 (d, J = 9.2 Hz, 1H), 7.45 (s, 1H), 7.33 (d, J = 2.8 Hz, 1H), 6.39-6.14 (m, 1H), 4.70 (d, J = 5.6 Hz, 2H), 4.63-4.58 (m, 1H), 4.22-4.06 (m, 3H), 3.82 (s, 3H), 2.89-2.71 (m, 3H), 2.64-2.59 (m, 1H), 1.96-1.91 (m, 2H) ppm |
| 138 | 659 | 1H NMR (400 MHz, DMSO-d6) δ = 9.60-9.57 (m, 1H), 9.02 (s, 1H), 8.36-8.27 (m, 2H), 8.23-8.16 (m, 2H), 7.48-7.42 (m, 2H), 6.73 (d, J = 2.4 Hz, 1H), 6.36-6.19 (m, 1H), 5.60-5.40 (m, 2H), 4.71-4.69 (m, 2H), 4.64-4.57 (m, 1H), 4.40-4.28 (m, 4H), 4.16 (m, 1H), 3.77-3.70 (m, 3H), 3.68-3.55 (m, 3H), 2.90-2.72 (m, 1H), 2.60 (m, 1H) ppm |
| 139 | 627.3 | 1H NMR (400 MHz, DMSO-d6) δ = 9.60-9.58 (m, 1H), 9.02 (s, 1H), 8.34-8.28 (m, 2H), 8.20-8.15 (m, 2H), 7.44 (s, 1H), 7.30 (d, J = 2.4 Hz, 1H), 6.59 (d, J = 2.4 Hz, 1H), 6.33-6.21 (m, 1H), 5.56-5.55 (m, 1H), 4.71 (br d, J = 6.0 Hz, 2H), 4.59 (m, 1H), 4.33-4.29 (m, 4H), 4.19-4.16 (m, 3H), 4.13-3.89 (m, 2H), 2.85-2.75 (m, 1H), 2.61-2.56 (m, 1H) ppm |
| 141 | 593.3 | 1H NMR (400 MHz, DMSO-d6) δ = 9.59-9.56 (m, 1H), 9.12 (s, 1H), 8.39-8.36 (m, 1H), 8.35-8.23 (m, 2H), 8.02-7.92 (m, 1H), 7.88-7.85 (m, 1H), 7.64 (d, J = 2.0 Hz, 1H), 7.61-7.54 (m, 2H), 6.86 (d, J = 2.0 Hz, 1H), 6.41-6.15 (m, 1H), 4.70 (d, J = 5.6 Hz, 2H), 4.69-4.63 (m, 1H), 4.35-4.29 (m, 2H), 4.14 (d, J = 11.6 Hz, 1H), 4.01-3.92 (m, 2H), 2.91-2.70 (m, 1H), 2.62-2.55 (m, 1H), 1.88-1.79 (m, 1H), 0.93-0.84 (m, 2H), 0.68-0.58 (m, 2H) ppm |
| 142 | 641.3 | 1H NMR (400 MHz, DMSO-d6) δ = 9.60-9.57 (m, 1H), 9.03 (s, 1H), 8.36-8.27 (m, 2H), 8.23-8.15 (m, 2H), 7.45 (s, 1H), 7.38 (d, J = 2.4 Hz, 1H), 6.63 (d, J = 2.4 Hz, 1H), 6.36-6.16 (m, 1H), 5.22-4.97 (m, 1H), 4.70 (d, J = 5.6 Hz, 2H), 4.61-4.59 (m, 1H), 4.36-4.23 (m, 5H), 4.19-4.05 (m, 2H), 3.62-3.55 (m, 1H), 2.90-2.72 (m, 1H), 2.64-2.58 (m, 1H), 1.46 (d, J = 6.4 Hz, 3H) ppm |
| 145 | 618.2 | 1H NMR (400 MHz, DMSO-d6) δ = 9.69-9.58 (m, 1H), 9.20-9.05 (m, 1H), 8.38-8.26 (m, 4H), 7.85 (d, J = 1.6 Hz, 1H), 7.53 (s, 1H), 7.34 (d, J = 1.6 Hz, 1H), 6.57-5.97 (m, 2H), 4.73 (d, J = 5.6 Hz, 2H), 4.65-4.57 (m, 1H), 4.35 (s, 4H), 4.22-4.11 (m, 1H), 3.23-3.12 (m, 2H), 2.93-2.71 (m, 1H), 2.57 (br s, 1H) ppm |

TABLE 5-continued

Compounds of the Invention

| # | LCMS (ESI/M + H) | 1HNMR |
|---|---|---|
| 147 | 598.2 | 1H NMR (400 MHz, DMSO-d6) δ = 9.61 (s, 1H), 9.10 (s, 1H), 8.34-8.32 (m, 2H), 8.28 (s, 2H), 7.91 (d, J = 5.2 Hz, 1H), 7.52 (s, 1H), 7.10 (d, J = 4.8 Hz, 1H), 6.34-6.21 (m, 1H), 4.73 (d, J = 5.4 Hz, 2H), 4.62-4.59 (m, 1H), 4.47 (s, 2H), 4.39-4.31 (m, 4H), 4.16-4.13 (m, 1H), 3.38 (s, 3H), 2.86-2.82 (m, 1H), 2.73-2.71 (m, 1H) ppm |
| 149 | 639.3 | 1H NMR (400 MHz, DMSO-d6) δ = 9.69-9.66 (m, 1H), 9.24 (s, 1H), 8.33 (s, 1H), 8.31-8.24 (m, 2H), 7.95 (d, J = 9.2 Hz, 1H), 7.84-7.71 (m, 2H), 7.17 (s, 1H), 6.40-6.16 (m, 1H), 4.80 (d, J = 5.2 Hz, 2H), 4.64-4.61 (m, 1H), 4.21-4.17 (m, 2H), 4.15-4.10 (m, 1H), 3.55-3.51 (m, 4H), 3.26 (s, 3H), 2.97 (s, 3H), 2.89-2.71 (m, 3H), 2.63-2.55 (m, 1H), 1.99-1.96 (m, 2H) ppm |
| 152 | 624.3 | 1H NMR (400 MHz, DMSO-d6) δ = 9.61 (s, 1H), 9.08 (s, 1H), 8.35-8.26 (m, 4H), 7.78 (d, J = 2.0 Hz, 1H), 7.49 (s, 1H), 7.01 (d, J = 2.4 Hz, 1H), 6.40-6.15 (m, 1H), 4.72 (d, J = 4.8 Hz, 2H), 4.66-4.56 (m, 1H), 4.32 (s, 4H), 4.19-4.13 (m, 1H), 3.39-3.35 (m, 4H), 2.88-2.71 (m, 1H), 2.63-2.56 (m, 1H), 2.15-2.00 (m, 1H), 1.27-1.15 (m, 1H), 1.08-1.07 (m, 1H) ppm |
| 153 | 583.1 | 1H NMR (400 MHz, DMSO-d6) δ = 9.62-9.54 (m, 1H), 9.10 (s, 1H), 8.36-8.25 (m, 2H), 7.95 (d, J = 8.8 Hz, 1H), 7.85-7.82 (m, 1H), 7.59 (d, J = 8.8 Hz, 2H), 7.53 (d, J = 2.4 Hz, 1H), 6.97 (d, J = 2.4 Hz, 1H), 6.34-6.19 (m, 1H), 4.69 (d, J = 5.6 Hz, 2H), 4.57 (s, 1H), 4.38-4.31 (m, 2H), 4.18-4.09 (m, 1H), 3.99-3.92 (m, 2H), 3.75 (s, 3H), 2.90-2.67 (m, 1H), 2.65-2.57 (m, 1H) ppm. |
| 154 | 612.3 | 1H NMR (400 MHz, DMSO-d6) δ = 9.61 (s, 1H), 9.10 (s, 1H), 8.37-8.28 (m, 4H), 7.88 (d, J = 2.0 Hz, 1H), 7.52 (s, 1H), 7.29 (d, J = 2.0 Hz, 1H), 6.41-6.15 (m, 1H), 4.73 (d, J = 6.0 Hz, 2H), 4.62-4.60 (m, 1H), 4.42 (s, 2H), 4.35 (s, 4H), 4.19-4.13 (m, 1H), 3.51-3.45 (m, 2H), 2.91-2.56 (m, 2H), 1.16-1.12 (m, 3H) ppm |
| 156 | 612.2 | 1H NMR (400 MHz, DMSO-d6) δ = 9.62-9.60 (m, 1H), 9.12 (s, 1H), 8.34-8.28 (m, 3H), 8.12 (d, J = 9.2 Hz, 1H), 7.51 (s, 1H), 7.25 (d, J = 8.0 Hz, 1H), 7.07 (d, J = 8.0 Hz, 1H), 6.33-6.21 (m, 1H), 4.93-4.76 (m, 1H), 4.73 (br d, J = 5.6 Hz, 2H), 4.60-4.59 (m, 1H), 4.32-4.27 (m, 4H), 4.25-4.16 (m, 1H), 2.85-2.71 (m, 1H), 2.60-2.55 (m, 2H), 1.49-1.43 (m, 1H), 1.23-1.17 (m, 1H) ppm |
| 157 | 596.2 | 1H NMR (400 MHz, DMSO-d6) δ = 9.69-9.55 (m, 1H), 9.08 (s, 1H), 8.37-8.25 (m, 4H), 7.84 (d, J = 1.6 Hz, 1H), 7.50 (s, 1H), 7.26 (d, J = 1.6 Hz, 1H), 6.42-6.13 (m, 1H), 4.72 (d, J = 5.6 Hz, 2H), 4.67-4.55 (m, 1H), 4.34 (s, 4H), 4.19-4.16 (m, 1H), 2.95-2.88 (m, 1H), 2.86-2.70 (m, 1H), 2.62 (d, J = 3.2 Hz, 1H), 1.22 (d, J = 6.8 Hz, 6H) ppm |
| 159 | 604.2 | 1H NMR (400 MHz, DMSO-d6) δ = 9.64-9.61 (m, 1H), 9.15 (s, 1H), 8.38-8.33 (m, 2H), 8.33-8.27 (m, 2H), 8.10 (d, J = 1.6 Hz, 1H), 7.56 (s, 1H), 7.50 (s, 1H), 7.29-6.83 (m, 1H), 6.42-6.13 (m, 1H), 4.74 (d, J = 5.6 Hz, 2H), 4.62-4.59 (m, 1H), 4.44-4.38 (m, 2H), 4.36 (d, J = 4.4 Hz, 2H), 4.16 (d, J = 11.6 Hz, 1H), 2.91-2.71 (m, 1H), 2.57 (s, 1H) ppm |
| 160 | 619.3 | 1H NMR (400 MHz, DMSO-d6) δ = 9.56-9.37 (m, 1H), 9.01 (s, 1H), 8.35-8.26 (m, 2H), 8.23-8.13 (m, 2H), 7.41 (s, 1H), 7.29 (d, J = 2.4 Hz, 1H), 6.49 (d, J = 2.4 Hz, 1H), 6.25-6.06 (m, 1H), 4.69 (d, J = 5.2 Hz, 2H), 4.57-4.47 (m, 1H), 4.37-4.26 (m, 4H), 4.14-4.05 (m, 1H), 4.03-3.94 (m, 1H), 3.90-3.82 (m, 1H), 3.59-3.48 (m, 1H), 2.93-2.68 (m, 1H), 2.64-2.56 (m, 1H), 2.40-2.36 (m, 1H), 2.34 (s, 3H), 2.06-1.98 (m, 1H), 1.40 (d, J = 6.0 Hz, 3H) ppm |
| 164 | 612.2 | 1H NMR (400 MHz, DMSO-d6) δ = 9.63-9.60 (m, 1H), 9.11 (s, 1H), 8.33-8.28 (m, 3H), 8.12 (d, J = 9.2 Hz, 1H), 7.50 (s, 1H), 7.26 (d, J = 8.0 Hz, 1H), 7.07 (d, J = 8.4 Hz, 1H), 6.33-6.20 (m, 1H), 4.92-4.90 (m, 1H), 4.75-4.71 (m, 2H), 4.61-4.58 (m, 1H), 4.31-4.24 (m, 4H), 4.18-4.15 (m, 1H), 2.84-2.75 (m, 1H), 2.59-2.55 (m, 2H), 1.50-1.43 (m, 1H), 1.22-1.16 (m, 1H) ppm |
| 165 | 639.2 | 1H NMR (400 MHz, DMSO-d6) δ = 9.61-9.58 (m, 1H), 9.02 (s, 1H), 8.59-8.37 (m, 2H), 8.30-8.08 (m, 2H), 7.44 (s, 1H), 7.29 (d, J = 2.4 Hz, 1H), 6.49 (d, J = 2.4 Hz, 1H), 6.36-6.12 (m, 1H), 4.70 (d, J = 6.0 Hz, 2H), 4.65-4.57 (m, 1H), 4.37-4.25 (m, 4H), 4.17-4.05 (m, 2H), 3.92-3.82 (m, 1H), 3.57-3.51 (m, 1H), 2.82-2.73 (m, 1H), 2.65-2.58 (m, 1H), 2.41-2.36 (m, 1H), 2.09-1.96 (m, 1H), 1.41 (d, J = 6.0 Hz, 3H) ppm |
| 166 | 630.3 | 1H NMR (400 MHz, DMSO-d6) δ = 9.62-9.59 (m, 1H), 9.10 (s, 1H), 8.34-8.29 (m, 4H), 7.88 (d, J = 2.0 Hz, 1H), 7.51 (s, 1H), 7.25 (d, J = 1.6 Hz, 1H), 6.33-6.21 (m, 1H), 4.72 (d, J = 5.6 Hz, 2H), 4.63-4.58 (m, 4H), 4.34 (s, 4H), 4.19-4.13 (m, 1H), 3.04-2.98 (m, 1H), 2.88-2.74 (m, 1H), 2.61-2.60 (m, 1H), 2.10-1.95 (m, 2H) ppm |
| 168 | 657.10 | 1H NMR (400 MHz, DMSO-d6) δ = 9.59-9.56 (m, 1H), 8.96 (s, 1H), 8.38-8.27 (m, 2H), 8.13 (s, 1H), 8.07 (d, J = 9.2 Hz, 1H), 7.80 (d, J = 9.2 Hz, 1H), 7.66 (d, J = 2.8 Hz, 1H), 7.42 (s, 1H), 7.01 (d, J = 2.8 Hz, 1H), 6.36-6.19 (m, 1H), 5.60-5.53 (m, 1H), 5.45-5.42 (m, 1H), 4.70 (br d, J = 6.0 Hz, 2H), 4.62-4.58 (m, 1H), 4.19-4.13 (m, 1H), 4.13-4.07 (m, 2H), 3.77-3.56 (m, 4H), 2.91-2.80 (m, 1H), 2.79-2.76 (m, 2H), 2.63-2.58 (m, 1H), 1.97-1.88 (m, 2H) ppm |
| 169 | 618.1 | 1H NMR (400 MHz, DMSO-d6) δ = 9.59 (m, 1H), 9.10 (s, 1H), 8.36-8.29 (m, 2H), 8.22 (s, 1H), 8.20 (d, J = 9.4 Hz, 1H), 8.14 (d, J = 6.0 Hz, 1H), 7.92 (d, J = 9.2 Hz, 1H), 7.66-7.46 (m, 2H), 6.93 (d, J = 5.6 Hz, 1H), 6.27 (m, 1H), 4.74 (m, 2H), 4.65-4.58 (m, 1H), 4.22-4.13 (m, 3H), 2.86 (m, 1H), 2.79-2.76 (m, 2H), 2.61 (m, 1H), 2.02-1.93 (m, 2H) ppm |

TABLE 5-continued

Compounds of the Invention

| # | LCMS (ESI/M + H) | 1HNMR |
|---|---|---|
| 171 | 632.2 | 1H NMR (400 MHz, DMSO-d6) δ = 9.60-9.57 (m, 1H), 9.02 (s, 1H), 8.39-8.27 (m, 2H), 8.22-8.15 (m, 2H), 7.45 (s, 1H), 7.30 (d, J = 2.4 Hz, 1H), 6.59 (d, J = 2.4 Hz, 1H), 5.63-5.39 (m, 1H), 4.70 (s, 2H), 4.31 (d, J = 7.6 Hz, 4H), 4.24-4.12 (m, 2H), 3.97-3.86 (m, 2H) ppm |
| 172 | 637.1 | 1H NMR (400 MHz, CHLOROFORM-d) δ = 8.93 (s, 1H), 8.26 (s, 1H), 8.10-8.08 (m, 1H), 7.98-7.92 (m, 2H), 7.91-7.88 (m, 1H), 7.82 (br s, 1H), 7.65-7.61 (m, 1H), 7.09 (d, J = 2.4 Hz, 1H), 5.66-5.50 (m, 1H), 4.88-4.87 (m, 2H), 4.67-4.64 (m, 1H), 4.33-4.25 (m, 2H), 4.15-4.06 (m, 1H), 3.92-3.87 (m, 4H), 3.18-3.14 (m, 4H), 3.12-2.99 (m, 1H), 2.88-2.84 (m, 2H), 2.54-2.44 (m, 1H), 2.08-2.04 (m, 3H) ppm |
| 176 | 618.2 | 1H NMR (400 MHz, DMSO-d6) δ = 9.66-9.62 (m, 1H), 9.14 (s, 1H), 8.35-8.28 (m, 4H), 8.10 (s, 1H), 7.55-7.50 (m, 2H), 6.34-6.21 (m, 1H), 4.74 (br d, J = 5.6 Hz, 2H), 4.59 (m, 1H), 4.40-4.34 (m, 4H), 4.16 (m, 1H), 2.85-2.72 (m, 1H), 2.60-2.58 (m, 1H), 2.05-1.96 (m, 3H) ppm |
| 178 | 598.4 | 1H NMR (400 MHz, METHANOL-d4) δ = 8.93 (s, 1H), 8.39-8.37 (m, 1H), 8.23 (s, 1H), 8.18-8.11 (m, 2H), 8.02 (d, J = 9.2 Hz, 1H), 7.56 (s, 1H), 5.97-5.81 (m, 1H), 4.80 (s, 2H), 4.67-4.62 (m, 1H), 4.30-4.28 (m, 2H), 4.19-4.13 (m, 1H), 3.08-2.92 (m, 1H), 2.86-2.83 (m, 2H), 2.61-2.54 (m, 1H), 2.36-2.23 (m, 1H), 2.11-2.03 (m, 2H), 1.19-1.11 (m, 2H), 1.05-0.95 (m, 2H) ppm |
| 180 | 620 | 1H NMR (400 MHz, DMSO-d6) δ = 9.64-9.59 (m, 1H), 9.11 (s, 1H), 8.34 (s, 1H), 8.32 (s, 1H), 8.31-8.28 (m, 1H), 8.25-8.21 (m, 1H), 7.86 (d, J = 2.8 Hz, 1H), 7.52 (s, 1H), 7.44-7.04 (m, 2H), 6.36-6.20 (m, 1H), 4.73 (d, J = 5.6 Hz, 2H), 4.65-4.56 (m, 1H), 4.39-4.33 (m, 4H), 4.21-4.11 (m, 1H), 3.45-3.40 (m, 2H), 2.59-2.56 (m, 1H) ppm |
| 182 | 641.10 | 1H NMR (400 MHz, DMSO-d6) δ = 9.60-9.57 (m, 1H), 9.03 (s, 1H), 8.34 (s, 1H), 8.31-8.28 (m, 1H), 8.21 (s, 2H), 8.13 (s, 1H), 7.46 (s, 1H), 7.42 (d, J = 2.6 Hz, 1H), 6.64 (d, J = 2.6 Hz, 1H), 6.39-6.19 (m, 1H), 5.58-5.34 (m, 1H), 4.71 (br d, J = 5.6 Hz, 2H), 4.63-4.58 (m, 1H), 4.41-4.27 (m, 4H), 4.19-4.13 (m, 1H), 3.61-3.50 (m, 2H), 3.43-3.38 (m, 2H), 2.87-2.74 (m, 2H), 2.31-2.09 (m, 2H) ppm |
| 183 | 641.10 | 1H NMR (400 MHz, DMSO-d6) δ = 9.60-9.57 (m, 1H), 9.03 (s, 1H), 8.36-8.27 (m, 2H), 8.21 (s, 2H), 8.13 (s, 1H), 7.50-7.39 (m, 2H), 6.64 (d, J = 1.6 Hz, 1H), 6.36-6.19 (m, 1H), 5.55-5.36 (m, 1H), 4.71 (br d, J = 5.6 Hz, 2H), 4.61 (br d, J = 12.8 Hz, 1H), 4.39-4.27 (m, 4H), 4.18-4.12 (m, 1H), 3.61-3.46 (m, 2H), 3.43-3.35 (m, 2H), 2.92-2.70 (m, 1H), 2.64-2.58 (m, 1H), 2.31-2.13 (m, 2H) ppm |
| 185 | 604.2 | 1H NMR (400 MHz, DMSO-d6) δ = 9.65-9.62 (m, 1H), 9.14 (s, 1H), 8.35 (s, 3H), 8.32-8.29 (m, 1H), 7.55 (s, 1H), 7.48 (d, J = 8.0 Hz, 1H), 7.35 (d, J = 8.0 Hz, 1H), 6.99-6.72 (m, 1H), 6.34-6.22 (m, 1H), 4.75 (d, J = 6.0 Hz, 2H), 4.61-4.59 (m, 1H), 4.41-4.38 (m, 4H), 4.19-4.16 (m, 1H), 2.85-2.76 (m, 1H), 2.62-2.57 (m, 1H) ppm |
| 187 | 591.3 | 1H NMR (400 MHz, DMSO-d6) δ = 9.58-9.55 (m, 1H), 9.05 (s, 1H), 8.55 (d, J = 2.0 Hz, 1H), 8.39-8.36 (m, 1H), 8.25-8.15 (m, 2H), 7.51 (d, J = 8.4 Hz, 1H), 7.46 (s, 1H), 7.28 (d, J = 2.4 Hz, 1H), 6.51 (d, J = 2.4 Hz, 1H), 6.31-6.15 (m, 1H), 4.74 (d, J = 5.6 Hz, 2H), 4.60-4.51 (m, 1H), 4.40-4.29 (m, 4H), 4.10-4.07 (m, 1H), 3.88-3.85 (m, 4H), 2.91-2.75 (m, 1H), 2.68-2.63 (m, 1H), 2.36 (s, 2H) ppm |
| 189 | 626.3 | 1H NMR (400 MHz, DMSO-d6) δ = 9.61-9.58 (m, 1H), 9.04 (s, 1H), 8.37-8.26 (m, 2H), 8.22 (s, 1H), 8.15 (d, J = 9.2 Hz, 1H), 8.04 (d, J = 6.0 Hz, 1H), 7.90 (d, J = 9.2 Hz, 1H), 7.48 (s, 1H), 6.81 (d, J = 6.0 Hz, 1H), 6.37-6.14 (m, 1H), 4.72 (d, J = 6.0 Hz, 2H), 4.65-4.56 (m, 1H), 4.23-4.21 (m, 2H), 4.17-4.09 (m, 3H), 3.72-3.65 (m, 2H), 3.33 (s, 3H), 2.94-2.73 (m, 1H), 2.69-2.66 (m, 2H), 2.64-2.55 (m, 1H), 1.98-1.87 (m, 2H) ppm |
| 190 | 609.3 | 1H NMR (400 MHz, DMSO-d6) δ = 9.63-9.54 (m, 1H), 9.01 (s, 1H), 8.40-8.25 (m, 2H), 8.24-8.12 (m, 2H), 7.43 (s, 1H), 7.23 (d, J = 2.0 Hz, 1H), 6.47 (d, J = 2.4 Hz, 1H), 6.38-6.16 (m, 1H), 4.70 (d, J = 6.0 Hz, 2H), 4.65-4.54 (m, 1H), 4.32-4.27 (m, 4H), 4.18-4.12 (m, 1H), 3.84-3.80 (m, 4H), 2.67 (s, 2H), 2.34-2.30 (m, 2H) ppm |
| 192 | 608.3 | 1H NMR (400 MHz, DMSO-d6) δ = 9.63-9.60 (m, 1H), 9.08 (s, 1H), 8.37-8.27 (m, 4H), 8.26 (s, 1H), 7.81 (d, J = 2.0 Hz, 1H), 7.50 (s, 1H), 7.15 (d, J = 2.0 Hz, 1H), 6.39-6.18 (m, 1H), 4.72 (d, J = 5.2 Hz, 2H), 4.63-4.60 (m, 1H), 4.34 (d, J = 2.4 Hz, 4H), 4.19-4.13 (m, 1H), 2.96-2.74 (m, 1H), 2.63-2.57 (m, 1H), 2.04-2.01 (m, 1H), 1.25-1.08 (m, 1H), 1.03-0.93 (m, 1H), 0.80 (d, J = 6.0 Hz, 3H), 0.70-0.69 (m, 1H) ppm |
| 194 | 596.2 | 1H NMR (400 MHz, DMSO-d6) δ = 9.63-9.60 (m, 1H), 9.09 (s, 1H), 8.38-8.25 (m, 4H), 7.82 (d, J = 4.8 Hz, 1H), 7.51 (s, 1H), 6.97 (d, J = 4.8 Hz, 1H), 6.38-6.20 (m, 1H), 4.72 (d, J = 5.6 Hz, 2H), 4.62-4.59 (m, 1H), 4.37-4.32 (m, 4H), 4.19-4.16 (m, 1H), 2.89-2.75 (m, 1H), 2.64-2.60 (m, 1H), 2.57-2.55 (m, 2H), 1.66-1.55 (m, 2H), 0.94-0.91 (m, 3H) ppm |
| 198 | 600.2 | 1H NMR (400 MHz, CHLOROFORM-d) δ = 9.03 (s, 1H), 8.47 (d, J = 9.2 Hz, 1H), 8.28 (s, 1H), 8.14-8.04 (m, 2H), 7.95-7.94 (m, 1H), 7.72 (s, 1H), 7.30 (d, J = 1.2 Hz, 1H), 5.76-5.50 (m, 2H), 4.92 (d, J = 5.2 Hz, 2H), 4.65-4.64 (m, 1H), 4.56-4.50 (m, 2H), 4.47-4.40 (m, 2H), 4.16-4.08 (m, 1H), 3.23-2.94 (m, 1H), 2.55-2.39 (m, 1H), 1.75-1.64 (m, 3H) ppm |
| 201 | 612.3 | 1H NMR (400 MHz, DMSO-d6) δ = 9.62-9.51 (m, 1H), 9.08 (s, 1H), 8.39-8.19 (m, 4H), 7.80 (d, J = 1.6 Hz, 1H), 7.50 (s, 1H), 7.26 (d, J = 1.6 Hz, 1H), 6.38-6.18 (m, 1H), 4.73-4.72 (m, 2H), 4.62-4.59 (m, 1H), 4.33 (s, 4H), 4.23-4.10 (m, 1H), 3.55-3.52 |

TABLE 5-continued

Compounds of the Invention

| # | LCMS (ESI/M + H) | 1HNMR |
|---|---|---|
| 203 | 609.2 | (m, 2H), 3.25 (s, 3H), 2.91-2.82 (m, 1H), 2.79-2.78 (m, 2H), 2.62 (s, 1H) ppm |
| 204 | 655.2 | 1H NMR (400 MHz, DMSO-d6) δ = 9.64-9.61 (m, 1H), 9.14 (s, 1H), 8.35-8.29 (m, 4H), 7.54 (s, 1H), 7.48 (d, J = 8.0 Hz, 1H), 7.34 (d, J = 8.0 Hz, 1H), 6.99-6.71 (m, 1H), 4.74 (br d, J = 5.6 Hz, 2H), 4.41-4.39 (m, 4H) ppm |
|  |  | 1H NMR (400 MHz, DMSO-d6) δ = 9.61-9.58 (m, 1H), 9.03 (s, 1H), 8.34-8.28 (m, 2H), 8.25-8.20 (m, 2H), 7.73 (d, J = 2.8 Hz, 1H), 7.45 (s, 1H), 7.03 (d, J = 2.8 Hz, 1H), 6.33-6.20 (m, 1H), 4.92-4.76 (m, 1H), 4.71 (d, J = 5.2 Hz, 2H), 4.63-4.58 (m, 1H), 4.33-4.30 (m, 4H), 4.19-4.13 (m, 1H), 3.38-3.33 (m, 2H), 3.17-3.11 (m, 2H), 2.89-2.72 (m, 1H), 2.61-2.58 (m, 1H), 2.00-1.91 (m, 2H), 1.81-1.74 (m, 2H) ppm |
| 212 | 635.2 | 1H NMR (400 MHz, DMSO-d6) δ = 9.62-9.60 (m, 1H), 9.05 (s, 1H), 8.37-8.19 (m, 4H), 7.63 (d, J = 5.2 Hz, 1H), 7.47 (s, 1H), 6.36-6.15 (m, 2H), 4.71 (d, J = 5.6 Hz, 2H), 4.65-4.55 (m, 1H), 4.29-4.28 (m, 4H), 4.16 (br s, 1H), 4.12 (s, 4H), 2.91-2.71 (m, 1H), 2.59-2.55 (m, 1H), 0.64 (s, 4H) ppm |
| 213 | 634.4 | 1H NMR (400 MHz, DMSO-d6) δ = 9.63-9.60 (m, 1H), 9.09 (s, 1H), 8.37-8.19 (m, 4H), 7.78 (d, J = 2.8 Hz, 1H), 7.51 (s, 1H), 7.21 (d, J = 2.4 Hz, 1H), 6.56-6.19 (m, 2H), 4.73 (d, J = 5.6 Hz, 2H), 4.65-4.56 (m, 1H), 4.44-4.34 (m, 4H), 4.18-4.15 (m, 1H), 2.87-2.80 (m, 1H), 2.61-2.60 (m, 1H) ppm |
| 214 | 623.3 | 1H NMR (400 MHz, DMSO-d6) δ = 9.59-9.57 (m, 1H), 8.99 (s, 1H), 8.34-8.27 (m, 2H), 8.25-8.21 (m, 2H), 7.47 (d, J = 9.2 Hz, 1H), 7.37 (s, 1H), 6.35-6.19 (m, 1H), 5.89 (s, 1H), 4.68 (d, J = 5.4 Hz, 2H), 4.62-4.58 (m, 1H), 4.31-4.17 (m, 6H), 3.85-3.82 (m, 1H), 3.66 (d, J = 8.4 Hz, 1H), 2.75-2.72 (m, 1H), 2.66-2.64 (m, 1H), 2.41-2.35 (m, 1H), 2.02-1.93 (m, 1H), 1.41 (d, J = 6.0 Hz, 3H) ppm |
| 216 | 610.3 | 1H NMR (400 MHz, DMSO-d6) δ = 9.63-9.60 (m, 1H), 9.07 (s, 1H), 8.52 (d, J = 2.0 Hz, 1H), 8.44 (d, J = 2.0 Hz, 1H), 8.36 (s, 1H), 8.32-8.23 (m, 2H), 7.79 (d, J = 2.0 Hz, 1H), 7.50 (s, 1H), 6.99 (d, J = 2.0 Hz, 1H), 6.36-6.16 (m, 1H), 4.72 (d, J = 5.6 Hz, 2H), 4.63-4.59 (m, 1H), 4.32 (s, 4H), 4.13-4.07 (m, 1H), 2.95-2.72 (m, 1H), 2.63-2.56 (m, 1H), 1.97-1.86 (m, 1H), 1.01-0.90 (m, 2H), 0.74-0.67 (m, 2H) ppm |
| 217 | 608.2 | 1H NMR (400 MHz, DMSO-d6) δ = 9.62-9.59 (m, 1H), 9.04 (s, 1H), 8.34-8.27 (m, 3H), 8.03 (d, J = 9.2 Hz, 1H), 7.49-7.22 (m, 2H), 6.34-6.22 (m, 1H), 4.71-4.70 (m, 2H), 4.60-4.59 (m, 1H), 4.29-4.27 (m, 2H), 4.16 (d, J = 11.6 Hz, 1H), 2.99-2.96 (m, 2H), 2.85-2.56 (m, 1H), 2.04-2.01 (m, 2H) ppm |
| 218 | 637.2 | 1H NMR (400 MHz, DMSO-d6) δ = 9.60-9.57 (m, 1H), 9.02 (s, 1H), 8.44-8.25 (m, 2H), 8.24-8.10 (m, 2H), 7.54-7.28 (m, 2H), 6.52 (d, J = 2.4 Hz, 1H), 6.40-6.14 (m, 1H), 4.70 (d, J = 5.6 Hz, 2H), 4.63-4.58 (m, 1H), 4.41-4.24 (m, 4H), 4.18-4.13 (m, 1H), 3.91-3.72 (m, 2H), 2.91-2.70 (m, 1H), 2.65-2.56 (m, 2H), 1.63-1.56 (m, 1H), 1.41 (d, J = 6.0 Hz, 6H) ppm |
| 219 | 651.90 | 1H NMR (400 MHz, DMSO-d6) δ = 9.61-9.58 (m, 1H), 9.02 (s, 1H), 8.37-8.22 (m, 3H), 7.60 (d, J = 9.2 Hz, 1H), 7.41 (s, 1H), 6.80 (d, J = 8.8 Hz, 1H), 6.49 (d, J = 2.0 Hz, 1H), 6.35-6.21 (m, 1H), 6.20-6.17 (m, 1H), 4.70 (br d, J = 5.2 Hz, 2H), 4.60 (br d, J = 13.2 Hz, 1H), 4.18 (br s, 5H), 3.77-3.74 (m, 2H), 3.49 (br d, J = 6.8 Hz, 2H), 3.44-3.41 (m, 2H), 3.26 (s, 3H), 2.91-2.70 (m, 2H), 2.64-2.58 (m, 1H) ppm |
| 223 | 608.3 | 1H NMR (400 MHz, DMSO-d6) δ = 9.63-9.60 (m, 1H), 9.07 (s, 1H), 8.38-8.23 (m, 4H), 7.76 (d, J = 2.0 Hz, 1H), 7.48 (s, 1H), 6.95 (d, J = 2.0 Hz, 1H), 6.38-6.15 (m, 1H), 4.72 (d, J = 5.6 Hz, 2H), 4.63-4.58 (m, 1H), 4.31 (s, 4H), 4.18-4.12 (m, 1H), 2.91-2.70 (m, 1H), 2.61-2.53 (m, 1H), 1.64-1.60 (m, 1H), 1.17-1.11 (m, 3H), 1.11-1.02 (m, 1H), 0.95-0.87 (m, 1H), 0.77-0.70 (m, 1H) ppm. |
| 224 | 598.3 | 1H NMR (400 MHz, DMSO-d6) δ = 9.63-9.60 (m, 1H), 9.15 (s, 1H), 8.38-8.26 (m, 4H), 7.89 (d, J = 1.6 Hz, 1H), 7.57 (s, 1H), 7.30 (d, J = 1.6 Hz, 1H), 6.37-6.19 (m, 1H), 4.74 (d, J = 5.6 Hz, 2H), 4.61-4.59 (m, 1H), 4.39 (s, 2H), 4.36 (s, 4H), 4.18-4.16 (m, 1H), 3.29 (s, 3H), 2.90-2.72 (m, 1H), 2.61-2.60 (m, 1H) ppm |
| 229 | 618 | 1H NMR (400 MHz, DMSO-d6) δ = 9.60 (t, J = 5.6 Hz, 1H), 9.06 (s, 1H), 8.34 (s, 1H), 8.33-8.29 (m, 1H), 8.19 (d, J = 9.2 Hz, 1H), 8.04 (d, J = 2.8 Hz, 1H), 7.88 (d, J = 9.2 Hz, 1H), 7.56 (d, J = 2.8 Hz, 1H), 7.50 (s, 1H), 7.38-7.02 (m, 1H), 6.20-6.32 (m, 1H), 4.72 (d, J = 5.6 Hz, 2H), 4.57-4.61 (m, 1H), 4.20-4.11 (m, 3H), 2.84-2.87 (m, 2H), 2.82-2.70 (m, 1H), 2.64-2.59 (m, 1H), 1.93-1.99 (m, 2H) ppm |
| 233 | 623.3 | 1H NMR (400 MHz, DMSO-d6) δ = 9.60-9.57 (m, 1H), 9.01 (s, 1H), 8.36-8.26 (m, 2H), 8.22-8.14 (m, 2H), 7.44 (s, 1H), 7.29 (d, J = 2.4 Hz, 1H), 6.49 (d, J = 2.4 Hz, 1H), 6.35-6.19 (m, 1H), 4.70 (d, J = 5.6 Hz, 2H), 4.61-4.59 (m, 1H), 4.38-4.24 (m, 4H), 4.20-4.06 (m, 2H), 3.90-3.83 (m, 1H), 3.53 (d, J = 8.0 Hz, 1H), 2.89-2.71 (m, 1H), 2.63-2.56 (m, 1H), 2.40-2.35 (m, 1H), 2.07-1.98 (m, 1H), 1.40 (d, J = 6.0 Hz, 3H) ppm. |
| 236 | 621.3 | 1H NMR (400 MHz, DMSO-d6) δ = 9.60-9.58 (m, 1H), 8.97 (s, 1H), 8.35-8.29 (m, 2H), 8.07 (d, J = 9.6 Hz, 1H), 7.78 (d, J = 9.2 Hz, 1H), 7.50 (d, J = 2.8 Hz, 1H), 7.42 (s, 1H), 6.82 (d, J = 2.4 Hz, 1H), 6.34-6.22 (m, 1H), 4.70 (br d, J = 5.6 Hz, 2H), 4.62-4.59 (m, 1H), 4.17-4.07 (m, 4H), 3.87-3.82 (m, 1H), 3.54 (br d, J = 8.0 Hz, 1H), 2.77-2.75 (m, 2H), 2.61 (br s, 1H), 2.37 (br s, 1H), 2.06-2.04 (m, 1H), 1.92-1.89 (m, 2H), 1.43 (d, J = 6.0 Hz, 3H) ppm |

TABLE 5-continued

Compounds of the Invention

| # | LCMS (ESI/M + H) | 1HNMR |
|---|---|---|
| 240 | 608.0 | 1HNMR (400 MHz, DMSO-d6) δ = 9.36 (d, J = 7.6 Hz, 1H), 9.08 (s, 1H), 8.38-8.29 (m, 2H), 8.28-8.23 (m, 2H), 7.79 (d, J = 2.0 Hz, 1H), 7.57 (s, 1H), 6.99 (d, J = 2.0 Hz, 1H), 6.36-6.13 (m, 1H), 5.41-5.19 (m, 1H), 4.61-4.57 (m, 1H), 4.37-4.24 (m, 4H), 4.17-4.11 (m, 1H), 2.89-2.75 (m, 1H), 2.62-2.58 (m, 1H), 1.96-1.85 (m, 1H), 1.60 (d, J = 7.2 Hz, 3H), 1.00-0.89 (m, 2H), 0.76-0.65 (m, 2H) ppm |
| 241 | 594.4 | 1H NMR (400 MHz, DMSO-d6) δ = 9.64 (m, 1H), 9.19 (s, 1H), 9.08-9.01 (m, 1H), 8.49-8.42 (m, 1H), 8.35-8.23 (m, 2H), 7.66 (d, J = 9.2 Hz, 1H), 7.53 (s, 1H), 7.28-6.97 (m, 1H), 6.36-6.16 (m, 1H), 4.74 (br d, J = 5.6 Hz, 2H), 4.66-4.57 (m, 1H), 4.53 (br d, J = 4.4 Hz, 2H), 4.31-4.24 (m, 2H), 4.13 (br d, J = 11.8 Hz, 1H), 2.87-2.73 (m, 1H), 2.64-2.58 (m, 1H), 2.23-2.11 (m, 1H), 1.18-1.10 (m, 2H), 1.07-0.99 (m, 2H) ppm |
| 243 | 637.3 | 1H NMR (400 MHz, DMSO-d6) δ = 9.61-9.59 (m, 1H), 9.00 (s, 1H), 8.38-8.26 (m, 2H), 8.18 (s, 2H), 7.49-7.33 (m, 2H), 6.56 (d, J = 2.4 Hz, 1H), 6.40-6.19 (m, 1H), 4.69 (d, J = 5.6 Hz, 2H), 4.62-4.58 (m, 1H), 4.43-4.24 (m, 4H), 4.18-4.15 (m, 1H), 3.94-3.82 (m, 1H), 3.39 (br s, 1H), 3.12-3.08 (m, 1H), 2.93-2.69 (m, 1H), 2.64-2.56 (m, 1H), 2.09-1.88 (m, 3H), 1.67 (br s, 1H), 1.10 (d, J = 6.2 Hz, 3H) ppm |
| 244 | 645.3 | 1H NMR (400 MHz, DMSO-d6) δ = 9.63-9.60 (m, 1H), 9.04 (s, 1H), 8.36-8.28 (m, 2H), 8.26-8.15 (m, 2H), 7.45 (s, 1H), 7.38 (d, J = 2.8 Hz, 1H), 6.71 (d, J = 2.4 Hz, 1H), 6.40-6.19 (m, 1H), 4.71 (d, J = 5.6 Hz, 2H), 4.61-4.59 (m, 1H), 4.39-4.26 (m, 8H), 4.15-4.13 (m, 1H), 2.91-2.72 (m, 1H), 2.64-2.55 (m, 1H) ppm |
| 246 | 627.3 | 1H NMR (400 MHz, DMSO-d6) δ = 9.62-9.59 (m, 1H), 9.09 (s, 1H), 8.43 (d, J = 9.2 Hz, 1H), 8.34-8.26 (m, 3H), 7.50 (s, 1H), 7.22 (d, J = 8.4 Hz, 1H), 6.33-6.21 (m, 1H), 6.17 (d, J = 8.4 Hz, 1H), 5.53-5.39 (m, 1H), 4.72 (br d, J = 5.6 Hz, 2H), 4.28-4.16 (m, 8H), 3.91-3.90 (m, 2H), 2.85-2.70 (m, 1H), 2.61-2.57 (m, 1H) ppm |
| 247 | 598 | 1H NMR (400 MHz, DMSO-d6) δ = 9.62-9.59 (m, 1H), 9.07 (s, 1H), 8.34 (s, 1H), 8.32-8.28 (m, 1H), 8.26-9.19 (m, 2H), 8.13 (s, 1H), 7.70 (d, J = 2.4 Hz, 1H), 7.49 (s, 1H), 7.07 (d, J = 2.4 Hz, 1H), 6.36-6.20 (m, 1H), 4.72 (br d, J = 5.6 Hz, 2H), 4.65-4.57 (m, 1H), 4.34 (br s, 4H), 4.16-4.15 (m, 1H), 4.10-4.05 (m, 2H), 2.90-2.72 (m, 1H), 2.64-2.55 (m, 1H), 1.34-1.31 (m, 3H) ppm |
| 248 | 641.3 | 1H NMR (400 MHz, DMSO-d6) δ = 9.60-9.57 (m, 1H), 9.02 (s, 1H), 8.37-8.27 (m, 2H), 8.22-8.14 (m, 2H), 7.44 (s, 1H), 7.27 (d, J = 2.8 Hz, 1H), 6.52 (d, J = 3.6 Hz, 1H), 6.36-6.16 (m, 1H), 4.72-4.55 (m, 5H), 4.36-4.26 (m, 4H), 4.19-4.13 (m, 1H), 3.96-3.92 (m, 2H), 3.66-3.63 (m, 2H), 3.14-3.02 (m, 1H), 2.91-2.70 (m, 1H), 2.56-2.54 (m, 1H) ppm |
| 254 | 645.2 | 1H NMR (400 MHz, DMSO-d6) δ = 9.61 (br t, J = 5.6 Hz, 1H), 9.10 (s, 1H), 8.42-8.33 (m, 2H), 8.33-8.26 (m, 2H), 7.50 (s, 1H), 7.27 (d, J = 8.6 Hz, 1H), 6.36-6.19 (m, 2H), 4.73 (br d, J = 5.3 Hz, 2H), 4.61 (td, J = 3.6, 12.9 Hz, 1H), 4.35-4.24 (m, 8H), 4.16 (br t, J = 11.8 Hz, 1H), 2.92-2.73 (m, 1H), 2.69-2.57 (m, 1H) ppm |
| 261 | 623.2 | 1H NMR (400 MHz, DMSO-d6) δ = 9.33 (d, J = 7.8 Hz, 1H), 9.02 (s, 1H), 8.41-8.28 (m, 2H), 8.25 (s, 1H), 8.22-8.12 (m, 2H), 7.52 (s, 1H), 7.24 (d, J = 2.6 Hz, 1H), 6.47 (d, J = 2.4 Hz, 1H), 6.39-6.13 (m, 1H), 5.32-5.28 (m, 1H), 4.62-4.60 (m, 1H), 4.40-4.26 (m, 4H), 4.14 (br d, J = 12.2 Hz, 1H), 3.83 (d, J = 7.2 Hz, 4H), 2.91-2.71 (m, 1H), 2.60 (br d, J = 5.0 Hz, 1H), 2.34-2.27 (m, 2H), 1.60 (d, J = 7.2 Hz, 3H) ppm |
| 262 | 626.3 | 1H NMR (400 MHz, DMSO-d6) δ = 9.58-9.55 (m, 1H), 9.12 (s, 1H), 8.41-8.25 (m, 3H), 8.21 (s, 1H), 7.97 (d, J = 2.8 Hz, 1H), 7.42 (s, 1H), 7.31-7.28 (m, 1H), 6.34-6.17 (m, 1H), 4.70 (d, J = 5.6 Hz, 2H), 4.61-4.56 (m, 1H), 4.29-4.24 (m, 1H), 4.22-4.12 (m, 1H), 4.04-4.02 (m, 2H), 2.88-2.72 (m, 1H), 2.59-2.55 (m, 3H), 1.94-1.77 (m, 2H), 0.81-0.73 (m, 2H), 0.71-0.63 (m, 2H) ppm |
| 263 | 623.2 | 1H NMR (400 MHz, DMSO-d6) δ = 9.62-9.59 (m, 1H), 9.05 (s, 1H), 8.34-8.20 (m, 4H), 7.61 (d, J = 5.2 Hz, 1H), 7.47 (s, 1H), 6.34-6.22 (m, 1H), 6.15 (d, J = 5.6 Hz, 1H), 4.71 (d, J = 5.6 Hz, 2H), 4.62-4.56 (m, 1H), 4.28-4.25 (m, 4H), 4.18-4.14 (m, 3H), 3.62-3.58 (m, 2H), 2.75-2.72 (m, 1H), 2.60 (br d, J = 6.8 Hz, 2H), 1.21 (d, J = 6.8 Hz, 3H) ppm |
| 264 | 609.2 | 1H NMR (400 MHz, DMSO-d6) δ = 9.62-9.59 (m, 1H), 9.07 (s, 1H), 8.49 (d, J = 9.6 Hz, 1H), 8.37-8.23 (m, 3H), 7.49 (s, 1H), 7.18 (d, J = 8.8 Hz, 1H), 6.39-6.15 (m, 1H), 6.08 (d, J = 8.4 Hz, 1H), 4.72 (d, J = 5.6 Hz, 2H), 4.65-4.56 (m, 1H), 4.29-4.12 (m, 5H), 3.87-3.83 (m, 4H), 2.86-2.71 (m, 1H), 2.62-2.61 (m, 1H), 2.31-2.23 (m, 2H) ppm |
| 265 | 622.2 | 1H NMR (400 MHz, DMSO-d6) δ = 9.65-9.62 (m, 1H), 9.18 (s, 1H), 8.40-8.37 (m, 1H), 8.34 (s, 1H), 8.33-8.27 (m, 2H), 8.24 (s, 1H), 7.69 (d, J = 2.4 Hz, 1H), 7.58 (s, 1H), 6.39-6.19 (m, 1H), 4.75 (d, J = 5.6 Hz, 2H), 4.64-4.56 (m, 1H), 4.47-4.40 (m, 2H), 4.37 (d, J = 4.4 Hz, 2H), 4.19-4.16 (m, 1H), 2.91-2.60 (m, 1H), 2.65-2.56 (m, 1H) ppm |
| 269 | 659.3 | 1H NMR (400 MHz, DMSO-d6) δ = 9.61 (s, 1H), 9.04 (s, 1H), 8.35-8.28 (m, 2H), 8.24-8.20 (m, 2H), 7.48-7.40 (m, 2H), 6.72 (d, J = 2.4 Hz, 1H), 6.41-6.17 (m, 1H), 4.75-4.66 (m, 2H), 4.62-4.59 (m, 1H), 4.52-4.40 (m, 1H), 4.39-4.24 (m, 5H), 4.20-4.12 (m, 1H), 4.11-4.02 (m, 1H), 2.92-2.70 (m, 1H), 2.64-2.55 (m, 1H), 1.42 (d, J = 6.4 Hz, 3H) ppm |
| 27 | 626.2 | 1H NMR (400 MHz, DMSO-d6) δ = 9.66-9.57 (m, 1H), 9.00 (s, 1H), 8.49-8.43 (m, 1H), 8.37-8.28 (m, 2H), 8.12 (d, J = 9.2 Hz, 1H), 7.91 (d, J = 3.2 Hz, 1H), 7.83 (d, J = 9.2 Hz, 1H), 7.45 (s, 1H), 7.34 (d, J = 2.8 Hz, 1H), |

TABLE 5-continued

Compounds of the Invention

| # | LCMS (ESI/M + H) | 1HNMR |
|---|---|---|
| | | 6.37-6.19 (m, 1H), 4.70 (d, J = 6.0 Hz, 2H), 4.65-4.56 (m, 1H), 4.20-4.08 (m, 5H), 3.70-3.63 (m, 2H), 3.31 (s, 3H), 2.92-2.68 (m, 4H), 1.96-1.91 (m, 2H) ppm. |
| 274 | 600.2 | 1H NMR (400 MHz, CHLOROFORM-d) δ = 9.04 (s, 1H), 8.43 (d, J = 9.2 Hz, 1H), 8.24 (s, 1H), 8.13-8.04 (m, 2H), 7.98-7.88 (m, 1H), 7.72-7.60 (m, 2H), 7.29 (s, 1H), 5.74-5.50 (m, 2H), 4.90 (d, J = 5.2 Hz, 2H), 4.75-4.62 (m, 1H), 4.55-4.49 (m, 2H), 4.45-4.39 (m, 2H), 4.14-4.11 (m, 1H), 3.24-2.98 (m, 1H), 2.57-2.41 (m, 1H), 1.76-1.64 (m, 3H) ppm |
| 276 | 635.30 | 1H NMR (400 MHz, DMSO-d6) δ = 9.60-9.57 (m, 1H), 9.01 (s, 1H), 8.36-8.28 (m, 2H), 8.22-8.15 (m, 2H), 7.45-7.36 (m, 2H), 6.60 (d, J = 2.0 Hz, 1H), 6.37-6.20 (m, 1H), 4.71-4.69 (m, 2H), 4.65-4.58 (m, 1H), 4.32 (m, 4H), 4.17 (m, 1H), 3.52 (d, J = 9.2 Hz, 2H), 3.21-3.14 (m, 2H), 2.90-2.72 (m, 1H), 2.62-2.57 (m, 1H), 1.73-1.66 (m, 2H), 0.76-0.68 (m, 1H), 0.27-0.26 (m, 1H) ppm |
| 277 | 612.2 | 1H NMR (400 MHz, DMSO-d6) δ = 9.62-9.59 (m, 1H), 9.09 (s, 1H), 8.34-8.24 (m, 4H), 7.51-7.48 (m, 1H), 7.30-7.27 (m, 1H), 7.09-7.05 (m, 1H), 6.33-6.21 (m, 1H), 5.01-4.81 (m, 1H), 4.73-4.72 (m, 2H), 4.63-4.53 (m, 1H), 4.39-4.26 (m, 2H), 4.19-4.07 (m, 2H), 2.88-2.72 (m, 1H), 2.61-2.57 (m, 1H), 2.29-2.25 (m, 1H), 1.71-1.61 (m, 1H), 1.19-1.10 (m, 1H) ppm |
| 279 | 618.3 | 1H NMR (400 MHz, DMSO-d6) δ = 9.63-9.60 (m, 1H), 9.13 (s, 1H), 8.35-8.24 (m, 5H), 7.53-7.50 (m, 1H), 7.42 (d, J = 8.0 Hz, 1H), 7.20 (d, J = 8.0 Hz, 1H), 6.33-6.21 (m, 1H), 5.86-5.82 (m, 1H), 4.95-4.76 (m, 4H), 4.75-4.72 (m, 1H), 4.37-4.34 (m, 4H), 4.22-4.15 (m, 1H), 2.93 (d, J = 1.2 Hz, 2H) ppm. |
| 281 | 578 | 1H NMR (400 MHz, CHLOROFORM-d) δ = 9.08 (br s, 1H), 8.67-8.52 (m, 2H), 8.39 (br s, 1H), 8.21-8.14 (m, 2H), 8.10 (s, 1H), 7.91 (s, 1H), 7.39 (S, 1H), 5.62-5.43 (m, 1H), 5.01 (br d, J = 4.0 Hz, 2H), 4.64 (br d, J = 12.4 Hz, 1H), 4.60-4.54 (m, 2H), 4.49-4.42 (m, 2H), 4.11-4.08 (m, 1H), 3.21 (s, 1H), 3.17-2.96 (m, 1H), 2.51-2.42 (m, 1H) ppm |
| 282 | 572.3 | 1H NMR (400 MHz, DMSO-d6) δ = 9.63-9.60 (m, 1H), 9.10 (s, 1H), 8.37-8.26 (m, 3H), 8.20 (d, J = 9.2 Hz, 1H), 7.95 (d, J = 2.4 Hz, 1H), 7.51 (s, 1H), 7.47-7.44 (m, 1H), 6.38-6.19 (m, 1H), 4.72 (d, J = 5.6 Hz, 2H), 4.62-4.59 (m, 1H), 4.47-4.27 (m, 4H), 4.19-4.16 (m, 1H), 2.92-2.71 (m, 1H), 2.61-2.59 (m, 1H) ppm |
| 284 | 655.3 | 1H NMR (400 MHz, DMSO-d6) δ = 9.60-9.57 (m, 1H), 9.00 (s, 1H), 8.38-8.28 (m, 2H), 8.23-8.12 (m, 2H), 7.46-7.34 (m, 2H), 6.62-6.55 (m, 1H), 6.36-6.19 (m, 1H), 5.31-5.11 (m, 1H), 4.75-4.67 (m, 2H), 4.62-4.59 (m, 1H), 4.37-4.27 (m, 4H), 4.18-4.14 (m, 1H), 3.70-3.49 (m, 3H), 3.44-3.13 (m, 1H), 2.97-2.92 (m, 1H), 2.89-2.75 (m, 1H), 2.60-2.57 (m, 1H), 1.14 (d, J = 6.8 Hz, 3H) ppm |
| 285 | 627.2 | 1H NMR (400 MHz, DMSO-d6) δ = 9.62-9.59 (m, 1H), 9.06 (s, 1H), 8.34-8.21 (m, 4H), 7.66 (d, J = 5.2 Hz, 1H), 7.48 (s, 1H), 6.26-6.23 (m, 2H), 5.52-5.37 (m, 1H), 4.71 (br d, J = 5.6 Hz, 2H), 4.70-4.65 (m, 1H), 4.37-4.29 (m, 6H), 4.10 (s, 2H), 4.06-4.04 (m, 1H), 2.60-2.58 (m, 2H) ppm |
| 286 | 655.1 | 1H NMR (400 MHz, DMSO-d6) δ = 9.61-9.58 (m, 1H), 9.03 (s, 1H), 8.36-8.28 (m, 2H), 8.23 (s, 2H), 7.72 (d, J = 2.4 Hz, 1H), 7.45 (s, 1H), 7.01 (d, J = 2.8 Hz, 1H), 6.40-6.14 (m, 1H), 4.89-4.56 (m, 4H), 4.36-4.25 (m, 4H), 4.19-4.13 (m, 1H), 3.47-3.36 (m, 2H), 3.20-3.04 (m, 2H), 2.93-2.72 (m, 1H), 2.64-2.55 (m, 1H), 1.93-1.72 (m, 3H), 1.60-1.55 (m, 1H) ppm |
| 293 | 608.1 | 1H NMR (400 MHz, DMSO-d6) δ = 9.62-9.60 (m, 1H), 9.07-9.03 (m, 1H), 8.37-8.28 (m, 2H), 8.16 (d, J = 9.2 Hz, 1H), 8.11-8.08 (m, 1H), 7.93 (d, J = 9.2 Hz, 1H), 7.78 (d, J = 2.4 Hz, 1H), 7.51-7.48 (m, 1H), 6.43-6.16 (m, 1H), 4.93-4.91 (m, 2H), 4.75-4.69 (m, 2H), 4.67-4.63 (m, 2H), 4.62-4.55 (m, 1H), 4.30-4.21 (m, 1H), 4.19-4.11 (m, 3H), 2.88-2.86 (m, 2H), 2.83-2.71 (m, 1H), 2.62-2.56 (m, 1H), 1.99-1.95 (m, 2H) ppm |
| 295 | 626.3 | 1H NMR (400 MHz, DMSO-d6) δ = 9.61-9.58 (m, 1H), 9.11 (s, 1H), 8.34-8.26 (m, 3H), 7.80 (d, J = 5.8 Hz, 1H), 7.52 (d, J = 9.2 Hz, 1H), 7.48 (s, 1H), 6.94 (d, J = 5.8 Hz, 1H), 6.37-6.11 (m, 1H), 4.71 (d, J = 5.8 Hz, 2H), 4.65-4.55 (m, 1H), 4.41-4.39 (m, 2H), 4.15 (d, J = 11.2 Hz, 1H), 4.03-4.00 (m, 2H), 3.68-3.66 (m, 2H), 3.31 (s, 3H), 2.90-2.69 (m, 1H), 2.65-2.60 (m, 2H), 2.53 (s, 1H), 1.98-1.87 (m, 2H) ppm |
| 296 | 597.3 | 1H NMR (400 MHz, METHANOL-d4) δ = 8.99 (s, 1H), 8.53-8.50 (m, 1H), 8.39 (s, 1H), 8.18-8.13 (m, 2H), 8.02 (d, J = 9.2 Hz, 1H), 7.70 (d, J = 5.2 Hz, 1H), 7.62 (s, 1H), 6.65 (d, J = 6.0 Hz, 1H), 5.94-5.81 (m, 1H), 4.82 (s, 2H), 4.65-4.62 (m, 1H), 4.39 (s, 4H), 4.19-4.13 (m, 1H), 3.05-2.98 (m, 6H), 2.60-2.58 (m, 2H) ppm |
| 299 | 685.2 | 1H NMR (400 MHz, DMSO-d6) δ = 9.61-9.58 (m, 1H), 9.01 (s, 1H), 8.65 (d, J = 2.0 Hz, 1H), 8.47 (d, J = 2.0 Hz, 1H), 8.21-8.14 (m, 2H), 7.44 (s, 1H), 7.29 (d, J = 2.4 Hz, 1H), 6.49 (d, J = 2.4 Hz, 1H), 6.30-6.18 (m, 1H), 4.70-4.69 (m, 2H), 4.60-4.57 (m, 1H), 4.34-4.28 (m, 4H), 4.15-4.00 (m, 2H), 3.86-3.85 (m, 1H), 3.53 (q, J = 8.4 Hz, 1H), 2.90-2.74 (m, 1H), 2.61-2.60 (m, 1H), 2.38-2.36 (m, 1H), 2.02-2.01 (m, 1H), 1.41 (d, J = 6.0 Hz, 3H) ppm |
| 300 | 608.3 | 1H NMR (400 MHz, DMSO-d6) δ = 9.63-9.60 (m, 1H), 9.08 (s, 1H), 8.36-8.26 (m, 4H), 7.81 (d, J = 2.0 Hz, 1H), 7.50 (s, 1H), 7.15 (d, J = 1.6 Hz, 1H), 6.37-6.18 (m, 1H), 4.72 (d, J = 5.2 Hz, 2H), 4.62-4.59 (m, 1H), 4.39-4.29 (m, 4H), 4.19-4.13 (m, 1H), 2.92-2.70 (m, 1H), 2.64-2.55 (m, 1H), 2.04-2.00 (m, 1H), 1.22-1.08 (m, 1H), 1.00-0.97 (m, 1H), 0.81-0.79 (m, 3H), 0.70-0.69 (m, 1H) ppm |

TABLE 5-continued

Compounds of the Invention

| # | LCMS (ESI/M + H) | 1HNMR |
|---|---|---|
| 303 | 603.2 | 1H NMR (400 MHz, DMSO-d6) δ = 9.61-9.58 (m, 1H), 9.19 (s, 1H), 8.39-8.27 (m, 2H), 8.04 (d, J = 8.8 Hz, 1H), 7.93-7.76 (m, 3H), 7.66 (s, 1H), 7.34 (s, 1H), 7.20-6.76 (m, 1H), 6.38-6.17 (m, 1H), 4.72 (br d, J = 5.6 Hz, 2H), 4.66-4.56 (m, 1H), 4.41-4.39 (m, 2H), 4.14-4.13 (m, 1H), 4.06-4.04 (m, 2H), 2.94-2.69 (m, 1H), 2.63-2.59 (m, 1H) ppm |
| 304 | 621.90 | 1H NMR (400 MHz, DMSO-d6) δ = 9.61-9.59 (m, 1H), 9.14 (s, 1H), 8.43-8.22 (m, 4H), 7.60 (d, J = 10.6 Hz, 1H), 7.55 (s, 1H), 7.16-6.89 (m, 1H), 6.32-6.20 (m, 1H), 4.74 (br d, J = 5.8 Hz, 2H), 4.65-4.55 (m, 1H), 4.44-4.40 (m, 4H), 4.19-4.16 (m, 1H), 2.90-2.72 (m, 1H), 2.64-2.55 (m, 1H) ppm |
| 305 | 581 | 1H NMR (400 MHz, CHLOROFORM-d) δ = 8.96 (s, 1H), 8.39 (s, 1H), 8.25 (s, 1H), 8.21-8.18 (m, 1H), 7.95-7.91 (m, 1H), 7.90-7.86 (m, 1H), 7.84 (d, J = 2.8 Hz, 1H), 7.79 (s, 1H), 7.43 (s, 1H), 7.08 (d, J = 2.4 Hz, 1H), 5.62-5.46 (m, 1H), 4.93 (br d, J = 6.0 Hz, 2H), 4.66-4.61 (m, 1H), 4.11-4.04 (m, 1H), 3.94-3.91 (m, 2H), 3.86 (s, 3H), 3.13-2.99 (m, 1H), 2.88-2.85 (m, 2H), 2.49-2.43 (m, 1H), 2.18-2.12 (m, 2H) ppm |

Preparation of (R)-9-chloro-N-((2-(6-((2S,6R)-2,6-dimethylmorpholino)pyridin-2-yl)-1,6-naphthyridin-7-)methyl)-4-fluoro-3,4-dihydro-2H-benzo[b][1,4]oxathiepine-7-carboxamide 5,5-dioxide (Compound 148)

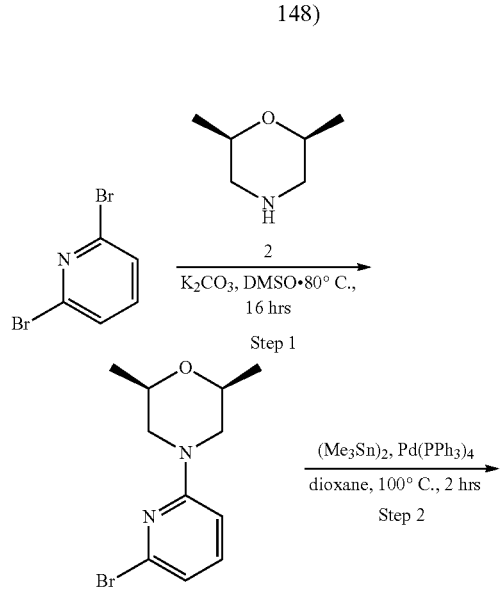

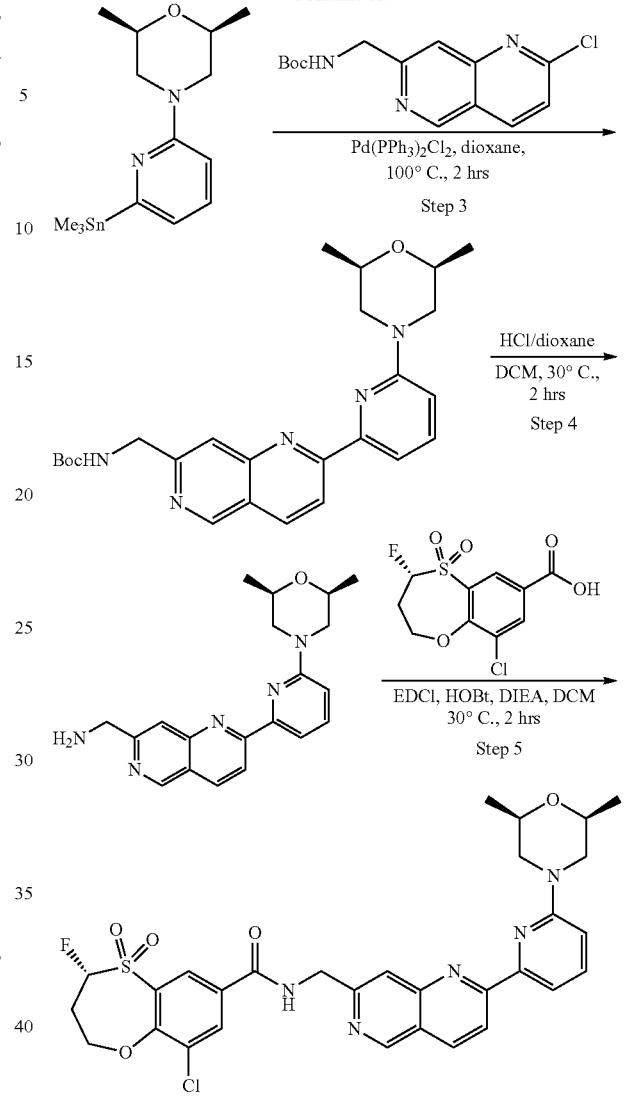

Step 1: Preparation of (2S,6R)-4-(6-bromo-2-pyridyl)-2,6-dimethyl-morpholine

To a solution of 2,6-dibromopyridine (50 g, 211.07 mmol) and (2S,6R)-2,6-dimethylmorpholine (36.46 g, 316.60 mmol) in DMSO (500 mL) was added K$_2$CO$_3$ (87.51 g, 633.20 mmol), the mixture was stirred at 80° C. for 16 hrs. The reaction mixture was poured into water (2 L), the solution was extracted with EA (2 L*3), the combined organic layer was washed with brine (2 L mL), dried over Na$_2$SO$_4$, filtered and concentrated to give a residue. The residue was purified by column chromatography (SiO$_2$, Petroleum ether/Ethyl acetate=10:1-1:1), the solution was concentrated to give (2S,6R)-4-(6-bromo-2-pyridyl)-2,6-dimethyl-morpholine (54 g, 199.15 mmol, 94.35% yield) as yellow oil. $^1$H NMR (400 MHz, DMSO-d$_6$) δ=7.31-7.27 (m, 1H), 6.76 (d, J=7.6 Hz, 1H), 6.50 (d, J=8.0 Hz, 1H), 4.03-3.99 (m, 2H), 3.69-3.66 (m, 2H), 2.55-2.49 (m, 2H), 1.28-1.25 (m, 5H) ppm Step 2: Preparation of [6-[(2R,6S)-2,6-dimethyl-morpholin-4-yl]-2-pyridyl]-trimethyl-stannane

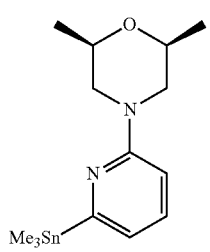

To a solution of (2S,6R)-4-(6-bromo-2-pyridyl)-2,6-dimethyl-morpholine (20 g, 73.76 mmol) and trimethyl(trimethylstannyl)stannane (29.00 g, 88.51 mmol) in dioxane (200 mL) was added Pd(PPh$_3$)$_4$ (4.26 g, 3.69 mmol), the mixture was stirred at 100° C. for 2 hrs under N$_2$. The reaction mixture was poured into water (500 mL), the solution was extracted with EA (500 mL*3), the combined organic layer was washed with brine (1000 mL), dried over Na$_2$SO$_4$, filtered and concentrated to give [6-[(2R,6S)-2,6-dimethyl-morpholin-4-yl]-2-pyridyl]-trimethyl-stannane (26.1 g, crude) was obtained as brown oil, which was used for the next step directly.

Step 3: Preparation of tert-butyl N-[[2-[6-[(2S,6R)-2,6-dimethylmorpholin-4-yl]-2-pyridyl]-1,6-naphthyridin-7-yl]methyl]carbamate

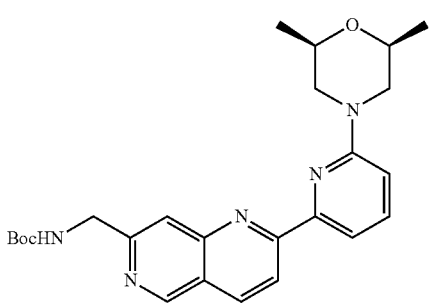 [SMILES: C[C@@H]1CN(c2cccc(-c3ccc4cnc(CNC(=O)OC(C)(C)C)cc4n3)n2)C[C@H](C)O1]

A mixture of [6-[(2R,6S)-2,6-dimethylmorpholin-4-yl]-2-pyridyl]-trimethyl-stannane (26 g, 73.23 mmol) and tert-butyl N-[(2-chloro-1,6-naphthyridin-7-yl)methyl]carbamate (described in example 1) (10.76 g, 36.61 mmol) in dioxane (120 mL) was added Pd(PPh$_3$)$_2$Cl$_2$ (2.57 g, 3.66 mmol), the mixture was stirred at 100° C. for 2 hrs under N$_2$. The reaction mixture was concentrated to give a residue. The residue was purified by column chromatography (SiO$_2$, Petroleum ether/Ethyl acetate=1:1-0:1), the solution was concentrated to give N-[[2-[6-[(2S,6R)-2,6-dimethylmorpholin-4-yl]-2-pyridyl]-1,6-naphthyridin-7-yl]methyl]carbamate (15 g, 32.78 mmol, 89.52% yield) as a yellow solid. LCMS (ESI) m/z: [$^{79}$BrM+H]$^+$=450.2. $^1$H NMR (400 MHz, DMSO-d$_6$) δ=9.35 (s, 1H), 8.66-8.59 (m, 2H), 7.93 (d, J=7.2 Hz, 1H), 7.79-7.74 (m, 2H), 7.62 (7.63-7.61, 1H), 7.04 (d, J=8.4 Hz, 1H), 4.45 (br d, J=6.0 Hz, 2H), 4.32 (br d, J=11.2 Hz, 2H), 3.69-3.65 (m, 2H), 2.52 (br s, 2H), 1.44-1.36 (m, 9H), 1.22 (d, J=6.0 Hz, 6H) ppm Step 4: Preparation of [2-[6-[(2S,6R)-2,6-dimethyl-morpholin-4-yl]-2-pyridyl]-1,6-naphthyridin-7-yl]methanamine

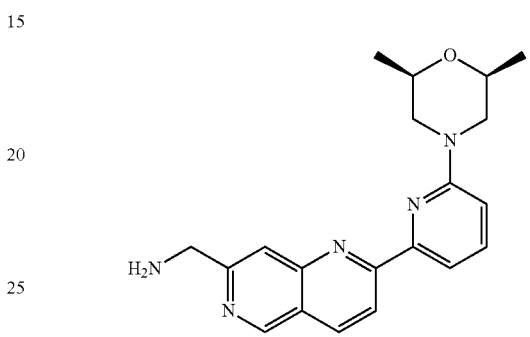

To HCl/dioxane (200 mL, 4M) was added a solution of N-[[2-[6-[(2S,6R)-2,6-dimethylmorpholin-4-yl]-2-pyridyl]-1,6-naphthyridin-7-yl]methyl]carbamate (15 g, 33.37 mmol) in DCM (200 mL), the mixture was stirred at 30° C. for 2 hrs. The reaction mixture was concentrated to give a residue. The residue was poured into MTBE (100 mL), the solution was filtered and the filter cake was dried in vacuum to give [2-[6-[(2S,6R)-2,6-dimethylmorpholin-4-yl]-2-pyridyl]-1,6-naphthyridin-7-yl]methanamine (15.5 g, crude, HCl salt) as a yellow solid. LCMS (ESI) m/z: [M+H]$^+$=350.1 $^1$H NMR (400 MHz, DMSO-d$_6$) δ=9.56 (s, 1H), 8.82-8.70 (m, 5H), 8.21 (s, 1H), 7.94 (d, J=7.6 Hz, 1H), 7.82-7.78 (m, 1H), 7.08 (d, J=8.4 Hz, 1H), 4.42-4.31 (m, 4H), 3.70-3.65 (m, 2H), 2.54-2.52 (m, 2H), 1.22-1.16 (m, 6H) ppm Step 5: Preparation of (R)-9-chloro-N-((2-(6-((2S,6R)-2,6-dimethylmorpholino)pyridin-2-yl)-1,6-naphthyridin-7-yl)methyl)-4-fluoro-3,4-dihydro-2H-benzo[b][1,4]oxathiepine-7-carboxamide 5,5-dioxide

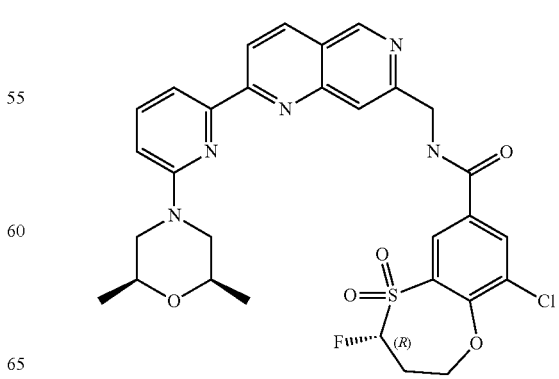

To a solution of Intermediate 3 (30 mg, 101.80 umol), [2-[6-[(2R,6S)-2,6-dimethylmorpholin-4-yl]-2-pyridyl]-1,6-naphthyridin-7-yl]methanamine (46.71 mg, 101.80 umol), HOBt (17.88 mg, 132.35 umol) and EDCl (25.37 mg, 132.35 umol) in DCM (1 mL) was added DIEA (65.79 mg, 509.02 umol). The mixture was stirred at 25° C. for 2 hrs. The reaction mixture was diluted with H₂O (20 mL) and extracted with DCM (10 mL*3). The combined organic layers were washed with brine (30 mL), dried over Na₂SO₄, filtered and concentrated under reduced pressure to give a residue. The crude product was purified by reversed-phase HPLC (0.1% FA condition), the eluent was lyophilized to give (R)-9-chloro-N-((2-(6-((2S,6R)-2,6-dimethylmorpholino)pyridin-2-yl)-1,6-naphthyridin-7-yl)methyl)-4-fluoro-3,4-dihydro-2H-benzo[b][1,4]oxathiepine-7-carboxamide 5,5-dioxide (43.55 mg, 69.30 umol, 68.07% yield) as a yellow solid. LCMS (ESI) m/z: [M+H]⁺=626.2. ¹H NMR (400 MHz, DMSO-d₆) δ=9.74-9.63 (m, 1H), 9.40 (s, 1H), 8.67-8.63 (m 2H), 8.54 (d, J=2.0 Hz, 1H), 8.46 (d, J=2.0 Hz, 1H), 8.14 (s, 1H), 7.92 (d, J=7.6 Hz, 1H), 7.85 (s, 1H), 7.78-7.74 (m, 1H), 7.04 (d, J=8.6 Hz, 1H), 6.36-6.17 (m, 1H), 4.81 (d, J=5.6 Hz, 2H), 4.69-4.57 (m, 1H), 4.32 (d, J=11.6 Hz, 2H), 4.14-4.08 (t, J=11.6 Hz, 1H), 3.71-3.63 (m, 2H), 2.94-2.72 (m, 1H), 2.64-2.56 (m, 1H), 2.53 (d, J=2.4 Hz, 2H), 1.22 (d, J=6.0 Hz, 6H). Chiral SFC: IG-3-MeOH+ACN(DEA)-60-3ML-5MIN-35T.lcm, Rt=1.655 min, ee %=100%

The following examples in Table 6 were prepared using standard chemical manipulations and procedures similar to those used for the preparation of Example 8.

TABLE 6

Compounds of the Invention

| # | LCMS (ESI/M + H) | ¹HNMR |
|---|---|---|
| 328 | 605.00 | 1H NMR (400 MHz, METHANOL-d4) δ = 9.32 (s, 1H), 8.53 (d, J = 8.6 Hz, 1H), 8.41-8.38 (m, 1H), 8.26 (d, J = 7.6 Hz, 1H), 8.21 (d, J = 8.6 Hz, 1H), 8.19-8.14 (m, 1H), 7.92 (s, 1H), 7.11 (d, J = 7.6 Hz, 1H), 6.21-6.20 (m, 1H), 5.96-5.79 (m, 1H), 4.90 (s, 2H), 4.65-4.60 (m, 1H), 4.19-4.13 (m, 1H), 4.06 (s, 3H), 3.42-3.35 (m, 1H), 3.09-2.84 (m, 1H), 2.64-2.50 (m, 1H), 1.45 (d, J = 7.0 Hz, 3H) ppm |
| 329 | 615.2 | 1H NMR (400 MHz, DMSO-d6) δ = 9.72-9.69 (m, 1H), 9.42 (s, 1H), 8.70 (d, J = 8.8 Hz, 1H), 8.57 (d, J = 8.4 Hz, 1H), 8.43 (d, J = 8.8 Hz, 1H), 8.24 (s, 1H), 8.03 (s, 1H), 7.87 (s, 1H), 7.76 (d, J = 8.4 Hz, 1H), 7.67-7.20 (m, 1H), 6.20-6.03 (m, 1H), 5.41 (d, J = 14.4 Hz, 1H), 4.91-4.75 (m, 3H), 4.47-4.29 (m, 2H), 3.99 (S, 3H), 2.47-2.42 (m, 1H), 1.19-1.18 (m, 2H), 1.12-1.10 (m, 2H) ppm |
| 330 | 541.2 | 1H NMR (400 MHz, DMSO-d6) δ = 9.68-9.66 (m, 1H), 9.41 (s, 1H), 8.69-8.61 (m, 2H), 8.35-8.30 (m, 2H), 8.19 (d, J = 7.6 Hz, 1H), 7.90-7.88 (m, 1H), 7.85 (s, 1H), 6.97 (d, J = 8.4 Hz, 1H), 6.33-6.21 (m, 1H), 4.82 (br d, J = 5.6 Hz, 2H), 4.63-4.59 (m, 1H), 4.53-4.48 (m, 2H), 4.19-4.16 (m, 1H), 2.86-2.73 (m, 1H), 2.61-2.55 (m, 1H), 1.42-1.39 (t, J = 7.0 Hz, 3H) ppm |
| 2 | 607.20 | 1H NMR (400 MHz, DMSO-d6) δ = 9.66 (m, 1H), 9.37 (s, 1H), 8.61 (d, J = 8.8 Hz, 1H), 8.36 (s, 1H), 8.33-8.30 (m, 1H), 8.23 (d, J = 8.8 Hz, 1H), 7.87 (s, 1H), 7.73 (d, J = 7.6 Hz, 1H), 7.61 (d, J = 8.0 Hz, 1H), 7.24 (m, 1H), 6.97 (s, 1H), 6.35-6.20 (m, 1H), 4.83 (d, J = 5.6 Hz, 2H), 4.61 (m, 1H), 4.38 (m, 2H), 4.17 (m, 1H), 3.64 (m, 2H), 3.22-3.20 (m, 3H), 2.89-2.75 (m, 1H), 2.62-2.58 (m, 1H), 2.48 (s, 3H) ppm |
| 5 | 624.3 | 1H NMR (400 MHz, DMSO-d6) δ = 9.68-9.65 (m, 1H), 9.39 (s, 1H), 8.67-9.61 (m, 2H), 8.39-8.36 (m, 2H), 7.91 (d, J = 7.2 Hz, 1H), 7.84 (s, 1H), 7.77-7.73 (m, 1H), 7.03 (d, J = 8.8 Hz, 1H), 6.06-5.94 (m, 1H), 4.81 (br d, J = 5.6 Hz, 2H), 4.42-4.29 (m, 4H), 3.69-3.65 (m, 2H), 2.58-2.56 (m, 2H), 2.46-2.35 (m, 2H), 1.75-1.61 (m, 2H), 1.24 (d, J = 6.4 Hz, 6H) ppm. |
| 14 | 610.1 | 1H NMR (400 MHz, DMSO-d6) δ = 9.68-9.66 (m, 1H), 9.39 (s, 1H), 8.67-8.61 (m, 2H), 8.35-8.30 (m, 2H), 7.92 (d, J = 7.2 Hz, 1H), 7.83 (s, 1H), 7.77-7.73 (m, 1H), 7.04 (d, J = 8.4 Hz, 1H), 6.34-6.33 (m, 1H), 4.81 (d, J = 5.6 Hz, 2H), 4.69-4.53 (m, 1H), 4.32 (d, J = 11.6 Hz, 2H), 4.19-4.16 (m, 1H), 3.70-3.65 (m, 2H), 2.61-2.56 (m, 1H), 1.22 (d, J = 6.0 Hz, 6H) ppm. |
| 22 | 592.3 | 1H NMR (400 MHz, DMSO-d6) δ = 9.63-9.60 (m, 1H), 9.40 (s, 1H), 8.66-8.65 (m, 2H), 8.52 (d, J = 2.4 Hz, 1H), 8.48 (s, 1H), 8.37-8.34 (m, 1H), 7.92 (d, J = 7.6 Hz, 1H), 7.82 (s, 1H), 7.75 (d, J = 8.0 Hz, 1H), 7.48 (d, J = 8.2 Hz, 1H), 7.03 (d, J = 8.4 Hz, 1H), 6.35-6.08 (m, 1H), 4.81 (d, J = 5.6 Hz, 2H), 4.58-4.47 (m, 1H), 4.32 (d, J = 11.6 Hz, 2H), 4.08-4.05 (m, 1H), 3.76-3.61 (m, 2H), 2.88-2.70 (m, 2H), 2.61-2.58 (m, 2H), 1.22 (d, J = 6.0 Hz, 6H) ppm |
| 60 | 586.90 | 1H NMR (400 MHz, DMSO-d6) δ = 9.66-9.65 (m, 1H), 9.44 (S, 1H), 8.72 (d, J = 8.6 Hz, 1H), 8.60 (d, J = 8.6 Hz, 1H), 8.46 (d, J = 8.0 Hz, 1H), 8.39-8.29 (m, 2H), 8.10 (d, J = 8.2 Hz, 1H), 7.88 (s, 1H), 7.64-7.37 (m, 1H), 6.32-6.20 (m, 1H), 4.82 (d, J = 5.6 Hz, 2H), 4.63-4.58 (m, 1H), 4.19-4.13 (m, 1H), 2.90-2.73 (m, 1H), 2.64-2.56 (m, 1H), 2.44-2.41 (m, 1H), 1.32-1.24 (m, 1H), 1.16-1.09 (m, 2H) ppm |
| 67 | 610.1 | 1H NMR (400 MHz, CHLOROFORM-d) δ = 9.29 (s, 1H), 8.85 (d, J = 8.6 Hz, 1H), 8.42 (d, J = 8.8 Hz, 1H), 8.31 (s, 1H), 8.22-8.05 (m, 3H), 7.99 (d, J = 7.4 Hz, 1H), 7.68 (d, J = 7.8 Hz, 1H), 6.55 (d, J = 8.4 Hz, 1H), 5.67-5.47 (m, 1H), 5.08-4.99 (m, 2H), 4.68- |

TABLE 6-continued

Compounds of the Invention

| # | LCMS (ESI/M + H) | 1HNMR |
|---|---|---|
| | | 4.64 (m,1H), 4.10 (t, J = 12.2 Hz, 1H), 3.93-3.77 (m, 2H), 3.75-3.69 (m, 1H), 3.67-3.61 (m, 1H), 3.46-3.42 (m, 3H), 3.29-3.26 (m,1H), 3.21-2.97 (m, 1H), 2.53-2.44 (m, 2H), 1.16 (d, J = 7.0 Hz, 3H) ppm |
| 68 | 581.20 | 1H NMR (400 MHz, DMSO-d6) δ = 9.66-9.63 (m, 1H), 9.36 (s, 1H), 8.60 (d, J = 8.8 Hz, 1H), 8.35 (s, 1H), 8.33-8.29 (m, 1H), 8.19 (d, J = 8.8 Hz, 1H), 7.88 (s, 1H), 7.70 (m, 1H), 7.12-6.99 (m, 2H), 6.36-6.18 (m, 1H), 4.82 (d, J = 5.6 Hz, 2H), 4.65-4.56 (m, 1H), 4.22-4.12 (m, 1H), 3.91 (d, J = 1.2 Hz, 3H), 2.85-2.73 (m, 1H), 2.61 (m, 1H), 2.46 (s, 3H) ppm |
| 84 | 582.2 | 1H NMR (400 MHz, DMSO-d6) δ = 9.68-9.66 (m, 1H), 9.42 (s, 1H), 8.64 (d, J = 8.6 Hz, 1H), 8.45 (d, J = 7.6 Hz, 1H), 8.40 (br s, 1H), 8.37-8.28 (m, 2H), 8.20 (d, J = 8.6 Hz, 1H), 7.83 (s, 1H), 7.48 (d, J = 7.6 Hz, 1H), 7.15-6.80 (m, 1H), 4.81 (br d, J = 5.6 Hz, 2H), 4.01 (s, 3H) ppm |
| 89 | 603.2 | 1H NMR (400 MHz, CHLOROFORM-d) δ = 9.29 (s, 1H), 8.66 (d, J = 8.6 Hz, 1H), 8.47 (d, J = 8.4 Hz, 1H), 8.39 (d, J = 8.8 Hz, 1H), 8.26 (s, 1H), 8.12-8.09 (m, 1H), 8.02 (s, 1H), 7.75 (br s, 1H), 7.57 (d, J = 8.4 Hz, 1H), 6.83-6.47 (m, 1H), 5.67-5.48 (m, 1H), 5.00 (d, J = 5.0 Hz, 2H), 4.69-4.64 (m, 1H), 4.13-4.07 (m, 1H), 3.20-2.98 (m, 1H), 2.57-2.46 (m, 2H), 1.30-1.26 (m, 2H), 1.15-1.08 (m, 2H) ppm |
| 92 | 610.1 | 1H NMR (400 MHz, CDCl3) δ = 9.26 (s, 1H), 8.75 (d, J = 8.4 Hz, 1H), 8.36 (d, J = 8.4 Hz, 1H), 8.25 (s, 1H), 8.10-8.08 (m, 1H), 8.01-7.91 (m, 2H), 7.67-7.63 (m, 2H), 6.52 (d, J = 8.4 Hz, 1H), 5.67-5.50 (m, 1H), 4.98 (d, J = 5.2 Hz, 2H), 4.68-4.65 (m, 1H), 4.30-4.22 (m, 1H), 4.14-4.11 (m, 1H), 3.83-3.55 (m, 6H), 3.21-2.99 (m, 1H), 2.56-2.42 (m, 1H), 2.22-2.17 (m, 2H), 1.26-1.23 (m, 3H) ppm |
| 97 | 614.1 | 1H NMR (400 MHz, DMSO-d6) δ = 9.66-9.63 (m, 1H), 9.39 (s, 1H), 8.67 (s, 2H), 8.37-8.29 (m, 2H), 7.89-7.83 (m, 2H), 7.75-7.71 (m, 1H), 6.71 (d, J = 8.4 Hz, 1H), 6.34-6.19 (m, 1H), 5.46-5.29 (m, 1H), 4.81 (d, J = 5.6 Hz, 2H), 4.63-4.59 (m, 1H), 4.22-4.12 (m, 2H), 3.94-3.70 (m, 3H), 3.40 (s, 3H), 2.92-2.71 (m, 2H) ppm |
| 98 | 591.2 | 1H NMR (400 MHz, DMSO-d6) δ = 9.69-9.67 (m, 1H), 9.41 (s, 1H), 8.63 (d, J = 8.8 Hz, 1H), 8.45 (s, 1H), 8.41 (d, J = 7.6 Hz, 1H), 8.37-8.27 (m, 2H), 8.20 (d, J = 8.8 Hz, 1H), 7.82 (s, 1H), 7.33 (d, J = 7.6 Hz, 1H), 6.39-6.18 (m, 1H), 6.07-5.81 (m, 1H), 5.12-4.86 (m, 2H), 4.81 (d, J = 5.6 Hz, 2H), 4.68-4.53 (m, 1H), 4.18-4.12 (m, 1H), 4.00 (s, 3H), 2.93-2.67 (m, 1H), 2.64-2.52 (m, 1H) ppm |
| 100 | 606.3 | 1H NMR (400 MHz, DMSO-d6) δ = 9.56-9.54 (m, 1H), 9.40 (s, 1H), 8.71-8.58 (m, 2H), 8.42 (s, 1H), 8.38-8.24 (m, 2H), 7.91 (d, J = 7.4 Hz, 1H), 7.82-7.69 (m, 2H), 7.03 (d, J = 8.6 Hz, 1H), 6.31-6.04 (m, 1H), 4.80 (d, J = 5.8 Hz, 2H), 4.60-4.48 (m, 1H), 4.31 (br d, J = 11.2 Hz, 2H), 3.99-3.97 (m, 1H), 3.73-3.60 (m, 2H), 2.89-2.68 (m, 1H), 2.54 (br s, 3H), 2.37-2.33 (m, 3H), 1.21 (d, J = 6.2 Hz, 6H) ppm |
| 104 | 610.1 | 1H NMR (400 MHz, CHLOROFORM-d) δ = 9.27 (s, 1H), 8.77 (d, J = 8.4 Hz, 1H), 8.38 (d, J = 8.8 Hz, 1H), 8.26 (s, 1H), 8.13-8.09 (m, 1H), 8.03 (s, 1H), 7.96 (d, J = 7.6 Hz, 1H), 7.76 (br s, 1H), 7.68-7.64 (M, 1H), 6.52 (d, J = 8.4 Hz, 1H), 5.65-5.51 (m, 1H), 5.00 (d, J = 4.8 Hz, 2H), 4.70-4.64 (m, 1H), 4.14-4.08 (m, 1H), 3.90-3.78 (m, 2H), 3.73-3.69 (m, 1H), 3.65-3.64 (m, 1H), 3.45 (s, 3H), 3.28-3.25 (m, 1H), 3.19-3.00 (m, 1H), 2.53-2.45 (m, 2H), 1.16 (d, J = 6.8 Hz, 3H) ppm |
| 117 | 552.3 | 1H NMR (400 MHz, DMSO-d6) δ = 9.67-9.65 (m, 1H), 9.38 (S, 1H), 8.69-8.64 (m, 1H), 8.62-8.56 (m, 1H), 8.38-8.29 (m, 2H), 7.87 (d, J = 7.6 Hz, 1H), 7.83 (s, 1H), 7.72-7.68 (m, 1H), 6.53 (d, J = 8.0 Hz, 1H), 6.36-6.17 (m, 1H), 4.81 (d, J = 5.6Hz, 2H), 4.63-4.59 (m, 1H), 4.19-4.16 (m, 1H), 4.08-4.04 (m, 4H), 2.90-2.72 (m, 1H), 2.62-2.57 (m, 1H), 2.41-2.35 (m, 2H) ppm |
| 120 | 577.2 | 1H NMR (400 MHz, DMSO-d6) δ = 9.69-9.66 (m, 1H), 9.42 (s, 1H), 8.68 (d, J = 8.4 Hz, 1H), 8.37-8.28 (m, 3H), 8.07 (d, J = 8.4 Hz, 1H), 8.02-7.60 (m, 2H), 7.33 (d, J = 7.6 Hz, 1H), 6.37-6.17 (m, 1H), 4.81 (d, J = 5.6 Hz, 2H), 4.63-4.57 (m, 1H), 4.18-4.12 (m, 1H), 2.88-2.71 (m, 1H), 2.63-2.58 (m, 1H), 2.53 (s, 3H) ppm |
| 135 | 580.2 | 1H NMR (400 MHz, DMSO-d6) δ = 9.68-9.67 (m, 1H), 9.42 (s, 1H), 8.65 (d, J = 8.8 Hz, 1H), 8.45 (d, J = 7.2 Hz, 1H), 8.34-8.30 (m, 2H), 8.21 (d, J = 8.4 Hz, 1H), 7.83 (s, 1H), 7.48 (d, J = 8.0 Hz, 1H), 7.11-6.84 (m, 1H), 6.33-6.21 (m, 1H), 4.82 (d, J = 5.6 Hz, 2H), 4.63-4.58 (m, 1H), 4.18-4.12 (m, 1H), 2.85-2.74 (m, 1H), 2.61-2.56 (m, 1H) ppm |
| 136 | 595.2 | 1H NMR (400 MHz, DMSO-d6) δ = 9.58-9.55 (m, 1H), 9.27 (S, 1H), 8.72 (d, J = 8.8 Hz, 1H), 8.50 (d, J = 7.6 Hz, 1H), 8.38-8.11 (m, 3H), 7.54 (d, J = 7.6 Hz, 1H), 7.21-6.80 (m, 1H), 6.46-6.06 (m, 1H), 4.86 (br s, 2H), 4.65-4.50 (m, 1H), 4.16-4.10 (m, 1H), 4.04 (s, 3H), 2.94-2.69 (m, 1H), 2.60-2.57 (m, 1H) ppm |

TABLE 6-continued

Compounds of the Invention

| # | LCMS (ESI/M + H) | ¹HNMR |
|---|---|---|
| 143 | 577.2 | 1H NMR (400 MHz, DMSO-d6) δ = 9.69-9.66 (m, 1H), 9.45 (s, 1H), 8.80-8.73 (m, 1H), 8.72-8.65 (m, 1H), 8.41-8.27 (m, 3H), 8.15 (d, J = 7.6 Hz, 1H), 7.88 (s, 1H), 7.42-6.90 (m, 1H), 6.46-6.11 (m, 1H), 4.82 (d, J = 5.6 Hz, 2H), 4.69-4.56 (m, 1H), 4.21-4.15 (m, 1H), 4.14 (s, 3H), 2.93-2.71 (m, 1H), 2.64-2.57 (m, 1H) ppm |
| 150 | 591.2 | 1HNMR (400 MHz, DMSO-d6) δ = 9.69-9.67 (m, 1H), 9.43 (s, 1H), 8.65 (d, J = 8.4 Hz, 1H), 8.45 (d, J = 7.6 Hz, 1H), 8.42 (s, 1H), 8.38-8.28 (m, 2H), 8.22 (d, J = 8.4 Hz, 1H), 7.84 (s, 1H), 7.48 (d, J = 7.6 Hz, 1H), 6.42-6.14 (m, 1H), 4.82 (d, J = 5.6 Hz, 2H), 4.66-4.58 (m, 1H), 4.16-4.14 (m, 1H), 4.03 (s, 3H), 2.89-2.74 (m, 1H), 2.64-2.59 (m, 1H), 2.10-2.01 (m, 3H) ppm |
| 151 | 591.2 | 1H NMR (400 MHz, DMSO-d6) δ = 9.68-9.65 (m, 1H), 9.42 (s, 1H), 8.64 (d, J = 8.8 Hz, 1H), 8.46 (d, J = 7.6 Hz, 1H), 8.39-8.28 (m, 2H), 8.24 (d, J = 8.4 Hz, 1H), 7.84 (s, 1H), 7.45 (d, J = 7.6 Hz, 1H), 7.19-6.78 (m, 1H), 6.40-6.15 (m, 1H), 4.81 (s, 2H), 4.66-4.56 (m, 1H), 4.51-4.46 (m, 2H), 4.18-4.12 (m, 1H), 2.93-2.71 (m, 1H), 2.65-2.59 (m, 1H), 1.38-1.35 (m, 3H) ppm |
| 155 | 569 | 1H NMR (400 MHz, CHLOROFORM-d) δ = 9.64 (s, 1H), 9.40 (s, 1H), 8.52-8.50 (m, 1H), 8.30 (m, 2H), 8.12-8.07 (m, 2H), 7.96-7.89 (m, 1H), 7.71-7.33 (m, 1H), 5.62-5.48 (m, 1H), 5.04-5.03 (m, 2H), 4.68-4.63 (m, 1H), 4.13-4.06 (m, 1H), 3.17-2.98 (m, 1H), 2.52-2.44 (m, 1H) ppm |
| 161 | 563.10 | 1H NMR (400 MHz, DMSO-d6) δ = 9.66-9.65 (m, 1H), 9.37 (s, 1H), 8.60 (d, J = 8.8 Hz, 1H), 8.46-8.40 (m, 1H), 8.37-8.29 (m, 2H), 8.24-8.21 (d, J = 8.8 Hz, 1H), 7.88 (s, 1H), 7.75-7.73 (d, J = 7.6 Hz, 1H), 7.61-7.56 (m, 1H), 7.27-7.25 (m, 1H), 7.00 (s, 1H), 6.36-6.19 (m, 1H), 4.83-4.81 (m, 2H), 4.63-4.58 (m, 1H), 4.17 (m, 1H), 3.75 (s, 3H), 2.87-2.77 (m, 1H), 2.61-2.59 (m, 1H), 2.48 (s, 3H) ppm |
| 173 | 573.2 | 1H NMR (400 MHz, DMSO-d6) δ = 9.69-9.67 (m, 1H), 9.40 (s, 1H), 8.62 (d, J = 8.4 Hz, 1H), 8.39-8.29 (m, 3H), 8.21 (d, J = 8.8 Hz, 1H), 7.81 (s, 1H), 7.28 (d, J = 8.0 Hz, 1H), 6.33-6.21 (m, 1H), 5.79-5.65 (m, 1H), 4.81 (br d, J = 5.6 Hz, 2H), 4.63-4.58 (m, 1H), 4.18-4.12 (m, 1H), 3.99 (s, 3H), 2.85-2.72 (m, 1H), 2.61-2.56 (m, 1H), 1.70-1.62 (m, 3H) ppm |
| 177 | 577.2 | 1H NMR (400 MHz, DMSO-d6) δ = 9.68-9.65 (m, 1H), 9.41 (s, 1H), 8.65 (d, J = 8.8 Hz, 1H), 8.45 (d, J = 7.6 Hz, 1H), 8.34-8.29 (m, 2H), 8.21 (d, J = 8.4 Hz, 1H), 7.83 (s, 1H), 7.48 (d, J = 7.6 Hz, 1H), 7.11-6.84 (m, 1H), 6.32-6.20 (m, 1H), 4.81 (d, J = 5.6 Hz, 2H), 4.62-4.58 (m, 1H), 4.18-4.12 (m, 1H), 4.01 (s, 3H), 2.85-2.74 (m, 1H), 2.61-2.56 (m, 1H) ppm |
| 181 | 567.2 | 1H NMR (400 MHz, DMSO-d6) δ = 9.68-9.65 (m, 1H), 9.35 (S, 1H), 8.65-8.59 (m, 1H), 8.57-8.50 (m, 1H), 8.39-8.29 (m, 1H), 7.81 (s, 1H), 7.51 (d, J = 8.8 Hz, 1H), 6.44-6.10 (m, 1H), 4.89-4.73 (m, 2H), 4.70-4.53 (m, 1H), 4.25-4.10 (m, 1H), 3.94 (s, 3H), 2.92-2.71 (m, 1H), 2.63-2.56 (m, 1H), 2.54 (s, 1H), 1.13-1.11 (m, 2H), 1.06-0.98 (m, 2H) ppm |
| 186 | 608.3 | 1H NMR (400 MHz, DMSO-d6) δ = 9.73-9.61 (m, 1H), 9.38 (s, 1H), 8.73-8.65 (m, 1H), 8.56 (d, J = 8.8 Hz, 1H), 8.44-8.38 (m, 1H), 8.37-8.29 (m, 2H), 7.87-7.83 (m, 1H), 7.79-7.73 (m, 1H), 7.65-7.11 (m, 1H), 4.81 (br d, J = 5.6 Hz, 2H), 2.62 (br d, J = 1.6 Hz, 1H), 1.22-1.16 (m, 2H), 1.14-1.07 (m, 2H) ppm |
| 188 | 567.2 | 1H NMR (400 MHz, DMSO-d6) δ = 9.68-9.65 (m, 1H), 9.46 (s, 1H), 8.75 (d, J = 8.4 Hz, 1H), 8.65 (d, J = 8.8 Hz, 1H), 8.56 (d, J = 5.2 Hz, 1H), 8.43 (s, 1H), 8.36-8.28 (m, 2H), 7.89 (s, 1H), 7.65 (d, J = 5.2 Hz, 1H), 6.40-6.15 (m, 1H), 4.82 (d, J = 6.0 Hz, 2H), 4.63-4.58 (m, 1H), 4.19-4.13 (m, 1H), 3.67-3.55 (m, 4H), 2.92-2.70 (m, 1H), 2.61 (s, 1H), 2.01-1.96 (m, 4H) ppm |
| 191 | 549.00 | 1H NMR (400 MHz, DMSO-d6) δ = 9.64-9.61 (m, 1H), 9.37 (s, 1H), 8.61 (d, J = 8.2 Hz, 1H), 8.36 (d, J = 2.0 Hz, 1H), 8.32-8.29 (m, 1H), 8.27-8.22 (m, 1H), 8.17 (s, 1H), 7.89 (s, 1H), 7.80 (d, J = 6.8 Hz, 1H), 7.65 (d, J = 8.2 Hz, 1H), 7.49 (d, J = 3.2 Hz, 1H), 7.36-7.32 (m, 1H), 7.24-7.15 (m, 1H), 6.37-6.19 (m, 1H), 4.82 (d, J = 5.8 Hz, 2H), 4.62-4.57 (m, 1H), 4.19-4.14 (m, 1H), 3.87 (s, 3H), 2.90-2.72 (m, 1H), 2.64-2.55 (m, 1H) ppm |
| 202 | 591.3 | 1H NMR (400 MHz, DMSO-d6) δ = 9.69-9.67 (m, 1H), 9.40 (s, 1H), 8.62 (d, J = 8.4 Hz, 1H), 8.45 (s, 1H), 8.40 (d, J = 7.6 Hz, 1H), 8.36-8.29 (m, 2H), 8.20 (d, J = 8.8 Hz, 1H), 7.82 (s, 1H), 7.33 (d, J = 7.6 Hz, 1H), 6.36-6.18 (m, 1H), 6.07-5.80 (m, 1H), 5.09-4.87 (m, 2H), 4.81 (d, J = 5.6 Hz, 2H), 4.60-4.58 (tm, 1H), 4.18-4.15 (m, 1H), 4.00 (s, 3H), 2.83-2.72 (m, 1H), 2.61-2.58 (m, 1H) ppm |
| 206 | 559.2 | 1H NMR (400 MHz, DMSO-d6) δ = 9.65-9.62 (m, 1H), 9.45 (s, 1H), 8.76 (d, J = 8.0 Hz, 1H), 8.66 (d, J = 8.8 Hz, 1H), 8.47-8.46 (m, 2H), 8.28-7.85 (m, 4H), 7.27 (d, J = 7.6 Hz, 1H), 6.35-5.93 (m, 1H), 5.21 (d, J = 14.5 Hz, 1H), 4.99 (d, J = 14.8 Hz, 1H), 4.83 (br d, J = 4.8 Hz, 2H), 4.56-4.24 (m, 2H), 2.52 (br s, 3H) ppm |

TABLE 6-continued

Compounds of the Invention

| # | LCMS (ESI/M + H) | ¹HNMR |
|---|---|---|
| 211 | 596.3 | 1H NMR (400 MHz, METHANOL-d4) δ = 9.27 (br d, J = 5.2 Hz, 1H), 8.72 (d, J = 8.8 Hz, 1H), 8.57 (d, J = 8.8 Hz, 1H), 8.41 (s, 1H), 8.19-8.14 (m, 1H), 8.00-7.89 (m, 2H), 7.78-7.69 (m, 1H), 7.17 (s, 1H), 5.96-5.81 (m, 1H), 4.91 (s, 2H), 4.66-4.62 (m, 1H), 4.21-4.13 (m, 1H), 3.46 (s, 3H), 3.43-3.38 (m, 1H), 3.25 (s, 3H), 3.06-2.86 (m, 1H), 2.73-2.68 (m, 1H), 2.63-2.55 (m, 1H), 1.26-1.20 (m, 1H), 1.00-0.91 (m, 1H) ppm |
| 215 | 596.3 | 1H NMR (400 MHz, DMSO-d6) δ = 9.70-9.63 (m, 1H), 9.44-9.38 (m, 1H), 8.67 (s, 2H), 8.41-8.26 (m, 2H), 7.95-7.90 (m, 1H), 7.88-7.84 (m, 1H), 7.78 (d, J = 8.0 Hz, 1H), 7.09 (d, J = 8.4 Hz, 1H), 6.40-6.10 (m, 1H), 4.86-4.76 (m, 2H), 4.68-4.55 (m, 1H), 4.23-4.10 (m, 1H), 3.37 (s, 3H), 3.30 (br d, J = 2.0 Hz, 1H), 3.22-3.18 (m, 3H), 2.91-2.74 (m, 1H), 2.74-2.70 (m, 1H), 2.60 (br d, J = 6.8 Hz, 1H), 1.27-1.19 (m, 1H), 0.98-0.80 (m, 1H) ppm |
| 220 | 567.2 | 1H NMR (400 MHz, DMSO-d6) δ = 9.71-9.68-9.65 (m, 1H), 9.41 (s, 1H), 8.87 (s, 1H), 8.71 (d, J = 8.4 Hz, 1H), 8.57 (d, J = 8.8 Hz, 1H), 8.39-8.27 (m, 2H), 8.11 (s, 1H), 7.87 (s, 1H), 6.35-6.21 (m, 1H), 4.82 (d, J = 5.2 Hz, 2H), 4.64-4.58 (m, 1H), 4.19-4.13 (m, 1H), 3.58 (br s, 4H), 2.90-2.72 (m, 1H), 2.63-2.56 (m, 1H), 2.05-1.95 (m, 4H) ppm |
| 226 | 535.9 | 1H NMR (400 MHz, DMSO-d6) δ = 9.69-9.63 (m, 2H), 9.37 (s, 1H), 8.65 (d, J = 8.8 Hz, 1H), 8.36 (d, J = 2.0 Hz, 1H), 8.32-8.29 (m, 1H), 8.24 (d, J = 8.8 Hz, 1H), 7.78 (s, 1H), 6.35-6.21 (m, 1H), 4.80 (d, J = 5.6 Hz, 2H), 4.64-4.59 (m, 1H), 4.19-4.14 (m, 1H), 2.88-2.81 (m, 1H), 2.64-2.61 (m, 2H) ppm |
| 227 | 591.2 | 1H NMR (400 MHz, DMSO-d6) δ = 9.70-9.68 (m, 1H), 9.43 (s, 1H), 8.78-8.71 (m, 1H), 8.71-8.64 (m, 1H), 8.37-8.28 (m, 3H), 7.99 (d, J = 7.6 Hz, 1H), 7.87 (s, 1H), 6.40-6.18 (m, 1H), 6.17-5.89 (m, 1H), 4.95-4.70 (m, 4H), 4.64-4.58 (m, 1H), 4.20-4.13 (m, 1H), 4.12 (s, 3H), 2.94-2.70 (m, 1H), 2.65-2.58 (m, 1H) ppm |
| 230 | 537.2 | 1H NMR (400 MHz, DMSO-d6) δ = 9.66-9.64 (m, 1H), 9.35 (s, 1H), 9.15 (s, 1H), 8.70-8.65 (m, 2H), 8.35-8.31 (m, 3H), 8.25-8.23 (m, 1H), 7.86 (s, 1H), 6.35-6.22 (m, 1H), 4.78 (d, J = 5.6 Hz, 2H), 4.64-4.59 (m, 1H), 4.17-4.12 (m, 1H), 2.76-2.71 (m, 1H), 2.62-2.57 (m, 1H), 2.33-2.29 (m, 1H), 1.13-1.10 (m, 4H) ppm |
| 245 | 541.2 | 1H NMR (400 MHz, DMSO-d6) δ = 9.68-9.66 (m, 1H), 9.37 (s, 1H), 8.57 (d, J = 8.4 Hz, 1H), 8.50-8.44 (m, 1H), 8.36-8.29 (m, 2H), 8.24 (d, J = 7.6 Hz, 1H), 8.19 (d, J = 8.6 Hz, 1H), 7.80 (S, 1H), 7.05 (d, J = 7.6 Hz, 1H), 6.37-6.19 (m, 1H), 4.80 (d, J = 6.0 Hz, 2H), 4.63-4.58 (m, 1H), 4.18-4.12 (m, 1H), 3.97 (s, 3H), 2.88-2.74 (m, 1H), 2.64-2.59 (m, 1H), 2.58 (s, 3H) ppm |
| 249 | 573.0 | 1HNMR (400 MHz, DMSO-d6) δ = 9.64-9.61 (m, 1H), 9.42 (s, 1H), 8.65 (d, J = 8.8 Hz, 1H), 8.51 (d, J = 2.4 Hz, 1H), 8.46-8.44 (m, 1H), 8.38-8.33 (m, 1H), 8.21 (d, J = 8.4 Hz, 1H), 7.81 (s, 1H), 7.48-7.45 (m, 2H), 6.34-6.09 (m, 1H), 4.81 (d, J = 5.6 Hz, 2H), 4.62-4.43 (m, 1H), 4.11-3.96 (m, 4H), 2.89-2.71 (m, 1H), 2.59-2.54 (m, 1H), 2.11-2.01 (m, 3H) ppm |
| 250 | 573.2 | 1H NMR (400 MHz, DMSO-d6) δ = 9.69-9.67 (m, 1H), 9.43 (s, 1H), 8.75-8.65 (m, 2H), 8.50 (d, J = 8.0 Hz, 1H), 8.36-8.30 (m, 2H), 8.02-7.98 (m, 1H), 7.87 (s, 1H), 7.64 (d, J = 7.6 Hz, 1H), 6.38-6.19 (m, 1H), 4.82 (d, J = 6.0 Hz, 2H), 4.61 (br d, J = 12.8 Hz, 1H), 4.19-4.13 (m, 1H), 3.39 (br s, 1H), 2.87 (br s, 1H), 2.63-2.56 (m, 2H), 2.14-2.07 (m, 1H) ppm |
| 252 | 537.2 | 1H NMR (400 MHz, DMSO-d6) δ = 9.68-9.65 (m, 1H), 9.41 (s, 1H), 8.70-8.59 (m, 2H), 8.37-8.29 (m, 3H), 7.89-7.80 (m, 2H), 7.47 (d, J = 7.6 Hz, 1H), 6.37-6.18 (m, 1H), 4.81 (d, J = 5.6 Hz, 2H), 4.63-4.58 (m, 1H), 4.19-4.13 (m, 1H), 2.90-2.72 (m, 1H), 2.63-2.56 (m, 1H), 2.27-2.20 (m, 1H), 1.13-1.08 (m, 2H), 1.07-1.02 (m, 2H) ppm. |
| 255 | 672.3 | 1H NMR (400 MHz, DMSO-d6) δ = 9.67 (t, J = 5.6 Hz, 1H), 9.43 (s, 1H), 8.67-8.63 (m, 3H), 8.48 (d, J = 2.0 Hz, 1H), 7.93-7.88 (m, 2H), 7.76 (t, J = 8.4 Hz, 1H), 7.04 (d, J = 8.4 Hz, 1H), 6.31-6.18 (m, 1H), 4.82-4.81 (m, 2H), 4.61-4.57 ( m, 1H), 4.33-4.30 (m, 4H), 4.0 9-4.03 (m, 1H), 3.70-3.65 (m, 2H), 2.91-2.75 (m, 1H), 2.60-2.59 (m, 1H), 2.42-2.38 (m, 2H), 1.21 (d, J = 6.0 Hz, 6H) ppm |
| 256 | 564.1 | 1H NMR (400 MHz, DMSO-d6) δ = 9.67-9.64 (m, 1H), 9.45 (s, 1H), 8.73 (d, J = 8.8 Hz, 1H), 8.44 (d, J = 5.2 Hz, 1H), 8.37-8.29 (m, 3H), 7.94 (s, 1H), 7.81-7.77 (m, 2H), 7.20 (d, J = 3.6 Hz, 1H), 6.33-6.21 (m, 1H), 4.87-4.83 (m, 2H), 4.63-4.58 (m, 1H), 4.43-4.35 (m, 2H), 4.19-4.13 (m, 1H), 2.89-2.72 (m, 1H), 2.61-2.59 (m, 1H), 1.43-1.40 (m, 3H) ppm |
| 257 | 570.2 | 1H NMR (400 MHz, DMSO-d6) δ = 9.68-9.65 (m, 1H), 9.35 (s, 1H), 8.63-8.52 (m, 2H), 8.38-8.30 (m, 3H), 7.81 (s, 1H), 7.50 (d, J = 8.4 Hz, 1H), 6.37-6.19 (m, 1H), 4.80 (br d, J = 5.6 Hz, 2H), 4.63-4.58 (m, 1H), 4.19-4.13 (m, 1H), 2.91-2.70 (m, 1H), 2.64-2.52 (m, 2H), 1.15-1.09 (m, 2H), 1.05-0.99 (m, 2H) ppm |

TABLE 6-continued

Compounds of the Invention

| # | LCMS (ESI/M + H) | ¹HNMR |
|---|---|---|
| 259 | 573.2 | 1H NMR (400 MHz, DMSO-d6) δ = 9.70-9.67 (m, 1H), 9.40 (s, 1H), 8.63 (d, J = 8.8 Hz, 1H), 8.40-8.31 (m, 3H) 8.22 (d, J = 8.8 Hz, 1H), 7.82 (s, 1H), 7.29 (d, J = 7.6 Hz, 1H), 6.34-6.22 (m, 1H), 5.79-5.66 (m, 1H), 4.82 (br d, J = 5.6 Hz, 2H), 4.63-4.59 (m, 1H), 4.19-4.16 (m, 1H), 4.00 (s, 3H), 2.86-2.72 (m, 1H), 2.63-2.60 (m, 1H), 1.71-1.63 (m, 3H) ppm |
| 266 | 544.2 | 1H NMR (400 MHz, DMSO-d6) δ = 9.68-9.65 (m, 1H), 9.37 (s, 1H), 8.54 (d, J = 8.8 Hz, 1H), 8.43 (br d, J = 2.0 Hz, 1H), 8.38-8.26 (m, 2H), 8.05 (d, J = 8.4 Hz, 1H), 7.88-7.84 (m, 1H), 7.79 (s, 1H), 7.15-7.12 (m, 1H), 6.94-6.93 (m, 1H), 6.37-6.14 (m, 1H), 4.80 (d, J = 5.6 Hz, 2H), 4.67-4.55 (m, 1H), 4.19-4.13 (m, 1H), 3.89 (s, 3H), 2.92-2.71 (m, 1H), 2.62-2.59 (m, 1H) ppm |
| 267 | 564.2 | 1H NMR (400 MHz, DMSO-d6) δ = 9.67-9.64 (m, 1H), 9.43 (S, 1H), 8.71 (d, J = 8.8 Hz, 1H), 8.35-8.29 (m, 4H), 7.94 (s, 1H), 7.76 (d, J = 4.8 Hz, 1H), 7.00 (s, 1H), 6.33-6.20 (m, 1H), 4.83 (br d, J = 5.6 Hz, 2H), 4.60 (br d, J = 13.2 Hz, 1H), 4.18 (br d, J = 12.0 Hz, 1H), 3.80 (s, 3H), 2.85 (br d, J = 2.0 Hz, 1H), 2.77-2.71 (m, 1H), 2.52 (br s, 3H) ppm |
| 273 | 603.3 | 1H NMR (400 MHz, DMSO-d6) δ = 9.67-9.64 (m, 1H), 9.38 (s, 1H), 8.67-8.60 (m, 2H), 8.54 (d, J = 8.8 Hz, 1H), 8.38-8.28 (m, 2H), 7.83 (s, 1H), 7.66 (d, J = 8.8 Hz, 1H), 6.37-6.19 (m, 1H), 4.81 (d, J = 5.2 Hz, 2H), 4.63-4.59 (m, 1H), 4.24-4.12 (m, 1H), 3.98 (s, 3H), 3.35 (d, J = 3.2 Hz, 1H), 2.90-2.71 (m, 1H), 2.62-2.60 (m, 1H), 2.38-2.36 (m, 1H), 2.11-2.05 (m, 1H) ppm |
| 275 | 581.3 | 1H NMR (400 MHz, DMSO-d6) δ = 9.69-9.68 (m, 1H), 9.41 (s, 1H), 8.70-8.59 (m, 2H), 8.37-8.31 (m, 3H), 7.91-7.89 (m, 1H), 7.85 (s, 1H), 7.59 (d, J = 8.0 Hz, 1H), 6.34-6.22 (m, 1H), 4.82 (br d, J = 5.6 Hz, 2H), 4.63-4.58 (m, 1H), 4.19-4.13 (m, 1H), 3.76 (s, 2H), 3.33 (s, 3H), 2.76-2.57 (m, 1H), 1.38-1.35 (m, 2H), 1.05-1.01 (m, 2H) ppm |
| 283 | 551.2 | 1H NMR (400 MHz, DMSO-d6) δ = 9.70-9.60 (m, 1H), 9.41-9.32 (m, 1H), 9.28-9.21 (m, 1H), 8.81-8.74 (m, 1H), 8.61-8.55 (m, 1H), 8.47-8.42 (m, 1H), 8.41-8.38 (m, 1H), 8.37-8.25 (m, 3H), 7.90-7.86 (m, 1H), 6.39-6.18 (m, 1H), 4.83-4.73 (m, 2H), 4.66-4.56 (m, 1H), 4.21-4.07 (m, 1H), 3.90-3.77 (m, 1H), 2.92-2.69 (m, 1H), 2.63-2.56 (m, 1H), 2.43 (br d, J = 2.4 Hz, 2H), 2.38-2.33 (m, 2H), 2.15-2.03 (m, 1H), 2.02-1.88 (m, 1H) ppm. |
| 287 | 609 | 1H NMR (400 MHz, CHLOROFORM-d) δ = 9.38-9.26 (m, 1H), 8.51 (d, J = 7.6 Hz, 1H), 8.38 (br d, J = 7.8 Hz, 1H), 8.26 (br s, 2H), 8.11 (br d, J = 9.0 Hz, 1H), 8.05 (s, 1H), 7.82-7.74 (m, 1H), 7.35 (d, J = 7.4 Hz, 1H), 6.46-6.13 (m, 1H), 5.66-5.47 (m, 1H), 5.01 (br d, J = 4.0 Hz, 2H), 4.71-4.64 (m, 1H), 4.16-4.10 (m, 1H), 4.08 (s, 3H), 3.20-3.00 (m, 1H), 2.54-2.45 (m, 1H) ppm |
| 288 | 533.1 | 1H NMR (400 MHz, CHLOROFORM-d) δ = 9.65-9.43 (m, 1H), 9.25 (br s, 1H), 8.48 (s, 1H), 8.45-8.22 (m, 2H), 8.10 (br d, J = 9.6 Hz, 1H), 7.95 (br s, 1H), 7.90-7.63 (m, 1H), 5.66-5.50 (m, 1H), 4.98 (br s, 2H), 4.73-4.61 (m, 1H), 4.23 (s, 3H), 4.10 (br t, J = 12.4 Hz, 1H), 3.18-2.99 (m, 1H), 2.52-2.45 (m, 1H) ppm |
| 291 | 536.2 | 1H NMR (400 MHz, DMSO-d6) δ = 9.63-9.61 (m, 1H), 9.32 (s, 1H), 8.61 (s, 1H), 8.39-8.28 (m, 3H), 8.20 (d, J = 8.8 Hz, 1H), 7.90 (d, J = 7.6 Hz, 1H), 7.85 (s, 1H), 7.79-7.70 (m, 1H), 7.33 (d, J = 7.6 Hz, 1H), 6.40-6.20 (m, 1H), 4.76 (d, J = 6.0 Hz, 2H), 4.64-4.59 (m, 1H), 4.17-4.11 (m, 1H), 2.96-2.70 (m, 1H), 2.64-2.57 (m, 1H), 2.23-2.16 (m, 1H), 1.12-0.98 (m, 4H) ppm |
| 292 | 591 | 1H NMR (400 MHz, METHANOL-d4) δ = 9.42 (s, 1H), 8.61 (d, J = 8.8 Hz, 1H), 8.39 (s, 1H), 8.32-8.29 (m, 2H), 8.16-8.14 (m, 1H), 8.07 (s, 1H), 8.03 (s, 1H), 7.13 (d, J = 7.6 Hz, 1H), 6.55-6.20 (m, 1H), 5.94-5.81 (m, 1H), 4.93 (s, 2H), 4.65-4.61 (m, 1H), 4.18-4.12 (m, 1H), 4.07 (s, 3H), 3.40-3.35 (m, 2H), 3.07-2.86 (m, 1H), 2.63-2.51 (m, 1H) ppm |
| 298 | 609.1 | 1H NMR (400 MHz, CHLOROFORM-d) δ = 9.31 (s, 1H), 8.50 (d, J = 7.6 Hz, 1H), 8.37 (d, J = 8.4 Hz, 1H), 8.29-8.22 (m, 2H), 8.11 (br d, J = 9.6 Hz, 1H), 8.02 (br s, 1H), 7.79-7.65 (m, 1H), 7.34 (d, J = 7.8 Hz, 1H), 6.31-6.28 (m, 1H), 5.67-5.46 (m, 1H), 5.00 (br d, J = 5.2 Hz, 2H), 4.69-4.65 (m, 1H), 4.15-4.08 (m, 1H), 4.07 (s, 3H), 3.20-3.00 (m, 1H), 2.55-2.43 (m, 1H) ppm |
| 306 | 593.2 | 1H NMR (400 MHz, DMSO-d6) δ = 9.70-9.67 (m, 1H), 9.42 (S, 1H), 8.66 (d, J = 8.8 Hz, 1H), 8.53 (d, J = 2.0 Hz, 1H), 8.45-8.43 (m, 2H), 8.21 (d, J = 8.4 Hz, 1H), 7.84 (s, 1H), 7.48 (d, J = 7.6 Hz, 1H), 7.12-6.84 (m, 1H), 6.31-6.18 (m, 1H), 4.81 (d, J = 5.6 Hz, 2H), 4.63-4.58 (m, 1H), 4.12-4.06 (m, 1H), 4.01 (s, 3H), 2.86-2.77 (m, 1H), 2.60-2.55 (m, 1H) ppm |
| 308 | 589.2 | 1H NMR (400 MHz, DMSO-d6) δ = 9.69-9.67 (m, 1H), 9.39 (s, 1H), 8.61 (d, J = 8.6 Hz, 1H), 8.53 (d, J = 1.8 Hz, 1H), 8.44 (d, J = 2.0 Hz, 1H), 8.38 (d, J = 7.6 Hz, 1H), 8.20 (d, J = 8.6 Hz, 1H), 7.83 (s, 1H), 7.27 (d, J = 7.6 Hz, 1H), 6.37-6.13 (m, 1H), 5.88-5.57 (m, 1H), 4.80 (br d, J = 5.6 Hz, 2H), 4.68-4.53 (m, 1H), 4.12-4.10 (m, 1H), 3.99 (s, 3H), 2.95-2.70 |

TABLE 6-continued

Compounds of the Invention

| # | LCMS (ESI/M + H) | ¹HNMR |
|---|---|---|
| 310 | 633.1 | (m, 1H), 2.59 (br d, J = 5.6 Hz, 1H), 1.75-1.55 (m, 3H) ppm<br>1H NMR (400 MHz, DMSO-d6) δ = 9.69-9.67 (m, 1H), 9.38 (s, 1H), 8.70-8.59 (m, 2H), 8.58-8.49 (m, 2H), 8.46 (d, J = 2.0 Hz, 1H), 7.84 (s, 1H), 7.64 (d, J = 8.8 Hz, 1H), 6.37-6.10 (m, 1H), 4.81 (d, J = 5.4 Hz, 2H), 4.66-4.57 (m, 1H), 4.34-4.19 (m, 2H), 4.16-4.03 (m, 1H), 3.40-3.35 (m, 1H), 2.92-2.74 (m, 1H), 2.64-2.58 (m, 2H), 2.13-2.02 (m, 1H), 1.44-1.40 (m, 3H) ppm |
| 311 | 593.3 | 1H NMR (400 MHz, DMSO-d6) δ = 9.66-9.63 (m, 1H), 9.37 (s, 1H), 8.62 (d, J = 8.2 Hz, 1H), 8.37-8.34 (m, 1H), 8.33-8.30 (m, 1H), 8.28 (s, 1H), 8.24 (d, J = 8.6 Hz, 1H), 7.87 (s, 1H), 7.77 (d, J = 7.0 Hz, 1H), 7.71 (d, J = 8.2 Hz, 1H), 7.52 (d, J = 3.2 Hz, 1H), 7.33-7.31 (m, 1H), 7.19 (d, J = 2.6 Hz, 1H), 6.36-6.17 (m, 1H), 4.82 (d, J = 5.6 Hz, 2H), 4.64-4.55 (m, 1H), 4.43-4.40 (m, 2H), 4.19-4.16 (m, 1H), 3.69-3.67 (m, H), 3.22 (s, 3H), 2.89-2.72 (m, 1H), 2.62-2.57 (m, 1H) ppm |
| 312 | 633.3 | 1H NMR (400 MHz, DMSO-d6) δ = 9.69-9.66 (m, 1H), 9.38 (S, 1H), 8.63-8.60 (m, 2H), 8.54-8.51 (m, 2H), 8.46 (d, J = 2.0 Hz, 1H), 7.84 (s, 1H), 7.65-7.63 (m, 1H), 6.33-6.20 (m, 1H), 4.81 (br d, J = 5.6 Hz, 2H), 4.63-4.60 (m, 1H), 4.27-4.23 (m, 2H), 4.14-4.11 (m, 1H), 3.40-3.36 (m, 1H), 2.88-2.78 (m, 1H), 2.62-2.60 (m, 2H), 2.10-2.06 (m, 1H), 1.44-1.41 (m, 3H) ppm |
| 313 | 617 | 1H NMR (400 MHz, DMSO-d6) δ = 9.66-9.63 (m, 1H), 9.37 (s, 1H), 8.65-8.60 (m, 2H), 8.51 (d, J = 8.8 Hz, 1H), 8.35-8.30 (m, 2H), 7.82 (s, 1H), 7.64 (d, J = 8.8 Hz, 1H), 6.33-6.21 (m, 1H), 4.80 (d, J = 5.6 Hz, 2H), 4.63-4.58 (m, 1H), 4.29-4.20 (m, 2H), 4.19-4.13 (m, 1H), 3.37-3.34 (m, 1H), 2.82-2.73 (m, 1H), 2.62-2.61 (m, 2H), 2.08-2.04 (m, 1H), 1.43-1.40 (m, 3H) ppm |
| 314 | 616.3 | 1H NMR (400 MHz, DMSO-d6) δ = 9.66-9.65 (m, 1H), 9.40 (s, 1H), 8.68-8.61 (m, 2H), 8.53-8.46 (m, 2H), 7.92 (d, J = 7.2 Hz, 1H), 7.84 (s, 1H), 7.79-7.68 (m, 1H), 7.03 (d, J = 8.4 Hz, 1H), 6.34-6.13 (m, 1H), 4.80 (d, J = 4.8 Hz, 2H), 4.67 (s, 1H), 4.63-4.54 (m, 1H), 4.31 (d, J = 12.4 Hz, 2H), 4.09-4.08 (m, 1H), 3.75-3.63 (m, 2H), 2.89-2.79 (m, 1H), 2.64-2.57 (m, 3H), 1.21 (br d, J = 6.4 Hz, 6H) ppm |
| 315 | 616.3 | 1H NMR (400 MHz, DMSO-d6) δ = 9.69-9.59 (m, 1H), 9.40 (s, 1H), 8.66-8.61 (m, 2H), 8.52-8.45 (m, 2H), 7.92 (d, J = 7.2 Hz, 1H), 7.84 (s, 1H), 7.79-7.71 (m, 1H), 7.03 (d, J = 8.4 Hz, 1H), 6.36-6.11 (m, 1H), 4.80 (d, J = 4.8 Hz, 2H), 4.67 (s, 1H), 4.64-4.53 (m, 1H), 4.33-4.30 (m, 2H), 4.14-4.03 (m, 1H), 3.70-3.65 (m, 2H), 2.92-2.71 (m, 1H), 2.57 (s, 1H), 2.55-2.52 (m, 2H), 1.21 (d, J = 6.0 Hz, 6H) ppm |
| 316 | 658.2 | 1H NMR (400 MHz, DMSO-d6) δ = 9.74-9.71 (m, 1H), 9.40 (s, 1H), 8.68-8.62 (m, 2H), 8.42 (d, J = 2.0 Hz, 1H), 8.26 (s, 1H), 7.91 (d, J = 7.2 Hz, 1H), 7.83 (s, 1H), 7.77-7.75 (m, 1H), 7.52-7.13 (m, 1H), 7.03 (br d, J = 8.4 Hz, 1H), 6.36-6.17 (m, 1H), 4.81 (br d, J = 4.8 Hz, 2H), 4.58 (br d, J = 12.4 Hz, 1H), 4.32 (br d, J = 12.4 Hz, 2H), 4.18-4.03 (m, 1H), 3.74-3.59 (m, 2H), 2.90-2.80 (m, 1H), 2.63-2.59 (m, 3H), 1.21 (br d, J = 6.4 Hz, 6H) ppm |
| 322 | 543.2 | 1H NMR (400 MHz, DMSO-d6) δ = 9.69 (br t, J = 5.7 Hz, 1H), 9.41 (s, 1H), 8.77-8.63 (m, 2H), 8.54 (d, J = 2.0 Hz, 1H), 8.46 (d, J = 2.0 Hz, 1H), 8.21 (d, J = 7.5 Hz, 1H), 7.98-7.79 (m, 2H), 7.00 (d, J = 8.2 Hz, 1H), 6.37-6.16 (m, 1H), 4.82 (br d, J = 5.6 Hz, 2H), 4.68-4.55 (m, 1H), 4.16-4.07 (m, 1H), 4.03 (s, 3H), 2.97-2.80 (m, 1H), 2.76-2.64 (m, 1H) ppm |
| 324 | 599.2 | 1H NMR (400 MHz, DMSO-d6) δ = 9.52 (s, 1H), 9.38 (s, 1H), 8.67-8.52 (m, 1H), 8.54-8.52(m, 1H), 8.39-8.37(m, 1H), 8.32-8.31(m, 1H), 8.27-8.26(m, 1H), 7.79 (s, 1H), 7.74-7.72(m, 1H), 7.57-7.20 (m, 1H), 6.20-6.08 (m, 1H), 4.78-4.71 ( m,2H), 4.58-4.49 (m, 1H), 4.02-3.91 (m, 1H), 2.84-2.70 (m, 1H), 2.56 (br s, 1H), 2.42-2.39 (m, 1H), 2.32 (s, 3H), 1.17-1.15(m, 2H), 1.10-1.06 (m, 2H) ppm |

Preparation of Intermediate 5 (2S,4S)—N-((2-(6-((2S,6R)-2,6-dimethylmorpholino)pyridin-2-yl)-1,6-naphthyridin-7-yl)methyl)-4,9-difluoro-2-methyl-3,4-dihydro-2H-benzo[b][1,4]oxathiepine-7-carboxamide 5,5-dioxide Step 1

HSO₃Cl
0~80° C., 5 hrs

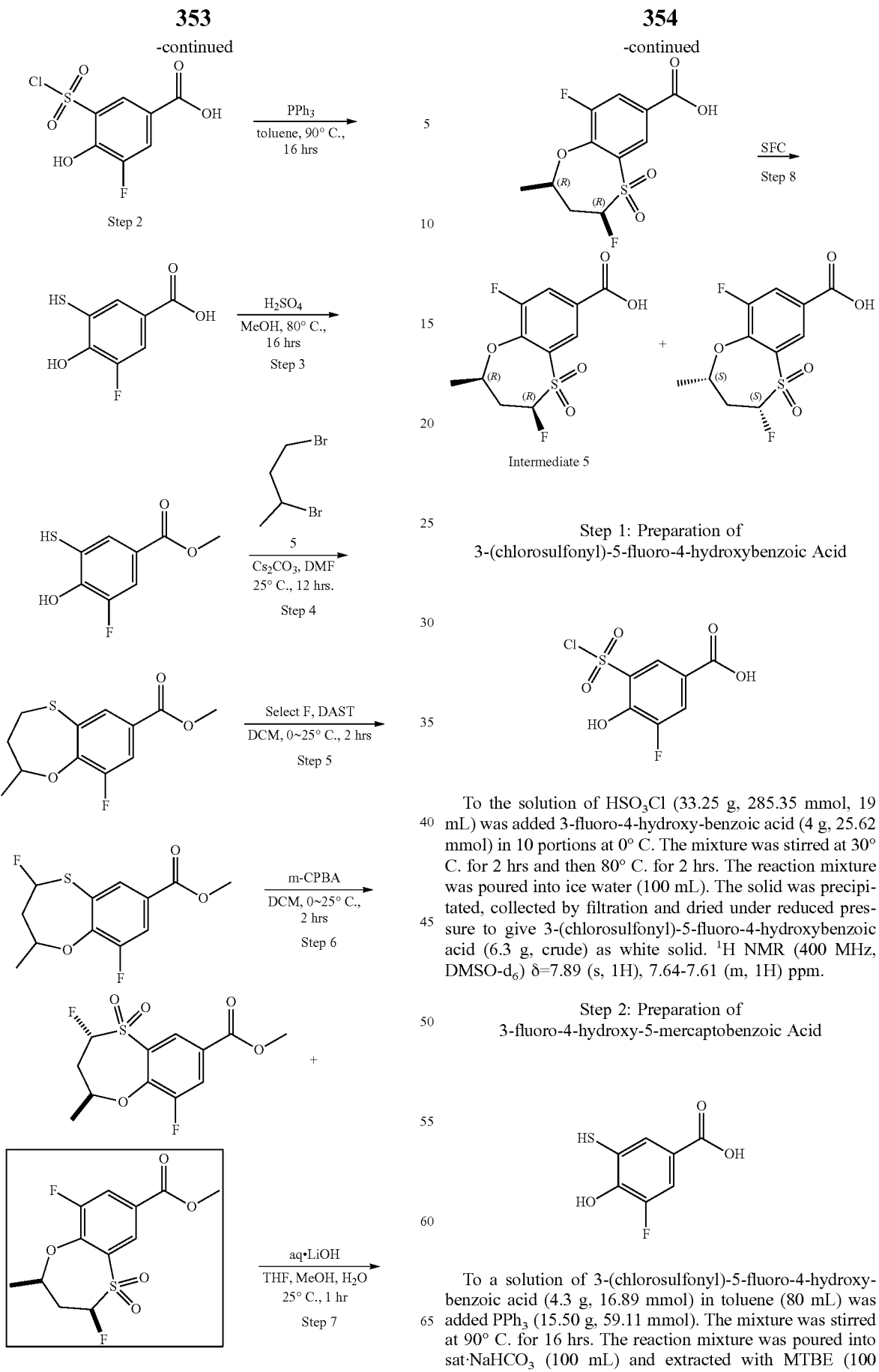

Step 1: Preparation of 3-(chlorosulfonyl)-5-fluoro-4-hydroxybenzoic Acid

To the solution of HSO₃Cl (33.25 g, 285.35 mmol, 19 mL) was added 3-fluoro-4-hydroxy-benzoic acid (4 g, 25.62 mmol) in 10 portions at 0° C. The mixture was stirred at 30° C. for 2 hrs and then 80° C. for 2 hrs. The reaction mixture was poured into ice water (100 mL). The solid was precipitated, collected by filtration and dried under reduced pressure to give 3-(chlorosulfonyl)-5-fluoro-4-hydroxybenzoic acid (6.3 g, crude) as white solid. $^1$H NMR (400 MHz, DMSO-$d_6$) δ=7.89 (s, 1H), 7.64-7.61 (m, 1H) ppm.

Step 2: Preparation of 3-fluoro-4-hydroxy-5-mercaptobenzoic Acid

To a solution of 3-(chlorosulfonyl)-5-fluoro-4-hydroxy-benzoic acid (4.3 g, 16.89 mmol) in toluene (80 mL) was added PPh₃ (15.50 g, 59.11 mmol). The mixture was stirred at 90° C. for 16 hrs. The reaction mixture was poured into sat·NaHCO₃ (100 mL) and extracted with MTBE (100 mL*3). The MTBE layer was discarded. The aqueous layer was adjusted to pH=3 by 12N aq·HCl and extracted with EA (100 mL*3). The organic layers were dried over Na$_2$SO$_4$, filtered and concentrated under reduced pressure to give 3-fluoro-4-hydroxy-5-mercaptobenzoic acid (3 g, crude) as white solid. $^1$H NMR (400 MHz, METHANOL-d$_4$) δ=7.71-7.69 (m, 1H), 7.48-7.45 (m, 1H) ppm.

Step 3: Preparation of methyl 3-fluoro-4-hydroxy-5-mercaptobenzoate

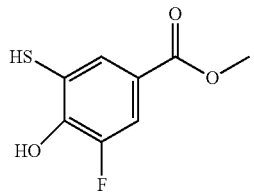

To a solution of 3-(chlorosulfonyl)-5-fluoro-4-hydroxy-benzoic acid (3 g, 15.94 mmol) in MeOH (30 mL) was added H$_2$SO$_4$ (5.52 g, 56.28 mmol, 3 mL). The mixture was stirred at 80° C. for 16 hrs. The reaction mixture was concentrated under reduced pressure to remove MeOH and diluted with H$_2$O (100 mL). The aqueous layer was adjusted to pH=3 with sat. NaHCO$_3$ and extracted with EA (500 mL*2). The combined organic layers were dried over anhydrous Na$_2$SO$_4$, filtered and concentrated in vacuum. The residue was purified by normal phase flash (column SiO$_2$, 20 g, PE/EA=1/0-9/1, Rf=0.5). The eluent was concentrated to give 3-fluoro-4-hydroxy-5-mercaptobenzoate (2.4 g, 11.87 mmol, 74.45% yield) as white solid. $^1$H NMR (400 MHz, DMSO-d$_6$) δ=7.86 (s, 1H), 7.77 (s, 1H), 7.63 (br d, J=10.8 Hz, 1H), 7.46-7.43 (m, 1H), 3.80 (s, 3H), 3.78 (s, 2H) ppm.

Step 4: Preparation of methyl 9-fluoro-2-methyl-3,4-dihydro-2H-benzo[b][1,4]oxathiepine-7-carboxylate

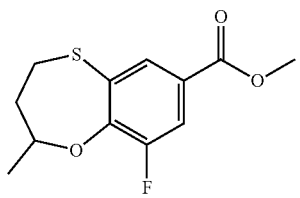

To a solution of 4 methyl 3-fluoro-4-hydroxy-5-mercaptobenzoate (1.2 g, 5.93 mmol) and 1,3-dibromobutane (1.28 g, 5.93 mmol, 719.87 uL) in DMF (50 mL) was added Cs$_2$CO$_3$ (9.67 g, 29.67 mmol). The mixture was stirred at 25° C. for 12 hrs. The mixture was diluted with H$_2$O (200 mL) and extracted with MTBE (200 mL*2). The combined organic layers were dried over anhydrous Na$_2$SO$_4$, filtered and concentrated. The residue was purified by normal phase flash (column SiO$_2$, Petroleum ether/Ethyl acetate=1/0 to 0/1, Rf=0.4). The eluent was concentrated to give methyl 9-fluoro-2-methyl-3,4-dihydro-2H-benzo[b][1,4]oxathi-epine-7-carboxylate (1.5 g, 5.54 mmol, 93.43% yield) as colorless oil. LCMS (ESI) m/z: [M+H]$^+$=256.8. $^1$H NMR (400 MHz, DMSO-d$_6$) δ=7.69-7.66 (m, 1H), 7.60-7.57 (m, 1H), 4.40-4.30 (m, 1H), 3.83 (s, 3H), 3.31-3.15 (m, 1H), 2.91-2.86 (m, 1H), 2.27-2.20 (m, 1H), 2.09-2.00 (m, 1H), 1.38 (d, J=6.4 Hz, 3H) ppm.

Step 5: Preparation of methyl 4,9-difluoro-2-methyl-3,4-dihydro-2H-benzo[b][1,4]oxathiepine-7-carboxylate

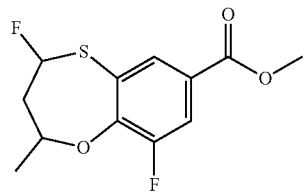 [SMILES: COC(=O)c1cc(F)c2c(c1)SC(F)CC(C)O2]

To a solution of methyl 9-fluoro-2-methyl-3,4-dihydro-2H-benzo[b][1,4]oxathiepine-7-carboxylate (1.3 g, 5.07 mmol) in ACN (13 mL) was added Select F (2.70 g, 7.61 mmol) and DAST (163.52 mg, 1.01 mmol, 134.03 uL) at 0° C. The mixture was stirred at 25° C. for 1 hr. Then DIEA (983.34 mg, 7.61 mmol, 1.33 mL) was added at 0° C. The mixture was stirred at 25° C. for 1 hr. The mixture was added to aq·NaHCO$_3$ (100 mL) at 0° C. and extracted with DCM (40 mL*3). The combined organic layers were dried over anhydrous Na$_2$SO$_4$, filtered and concentrated to afford methyl 4,9-difluoro-2-methyl-3,4-dihydro-2H-benzo[b][1,4]oxathiepine-7-carboxylate (1.3 g, crude) was obtained as yellow oil. LCMS (ESI) m/z: [M+H]$^+$=274.9.

Step 6: Preparation of methyl (trans)-4,9-difluoro-2-methyl-3,4-dihydro-2H-benzo[b][1,4]oxathiepine-7-carboxylate 5,5-dioxide and methyl (cis)-4,9-difluoro-2-methyl-3,4-dihydro-2H-benzo[b][1,4]oxathiepine-7-carboxylate 5,5-dioxide

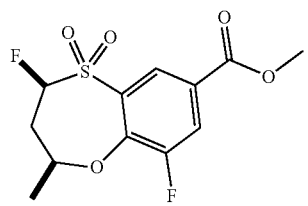

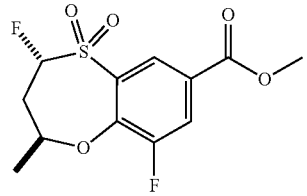

To a solution of methyl 4,9-difluoro-2-methyl-3,4-dihydro-2H-benzo[b][1,4]oxathiepine-7-carboxylate (1.3 g, 4.74 mmol) in DCM (33 mL) was added m-CPBA (3.37 g, 16.59 mmol, 85% purity) at 0° C. The mixture was stirred at 25° C. for 2 hrs. The mixture was poured into water (50 mL) and extracted with EA (50 mL*3). The organic layer was dried over anhydrous Na$_2$SO$_4$, filtered and concentrated in vacuum. The residue was purified by normal phase flash (column SiO$_2$, PE/EA=1/0-0/1). The eluent was concentrated under vacuum. The residue was purified by reverse phase flash (0.1% FA condition). The eluent was concentrated in vacuum to remove MeCN and extracted with EA (50 mL*3). The organic layer was dried over anhydrous Na₂SO₄, filtered and concentrated in vacuum. The product was purified by normal phase flash (column SiO₂, PE/EA=1/0-0/1, Rf=0.3, 0.2). The eluent was concentrated in vacuum to give (trans)-4,9-difluoro-2-methyl-3,4-dihydro-2H-benzo[b][1,4]oxathiepine-7-carboxylate 5,5-dioxide (390 mg, 1.27 mmol, 26.87% yield) as yellow oil. LCMS (ESI) m/z: [M+H]⁺=306.9. ¹H NMR (400 MHz, DMSO-d₆) δ=8.24-8.16 (m, 2H), 6.35-6.19 (m, 1H), 4.39-4.31 (m, 1H), 3.91 (s, 3H), 2.80-2.60 (m, 2H), 1.50 (d, J=6.4 Hz, 3H) ppm and (cis)-4,9-difluoro-2-methyl-3,4-dihydro-2H-benzo[b][1,4]oxathiepine-7-carboxylate 5,5-dioxide (60 mg, 195.90 umol, 4.13% yield) as colorless oil. LCMS (ESI) m/z: [M+H]⁺= 306.8.¹H NMR (400 MHz, DMSO-d₆) δ=8.25-8.18 (m, 2H), 6.21-6.05 (m, 1H), 4.71-4.61 (m, 1H), 3.91 (s, 3H), 2.78-2.69 (m, 1H), 2.63-2.54 (m, 1H), 1.47 (d, J=6.8 Hz, 3H) ppm.

Step 7: Preparation of (cis)-4,9-difluoro-2-methyl-3,4-dihydro-2H-benzo[b][1,4]oxathiepine-7-carboxylic Acid 5,5-dioxide

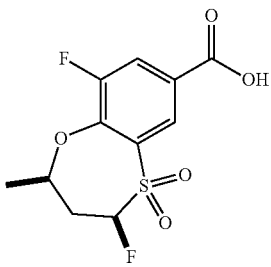 [SMILES: C[C@@H]1C[C@H](F)S(=O)(=O)c2cc(C(=O)O)cc(F)c2O1]

To a mixture of (cis)-4,9-difluoro-2-methyl-3,4-dihydro-2H-benzo[b][1,4]oxathiepine-7-carboxylate 5,5-dioxide (60.00 mg, 195.90 umol) in THF (0.8 mL) and MeOH (0.8 mL) was added LiOH (14.08 mg, 587.69 umol) and H₂O (0.4 mL). The mixture was stirred at 25° C. for 1 hr. The reaction mixture was adjusted to pH=3~4 by aq. HCl (1 N) and extracted with EA (5 mL*3). The combined organic layer was washed by brine (10 mL), dried over Na₂SO₄, filtered and concentrated under vacuum to give (cis)-4,9-difluoro-2-methyl-3,4-dihydro-2H-benzo[b][1,4]oxathiepine-7-carboxylic acid 5,5-dioxide (60 mg, crude) as yellow oil. ¹H NMR (400 MHz, DMSO-d₆) δ=8.29-8.12 (m, 2H), 6.24-6.04 (m, 1H), 4.76-4.57 (m, 1H), 3.92 (s, 3H), 2.80-2.55 (m, 2H), 1.48 (d, J=6.4 Hz, 3H) ppm.

Step 8: Preparation of (2R,4R)-4,9-difluoro-2-methyl-3,4-dihydro-2H-benzo[b][1,4]oxathiepine-7-carboxylic acid 5,5-dioxide and (2S,4S)-4,9-difluoro-2-methyl-3,4-dihydro-2H-benzo[b][1,4]oxathiepine-7-carboxylic acid 5,5-dioxide

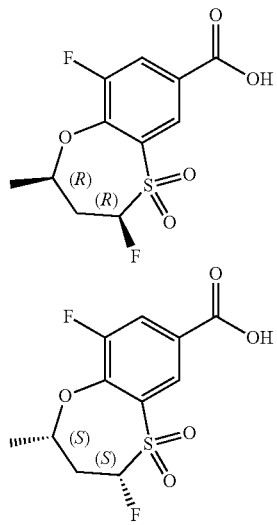

(cis)-4,9-difluoro-2-methyl-3,4-dihydro-2H-benzo[b][1,4]oxathiepine-7-carboxylic (60 mg, crude) was separated by SFC (column: DAICEL CHIRALPAK IG (250 mm*30 mm, 10 um); mobile phase: [MeOH (0.1% IPAm)]; B %: 20%-20%, A5.4; 54 min). The eluent was concentrated under vacuum to give impure (2S,4S)-4,9-difluoro-2-methyl-3,4-dihydro-2H-benzo[b][1,4]oxathiepine-7-carboxylic acid 5,5-dioxide and pure (2R,4R)-4,9-difluoro-2-methyl-3,4-dihydro-2H-benzo[b][1,4]oxathiepine-7-carboxylic acid 5,5-dioxide (Intermediate 5) (23 mg, 77.30 umol, 37.65% yield) as yellow oil. ¹H NMR (400 MHz, DMSO-d₆) δ=8.29-8.12 (m, 2H), 6.24-6.04 (m, 1H), 4.76-4.57 (m, 1H), 3.92 (s, 3H), 2.80-2.55 (m, 2H), 1.48 (d, J=6.4 Hz, 3H) ppm. Chiral SFC: G-3-MeOH (DEA)-5-40-3 mL-35T.lcm, Rt=1.313 mins, ee %=100%.

Preparation of (2R,4R)—N-((2-(6-((2S,6R)-2,6-dimethylmorpholino)pyridin-2-yl)-1,6-naphthyridin-7-yl)methyl)-4,9-difluoro-2-methyl-3,4-dihydro-2H-benzo[b][1,4]oxathiepine-7-carboxamide 5,5-dioxide

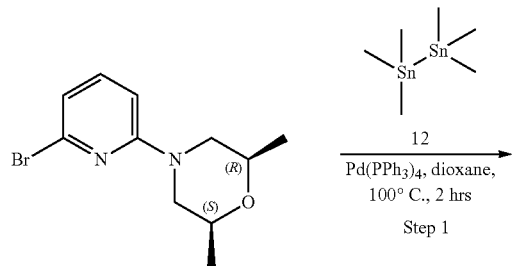

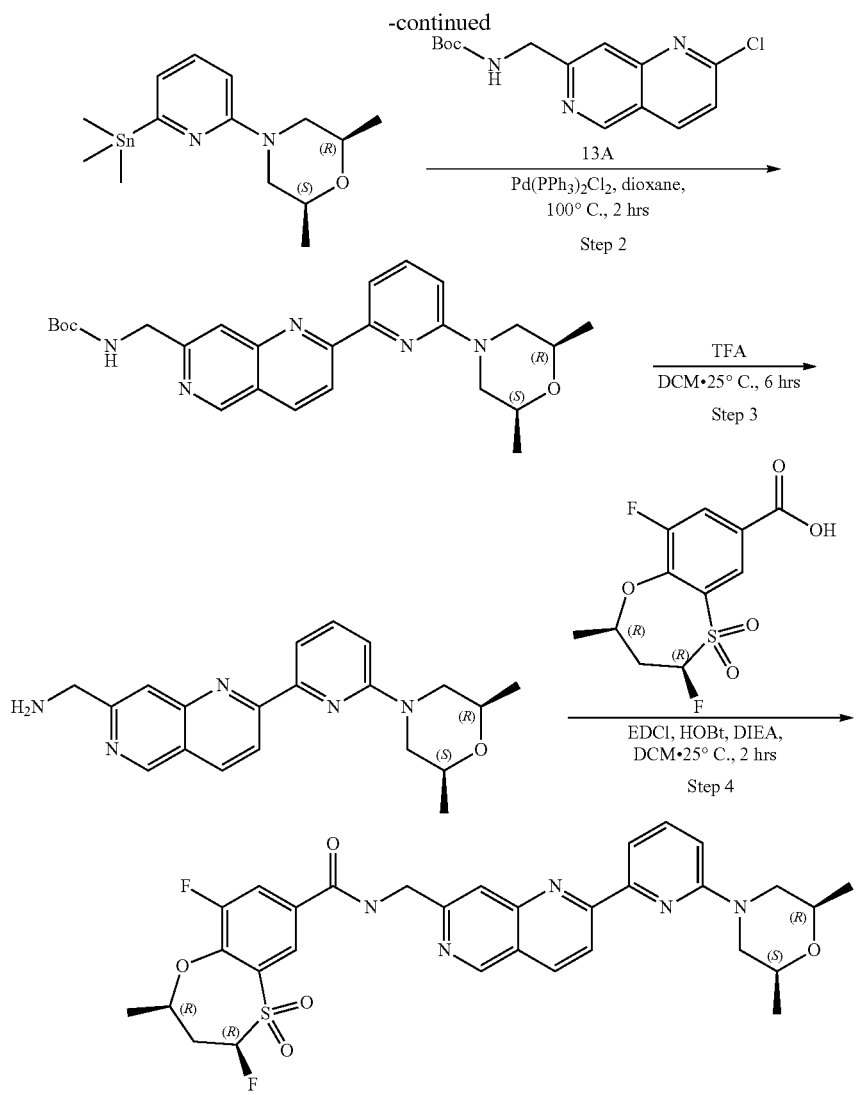

Step 1: Preparation of (2S,6R)-2,6-dimethyl-4-(6-(trimethylstannyl)pyridin-2-yl)morpholine

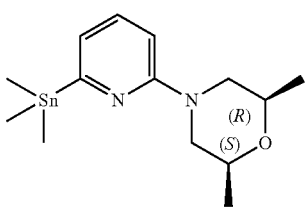

To a solution of (2R,6S)-4-(6-bromo-2-pyridyl)-2,6-dimethyl-morpholine (Prepared according to the method in example 6) (600 mg, 2.21 mmol) and trimethyl(trimethylstannyl)stannane (869.96 mg, 2.66 mmol, 550.60 uL) in dioxane (7 mL) was added Pd(PPh₃)₄ (127.85 mg, 110.64 umol). The mixture was degassed and purged with N₂ and stirred at 100° C. for 2 hrs. The mixture was poured into water (100 mL) and extracted with EA (30 mL*3). The combined organic layer was washed by brine (50 mL), dried over anhydrous Na₂SO₄, filtered and concentrated under vacuum to give (2S,6R)-2,6-dimethyl-4-(6-(trimethylstannyl)pyridin-2-yl)morpholine (780 mg, crude) as yellow oil which was used to next step directly. LCMS (ESI) m/z: [M+H]⁺=356.7.

Step 2: Preparation of tert-butyl ((2-(6-((2S,6R)-2,6-dimethylmorpholino)pyridin-2-yl)-1,6-naphthyridin-7-yl)methyl)carbamate To a solution of (2S,6R)-2,6-dimethyl-4-(6-(trimethylstannyl)pyridin-2-yl)morpholine (779.63 mg, 2.20 mmol) and tert-butyl N-[(2-chloro-1,6-naphthyridin-7-yl)methyl]carbamate (430 mg, 1.46 mmol) in dioxane (5 mL) was added Pd(PPh$_3$)$_2$Cl$_2$ (102.75 mg, 146.38 umol). The mixture was degassed and purged with N$_2$ and stirred at 100° C. for 2 hrs. The mixture was poured into water (100 mL) and extracted with EA (30 mL*3). The combined organic layer was washed by brine (50 mL), dried over anhydrous Na$_2$SO$_4$, filtered and concentrated under vacuum. The residue was purified by normal phase flash (column: SiO$_2$, PE:EA=1:0-0:1, RF=0.2). The eluent was concentrated under vacuum to give ((2-(6-((2S,6R)-2,6-dimethylmorpholino)pyridin-2-yl)-1,6-naphthyridin-7-yl)methyl)carbamate (600 mg, 1.27 mmol, 86.62% yield) as yellow solid. LCMS (ESI) m/z: [M+H]$^+$=450.0. $^1$H NMR (400 MHz, DMSO-d$_6$) δ=9.35 (s, 1H), 8.71-8.55 (m, 2H), 7.93 (d, J=7.4 Hz, 1H), 7.82-7.73 (m, 2H), 7.60-7.58 (m, 1H), 7.03 (d, J=8.4 Hz, 1H), 4.45 (br d, J=5.8 Hz, 2H), 4.31 (br d, J=12.6 Hz, 2H), 3.76-3.57 (m, 2H), 1.44 (s, 9H), 1.22 (d, J=6.2 Hz, 6H) ppm.

Step 3: Preparation of (2-(6-((2S,6R)-2,6-dimethylmorpholino)pyridin-2-yl)-1,6-naphthyridin-7-yl)methanamine

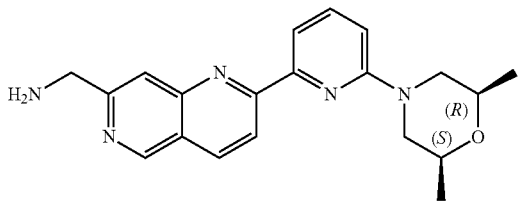

To a solution of ((2-(6-((2S,6R)-2,6-dimethylmorpholino)pyridin-2-yl)-1,6-naphthyridin-7-yl)methyl)carbamate (200 mg, 444.90 umol) in DCM (2 mL) was added TFA (0.6 mL). The mixture was stirred at 25° C. for 6 hrs. The mixture was poured into sat·NaHCO$_3$ (20 mL) and extracted with DCM (10 ml*3). The combined organic layer was washed by brine (10 mL), dried over anhydrous Na$_2$SO$_4$, filtered and concentrated under vacuum to give (2-(6-((2S,6R)-2,6-dimethylmorpholino)pyridin-2-yl)-1,6-naphthyridin-7-yl)methanamine (160 mg, crude) as yellow oil. LCMS (ESI) m/z: [M+H]$^+$=350.0

Step 4: Preparation of (2S,4S)—N-((2-(6-((2S,6R)-2,6-dimethylmorpholino)pyridin-2-yl)-1,6-naphthyridin-7-yl)methyl)-4,9-difluoro-2-methyl-3,4-dihydro-2H-benzo[b][1,4]oxathiepine-7-carboxamide 5,5-dioxide (Compound 34)

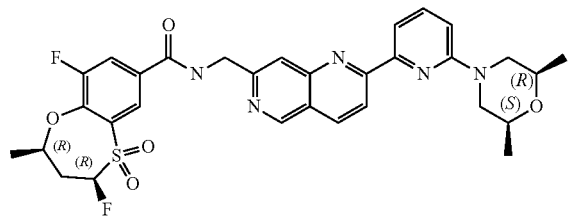

To a solution of (2R,4R)-4,9-difluoro-2-methyl-3,4-dihydro-2H-benzo[b][1,4]oxathiepine-7-carboxylic acid 5,5-dioxide (Intermediate 5) (18.40 mg, 62.96 umol) in DCM (1 mL) was added EDCl (16.46 mg, 85.86 umol), HOBT (11.60 mg, 85.86 umol) and DIEA (36.99 mg, 286.20 umol, 49.85 uL). Then (2-(6-((2S,6R)-2,6-dimethylmorpholino)pyridin-2-yl)-1,6-naphthyridin-7-yl)methanamine (20 mg, 57.24 umol) was added. The mixture was stirred at 25° C. for 2 hrs. The mixture was poured into water (10 mL) and extracted with EA (5 mL*3). The combined organic layer was washed by brine (5 mL), dried over anhydrous Na$_2$SO$_4$, filtered and concentrated under vacuum. The residue was purified by prep-HPLC (column: Phenomenex luna C18 150*25 mm*10 um; mobile phase: [water (FA)-ACN]; B %: 50%-80%, 10 min). Then the eluent was concentrated and lyophilized to give (2S,4S)—N-((2-(6-((2S,6R)-2,6-dimethylmorpholino)pyridin-2-yl)-1,6-naphthyridin-7-yl)methyl)-4,9-difluoro-2-methyl-3,4-dihydro-2H-benzo[b][1,4]oxathiepine-7-carboxamide 5,5-dioxide (7.23 mg, 11.35 umol, 19.83% yield) as yellow solid. LCMS (ESI) m/z: [M+H]$^+$=623.9. $^1$H NMR (400 MHz, DMSO-d$_6$) δ=9.68-9.66 (m, 1H), 9.40 (s, 1H), 8.71-8.58 (m, 2H), 8.40-8.30 (m, 2H), 7.91 (d, J=7.6 Hz, 1H), 7.83 (s, 1H), 7.78-7.75 (m, 1H), 7.04 (d, J=8.4 Hz, 1H), 6.24-6.01 (m, 1H), 4.82 (br d, J=6.0 Hz, 2H), 4.67-4.56 (m, 1H), 4.32 (br d, J=12.0 Hz, 2H), 3.72-3.64 (m, 2H), 2.80-2.56 (m, 4H), 1.49 (br d, J=6.2 Hz, 3H), 1.22 (d, J=6.2 Hz, 6H) ppm.

Chiral SFC: (S, S) Whelk-O1-IPA+ACN(DEA)-40-3 mL-35T.lcm, Rt=2.237 mins, ee %=97.69%.

The following examples in Table 7 were prepared using standard chemical manipulations and procedures like those used for the preparation of Compound 34.

TABLE 7

Compounds of the Invention

| # | LCMS (ESI/ M + H) | $^1$HNMR |
|---|---|---|
| 134 | 623.9 | 1H NMR (400 MHZ, DMSO-d6) δ = 9.75-9.72 (m, 1H), 9.41 (s, 1H), 8.69-8.62 (m, 2H), 8.49 (d, J = 1.2 Hz, 1H), 8.47-8.45 (m, 1H), 8.28-8.25 (m, 1H), 7.92 (d, J = 7.2 Hz, 1H), 7.85 (s, 1H), 7.77-7.74 (m, 1H), 7.04 (d, J = 8.4 Hz, 1H), 6.28-6.03 (m, 1H), 5.54-5.49 (m, 1H), 4.83 (d, J = 5.6 Hz, 2H), 4.69-4.50 (m, 1H), 4.32 (d, J = 11.2 Hz, 2H), 4.03-3.82 (m, 1H), 3.79-3.62 (m, 2H), 2.55-2.53 (m, 2H), 1.56 (d, J = 6.8 Hz, 3H), 1.22 (d, J = 6.4 Hz, 6H) ppm = |
| 162 | 590.3 | 1H NMR (400 MHZ, DMSO-d6) δ = 9.65-9.62 (m, 1H), 9.08 (s, 1H), 8.63 (d, J 2.0 Hz, 1H), 8.36-8.33 (m, 1H), 8.27 (s, 2H), 7.82-7.75 (m, 2H), 7.48 (S, 1H), 6.99 (d, J = 2.0 Hz, 1H), 6.17-5.90 (m, 1H), 5.32-5.27 (m, 1H), 4.73 (d, J = 5.6 Hz, 2H), 4.57-4.44 (m, 1H), 4.31 (s, 4H), 4.10-4.02 (m, 1H), 2.01-1.85 (m, 1H), 1.62 (d, J = 6.8 Hz, 3H), 1.02-0.89 (m, 2H), 0.76-0.66 (m, 2H) ppm |

TABLE 7-continued

Compounds of the Invention

| # | LCMS (ESI/ M + H) | ¹HNMR |
|---|---|---|
| 197 | 573.3 | 1H NMR (400 MHZ, DMSO-d6) δ = 9.72-9.69 (m, 1H), 9.43 (s, 1H), 8.69-8.61 (m, 2H), 8.46 (d, J = 7.2 Hz, 2H), 8.38-8.36 (m, 1H), 8.21 (d, J = 8.8 Hz, 1H), 7.88-7.81 (m, 2H), 7.47 (d, J = 7.6 Hz, 1H), 7.16-6.78 (m, 1H), 6.21-5.98 (m, 1H), 5.36-5.33 (m, 1H), 4.83 (d, J = 5.6 Hz, 2H), 4.60-4.34 (m, 2H), 4.02 (s, 3H), 1.65 (d, J = 6.4 Hz, 3H) ppm. |
| 200 | 606.0 | 1H NMR (400 MHz, DMSO-d6) δ = 9.69-9.66 (m, 1H), 9.40 (s, 1H), 8.68-8.61 (m, 3H), 8.38-8.36 (m, 1H), 8.35 (d, J = 1.6 Hz, 1H), 7.91 (d, J = 7.6 Hz, 1H), 7.81-7.72 (m, 3H), 7.03 (d, J = 8.8 Hz, 1H), 6.08-5.93 (m, 1H), 5.34-5.27 (m, 1H), 4.83-4.80 (m, 2H), 4.53-4.46 (m, 1H), 4.30-4.29 (m, 2H), 4.10-4.03 (m, 1H), 3.69-3.65 (m, 2H), 2.53-2.52 (m, 2H), 1.63 (d, J = 6.4 Hz, 3H), 1.21 (d, J = 6.4 Hz, 6H) ppm |
| 222 | 624.3 | 1H NMR (400 MHZ, DMSO-d6) δ = 9.75-9.73 (m, 1H), 9.40 (s, 1H), 8.70-8.59 (m, 2H), 8.53 (s, 1H), 8.48-8.39 (m, 1H), 8.26-8.23 (m, 1H), 7.91 (d, J = 7.2 Hz, 1H), 7.84 (s, 1H), 7.77-7.75 (m, 1H), 7.03 (d, J = 8.4 Hz, 1H), 6.27-6.03 (m, 1H), 5.53-5.48 (m, 1H), 4.82 (br d, J = 5.6 Hz, 2H), 4.42-4.27 (m, 4H), 3.73-3.60 (m, 2H), 2.58-2.55 (m, 2H), 1.63-1.61 (m, 3H), 1.21 (d, J = 6.4 Hz, 6H) ppm |

Preparation of (S)—N-((2-(6-((2S,6R)-2,6-dimethyl-morpholino)pyridin-2-yl)-1,6-naphthyridin-7-yl)methyl)-2-fluoro-4-methyl-2,3,4,5-tetrahydrobenzo[f][1,4]thiazepine-8-carboxamide 1,1-dioxide (Compound 1)

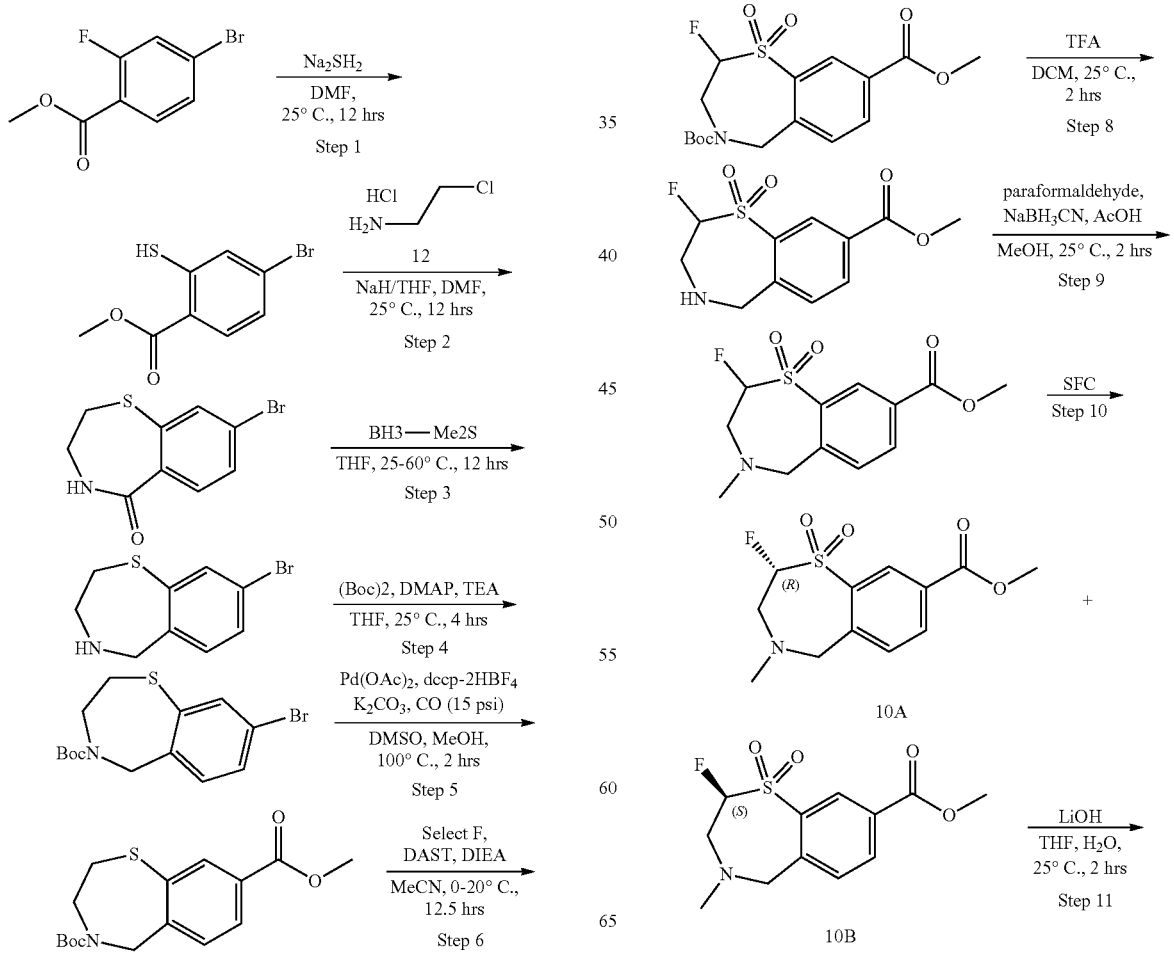

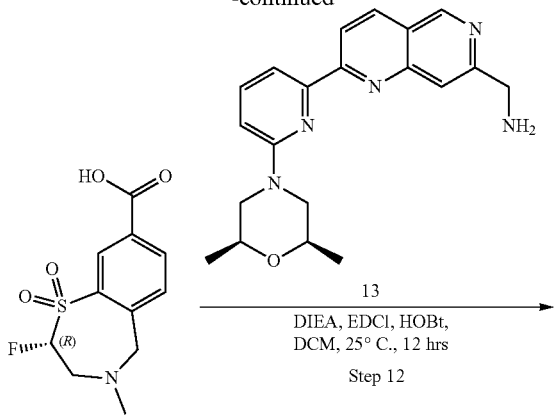

→ 13
DIEA, EDCl, HOBt,
DCM, 25° C., 12 hrs
Step 12

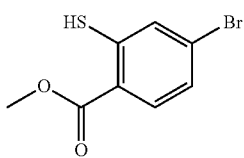

Step 1: Preparation of methyl
4-bromo-2-mercaptobenzoate

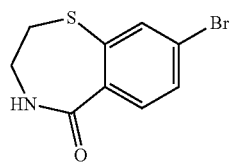 [SMILES: O=C1NCCSc2cc(Br)ccc21]

To a solution of methyl 4-bromo-2-fluoro-benzoate (5 g, 21.46 mmol) in DMF (50 mL) was added Na₂S (1.95 g, 22.53 mmol, 90% purity). The mixture was stirred at 25° C. for 12 hrs. The mixture of methyl 4-bromo-2-mercaptobenzoate (5.3 g, crude) as a brown liquid in DMF (50 mL) used in the next step directly without further purification. LCMS (ESI) m/z: [Br$^{81}$M+H]$^+$=204.0.

Step 2: Preparation of 8-bromo-3,4-dihydrobenzo[f][1,4]thiazepin-5(2H)-one

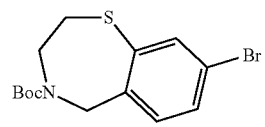

To a solution of methyl 4-bromo-2-mercaptobenzoate (5.3 g, 21.45 mmol) in DMF (50 mL) and THF (50 mL) was added 2-chloroethanamine (4.98 g, 42.90 mmol), then NaH (2.57 g, 64.34 mmol, 60% purity) was added to the mixture at 0° C. under N₂ atmosphere. The mixture was stirred at 25° C. for 12 hrs. The mixture was diluted with NH₄Cl solution (500 mL) and extracted with EA (500 mL*2), the combined organic layer was washed by brine (300 mL*2). Then the organic layer was dried with anhydrous Na₂SO₄ and concentrated to afford residue. The residue was diluted with MTBE and filtered. The filtered cake was dried in vacuo to give 8-bromo-3,4-dihydrobenzo[f][1,4]thiazepin-5(2H)-one (1 g, 3.87 mmol, 18.06% yield) was obtained as an off-white solid. LCMS (ESI) m/z: [Br$^{81}$M+H]$^+$=260.2

Step 3: Preparation of 8-bromo-2,3,4,5-tetrahydrobenzo[f][1,4]thiazepine

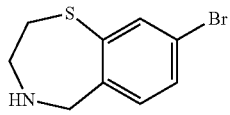 [SMILES: Brc1ccc2c(c1)SCCNC2]

To a solution of 8-bromo-3,4-dihydrobenzo[f][1,4]thiazepin-5(2H)-one (1 g, 3.87 mmol) in THF (10 mL) was added BH3-Me2S (10 M, 774.79 uL) at 25° C. The mixture was stirred at 60° C. for 12 hrs. The reaction mixture was diluted with MeOH (2 mL) and stirred at 60° C. for 12 hrs. The mixture was concentrated to give 8-bromo-2,3,4,5-tetrahydrobenzo[f][1,4]thiazepine (945 mg, crude) as a yellow oil. LCMS (ESI) m/z: [Br$^{81}$M+H]$^+$=246.0.

Step 4: Preparation of tert-butyl 8-bromo-2,3-dihydrobenzo[f][1,4]thiazepine-4(5H)-carboxylate To a solution of 8-bromo-2,3,4,5-tetrahydrobenzo[f][1,4]thiazepine (945 mg, 3.87 mmol) in THF (10 mL) was added (Boc)₂O (1.69 g, 7.74 mmol) and DMAP (47.29 mg, 387.06 umol) and TEA (1.17 g, 11.61 mmol). The mixture was stirred at 25° C. for 4 hrs. The mixture was diluted with water (20 mL) and extracted with EA (20 mL*2). The combined organic layer was dried with anhydrous Na₂SO₄ and concentrated to afford residue. The residue was purified by flash silica gel chromatography (ISCO®; 12 g SepaFlash® Silica Flash Column, Eluent of 0-100% Ethylacetate/Petroleum ether). The eluent was concentrated to give tert-butyl 8-bromo-2,3-dihydrobenzo[f][1,4]thiazepine-4(5H)-carboxylate (600 mg, 1.74 mmol, 45.03% yield) was obtained as a white solid. LCMS (ESI) m/z: [Br$^{81}$M+H]$^+$=290.0. $^1$HNMR (400 MHz, DMSO-d₆) δ=7.70-7.64 (m, 1H), 7.52-7.43 (m, 1H), 7.33-7.25 (m, 1H), 4.49-4.39 (m, 2H), 3.79 (s, 2H), 2.89-2.76 (m, 2H), 1.33 (s, 9H) ppm.

Step 5: Preparation of 4-(tert-butyl) 8-methyl 2,3-dihydrobenzo[f][1,4]thiazepine-4,8(5H)-dicarboxylate

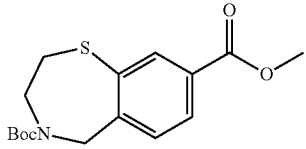 [SMILES: COC(=O)c1ccc2c(c1)SCCN(C(=O)OC(C)(C)C)C2]

To a solution of tert-butyl 8-bromo-2,3-dihydrobenzo[f][1,4]thiazepine-4(5H)-carboxylate (600 mg, 1.74 mmol) in DMSO (6 mL) and MeOH (279.22 mg, 8.71 mmol) was added dicyclohexyl(3-dicyclohexylphosphaniumylpropyl)phosphonium; ditetrafluoroborate (106.71 mg, 174.28 umol), K$_2$CO$_3$ (361.32 mg, 2.61 mmol) and Pd(OAc)$_2$ (39.13 mg, 174.28 umol). Then the mixture was degassed and purged with CO for 3 times, and was stirred at 100° C. for 2 hrs under CO (15 psi) atmosphere. The mixture was filtered and the filtered cake was washed by EA (100 mL) and water (100 mL). Then the mixture was diluted with water (100 mL) and extracted with EA (100 mL*2). The combined organic layer dried with anhydrous Na$_2$SO$_4$ and concentrated to afford product. The residue was purified by flash silica gel chromatography (ISCO®; 12 g SepaFlash® Silica Flash Column, Eluent of 0-100% Ethylacetate/Petroleum ether). The eluent was concentrated to give 4-(tert-butyl) 8-methyl 2,3-dihydrobenzo[f][1,4]thiazepine-4,8(5H)-dicarboxylate (450 mg, 1.39 mmol, 79.84% yield) as a white solid. LCMS (ESI) m/z: [M+H]$^+$=224.1 $^1$HNMR (400 MHz, DMSO-d$_6$) δ=8.04-7.98 (m, 1H), 7.88-7.80 (m, 1H), 7.54-7.46 (m, 1H), 4.58-4.49 (m, 2H), 3.88-3.77 (m, 5H), 2.93-2.82 (m, 2H), 1.34-1.29 (m, 9H) ppm.

Step 6: Preparation of 4-(tert-butyl) 8-methyl (S)-2-fluoro-2,3-dihydrobenzo[f][1,4]thiazepine-4,8(5H)-dicarboxylate

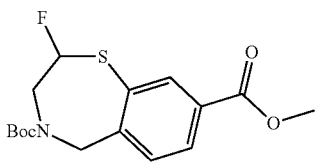 [SMILES: COC(=O)c1ccc2c(c1)SC(F)CN(C(=O)OC(C)(C)C)C2]

To a solution of 4-(tert-butyl) 8-methyl 2,3-dihydrobenzo[f][1,4]thiazepine-4,8(5H)-dicarboxylate (450 mg, 1.39 mmol) in ACN (6 mL) was added Select F (985.86 mg, 2.78 mmol) and then DAST (44.86 mg, 278.29 umol) was added under ice-bath (0° C.). The solution was stirred at 25° C. for 0.5 hr. Then DIEA (269.75 mg, 2.09 mmol) was added under ice-bath (0° C.) and the solution was stirred at 25° C. for 12 hrs. The mixture was diluted with water (30 mL) and extracted with DCM (30 mL*2). The combined organic layer was dried with anhydrous Na$_2$SO$_4$ and concentrated to 4-(tert-butyl) 8-methyl (S)-2-fluoro-2,3-dihydrobenzo[f][1,4]thiazepine-4,8(5H)-dicarboxylate (475 mg, crude) as a black solid that was used without purification.

Step 7: Preparation of 4-(tert-butyl) 8-methyl (S)-2-fluoro-2,3-dihydrobenzo[f][1,4]thiazepine-4,8(5H)-dicarboxylate 1,1-dioxide

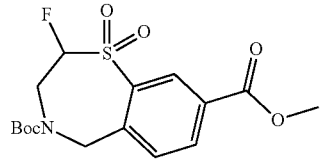 [SMILES: COC(=O)c1ccc2c(c1)S(=O)(=O)C(F)CN(C(=O)OC(C)(C)C)C2]

To a solution of 4-(tert-butyl) 8-methyl (S)-2-fluoro-2,3-dihydrobenzo[f][1,4]thiazepine-4,8(5H)-dicarboxylate (475 mg, 1.39 mmol) in DCM (6 mL) was added m-CPBA (1.41 g, 6.96 mmol, 85% purity) at 0° C. The mixture was stirred at 25° C. for 12 hrs. The mixture was diluted with water (30 mL) and extracted with DCM (30 mL*2). Then the combined organic layers were washed by sat·Na$_2$SO$_3$ (30 mL*2) and sat. NaHCO$_3$ solution (30 mL*2) and then dried over Na$_2$SO$_4$, filtered and concentrated to obtained a residue. The residue was purified by flash silica gel chromatography (ISCO®; 20 g SepaFlash® Silica Flash Column, Eluent of 0-100% Ethylacetate/Petroleum ether). The eluent was concentrated to give 4-(tert-butyl) 8-methyl (S)-2-fluoro-2,3-dihydrobenzo[f][1,4]thiazepine-4,8(5H)-dicarboxylate 1,1-dioxide (180 mg, 448.32 umol, 32.22% yield) as a white solid. LCMS (ESI) m/z: [M+H]$^+$=318.0. $^1$HNMR (400 MHz, DMSO-d6) δ=8.48 (d, J=2.8 Hz, 1H), 8.38-8.28 (m, 1H), 7.85-7.73 (m, 1H), 6.28-6.10 (m, 1H), 4.91-4.79 (m, 1H), 4.69-4.49 (m, 2H), 3.99-3.81 (m, 4H), 1.35-1.26 (m, 9H) ppm.

Step 8: Preparation of methyl 2-fluoro-2,3,4,5-tetrahydrobenzo[f][1,4]thiazepine-8-carboxylate 1,1-dioxide

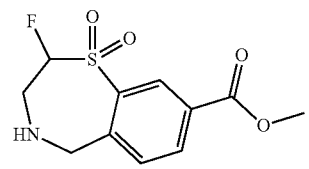 [SMILES: COC(=O)c1ccc2c(c1)S(=O)(=O)C(F)CNC2]

To a solution of 4-(tert-butyl) 8-methyl (S)-2-fluoro-2,3-dihydrobenzo[f][1,4]thiazepine-4,8(5H)-dicarboxylate 1,1-dioxide (180 mg, 482.06 umol) in DCM (2 mL) was added TFA (1.10 g, 9.64 mmol). The mixture was stirred at 25° C. for 2 hrs. The mixture was diluted with ice water (10 mL) and adjusted pH=8 with saturated NaHCO$_3$ solution. Then the mixture was extracted with DCM (10 mL*2). The combined organic layer was dried with anhydrous Na$_2$SO$_4$ and concentrated to give methyl 2-fluoro-2,3,4,5-tetrahydrobenzo[f][1,4]thiazepine-8-carboxylate 1,1-dioxide (130 mg, 475.70 umol, 98.68% yield) as a yellow solid. LCMS (ESI) m/z: [M+H]$^+$=274.0

Step 9: Preparation of methyl 2-fluoro-4-methyl-2, 3,4,5-tetrahydrobenzo[f][1,4]thiazepine-8-carboxylate 1,1-dioxide

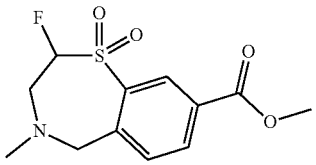

To a solution of methyl 2-fluoro-2,3,4,5-tetrahydrobenzo[f][1,4]thiazepine-8-carboxylate 1,1-dioxide (130 mg, 475.70 umol) in MeOH (2 mL) was added HCHO (115.83 mg, 1.43 mmol, 37% purity) and AcOH (2.86 mg, 47.57 umol), then NaBH$_3$CN (89.68 mg, 1.43 mmol) was added at 0° C. The mixture was stirred at 25° C. for 2 hrs. The mixture was diluted with water (10 mL) and extracted with EA (10 mL*2). The combined organic layer was dried with anhydrous Na$_2$SO$_4$ and concentrated to afford residue. The residue was purified by flash silica gel chromatography (ISCO®; 20 g SepaFlash® Silica Flash Column, Eluent of 0-100% Ethylacetate/Petroleum ether). The eluent was concentrated to give methyl 2-fluoro-4-methyl-2,3,4,5-tetrahydrobenzo[f][1,4]thiazepine-8-carboxylate 1,1-dioxide (120 mg, 417.67 umol, 87.80% yield) as a brown oil. LCMS (ESI) m/z: [M+H]$^+$=288.1. $^1$HNMR (400 MHz, DMSO-d$_6$) δ=8.48 (d, J=1.6 Hz, 1H), 8.29-8.26 (m, 1H), 7.77 (d, J=7.6 Hz, 1H), 6.12-6.08 (m, 1H), 4.50-4.44 (m, 1H), 4.10-4.06 (m, 1H), 3.92 (s, 3H), 3.61-3.53 (m, 2H), 2.52 (s, 3H) ppm.

Step 10: Preparation of methyl (R)-2-fluoro-4-methyl-2,3,4,5-tetrahydrobenzo[f][1,4]thiazepine-8-carboxylate 1,1-dioxide and methyl (S)-2-fluoro-4-methyl-2,3,4,5-tetrahydrobenzo[f][1,4]thiazepine-8-carboxylate 1,1-dioxide

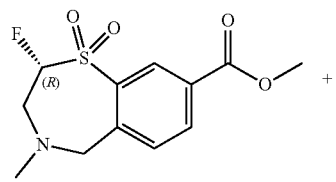

+

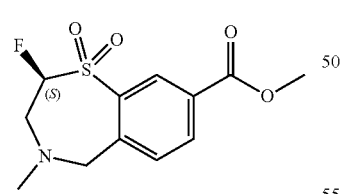

Methyl 2-fluoro-4-methyl-2,3,4,5-tetrahydrobenzo[f][1,4]thiazepine-8-carboxylate 1,1-dioxide (120 mg, 417.67 umol) was separated by SFC. The solid was separated by SFC (column: DAICEL CHIRALPAK AD (250 mm*30 mm, 10 um); mobile phase: [0.1% NH$_3$H$_2$O MEOH]; B %: 25%-25%, 6.8 min). The eluent of Peak 1 was concentrated to afford (R)-2-fluoro-4-methyl-2,3,4,5-tetrahydrobenzo[f][1,4]thiazepine-8-carboxylate 1,1-dioxide and methyl (30 mg, 104.42 umol, 25.00% yield) as a white solid. Chiral SFC: AD-3-MeOH(DEA)-5-40-3 mL-35T.lcm; Rt=1.127 mins, ee %=100%.

The eluent of Peak 2 was concentrated to afford (S)-2-fluoro-4-methyl-2,3,4,5-tetrahydrobenzo[f][1,4]thiazepine-8-carboxylate 1,1-dioxide (35 mg, 118.17 umol, 28.29% yield) as a white solid. Chiral SFC: AD-3-MeOH(DEA)-5-40-3 mL-35T.lcm; Rt=1.957 mins, ee %=99.49%.

Step 11: Preparation of (R)-2-fluoro-4-methyl-2,3,4,5-tetrahydrobenzo[f][1,4]thiazepine-8-carboxylic Acid 1,1-dioxide

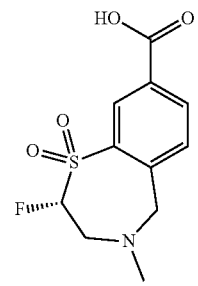 [SMILES: CN1Cc2ccc(C(=O)O)cc2S(=O)(=O)[C@@H](F)C1]

To a solution of (R)-2-fluoro-4-methyl-2,3,4,5-tetrahydrobenzo[f][1,4]thiazepine-8-carboxylate 1,1-dioxide and methyl (20 mg, 69.61 umol) in THF (0.2 mL) and Water (0.1 mL) was added LiOH·H$_2$O (8.76 mg, 208.84 umol). The mixture was stirred at 25° C. for 2 hrs. The reaction mixture was adjusted pH=5 by 1 N HCl, after that the mixture was adjusted pH=9 by NaHCO$_3$ solid. Then the mixture was concentrated to give (R)-2-fluoro-4-methyl-2,3,4,5-tetrahydrobenzo[f][1,4]thiazepine-8-carboxylic acid 1,1-dioxide (19 mg, 69.53 umol, 99.88% yield) as a yellow solid. LCMS (ESI) m/z: [M+H]$^+$=274.1.

Step 12: Preparation of (R)—N-((2-(6-((2S,6R)-2,6-dimethylmorpholino)pyridin-2-yl)-1,6-naphthyridin-7-yl)methyl)-2-fluoro-4-methyl-2,3,4,5-tetrahydrobenzo[f][1,4]thiazepine-8-carboxamide 1,1-dioxide (Compound 1)

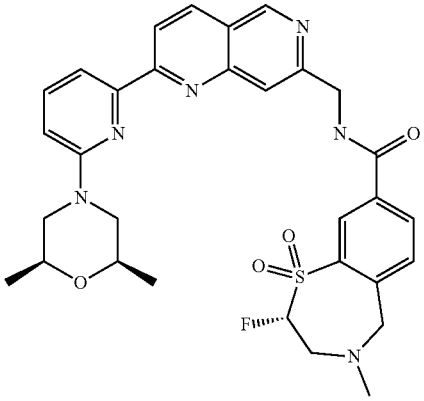 [SMILES: C[C@@H]1CN(c2cccc(-c3ccc4cnc(CNC(=O)c5ccc6c(c5)S(=O)(=O)[C@@H](F)CN(C)C6)cc4n3)n2)C[C@H](C)O1]

To a solution of (R)-2-fluoro-4-methyl-2,3,4,5-tetrahydrobenzo[f][1,4]thiazepine-8-carboxylic acid 1,1-dioxide (19 mg, 69.53 umol) and [2-[6-[(2R,6S)-2,6-dimethylmorpholin-4-yl]-2-pyridyl]-1,6-naphthyridin-7-yl]methanamine (26.83 mg, 69.53 umol) (Prepared according to the method in Example 9) in DMF (0.5 mL) was added HOBt (14.09 mg, 104.29 umol), EDCl (19.99 mg, 104.29 umol) and DIPEA (26.96 mg, 208.58 umol). The mixture was stirred at 25° C. for 12 hrs. The reaction mixture was diluted with water (10 mL) and extracted with DCM (10 mL*2). The combined organic layer was dried with anhydrous $Na_2SO_4$ and concentrated to afford residue. The residue was purified by reversed-phase HPLC (0.1% $NH_3 \cdot H_2O$). The eluent was concentrated to remove ACN and lyophilized to give (R)—N-((2-(6-((2S,6R)-2,6-dimethylmorpholino)pyridin-2-yl)-1,6-naphthyridin-7-yl)methyl)-2-fluoro-4-methyl-2,3,4,5-tetrahydrobenzo[f][1,4]thiazepine-8-carboxamide 1,1-dioxide (2.65 mg, 4.38 umol, 6.30% yield) as a yellow solid. LCMS (ESI) m/z: [M+H]$^+$=605.3. $^1$H NMR (400 MHz, DMSO-d)) 5=9.70-9.61 (m, 1H), 9.40 (s, 1H), 8.70-8.60 (m, 2H), 8.58 (m, 1H), 8.32 (d, J=7.6 Hz, 1H), 7.92 (d, J=7.6 Hz, 1H), 7.84 (5, 1H), 7.78-7.72 (m, 2H), 7.03 (d, J=8.0 Hz, 1H), 6.11-5.94 (m, 1H), 4.82 (d, J=5.6 Hz, 2H), 4.47 (d, J=14.8 Hz, 1H), 4.31 (d, J=12.8 Hz, 2H), 4.14-4.03 (m, 1H), 3.75-3.62 (m, 3H), 3.57-3.48 (m, 1H), 2.63-2.56 (m, 2H), 2.30 (z, 3H), 1.21 (d, J=6.0 Hz, 6H) ppm. Chiral SF0: IA-3-ETOH(DEA)-40_1 ML_T35.M; Rt=4.133 mins, ee %=100%.

The following examples in Table 8 were prepared using standard chemical manipulations and procedures similar to those used for the preparation of Compound 1.

TABLE 8

Compounds of the Invention

| # | LCMS (ESI/M + H) | $^1$HNMR |
|---|---|---|
| 317 | 605.3 | 1H NMR (400 MHZ, DMSO-d6) δ = 9.67-9.65 (m, 1H), 9.40 (s, 1H), 8.68-8.58 (m, 3H), 8.34-8.31(m, 1H), 7.92 (d, J = 7.6 Hz, 1H), 7.84 (s, 1H), 7.76-7.74 (m, 2H), 7.03 (d, J = 8.4 Hz, 1H), 6.09-5.97 (m, 1H), 4.82 (br d, J = 5.2 Hz, 2H), 4.47 (br d, J = 15.2 Hz, 1H), 4.31 (br d, J = 11.2 Hz, 2H), 4.08 (br d, J = 15.2 Hz, 1H), 3.69-3.66 (m, 3H), 3.67-3.51 (m, 1H), 2.54 (br s, 2H), 2.29 (d, J = 0.8 Hz, 3H), 1.21 (d, J = 6.0 Hz, 6H) ppm |
| 318 | 605.3 | 1H NMR (400 MHZ, DMSO-d6) δ = 9.41-9.39 (m, 2H), 8.67-8.60 (m, 2H), 8.49 (d, J = 2.4 Hz, 1H), 8.22-8.19 (m, 1H), 7.91 (d, J = 7.2 Hz, 1H), 7.76-7.71 (m, 2H), 7.29 (d, J = 8.8 Hz, 1H), 7.03 (d, J = 8.4 Hz, 1H), 6.05-5.92 (m, 1H), 4.78 (br d, J = 6.0 Hz, 2H), 4.31 (br d, J = 11.6 Hz, 2H), 3.69-3.65 (m, 2H), 3.56-3.51 (m, 1H), 3.28 (br s, 1H), 3.06 (s, 3H), 2.58 (br s, 2H), 2.39 (br d, J = 1.6 Hz, 1H), 2.29-2.25 (m, 1H), 1.21 (d, J = 6.0 Hz, 6H) ppm |
| 319 | 605.4 | 1H NMR (400 MHZ, DMSO-d6) δ = 9.51-9.29 (m, 2H), 8.76-8.57 (m, 2H), 8.49 (d, J = 2.0 Hz, 1H), 8.22-8.19 (m , 1H), 7.91 (d, J = 7.2 Hz, 1H), 7.82-7.64 (m, 2H), 7.29 (d, J = 8.8 Hz, 1H), 7.03 (d, J = 8.8 Hz, 1H), 6.12-5.80 (m, 1H), 4.78 (d, J = 5.6 Hz, 2H), 4.31 (br d, J = 11.2 Hz, 2H), 3.69-3.65 (m, 2H), 3.58-3.49 (m, 1H), 3.25 (br s, 1H), 3.07 (s, 3H), 2.64-2.54 (m, 1H), 2.52 (br s, 2H), 2.31-2.20 (m, 1H), 1.21 (d, J = 6.4 Hz, 6H) ppm |

Preparation of (R)-9-bromo-4-fluoro-N-((2-(7-((S)-2-(fluoromethyl)azetidin-1-yl)-2,3-dihydro-4H-pyrido[3,2-b][1,4]oxazin-4-yl)-1,6-naphthyridin-7-yl)methyl)-3,4-dihydro-2H-benzo[b][1,4]oxathiepine-7-carboxamide 5,5-dioxide (Compound 210)

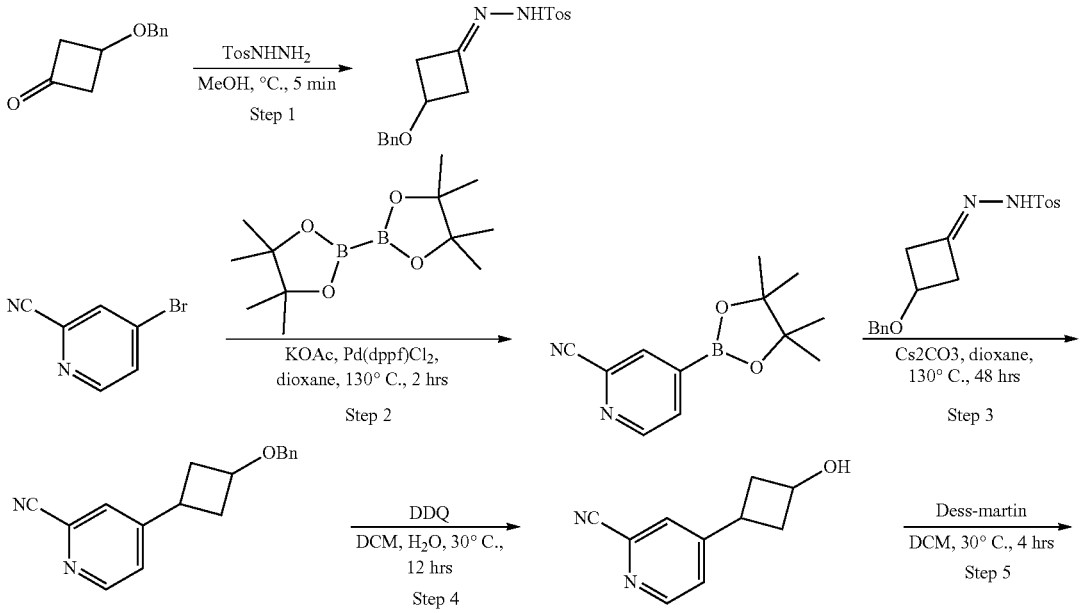

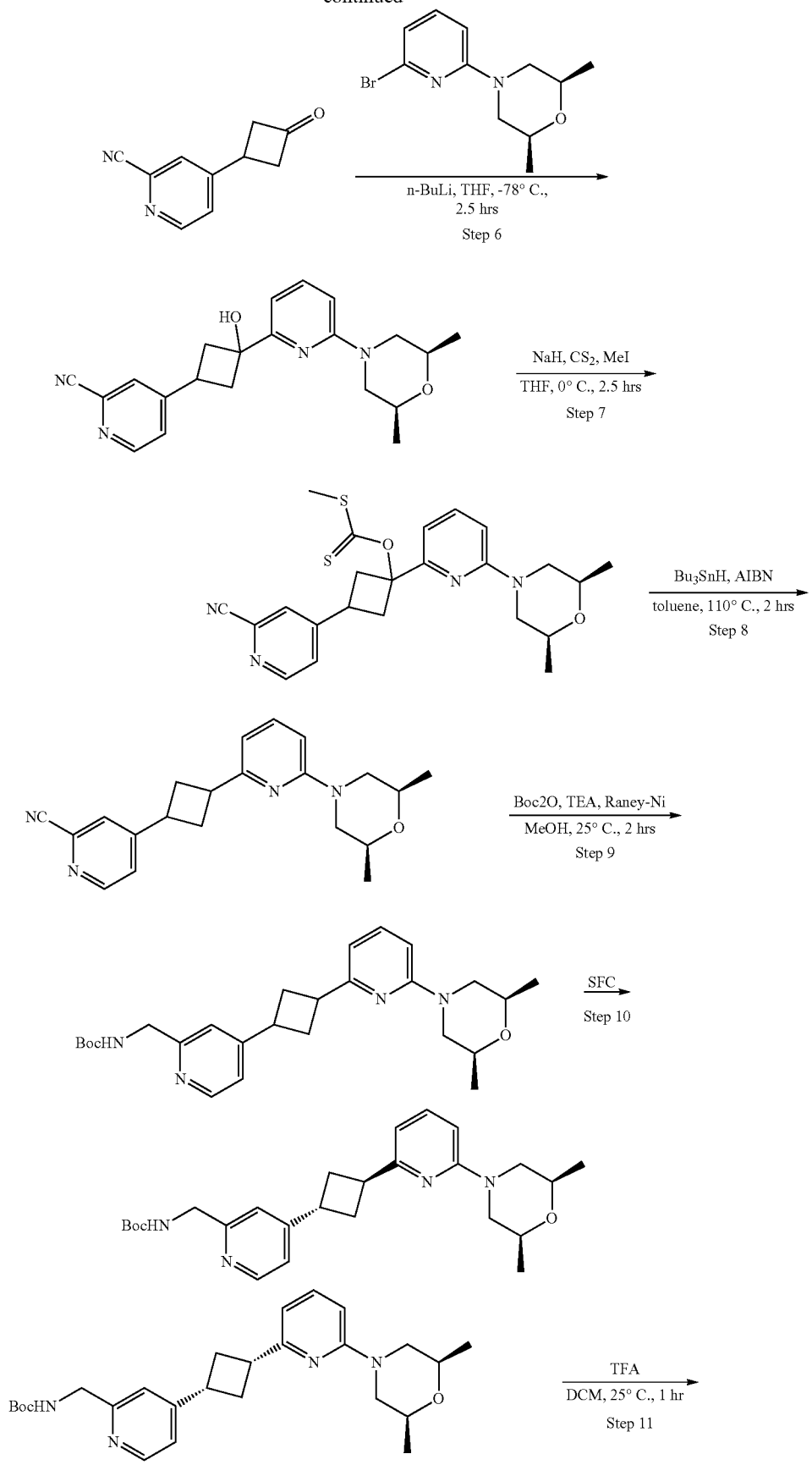

-continued

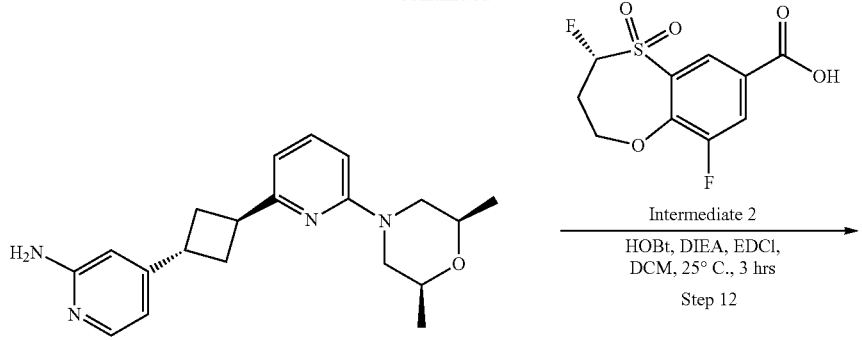

Intermediate 2

HOBt, DIEA, EDCl,
DCM, 25° C., 3 hrs

Step 12

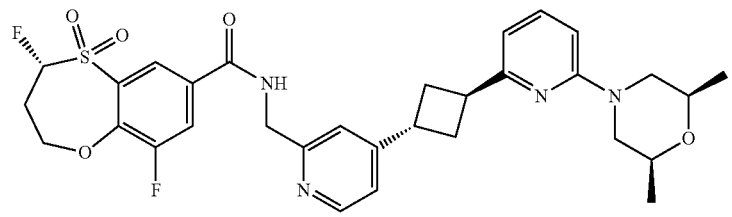

Step 1: Preparation of N'-(3-(benzyloxy)cyclobutyl-idene)-4-methylbenzenesulfonohydrazide

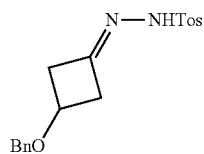

To a solution of 3-benzyloxycyclobutanone (10 g, 56.75 mmol) in MeOH (100 mL) was added 4-methylbenzenesulfonohydrazide (10.57 g, 56.75 mmol). The mixture was stirred at 25° C. for 5 min. The reaction mixture was filtered and the filter cake was washed MeOH (20 mL) and dried under reduced pressure to give N'-(3-(benzyloxy)cyclobutylidene)-4-methylbenzenesulfonohydrazide (13.88 g, 40.30 mmol, 71.01% yield) as a white solid. $^1$H NMR (400 MHz, DMSO-d$_6$) δ=10.34 (s, 1H), 7.69 (d, J=8.4 Hz, 2H), 7.39 (d, J=8.0 Hz, 3H), 7.34-7.30 (m, 5H), 4.39 (d, J=2.8 Hz, 2H), 4.16-4.13 (m, 1H), 3.12-2.98 (m, 3H), 2.38 (s, 4H) ppm.

Step 2: Preparation of 4-(4,4,5,5-tetramethyl-1,3,2-dioxaborolan-2-yl)picolinonitrile

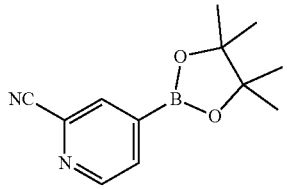 [SMILES: CC1(C)OB(c2ccnc(C#N)c2)OC1(C)C]

To a solution of 4-bromopyridine-2-carbonitrile (20 g, 109.29 mmol) and 4,4,5,5-tetramethyl-2-(4,4,5,5-tetramethyl-1,3,2-dioxaborolan-2-yl)-1,3,2-dioxaborolane (83.26 g, 327.86 mmol) in dioxane (200 mL) was added KOAc (32.18 g, 327.86 mmol) and Pd(dppf)Cl$_2$ (8.00 g, 10.93 mmol). The mixture was stirred at 130° C. for 2 hrs under N$_2$. The mixture was filtered and the filtrate was concentrated under reduced pressure to give a residue. The residue was purified by column chromatography (SiO$_2$, PE:EA=1:0-3:1). The eluent was concentrated to afford 4-(4,4,5,5-tetramethyl-1,3,2-dioxaborolan-2-yl)picolinonitrile (20 g, 86.93 mmol, 79.54% yield) as a white solid. LCMS (ESI) m/z: [M+H]$^+$=231.4. $^1$H NMR (400 MHz, CDCl$_3$) δ=8.75-8.74 (m, 1H), 8.04 (s, 1H), 7.84-7.83 (m, 1H), 1.37 (s, 12H) ppm.

Step 3: Preparation of 4-(3-(benzyloxy)cyclobutyl)picolinonitrile

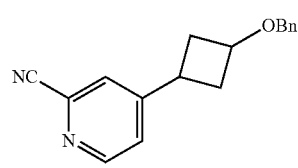 [SMILES: N#Cc1cc(C2CC(OCc3ccccc3)C2)ccn1]

To a solution of N'-(3-(benzyloxy)cyclobutylidene)-4-methylbenzenesulfonohydrazide (12.88 g, 37.40 mmol) and 4-(4,4,5,5-tetramethyl-1,3,2-dioxaborolan-2-yl)picolinonitrile (12.91 g, 56.09 mmol) in dioxane (260 mL) was added Cs$_2$CO$_3$ (36.55 g, 112.19 mmol). The mixture was stirred at 130° C. for 48 hrs. The mixture was concentrated to give a residue. The residue was purified by column chromatography (SiO$_2$, PE:EA=1:0-3:1). The eluent was concentrated to afford 4-(3-(benzyloxy)cyclobutyl)picolinonitrile (1.53 g, 5.79 mmol, 15.48% yield) as red oil which was used for next step directly. LCMS (ESI) m/z: [M+H]$^+$=265.2;

Step 4: Preparation of 4-(3-hydroxycyclobutyl)picolinonitrile

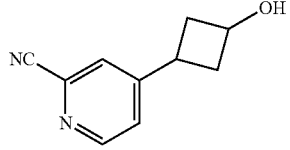 [SMILES: N#Cc1cc(C2CC(O)C2)ccn1]

To a solution of 4-(3-(benzyloxy)cyclobutyl)picolinonitrile (1.53 g, 5.79 mmol) in DCM (45 mL) and H$_2$O (4.5 mL) was added DDQ (7.23 g, 31.84 mmol). The mixture was stirred at 30° C. for 12 hrs. The mixture was diluted with aq. Na$_2$SO$_3$ (100 mL) and extracted with DCM (100 mL*2). The combined organic layers were dried over anhydrous Na$_2$SO$_4$, filtered and concentrated under reduced pressure to give a residue. The residue was purified by column chromatography (SiO$_2$, PE:EA=1:0-0:1). The eluent was concentrated to afford 4-(3-hydroxycyclobutyl)picolinonitrile (670 mg, 3.85 mmol, 66.45% yield) as a yellow solid. LCMS (ESI) m/z: [M+H]$^+$=175.1.

Step 5: Preparation of 4-(3-oxocyclobutyl)picolinonitrile

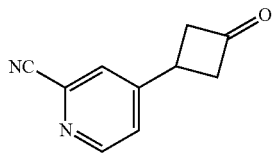 [SMILES: N#Cc1cc(C2CC(=O)C2)ccn1]

To a solution of 4-(3-hydroxycyclobutyl)picolinonitrile (670 mg, 3.85 mmol) in DCM (7 mL) was added Dess-martin (4.89 g, 11.54 mmol) at 0° C. The mixture was stirred at 30° C. for 4 hrs. The mixture was added to aq·NaHCO$_3$ to adjust pH=9 and extracted with DCM (50 mL*2). The combined organic layers were dried over anhydrous Na$_2$SO$_4$, filtered and concentrated under reduced pressure to give a residue. The residue was purified by column chromatography (SiO$_2$, PE:EA=10:1). The eluent was concentrated to afford 4-(3-oxocyclobutyl)picolinonitrile (576 mg, 3.35 mmol, 86.98% yield) as a white solid. LCMS (ESI) m/z: [M+H]$^+$=173.2. $^1$H NMR (400 MHz, CDCl$_3$) δ=8.71 (d, J=4.8 Hz, 1H), 7.65 (s, 1H), 7.47-7.46 (m, 1H), 3.74-3.66 (m, 1H), 3.62-3.59 (m, 2H), 3.32-3.25 (m, 2H) ppm.

Step 6: Preparation of 4-(3-(6-((2S,6R)-2,6-dimethylmorpholino)pyridin-2-yl)-3-hydroxycyclobutyl)picolinonitrile

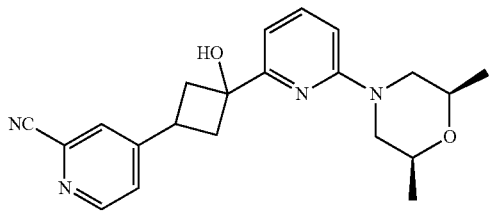 [SMILES: C[C@@H]1CN(c2cccc(C3(O)CC(c4ccnc(C#N)c4)C3)n2)C[C@H](C)O1]

To a solution of (2S,6R)-4-(6-bromo-2-pyridyl)-2,6-dimethyl-morpholine (629.92 mg, 2.32 mmol) (EW9303-1833-P1) in THF (4 mL) was added n-BuLi (2.5 M, 929.24 uL) at −78° C. under N$_2$, the mixture was stirred at −78° C. for 0.5 hr. Then the mixture was added to the solution of 4-(3-oxocyclobutyl)picolinonitrile (200 mg, 1.16 mmol) in THF (4 mL) at −78° C. under N$_2$ and the mixture was stirred at −78° C. for 2 hrs. The mixture was poured into aq·NH$_4$Cl (50 mL), then extracted with EA (50 mL*2), the combined organic layers was dried over Na$_2$SO$_4$, filtered and concentrated under vacuum to give a residue. The residue was purified by column chromatography (SiO$_2$, PE:EA=1:0-1:1). The eluent was concentrated to afford 4-(3-(6-((2S,6R)-2,6-dimethylmorpholino)pyridin-2-yl)-3-hydroxycyclobutyl)picolinonitrile (455 mg, crude) as a yellow solid. LCMS (ESI) m/z: [M+H]$^+$=365.1. $^1$H NMR (400 MHz, DMSO-d$_6$) δ=8.67 (d, J=4.4 Hz, 1H), 8.08 (s, 1H), 7.71-7.69 (m, 1H), 7.57-7.53 (m, 1H), 6.92 (d, J=7.2 Hz, 1H), 6.73 (d, J=8.8 Hz, 1H), 5.82 (s, 1H), 4.20-4.17 (m, 2H), 3.66-3.63 (m, 2H), 3.50 (m, 1H), 2.97-2.92 (m, 2H), 2.42-2.37 (m, 4H), 1.18 (d, J=6.0 Hz, 6H) ppm.

Step 7: Preparation of O-(3-(2-cyanopyridin-4-yl)-1-(6-((2S,6R)-2,6-dimethylmorpholino)pyridin-2-yl)cyclobutyl)S-methyl carbonodithioate

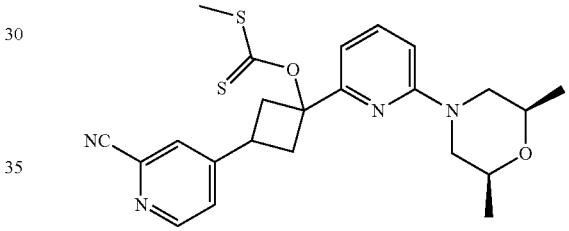

To a solution of NaH (111.12 mg, 2.78 mmol, 60% purity) in THF (4 mL) was added a solution of 4-(3-(6-((2S,6R)-2,6-dimethylmorpholino)pyridin-2-yl)-3-hydroxycyclobutyl)picolinonitrile (405 mg, 1.11 mmol) in THF (4 mL) dropwise at 0° C. under N$_2$, the mixture was stirred at 0° C. for 0.5 hr under N$_2$, then CS$_2$ (359.27 uL, 5.95 mmol) was added dropwise at 0° C., the mixture was stirred at 0° C. for 1 hr. Then MeI (179.88 uL, 2.89 mmol) was added to the mixture dropwise at 0° C., the mixture was stirred at 0° C. for 1 hr. The mixture was poured into aq·NH$_4$Cl (50 mL) and extracted with EA (50 mL*2). The combined organic layers were dried over Na$_2$SO$_4$, filtered and concentrated under reduced pressure to give a residue. The residue was purified by column chromatography (SiO$_2$, PE:EA=1:0-3:1). The eluent was concentrated to afford O-(3-(2-cyanopyridin-4-yl)-1-(6-((2S,6R)-2,6-dimethylmorpholino)pyridin-2-yl)cyclobutyl)S-methyl carbonodithioate (490 mg, 1.08 mmol, 96.99% yield) as a yellow solid. LCMS (ESI) m/z: [M+H]$^+$=455.0. $^1$H NMR (400 MHz, CDCl$_3$) δ=8.66 (d, J=5.2 Hz, 1H), 7.61 (s, 1H), 7.51-7.47 (m, 1H), 7.43-7.42 (m, 1H), 6.65 (d, J=7.6 Hz, 1H), 6.55 (d, J=8.4 Hz, 1H), 4.12-4.08 (m, 2H), 3.77-3.76 (m, 2H), 3.69 (s, 1H), 3.43-3.40 (m, 2H), 2.80-2.74 (m, 2H), 2.61-2.55 (m, 5H), 1.30 (d, J=6.0 Hz, 6H) ppm.

Step 8: Preparation of 4-(3-(6-((2S,6R)-2,6-dimethylmorpholino)pyridin-2-yl)cyclobutyl)picolinonitrile

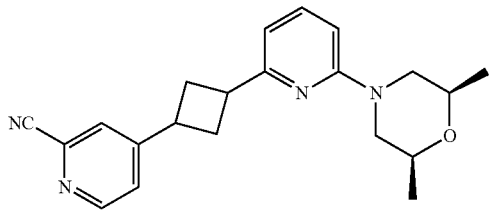 [SMILES: C[C@@H]1CN(c2cccc(C3CC(c4ccnc(C#N)c4)C3)n2)C[C@H](C)O1]

To a solution of O-(3-(2-cyanopyridin-4-yl)-1-(6-((2S,6R)-2,6-dimethylmorpholino)pyridin-2-yl)cyclobutyl)S-methyl carbonodithioate (300 mg, 659.91 umol) in toluene (7.5 mL) was added Bu₃SnH (663.64 uL, 2.51 mmol), then AIBN (21.67 mg, 131.98 umol) was added to the mixture. The reaction mixture was stirred at 110° C. for 2 hrs. The mixture was quenched with sat·KF 50 mL and extracted with EA (50 mL*3). The combined organic layers were dried over Na₂SO₄, filtered and concentrated under reduced pressure to give a residue. The residue was purified by column chromatography (SiO₂, PE:EA=1:0-3:1). The eluent was concentrated to afford 4-(3-(6-((2S,6R)-2,6-dimethylmorpholino)pyridin-2-yl)cyclobutyl)picolinonitrile (150 mg, 430.49 umol, 65.23% yield) as a yellow solid. LCMS (ESI) m/z: [M+H]⁺=349.2. ¹H NMR (400 MHz, CDCl₃) δ=8.65-8.61 (m, 1H), 7.65-7.64 (m, 1H), 7.48-7.41 (m, 2H), 6.56-6.47 (m, 2H), 4.14-4.09 (m, 2H), 3.77-3.74 (m, 2H), 2.78-2.75 (m, 2H), 2.55-2.49 (m, 4H), 1.31-1.28 (m, 6H) ppm.

Step 9: Preparation of tert-butyl ((4-(3-(6-((2S,6R)-2,6-dimethylmorpholino)pyridin-2-yl)cyclobutyl)pyridin-2-yl)methyl)carbamate

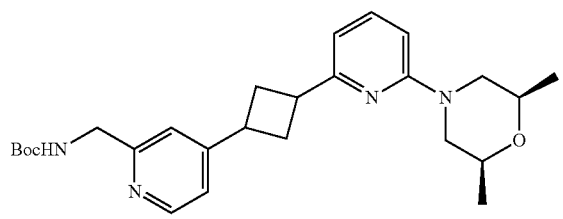 [SMILES: C[C@@H]1CN(c2cccc(C3CC(c4ccnc(CNC(=O)OC(C)(C)C)c4)C3)n2)C[C@H](C)O1]

To a solution of 4-(3-(6-((2S,6R)-2,6-dimethylmorpholino)pyridin-2-yl)cyclobutyl)picolinonitrile (150 mg, 430.49 umol) in MeOH (3 mL) was added Boc₂O (197.80 uL, 860.98 umol), TEA (179.76 uL) and Raney-Ni (100 mg, 1.17 mmol). The suspension was degassed under vacuum and purged with H₂ several times. The mixture was stirred under H2 (15 psi) at 25° C. for 2 hours. The mixture was diluted with MeOH (10 mL) and stranded for 10 min, then the supernatant was removed and filtered. Repeat this work up for 3 times. The filtrate was concentrated to afford the crude product. The crude product was purified by column chromatography (SiO₂, PE:EA=1:0-1:1). The eluent was concentrated to afford tert-butyl ((4-(3-(6-((2S,6R)-2,6-dimethylmorpholino)pyridin-2-yl)cyclobutyl)pyridin-2-yl)methyl)carbamate (140 mg, 309.33 umol, 71.86% yield) as colorless oil. LCMS (ESI) m/z: [M+H]⁺=453.3. ¹H NMR (400 MHz, CDCl₃) δ=8.48-8.44 (m, 1H), 7.44-7.40 (m, 1H), 7.22-7.15 (m, 2H), 6.57-6.45 (m, 2H), 5.59 (br d, J=2.4 Hz, 1H), 4.45-4.43 (m, 2H), 4.14-4.10 (m, 2H), 3.77-3.73 (m, 2H), 2.77-2.72 (m, 2H), 2.54-2.46 (m, 4H), 1.31-1.27 (m, 6H) ppm. Chiral SFC: AD-3_5CM_ETOH (DEA)_5_40_3ML_T35.M, Rt=1.198 mins, 1.504 mins.

Step 10: Preparation of tert-butyl ((4-((1R,3r)-3-(6-((2S,6R)-2,6-dimethylmorpholino)pyridin-2-yl)cyclobutyl)pyridin-2-yl)methyl)carbamate and tert-butyl ((4-((1S,3s)-3-(6-((2S,6R)-2,6-dimethylmorpholino)pyridin-2-yl)cyclobutyl)pyridin-2-yl)methyl)carbamate

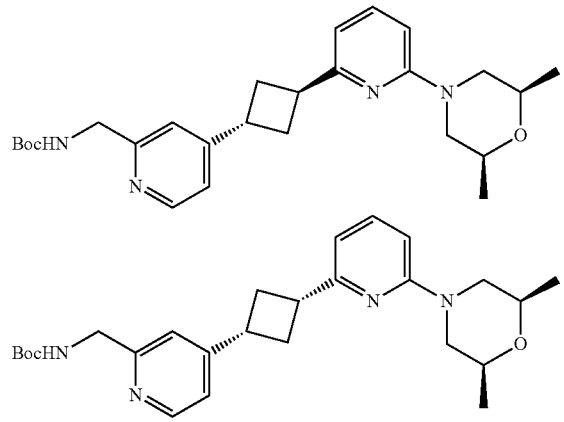

4-(3-(6-((2S,6R)-2,6-dimethylmorpholino)pyridin-2-yl)cyclobutyl)picolinonitrile (140 mg, 309.33 umol) was separated by Chiral SFC (column: DAICEL CHIRALPAK AD (250 mm*30 mm, 10 um); mobile phase: [0.1% NH₃H₂O ETOH]; B %: 30%-30%, 4.3 min). The eluent of peak 1 was concentrated to afford tert-butyl ((4-((1R,3r)-3-(6-((2S,6R)-2,6-dimethylmorpholino)pyridin-2-yl)cyclobutyl)pyridin-2-yl)methyl)carbamate and tert-butyl (40 mg, 88.38 umol, 28.57% yield) as colorless oil. LCMS (ESI) m/z: [M+H]⁺=453.3. ¹H NMR (400 MHz, CDCl₃) δ=8.47 (d, J=4.8 Hz, 1H), 7.47-7.43 (m, 1H), 7.21 (s, 1H), 7.14 (d, J=5.2 Hz, 1H), 6.57-6.48 (m, 2H), 5.58 (br s, 1H), 4.45 (br d, J=5.2 Hz, 2H), 4.16 (br d, J=11.6 Hz, 2H), 3.79-3.75 (m, 3H), 2.81-2.77 (m, 2H), 2.56-2.51 (m, 4H), 1.48 (s, 9H), 1.30 (d, J=6.4 Hz, 6H) ppm. Chiral SFC: AD-3_5CM_ETOH (DEA)_5_40_3ML_T35.M; Rt=1.177 mins, ee %=98.82%.

The eluent of peak 2 was concentrated to afford tert-butyl ((4-((1S,3s)-3-(6-((2S,6R)-2,6-dimethylmorpholino)pyridin-2-yl)cyclobutyl)pyridin-2-yl)methyl)carbamate. (86 mg, 189.11 umol, 61.13% yield) as colorless oil. LCMS (ESI) m/z: [M+H]⁺=453.3. ¹H NMR (400 MHz, CDCl₃) δ=8.45 (d, J=4.8 Hz, 1H), 7.44-7.40 (m, 1H), 7.17 (d, J=5.2 Hz, 1H), 7.13 (s, 1H), 6.53-6.45 (m, 2H), 5.57 (br s, 1H), 4.43 (br d, J=5.2 Hz, 2H), 4.13-4.10 (m, 2H), 3.75-3.73 (m, 2H), 2.74-2.71 (m, 2H), 2.54-2.46 (m, 4H), 1.47 (s, 9H), 1.28 (d, J=6.4 Hz, 6H) ppm. Chiral SFC: AD-3_5CM_ETOH (DEA)_5_40_3ML_T35.M: Rt=1.505 mins, ee %=100%.

Step 11: Preparation of 4-((1R,3r)-3-(6-((2S,6R)-2,6-dimethylmorpholino)pyridin-2-yl)cyclobutyl)pyridin-2-methamine

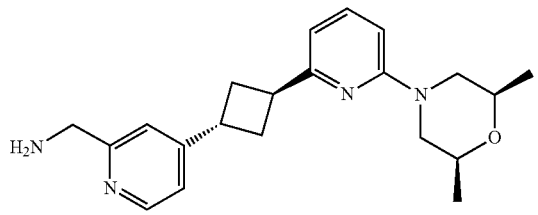 [SMILES: C[C@@H]1CN(c2cccc([C@H]3C[C@H](c4ccnc(CN)c4)C3)n2)C[C@H](C)O1]

A solution of ((4-((1R,3r)-3-(6-((2S,6R)-2,6-dimethylmorpholino)pyridin-2-yl)cyclobutyl)pyridin-2-yl)methyl)carbamate and tert-butyl (40 mg, 88.38 umol) in HCl/dioxane (4 M, 1 mL). The mixture was stirred at 25° C. for 1 hr. The mixture was concentrated to afford 4-((1R,3r)-3-(6-((2S,6R)-2,6-dimethylmorpholino)pyridin-2-yl)cyclobutyl)pyridin-2-methamine (35 mg, crude, HCl) as colorless oil. LCMS (ESI) m/z: [M+H]$^+$=353.3.

Step 12: Preparation of compound 210 (R)-9-bromo-4-fluoro-N-((2-(7-((S)-2-(fluoromethyl)azetidin-1-yl)-2,3-dihydro-4H-pyrido[3,2-b][1,4]oxazin-4-yl)-1,6-naphthyridin-7-yl)methyl)-3,4-dihydro-2H-benzo[b][1,4]oxathiepine-7-carboxamide 5,5-dioxide

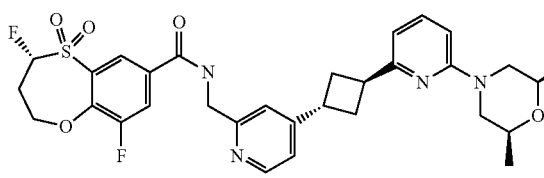

To a solution of 4-((1R,3r)-3-(6-((2S,6R)-2,6-dimethylmorpholino)pyridin-2-yl)cyclobutyl)pyridin-2-amine. (35 mg, 89.99 umol) and (4R)-4,9-difluoro-5,5-dioxo-3,4-dihydro-2H-1,5λ$^6$-benzoxathiepine-7-carboxylic acid (25 mg, 89.85 umol) (Intermediate 2) in DCM (1 mL) was added HOBt (18.21 mg, 134.78 umol), DIEA (78.25 uL, 449.27 umol) and EDCl (25.84 mg, 134.78 umol). The mixture was stirred at 25° C. for 3 hrs. The mixture was diluted with aq·NaHCO$_3$ (5 mL) and extracted with DCM (5 mL*3). The combined organic layers were dried over anhydrous Na$_2$SO$_4$, filtered and concentrated under reduced pressure to give a residue. The residue was purified by reversed-phase (0.1% FA condition). The eluent was concentrated to remove the ACN and lyophilized to afford (R)-9-bromo-4-fluoro-N-((2-(7-((S)-2-(fluoromethyl)azetidin-1-yl)-2,3-dihydro-4H-pyrido[3,2-b][1,4]oxazin-4-yl)-1,6-naphthyridin-7-yl)methyl)-3,4-dihydro-2H-benzo[b][1,4]oxathiepine-7-carboxamide 5,5-dioxide (14.02 mg, 21.95 umol, 24.43% yield) as a white solid. LCMS (ESI) m/z: [M+H]$^+$=613.2; $^1$H NMR (400 MHz, DMSO-d$_6$) δ=9.50-9.47 (m, 1H), 8.46-8.45 (m, 1H), 8.29-8.24 (m, 2H), 7.49-7.45 (m, 1H), 7.30 (s, 2H), 6.67-6.59 (m, 2H), 6.32-6.21 (m, 1H), 4.61-4.58 (m, 3H), 4.20-4.16 (m, 3H), 3.64-3.60 (m, 1H), 2.61 (br s, 4H), 2.46-2.34 (m, 3H), 1.14 (d, J=6.4 Hz, 6H) ppm. Chiral SFC: IC-3-MeOH+ACN (DEA)-40-3ML-35T.lcm; Rt=1.113 mins, ee %=100%.

Preparation of (R)-9-chloro-N-((2-(6-(difluoromethyl)-2-ethoxypyridin-3-yl)-1,6-naphthyridin-7-yl)methyl)-4-fluoro-3,4-dihydro-2H-benzo[b][1,4]oxathiepine-7-carboxamide 5,5-dioxide (Compound 331)

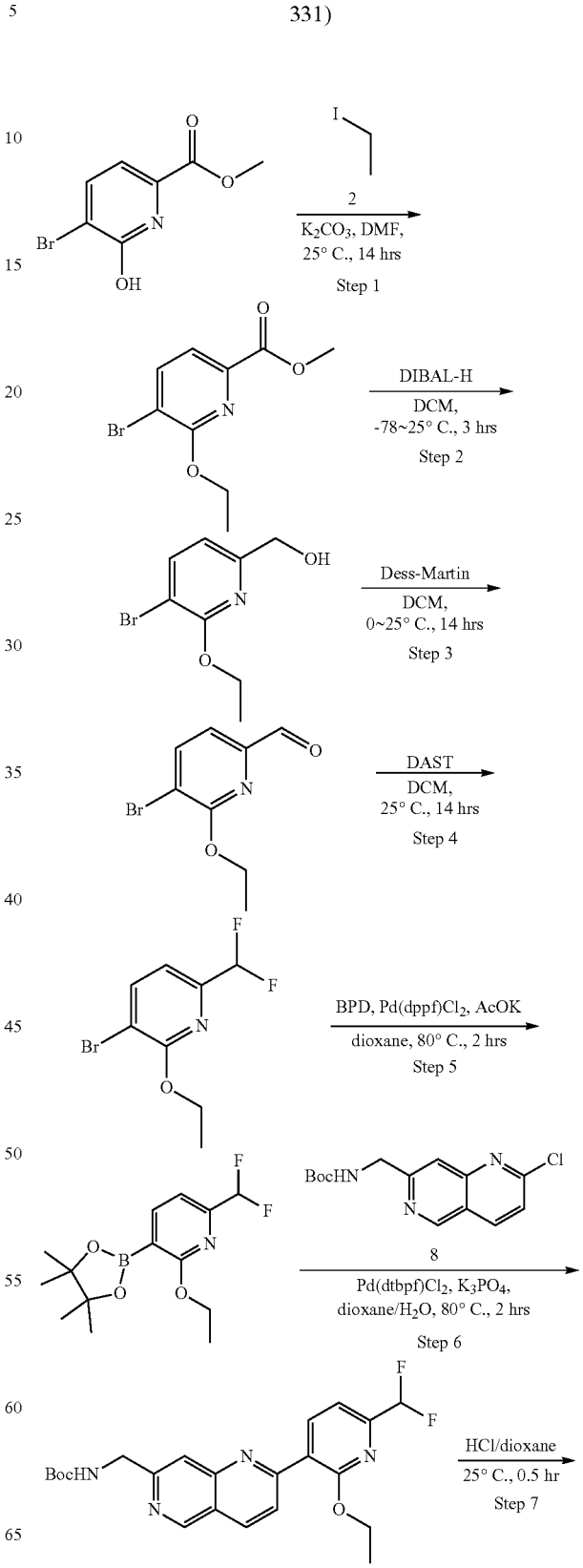

383
-continued

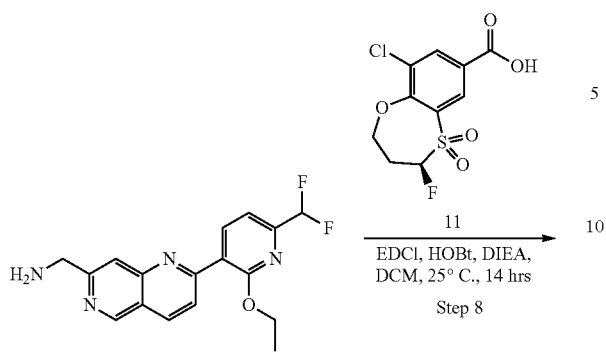

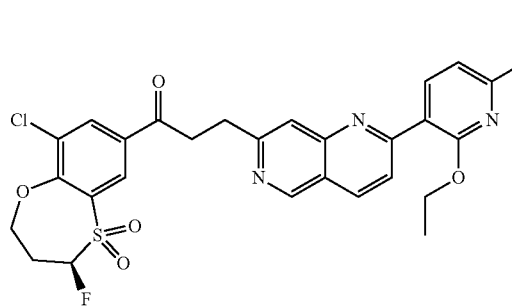

Step 1: Preparation of methyl 5-bromo-6-ethoxypicolinate

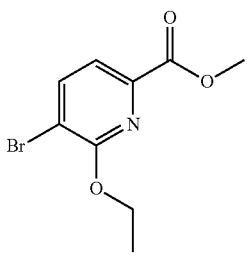

To a solution of methyl 5-bromo-6-hydroxy-pyridine-2-carboxylate (100 g, 430.98 mmol) in DMF (1000 mL) was added K$_2$CO$_3$ (119.13 g, 861.95 mmol) and iodoethane (73.94 g, 474.07 mmol, 37.92 mL). The mixture was stirred at 25° C. for 14 hrs. The reaction mixture was diluted with H$_2$O (1000 mL), extracted with MTBE (1000 mL) and EA (1000 mL*2). The combined organic layers were washed with brine (800 mL*3), dried over anhydrous Na$_2$SO$_4$, filtered and concentrated under reduced pressure to give the residue. The residue was purified by column chromatography (SiO$_2$, Petroleum ether/Ethyl acetate=20/1 to 10/1). The fraction was concentrated under reduced pressure to give methyl 5-bromo-6-ethoxypicolinate (54 g, 140.44 mmol, 48.17% yield) as off-white solid.

LCMS (ESI) m/z: [$^{81}$Br M+H]$^+$=262.1.

$^1$H NMR (400 MHz, DMSO-d$_6$) δ=8.20 (d, J=8.0 Hz, 1H), 7.56 (d, J=8.0 Hz, 1H), 4.44-4.39 (m, 2H), 3.86 (s, 3H), 1.43-1.28 (m, 3H) ppm 384
Step 2: Preparation of (5-bromo-6-ethoxypyridin-2-yl)methanol

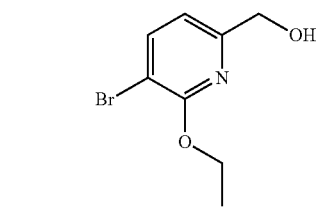

To a solution of methyl 5-bromo-6-ethoxypicolinate (54 g, 207.63 mmol) in DCM (550 mL) was added dropwise DIBAL-H (1 M, 415.25 mL) at −78° C. After the completion of the dropwise addition, the mixture was stirred at 25° C. for 3 hrs. The reaction mixture was poured into HCl (1 M) (1500 mL) and then adjust pH=8 with sat·NaHCO$_3$. The mixture was extracted with DCM (2000 mL*3), dried over anhydrous Na$_2$SO$_4$, filtered and concentrated under reduced pressure to give (5-bromo-6-ethoxypyridin-2-yl)methanol (46 g, 130.01 mmol, 62.62% yield) as yellow oil. $^1$H NMR (400 MHz, DMSO-d$_6$) δ=7.97 (d, J=8.0 Hz, 1H), 6.98 (d, J=8.0 Hz, 1H), 5.66-5.12 (m, 1H), 4.43 (s, 2H), 4.36-4.31 (m, 2H), 1.33-1.30 (m, 3H) ppm.

Step 3: Preparation of 5-bromo-6-ethoxypicolinaldehyde

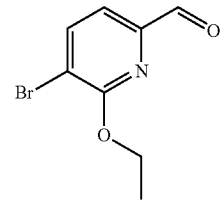

To a solution of (5-bromo-6-ethoxypyridin-2-yl)methanol (46 g, 198.21 mmol) in DCM (460 mL) was added Dess-Martin (100.88 g, 237.86 mmol) at 0° C. The mixture was stirred at 25° C. for 14 hrs. The reaction mixture was filtered to remove the white solid. Then the filtrate was diluted with sat·NaHCO$_3$ (1000 mL) and extracted with DCM (1000 mL*3). The combined organic layers were dried over anhydrous Na$_2$SO$_4$, filtered and concentrated under reduced pressure to give the residue. The residue was purified by column chromatography (SiO$_2$, Petroleum ether/Ethyl acetate=20/1 to 10/1). The fraction was concentrated under reduced pressure to give 5-bromo-6-ethoxypicolinaldehyde (35 g, 152.14 mmol, 76.75% yield) as off-white solid.

$^1$H NMR (400 MHz, DMSO-d$_6$) δ=9.84 (s, 1H), 8.27 (d, J=8.0 Hz, 1H), 7.46 (d, J=8.0 Hz, 1H), 4.49-4.44 (m, 2H), 1.40-1.36 (m, 3H) ppm

Step 4: Preparation of 3-bromo-6-(difluoromethyl)-2-ethoxypyridine

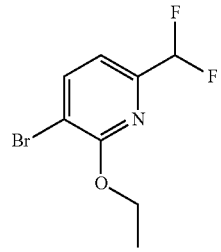

To a solution of 5-bromo-6-ethoxypicolinaldehyde (35 g, 152.14 mmol) in DCM (350 mL) was added DAST (60.30 mL, 456.41 mmol). The mixture was stirred at 25° C. for 14 hrs. The reaction mixture was poured into saturated sat·NaHCO$_3$ (500 mL) and extracted with DCM (500 mL*3). The combined organic layer was dried over anhydrous Na$_2$SO$_4$, filtered and concentrated in vacuum to give the residue. The residue was purified by column chromatography (SiO$_2$, Petroleum ether/Ethyl acetate=10/1 to 3/1). The fraction was concentrated under reduced pressure to give 3-bromo-6-(difluoromethyl)-2-ethoxypyridine (29 g, 100.21 mmol, 65.87% yield) as yellow oil.

LCMS (ESI) m/z: [$^{81}$Br M+H]$^+$=252.1.

$^1$H NMR (400 MHz, DMSO-d$_6$) δ=8.20 (d, J=8.0 Hz, 1H), 7.20 (d, J=8.0 Hz, 1H), 7.07-6.66 (m, 1H), 4.42-4.37 (m, 2H), 1.37-1.33 (m, 3H) ppm.

Step 5: Preparation of 6-(difluoromethyl)-2-ethoxy-3-(4,4,5,5-tetramethyl-1,3,2-dioxaborolan-2-yl)pyridine

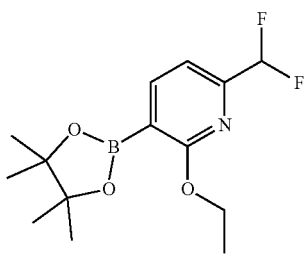 [SMILES: CCOc1nc(C(F)F)ccc1B1OC(C)(C)C(C)(C)O1]

To a solution of 4,4,5,5-tetramethyl-2-(4,4,5,5-tetramethyl-1,3,2-dioxaborolan-2-yl)-1,3,2-dioxaborolane (BPD) (34.96 g, 137.66 mmol) and 3-bromo-6-(difluoromethyl)-2-ethoxypyridine (29 g, 115.05 mmol) in dioxane (400 mL) was added AcOK (33.77 g, 344.15 mmol) and cyclopentyl(diphenyl)phosphane; dichloropalladium; iron (4.20 g, 5.74 mmol) under N$_2$. The reaction mixture was stirred at 80° C. for 2 hrs under N$_2$ atmosphere. The reaction mixture was diluted with EA (100 mL) and then filtered. The filtrate was concentrated in vacuum to give 6-(difluoromethyl)-2-ethoxy-3-(4,4,5,5-tetramethyl-1,3,2-dioxaborolan-2-yl)pyridine (33.5 g, 111.99 mmol, 97.63% yield) as brown oil.

LCMS (ESI) m/z: [M+H]$^+$=300.3.

Step 6: Preparation of tert-butyl ((2-(6-(difluoromethyl)-2-ethoxypyridin-3-yl)-1,6-naphthyridin-7-yl)methyl)carbamate

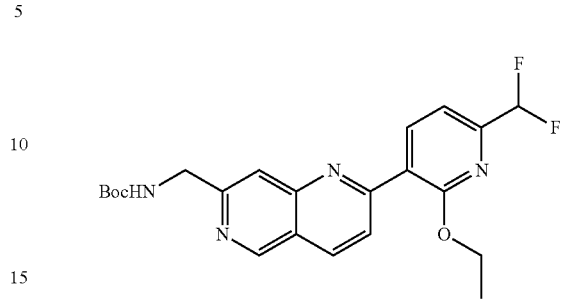

A mixture of (2-chloro-1,6-naphthyridin-7-yl)methanamine (25 g, 85.11 mmol), 6-(difluoromethyl)-2-ethoxy-3-(4,4,5,5-tetramethyl-1,3,2-dioxaborolan-2-yl)pyridine (33.09 g, 110.64 mmol), K$_3$PO$_4$ (54.20 g, 255.32 mmol) and ditert-butyl(cyclopentyl)phosphane; dichloropalladium; iron (2.77 g, 4.26 mmol) in dioxane (400 mL) and H$_2$O (40 mL) was degassed and purged with N$_2$ for 3 times, and then the mixture was stirred at 80° C. for 2 hrs under N$_2$ atmosphere. The reaction mixture was diluted with H$_2$O (300 mL) and extracted with EA (300 mL*3). The combined organic layer was dried over anhydrous Na$_2$SO$_4$, filtered and concentrated under reduced pressure to give the residue. The residue was purified by column chromatography (SiO$_2$, Petroleum ether/Ethyl acetate=1/0 to 1/3). The fraction was concentrated under reduced pressure to give the brown solid. Then PE (100 mL) was added into the brown solid, and then the mixture was stirred for 30 mins. The mixture was filtered to give the solid. The solid was washed with PE (40 mL*2), filtered and concentrated in vacuum to give tert-butyl ((2-(6-(difluoromethyl)-2-ethoxypyridin-3-yl)-1,6-naphthyridin-7-yl)methyl)carbamate (21 g, 41.77 mmol, 49.08% yield) as yellow solid.

LCMS (ESI) m/z: [M+H]$^+$=431.3.

$^1$H NMR (400 MHz, DMSO-d$_6$) δ=9.37 (s, 1H), 8.62 (d, J=8.8 Hz, 1H), 8.46 (d, J=7.6 Hz, 1H), 8.21 (d, J=8.8 Hz, 1H), 7.74 (s, 1H), 7.63-7.61 (m, 1H), 7.48 (d, J=8.0 Hz, 1H), 7.15-6.80 (m, 1H), 4.53-4.47 (m, 2H), 4.47-4.43 (m, 2H), 1.43 (s, 9H), 1.38-1.35 (m, 3H) ppm.

Step 7: Preparation of (2-(6-(difluoromethyl)-2-ethoxypyridin-3-yl)-1,6-naphthyridin-7-yl)methanamine

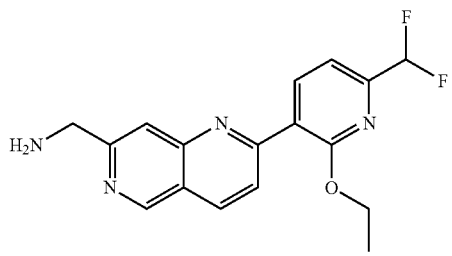 [SMILES: CCOc1nc(C(F)F)ccc1-c1ccc2cnc(CN)cc2n1]

A mixture of tert-butyl ((2-(6-(difluoromethyl)-2-ethoxypyridin-3-yl)-1,6-naphthyridin-7-yl)methyl)carbamate (21 g, 48.79 mmol) in HCl/dioxane (4 M, 180 mL) was stirred at 25° C. for 0.5 hr. The reaction mixture was concentrated under reduced pressure to give (2-(6-(difluoromethyl)-2-ethoxypyridin-3-yl)-1,6-naphthyridin-7-yl)methanamine (17.5 g, 47.71 mmol, 97.80% yield, HCl salt) as yellow solid.

LCMS (ESI) m/z: [M+H]+=331.3.

Step 8: Preparation of (R)-9-chloro-N-((2-(6-(difluoromethyl)-2-ethoxypyridin-3-yl)-1,6-naphthyridin-7-yl)methyl)-4-fluoro-3,4-dihydro-2H-benzo[b][1,4]oxathiepine-7-carboxamide 5,5-dioxide

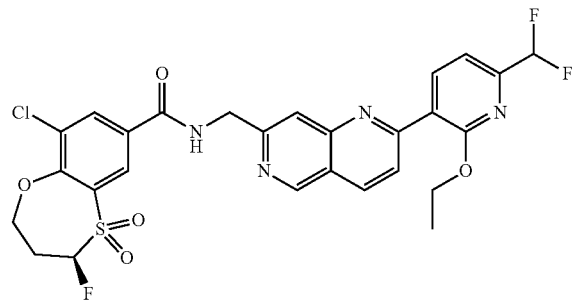 [SMILES: CCOc1nc(C(F)F)ccc1-c1ccc2cnc(CNC(=O)c3cc(Cl)c4c(c3)S(=O)(=O)[C@@H](F)CCO4)cc2n1]

To a solution of (4R)-9-chloro-4-fluoro-5,5-dioxo-3,4-dihydro-2H-1,5benzoxathiepine-7-carboxylic acid (15.47 g, 52.48 mmol) in DCM (30 mL) was added (2-(6-(difluoromethyl)-2-ethoxypyridin-3-yl)-1,6-naphthyridin-7-yl)methanamine (17.5 g, 47.71 mmol), EDCl (13.72 g, 71.57 mmol), HOBt (9.67 g, 71.57 mmol) and DIEA (41.55 mL, 238.55 mmol). The reaction mixture was stirred at 25° C. for 14 hrs. The reaction mixture was diluted with H₂O (100 mL) and extracted with DCM (100 mL*2). The combined organic layer was dried over anhydrous Na₂SO₄, filtered and concentrated under reduced pressure to give the residue. The residue was purified by flash silica gel chromatography (ISCO®; 330 g SepaFlash® Silica Flash Column, Eluent of 0-80% Ethyl acetate/Petroleum ether gradient @ 200 mL/min). Then the fraction was concentrated under reduced pressure to give the residue. The residue was dissolved in MeCN (20 mL) and H₂O (200 mL), then the mixture was concentrated under reduced pressure to remove MeCN and then lyophilized to give Compound 331, (R)-9-chloro-N-((2-(6-(difluoromethyl)-2-ethoxypyridin-3-yl)-1,6-naphthyridin-7-yl)methyl)-4-fluoro-3,4-dihydro-2H-benzo[b][1,4]oxathiepine-7-carboxamide 5,5-dioxide (21.37 g, 35.21 mmol, 73.79% yield) as off-white solid.

LCMS (ESI) m/z: [M+H]+=607.2.

$^1$H NMR (400 MHz, DMSO-d₆) δ=9.69-9.66 (m, 1H), 9.41 (s, 1H), 8.64 (d, J=8.8 Hz, 1H), 8.52 (d, J=2.0 Hz, 1H), 8.50-8.42 (m, 2H), 8.24 (d, J=8.8 Hz, 1H), 7.85 (s, 1H), 7.45 (d, J=7.6 Hz, 1H), 7.13-6.78 (m, 1H), 6.34-6.14 (m, 1H), 4.81 (d, J=5.6 Hz, 2H), 4.63-4.58 (m, 1H), 4.51-4.46 (m, 2H), 4.12-4.06 (m, 1H), 2.93-2.71 (m, 1H), 2.64-2.55 (m, 1H), 1.38-1.34 (m, 3H) ppm.

Chiral SFC: OJ-3-IPA (DEA)-5-40-3ML-35T.lcm, Rt=2.084 mins, ee %=100%.

Preparation of (4R)—N-[[2-[2-(cyclopropylmethoxy)-6-(difluoromethyl)-3-pyridyl]-1,6-naphthyridin-7-yl]methyl]-4,9-difluoro-5,5-dioxo-3,4-dihydro-2H-1,5benzoxathiepine-7-carboxamide (Compound 332)

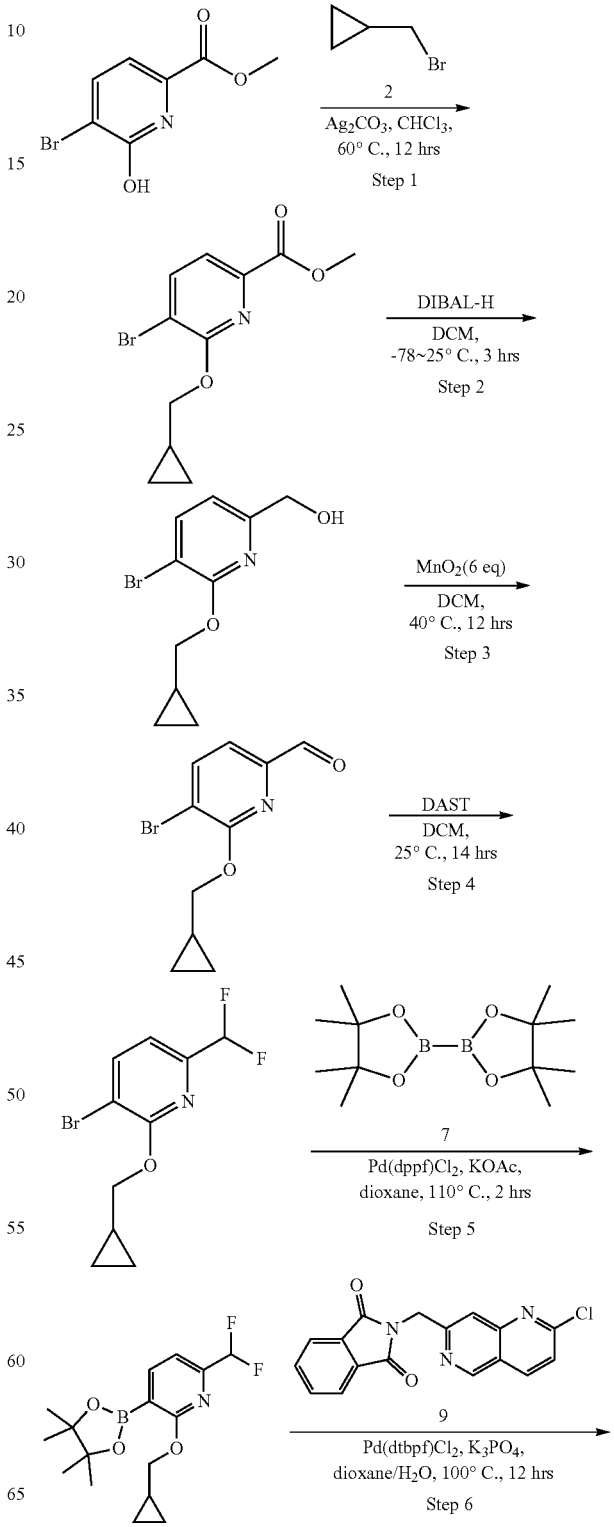

389
-continued

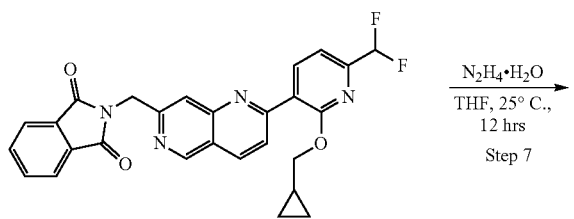

N₂H₄·H₂O
THF, 25° C.,
12 hrs
Step 7

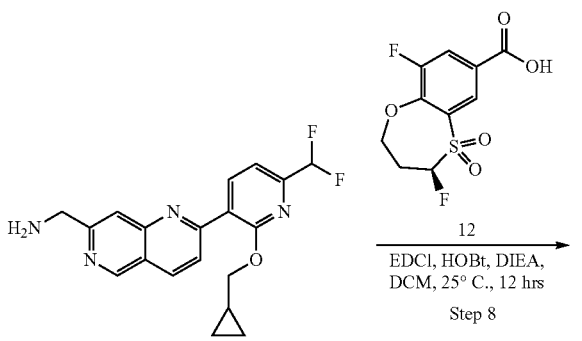

12
EDCl, HOBt, DIEA,
DCM, 25° C., 12 hrs
Step 8

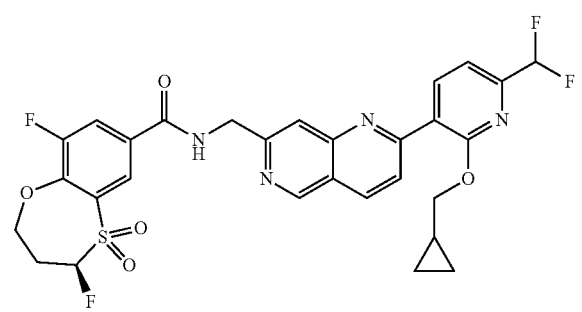

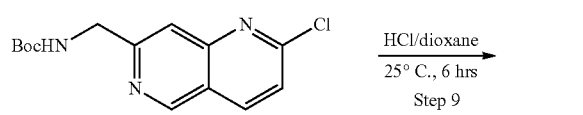

HCl/dioxane
25° C., 6 hrs
Step 9

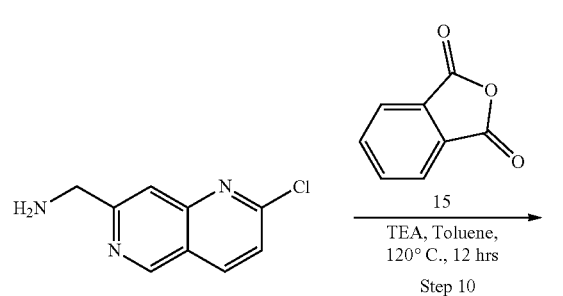

15
TEA, Toluene,
120° C., 12 hrs
Step 10

390

Step 1: Preparation of methyl 5-bromo-6-(cyclopropylmethoxy)pyridine-2-carboxylate

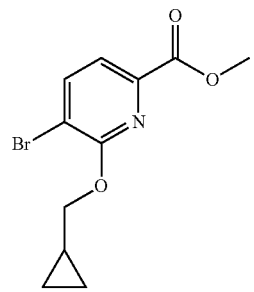 [SMILES: COC(=O)c1ccc(Br)c(OCC2CC2)n1]

To a solution of methyl 5-bromo-6-hydroxy-pyridine-2-carboxylate (146 g, 629.23 mmol) and bromomethylcyclopropane (254.84 g, 1.89 mol, 180.23 mL) in CHCl₃ (1500 mL) was added Ag₂CO₃ (208.21 g, 755.07 mmol), the mixture was stirred at 60° C. for 12 hrs. The reaction mixture was filtered and the filter cake was washed with EA (200 mL*2) to give yellow filtrate. The filtrate was concentrated under reduced pressure to give a yellow oil, which was purified by column chromatography (SiO₂, PE/EA=20:1) and the eluent was concentrated under reduced pressure to give methyl 5-bromo-6-(cyclopropylmethoxy) picolinate (166 g, 580.17 mmol, 92.20% yield) as a light yellow oil $^1$H NMR (400 MHz, DMSO-$d_6$) δ=8.20 (d, J=7.6 Hz, 1H), 7.55 (d, J=7.6 Hz, 1H), 4.22 (d, J=7.2 Hz, 2H), 3.86 (s, 3H), 1.30-1.28 (m, 1H), 0.64-0.50 (m, 2H), 0.47-0.31 (m, 2H) ppm.

Step 2: Preparation of 5-bromo-6-(cyclopropylmethoxy)-2-pyridyl]methanol

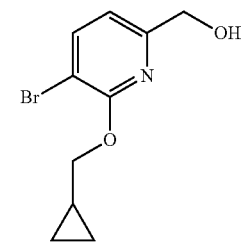

To a solution of methyl 5-bromo-6-(cyclopropylmethoxy) picolinate (83000 mg, 290.09 mmol) in DCM (850 mL) was added DIBAL-H (1 M, 638.19 mL) under N₂ at −60° C., the mixture was warmed to 0° C. over 2 hrs. The reaction mixture was poured into 1 N HCl (1600 mL) slowly and extracted with DCM (500 mL*2), the combined organic layers were concentrated under reduced pressure to give (5-bromo-6-(cyclopropylmethoxy)pyridin-2-yl)methanol (140 g, crude) as a light yellow oil, which was used for next step directly and without further purification.

Step 3: Preparation of 5-bromo-6-(cyclopropylmethoxy)picolinaldehyde

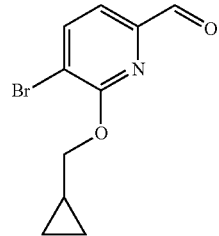 [SMILES: O=Cc1ccc(Br)c(OCC2CC2)n1]

To a solution of (5-bromo-6-(cyclopropylmethoxy)pyridin-2-yl)methanol (140 g, 542.40 mmol) in DCM (1500 mL) was added MnO$_2$ (398.92 g, 4.59 mol), the mixture was warmed to 40° C. for 12 hrs. The reaction mixture was filtered and the filter cake was washed with DCM (2 L), the filtrate was concentrated under reduced pressure to give 5-bromo-6-(cyclopropylmethoxy)picolinaldehyde (144 g, crude) as a light yellow oil, which was used for next step directly and without further purification.

$^1$H NMR (400 MHz, DMSO-d$_6$) δ=9.84 (s, 1H), 8.27 (d, J=7.6 Hz, 1H), 7.46 (d, J=7.6 Hz, 1H), 4.27 (d, J=7.2 Hz, 2H), 1.42-1.21 (m, 1H), 0.65-0.35 (m, 4H) ppm.

Step 4: Preparation of 3-bromo-2-(cyclopropylmethoxy)-6-(difluoromethyl)pyridine

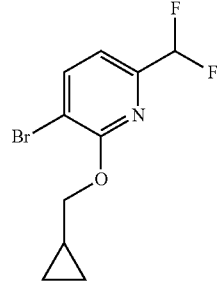 [SMILES: FC(F)c1ccc(Br)c(OCC2CC2)n1]

To a solution of 5-bromo-6-(cyclopropylmethoxy)picolinaldehyde (144 g, 562.29 mmol) in DCM (1500 mL) was added DAST (226.59 g, 1.41 mol) at 0° C., the mixture was stirred at 20° C. for 12 hrs. The reaction mixture was poured into sat. NaHCO$_3$ (2 L) slowly and extracted with DCM (500 mL*2), the combined organic layers were dried over Na$_2$SO$_4$, filtered and concentrated under reduced pressure to give a residue, which was purified by column chromatography (SiO$_2$, PE) and the eluent was concentrated under reduced pressure to give 3-bromo-2-(cyclopropylmethoxy)-6-(difluoromethyl)pyridine (130 g, 466.39 mmol, 82.95% yield) as a light yellow oil.

LCMS (ESI) m/z: [$^{79}$BrM+H]$^+$=278.0.

$^1$H NMR (400 MHz, DMSO-d$_6$) δ=8.21 (d, J=7.6 Hz, 1H), 7.20 (d, J=8.0 Hz, 1H), 7.03-6.64 (m, 1H), 4.21 (d, J=7.2 Hz, 2H), 1.34-1.20 (m, 1H), 0.63-0.50 (m, 2H), 0.44-0.29 (m, 2H) ppm.

Step 5: Preparation of 2-(cyclopropylmethoxy)-6-(difluoromethyl)-3-(4,4,5,5-tetramethyl-1,3,2-dioxaborolan-2-yl)pyridine To a solution of 3-bromo-2-(cyclopropylmethoxy)-6-(difluoromethyl)pyridine (20 g, 71.92 mmol) in dioxane (400 mL) was added 4,4,5,5-tetramethyl-2-(4,4,5,5-tetramethyl-1,3,2-dioxaborolan-2-yl)-1,3,2-dioxaborolane (21.92 g, 86.30 mmol), Pd(dppf)Cl$_2$ (5.26 g, 7.19 mmol) and KOAc (21.17 g, 215.76 mmol). The mixture was degassed and purged with N$_2$ for 3 times, and the mixture was stirred at 110° C. for 2 hrs under N$_2$. The reaction mixture was filtered and the filter cake was washed with EA (30 mL*3). The combined filtrate were concentrated under reduced pressure to give 2-(cyclopropylmethoxy)-6-(difluoromethyl)-3-(4,4,5,5-tetramethyl-1,3,2-dioxaborolan-2-yl)pyridine (23.38 g, crude) as brown oil, which was used for next step directly and without further purification.

Step 6: Preparation of 2-[[2-[2-(cyclopropylmethoxy)-6-(difluoromethyl)-3-pyridyl]-1,6-naphthyridin-7-yl]methyl]isoindoline-1,3-dione To a solution of 2-(cyclopropylmethoxy)-6-(difluoromethyl)-3-(4,4,5,5-tetramethyl-1,3,2-dioxaborolan-2-yl)pyridine (22.60 g, 69.50 mmol) in dioxane (300 mL) and H$_2$O (30 mL) was added 4,2-[(2-chloro-1,6-naphthyridin-7-yl)methyl]isoindoline-1,3-dione (15 g, 46.33 mmol), ditert-butyl(cyclopentyl)phosphane; dichloropalladium; iron (3.02 g, 4.63 mmol) and K$_3$PO$_4$ (29.51 g, 139.00 mmol). The mixture was degassed and purged with N$_2$ for 3 times, and the mixture was stirred at 80° C. for 12 hrs under N$_2$. The reaction mixture was concentrated under reduced pressure to give a residue. The residue was diluted with H$_2$O (200 mL) and extracted with EA (300 mL*2). The combined layers were washed with brine (500 mL*2), dried over Na$_2$SO$_4$, filtered and concentrated under reduced pressure to give the crude, which was purified by column chromatography (SiO$_2$, Petroleum ether/Ethyl acetate=10/1 to 1/1), the eluent was concentrated under reduced pressure to give 2-((2-(2-(cyclopropylmethoxy)-6-(difluoromethyl)pyridin-3-yl)-1,6-naphthyridin-7-yl)methyl)isoindoline-1,3-dione (16.31 g, 33.53 mmol, 72.36% yield) as a yellow solid LCMS (ESI) m/z: [M+H]$^+$=487.2.

$^1$H NMR (400 MHz, DMSO-d$_6$) δ=9.35 (s, 1H), 8.64-8.62 (m, 1H), 8.47 (d, J=7.6 Hz, 1H), 8.29-8.26 (m, 1H), 8.02-7.84 (m, 5H), 7.45 (d, J=7.6 Hz, 1H), 7.14-6.78 (m, 1H), 5.12 (s, 2H), 4.31-4.29 (m, 2H), 1.34-1.26 (m, 1H), 0.60-0.50 (m, 2H), 0.42-0.35 (m, 2H) ppm.

Step 7: Preparation of [2-[2-(cyclopropylmethoxy)-6-(difluoromethyl)-3-pyridyl]-1,6-naphthyridin-7-yl]methanamine

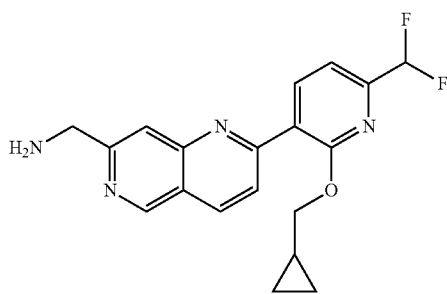 [SMILES: NCc1cc2nc(-c3ccc(C(F)F)nc3OCC3CC3)ccc2cn1]

To a solution of 2-((2-(2-(cyclopropylmethoxy)-6-(difluoromethyl)pyridin-3-yl)-1,6-naphthyridin-7-yl)methyl)isoindoline-1,3-dione (16.31 g, 33.53 mmol) in THF (200 mL) was added NH$_2$NH$_2$·H$_2$O (35.62 g, 697.31 mmol). The mixture was stirred at 25° C. for 12 hrs. The reaction mixture was poured into H$_2$O (300 mL) and extracted with EA (200 mL*3). The combined organic layers were washed with brine (300 mL*2), dried over Na$_2$SO$_4$, filtered and concentrated under reduced pressure to give (2-(2-(cyclopropylmethoxy)-6-(difluoromethyl)pyridin-3-yl)-1,6-naphthyridin-7-yl)methanamine (11.71 g, 32.86 mmol, 98.01% yield) as a yellow solid, which was used for next step directly and without further purification.

LCMS (ESI) m/z: [M+H]$^+$=357.1.

1H NMR (400 MHz, DMSO-d$_6$) δ=9.36 (s, 1H), 8.63-9.61 (m, 1H), 8.48 (d, J=7.6 Hz, 1H), 8.25-8.23 (m, 1H), 7.99 (s, 1H), 7.50-7.48 (m, 1H), 7.21-6.77 (m, 1H), 4.32-4.30 (m, 2H), 4.09-3.98 (m, 2H), 2.23-2.00 (m, 2H), 1.41-1.24 (m, 1H), 0.67-0.49 (m, 2H), 0.40-0.39 (m, 2H) ppm.

Step 8: Preparation of (4R)—N-[[2-[2-(cyclopropylmethoxy)-6-(difluoromethyl)-3-pyridyl]-1,6-naphthyridin-7-yl]methyl]-4,9-difluoro-5,5-dioxo-3,4-dihydro-2H-1,5benzoxathiepine-7-carboxamide

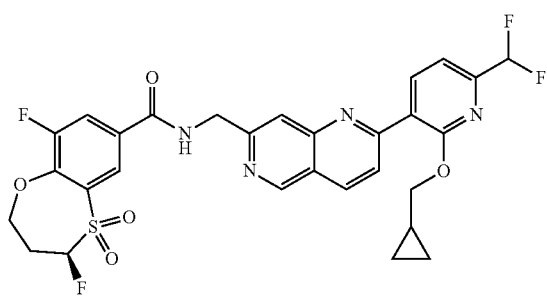 [SMILES: O=C(NCc1cc2nc(-c3ccc(C(F)F)nc3OCC3CC3)ccc2cn1)c1cc(F)c2c(c1)S(=O)(=O)[C@@H](F)CCO2]

To a solution of (4R)-9-chloro-4-fluoro-5,5-dioxo-3,4-dihydro-2H-1,5benzoxathiepine-7-carboxylic acid (9.14 g, 32.86 mmol) in DCM (150 mL) was added EDCl (8.19 g, 42.72 mmol), HOBt (5.77 g, 42.72 mmol) and DIEA (12.74 g, 98.58 mmol), then (2-(2-(cyclopropylmethoxy)-6-(difluoromethyl)pyridin-3-yl)-1,6-naphthyridin-7-yl)methanamine (11.71 g, 32.86 mmol) was added. The mixture was stirred at 25° C. for 12 hrs. The reaction mixture was diluted with H$_2$O (200 mL) and extracted with DCM (100 mL*2). The combined organic layers were washed with brine (300 mL*2), dried over Na$_2$SO$_4$, filtered and concentrated under reduced pressure to give a residue, which was purified by column chromatography (SiO$_2$, PE/EA=10/1 to 1/2), the eluent was concentrated under reduced pressure to give a yellow gum. The gum was dissolved in MeCN (100 mL) and H$_2$O (300 mL), then the solution was concentrated under reduced pressure to remove MeCN and lyophilized to give the title compound, Compound 332 (16.34 g, 26.37 mmol, 80.24% yield) as an off-white solid.

LCMS (ESI) m/z: [M+H]$^+$=617.3.

$^1$H NMR (400 MHz, DMSO-d$_6$) δ=9.69-9.67 (m, 1H), 9.41 (s, 1H), 8.65 (d, J=8.4 Hz, 1H), 8.46 (d, J=7.6 Hz, 1H), 8.38-8.23 (m, 3H), 7.84 (s, 1H), 7.46-7.44 (m, 1H), 7.17-6.76 (m, 1H), 6.41-6.16 (m, 1H), 4.81 (d, J=5.6 Hz, 2H), 4.63-4.59 (m, 1H), 4.31-4.29 (m, 2H), 4.19-4.16 (m, 1H), 2.93-2.71 (m, 1H), 2.65-2.53 (m, 1H), 1.39-1.22 (m, 1H), 0.59-0.51 (m, 2H), 0.40-0.37 (m, 2H) ppm.

Chiral SFC: AD-3-IPA+ACN(DEA)-40-3ML-35T.lcm, Rt=0.836 min, ee %=100.00%

Step 9: Preparation of (2-chloro-1,6-naphthyridin-7-yl)methanamine

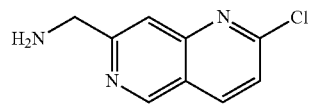 [SMILES: NCc1cc2nc(Cl)ccc2cn1]

A mixture of tert-butyl ((2-chloro-1,6-naphthyridin-7-yl)methyl)carbamate (30 g, 102.13 mmol) in HCl/dioxane (4 M, 100 mL) was stirred at 25° C. for 6 hrs. The reaction mixture was concentrated under reduced pressure to give (2-chloro-1,6-naphthyridin-7-yl)methanamine (23.5 g, 102.13 mmol, 100.00% yield, HCl Salt) as a brown solid, which was used for next step directly and without further purification.

LCMS (ESI) m/z: [M+H]$^+$=294.1.

$^1$H NMR (400 MHz, DMSO-d$_6$) δ=9.53 (s, 1H), 8.73-8.70 (m, 3H), 8.05 (s, 1H), 7.82 (d, J=8.8 Hz, 1H), 4.39-4.34 (m, 2H) ppm.

Step 10: Preparation of Intermediate 4,2-[(2-chloro-1,6-naphthyridin-7-yl)methyl]isoindoline-1,3-dione

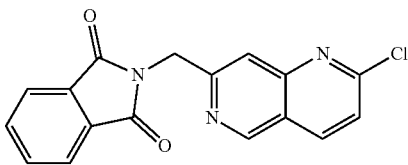 [SMILES: O=C1c2ccccc2C(=O)N1Cc1cc2nc(Cl)ccc2cn1]

To a solution of (2-chloro-1,6-naphthyridin-7-yl)methanamine (23.5 g, 102.13 mmol) in toluene (700 mL) was added TEA (31.00 g, 306.40 mmol) and isobenzofuran-1,3-dione (15.13 g, 102.13 mmol). The mixture was stirred at 120° C. for 2 hrs. The reaction mixture was concentrated under reduced pressure to remove toluene and the residue was diluted with H₂O (100 mL) and extracted with EA (200 mL*3). The combined organic layers were washed with brine (500 mL), dried over Na₂SO₄, filtered and concentrated under reduced pressure to give a residue, which was purified by column chromatography (SiO₂, PE/EA=10/1 to 1/1). The eluent was concentrated under reduced pressure to give 9 (25.35 g, 78.31 mmol, 76.67% yield) was obtained as a yellow solid.

LCMS (ESI) m/z: [M+H]⁺=324.1.

¹H NMR (400 MHz, DMSO-d₆) δ=9.35 (s, 1H), 8.62-8.60 (m, 1H), 8.06-7.83 (m, 5H), 7.75-7.73 (m, 1H), 5.10 (s, 2H) ppm.

Preparation of (4R)—N-[[2-[6-[(2R,6S)-2,6-dimethylmorpholin-4-yl]-2-pyridyl]pyrido[3,4-b]pyrazin-7-yl]methyl]-4,9-difluoro-5,5-dioxo-3,4-dihydro-2H-1,5λ6-benzoxathiepine-7-carboxamide (Compound 405)

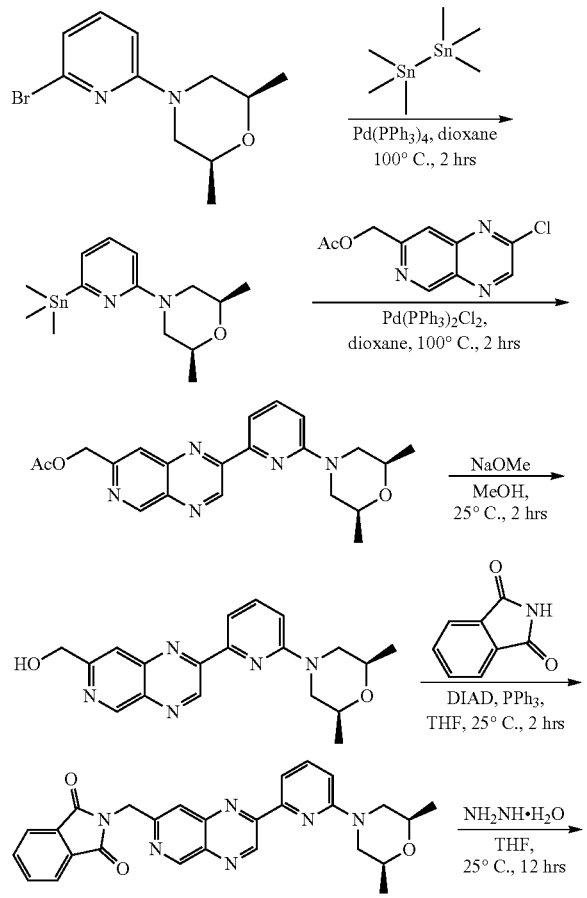

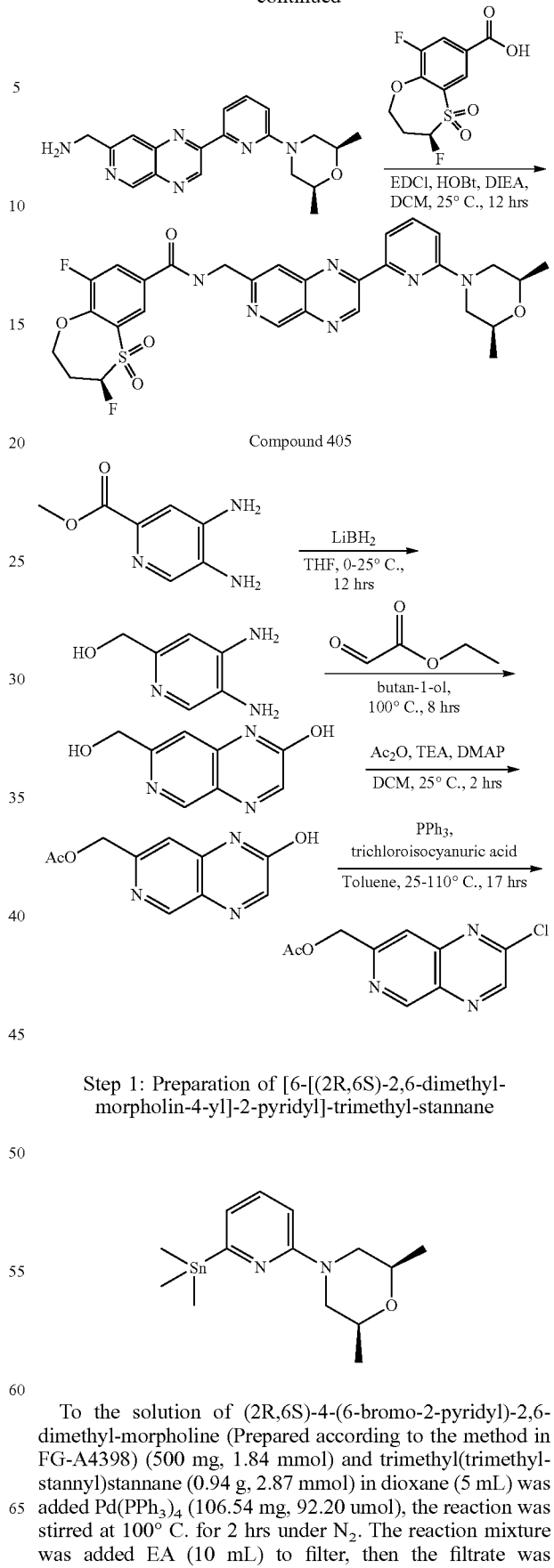

Compound 405

Step 1: Preparation of [6-[(2R,6S)-2,6-dimethyl-morpholin-4-yl]-2-pyridyl]-trimethyl-stannane To the solution of (2R,6S)-4-(6-bromo-2-pyridyl)-2,6-dimethyl-morpholine (Prepared according to the method in FG-A4398) (500 mg, 1.84 mmol) and trimethyl(trimethyl-stannyl)stannane (0.94 g, 2.87 mmol) in dioxane (5 mL) was added Pd(PPh₃)₄ (106.54 mg, 92.20 umol), the reaction was stirred at 100° C. for 2 hrs under N₂. The reaction mixture was added EA (10 mL) to filter, then the filtrate was concentrated to give [6-[(2R,6S)-2,6-dimethylmorpholin-4-yl]-2-pyridyl]-trimethyl-stannane (650 mg, crude) as a yellow solid, which was used into the next step without further purification.

LCMS (ESI) m/z: [M+H]$^+$=357.0.

Step 2: Preparation of [2-[6-[(2R,6S)-2,6-dimethyl-morpholin-4-yl]-2-pyridyl]pyrido[3,4-b]pyrazin-7-yl]methyl Acetate

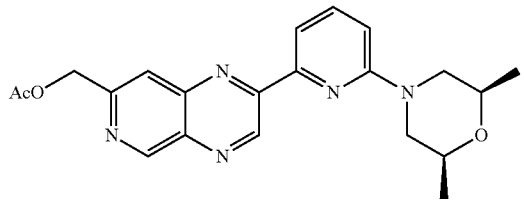 [SMILES: CC(=O)OCc1cc2nc(-c3cccc(N4C[C@@H](C)O[C@@H](C)C4)n3)cnc2cn1]

To the solution of 4 (650 mg, 1.83 mmol) in dioxane (6 mL) was added (2-chloropyrido[3,4-b]pyrazin-7-yl)methyl acetate (290.03 mg, 1.22 mmol) and dichloropalladium; triphenylphosphane (85.66 mg, 122.04 umol), the reaction was stirred at 100° C. for 12 hrs under N$_2$. The reaction mixture was poured into water (10 mL), the solution was extracted with EA (10 mL*3), the combined organic layer was washed with brine (10 mL), dried over Na$_2$SO$_4$, filtered and concentrated to give a residue. The residue was purified by column chromatography (SiO2, Petroleum ether/Ethyl acetate=10:1-5:1), the solution was concentrated to give [2-[6-[(2R,6S)-2,6-dimethylmorpholin-4-yl]-2-pyridyl]pyrido[3,4-b]pyrazin-7-yl]methyl acetate (160 mg, crude) as a yellow solid.

LCMS (ESI) m/z: [M+H]$^+$=294.1.

Step 3: Preparation of [2-[6-[(2R,6S)-2,6-dimethyl-morpholin-4-yl]-2-pyridyl]pyrido[3,4-b]pyrazin-7-yl]methanol

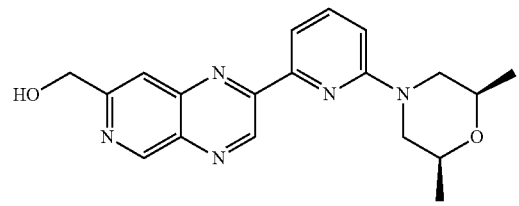 [SMILES: C[C@@H]1CN(c2cccc(-c3cnc4cnc(CO)cc4n3)n2)C[C@H](C)O1]

To the solution of 5 (160 mg, 406.67 umol) in MeOH (3 mL) was added NaOMe (43.94 mg, 813.34 umol), the reaction was stirred at 25° C. for 2 hrs under N$_2$. The reaction mixture was poured into water (10 mL), the solution was extracted with EA (10 mL*3), the combined organic layer was washed with brine (10 mL), dried over Na$_2$SO$_4$, filtered and concentrated to give a residue. The residue was purified by column chromatography (SiO2, Petroleum ether/Ethyl acetate=10:1-5:1), the solution was concentrated to give [2-[6-[(2R,6S)-2,6-dimethylmorpholin-4-yl]-2-pyridyl]pyrido[3,4-b]pyrazin-7-yl]methanol (100 mg, 284.57 umol, 69.98% yield) as a yellow solid.

LCMS (ESI) m/z: [M+H]$^+$=352.2.

Step 4: Preparation of 2-[[2-[6-[(2R,6S)-2,6-dimethylmorpholin-4-yl]-2-pyridyl]pyrido[3,4-b]pyrazin-7-yl]methyl]isoindoline-1,3-dione

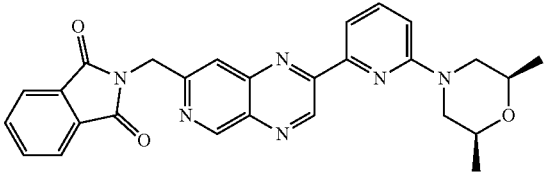 [SMILES: C[C@@H]1CN(c2cccc(-c3cnc4cnc(CN5C(=O)c6ccccc6C5=O)cc4n3)n2)C[C@H](C)O1]

The solution of 6 (100 mg, 284.57 umol) and isoindoline-1,3-dione (46.06 mg, 313.03 umol) in THF (2 mL) was added PPh$_3$ (89.57 mg, 341.49 umol), then DIAD (86.31 mg, 426.86 umol) was added to the mixture at 0° C., the reaction was stirred at 25° C. for 2 hrs under N$_2$. The reaction mixture was poured into water (20 mL), the solution was extracted with EA (20 mL*3), the combined organic layer was washed with brine (20 mL*3), dried over Na$_2$SO$_4$, filtered and concentrated to give a residue. The residue was purified by column chromatography (SiO$_2$, Petroleum ether/Ethyl acetate=10:1-5:1), the solution was concentrated to give 2-[[2-[6-[(2R,6S)-2,6-dimethylmorpholin-4-yl]-2-pyridyl]pyrido[3,4-b]pyrazin-7-yl]methyl]isoindoline-1,3-dione (90 mg, 187.30 umol, 65.82% yield) as a yellow solid.

LCMS (ESI) m/z: [M+H]$^+$=481.0.

Step 5: Preparation of [2-[6-[(2R,6S)-2,6-dimethyl-morpholin-4-yl]-2-pyridyl]pyrido[3,4-b]pyrazin-7-yl]methanamine

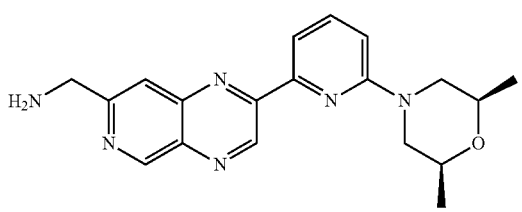 [SMILES: C[C@@H]1CN(c2cccc(-c3cnc4cnc(CN)cc4n3)n2)C[C@H](C)O1]

To the solution of 8 (50 mg, 104.05 umol) in THF (0.5 mL) was added hydrazine; hydrate (0.14 g, 2.74 mmol) at 25° C., the reaction was stirred at 25° C. for 12 hrs. The reaction mixture was poured into water (10 mL), the solution was extracted with EA (10 mL*3), the combined organic layer was washed with brine (20 mL), dried over Na2SO4, filtered and concentrated to give [2-[6-[(2R,6S)-2,6-dimethylmorpholin-4-yl]-2-pyridyl]pyrido[3,4-b]pyrazin-7-yl]methanamine (35 mg, crude) as a yellow solid, which was used directly in the next step.

LCMS (ESI) m/z: [M+H]$^+$=351.1.

Step 6: Preparation of Compound 405

(4R)—N-[[2-[6-[(2R,6S)-2,6-dimethylmorpholin-4-yl]-2-pyridyl]pyrido[3,4-b]pyrazin-7-yl]methyl]-4,9-difluoro-5,5-dioxo-3,4-dihydro-2H-1,5λ6-benzoxathiepine-7-carboxamide Compound 405

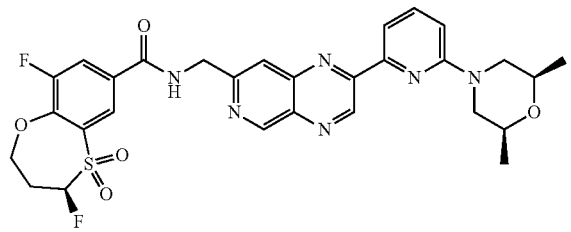

To the solution of 9 (35 mg, 99.88 umol) in DCM (1.5 mL) was added (4R)-4,9-difluoro-5,5-dioxo-3,4-dihydro-2H-1,5λ6-benzoxathiepine-7-carboxylic acid (Prepared according to the method in FG-A5321A) (27.79 mg, 99.88 umol), EDCl (28.72 mg, 149.82 umol), HOBt (20.24 mg, 149.82 umol) and DIEA (64.54 mg, 499.41 umol), the reaction was stirred at 25° C. for 12 hrs. The reaction mixture was diluted with H$_2$O (10 mL), the solution was extracted with EA (10 mL*3), the combined organic layer was washed with brine (10 mL), dried over Na2SO4, filtered and concentrated to give a residue. The residue was purified by reversed-phase HPLC (0.1% FA condition). The solution was lyophilized to give Compound 405 (12.96 mg, 19.74 umol, 19.76% yield, FA) as a yellow solid.

LCMS (ESI) m/z: [M+H]$^+$=611.4.

$^1$H NMR (400 MHz, DMSO-d$_6$) δ=9.96 (s, 1H), 9.75-9.69 (m, 1H), 9.50 (s, 1H), 8.44 (s, 1H), 8.39-8.28 (m, 2H), 7.94 (s, 1H), 7.90-7.84 (m, 1H), 7.83-7.76 (m, 1H), 7.11 (d, J=8.4 Hz, 1H), 6.37-6.19 (m, 1H), 4.85 (br d, J=5.6 Hz, 2H), 4.66-4.56 (m, 1H), 4.35 (br d, J=11.6 Hz, 2H), 4.19-4.15 (m, 1H), 3.75-3.62 (m, 2H), 2.92-2.73 (m, 1H), 2.66-2.55 (m, 3H), 1.22 (d, J=6.2 Hz, 6H) ppm.

Chiral SFC: OJ-3-IPA(DEA)-5-40-3ML-35T.lcm, Rt=2.121 mins, ee %=100%.

Step 7: Preparation of (4,5-diaminopyridin-2-yl)methanol

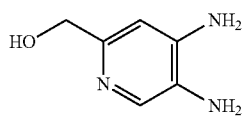

To a solution of methyl 4,5-diaminopyridine-2-carboxylate (8 g, 47.86 mmol) in THF (80 mL) was added and LiBH$_4$ (2 M, 103.98 mL) dropwise at 0° C. The mixture was stirred at 25° C. for 12 hrs. The reaction mixture was poured into aq·NaHCO$_3$ (300 mL) slowly. The suspension was filtered. The filtrate was concentrate to remove THF, then lyophilized to get the crude.

The crude was washed by column (Al$_2$O$_3$, DCM/MeOH=10:1 to 2:1) to get (4,5-diaminopyridin-2-yl)methanol (12 g, crude) as a white solid.

LCMS (ESI) m/z: [M+H]$^+$=140.4

Step 8: Preparation of 7-(hydroxymethyl)pyrido[3,4-b]pyrazin-2-ol

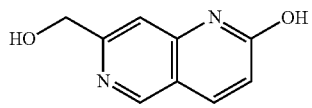 [SMILES: OCc1cc2nc(O)ccc2cn1]

To a solution of 2A (5 g, 35.93 mmol) in n-BuOH (50 mL) was added ethyl 2-oxoacetate (7.70 g, 37.73 mmol, 50% in toluene). The mixture was stirred at 100° C. for 8 hrs.

The reaction mixture was filtered. The filter cake was washed MeOH (50 mL) to get the filtrate A and filter cake B. The filtrate A was concentrated to get the residue. The residue was triturated by PE: EA (1:1, 100 mL) and then MeOH (20 mL) to get the 7-(hydroxymethyl)pyrido[3,4-b]pyrazin-2-ol (3.3 g, 18.63 mmol, 51.84% yield) as an off-white solid $^1$H NMR (400 MHz, DMSO-d$_6$) δ=8.81 (s, 1H), 8.15 (s, 1H), 7.33 (s, 1H), 5.79-5.46 (m, 1H), 4.62 (s, 2H) ppm.

Step 9: Preparation of (2-hydroxypyrido[3,4-b]pyrazin-7-yl)methyl Acetate

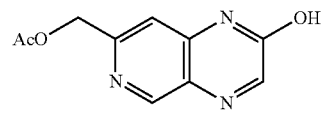 [SMILES: CC(=O)OCc1cc2nc(O)cnc2cn1]

To a solution of 4A (150 mg, 846.69 μmol) and DMAP (51.72 mg, 423.35 μmol) in DCM (3 mL) were added Ac$_2$O (259.31 mg, 2.54 mmol) and TEA (128.51 mg, 1.27 mmol). The mixture was stirred at 25° C. for 2 hrs. The reaction was concentrated to get the residue. The residue was purified by column chromatography (SiO$_2$, Petroleum ether/Ethyl acetate=2/1 to 1/1) to get (2-hydroxypyrido[3,4-b]pyrazin-7-yl)methyl acetate (100 mg, 456.21 μmol, 53.88% yield) as a yellow solid.

$^1$H NMR (400 MHz, DMSO-d$_6$) δ=12.65 (br s, 1H), 8.89 (s, 1H), 8.21 (s, 1H), 7.22 (s, 1H), 5.20 (s, 2H), 2.15 (s, 3H) ppm.

Step 10: Preparation of (2-chloropyrido[3,4-b]pyrazin-7-yl)methyl Acetate

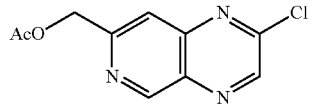 [SMILES: CC(=O)OCc1cc2nc(Cl)cnc2cn1]

To a solution of PPh$_3$ (344.62 mg, 1.31 mmol) in toluene (4 mL) was added trichloroisocyanuric acid (101.79 mg, 437.96 μmol). The resulting mixture was stirred at 25° C. for 12 hrs. To the above mixture, 5A (60 mg, 273.73 μmol) was added. The resulting mixture was stirred at 110° C. for 5 hrs. The reaction was concentrated to get the residue. The residue was purified by column chromatography (SiO$_2$, Petroleum ether/Ethyl acetate=10/1 to 5/1) to get (2-chloropyrido[3,4-b]pyrazin-7-yl)methyl acetate (40 mg, 164.95 μmol, 60.26% yield) as a white solid.

LCMS (ESI) m/z: [M+H]$^+$=238.1

$^1$H NMR (400 MHz, DMSO-d$_6$) δ=9.52 (s, 1H), 9.14 (s, 1H), 7.97 (s, 1H), 5.39 (s, 2H), 2.18 (s, 3H) ppm.

Preparation of (2R)—N-[[2-[3-(difluoromethoxy)-4-fluoro-pyrazol-1-yl]-1,6-naphthyridin-7-yl]methyl]-6-(difluoromethyl)-2-fluoro-1,1-dioxo-3,5-dihydro-2H-4,1benzoxathiepine-8-carboxamide (Compound 514)

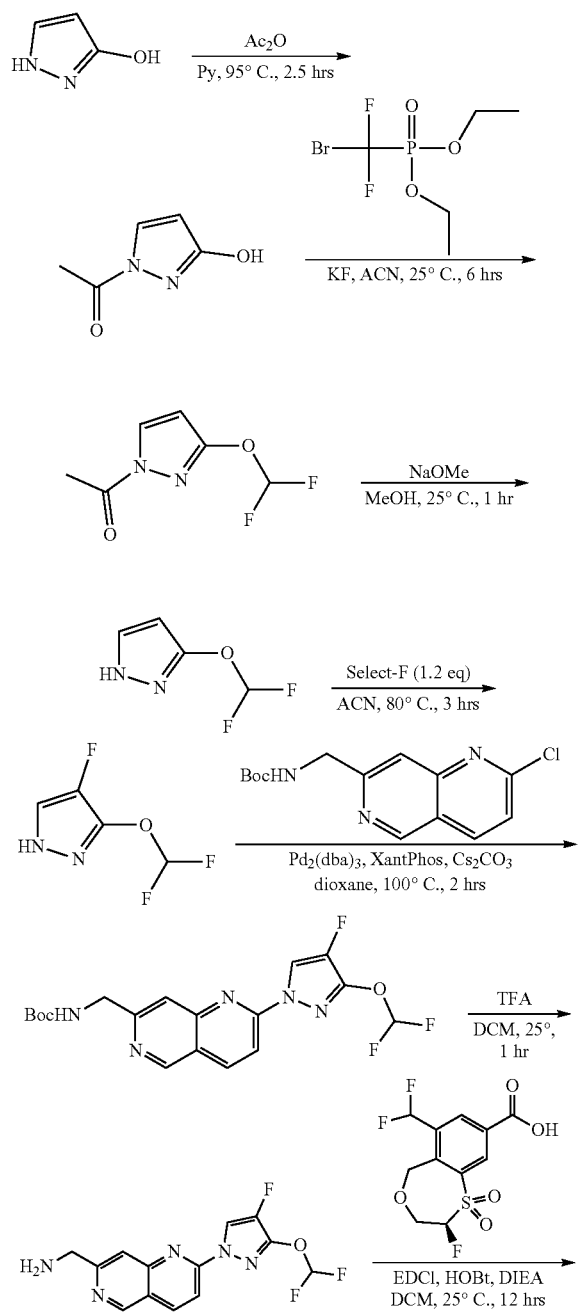

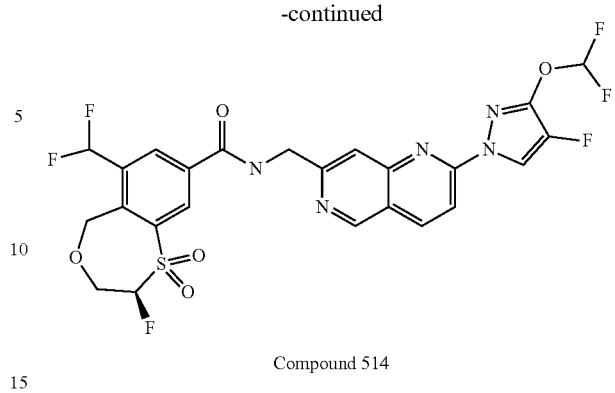

Compound 514

Step 1: Preparation of 1-(3-hydroxy-1H-pyrazol-1-yl)ethan-1-one

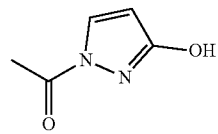

To a solution of 1H-pyrazol-3-ol (3 g, 35.68 mmol) in PYRIDINE (50 mL) was added a solution of Ac$_2$O (3.82 g, 37.47 mmol) in PYRIDINE (20 mL) at 95° C. for 30 min, then the mixture was stirred at 95° C. for 2 hrs. The reaction mixture was concentrated to get the residue. The residue was triturated by MeOH (100 mL) and filtered. The filter cake was washed with MeOH (20 mL*3) and dried to get 1-(3-hydroxy-1H-pyrazol-1-yl)ethan-1-one (4 g, 31.72 mmol, 88.89% yield) as a yellow solid.

Step 2: Preparation of 1-(3-(difluoromethoxy)-1H-pyrazol-1-yl)ethan-1-one

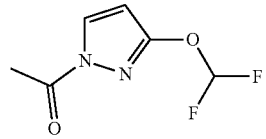

To a solution of 1-(3-hydroxy-1H-pyrazol-1-yl)ethan-1-one (2 g, 15.86 mmol) in ACN (20 mL) was added 1-[[bromo(difluoro)methyl]-ethoxy-phosphoryl]oxyethane (8.47 g, 31.72 mmol) and KF (1.84 g, 31.72 mmol). The mixture was stirred at 25° C. for 6 hrs. The reaction was diluted with water (100 mL), extract with EA (20 mL*4). The combined organic layers were dried over Na$_2$SO$_4$, filtered and concentrated to get the residue. The residue was purified by column chromatography (SiO$_2$, Petroleum ether/Ethyl acetate=10/1 to 3/1) to get 1-(3-(difluoromethoxy)-1H-pyrazol-1-yl)ethan-1-one (860 mg, 4.88 mmol, 30.79% yield) as a colorless oil.

$^1$H NMR (400 MHz, DMSO-d$_6$) δ=8.41 (d, J=2.8 Hz, 1H), 7.64-7.28 (m, 1H), 6.48 (d, J=3.2 Hz, 1H), 2.57 (s, 3H) ppm.

Step 3: Preparation of 3-(difluoromethoxy)-1H-pyrazole

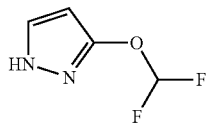

To a solution of 1-(3-(difluoromethoxy)-1H-pyrazol-1-yl)ethan-1-one (700 mg, 3.97 mmol) in MeOH (10 mL) was added NaOMe (429.44 mg, 7.95 mmol). The mixture was stirred at 25° C. for 1 hr. The reaction diluted with water (100 mL), extract with EA (50 mL*3). The combined organic layers were dried over $Na_2SO_4$, filtered and concentrated to get 3-(difluoromethoxy)-1H-pyrazole (460 mg, 3.43 mmol, 86.32% yield) as a colorless oil. $^1$H NMR (400 MHz, DMSO-$d_6$) δ=12.49 (br s, 1H), 7.69 (s, 1H), 7.41-7.04 (m, 1H), 5.97 (s, 1H) ppm.

Step 4: Preparation of 3-(difluoromethoxy)-4-fluoro-1H-pyrazole

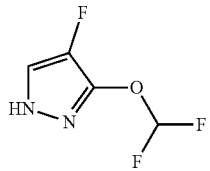

To a solution of 3-(difluoromethoxy)-1H-pyrazole (400 mg, 2.98 mmol) in ACN (10 mL) was added Select F (1.27 g, 3.58 mmol). The mixture was stirred at 80° C. for 3 hrs. The reaction mixture was filtered to get the filtrate. The filtrate was purified by reversed-phase HPLC (0.1% FA condition). The fraction was concentrated to remove MeCN. The liquid was extracted with EA (20 mL*3). The combined organic layers were dried over $Na_2SO_4$, filtered and concentrated to get 3-(difluoromethoxy)-4-fluoro-1H-pyrazole (180 mg, 1.18 mmol, 39.68% yield) as a colorless oil.

$^1$H NMR (400 MHz, DMSO-$d_6$) δ=12.56 (br s, 1H), 7.91-7.90 (m, 1H), 7.41-7.05 (m, 1H) ppm.

Step 5: Preparation of tert-butyl ((2-(3-(difluoromethoxy)-4-fluoro-1H-pyrazol-1-yl)-1,6-naphthyridin-7-yl)methyl)carbamate

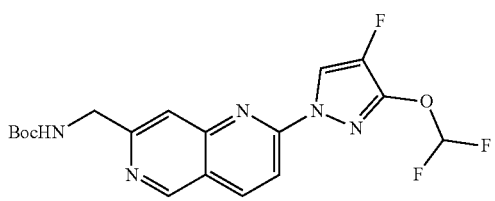 [SMILES: CC(C)(C)OC(=O)NCc1cc2nc(-n3cc(F)c(OC(F)F)n3)ccc2cn1]

A mixture of tert-butyl N-[(2-chloro-1,6-naphthyridin-7-yl)methyl]carbamate (Prepared according to the method in FG-A3432C) (120 mg, 408.51 μmol), 3-(difluoromethoxy)-4-fluoro-1H-pyrazole (68.34 mg, 449.36 μmol), $Pd_2(dba)_3$ (37.41 mg, 40.85 μmol), Xantphos (47.27 mg, 81.70 μmol) and $Cs_2CO_3$ (399.30 mg, 1.23 mmol) in dioxane (2 mL) was degassed and purged with $N_2$ for 3 times, and then the mixture was stirred at 100° C. for 2 hrs under $N_2$ atmosphere. The reaction was diluted with water (10 mL), extract with EA (5 mL*3). The combined organic layers were dried over $Na_2SO_4$, filtered and concentrated to get the residue. The residue was purified by prep-HPLC (column: Phenomenex luna C18 150*25 mm*10 um; mobile phase: [water (FA)-ACN]; B %: 47%-77%, 10 min). The fraction was concentrated to remove MeCN. The liquid was extract with DCM (5 mL*3). The combined organic layers were dried over $Na_2SO_4$, filtered and concentrated to get tert-butyl ((2-(3-(difluoromethoxy)-4-fluoro-1H-pyrazol-1-yl)-1,6-naphthyridin-7-yl)methyl)carbamate (120 mg, 293.14 μmol, 71.76% yield) as a white solid. $^1$H NMR (400 MHz, DMSO-$d_6$) δ=9.33 (s, 1H), 9.08 (d, J=4.0 Hz, 1H), 8.74 (d, J=8.8 Hz, 1H), 8.08 (d, J=9.2 Hz, 1H), 7.75-7.36 (m, 3H), 4.42 (br d, J=6.0 Hz, 2H), 1.43 (s, 9H) ppm.

Step 6: Preparation of (2-(3-(difluoromethoxy)-4-fluoro-1H-pyrazol-1-yl)-1,6-naphthyridin-7-yl)methanamine

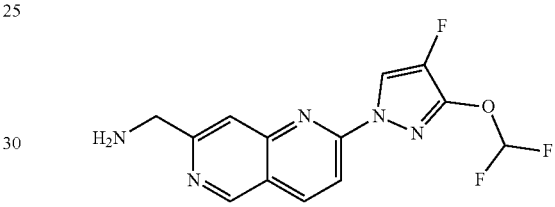

A mixture of tert-butyl ((2-(3-(difluoromethoxy)-4-fluoro-1H-pyrazol-1-yl)-1,6-naphthyridin-7-yl)methyl)carbamate (80 mg, 195.43 μmol) in TFA (0.2 mL) and DCM (1 mL) was stirred at 25° C. for 1 hr. The reaction mixture was diluted with aq·$NaHCO_3$ (5 mL), extract with EA (3 mL*5). The combined organic layers were dried over $Na_2SO_4$, filtered and concentrated to get (2-(3-(difluoromethoxy)-4-fluoro-1H-pyrazol-1-yl)-1,6-naphthyridin-7-yl)methanamine (60 mg, 194.02 μmol, 99.28% yield) as a yellow solid.

LCMS (ESI) m/z: $[M+H]^+$=310.0

Step 7: Preparation of (2R)—N-[[2-[3-(difluoromethoxy)-4-fluoro-pyrazol-1-yl]-1,6-naphthyridin-7-yl]methyl]-6-(difluoromethyl)-2-fluoro-1,1-dioxo-3,5-dihydro-2H-4,1benzoxathiepine-8-carboxamide Compound 514

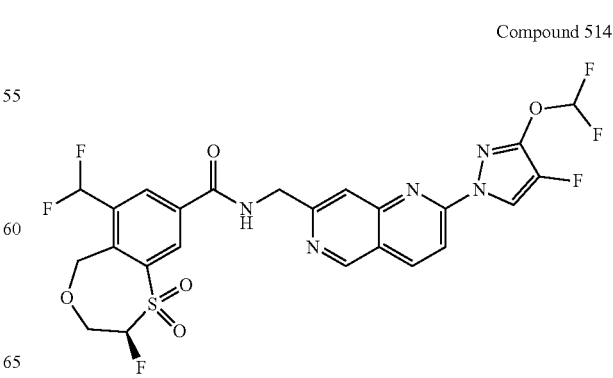

To a solution of (2R)-6-(difluoromethyl)-2-fluoro-1,1-dioxo-3,5-dihydro-2H-4,1 benzoxathiepine-8-carboxylic acid (60.19 mg, 194.02 μmol) in DCM (1 mL) was added EDCl (37.19 mg, 194.02 μmol), HOBt (26.22 mg, 194.02 μmol) and DIEA (62.69 mg, 485.05 μmol), then [2-[3-(difluoromethoxy)-4-fluoropyrazol-1-yl]-1,6-naphthyridin-7-yl]methanamine (50 mg, 161.68 μmol) was added. The mixture was stirred at 25° C. for 12 hrs. The reaction mixture was filtered and the filter cake was washed with PE (1 mL*3). The resulting solid was filtered under reduced pressure to give Compound 514 (54.32 mg, 90.31 μmol, 55.86% yield) as a white solid.

LCMS (ESI) m/z: [M+H]$^+$=602.1.

$^1$H NMR (400 MHz, DMSO-d$_6$) δ=9.91-9.88 (m, 1H), 9.38 (s, 1H), 9.05 (d, J=4.4 Hz, 1H), 8.83-8.71 (m, 2H), 8.60 (s, 1H), 8.11-8.09 (m, 1H), 7.77-7.33 (m, 3H), 6.35-6.12 (m, 1H), 5.31-5.27 (m, 1H), 5.12-5.08 (m, 1H), 4.83-4.82 (m, 2H), 4.58-4.41 (m, 2H) ppm.

Chiral SFC: OJ-3-EtOH(DEA)-5-40-3ML-35T.lcm, Rt=2.043 mins, ee %=100%.

The following examples in Table 9 were prepared using standard chemical manipulations and procedures similar to those described herein.

TABLE 9

Compounds of the Invention

| # | LCMS (ESI/M + H) | $^1$HNMR |
|---|---|---|
| 317 | 605.3 | 1H NMR (400 MHZ, DMSO-d6) δ = 9.67-9.65 (m, 1H), 9.40 (s, 1H), 8.68-8.58 (m, 3H), 8.34-8.31(m, 1H), 7.92 (d, J = 7.6 Hz, 1H), 7.84 (s, 1H), 7.76-7.74 (m, 2H), 7.03 (d, J = 8.4 Hz, 1H), 6.09-5.97 (m, 1H), 4.82 (br d, J = 5.2 Hz, 2H), 4.47 (br d, J = 15.2 Hz, 1H), 4.31 (br d, J = 11.2 Hz, 2H), 4.08 (br d, J = 15.2 Hz, 1H), 3.69-3.66 (m, 3H), 3.67-3.51 (m, 1H), 2.54 (br s, 2H), 2.29 (d, J = 0.8 Hz, 3H), 1.21 (d, J = 6.0 Hz, 6H) ppm |
| 318 | 605.3 | 1H NMR (400 MHZ, DMSO-d6) δ = 9.41-9.39 (m, 2H), 8.67-8.60 (m, 2H), 8.49 (d, J = 2.4 Hz, 1H), 8.22-8.19 (m, 1H), 7.91 (d, J = 7.2 Hz, 1H), 7.76-7.71 (m, 2H), 7.29 (d, J = 8.8 Hz, 1H), 7.03 (d, J = 8.4 Hz, 1H), 6.05-5.92 (m, 1H), 4.78 (br d, J = 6.0 Hz, 2H), 4.31 (br d, J = 11.6 Hz, 2H), 3.69-3.65 (m, 2H), 3.56-3.51 (m, 1H), 3.28 (br s, 1H), 3.06 (s, 3H), 2.58 (br s, 2H), 2.39 (br d, J = 1.6 Hz, 1H), 2.29-2.25 (m, 1H), 1.21 (d, J = 6.0 Hz, 6H) ppm |
| 319 | 605.4 | 1H NMR (400 MHZ, DMSO-d6) δ = 9.51-9.29 (m, 2H), 8.76-8.57 (m, 2H), 8.49 (d, J = 2.0 Hz, 1H), 8.22-8.19 (m , 1H), 7.91 (d, J = 7.2 Hz, 1H), 7.82-7.64 (m, 2H), 7.29 (d, J = 8.8 Hz, 1H), 7.03 (d, J = 8.8 Hz, 1H), 6.12-5.80 (m, 1H), 4.78 (d, J = 5.6 Hz, 2H), 4.31 (br d, J = 11.2 Hz, 2H), 3.69-3.65 (m, 2H), 3.58-3.49 (m, 1H), 3.25 (br s, 1H), 3.07 (s, 3H), 2.64-2.54 (m, 1H), 2.52 (br s, 2H), 2.31-2.20 (m, 1H), 1.21 (d, J = 6.4 Hz, 6H) ppm |
| 521 | 704.20 | 1H NMR (400 MHZ, DMSO-d6) δ = 9.71-9.68 (m, 1H), 9.06 (s, 1H), 8.64-8.60 (m, 2H), 8.32-8.16 (m, 2H), 7.72 (d, J = 2.8 Hz, 1H), 7.51 (s, 1H), 7.10 (d, J = 2.4 Hz, 1H), 6.36-6.11 (m, 1H), 5.37 (d, J = 14.8 Hz, 1H), 5.16 (d, J = 14.4 Hz, 1H), 4.72 (d, J = 5.6 Hz, 2H), 4.52-4.38 (m, 2H), 4.34 (d, J = 1.6 Hz, 4H), 4.18-4.11 (m, 2H), 3.73-3.68 (m, 2H), 3.53-3.49 (m, 2H), 1.15-1.11 (m, 3H) ppm. |
| 520 | 634.20 | 1H NMR (400 MHZ, DMSO-d6) δ = 9.76-9.73 (m, 1H), 9.42 (s, 1H), 8.57 (d, J = 8.8 Hz, 1H), 8.53-8.45 (m, 2H), 8.29-8.20 (m, 2H), 7.98-7.92 (m, 1H), 7.91-7.85 (m, 2H), 7.64-7.60 (m, 1H), 7.40 (d, J = 3.2 Hz, 1H), 6.30-6.13 (m, 1H), 5.30-5.08 (m, 2H), 4.94-4.81 (m, 3H), 4.52-4.29 (m, 4H), 1.56 (d, J = 6.0 Hz, 3H) ppm. |
| 366 | 605.00 | 1H NMR (400 MHZ, METHANOL-d4) δ = 9.32 (s, 1H), 8.53 (d, J = 8.6 Hz, 1H), 8.41-8.38 (m, 1H), 8.26 (d, J = 7.6 Hz, 1H), 8.21 (d, J = 8.6 Hz, 1H), 8.19-8.14 (m, 1H), 7.92 (s, 1H), 7.11 (d, J = 7.6 Hz, 1H), 6.21-6.20 (m, 1H), 5.96-5.79 (m, 1H), 4.90 (m, 2H), 4.65-4.60 (m, 1H), 4.19-4.13 (m, 1H), 4.06 (s, 3H), 3.42-3.35 (m, 1H), 3.09-2.84 (m, 1H), 2.64-2.50 (m, 1H), 1.45 (d, J = 7.0 Hz, 3H) ppm |
| 358 | 541.2 | 1H NMR (400 MHZ, DMSO-d6) δ = 9.68-9.66 (m, 1H), 9.41 (s, 1H), 8.69-8.61 (m, 2H), 8.35-8.30 (m, 2H), 8.19 (d, J = 7.6 Hz, 1H), 7.90-7.88 (m, 1H), 7.85 (s, 1H), 6.97 (d, J = 8.4 Hz, 1H), 6.33-6.21 (m, 1H), 4.82 (br d, J = 5.6 Hz, 2H), 4.63-4.59 (m, 1H), 4.53-4.48 (m, 2H), 4.19-4.16 (m, 1H), 2.86-2.73 (m, 1H), 2.61-2.55 (m, 1H), 1.42-1.39 (t, J = 7.0 Hz, 3H) ppm |
| 523 | 586.20 | 1H NMR (400 MHZ, DMSO-d6 ) δ = 9.75-9.73 (m, 1H), 9.35 (s, 1H), 8.63-8.57 (m, 2H), 8.56-8.48 (m, 2H), 8.37 (d, J = 8.8 Hz, 1H), 7.85 (s, 1H), 7.50 (d, J = 8.8 Hz, 1H), 6.31-6.12 (m, 1H), 5.41 (d, J = 14.4 Hz, 1H), 5.09 (d, J = 14.4 Hz, 1H), 4.81(d, J = 5.6 Hz, 2H), 4.54-4.29 (m, 2H), 2.44 (s, 1H), 1.15-1.08 (m, 2H), 1.05-0.98 (m, 2H) ppm. |
| 522 | 632.10 | 1H NMR (400 MHZ, DMSO-d6 ) δ = 9.75-9.73 (m, 1H), 9.35 (s, 1H), 8.65 (d, J = 1.6 Hz, 1H), 8.63-8.58 (m, 2H), 8.57-8.50 (m, 1H), 8.37 (d, J = 8.8 Hz, 1H), 7.85 (s, 1H), 7.50 (d, J = 8.4 Hz, 1H), 6.39-6.08 (m, 1H), 5.38 (d, J = 14.8 Hz, 1H), 5.17 (d, J = 14.4 Hz, 1H), 4.81 (d, J = 5.6 Hz, 2H), 4.55-4.33 (m, 2H), 2.46 (s, 1H), 1.16-1.09 (m, 2H), 1.03-1.01 ( m, 2H) ppm. |
| 513 | 637.00 | 1H NMR (400 MHZ, DMSO-d6) δ = 9.71 (s, 1H), 9.43 (s, 1H), 8.71 (s, 1H), 8.59 (d, J = 7.6 Hz, 1H), 8.54 (s, 1H), 8.45 (s, 1H), 8.22 (d, J = 8.4 Hz, 1H), 8.06 (d, J = 8.8 Hz, 1H), 7.99 (d, J = 7.2 Hz, 1H), 7.94 (s, 1H), 7.86 (s, 1H), 7.73-7.70 ( m, 1H), 6.35-6.17 (m, 1H), 4.83 (s, 2H), 4.60 (d, J = 11.6 Hz, 1H), 4.32 (s, 2H), 4.13-4.10 (m, 1H), 3.77 (s, 2H), 3.41-3.36 (m, 3H), 2.92-2.72 (m, 1H), 2.63-2.54 (m, 1H) ppm. |

TABLE 9-continued

Compounds of the Invention

| # | LCMS (ESI/M + H) | ¹HNMR |
|---|---|---|
| 512 | 594.00 | 1H NMR (400 MHZ, DMSO-d6) δ = 9.79-9.76 (m, 1H), 9.31 (s, 1H), 8.85 (d, J = 4.4 Hz, 1H), 8.67 (d, J = 9.2 Hz, 1H), 8.57 (d, J = 1.2 Hz, 1H), 8.49 (d, J = 1.2 Hz, 1H), 8.06 (d, J = 9.2 Hz, 1H), 7.67 (s, 1H), 6.29-6.18 (m, 1H), 5.41 (d, J = 14.8 Hz, 1H), 5.09 (d, J = 14.8 Hz, 1H), 4.79 (br d, J = 5.6 Hz, 2H), 4.50-4.42 (m, 4H), 3.74-3.72 (m, 2H), 3.33 (s, 3H) ppm. |
| 511 | 610.10 | 1H NMR (400 MHZ, DMSO-d6) δ = 9.90-9.87 (m, 1H), 9.32 (s, 1H), 8.86 (d, J = 4.4 Hz, 1H), 8.79 (s, 1H), 8.67 (d, J = 8.8 Hz, 1H), 8.60 (s, 1H), 8.44-8.43 (m, 1H), 8.06 (d, J = 8.8 Hz, 1H), 7.67-7.54 (m, 2H), 6.29-6.18 (m, 1H), 5.28 (d, J = 14.8 Hz, 1H), 5.10 (d, J = 14.8 Hz, 1H), 4.80 (br d, J = 5.6 Hz, 2H), 4.52-4.44 (m, 4H), 3.74-3.72 (m, 2H), 3.32 (br s, 3H) ppm. |
| 508 | 578.10 | 1H NMR (400 MHZ, DMSO-de) δ = 9.68-9.65 (m, 1H), 9.30 (s, 1H), 8.84 (d, J = 4.4 Hz, 1H), 8.66 (d, J = 8.8 Hz, 1H), 8.35-8.29 (m, 2H), 8.05 (d, J = 8.8 Hz, 1H), 7.64 (s, 1H), 6.34-6.22 (m, 1H), 4.77 (d, J = 5.6 Hz, 2H), 4.60 (s, 1H), 4.49-4.47 (m, 2H), 4.15 (s, 1H), 3.74-3.72 (m, 2H), 3.32 (s, 3H), 2.62-2.59 (m, 1H) ppm. |
| 507 | 622.30 | 1H NMR (400 MHz, DMSO-de) δ = 9.78-9.75 (m, 1H), 9.39 (s, 1H), 8.67-8.61 (m, 2H), 8.59 (d, J = 1.6 Hz, 1H), 8.56 (d, J = 8.4 Hz, 1H), 8.51 (d, J = 1.6 Hz, 1H), 7.88 (s, 1H), 7.66 (d, J = 8.4 Hz, 1H), 6.33-6.16 (m, 1H), 5.42 (d, J = 14.8 Hz, 1H), 5.10 (d, J = 14.4 Hz, 1H), 4.83 (d, J = 5.6 Hz, 2H), 4.55-4.38 (m, 2H), 3.36 (s, 1H), 2.66-2.58 (m, 1H), 2.14-2.01 (m, 1H) |
| 506 | 622.10 | 1H NMR (400 MHz, DMSO-de) δ = 9.78-9.75 (m, 1H), 9.38 (s, 1H), 8.66-8.61 (m, 2H), 8.58 (s, 1H), 8.55 (d, J = 8.8 Hz, 1H), 8.51 (s, 1H), 7.87 (s, 1H), 7.65 (d, J = 8.8 Hz, 1H), 6.29-6.19 (m, 1H), 5.41 (d, J = 14.8 Hz, 1H), 5.09 (d, J = 14.8 Hz, 1H), 4.82 (br d, J = 6.0 Hz, 2H), 4.50-4.39 (m, 2H), 3.30 (br s, 1H), 2.62-2.57 (m, 1H), 2.11-2.04 (m, 1H) ppm. |
| 504 | 621.40 | 1H NMR (400 MHZ, DMSO-d6) δ = 9.68-9.66 (m, 1H), 9.42 (s, 1H), 8.71 (d, J = 3.2 Hz, 1H), 8.59 (d, J = 8.8 Hz, 1H), 8.38-8.28 (m, 2H), 8.22 (d, J = 8.8 Hz, 1H), 8.05 (d, J = 7.6 Hz, 1H), 8.01-7.97 (m, 1H), 7.93 (d, J = 3.2Hz, 1H), 7.84 (s, 1H), 7.73-7.69 (m, 1H), 6.35-6.18 (m, 1H), 4.82 (d, J = 6.0 Hz, 2H), 4.64-4.55 (m, 1H), 4.36-4.28 (m, 2H), 4.18-4.12 (m, 1H), 3.80-3.72 (m, 2H), 3.33 (s, 3H), 2.90-2.70 (m, 1H), 2.64-2.55 (m, 1H) ppm. |
| 503 | 608.00 | 1H NMR (400 MHZ, DMSO-d6) δ = 9.88-9.84 (m, 1H), 9.45 (s, 1H), 8.83-8.71 (m, 2H), 8.59 (s, 1H), 8.19 (d, J = 8.8 Hz, 1H), 8.10 (d, J = 8.4 Hz, 1H), 7.91 (s, 1H), 7.69-7.36 (m, 3H), 6.32-6.14 (m, 1H), 5.35-5.03 (m, 2H), 4.86 (d, J = 5.6 Hz, 2H), 4.59-4.38 (m, 2H) ppm. |
| 502 | 639.20 | 1H NMR (400 MHZ, DMSO-d6) δ = 9.78-9.76 (m, 1H), 9.41 (s, 1H), 8.65 (d, J = 1.6 Hz, 1H), 8.63 (d, J = 8.4 Hz, 1H), 8.61 (s, 1H), 8.40 (d, J = 7.6 Hz, 1H), 8.22 (d, J = 8.8 Hz, 1H), 7.87 (s, 1H), 7.29 (d, J = 7.6 Hz, 1H), 6.31-6.14 (m, 1H), 5.38 (d, J = 14.8 Hz, 1H), 5.17 (d, J = 14.8 Hz, 1H), 4.83 (d, J = 5.6 Hz, 2H), 4.53-4.38 (m, 2H), 4.01 (s, 3H) ppm. |
| 501 | 580.10 | 1H NMR (400 MHZ, DMSO-d6) δ = 9.88-9.86 (m, 1H), 9.31 (s, 1H), 8.84 (d, J = 4.4 Hz, 1H), 8.79 (s, 1H), 8.67 (d, J = 9.2 Hz, 1H), 8.59 (s, 1H), 8.07-8.05 (m, 1H), 7.73-7.35 (m, 2H), 6.39-6.12 (m, 1H), 5.28 (d, J = 15.2 Hz, 1H), 5.14-5.06 (m, 1H), 4.80 (d, J = 5.6 Hz, 2H), 4.56-4.48 (m, 1H), 4.47-4.38 (m, 3H), 1.43-1.39 (m, 3H) ppm. |
| 500 | 667.20 | 1H NMR (400 MHZ, DMSO-d6) δ = 9.82-9.80 (m, 1H), 9.06 (s, 1H), 8.78 (S, 1H), 8.59 (s, 1H), 8.39 (s, 1H), 8.26-8.20 (m, 2H), 7.71 (d, J = 2.8 Hz, 1H), 7.66-7.39 (m, 2H), 7.09 (d, J = 2.8 Hz, 1H), 6.28-6.17 (m, 1H), 5.31-5.26 (m, 1H), 5.11-5.07 (m, 1H), 4.74 (d, J = 5.6 Hz, 2H), 4.55-4.44 (m, 2H), 4.34-4.32 (m, 4H) ppm. |
| 499 | 626.10 | 1H NMR (400 MHZ, DMSO-d6) δ = 9.79-9.76 (m, 1H), 9.42 (s, 1H), 8.65-8.63 (m, 1H), 8.57 (s, 1H), 8.52-8.44 (m, 2H), 8.26-8.24 (m, 1H), 7.88 (s, 1H), 7.46-7.44 (m, 1H), 6.35-6.14 (m, 1H), 5.42-5.39 (m, 1H), 5.09 (d, J = 14.8 Hz, 1H), 4.83-4.82 (m, 2H), 4.55-4.36 (m, 2H), 2.11-1.97 (m, 3H) ppm. |
| 498 | 632.30 | 1H NMR (400 MHZ, DMSO-d6) δ = 9.81-9.73 (m, 1H), 9.42 (s, 1H), 8.61-8.42 (m, 4H), 8.23 (d, J = 8.4 Hz, 1H), 7.97-7.80 (m, 3H), 7.65-7.54 (m, 1H), 7.31-7.24 (m, 1H), 6.40-6.08 (m, 1H), 5.40 (d, J = 14.4 Hz, 1H), 5.08 (d, J = 14.4 Hz, 1H), 4.84 (d, J = 5.6 Hz, 2H), 4.56-4.40 (m, 2H), 4.39-4.27 (m, 1H), 4.12-3.98 (m, 1H), 3.85-3.63 (m, 1H), 2.47-2.36 (m, 1H), 2.17-2.08 (m, 1H), 1.51 (d, J = 6.0 Hz, 3H) ppm. |
| 497 | 632.20 | 1H NMR (400 MHZ, DMSO-de) δ = 9.70-9.67 (m, 1H), 9.41 (s, 1H), 8.56-8.52 (m, 2H), 8.44-8.42 (m, 2H), 8.21 (d, J = 8.8 Hz, 1H), 7.91 (d, J = 7.2 Hz, 1H), 7.84-7.80 (m, 2H), 7.60-7.57 (m, 1H), 7.24 (d, J = 2.8 Hz, 1H), 6.30-6.18 (m, 1H), 4.82 (d, J = 5.6 Hz, 2H), 4.61-4.57 (m, 1H), 4.35-4.27 (m, 1H), 4.12-4.01 (m, 2H), 3.76-3.70 (m, 1H), 2.89-2.73 (m, 1H), 2.61-2.50 (m, 2H), 2.13-2.07 (m, 1H), 1.51 (d, J = 6.0 Hz, 3H) ppm. |
| 496 | 616.20 | 1H NMR (400 MHz, DMSO-d6) δ = 9.76-9.73 (m, 1H), 9.41 (s, 1H), 8.56-8.42 (m, 3H), 8.27-8.20 (m, 2H), 7.92-7.87 (m, 2H), 7.82 (d, J = 7.2 Hz, 1H), 7.61-7.57 (m, 1H), 7.24 (d, J = 2.8 Hz, 1H), 6.26-6.15 (m, 1H), 5.23 (d, J = 14.4 Hz, 1H), 4.90-4.82 (m, 3H), 4.47-4.28 (m, 3H), 4.04-4.01 (m, 1H), 3.78-3.67 (m, 1H), 2.59-2.50 (m, 1H), 2.11-2.07 (m, 1H), 1.50 (d, J = 6.0 Hz, 3H) ppm. |

TABLE 9-continued

Compounds of the Invention

| # | LCMS (ESI/M + H) | $^1$HNMR |
|---|---|---|
| 495 | 612.10 | 1H NMR (400 MHZ, DMSO-d6) δ = 9.69-9.66 (m, 1H), 9.41 (s, 1H), 8.64 (d, J = 8.4 Hz, 1H), 8.53 (d, J = 2.0 Hz, 1H), 8.49-8.42 (m, 2H), 8.24 (d, J = 8.8 Hz, 1H), 7.85 (s, 1H), 7.45 (d, J = 7.6 Hz, 1H), 7.13-6.79 (m, 1H), 6.35-6.16 (m, 1H), 4.81 (d, J = 5.6 Hz, 2H), 4.63-4.58 (m, 1H), 4.12-4.06 (m, 1H), 2.94-2.71 (m, 1H), 2.65-2.53 (m, 1H) ppm. |
| 494 | 674.30 | 1H NMR (400 MHZ, DMSO-d6) δ = 9.81-9.79 (m, 1H), 9.06 (s, 1H), 8.78 (s, 1H), 8.59 (s, 1H), 8.24-8.20 (m, 2H), 7.72 (d, J = 2.4 Hz, 1H), 7.68-7.37 (m, 2H), 7.09 (d, J = 2.4 Hz, 1H), 6.34-6.11 (m, 1H), 5.30-5.26 (m, 1H), 5.11-5.07 (m, 1H), 4.74 (d, J = 5.6 Hz, 2H), 4.57-4.42 (m, 2H), 4.34 (d, J = 1.2 Hz, 4H), 4.19-4.12 (m, 2H), 3.73-3.65 (m, 2H), 3.56-3.45 (m, 2H), 1.15-1.11 (m, 3H) ppm. |
| 493 | 668.10 | 1H NMR (400 MHZ, DMSO-d6) δ = 9.77-9.74 (m, 1H), 9.39 (s, 1H), 8.69-8.60 (m, 4H), 8.56 (d, J = 8.8 Hz, 1H), 7.87 (s, 1H), 7.66 (d, J = 8.8 Hz, 1H), 6.36-6.14 (m, 1H), 5.39 (d, J = 14.8 Hz, 1H), 5.18 (d, J = 14.0 Hz, 1H), 4.82 (d, J = 5.6 Hz, 2H), 4.56-4.37 (m, 2H), 3.25-3.22 (m, 1H), 2.61-2.57 (m, 1H), 2.09-2.05 (m, 1H) ppm. |
| 492 | 681.00 | 1H NMR (400 MHZ, DMSO-d6) δ = 9.79-9.76 (m, 1H), 9.44 (s, 1H), 8.75-8.59 (m, 4H), 8.46 (br d, J = 8.4 Hz, 1H), 8.01 (br d, J = 8.0 Hz, 1H), 7.92 (s, 1H), 6.81-6.42 (m, 2H), 6.24 (br d, J = 42.0 Hz, 1H), 5.39 (br d, J = 14.8 Hz, 1H), 5.18 (br d, J = 14.4 Hz, 1H), 4.84 (br d, J = 5.6 Hz, 2H), 4.55-4.38 (m, 2H), 2.44-2.38 (m, 1H), 1.26-1.22 (m, 2H), 1.09-1.08 (m, 2H) ppm. |
| 491 | 635.10 | 1H NMR (400 MHZ, DMSO-d6) δ = 9.71-9.68 (m, 1H), 9.44 (s, 1H), 8.72 (d, J = 8.8 Hz, 1H), 8.61 (d, J = 8.8 Hz, 1H), 8.55 (d, J = 2.0 Hz, 1H), 8.50-8.43 (m, 2H), 8.02 (d, J = 8.2 Hz, 1H), 7.89 (s, 1H), 6.80-6.42 (m, 2H), 6.33-6.21 (m, 1H), 4.83 (d, J = 5.6 Hz, 2H), 4.63 (br d, J = 12.8 Hz, 1H), 4.13-4.07 (m, 1H), 2.95-2.74 (m, 1H), 2.64-2.55 (m, 1H), 2.45-2.38 (m, 1H), 1.29-1.20 (m, 2H), 1.13-1.04 (m, 2H) ppm. |
| 490 | 651.10 | 1H NMR (400 MHZ, DMSO-d6) δ = 9.89-9.86 (m, 1H), 9.45 (s, 1H), 8.80 (s, 1H), 8.73 (d, J = 8.4 Hz, 1H), 8.63-8.58 (m, 2H), 8.47 (d, J = 8.0 Hz, 1H), 8.01 (d, J = 8.0 Hz, 1H), 7.92 (s, 1H), 7.54-7.40 (m, 1H), 6.80-6.43 (m, 2H), 6.33-6.17 (m, 1H), 5.29 (d, J = 15.2 Hz, 1H), 5.11 (d, J = 14.8 Hz, 1H), 4.86 (br d, J = 5.6 Hz, 2H), 4.58-4.40 (m, 2H), 2.44-2.37 (m, 1H), 1.33-1.18 (m, 2H), 1.14-1.04 (m, 2H) ppm. |
| 489 | 672.10 | 1H NMR (400 MHZ, DMSO-d6) δ = 9.77-9.74 (m, 1H), 9.41 (s, 1H), 8.66-8.58 (m, 3H), 8.43 (d, J = 8.0 Hz, 1H), 8.24 (d, J = 8.8 Hz, 1H), 7.87 (s, 1H), 7.31 (d, J = 8.0 Hz, 1H), 6.32-6.15 (m, 1H), 6.03-5.79 (m, 1H), 5.37 (d, J = 14.8 Hz, 1H), 5.16 (d, J = 14.8 Hz, 1H), 5.09-4.85 (m, 2H), 4.82 (d, J = 5.6 Hz, 2H), 4.52-4.36 (m, 2H) ppm. |
| 488 | 617.00 | 1H NMR (400 MHZ, DMSO-d6) δ = 9.78-9.76 (m, 1H), 9.43 (s, 1H), 8.66 (d, J = 8.4 Hz, 1H), 8.51-8.44 (m, 2H), 8.31-8.24 (m, 2H), 7.88 (s, 1H), 7.46 (d, J = 7.6 Hz, 1H), 7.18-6.76 (m, 1H), 6.33-6.10 (m, 1H), 5.26-5.23 (m, 1H), 4.92-4.88 (m, 1H), 4.83 (d, J = 5.6 Hz, 2H), 4.48 (s, 1H), 4.46-4.35 (m, 1H), 4.31-4.30 (m, 2H), 1.35-1.27 (m, 1H), 0.59-0.52 (m, 2H), 0.40-0.38 (m, 2H) ppm. |
| 487 | 627.00 | 1H NMR (400 MHZ, DMSO-d6 ) δ = 9.75-9.72 (m, 1H), 9.34 (s, 1H), 8.64 (d, J = 1.6 Hz, 1H), 8.62-8.58 (m, 2H), 8.55-8.49 (m, 1H), 8.37 (d, J = 8.8 Hz, 1H), 7.84 (s, 1H), 7.49 (d, J = 8.8 Hz, 1H), 6.29-6.14 (m, 1H), 5.37 (d, J = 14.8 Hz, 1H), 5.16 (d, J = 14.4 Hz, 1H), 4.80 (d, J = 5.6 Hz, 2H), 4.53-4.37 (m, 2H), 3.93 (s, 3H), 2.45 (s, 1H), 1.16-1.07 (m, 2H), 1.06-0.97 (m, 2H) ppm. |
| 486 | 658.00 | 1H NMR (400MHZ, DMSO-d6) δ = 9.78-9.75 (m, 1H), 9.42 (s, 1H), 8.65-8.59 (m, 3H), 8.47 (d, J = 7.6 Hz, 1H), 8.24 (d, J = 8.4 Hz, 1H), 7.88 (s, 1H), 7.45 (d, J = 8.0 Hz, 1H), 7.10-6.82 (m, 1H), 6.27-6.17 (m, 1H), 5.37 (d, J = 14.4 Hz, 1H), 5.16 (d, J = 14.4 Hz, 1H), 4.82 (d, J = 5.6 Hz, 2H), 4.50-4.41 (m, 2H) ppm. |
| 485 | 672.00 | 1H NMR (400 MHZ, DMSO-d6) δ = 9.77-9.75 (m, 1H), 9.41 (s, 1H), 8.64-8.59 (m, 3H), 8.42 (d, J = 7.6 Hz, 1H), 8.24 (d, J = 8.4 Hz, 1H), 7.87 (s, 1H), 7.33-7.30 (m, 1H), 6.27-6.16 (m, 1H), 6.02-5.81 (m, 1H), 5.37 (d, J = 14.4 Hz, 1H), 5.20-5.12 (m, 1H), 5.06-4.90 (m, 2H), 4.82-4.79 (m, 2H), 4.50-4.36 (m, 2H) ppm. |
| 484 | 663.20 | 1H NMR (400 MHZ, DMSO-d6) δ = 9.83-9.80 (m, 1H), 9.06 (s, 1H), 8.78 (S, 1H), 8.59 (s, 1H), 8.37-8.34 (m, 1H), 8.27-8.19 (m, 2H), 7.71 (d, J = 2.4 Hz, 1H), 7.66-7.39 (m, 2H), 7.09 (d, J = 2.0 Hz, 1H), 6.28-6.17 (m, 1H), 5.28 (d, J = 14.4 Hz, 1H), 5.09 (d, J = 15.6 Hz, 1H), 4.74 (d, J = 5.6 Hz, 2H), 4.51-4.44 (m, 2H), 4.33 (s, 4H), 4.15-4.13 (m, 2H), 3.66-3.64 (m, 2H) ppm. |
| 483 | 681.00 | 1H NMR (400 MHZ, DMSO-d6) δ = 9.79-9.76 (m, 1H), 9.44 (s, 1H), 8.73 (d, J = 6.8 Hz, 1H), 8.66 (d, J = 1.6 Hz, 1H), 8.63-8.58 (m, 2H), 8.47 (d, J = 8.0 Hz, 1H), 8.02 (d, J = 8.4 Hz, 1H), 7.92 (s, 1H), 6.77-6.41 (m, 2H), 6.36-6.14 (m, 1H), 5.39 (d, J = 14.8 Hz, 1H), 5.18 (d, J = 14.4 Hz, 1H), 4.84 (d, J = 5.6 Hz, 2H), 4.55-4.35 (m, 2H), 2.45-2.36 (m, 1H), 1.31-1.21 (m, 2H), 1.10-1.08 (m, 2H) ppm. |

TABLE 9-continued

Compounds of the Invention

| # | LCMS (ESI/M + H) | ¹HNMR |
|---|---|---|
| 482 | 635.00 | 1H NMR (400 MHZ, DMSO-d6) δ = 9.71-9.68 (m, 1H), 9.44 (s, 1H), 8.73 (d, J = 8.4 Hz, 1H), 8.61 (d, J = 8.8 Hz, 1H), 8.55 (d, J = 2.0 Hz, 1H), 8.47-8.45 (m, 2H), 8.02 (d, J = 8.4 Hz, 1H), 7.89 (s, 1H), 6.81-6.41 (m, 2H), 6.36-6.17 (m, 1H), 4.83 (d, J = 5.4 Hz, 2H), 4.65-4.60 (m, 1H), 4.13-4.07 (m, 1H), 2.93-2.73 (m, 1H), 2.63-2.58 (m, 1H), 2.44-2.39 (m, 1H), 1.26-1.20 (m, 2H), 1.10-1.08 (m, 2H) ppm. |
| 481 | 621.20 | 1H NMR (400 MHZ, DMSO-d6) δ = 9.78-9.75 (m, 1H), 9.40 (s, 1H), 8.62 (d, J = 8.8 Hz, 1H), 8.57 (d, J = 1.6 Hz, 1H), 8.49 (d, J = 1.6 Hz, 1H), 8.42 (d, J = 7.6 Hz, 1H), 8.24 (d, J = 8.4 Hz, 1H), 7.87 (s, 1H), 7.31 (d, J = 7.6 Hz, 1H), 6.31-6.11 (m, 1H), 6.03-5.78 (m, 1H), 5.41 (d, J = 14.8 Hz, 1H), 5.19-4.75 (m, 5H), 4.55-4.36 (m, 4H), 1.38-1.34 (m, 3H) ppm. |
| 480 | 668.00 | 1H NMR (400 MHZ, DMSO-d6) δ = 9.77-9.74 (m, 1H), 9.38 (s, 1H), 8.63 (d, J = 15.6 Hz, 4H), 8.55 (d, J = 8.8 Hz, 1H), 7.87 (s, 1H), 7.65 (d, J = 8.8 Hz, 1H), 6.32-6.14 (m, 1H), 5.38 (d, J = 14.8 Hz, 1H), 5.17 (d, J = 14.8 Hz, 1H), 4.82 (d, J = 4.8 Hz, 2H), 4.56-4.38 (m, 2H), 3.29-3.23 (m, 1H), 2.59 (d, J = 5.6 Hz, 1H), 2.15-1.98 (m, 1H) ppm. |
| 479 | 642.20 | 1H NMR (400 MHZ, DMSO-d6) δ = 9.89-9.84 (m, 1H), 9.41 (s, 1H), 8.78 (s, 1H), 8.65-8.57 (m, 2H), 8.42 (d, J = 7.6 Hz, 1H), 8.24 (d, J = 8.8 Hz, 1H), 7.86 (s, 1H), 7.68-7.37 (m, 1H), 7.31 (d, J = 8.0 Hz, 1H), 6.31-6.15 (m, 1H), 6.05-5.77 (m, 1H), 5.32-5.23 (m, 1H), 5.17-5.02 (m, 2H), 5.00-4.91 (m, 1H), 4.84 (d, J = 5.6 Hz, 2H), 4.52-4.43 (m, 2H) ppm. |
| 478 | 642.20 | 1H NMR (400 MHZ, DMSO-d6 ) δ = 9.87-9.85 (m, 1H), 9.41 (s, 1H), 8.78 (s, 1H), 8.63-8.59 (m, 2H), 8.42 (d, J = 7.6 Hz, 1H), 8.24 (d, J = 8.4 Hz, 1H), 7.86 (s, 1H), 7.69-7.43 (m, 1H), 7.30 (d, J = 7.6 Hz, 1H), 6.28-6.16 (m, 1H), 6.02-5.79 (m, 1H), 5.27 (d, J = 14.8 Hz, 1H), 5.10-4.83 (m, 5H), 4.54-4.39 (m, 2H) ppm. |
| 477 | 614.10 | 1H NMR (400 MHz, MeOD) δ = 9.07 (s, 1H), 8.50 (d, J = 2.0 Hz, 1H), 8.48-8.44 (m, 1H), 8.42 (d, J = 2.0 Hz, 1H), 8.34 (d, J = 8.8 Hz, 1H), 7.66 (d, J = 8.8 Hz, 2H), 7.56 (d, J = 5.6 Hz, 1H), 7.11 (d, J = 5.6 Hz, 1H), 5.97-5.79 (m, 1H), 4.84 (s, 2H), 4.68-4.63 (m, 1H), 4.46-4.35 (m, 4H), 4.30-4.21 (m, 2H), 4.18-4.05 (m, 1H), 3.10-2.90 (m, 1H), 2.64-2.51 (m, 1H), 1.43-1.39 (m, 3H) ppm. |
| 476 | 651.10 | 1H NMR (400 MHZ, DMSO-d6) δ = 9.89-9.86 (m, 1H), 9.45 (s, 1H), 8.80 (s, 1H), 8.73 (d, J = 8.4 Hz, 1H), 8.61 (d, J = 8.8 Hz, 2H), 8.47 (d, J = 8.4 Hz, 1H), 8.01 (d, J = 8.0 Hz, 1H), 7.91 (s, 1H), 7.67-7.40 (m, 1H), 6.81-6.43 (m, 2H), 6.28-6.18 (m, 1H), 5.30 (d, J = 14.8 Hz, 1H), 5.10 (d, J = 14.8 Hz, 1H), 4.86 (d, J = 5.6 Hz, 2H), 4.59-4.42 (m, 2H), 2.44-2.38 (m, 1H), 1.30-1.21 (m, 2H), 1.15-1.03 (m, 2H) ppm. |
| 475 | 621.00 | 1H NMR (400 MHZ, DMSO-de ) δ = 9.77-9.74 (m, 1H), 9.40 (s, 1H), 8.62 (d, J = 8.4 Hz, 1H), 8.57 (d, J = 1.2 Hz, 1H), 8.49 (d, J = 1.2 Hz, 1H), 8.42 (d, J = 7.8 Hz, 1H), 8.24 (d, J = 8.8 Hz, 1H), 7.87 (s, 1H), 7.31 (d, J = 7.6 Hz, 1H), 6.31-6.16 (m, 1H), 6.03-5.78 (m, 1H), 5.41 (d, J = 14.4 Hz, 1H), 5.12-4.79 (m, 5H), 4.53-4.37 (m, 4H), 1.38-1.34 (m, 3H) ppm. |
| 474 | 586.00 | 1H NMR (400 MHZ, DMSO-d6) δ = 9.82-9.79 (m, 1H), 9.38 (s, 1H), 9.06 (d, J = 4.0 Hz, 1H), 8.76 (d, J = 8.0 Hz, 1H), 8.60-8.48 (m, 2H), 8.10 (d, J = 9.2 Hz, 1H), 7.77-7.34 (m, 2H), 6.25 (br d, J = 41.6 Hz, 1H), 5.41 (d, J = 14.8 Hz, 1H), 5.09 (d, J = 14.4 Hz, 1H), 4.81 (br d, J = 5.6 Hz, 2H), 4.52-4.36 (m, 2H) ppm. |
| 473 | 570.00 | 1H NMR (400 MHZ, DMSO-d6) δ = 9.72-9.69 (m, 1H), 9.38 (s, 1H), 9.06 (d, J = 4.0 Hz, 1H), 8.76 (d, J = 8.8 Hz, 1H), 8.36 (s, 1H), 8.35-8.29 (m, 1H), 8.10 (d, J = 8.8 Hz, 1H), 7.75-7.35 (m, 2H), 6.35-6.23 (m, 1H), 4.79 (br d, J = 5.6 Hz, 2H), 4.68-4.58 (m, 1H), 4.19-4.13 (m, 1H), 2.92-2.73 (m, 1H), 2.65-2.57 (m, 1H) ppm. |
| 472 | 564.10 | 1H NMR (400 MHZ, DMSO-d6) δ = 9.83-9.71 (m, 1H), 9.31 (s, 1H), 8.84 (d, J = 4.4 Hz, 1H), 8.67 (d, J = 8.8 Hz, 1H), 8.57 (d, J = 1.6 Hz, 1H), 8.49 (d, J = 1.6 Hz, 1H), 8.06 (d, J = 8.8 Hz, 1H), 7.67 (s, 1H), 6.42-6.08 (m, 1H), 5.41 (d, J = 14.4 Hz, 1H), 5.11-5.07 (m, 1H), 4.79 (d, J = 5.6 Hz, 2H), 4.52-4.36 (m, 4H), 1.43-1.39 (m, 3H) ppm. |
| 471 | 605.10 | 1H NMR (400 MHZ, DMSO-d6 ) δ = 9.69-9.66 (m, 1H), 9.42 (s, 1H), 8.64 (d, J = 8.8 Hz, 1H), 8.46 (d, J = 7.6 Hz, 1H), 8.34-8.30 (m, 2H), 8.25 (d, J = 8.6 Hz, 1H), 7.83 (s, 1H), 7.45 (d, J = 8.0 Hz, 1H), 6.34-6.22 (m, 1H), 4.81 (br d, J = 5.6 Hz, 2H), 4.65-4.58 (m, 1H), 4.53-4.48 (m, 2H), 4.19-4.13 (m, 1H), 2.90-2.72 (m, 1H), 2.63-2.58 (m, 1H), 2.10-2.00 ( m, 3H), 1.40-1.36 (m, 3H) ppm. |
| 470 | 616.30 | 1H NMR (400MHz, DMSO-d6) δ = 9.68-9.65 (m, 1H), 9.41 (s, 1H), 8.55 (d, J = 8.8 Hz, 1H), 8.42 (d, J = 2.8 Hz, 1H), 8.34-8.30 (m, 2H), 8.21 (d, J = 8.8 Hz, 1H), 7.91 (d, J = 8.4 Hz, 1H), 7.83-7.80 (m, 2H), 7.60-7.57 (m, 1H), 7.24 (d, J = 2.8 Hz, 1H), 6.35-6.18 (m, 1H), 4.81 (d, J = 5.6 Hz, 2H), 4.61-4.57 (m, 1H), 4.35-4.27 (m, 1H), 4.21-4.12 (m, 1H), 4.08-4.01 (m, 1H), 3.76-3.70 (m, 1H), 2.84-2.70 (m, 1H), 2.62-2.55 (m, 2H), 2.15-2.05 (m, 1H), 1.51 (d, J = 6.4 Hz, 3H) ppm. |

TABLE 9-continued

Compounds of the Invention

| # | LCMS (ESI/M + H) | ¹HNMR |
|---|---|---|
| 469 | 576.10 | 1H NMR (400 MHZ, DMSO-d6) δ = 9.80-9.77 (m, 1H), 9.33 (s, 1H), 8.87 (d, J = 4.4 Hz, 1H), 8.70 (d, J = 9.2 Hz, 1H), 8.58 (s, 1H), 8.51 (s, 1H), 8.09 (d, J = 8.8 Hz, 1H), 7.69 (s, 1H), 6.35-6.14 (m, 1H), 5.42 (d, J = 14.8 Hz, 1H), 5.10 (d, J = 14.8 Hz, 1H), 4.80 (d, J = 5.6 Hz, 2H), 4.57-4.41 (m, 2H), 4.35-4.34(m, 1H), 0.87-0.80 (m, 4H) ppm. |
| 468 | 605.20 | 1H NMR (400 MHZ, DMSO-d6 ) δ = 9.78-9.75 (m, 1H), 9.42 (s, 1H), 8.64 (d, J = 8.4 Hz, 1H), 8.52-8.41 (m, 2H), 8.36 (s, 1H), 8.29-8.18 (m, 2H), 7.87 (s, 1H), 7.45 (d, J = 7.6 Hz, 1H), 6.36-6.09 (m, 1H), 5.24 (d, J = 14.4 Hz, 1H), 4.96-4.78 (m, 3H), 4.59-4.31 (m, 4H), 2.08-1.98 (m, 3H), 1.39-1.36 (m, 3H) ppm. |
| 467 | 623.10 | 1H NMR (400 MHZ, DMSO-d6 ) δ = 9.86 (s, 1H), 9.43 (s, 1H), 8.78 (s, 1H), 8.65 (d, J = 8.4 Hz, 1H), 8.59 (s, 1H), 8.46 (d, J = 7.6 Hz, 1H), 8.22 (d, J = 8.8 Hz, 1H), 7.88 (s, 1H), 7.66-7.39 (m, 2H), 6.28-6.17 (m, 1H), 5.30-5.07 (m, 2H), 4.84 (d, J = 5.6 Hz, 2H), 4.51-4.44 (m, 2H), 4.03 (s, 3H), 2.10-2.00 (m, 3H) ppm. |
| 466 | 592.00 | 1H NMR (400 MHZ, DMSO-d6) δ = 9.76-9.73 (m, 1H), 9.45 (s, 1H), 8.76 (d, J = 8.8 Hz, 1H), 8.66 (d, J = 8.8 Hz, 1H), 8.57 (s, 1H), 8.51-8.44 (m, 2H), 8.29-7.87 (m, 3H), 7.27 (d, J = 8.0 Hz, 1H), 6.20-6.02 (m, 1H), 4.84 (d, J = 5.6 Hz, 2H), 4.52 (d, J = 1.6 Hz, 2H), 3.77-3.49 (m, 2H), 2.36 (s, 3H) ppm. |
| 465 | 636.20 | 1H NMR (400 MHZ, DMSO-d6) δ = 9.89-9.86 (m, 1H), 9.44 (s, 1H), 9.10 (s, 1H), 8.78 (d, J = 1.2 Hz, 1H), 8.73 (d, J = 8.8 Hz, 1H), 8.59 (s, 1H), 8.48 (d, J = 8.5 Hz, 1H), 8.06-7.35 (m, 3H), 6.32-6.13 (m, 1H), 5.28 (d, J = 14.8 Hz, 1H), 5.09 (d, J = 14.8 Hz, 1H), 4.85 (d, J = 5.6 Hz, 2H), 4.54-4.43 (m, 2H), 2.42-2.38 (m, 1H), 1.25-1.19 (m, 4H) ppm. |
| 464 | 622.30 | 1H NMR (400 MHZ, DMSO-d6) δ = 9.76-9.73 (m, 1H), 9.37 (s, 1H), 8.67-8.58 (m, 2H), 8.55-8.46 (m, 2H), 8.27 (d, J = 9.6 Hz, 1H), 7.85 (s, 1H), 7.62 (d, J = 8.8 Hz, 1H), 6.32-6.15 (m, 1H), 5.25 (d, J = 14.8 Hz, 1H), 4.95-4.86 (m, 1H), 4.82 ( d, J =5.6 Hz, 2H), 4.52-4.34 (m, 2H), 3.32-3.25 (m, 1H), 2.60-2.54 (m, 1H), 2.15-2.01 (m, 1H) ppm. |
| 463 | 622.10 | 1H NMR (400 MHZ, DMSO-d6) δ = 9.75-9.72 (m, 1H), 9.37 (s, 1H), 8.69-8.57 (m, 2H), 8.54-8.47 (m, 2H), 8.27 (d, J = 9.6Hz, 1H), 7.86 (s, 1H), 7.63 (d, J = 8.8 Hz, 1H), 6.35-6.07 (m, 1H), 5.25 (d, J = 14.4 Hz, 1H), 4.90 (d, J = 15.2 Hz, 1H), 4.82(d, J = 5.6 Hz, 2H), 4.52-4.33 (m, 2H), 3.30-3.22 (m, 1H), 2.60-2.55 (m, 1H), 2.10-2.01 (m, 1H) ppm. |
| 462 | 724.10 | 1H NMR (400 MHZ, DMSO-d6) δ = 9.63-9.60 (m, 1H), 9.11 (s, 1H), 8.66 (d, J = 2.0 Hz, 1H), 8.47 (d, J = 2.0 Hz, 1H), 8.27 (d, J = 9.6 Hz, 1H), 8.21 (d, J = 2.8 Hz, 1H), 7.96 (d, J = 8.8 Hz, 1H), 7.71 (d, J = 2.4 Hz, 1H), 7.53 (s, 1H), 6.41-6.09 (m, 1H),4.73 (d, J = 5.6 Hz, 2H), 4.61-4.57 (m, 1H), 4.43-4.28 (m, 2H), 4.25-4.16 (m, 2H), 4.13-3.97 (m, 1H), 3.72-3.65 (m, 2H),3.31 (s, 3H), 2.93-2.72 (m, 1H), 2.70-2.56 (m, 3H) ppm. |
| 461 | 667.10 | 1H NMR (400 MHZ, DMSO-d6) δ = 9.77-9.74 (m, 1H), 9.40 (s, 1H), 8.71-8.54 (m, 3H), 8.42 (d, J = 7.6 Hz, 1H), 8.24 (d, J = 8.8 Hz, 1H), 7.86 (s, 1H), 7.31 (d, J = 7.6 Hz, 1H), 6.35-6.12 (m, 1H), 6.02-5.80 (m, 1H), 5.37 (d, J = 14.8 Hz, 1H), 5.16 (d, J = 14.8 Hz, 1H), 5.07-4.76 (m, 4H), 4.55-4.34 (m, 4H), 1.38-1.34 (m, 3H) ppm. |
| 460 | 637.20 | 1H NMR (400 MHZ, DMSO-d6) δ = 9.87-9.84 (m, 1H), 9.41 (s, 1H), 8.78 (s, 1H), 8.67-8.55 (m, 2H), 8.42 (d, J = 7.6 Hz, 1H), 8.24 (d, J = 8.4 Hz, 1H), 7.86 (s, 1H), 7.70-7.37 (m, 1H), 7.31 (d, J = 7.6 Hz, 1H), 6.33-6.12 (m, 1H), 6.05-5.77 (m, 1H), 5.28 (d, J = 14.8 Hz, 1H), 5.14-4.80 (m, 5H), 4.58-4.39 (m, 4H), 1.38-1.34 (m, 3H) ppm. |
| 459 | 638.30 | 1H NMR (400 MHZ, DMSO-d6) δ = 9.87-9.84 (m, 1H), 9.39 (s, 1H), 8.79 (s, 1H), 8.67-8.59 (m, 3H), 8.55 (d, J = 8.8 Hz, 1H), 7.87 (s, 1H), 7.68-7.39 (m, 2H), 6.34-6.12 (m, 1H), 5.29 (d, J = 14.4 Hz, 1H), 5.17-5.03 (m, 1H), 4.84 (d, J = 5.6 Hz, 2H), 4.63-4.38 (m, 2H), 3.31 (s, 1H), 2.45-2.40 (m, 1H), 2.18-1.96 (m, 1H) ppm. |
| 458 | 576.10 | 1H NMR (400 MHZ, DMSO-d6) δ = 9.68-9.67 (m, 1H), 9.44 (s, 1H), 8.76 (d, J = 8.8 Hz, 1H), 8.35-8.34 (m, 2H), 8.19 (d, J =8.8 Hz, 1H), 8.10-8.08 (m, 1H), 7.87 (s, 1H), 7.61-7.59 (m, 1H), 7.43-7.39 (m, 1H), 6.33-6.20 (m, 1H), 4.83 (d, J = 5.6 Hz, 2H),4.63-4.58 (m, 2H), 4.19-4.13(m, 1H), 2.75 (d, J = 3.6 Hz, 1H), 2.56-2.50(m, 1H) ppm |
| 457 | 637.10 | 1H NMR (400 MHZ, DMSO-d6) δ = 9.87-8.84 (m, 1H), 9.41 (s, 1H), 8.78 (S, 1H), 8.66-8.56 (m, 2H), 8.42 (d, J = 7.6 Hz, 1H), 8.24 (d, J = 8.8 Hz, 1H), 7.86 (s, 1H), 7.71-7.36 (m, 1H), 7.31 (d, J = 7.6 Hz, 1H), 6.32-6.10 (m, 1H), 6.04-5.76 (m, 1H), 5.28 (d, J = 15.0 Hz, 1H), 5.12-4.80 (m, 5H), 4.55-4.42 (m, 4H), 1.38-1.34 (m, 3H) ppm. |
| 456 | 666.90 | 1H NMR (400 MHz, DMSO-d6 ) δ = 9.77-9.74 (m, 1H), 9.40 (s, 1H), 8.69-8.56 (m, 3H), 8.43 (d, J = 8.0 Hz, 1H), 8.24 (d, J = 8.8 Hz, 1H), 7.87 (s, 1H), 7.31 (d, J = 7.6 Hz, 1H), 6.33-6.15 (m, 1H), 6.02-5.78 (m, 1H), 5.38 (d, J = 14.4 Hz, 1H), 5.17 (d, J = 14.2 Hz, 1H), 5.09-4.79 (m, 4H), 4.57-4.37 (m, 4H), 1.38-1.35 (m, 3H) ppm. |

TABLE 9-continued

Compounds of the Invention

| # | LCMS (ESI/M + H) | ¹HNMR |
|---|---|---|
| 455 | 638.10 | 1H NMR (400 MHz, DMSO-d6 ) δ = 9.86 (s, 1H), 9.37 (s, 1H), 8.80 (s, 1H), 8.61 (d, J = 5.2 Hz, 3H), 8.54 (d, J = 8.4 Hz, 1H), 7.86 (s, 1H), 7.68-7.38 (m, 2H), 6.31-6.16 (m, 1H), 5.29 (d, J = 14.8 Hz, 1H), 5.10 (d, J = 15.2 Hz, 1H), 4.84 (d, J = 4.4 Hz, 2H), 4.57-4.40 (m, 2H), 3.27 (s, 1H), 2.62-2.56 (m, 1H), 2.14-2.00 (m, 1H) ppm. |
| 454 | 626.10 | 1H NMR (400 MHZ, DMSO-d6) δ = 9.68-9.65 (m, 1H), 9.40 (s, 1H), 8.62 (d, J = 8.8 Hz, 1H), 8.53 (d, J = 2.0 Hz, 1H), 8.44 (d, J = 2.0 Hz, 1H), 8.42 (d, J = 8.0 Hz, 1H), 8.23 (d, J = 8.8 Hz, 1H), 7.83 (s, 1H), 7.31 (d, J = 7.6 Hz, 1H), 6.35-6.17 (m, 1H), 6.02-5.79 (m, 1H), 5.09-4.84 (m, 2H), 4.81 (d, J = 6.0 Hz, 2H), 4.63-4.58 (m, 1H), 4.12-4.07 (m, 1H), 2.95-2.71 (m, 1H), 2.65-2.55 (m, 1H) ppm. |
| 453 | 619.20 | 1H NMR (400 MHZ, DMSO-d6) δ = 9.69-9.67 (m, 1H), 9.44 (s, 1H), 8.73 (d, J = 8.8 Hz, 1H), 8.61 (d, J = 8.6 Hz, 1H), 8.46 (d, J = 8.4 Hz, 1H), 8.40-8.29 (m, 2H), 8.02 (d, J = 8.0 Hz, 1H), 7.88 (s, 1H), 6.81-6.42 (m, 2H), 6.38-6.20 (m, 1H), 4.83 (d, J = 6.0 Hz, 2H), 4.64-4.59 (m, 1H), 4.20-4.14 (m, 1H), 2.90-2.72 (m, 1H), 2.64-2.59 (m, 1H), 2.43-2.40 (m, 1H), 1.25-1.20 (m, 2H), 1.13-1.05 (m, 2H) ppm. |
| 452 | 580.00 | 1H NMR (400 MHZ, DMSO-d6) δ = 9.82-9.79 (m, 1H), 9.59 (s, 1H), 9.49 (s, 1H), 8.83 (d, J = 8.4 Hz, 1H), 8.75 (s, 1H), 8.62 (d, J = 8.4 Hz, 1H), 8.58 (d, J = 1.6 Hz, 1H), 8.51 (d, J = 1.6 Hz, 1H), 8.28-7.85 (m, 2H), 6.36-6.12 (m, 1H), 5.44-5.40 (m, 1H), 5.12-5.08 (m, 1H), 4.86 (d, J = 5.6 Hz, 2H), 4.50 (s, 1H), 4.47-4.38 (m, 1H) ppm. |
| 451 | 671.10 | 1H NMR (400 MHZ, DMSO-d6) δ = 9.89-9.86 (m, 1H), 9.44 (s, 1H), 8.80 (s, 1H), 8.73-8.71 (m, 1H), 8.66-8.60 (m, 3H), 7.91-7.89 (m, 2H), 7.65-7.28 (m, 2H), 6.29-6.18 (m, 1H), 5.29 (d, J = 14.8 Hz, 1H), 5.10 (d, J = 14.8 Hz, 1H), 4.85 (d, J = 5.6 Hz, 2H), 4.55-4.44 (m, 2H), 3.38 (br d, J = 4.0 Hz, 1H), 2.64-2.60 (m, 1H), 2.19-2.13 (m, 1H) ppm. |
| 450 | 651.00 | 1H NMR (400 MHZ, DMSO-d6) δ = 9.78-9.75 (m, 1H), 9.42 (s, 1H), 8.65-8.60 (m, 3H), 8.42 (d, J = 7.6 Hz, 1H), 8.21 (d, J =8.8 Hz, 1H), 7.87 (s, 1H), 7.34 (d, J = 7.6 Hz, 1H), 6.28-6.18 (m, 1H), 5.85-5.84 (m, 1H), 5.38 (d, J = 14.8 Hz, 1H), 5.17 (d, J = 14.8 Hz, 1H), 5.07-4.89 (m, 2H), 4.82 (d, J = 6.0 Hz, 2H), 4.50-4.42 (m, 2H), 4.01 (s, 3H) ppm. |
| 449 | 655.00 | 1H NMR (400 MHZ, DMSO-d6) δ = 9.80-9.70 (m, 1H), 9.40 (s, 1H), 8.71-8.67 (m, 1H), 8.64-8.61 (m, 1H), 8.58 (d, J = 8.8 Hz, 1H), 8.54 (d, J = 1.6 Hz, 1H), 8.47 (d, J = 1.6 Hz, 1H), 8.40 (s, 1H), 7.98-7.80 (m, 2H), 7.71-7.18 (m, 1H), 6.35-6.08 (m, 1H), 5.40-5.36 (m, 1H), 5.06 (d, J = 14.4 Hz, 1H), 4.80 (d, J = 5.2 Hz, 2H), 4.45 (d, J = 2.4 Hz, 1H), 4.43-4.38 (m, 1H), 3.38-3.36 (m, 1H), 2.61-2.56 (m, 1H), 2.16-2.10 (m, 1H) ppm. |
| 448 | 700.90 | 1H NMR (400 MHZ, DMSO-d6) δ = 9.70-9.68 (m, 1H), 9.43 (s, 1H), 8.74-8.70 (m, 1H), 8.68-8.59 (m, 3H), 8.48 (d, J = 2.0 Hz, 1H), 8.37-8.29 (m, 1H), 8.03-7.84 (m, 2H), 7.77-7.17 (m, 1H), 6.39-6.15 (m, 1H), 4.82 (d, J = 5.6 Hz, 2H), 4.67-4.47 (m, 1H), 4.16-4.01 (m, 1H), 3.41-3.38 (m, 1H), 2.84-2.72 (m, 1H), 2.64-2.61 (m, 1H), 2.44 (d, J = 4.0 Hz, 1H), 2.20-2.14 (m, 1H) ppm. |
| 447 | 655.00 | 1H NMR (400 MHZ, DMSO-d6) δ = 9.79-9.77 (m, 1H), 9.44 (s, 1H), 8.75-8.68 (m, 1H), 8.68-8.59 (m, 2H), 8.58 (d, J = 2.0 Hz, 1H), 8.51 (d, J = 2.0 Hz, 1H), 7.93-7.87 (m, 2H), 7.70-7.22 (m, 1H), 6.36-6.07 (m, 1H), 5.42 (d, J = 14.4 Hz, 1H), 5.10 (d, J = 14.8 Hz, 1H), 4.84 (d, J = 6.0 Hz, 2H), 4.55-4.46 (m, 1H), 4.46-4.38 (m, 1H), 3.41-3.37 (m, 1H), 2.63 (d, J = 5.2 Hz, 1H), 2.24-2.07 (m, 1H) ppm. |
| 446 | 628.20 | 1H NMR (400 MHZ, DMSO-de) δ = 9.88-9.85 (m, 1H), 9.43 (s, 1H), 8.78 (s, 1H), 8.65 (d, J = 8.8 Hz, 1H), 8.59 (s, 1H), 8.46 (d, J = 7.6 Hz, 1H), 8.25 (d, J = 8.8 Hz, 1H), 7.88 (s, 1H), 7.70-7.36 (m, 2H), 7.11-6.82 (m, 1H), 6.29-6.16 (m, 1H), 5.28 (d, J = 15.0 Hz, 1H), 5.09 (d, J = 14.8 Hz, 1H), 4.84 (d, J = 5.6 Hz, 2H), 4.56-4.40 (m, 2H) ppm. |
| 445 | 621.10 | 1H NMR (400 MHZ, DMSO-d6) δ = 9.79-7.60 (m, 1H), 9.42 (s, 1H), 8.64 (d, J = 8.8 Hz, 1H), 8.56 (s, 1H), 8.52-8.41 (m, 2H), 8.25 (d, J = 8.8 Hz, 1H), 7.88 (s, 1H), 7.45 (d, J = 7.6 Hz, 1H), 6.33-6.14 (m, 1H), 5.41 (d, J = 14.4 Hz, 1H), 5.09 (d, J = 14.8 Hz, 1H), 4.83 (br d, J = 5.6 Hz, 2H), 4.57-4.40 (m, 4H), 2.08-1.99 (m, 3H), 1.40-1.36 (m, 3H) ppm. |
| 444 | 596.00 | 1H NMR (400 MHZ, DMSO-d6) δ = 9.86-9.73 (m, 1H), 9.46 (s, 1H), 8.72 (d, J = 8.8 Hz, 1H), 8.63-8.46 (m, 2H), 8.07-8.04 (m, 1H), 7.97-7.82 (m, 2H), 7.68-7.04 (m, 3H), 6.33-6.08 (m, 1H), 5.40 (d, J = 14.4 Hz, 1H), 5.09 (d, J = 14.8 Hz, 1H), 4.83 (d, J = 5.6 Hz, 2H), 4.53-4.38 (m, 2H) ppm. |
| 443 | 636.20 | 1H NMR (400 MHZ, DMSO-d6) δ = 9.74-9.73 (m, 1H), 9.40 (s, 1H), 8.70-8.60 (m, 2H), 8.56 (d, J = 2.4 Hz, 1H), 8.51 (d, J = 2.0 Hz, 1H), 7.91 (d, J = 7.6 Hz, 1H), 7.84 (s, 1H), 7.76-7.72 (m, 1H), 7.03 (d, J = 8.4 Hz, 1H), 6.37-6.13 (m, 1H), 5.68-5.42 (m, 1H), 5.38-5.33 (m, 1H), 4.82 (d, J = 5.2 Hz, 2H), 4.67-4.53 (m, 1H), 4.31 (d, J = 11.2 Hz, 2H), 4.15-3.99 (m, 1H), 3.73-3.63 (m, 2H), 2.91-2.73 (m, 1H), 2.64-2.57 (m, 1H), 2.47 (s, 2H), 1.21 (d, J = 6.0 Hz, 6H) ppm. |

TABLE 9-continued

Compounds of the Invention

| # | LCMS (ESI/M + H) | ¹HNMR |
|---|---|---|
| 442 | 647.10 | 1H NMR (400 MHZ, DMSO-d6) δ = 9.74 (s, 1H), 9.03 (s, 1H), 8.80 (s, 2H), 8.25-8.17 (m, 2H), 7.51 (s, 1H), 7.30 (d, J = 2.4 Hz, 1H), 6.49 (d, J = 2.4 Hz, 1H), 6.34 (s, 1H), 5.30-5.13 (m, 2H), 4.73 (s, 2H), 4.56-4.42 (m, 2H), 4.38-4.25 (m, 4H), 4.16-4.03 (m, 1H), 3.93-3.79 (m, 1H), 3.53 (d, J = 7.6 Hz, 1H), 2.36 (d, J = 2.4 Hz, 1H), 2.06-1.96 (m, 1H), 1.41 (d, J = 6.0 Hz, 3H) ppm. |
| 441 | 620.10 | 1H NMR (400 MHZ, DMSO-d6) δ = 9.68-9.65 (m, 1H), 9.43 (s, 1H), 8.75-8.67 (m, 1H), 8.66-8.59 (m, 1H), 8.40-8.28 (m, 2H), 8.08-7.95 (m, 2H), 7.87 (s, 1H), 7.34-6.95 (m, 1H), 6.38-6.18 (m, 1H), 5.70-5.39 (m, 1H), 4.82 (d, J = 5.6 Hz, 2H), 4.67-4.49 (m, 3H), 4.40-4.25 (m, 2H), 4.22-4.11 (m, 1H), 2.90-2.72 (m, 1H), 2.64-2.55 (m, 1H) ppm. |
| 440 | 654.30 | 1H NMR (400MHZ, DMSO-d6) δ = 9.85 (s, 1H), 9.38 (s, 1H), 8.80 (s, 1H), 8.63-8.59 (m, 3H), 8.52 (d, J = 8.4 Hz, 1H), 7.86 (s, 1H), 7.66-7.39 (m, 2H), 6.28-6.17 (m, 1H), 5.28 (d, J = 14.8 Hz, 1H), 5.10 (d, J = 14.4 Hz, 1H), 4.83 (d, J = 4.8 Hz, 2H), 4.55-4.40 (m, 2H), 3.30-3.25 (m, 1H), 2.60-2.56 (m, 1H), 2.10-2.03 (m, 1H) ppm. |
| 439 | 658.40 | 1H NMR (400 MHZ, DMSO-d6) δ = 9.80-9.78 (m, 1H), 9.01 (s, 1H), 8.78 (s, 1H), 8.58 (s, 1H), 8.35 (d, J = 2.8 Hz, 1H), 8.12 (d, J = 8.8 Hz, 1H), 7.90 (d, J = 1.6 Hz, 1H), 7.83 (d, J = 8.8 Hz, 1H), 7.65-7.39 (m, 2H), 7.34 (s, 1H), 6.33-6.14 (m, 1H), 5.27 (d, J = 14.8 Hz, 1H), 5.09 (d, J = 14.8 Hz, 1H), 4.73 (d, J = 5.2 Hz, 2H), 4.56-4.43 (m, 2H), 4.18-4.10 (m, 4H), 3.67-3.65 (m, 2H), 3.36-3.35 (m, 3H), 2.81-2.78 (m, 2H), 1.96-1.89 (m, 2H) ppm. |
| 437 | 660.40 | 1H NMR (400 MHZ, DMSO-d6) δ = 9.82-9.79 (m, 1H), 9.06 (s, 1H), 8.78 (s, 1H), 8.59 (s, 1H), 8.31-8.17 (m, 2H), 7.72 (d, J = 2.4 Hz, 1H), 7.68-7.35 (m, 2H), 7.09 (d, J = 2.4 Hz, 1H), 6.34-6.12 (m, 1H), 5.30-5.26 (m, 1H), 5.09 (d, J = 15.2 Hz, 1H), 4.74 (d, J = 5.2 Hz, 2H), 4.57-4.41 (m, 2H), 4.34 (s, 4H), 4.20-4.09 (m, 2H), 3.71-3.61 (m, 2H), 3.31 (s, 3H) ppm. |

Example 2. Assay for ATPase Catalytic Activity of BRM and BRG-1

The ATPase catalytic activity of BRM or BRG-1 was measured by an in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG-1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh DTT (Pierce™ DTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then, following addition of 5 μL of ADP-Glo™ Reagent provided in the kit, the reaction incubates at room temperature for 40 minutes. Then, 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG-1 were synthesized from high five insect cell lines with a purity of greater than 90%. $IC_{50}$ data from the ATPase catalytic activity assay described herein are shown in Table 10 below.

TABLE 10

BRM and BRG-1 Inhibition Data for Compounds of the Invention

| cpd # | BRM IC50 (μM) | BRG1 IC50 (μM) | Ratio* |
|---|---|---|---|
| 1 | 0.0029 | 0.0214 | 7.29 |
| 2 | 0.0006 | 0.0105 | 18.80 |
| 3 | 0.0008 | 0.0252 | 27.70 |
| 4 | 0.0011 | 0.0169 | 12.99 |
| 5 | 0.0011 | 0.0109 | 9.64 |
| 6 | 0.0012 | 0.0213 | 18.28 |
| 7 | 0.0012 | 0.0179 | 12.72 |
| 8 | 0.0013 | 0.0223 | 14.89 |
| 9 | 0.0013 | 0.0302 | 23.22 |
| 10 | 0.0013 | 0.0157 | 11.90 |
| 11 | 0.0014 | 0.0142 | 9.50 |
| 12 | 0.0014 | 0.0162 | 11.63 |
| 13 | 0.0015 | 0.0243 | 14.77 |
| 14 | 0.0015 | 0.0160 | 9.92 |
| 15 | 0.0015 | 0.0166 | 11.06 |
| 16 | 0.0015 | 0.0178 | 10.27 |
| 17 | 0.0015 | 0.0234 | 12.76 |
| 18 | 0.0015 | 0.0240 | 15.43 |
| 19 | 0.0016 | 0.0207 | 13.20 |
| 20 | 0.0016 | 0.0447 | 26.66 |
| 21 | 0.0016 | 0.0283 | 16.50 |
| 22 | 0.0016 | 0.0162 | 9.93 |
| 23 | 0.0016 | 0.0379 | 19.69 |
| 24 | 0.0017 | 0.0311 | 18.65 |
| 25 | 0.0017 | 0.0439 | 21.51 |
| 26 | 0.0017 | 0.0391 | 21.77 |
| 27 | 0.0018 | 0.0195 | 11.52 |
| 28 | 0.0018 | 0.0422 | 22.66 |
| 29 | 0.0018 | 0.0350 | 22.36 |
| 30 | 0.0018 | 0.0391 | 19.40 |
| 31 | 0.0018 | 0.0330 | 18.05 |
| 32 | 0.0019 | 0.0367 | 18.96 |
| 33 | 0.0019 | 0.0189 | 11.17 |
| 34 | 0.1204 | 1.4650 | 12.17 |

TABLE 10-continued

BRM and BRG-1 Inhibition Data for Compounds of the Invention

| cpd # | BRM IC50 (μM) | BRG1 IC50 (μM) | Ratio* |
|---|---|---|---|
| 35 | 0.0019 | 0.0233 | 13.74 |
| 36 | 0.0019 | 0.0399 | 21.51 |
| 37 | 0.0020 | 0.0319 | 15.93 |
| 38 | 0.0020 | 0.0339 | 16.77 |
| 39 | 0.0020 | 0.0246 | 13.44 |
| 40 | 0.0020 | 0.0385 | 16.70 |
| 41 | 0.0020 | 0.0464 | 20.00 |
| 42 | 0.0020 | 0.0270 | 13.35 |
| 43 | 0.0020 | 0.0406 | 19.89 |
| 44 | 0.0021 | 0.0641 | 23.96 |
| 45 | 0.0021 | 0.0258 | 12.59 |
| 46 | 0.0023 | 0.0477 | 20.83 |
| 47 | 0.0023 | 0.0543 | 16.31 |
| 48 | 0.0023 | 0.0341 | 13.42 |
| 49 | 0.0024 | 0.0440 | 14.43 |
| 50 | 0.0025 | 0.0387 | 15.78 |
| 51 | 0.0025 | 0.0421 | 18.72 |
| 52 | 0.0025 | 0.0560 | 22.78 |
| 53 | 0.0025 | 0.0543 | 19.48 |
| 54 | 0.0025 | 0.0279 | 9.72 |
| 55 | 0.0025 | 0.1237 | 35.69 |
| 56 | 0.0025 | 0.0582 | 23.00 |
| 57 | 0.0025 | 0.0368 | 17.61 |
| 58 | 0.0025 | 0.0644 | 23.60 |
| 59 | 0.0025 | 0.0725 | 28.47 |
| 60 | 0.0026 | 0.0531 | 18.66 |
| 61 | 0.0026 | 0.0485 | 21.08 |
| 62 | 0.0026 | 0.0797 | 28.84 |
| 63 | 0.0026 | 0.0587 | 23.13 |
| 64 | 0.0026 | 0.0298 | 11.59 |
| 65 | 0.0026 | 0.0462 | 21.94 |
| 66 | 0.0026 | 0.0785 | 24.64 |
| 67 | 0.0027 | 0.0462 | 17.37 |
| 68 | 0.0027 | 0.0362 | 13.58 |
| 69 | 0.0027 | 0.0375 | 13.99 |
| 70 | 0.0027 | 0.0396 | 12.79 |
| 71 | 0.0027 | 0.0483 | 17.64 |
| 72 | 0.0028 | 0.0666 | 21.76 |
| 73 | 0.0028 | 0.0571 | 20.62 |
| 74 | 0.0028 | 0.0267 | 9.59 |
| 75 | 0.0028 | 0.0801 | 26.00 |
| 76 | 0.0028 | 0.0451 | 16.02 |
| 77 | 0.0028 | 0.0670 | 23.82 |
| 78 | 0.0029 | 0.0949 | 24.83 |
| 79 | 0.0030 | 0.0344 | 12.12 |
| 80 | 0.0030 | 0.0484 | 16.24 |
| 81 | 0.0030 | 0.0467 | 14.31 |
| 82 | 0.0031 | 0.0680 | 22.96 |
| 83 | 0.0031 | 0.0496 | 19.36 |
| 84 | 0.0031 | 0.0957 | 25.97 |
| 85 | 0.0031 | 0.0699 | 20.37 |
| 86 | 0.0032 | 0.0512 | 17.70 |
| 87 | 0.0032 | 0.0783 | 20.66 |
| 88 | 0.0032 | 0.0889 | 21.33 |
| 89 | 0.0032 | 0.1315 | 28.75 |
| 90 | 0.0032 | 0.0512 | 15.80 |
| 91 | 0.0032 | 0.0467 | 14.38 |
| 92 | 0.0033 | 0.0390 | 11.88 |
| 93 | 0.0033 | 0.0423 | 14.45 |
| 94 | 0.0033 | 0.0586 | 16.88 |
| 95 | 0.0033 | 0.0337 | 10.07 |
| 96 | 0.0034 | 0.0864 | 22.86 |
| 97 | 0.0034 | 0.0657 | 17.66 |
| 98 | 0.0035 | 0.1225 | 31.77 |
| 99 | 0.0035 | 0.0427 | 12.19 |
| 100 | 0.0035 | 0.0448 | 13.01 |
| 101 | 0.0035 | 0.0834 | 23.62 |
| 102 | 0.0036 | 0.0954 | 26.75 |
| 103 | 0.0036 | 0.0434 | 12.05 |
| 104 | 0.0036 | 0.0427 | 10.21 |
| 105 | 0.0037 | 0.0367 | 9.68 |
| 106 | 0.0038 | 0.0353 | 10.13 |
| 107 | 0.0038 | 0.0990 | 25.68 |
| 108 | 0.0039 | 0.0644 | 16.69 |
| 109 | 0.0039 | 0.0872 | 17.52 |
| 110 | 0.0039 | 0.0694 | 15.35 |
| 111 | 0.0039 | 0.0791 | 19.81 |
| 112 | 0.0039 | 0.0572 | 14.50 |
| 113 | 0.0040 | 0.0839 | 21.12 |
| 114 | 0.0040 | 0.1179 | 29.13 |
| 115 | 0.0040 | 0.1055 | 22.17 |
| 116 | 0.0040 | 0.0483 | 12.04 |
| 117 | 0.0040 | 0.0871 | 21.61 |
| 118 | 0.0040 | 0.0630 | 19.47 |
| 119 | 0.0041 | 0.0422 | 10.33 |
| 120 | 0.0041 | 0.0983 | 24.03 |
| 121 | 0.0041 | 0.0567 | 13.86 |
| 122 | 0.0042 | 0.0459 | 10.93 |
| 123 | 0.0042 | 0.0506 | 12.84 |
| 124 | 0.0043 | 0.0749 | 15.93 |
| 125 | 0.0043 | 0.0815 | 19.09 |
| 126 | 0.0044 | 0.0889 | 20.36 |
| 127 | 0.0044 | 0.0725 | 17.26 |
| 128 | 0.0044 | 0.1233 | 23.54 |
| 129 | 0.0045 | 0.1107 | 18.60 |
| 130 | 0.0045 | 0.0711 | 15.94 |
| 131 | 0.0045 | 0.0708 | 17.91 |
| 132 | 0.0045 | 0.0772 | 17.90 |
| 133 | 0.0045 | 0.0942 | 18.45 |
| 134 | 0.0046 | 0.0986 | 20.63 |
| 135 | 0.0046 | 0.1100 | 23.88 |
| 136 | 0.0046 | 0.0749 | 13.12 |
| 137 | 0.0047 | 0.0997 | 21.45 |
| 138 | 0.0047 | 0.0882 | 18.95 |
| 139 | 0.0047 | 0.1470 | 24.09 |
| 140 | 0.0047 | 0.0831 | 17.66 |
| 141 | 0.0047 | 0.0763 | 16.19 |
| 142 | 0.0047 | 0.0891 | 19.04 |
| 143 | 0.0047 | 0.0985 | 21.43 |
| 144 | 0.0048 | 0.1088 | 25.02 |
| 145 | 0.0048 | 0.0772 | 16.05 |
| 146 | 0.0048 | 0.0729 | 15.71 |
| 147 | 0.0048 | 0.0581 | 11.98 |
| 148 | 0.0049 | 0.0826 | 17.59 |
| 149 | 0.0049 | 0.0677 | 13.78 |
| 150 | 0.0049 | 0.1190 | 21.42 |
| 151 | 0.0049 | 0.0766 | 16.49 |
| 152 | 0.0050 | 0.0530 | 11.35 |
| 153 | 0.0050 | 0.0695 | 13.92 |
| 154 | 0.0050 | 0.0680 | 15.21 |
| 155 | 0.0050 | 0.0880 | 19.80 |
| 156 | 0.0050 | 0.0970 | 23.13 |
| 157 | 0.0051 | 0.0968 | 18.45 |
| 158 | 0.0051 | 0.0867 | 17.08 |
| 159 | 0.0051 | 0.1000 | 14.72 |
| 160 | 0.0051 | 0.0760 | 17.82 |
| 161 | 0.0051 | 0.0493 | 9.63 |
| 162 | 0.0113 | 0.2210 | 17.63 |
| 163 | 0.0052 | 0.1158 | 22.36 |
| 164 | 0.0052 | 0.1723 | 32.00 |
| 165 | 0.0053 | 0.1434 | 22.18 |
| 166 | 0.0053 | 0.0838 | 15.93 |
| 167 | 0.0053 | 0.0567 | 10.82 |
| 168 | 0.0053 | 0.0795 | 15.00 |
| 169 | 0.0053 | 0.0583 | 10.91 |
| 170 | 0.0053 | 0.1224 | 24.59 |
| 171 | 0.0055 | 0.0891 | 16.27 |
| 172 | 0.0055 | 0.0741 | 13.09 |
| 173 | 0.0055 | 0.1783 | 30.21 |
| 174 | 0.0056 | 0.1582 | 28.19 |
| 175 | 0.0056 | 0.0493 | 12.83 |
| 176 | 0.0056 | 0.1225 | 17.02 |
| 177 | 0.0056 | 0.1131 | 22.67 |
| 178 | 0.0056 | 0.2069 | 34.29 |
| 179 | 0.0056 | 0.0599 | 10.62 |
| 180 | 0.0057 | 0.1035 | 18.29 |

TABLE 10-continued

BRM and BRG-1 Inhibition Data for Compounds of the Invention

| cpd # | BRM IC50 (µM) | BRG1 IC50 (µM) | Ratio* |
|---|---|---|---|
| 181 | 0.0057 | 0.1456 | 29.09 |
| 182 | 0.0057 | 0.0839 | 16.19 |
| 183 | 0.0057 | 0.0899 | 12.89 |
| 184 | 0.1429 | 3.4163 | 23.91 |
| 185 | 0.0057 | 0.1103 | 21.73 |
| 186 | 0.0057 | 0.1019 | 16.18 |
| 187 | 0.0058 | 0.0766 | 13.32 |
| 188 | 0.0058 | 0.1319 | 20.95 |
| 189 | 0.0058 | 0.1069 | 16.84 |
| 190 | 0.0058 | 0.1267 | 20.33 |
| 191 | 0.0058 | 0.0621 | 10.64 |
| 192 | 0.0059 | 0.0665 | 11.37 |
| 193 | 0.0059 | 0.1098 | 16.06 |
| 194 | 0.0059 | 0.0692 | 11.72 |
| 195 | 0.0059 | 0.1681 | 24.88 |
| 196 | 0.0998 | 3.8430 | 38.53 |
| 197 | 0.0060 | 0.0846 | 14.25 |
| 198 | 0.0060 | 0.1029 | 17.01 |
| 199 | 0.0061 | 0.0664 | 10.91 |
| 200 | 0.0061 | 0.1009 | 16.77 |
| 201 | 0.0061 | 0.0640 | 10.41 |
| 202 | 0.0061 | 0.1252 | 15.85 |
| 203 | 0.0061 | 0.0920 | 14.89 |
| 204 | 0.0061 | 0.0717 | 11.71 |
| 205 | 0.0061 | 0.1283 | 23.40 |
| 206 | 0.0062 | 0.1971 | 31.39 |
| 207 | 0.0062 | 0.1132 | 18.77 |
| 208 | 0.0063 | 0.2386 | 36.06 |
| 209 | 0.0063 | 0.1030 | 21.93 |
| 210 | 0.0063 | 0.0853 | 13.52 |
| 211 | 0.0063 | 0.0616 | 9.76 |
| 212 | 0.0064 | 0.1356 | 21.18 |
| 213 | 0.0064 | 0.0903 | 14.08 |
| 214 | 0.0064 | 0.0720 | 11.03 |
| 215 | 0.0065 | 0.0893 | 13.76 |
| 216 | 0.0065 | 0.1484 | 21.18 |
| 217 | 0.0065 | 0.0634 | 9.68 |
| 218 | 0.0067 | 0.0906 | 11.41 |
| 219 | 0.0067 | 0.1667 | 19.94 |
| 220 | 0.0068 | 0.1482 | 21.81 |
| 221 | 0.0069 | 0.1785 | 27.18 |
| 222 | 0.0070 | 0.0798 | 11.79 |
| 223 | 0.0070 | 0.1020 | 13.44 |
| 224 | 0.0071 | 0.1154 | 15.91 |
| 225 | 0.0071 | 0.4609 | 49.95 |
| 226 | 0.0071 | 0.1056 | 14.90 |
| 227 | 0.0071 | 0.0705 | 9.91 |
| 228 | 0.0071 | 0.1082 | 14.53 |
| 229 | 0.0072 | 0.0723 | 10.03 |
| 230 | 0.0072 | 0.1534 | 18.99 |
| 231 | 0.0072 | 0.1015 | 14.03 |
| 232 | 0.0073 | 0.1399 | 19.46 |
| 233 | 0.0073 | 0.0762 | 10.41 |
| 234 | 0.0073 | 0.0830 | 15.92 |
| 235 | 0.0074 | 0.1632 | 23.91 |
| 236 | 0.0074 | 0.1602 | 21.61 |
| 237 | 0.0076 | 0.1725 | 25.36 |
| 238 | 0.0076 | 0.1323 | 17.11 |
| 239 | 0.0076 | 0.0932 | 12.22 |
| 240 | 0.0076 | 0.1852 | 19.83 |
| 241 | 0.0077 | 0.0824 | 11.31 |
| 242 | 0.0077 | 0.2457 | 34.12 |
| 243 | 0.0077 | 0.1107 | 14.29 |
| 244 | 0.0078 | 0.2454 | 25.74 |
| 245 | 0.0078 | 0.1662 | 17.91 |
| 246 | 0.0078 | 0.2172 | 23.74 |
| 247 | 0.0078 | 0.0985 | 13.39 |
| 248 | 0.0078 | 0.1281 | 16.34 |
| 249 | 0.0079 | 0.0845 | 10.70 |
| 250 | 0.0080 | 0.2198 | 26.90 |
| 251 | 0.0080 | 0.1261 | 15.83 |
| 252 | 0.0080 | 0.2187 | 23.94 |
| 253 | 0.0080 | 0.1710 | 22.99 |
| 254 | 0.0080 | 0.1900 | 21.58 |
| 255 | 0.0081 | 0.2065 | 23.96 |
| 256 | 0.0081 | 0.1120 | 13.83 |
| 257 | 0.0082 | 0.1079 | 13.20 |
| 258 | 0.0082 | 0.1021 | 12.41 |
| 259 | 0.0083 | 0.2736 | 27.15 |
| 260 | 0.0085 | 0.2878 | 34.05 |
| 261 | 0.0085 | 0.2421 | 25.34 |
| 262 | 0.0085 | 0.1660 | 19.49 |
| 263 | 0.0085 | 0.0897 | 10.51 |
| 264 | 0.0086 | 0.1770 | 21.59 |
| 265 | 0.0087 | 0.1005 | 11.56 |
| 266 | 0.0087 | 0.1535 | 18.84 |
| 267 | 0.0088 | 0.0918 | 10.49 |
| 268 | 0.0088 | 0.1988 | 22.51 |
| 269 | 0.0089 | 0.1105 | 11.77 |
| 270 | 0.0089 | 0.1740 | 22.02 |
| 271 | 0.0089 | 0.2939 | 29.78 |
| 272 | 0.0089 | 0.1990 | 23.60 |
| 273 | 0.0089 | 0.2099 | 23.61 |
| 274 | 0.0089 | 0.1921 | 22.22 |
| 275 | 0.0091 | 0.1280 | 14.02 |
| 276 | 0.0091 | 0.1316 | 14.41 |
| 277 | 0.0091 | 0.0900 | 19.61 |
| 278 | 0.0092 | 0.0755 | 9.67 |
| 279 | 0.0092 | 0.1642 | 18.19 |
| 280 | 0.0092 | 0.1060 | 11.58 |
| 281 | 0.0093 | 0.0943 | 10.16 |
| 282 | 0.0094 | 0.1628 | 17.58 |
| 283 | 0.0094 | 0.3849 | 28.86 |
| 284 | 0.0095 | 0.1048 | 11.05 |
| 285 | 0.0095 | 0.0946 | 9.97 |
| 286 | 0.0096 | 0.1964 | 20.51 |
| 287 | 0.0096 | 0.1131 | 11.77 |
| 288 | 0.0096 | 0.2030 | 26.09 |
| 289 | 0.0096 | 0.1152 | 11.49 |
| 290 | 0.0096 | 0.1872 | 17.27 |
| 291 | 0.0097 | 0.2063 | 21.54 |
| 292 | 0.0098 | 0.2258 | 23.12 |
| 293 | 0.0098 | 0.1680 | 17.20 |
| 294 | 0.0098 | 0.3443 | 35.16 |
| 295 | 0.0098 | 0.1743 | 16.68 |
| 296 | 0.0099 | 0.1141 | 11.58 |
| 297 | 0.0099 | 0.2663 | 29.64 |
| 298 | 0.0099 | 0.1428 | 14.40 |
| 299 | 0.0099 | 0.2950 | 29.29 |
| 300 | 0.0099 | 0.1181 | 11.89 |
| 301 | 0.0100 | 0.1754 | 18.66 |
| 302 | 0.0100 | 0.3479 | 30.11 |
| 303 | 0.0101 | 0.1076 | 10.70 |
| 304 | 0.0101 | 0.1584 | 15.65 |
| 305 | 0.0103 | 0.1250 | 12.14 |
| 306 | 0.0103 | 0.3597 | 32.74 |
| 307 | 0.0104 | 0.1611 | 20.42 |
| 308 | 0.0104 | 0.3291 | 28.69 |
| 309 | 0.0105 | 0.1151 | 11.01 |
| 313 | 0.0130 | 0.5538 | 36.05 |
| 314 | 0.5468 | 4.1269 | 7.55 |
| 315 | 0.0249 | 1.0849 | 43.60 |
| 316 | 0.0183 | 0.3251 | 17.77 |
| 317 | 0.2268 | 1.7642 | 7.78 |
| 318 | 0.0123 | 0.1046 | 8.51 |
| 319 | 0.1925 | 4.9919 | 25.94 |
| 322 | 0.0322 | 1.1769 | 30.39 |
| 323 | 0.0118 | 0.1638 | 13.90 |
| 324 | 0.0161 | 0.3566 | 22.15 |
| 325 | 0.0297 | 0.3880 | 13.06 |
| 326 | 0.1219 | 3.5059 | 28.75 |
| 327 | 0.0035 | 0.0407 | 11.57 |

TABLE 10-continued

BRM and BRG-1 Inhibition Data for Compounds of the Invention

| cpd # | BRM IC50 (μM) | BRG1 IC50 (μM) | Ratio* |
|---|---|---|---|
| 328 | 0.0241 | 0.7232 | 29.97 |
| 329 | 0.0407 | 1.3463 | 29.14 |
| 330 | 0.0153 | 0.3508 | 27.40 |

*Ratio is a numeric value produced by dividing BRG1 $IC_{50}$ (μM) by BRM $IC_{50}$ (μM).

Example 3. Assay for Inhibitory Effects on BRG1 and BRM-Dependent Transcription The potential inhibitory effects of compounds on BRG1 and BRM dependent transcription was study by testing the activity of against the BRG1 mutant lung cancer cell line A549 and a MDA cell line with BRM removed by CRISPR. Both cell lines were genetically engineered with a BRG1 or BRM-dependent mouse mammary tumor virus luciferase reporter. Luciferase transcription was induced by dexamethasone in the presence of compound at different concentrations and luminescence was measured using a plate reader 6 hours after stimulation.

$IC_{50}$ data from the assay described herein are shown in Table 11 below.

TABLE 11

BRM and BRG-1 Inhibition Data for Compounds of the Invention

| cpd # | BRM IC50 (μM) | Ratio* | cpd # | BRM IC50 (μM) | Ratio* |
|---|---|---|---|---|---|
| 331 | 0.0169 | 33.18 | 427 | 0.0206 | 32.84 |
| 332 | 0.0210 | 28.13 | 428 | 0.0203 | 26.26 |
| 333 | 0.0154 | 31.11 | 429 | 0.0169 | 32.94 |
| 334 | 0.0190 | 26.38 | 430 | 0.0081 | 40.24 |
| 335 | 0.0163 | 30.32 | 431 | 0.0095 | 31.77 |
| 336 | 0.0153 | 22.47 | 432 | 0.0130 | 25.93 |
| 337 | 0.0201 | 30.81 | 433 | 0.0030 | 27.74 |
| 338 | 0.0141 | 21.68 | 434 | 0.0087 | 41.19 |
| 339 | 0.0194 | 40.09 | 435 | 0.0230 | 25.82 |
| 340 | 0.0158 | 26.04 | 436 | 0.0131 | 43.58 |
| 341 | 0.1220 | 28.75 | 437 | 0.0058 | 35.93 |
| 342 | 0.0179 | 23.62 | 439 | 0.0133 | 27.20 |
| 343 | 0.0111 | 24.93 | 440 | 0.0161 | 53.01 |
| 344 | 0.0186 | 25.42 | 441 | 0.0089 | 21.14 |
| 345 | 0.0156 | 21.59 | 442 | 0.0085 | 25.83 |
| 346 | 0.0199 | 44.98 | 443 | 0.0152 | 27.83 |
| 347 | 0.0172 | 25.03 | 444 | 0.0226 | 24.79 |
| 348 | 0.0139 | 30.79 | 445 | 0.0212 | 22.07 |
| 349 | 0.0130 | 34.91 | 446 | 0.0135 | 29.71 |
| 350 | 0.0170 | 25.08 | 447 | 0.0138 | 22.11 |
| 351 | 0.0200 | 25.07 | 448 | 0.0190 | 37.60 |
| 352 | 0.0163 | 23.28 | 449 | 0.0074 | 37.87 |
| 353 | 0.0155 | 21.63 | 450 | 0.0154 | 35.43 |
| 354 | 0.0172 | 26.53 | 451 | 0.0056 | 25.86 |
| 355 | 0.0131 | 23.10 | 452 | 0.0204 | 28.85 |
| 356 | 0.0146 | 23.98 | 453 | 0.0088 | 28.72 |
| 357 | 0.0124 | 22.68 | 454 | 0.0142 | 29.67 |
| 358 | 0.0153 | 27.40 | 455 | 0.0104 | 45.81 |
| 359 | 0.0188 | 29.73 | 456 | 0.0097 | 40.89 |
| 360 | 0.0199 | 23.20 | 457 | 0.0072 | 33.28 |
| 361 | 0.0179 | 22.13 | 458 | 0.0156 | 23.65 |
| 362 | 0.0222 | 31.16 | 459 | 0.0153 | 27.87 |
| 363 | 0.0169 | 22.45 | 460 | 0.0100 | 41.47 |
| 364 | 0.0019 | 22.21 | 461 | 0.0259 | 56.88 |
| 365 | 0.0213 | 24.82 | 462 | 0.0081 | 25.94 |
| 366 | 0.0241 | 29.97 | 463 | 0.0062 | 35.00 |
| 367 | 0.0030 | 17.70 | 464 | 0.0071 | 39.23 |
| 368 | 0.0022 | 17.34 | 465 | 0.0226 | 55.20 |
| 369 | 0.0171 | 26.85 | 466 | 0.0246 | 48.16 |
| 370 | 0.0205 | 27.27 | 467 | 0.0170 | 24.85 |
| 371 | 0.0079 | 21.86 | 468 | 0.0042 | 25.28 |
| 372 | 0.0076 | 21.84 | 469 | 0.0215 | 21.59 |
| 373 | 0.0149 | 23.16 | 470 | 0.0041 | 29.42 |
| 374 | 0.0178 | 54.50 | 471 | 0.0082 | 25.44 |
| 375 | 0.0065 | 36.69 | 472 | 0.0110 | 39.75 |
| 376 | 0.0153 | 22.09 | 473 | 0.0171 | 22.61 |
| 377 | 0.0132 | 46.76 | 474 | 0.0186 | 42.97 |
| 378 | 0.0111 | 43.63 | 475 | 0.0071 | 37.21 |
| 379 | 0.0200 | 22.55 | 476 | 0.0224 | 21.45 |
| 380 | 0.0091 | 33.44 | 477 | 0.0074 | 52.71 |
| 381 | 0.0068 | 29.06 | 478 | 0.0104 | 33.55 |
| 382 | 0.0096 | 40.88 | 479 | 0.0062 | 35.46 |
| 383 | 0.0218 | 24.64 | 480 | 0.0094 | 38.09 |
| 384 | 0.0064 | 29.60 | 481 | 0.0102 | 50.79 |
| 385 | 0.0209 | 22.49 | 482 | 0.0120 | 25.21 |
| 386 | 0.0260 | 23.22 | 483 | 0.0111 | 28.21 |
| 387 | 0.0173 | 34.06 | 484 | 0.0054 | 28.00 |
| 388 | 0.0073 | 26.43 | 485 | 0.0120 | 49.42 |
| 389 | 0.0032 | 26.77 | 486 | 0.0133 | 33.87 |
| 390 | 0.0074 | 22.68 | 487 | 0.0134 | 53.94 |
| 391 | 0.0021 | 24.21 | 488 | 0.0079 | 26.53 |
| 392 | 0.0047 | 24.22 | 489 | 0.0118 | 35.95 |
| 393 | 0.0203 | 36.31 | 490 | 0.0079 | 26.59 |
| 394 | 0.0092 | 24.90 | 491 | 0.0182 | 23.59 |
| 395 | 0.0047 | 21.65 | 492 | 0.0166 | 24.09 |
| 396 | 0.0138 | 25.74 | 493 | 0.0194 | 49.65 |
| 397 | 0.0053 | 29.48 | 494 | 0.0057 | 28.82 |
| 398 | 0.0053 | 26.52 | 495 | 0.0151 | 32.03 |
| 399 | 0.0129 | 24.67 | 496 | 0.0016 | 21.18 |
| 400 | 0.0251 | 47.75 | 497 | 0.0124 | 29.41 |
| 401 | 0.0185 | 33.01 | 498 | 0.0059 | 38.20 |
| 402 | 0.0217 | 26.98 | 499 | 0.0150 | 24.97 |
| 403 | 0.0140 | 27.49 | 500 | 0.0077 | 21.12 |
| 404 | 0.0156 | 36.02 | 501 | 0.0130 | 30.55 |
| 405 | 0.0028 | 22.10 | 502 | 0.0096 | 38.00 |
| 406 | 0.0059 | 27.42 | 503 | 0.0173 | 33.25 |
| 407 | 0.0117 | 29.00 | 504 | 0.0075 | 24.06 |
| 408 | 0.0165 | 32.34 | 505 | 0.0106 | 21.63 |
| 409 | 0.0141 | 25.36 | 506 | 0.0102 | 42.09 |
| 410 | 0.0143 | 27.39 | 507 | 0.0135 | 30.86 |
| 411 | 0.0086 | 24.27 | 508 | 0.0115 | 21.72 |
| 412 | 0.0119 | 21.10 | 509 | 0.0202 | 25.33 |
| 413 | 0.0062 | 27.54 | 510 | 0.0146 | 22.06 |
| 414 | 0.0151 | 22.34 | 511 | 0.0131 | 21.48 |
| 415 | 0.0076 | 35.99 | 512 | 0.0100 | 23.26 |
| 416 | 0.0199 | 50.12 | 513 | 0.0137 | 27.47 |
| 417 | 0.0275 | 39.11 | 514 | 0.0210 | 32.01 |
| 418 | 0.0239 | 52.60 | 515 | 0.0167 | 23.82 |
| 419 | 0.0174 | 28.69 | 516 | 0.0121 | 31.51 |
| 420 | 0.0257 | 24.69 | 517 | 0.0204 | 35.51 |
| 421 | 0.0080 | 23.62 | 518 | 0.0210 | 35.47 |
| 422 | 0.0244 | 23.20 | 519 | 0.0226 | 28.12 |
| 423 | 0.0104 | 32.08 | 520 | 0.0034 | 20.93 |
| 424 | 0.0237 | 31.82 | 521 | 0.0078 | 21.02 |
| 425 | 0.0023 | 24.38 | 522 | 0.0214 | 29.68 |
| 426 | 0.0102 | 25.72 | 523 | 0.0162 | 26.20 |

*Ratio is a numeric value produced by dividing MDA-MMTV $IC_{50}$ (μM) by A549-MMTV $IC_{50}$ (μM).

425

Example 4. Synthesis of Compound A

BRG1/BRM Inhibitor compound A has the structure:

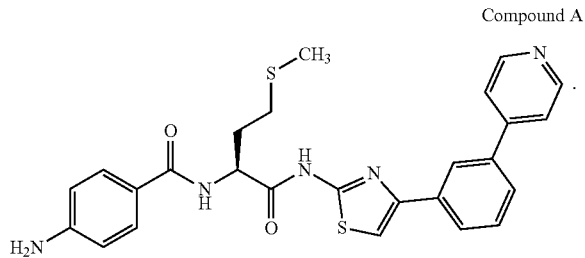 [SMILES: CSCC[C@H](NC(=O)c1ccc(N)cc1)C(=O)Nc1nc(-c2cccc(-c3ccncc3)c2)cs1]

Compound A was synthesized as shown in Scheme 1 below.

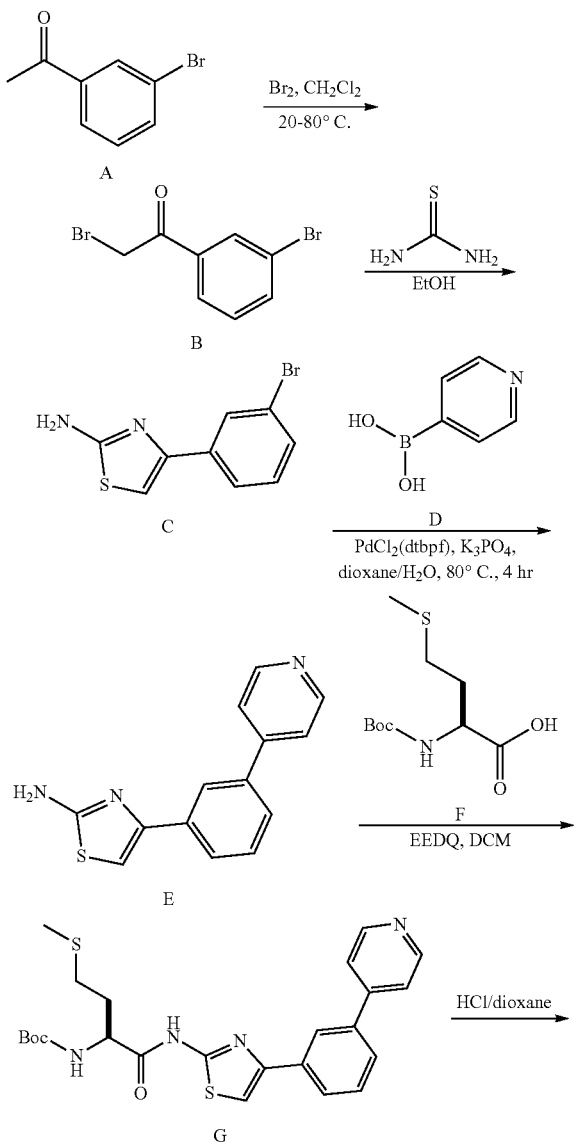

426

-continued

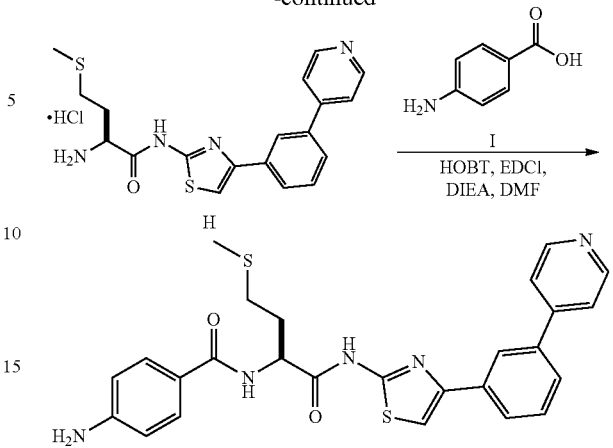

The ATPase catalytic activity of BRM or BRG-1 in the presence of Compound A was measured by the in vitro biochemical assay using ADP-Glo™ (Promega, V9102) described above. Compound A was found to have an $IC_{50}$ of 10.4 nM against BRM and 19.3 nM against BRG1 in the assay.

Example 5. Effects of BRG1/BRM ATPase Inhibition on the Growth of Uveal Melanoma and Hematological Cancer Cell Lines Procedure: Uveal melanoma cell lines (92-1, MP41, MP38, MP46), prostate cancer cell lines (LNCAP), lung cancer cell lines (NCI-H1299), and immortalized embryonic kidney lines (HEK293T) were plated into 96 well plates with growth media (see Table 9). BRG1/BRM ATPase inhibitor, Compound A, was dissolved in DMSO and added to the cells in a concentration gradient from 0 to 10 micromolar at the time of plating. Cells were incubated at 37 degrees Celsius for 3 days. After three days of treatment, the media was removed from the cells and 30 microliters of TrypLE (Gibco) was added to cells for 10 minutes. Cells were detached from the plates and resuspended with the addition of 170 microliters of growth media. Cells from two DMSO-treated control wells were counted, and the initial number of cells plated at the start of the experiment, were re-plated into fresh-compound containing plates for an additional four days at 37 degrees Celsius. At day 7, cells were harvested as described above. On day 3 and day 7, relative cell growth was measured by the addition of Cell-titer glo (Promega) and luminescence was measured on an Envision plate reader (Perkin Elmer). The concentration of compound at which each cell line's growth was inhibited by 50% ($GI_{50}$), was calculated using Graphpad Prism, and is plotted below. For multiple myeloma cell lines (OPM2, MM1S, LP1), ALL cell lines (TALL1, JURKAT, RS411), DLBCL cell lines (SUDHL6, SUDHL4, DB, WSUDLCL2, PFE-IFFER), AML cell lines (OCIAML5), MDS cell lines (SKM1), ovarian cancer cell lines (OV7, TYKNU), esophageal cancer cell lines (KYSE150), rhabdoid tumor lines (RD, G402, G401, HS729, A204), liver cancer cell lines (HLF, HLE, PLCRPF5), and lung cancer cell lines (SW1573, NCIH2444), the above methods were performed with the following modifications: Cells were plated in 96 well plates, and the next day, BRG1/BRM ATPase inhibitor, Compound A, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 12 lists the tested cell lines and growth media used.

TABLE 12

Cell Lines and Growth Media

| Cell Line | Source | Growth Media |
|---|---|---|
| 92-1 | SIGMA | RPMI 1640 + 20% FBS |
| A204 | ATCC | McCoy's 5A +10% FBS |
| DB | ATCC | RPMI 1640 + 10% FBS |
| G401 | ATCC | McCoy's 5A +10% FBS |
| G402 | ATCC | McCoy's 5A +10% FBS |
| HEK293T | ATCC | DMEM + 10% FBS |
| HLE | JCRB | DMEM + 10% FBS |
| HLF | JCRB | DMEM + 10% FBS |
| HS729 | ATCC | DMEM + 10% FBS |
| JURKAT | ATCC | RPMI 1640 + 10% FBS |
| KYSE150 | DSMZ | RPMI 1640/Ham's F12 + 10% FBS |
| LNCAP | ATCC | RPMI 1640 + 10% FBS |
| LP1 | DSMZ | IMDM + 20% FBS |
| MM1S | ATCC | RPMI 1640 + 10% FBS |
| MP38 | ATCC | RPMI 1640 + 20% FBS |
| MP41 | ATCC | RPMI 1640 + 20% FBS |
| MP46 | ATCC | RPMI 1640 + 20% FBS |
| NCIH1299 | ATCC | RPMI 1640 + 10% FBS |
| NCIH2444 | ATCC | RPMI 1640 + 20% FBS |
| OCIAML5 | DSMZ | alpha-MEM + 20% FBS +10 ng/ml GM-CSF |
| OPM2 | DSMZ | RPMI 1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI 1640 + 10% FBS |
| PLCPRF5 | ATCC | EMEM + 10% FBS |
| RD | ATCC | DMEM + 10% FBS |
| RS411 | ATCC | RPMI 1640 + 10% FBS |
| SKM1 | JCRB | RPMI1640 + 10% FBS |
| SUDHL4 | DSMZ | RPMI 1640 + 10% FBS |
| SUDHL6 | ATCC | RPMI 1640 + 20% FBS |
| SW1573 | ATCC | DMEM + 10% FBS |
| TALL1 | JCRB | RPMI 1640 + 10% FBS |
| TYKNU | JCRB | EMEM + 20% FBS |
| WSUDLCL2 | DSMZ | RPMI 1640 + 10% FBS |

Results: As shown in FIG. 1, the uveal melanoma and hematologic cancer cell lines were more sensitive to BRG1/BRM inhibition than the other tested cell lines. Inhibition of the uveal melanoma and hematologic cancer cell lines was maintained through day 7.

Example 6. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 12). BAF ATPase inhibitors (Compound A), PKC inhibitor (LXS196; MedChemExpress), or MEK inhibitor (Selumetinib; Selleck Chemicals) were dissolved in DMSO and added to the cells in a concentration gradient from 0 to 10 micromolar at the time of plating. Cells were incubated at 37 degrees Celsius for 3 days. After three days of treatment, cell growth was measured with Cell-titer glow (Promega), and luminescence was read on an Envision plate reader (Perkin Elmer).

Figure 2A:
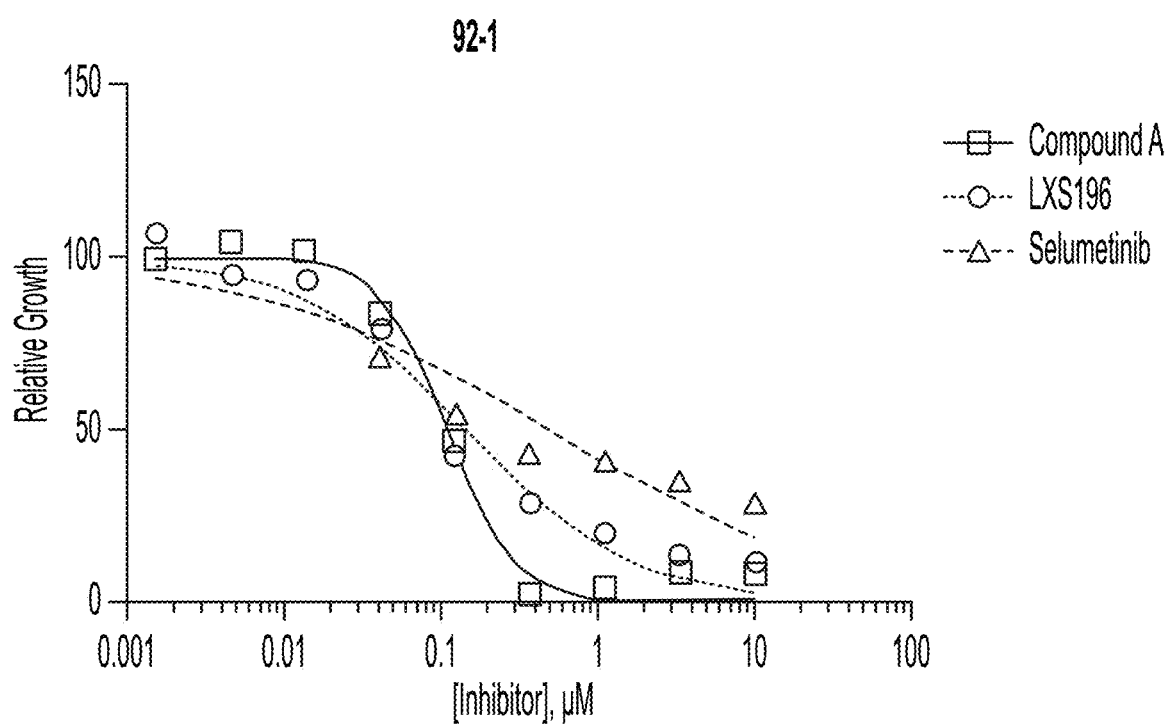
FIG. 2A is a graph illustrating inhibition of cell proliferation of uveal melanoma cell line 92-1 by a BRG1/BRM inhibitor (Compound A), a MEK inhibitor (Selumetinib), and a PKC inhibitor (LXS196).
Figure 2B:
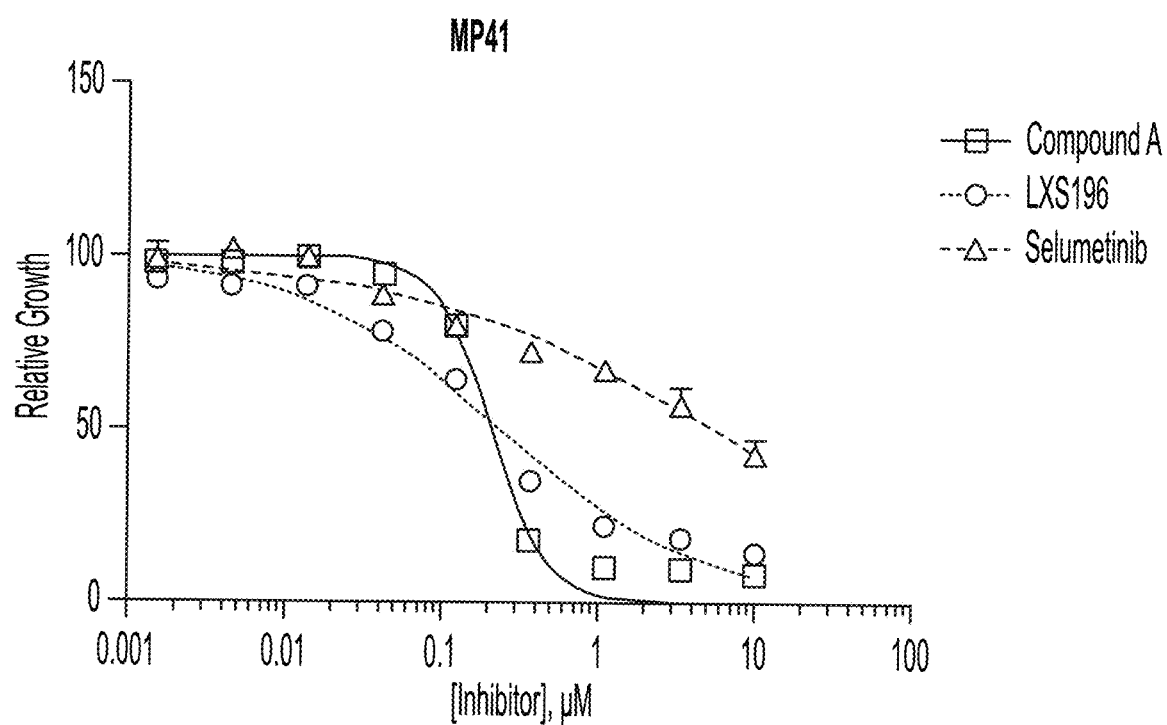
FIG. 2B is a graph illustrating inhibition of cell proliferation of uveal melanoma cell line MP41 by a BRG1/BRM inhibitor (Compound A), a MEK inhibitor (Selumetinib), and a PKC inhibitor (LXS196).

Results: As shown in FIG. 2A and FIG. 2B, Compound A showed comparable growth inhibition of uveal melanoma cells as the clinical PKC and MEK inhibitors. Further, compound A was found to result in a faster onset of inhibition than the clinical PKC and MEK inhibitors.

Example 7. Synthesis of Compound B

BRG1/BRM Inhibitor Compound B has the structure:

Scheme 2. Synthesis of Compound B

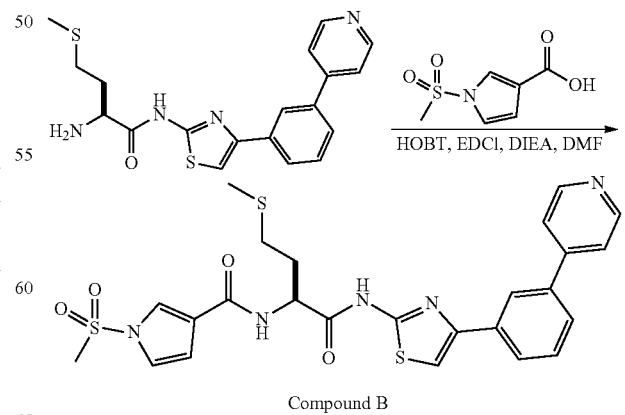

Compound B

Compound B was synthesized as shown in Scheme 2 below.

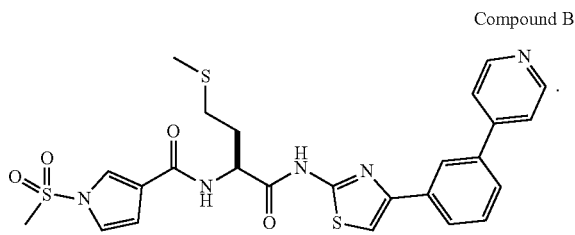 [SMILES: CSCC[C@H](NC(=O)c1ccn(S(C)(=O)=O)c1)C(=O)Nc1nc(-c2cccc(-c3ccncc3)c2)cs1]

Compound B

Preparation of (S)-1-(methylsulfonyl)-N-(4-(methyl-thio)-1-oxo-1-((4-(3-(pyridin-4-yl)phenyl)thiazol-2-yl)amino)butan-2-yl)-1H-pyrrole-3-carboxamide (Compound B)

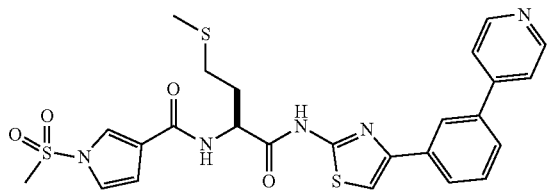 [SMILES: CSCC[C@H](NC(=O)c1ccn(S(C)(=O)=O)c1)C(=O)Nc1nc(-c2cccc(-c3ccncc3)c2)cs1]

To a mixture of (2S)-2-amino-4-methylsulfanyl-N-[4-[3-(4-pyridyl)phenyl]thiazol-2-yl]butanamide (2 g, 4.75 mmol, HCl salt) and 1-methylsulfonylpyrrole-3-carboxylic acid (898.81 mg, 4.75 mmol) in DMF (20 mL) was added EDCl (1.37 g, 7.13 mmol), HOBt (962.92 mg, 7.13 mmol), and DIEA (2.46 g, 19.00 mmol, 3.31 mL) and the mixture was stirred at 25° C. for 3 hours. The mixture was poured into H₂O (100 mL) and the precipitate was collected by filtration. The solid was triturated in MeOH (20 mL) and the precipitate was collected by filtration. The solid was dissolved in DMSO (10 mL) and then the mixture was poured into MeOH (50 mL) and the formed precipitate was collected by filtration and lyophilized to give Compound B (2.05 g, 3.66 mmol, 77.01% yield) as a white solid. LCMS (ESI) m/z [M+H]⁺=555.9. ¹H NMR (400 MHz, DMSO) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H). SFC: AS-3-MeOH (DEA)-40-3 mL-35T.lcm, t=0.932 min, ee %=100%.

Example 8. Effects of BRG1/BRM ATPase Inhibition on the Growth of Uveal Melanoma, Hematological Cancer, Prostate Cancer, Breast Cancer, and Ewing's Sarcoma Cell Lines Procedure: All cell lines described above in Example 4 were also tested as described above with Compound B. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COLO829, SKMEL3, A375), breast cancer cell lines (MDAMB415, CAMA1, MCF7, BT474, HCC1419, DU4475, BT549), B-ALL cell lines (SUPB15), CML cell lines (K562, MEG01), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, Compound B, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 13 lists the tested cell lines and growth media used.

TABLE 13

Cell Lines And Growth Media

| Cell Line | Source | Growth Media |
|---|---|---|
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COLO829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KASUMI1 | ATCC | RPMI1640 + 10% FBS |
| MCF7 | ATCC | EMEM +0.01 mg/ml bovine insulin+ 10% FBS |
| MDAMB415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |

TABLE 13-continued

Cell Lines And Growth Media

| Cell Line | Source | Growth Media |
|---|---|---|
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 3:
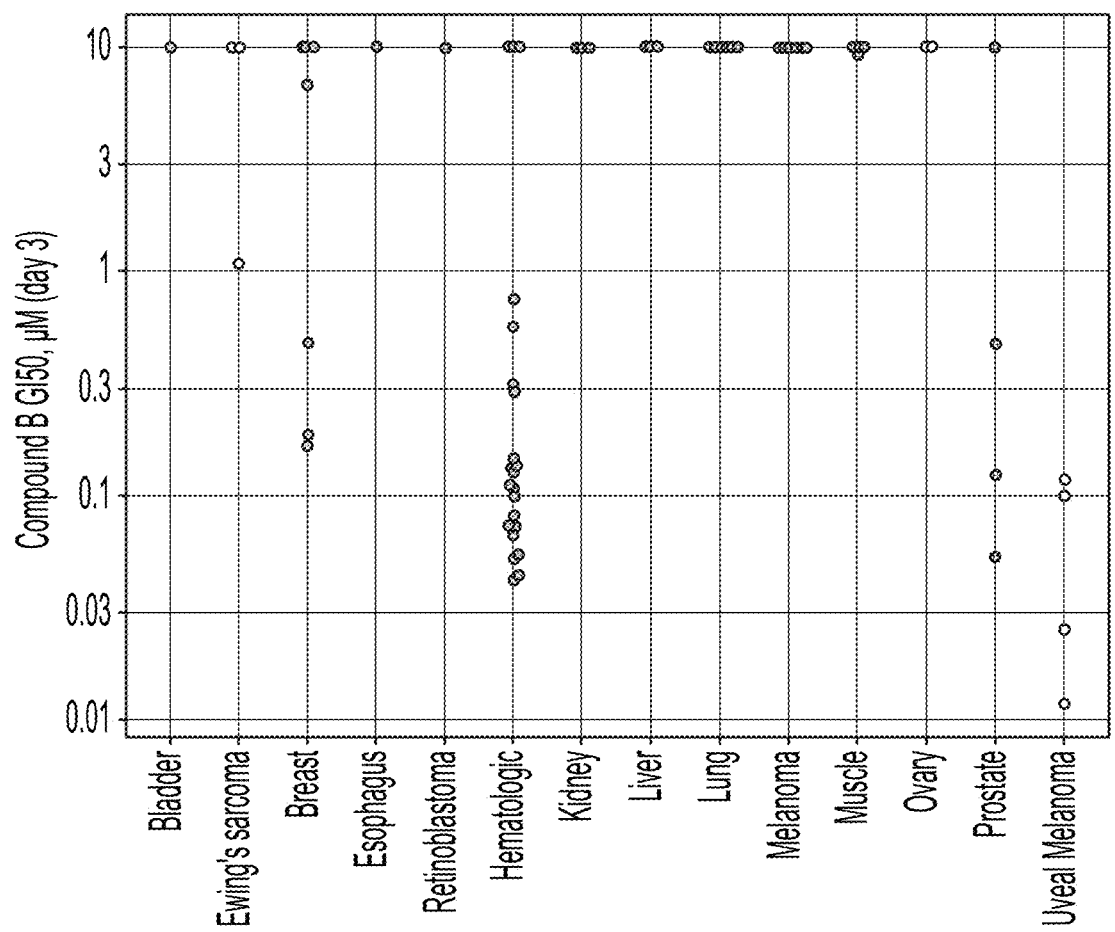
FIG. 3 is a graph illustrating inhibition of cell proliferation of several cancer cell lines by a BRG1/BRM inhibitor (Compound B).

Results: As shown in FIG. 3, the uveal melanoma, hematologic cancer, prostate cancer, breast cancer, and Ewing's sarcoma cell lines were more sensitive to BRG1/BRM inhibition than the other tested cell lines. Inhibition of the uveal melanoma, hematologic cancer, prostate cancer, breast cancer, and Ewing's sarcoma cell lines was maintained through day 7.

Example 9. Effects of BRG1/BRM ATPase Inhibition on the Growth of Cancer Cell Lines Procedure: A pooled cell viability assay was performed using PRISM (Profiling Relative Inhibition Simultaneously in Mixtures) as previously described ("High-throughput identification of genotype-specific cancer vulnerabilities in mixtures of barcoded tumor cell lines", Yu et al, Nature Biotechnology 34, 419-423, 2016), with the following modifications. Cell lines were obtained from the Cancer Cell Line Encyclopedia (CCLE) collection and adapted to RPMI-1640 medium without phenol red, supplemented with 10% heat-inactivated fetal bovine serum (FBS), in order to apply a unique infection and pooling protocol to such a big compendium of cell lines. A lentiviral spin-infection protocol was executed to introduce a 24 nucleotide-barcode in each cell line, with an estimated multiplicity of infection (MOI) of 1 for all cell lines, using blasticidin as selection marker. Over 750 PRISM cancer cell lines stably barcoded were then pooled together according to doubling time in pools of 25. For the screen execution, instead of plating a pool of 25 cell lines in each well as previously described (Yu et al.), all the adherent or all the suspension cell line pools were plated together using T25 flasks (100,000 cells/flask) or 6-well plates (50,000 cells/well), respectively. Cells were treated with either DMSO or compound in a 8-point 3-fold dose response in triplicate, starting from a top concentration of 10 µM. As control for assay robustness, cells were treated in parallel with two previously validated compounds, the pan-Raf inhibitor AZ-628, and the proteasome inhibitor bortezomib, using a top concentration of 2.5 µM and 0.039 µM, respectively.

Figure 4:
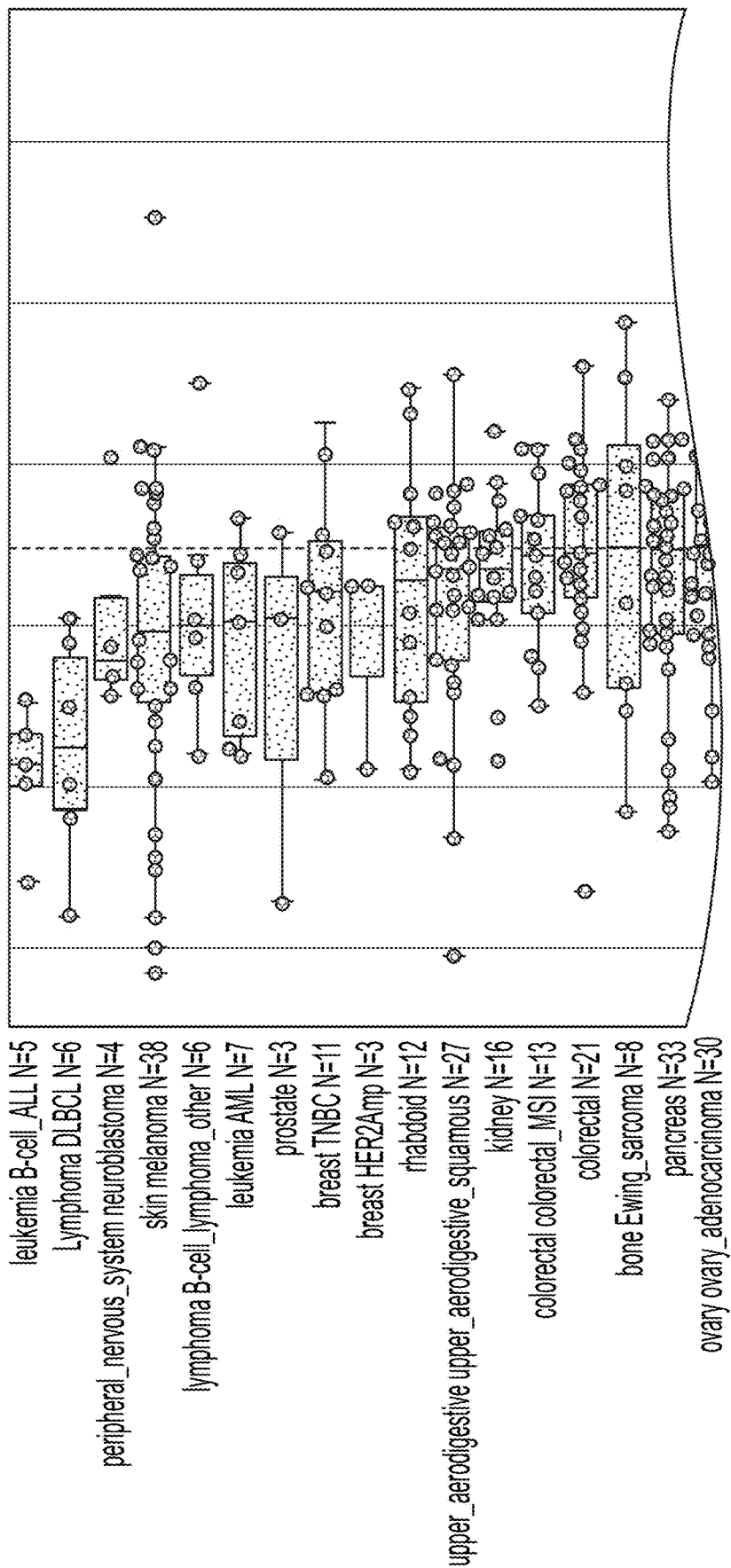
FIG. 4 is a graph illustrating the area under the curves (AUCs) calculated from dose-response curves for cancer cell lines treated with a BRG1/BRM inhibitor.
Figure 4:
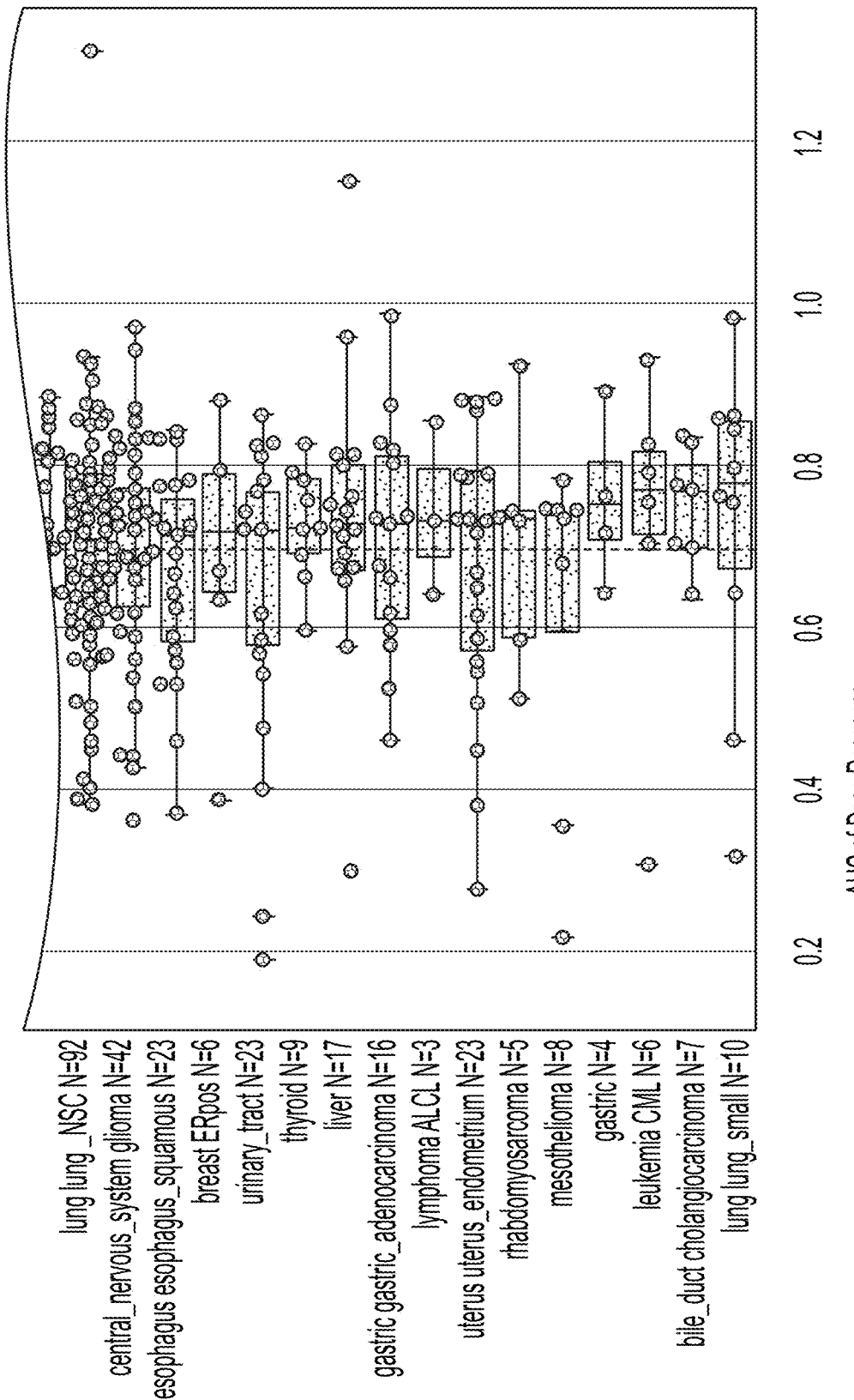

Following 3 days of treatment with compounds, cells were lysed, genomic DNA was extracted, barcodes were amplified by PCR and detected with Next-Generation Sequencing. Cell viability was determined by comparing the counts of cell-line specific barcodes in treated samples to those in the DMSO-control and Day 0 control. Dose-response curves were fit for each cell line and corresponding area under the curves (AUCs) were calculated and compared to the median AUC of all cell lines (FIG. 4). Cell lines with AUCs less than the median were considered most sensitive.

Example 10. Effects of BRG1/BRM ATPase Inhibitors on the Growth of Uveal Melanoma Cell Lines Procedure: Uveal melanoma cell lines (92-1, MP41, MP38, MP46) and Non-small cell lung cancer cells (NCIH1299) were plated into 96 well plates with growth media (see Table 9). BRG1/BRM ATPase inhibitor, compound 67, was dissolved in DMSO and added to the cells in a concentration gradient from 0 to 10 micromolar at the time of plating. Cells were incubated at 37° C. for 3 days. After three days of treatment, cell growth was measured with Cell-titer glow (Promega), and luminescence was read on an Envision plate reader (Perkin Elmer).

Figure 5:
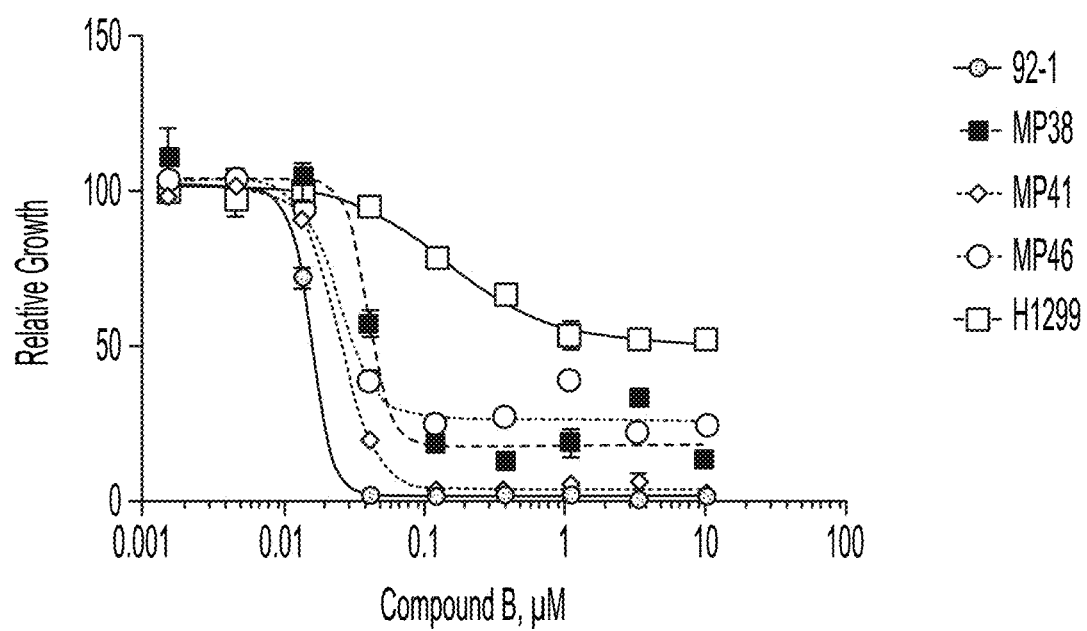
FIG. 5 is a graph illustrating inhibition of cell proliferation of uveal melanoma and non-small cell lung cancer cell lines by a BRG1/BRM inhibitor (Compound B).

Results: As shown in FIG. 5, Compound B resulted in potent growth inhibition in the uveal melanoma cell lines.

Example 11. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 9). BAF ATPase inhibitor (Compound B), PKC inhibitor (LXS196; MedChemExpress), and MEK inhibitor (Selumetinib; Selleck Chemicals) were dissolved in DMSO and added to the cells in a concentration gradient from 0 to 10 micromolar at the time of plating. Cells were incubated at 37° C. for 3 days. After three days of treatment, cell growth was measured with Cell-titer glow (Promega), and luminescence was read on an Envision plate reader (Perkin Elmer).

Figure 6A:
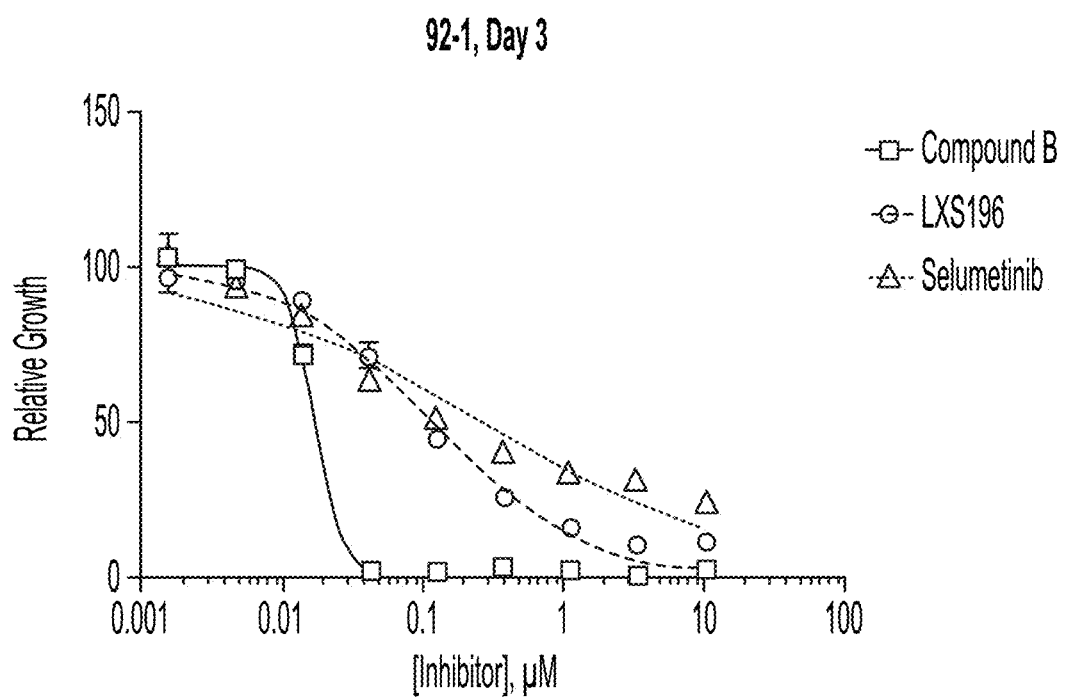
FIG. 6A is a graph illustrating inhibition of cell proliferation of uveal melanoma cell line 92-1 by a BRG1/BRM inhibitor (Compound B), a MEK inhibitor (Selumetinib), and a PKC inhibitor (LXS196).
Figure 6B:
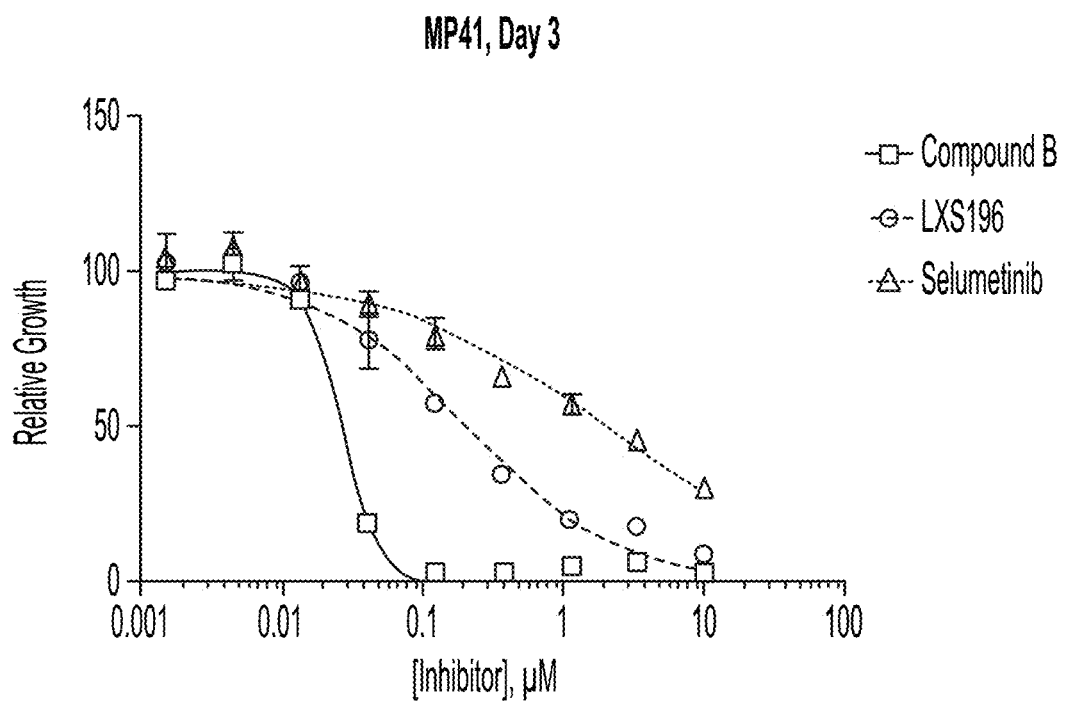
FIG. 6B is a graph illustrating inhibition of cell proliferation of uveal melanoma cell line MP41 by a BRG1/BRM inhibitor (Compound B), a MEK inhibitor (Selumetinib), and a PKC inhibitor (LXS196).

Results: As shown in FIG. 6A and FIG. 6B, Compound B showed more potent effects on growth inhibition of uveal melanoma cells as compared to the clinical PKC and MEK inhibitors. Further, Compound B was found to result in a faster onset of growth inhibition than the clinical PKC and MEK inhibitors.

Example 12. BRG1/BRM ATPase Inhibitors are Effective at Inhibiting the Growth of PKC Inhibitor-Resistant Cells Procedure: MP41 uveal melanoma cells were made resistant to the PKC inhibitor (LXS196; MedChemExpress), by long-term culture in growth media (see Table 9) containing increasing concentrations of the compound, up to 1 micromolar. After 3 months, sensitivity of the parental MP41 cells and the PKC inhibitor (PKCi)-resistant cells to the PKC inhibitor (LXS196) or the BRG1/BRM ATPase inhibitor (Compound B) was tested in a 7-day growth inhibition assay as described above in Example 6.

Figure 7A:
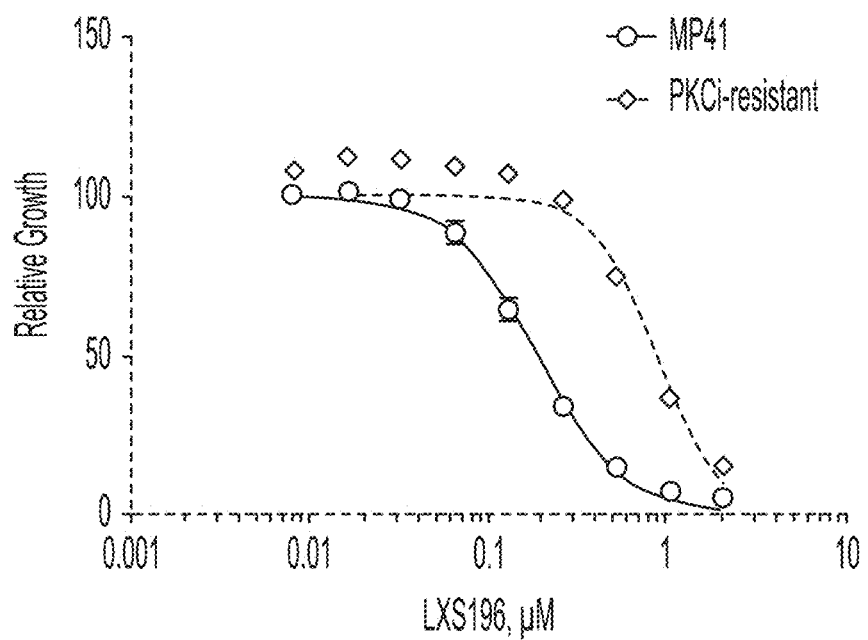
FIG. 7A is a graph illustrating inhibition of cell proliferation of parental and PKC-inhibitor refractory uveal melanoma cell lines by a PKC inhibitor (LXS196).
Figure 7B:
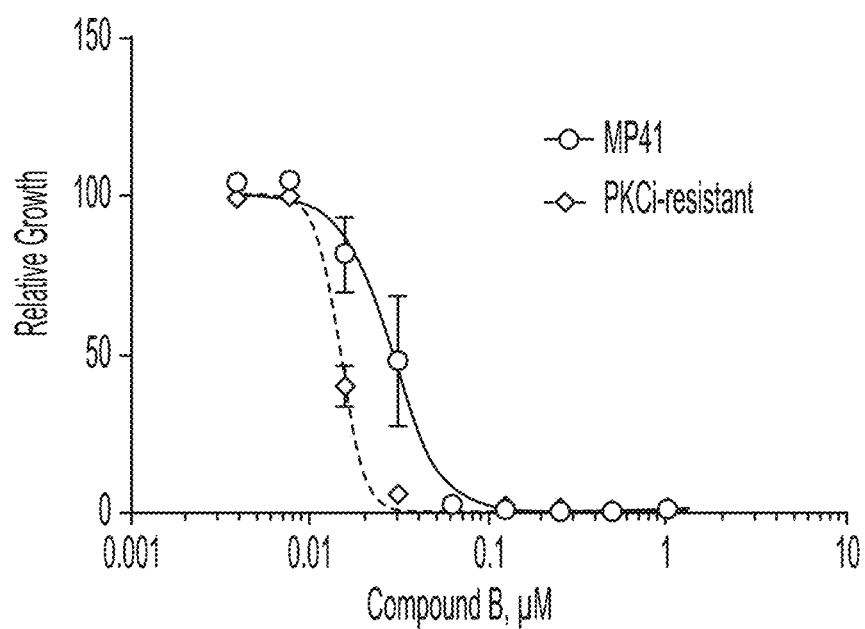
FIG. 7B is a graph illustrating inhibition of cell proliferation of parental and PKC-inhibitor refractory uveal melanoma cell lines by a BRG1/BRM inhibitor (Compound B).

Results: While the PKCi-resistant cells could tolerate growth at higher concentrations of LXS196 than could the parental MP41 cell line (FIG. 7A), the BRG1/BRM ATPase inhibitor (Compound B) still resulted in strong growth inhibition of both the PKCi-resistant and parental cell lines

Example 13. Synthesis of Compound C

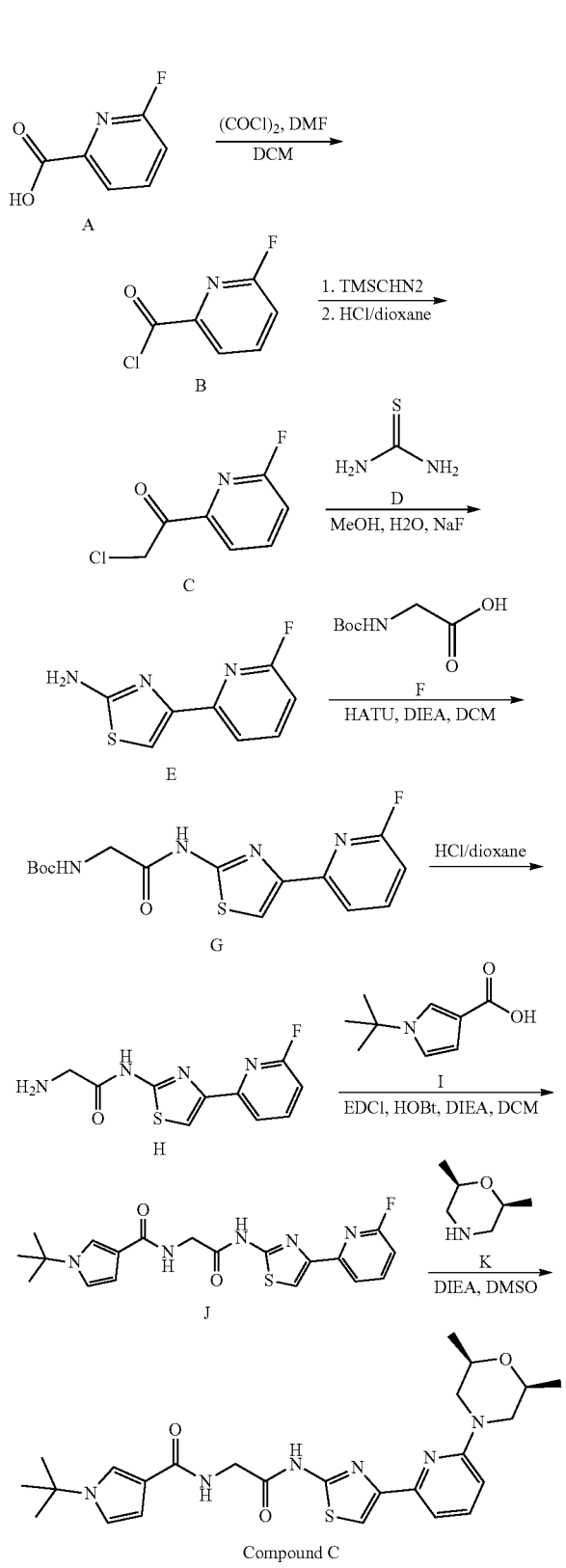

Compound C

Step 1. Preparation of 6-fluoropyridine-2-carbonyl Chloride (Intermediate B)

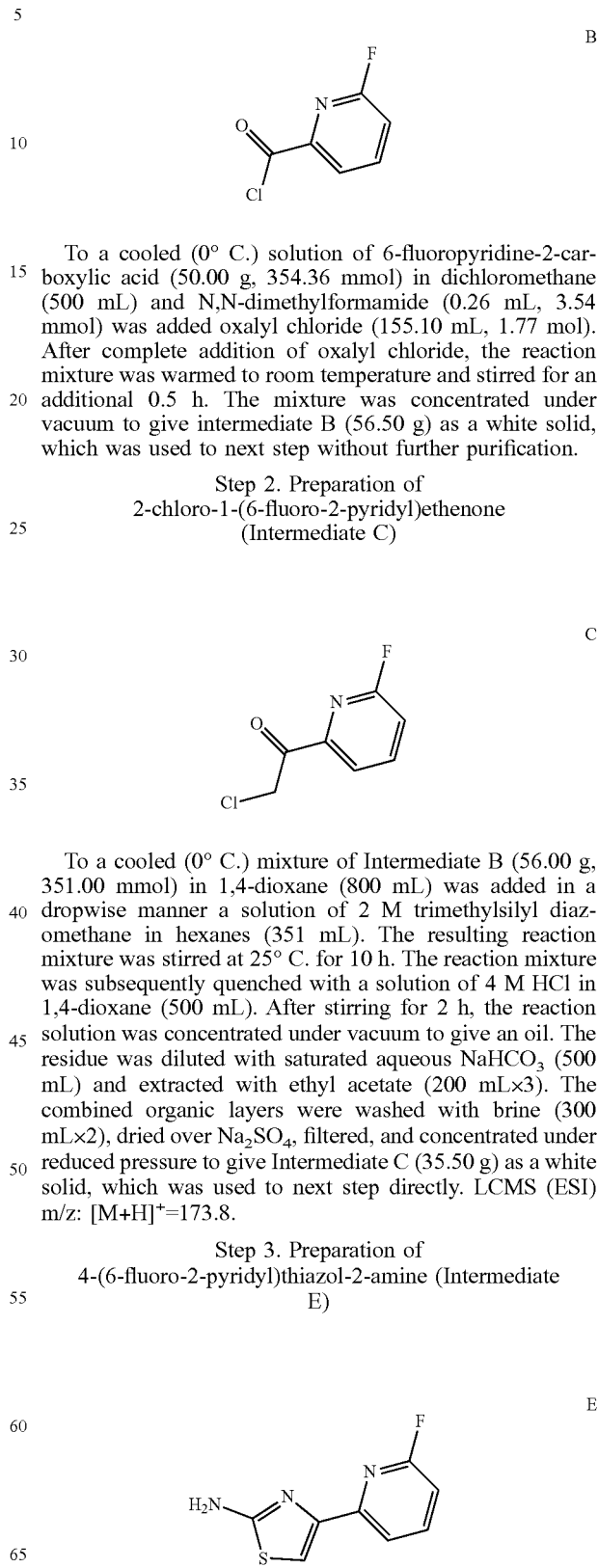

To a cooled (0° C.) solution of 6-fluoropyridine-2-carboxylic acid (50.00 g, 354.36 mmol) in dichloromethane (500 mL) and N,N-dimethylformamide (0.26 mL, 3.54 mmol) was added oxalyl chloride (155.10 mL, 1.77 mol). After complete addition of oxalyl chloride, the reaction mixture was warmed to room temperature and stirred for an additional 0.5 h. The mixture was concentrated under vacuum to give intermediate B (56.50 g) as a white solid, which was used to next step without further purification.

Step 2. Preparation of 2-chloro-1-(6-fluoro-2-pyridyl)ethenone (Intermediate C)

To a cooled (0° C.) mixture of Intermediate B (56.00 g, 351.00 mmol) in 1,4-dioxane (800 mL) was added in a dropwise manner a solution of 2 M trimethylsilyl diazomethane in hexanes (351 mL). The resulting reaction mixture was stirred at 25° C. for 10 h. The reaction mixture was subsequently quenched with a solution of 4 M HCl in 1,4-dioxane (500 mL). After stirring for 2 h, the reaction solution was concentrated under vacuum to give an oil. The residue was diluted with saturated aqueous NaHCO$_3$ (500 mL) and extracted with ethyl acetate (200 mL×3). The combined organic layers were washed with brine (300 mL×2), dried over Na$_2$SO$_4$, filtered, and concentrated under reduced pressure to give Intermediate C (35.50 g) as a white solid, which was used to next step directly. LCMS (ESI) m/z: [M+H]$^+$=173.8.

Step 3. Preparation of 4-(6-fluoro-2-pyridyl)thiazol-2-amine (Intermediate E)

To a solution of Intermediate C (35.50 g, 204.53 mmol) and thiourea (14.01 g, 184.07 mmol) in a mixture of MeOH (250 mL) and H₂O (250 mL) at room temperature was added NaF (3.56 g, 84.82 mmol). After stirring for 0.5 h, the reaction mixture was partially concentrated under vacuum to remove MeOH, and the resulting solution was acidified to pH ~3 with aqueous 2 M HCl. After 15 min, the solution was extracted with ethyl acetate (200 mL×3), the organic layers were discarded and the aqueous phase was alkalized with NaHCO₃ (500 mL) and stirred for 30 min, then extracted with ethyl acetate (325 mL*3), the combined organic layers were washed with brine (225 mL*3), dried over Na₂SO₄, filtered, and concentrated under reduced pressure. The residue was triturated with petroleum ether (300 mL) and stirred at 25° C. for 10 min and filtered. The resultant solids were dried under vacuum to give Intermediate E (28.00 g, 143.43 mmol, 70.13% yield, 100% purity) as a white solid. LCMS (ESI) m/z: [M+H]⁺=195.8; ¹H NMR (400 MHz, DMSO-d₆) δ 8.00-7.96 (m, 1H), 7.72 (d, J=7.2 Hz, 1H), 7.24 (s, 1H), 7.16 (s, 2H), 7.02 (d, J=8.0 Hz, 1H).

Step 4. Preparation of tert-butyl N-[2-[[4-(6-fluoro-2-pyridyl)thiazol-2-yl]amino]-2-oxo-ethyl]carbamate (Intermediate G)

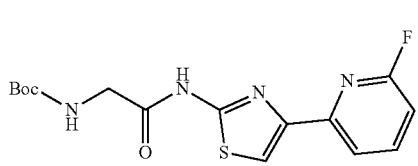

To a solution of N-Boc-glycine (5.92 g, 33.81 mmol), HATU (12.86 g, 33.81 mmol), and DIEA (15.89 g, 122.94 mmol, 21.41 mL) in dichloromethane (100 mL) was added Intermediate E (6.00 g, 30.74 mmol). After stirring for 2 h, the reaction mixture was concentrated and subsequently diluted with water (100 mL) and extracted with ethyl acetate (60 mL×4). The combined organic layers were washed with brine (100 mL×2), dried over Na₂SO₄, filtered, and concentrated under reduced pressure to give a residue. The residue was triturated with a 1:1 mixture of petroleum ether and MeOH (40 mL). After stirring at 25° C. for 20 min, the suspension was filtered, the filter cake was washed with MTBE (20 mL), and dried in vacuo to give Intermediate G (7.7 g, 21.63 mmol, 70.4% yield, 99.0% purity) as a white solid. LCMS (ESI) m/z: [M+H]⁺=353.1.

Step 5. Preparation of 2-((4-(6-fluoropyridin-2-yl)thiazol-2-yl)amino)-2-oxoethane-1-aminium Chloride (Intermediate H)

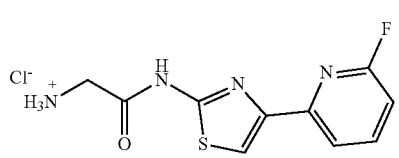

A solution of Intermediate G (5.40 g, 15.32 mmol) in 4 M HCl in 1,4-dioxane (35 mL) was stirred at 25° C. for 1.5 h. The mixture was concentrated under vacuum to give Intermediate H (4.42 g) as a white solid, which was used to next step directly without further purification. LCMS (ESI) m/z: [M+H]⁺=252.9.

Step 6. Preparation of 1-tert-butyl-N-[2-[[4-(6-fluoro-2-pyridyl)thiazol-2-yl]amino]-2-oxo-ethyl]pyrrole-3-carboxamide (Intermediate J)

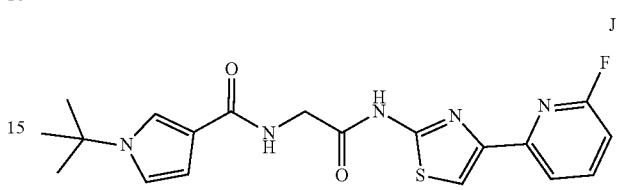

To a solution of Intermediate H (3.00 g, 10.39 mmol), 1-tert-butylpyrrole-3-carboxylic acid (1.74 g, 10.39 mmol), and DIEA (6.71 g, 51.95 mmol, 9.05 mL) in dichloromethane (40 mL) was sequentially added HOBt (1.68 g, 12.47 mmol) and EDCl (2.39 g, 12.47 mmol). After stirring for 4 h, the mixture was concentrated under vacuum. The residue was diluted with water (250 mL) and extracted with ethyl acetate (200 mL×3). The combined organic layers were washed with brine (300 mL×3), dried over Na₂SO₄, filtered, and concentrated under reduced pressure. The resulting solids were triturated with a 1:1 mixture of MTBE/ethyl acetate (400 mL) and after 30 min, the suspension was filtered. The solids were washed with MTBE (85 mL×3) and then dried under vacuum to give Intermediate J (3.10 g, 7.64 mmol, 73.6% yield, 99.0% purity) as a white solid.
LCMS (ESI) m/z: [M+H]⁺=402.3.
¹H NMR (400 MHz, DMSO-d₆) δ 12.40 (s, 1H), 8.18-8.15 (m, 1H), 8.09-8.08 (m, 1H), 7.87-7.83 (m, 2H), 7.52 (s, 1H), 7.11 (d, J=8.0 Hz, 1H), 6.97 (m, 1H), 6.47 (s, 1H), 4.10 (d, J=5.6 Hz, 2H), 1.49 (s, 9H).

Step 7. Preparation of 1-(tert-butyl)-N-(2-((4-(6-(cis-2,6-dimethylmorpholino)pyridin-2-yl)thiazol-2-yl)amino)-2-oxoethyl)-1H-pyrrole-3-carboxamide (Compound C)

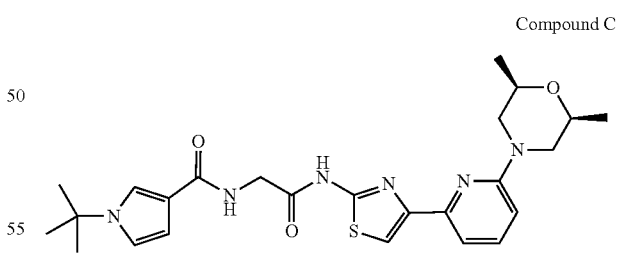

To a solution of Intermediate J (0.100 g, 0.249 mmol) in DMSO (1 mL) was added DIEA (0.130 mL, 0.747 mmol) and cis-2,6-dimethylmorpholine (0.057 g, 0.498 mmol) and the mixture was stirred at 120° C. After 12 h, the solution was cooled to room temperature and reaction mixture was diluted with MeOH (3 mL). The residue was purified by prep-HPLC (0.1% TFA; column: Luna C18 150*25 5u; mobile phase: [water (0.075% TFA)-ACN]; B %: 30%-60%, 2 min). The appropriate fractions were collected and lyophilized to give Compound C (0.079 g, 0.129 mmol, 51.94% yield, 100% purity) as a white solid. LCMS (ESI) m/z: [M+H]$^+$=497.5. $^1$H NMR (400 MHz, DMSO-d$_6$) δ 12.27 (s, 1H), 8.17-8.14 (m, 1H), 7.75 (s, 1H), 7.63-7.59 (m, 1H), 7.51 (s, 1H), 7.25 (d, J=7.2 Hz, 1H), 6.96 (s, 1H), 6.79 (d, J=8.8 Hz, 1H), 6.47 (s, 1H), 4.24 (d, J=12.4 Hz, 2H), 4.08 (d, J=5.6 Hz, 2H), 3.64-3.61 (m, 2H), 2.44-2.38 (m, 2H), 1.49 (s, 9H), 1.18 (d, J=5.6 Hz, 6H).

Example 14. BRG1/BRM ATPase Inhibitors Cause Uveal Melanoma Tumor Growth Inhibition In Vivo Procedure: Nude mice (Envigo) were engrafted subcutaneously in the axillary region with 5×10$^6$ 92-1 uveal melanoma cells in 50% Matrigel. Tumors were grown to a mean of ~200 mm$^3$, at which point mice were grouped and dosing was initiated. Mice were dosed once daily by oral gavage with vehicle (20% 2-Hydroxypropyl-β-Cyclodextrin) or increasing doses of Compound C. Tumor volumes and body weights were measured over the course of 3 weeks, and doses were adjusted by body weight to achieve the proper dose in terms of mg/kg. At this time, animals were sacrificed, and tumors were dissected and imaged.

Figure 8A:
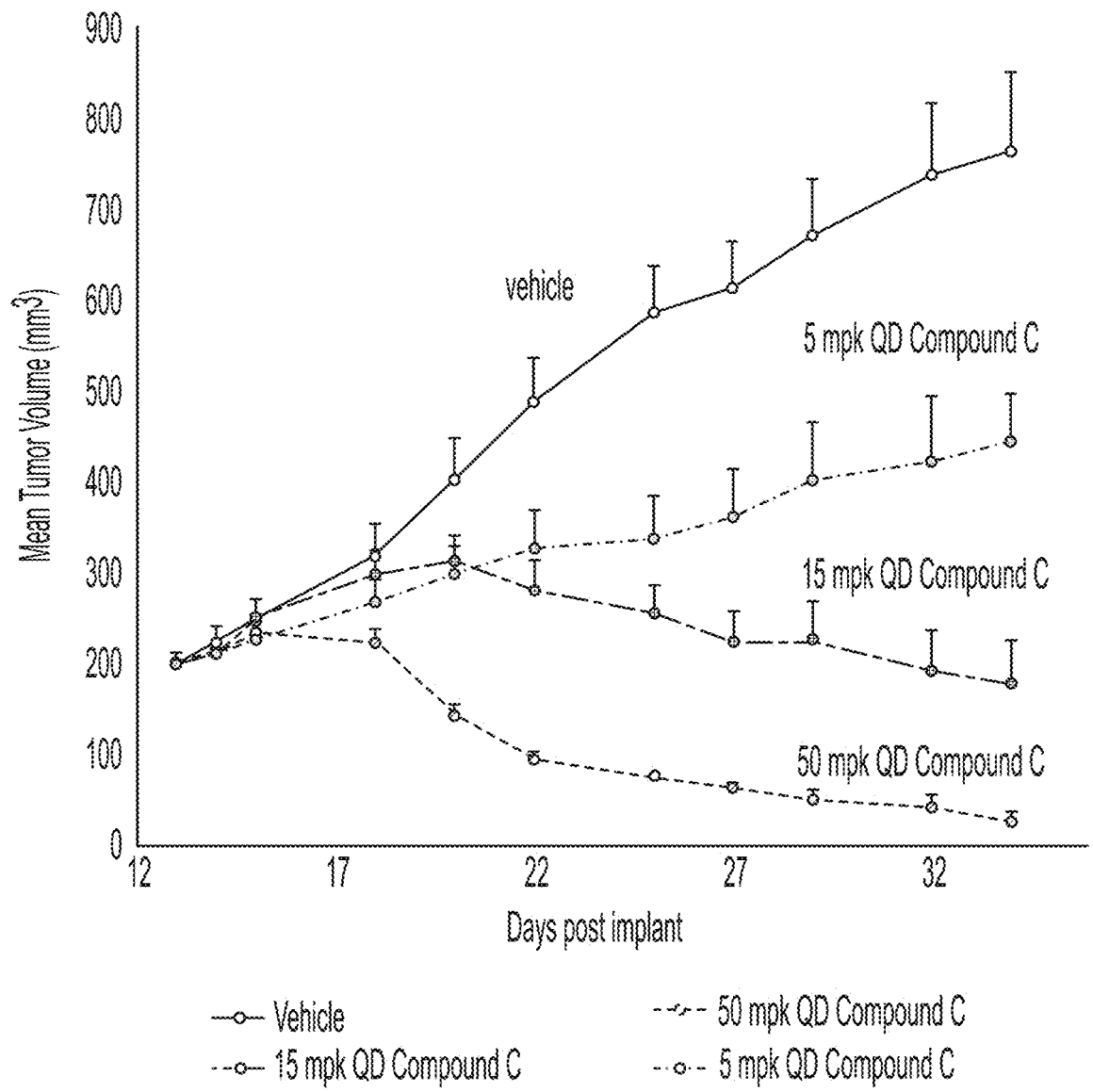
FIG. 8A is a graph illustrating inhibition of tumor growth in mice engrafted with uveal melanoma cell lines by a BRG1/BRM inhibitor (Compound C).
Figure 8B:
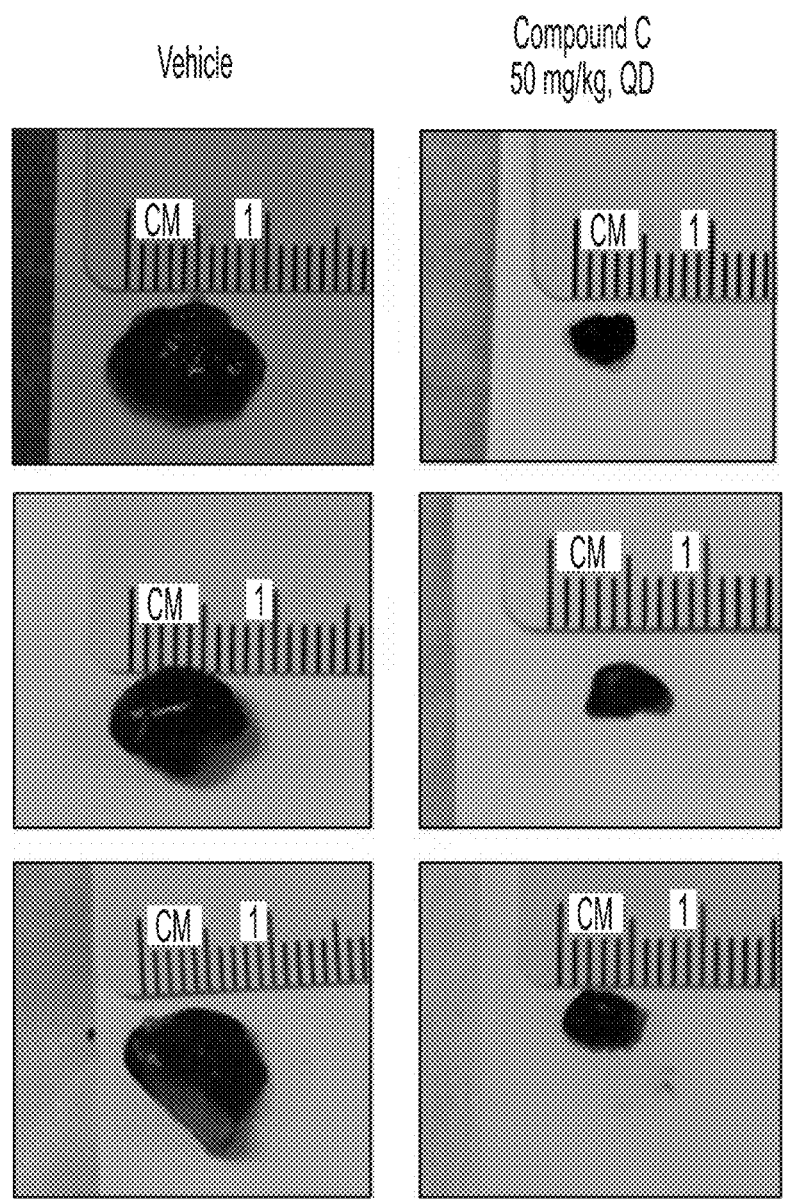
FIG. 8B is an illustration of the size of tumors from mice engrafted with uveal melanoma cell lines and dosed with a BRG1/BRM inhibitor (Compound C).
Figure 8C:
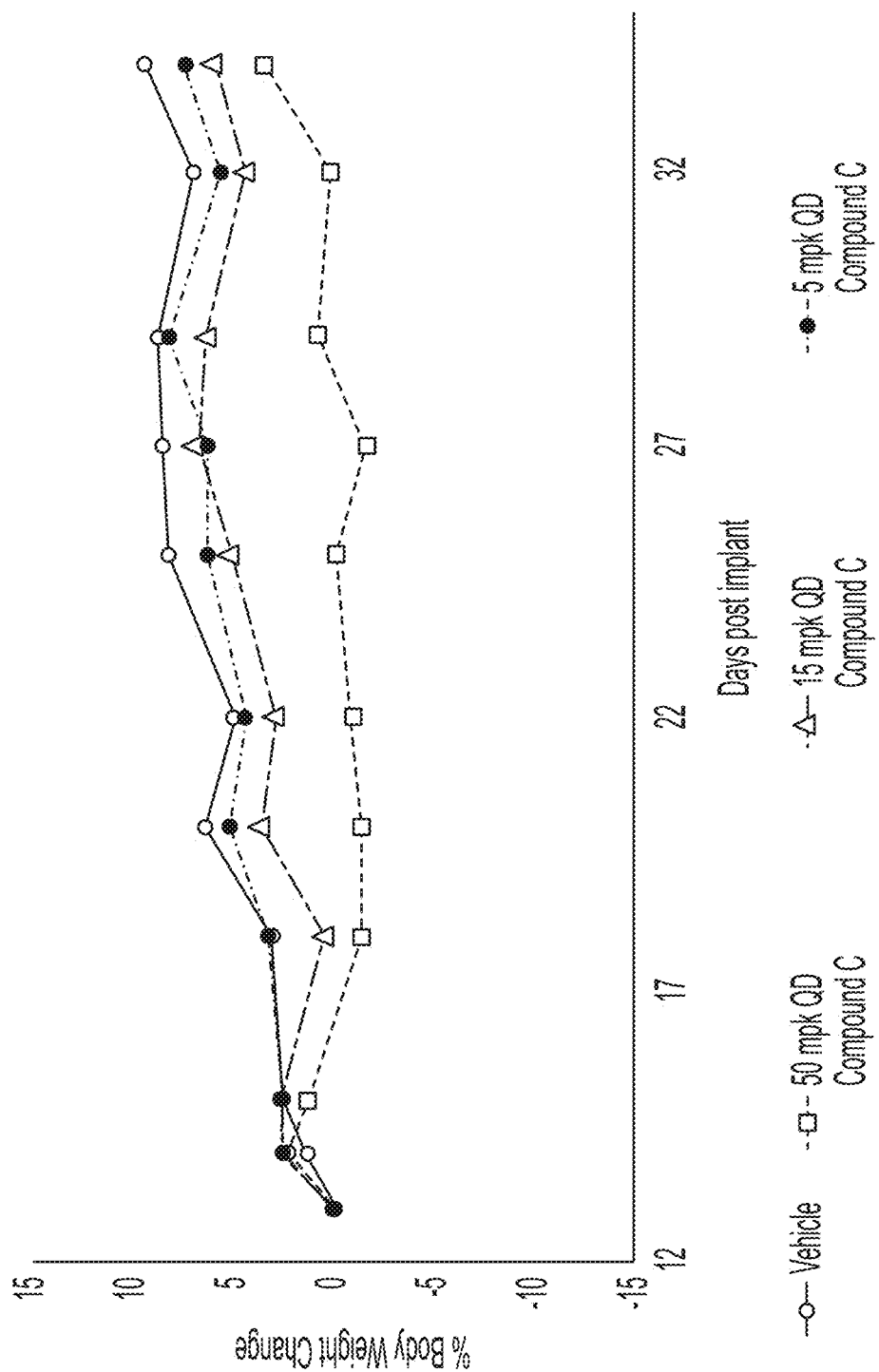
FIG. 8C is a graph illustrating body weight change of mice engrafted with uveal melanoma cell lines and dosed with a BRG1/BRM inhibitor (Compound C).

Results: Treatment with Compound C led to tumor growth inhibition in a dose-dependent manner with tumor regression observed at the highest (50 mg/kg) dose. (FIG. 8A and FIG. 8B). All treatments were well tolerated with no body weight loss observed (FIG. 8C).

Other Embodiments

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:
1. A compound having the structure:

Formula I

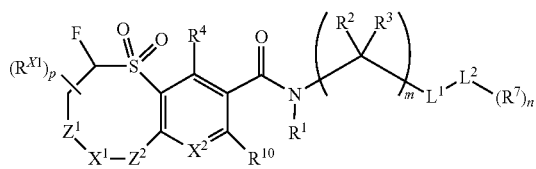

wherein
m is 0, 1, 2, or 3;
n is 0, 1, 2, 3, or 4;
p is 0, 1, 2, or 3;
X$^1$ is O, NR$^5$, or (C(R$^5$)(R$^6$)), and each of Z$^1$ and Z$^2$ is independently absent or (C(R$^9$)$_2$) or O, provided that, if X$^1$ is O, then each of Z$^1$ and Z$^2$ is independently absent or (C(R$^9$)$_2$);
X$^2$ is N or CR$^8$;
each R$^{X1}$ is independently deuterium, optionally substituted C$_1$-C$_6$ alkyl, or halo, or two geminal R$^{X1}$ groups, together with the atom to which they are attached, combine to form a carbonyl;

L$^1$ is optionally substituted 9- or 10-membered bicyclic heterocyclyl, optionally substituted 9- or 10-membered bicyclic heteroaryl, optionally substituted monocyclic 6-membered heteroarylvinyl, optionally substituted monocyclic 6-membered heteroaryl-C$_3$-C$_8$-cycloalkyl, or optionally substituted monocyclic 6-membered heteroarylethynyl;
L$^2$ is absent, optionally substituted C$_3$-C$_{10}$ cycloalkyl, optionally substituted C$_6$-C$_{10}$ aryl, optionally substituted 5- to 10-membered heteroaryl, or optionally substituted 4- to 10-membered heterocyclyl;
R$^1$ is hydrogen or optionally substituted C$_1$-C$_6$ alkyl;
each R$^2$ and each R$^3$ are independently hydrogen, optionally substituted C$_1$-C$_6$ alkyl, or optionally substituted C$_1$-C$_6$ heteroalkyl;
R$^4$ is hydrogen, halo, optionally substituted C$_1$-C$_6$ alkyl, or optionally substituted C$_3$-C$_{10}$ cycloalkyl;
R$^5$ is hydrogen, deuterium, or optionally substituted C$_1$-C$_6$ alkyl;
R$^6$ is hydrogen, deuterium, optionally substituted C$_1$-C$_6$ alkyl, or halo, and each R$^9$ is independently hydrogen, deuterium, optionally substituted C$_1$-C$_6$ alkyl, or halo; or R$^6$ and one vicinal R$^9$, together with the atoms to which they are attached, combine to form optionally substituted C$_3$-C$_8$ cycloalkyl, and the remaining R$^9$ groups, if present, are independently deuterium, optionally substituted C$_1$-C$_6$ alkyl, or halo;
each R$^7$ is independently optionally substituted C$_1$-C$_6$ alkyl, optionally substituted C$_1$-C$_6$ heteroalkyl, halo, optionally substituted C$_3$-C$_{10}$ cycloalkyl, optionally substituted 5- to 10-membered heteroaryl, optionally substituted 4- to 10-membered heterocyclyl, —N(R$^{7A}$)$_2$, or —OR$^{7A}$, wherein each R$^{7A}$ is independently H, optionally substituted C$_1$-C$_6$ alkyl, optionally substituted C$_1$-C$_6$ heteroalkyl, optionally substituted C$_3$-C$_{10}$ cycloalkyl, optionally substituted C$_6$-C$_{10}$ aryl, optionally substituted 5- to 10-membered heteroaryl, or optionally substituted 4- to 10-membered heterocyclyl, or two geminal R$^{7A}$ groups, together with the atom to which they are attached, combine to form optionally substituted 5- to 10-membered heteroaryl or optionally substituted 4- to 10-membered heterocyclyl;
R$^8$ is hydrogen, halo, cyano, optionally substituted C$_1$-C$_6$ alkyl, optionally substituted C$_2$-C$_6$ alkynyl, optionally substituted C$_1$-C$_6$ heteroalkyl, or optionally substituted C$_3$-C$_{10}$ cycloalkyl; and
R$^{10}$ is hydrogen or halo;
or a pharmaceutically acceptable salt thereof.

2. The compound of claim 1, or a pharmaceutically acceptable salt thereof, wherein Z$^1$ is (C(R$^9$)$_2$).

3. The compound of claim 1, or a pharmaceutically acceptable salt thereof, wherein Z$^1$ is absent.

4. The compound of claim 1, or a pharmaceutically acceptable salt thereof, wherein Z$^1$ is O.

5. The compound of claim 1, or a pharmaceutically acceptable salt thereof, wherein Z$^2$ is (C(R$^9$)$_2$).

6. The compound of claim 1, or a pharmaceutically acceptable salt thereof, wherein Z$^2$ is absent.

7. The compound of claim 1, or a pharmaceutically acceptable salt thereof, wherein Z$^2$ is O.

8. The compound of claim 1, or a pharmaceutically acceptable salt thereof, wherein X$^1$ is O.

9. The compound of claim 1, or a pharmaceutically acceptable salt thereof, wherein X$^1$ is NR$^5$.

10. The compound of claim 1, or a pharmaceutically acceptable salt thereof, wherein X$^1$ is (C(R$^5$)(R$^6$)).

11. The compound of claim 1, or a pharmaceutically acceptable salt thereof, wherein $X^2$ is $CR^8$.

12. The compound of claim 1, or a pharmaceutically acceptable salt thereof, wherein

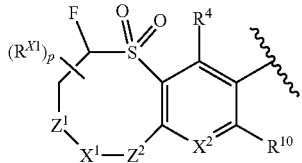

is a group of the following structure

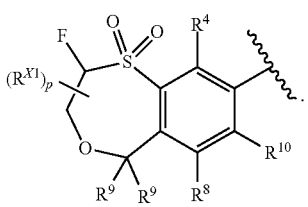

13. The compound of claim 1, or a pharmaceutically acceptable salt thereof, wherein

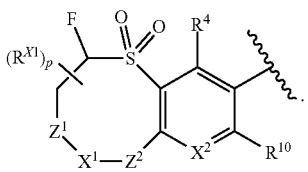

is a group of the following structure

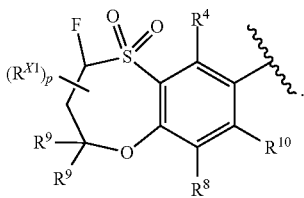

14. The compound of claim 13, or a pharmaceutically acceptable salt thereof, wherein

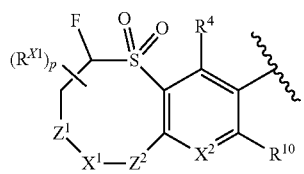

is a group of the following structure

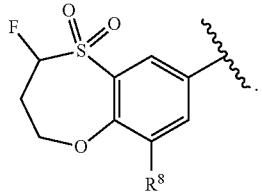

15. The compound of claim 1, or a pharmaceutically acceptable salt thereof, wherein

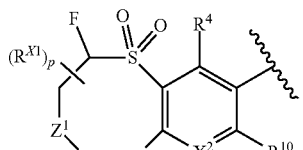

is a group of the following structure

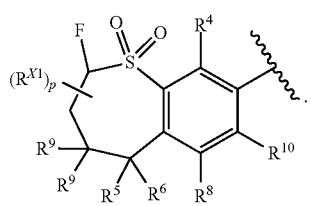

16. The compound of claim 1, or a pharmaceutically acceptable salt thereof, wherein

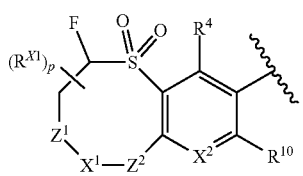

is a group of the following structure

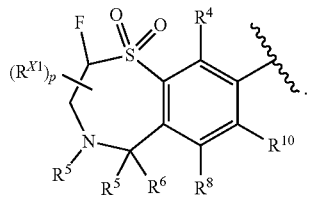

17. The compound of claim 1, or a pharmaceutically acceptable salt thereof, wherein

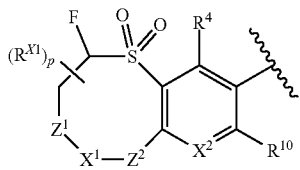

is a group of the following structure

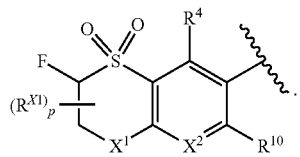

18. The compound of claim 1, or a pharmaceutically acceptable salt thereof, wherein

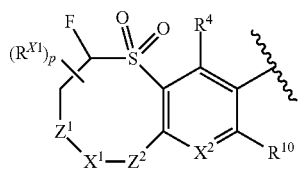

is a group of the following structure

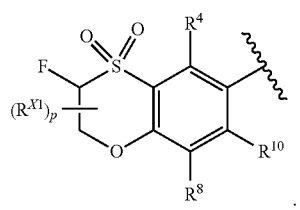

19. The compound of claim 1, or a pharmaceutically acceptable salt thereof, wherein

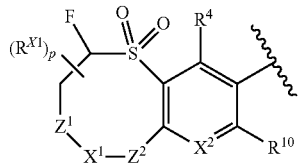

is a group of the following structure

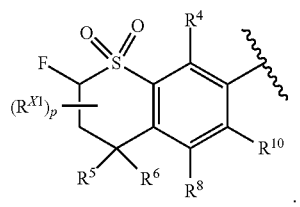

20. The compound of claim 1, or a pharmaceutically acceptable salt thereof, wherein

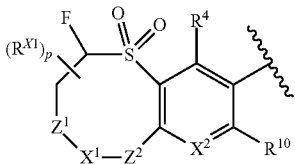

is a group of the following structure

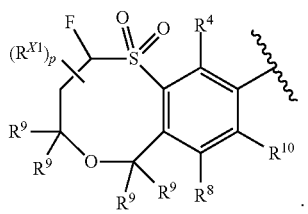

21. The compound of claim 1, or a pharmaceutically acceptable salt thereof, wherein

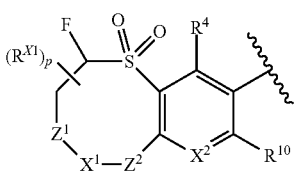

is a group of the following structure

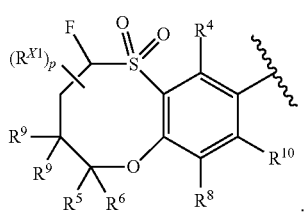

22. The compound of claim 1, or a pharmaceutically acceptable salt thereof, wherein $R^8$ is hydrogen.

23. The compound of claim 1, or a pharmaceutically acceptable salt thereof, wherein $R^8$ is halo.

24. The compound of claim 23, or a pharmaceutically acceptable salt thereof, wherein $R^8$ is fluoro.

25. The compound of claim 1, or a pharmaceutically acceptable salt thereof, wherein $R^8$ is optionally substituted $C_2$-$C_6$ alkynyl.

26. The compound of claim 1, or a pharmaceutically acceptable salt thereof, wherein $R^8$ is optionally substituted $C_1$-$C_6$ heteroalkyl.

27. The compound of claim 1, or a pharmaceutically acceptable salt thereof, wherein $R^8$ is optionally substituted $C_3$-$C_{10}$ cycloalkyl.

28. The compound of claim 1, or a pharmaceutically acceptable salt thereof, wherein $X^2$ is N.

29. The compound of claim 1, or a pharmaceutically acceptable salt thereof, wherein

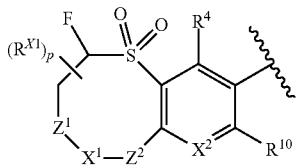

is a group of the following structure

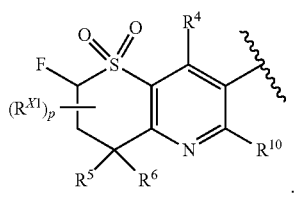

30. The compound of claim 1, or a pharmaceutically acceptable salt thereof, wherein $R^4$ is hydrogen.
31. The compound of claim 1, or a pharmaceutically acceptable salt thereof, wherein $R^4$ is halogen.
32. The compound of claim 1, or a pharmaceutically acceptable salt thereof, wherein $R^{10}$ is hydrogen.
33. The compound of claim 1, or a pharmaceutically acceptable salt thereof, wherein $R^{10}$ is halogen.
34. The compound of claim 1, or a pharmaceutically acceptable salt thereof, wherein at least one $R^{X1}$ is optionally substituted $C_1$-$C_6$ alkyl.
35. The compound of claim 1, or a pharmaceutically acceptable salt thereof, wherein at least one $R^{X1}$ is halo.
36. The compound of claim 1, or a pharmaceutically acceptable salt thereof, wherein at least one $R^{X1}$ is deuterium.
37. The compound of claim 1, or a pharmaceutically acceptable salt thereof, wherein p is 3.
38. The compound of claim 1, or a pharmaceutically acceptable salt thereof, wherein p is 2.
39. The compound of claim 1, or a pharmaceutically acceptable salt thereof, wherein p is 1.
40. The compound of claim 1, or a pharmaceutically acceptable salt thereof, wherein p is 0.
41. The compound of claim 1, or a pharmaceutically acceptable salt thereof, wherein $L^1$ is optionally substituted 9- or 10-membered bicyclic heteroaryl.
42. The compound of claim 1, or a pharmaceutically acceptable salt thereof, wherein $L^1$ is

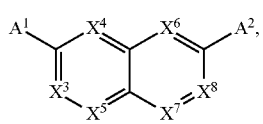

Formula A wherein
each of $X^3$, $X^4$, $X^5$, $X^6$, $X^7$, and $X^8$ is independently N or $CR^{L1}$;
each $R^{L1}$ is independently H, halo, optionally substituted $C_1$-$C_6$ alkyl;
$A^1$ is a bond to —$(C(R^2)(R^3))_m$—; and
$A^2$ is a bond to $L^2$.

43. The compound of claim 42, or a pharmaceutically acceptable salt thereof, wherein $L^1$ is

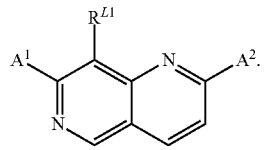

44. The compound of claim 43, or a pharmaceutically acceptable salt thereof, wherein $R^{L1}$ is hydrogen.
45. The compound of claim 42, or a pharmaceutically acceptable salt thereof, wherein $L^1$ is

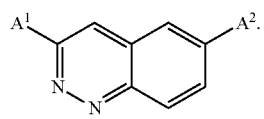

46. The compound of claim 42, or a pharmaceutically acceptable salt thereof, wherein $L^1$ is

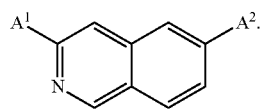

47. The compound of claim 1, or a pharmaceutically acceptable salt thereof, wherein $L^1$ is optionally substituted monocyclic 6-membered heteroarylvinyl.
48. The compound of claim 1, or a pharmaceutically acceptable salt thereof, wherein $L^1$ is

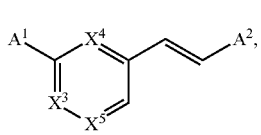

Formula B wherein
each of $X^3$, $X^4$, and $X^5$ is independently N or $CR^{L1}$;
each $R^{L1}$ is independently H, halo, optionally substituted $C_1$-$C_6$ alkyl;
$A^1$ is a bond to —$(C(R^2)(R^3))_m$—; and
$A^2$ is a bond to $L^2$.

49. The compound of claim 48, or a pharmaceutically acceptable salt thereof, wherein $L^1$ is

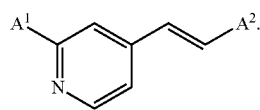

50. The compound of claim 1, or a pharmaceutically acceptable salt thereof, wherein $L^1$ is optionally substituted monocyclic 6-membered heteroarylethynyl.

51. The compound of claim 1, or a pharmaceutically acceptable salt thereof, wherein L¹ is

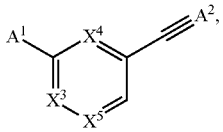   Formula C wherein
each of X³, X⁴, and X⁵ is independently N or CR$^{L1}$;
each R$^{L1}$ is independently H, halo, optionally substituted C₁-C₆ alkyl;
A¹ is a bond to —(C(R²)(R³))$_m$—; and
A² is a bond to L².

52. The compound of claim 51, or a pharmaceutically acceptable salt thereof, wherein L¹ is

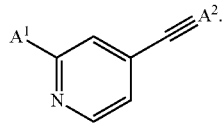

53. The compound of claim 1, or a pharmaceutically acceptable salt thereof, wherein L¹ is optionally substituted monocyclic 6-membered heteroaryl-C₃-C₈-cycloalkyl.

54. The compound of claim 1, or a pharmaceutically acceptable salt thereof, wherein L¹ is

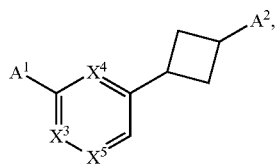   Formula D wherein
each of X³, X⁴, and X⁵ is independently N or CR$^{L1}$;
each R$^{L1}$ is independently H, halo, optionally substituted C₁-C₆ alkyl;
A¹ is a bond to —(C(R²)(R³))$_m$—; and
A² is a bond to L².

55. The compound of claim 54, or a pharmaceutically acceptable salt thereof, wherein L¹ is

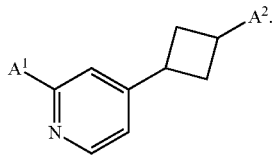

56. The compound of claim 1, or a pharmaceutically acceptable salt thereof, wherein L¹ is optionally substituted 9- or 10-membered bicyclic heterocyclyl.

57. The compound of claim 1, or a pharmaceutically acceptable salt thereof, wherein the compound has the structure:

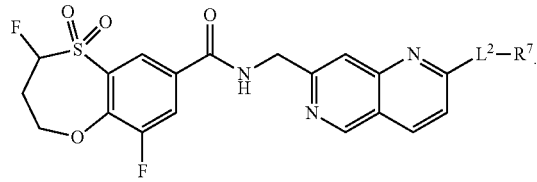

58. The compound of claim 1, or a pharmaceutically acceptable salt thereof, wherein L² is optionally substituted 5- to 10-membered heteroaryl.

59. The compound of claim 1, or a pharmaceutically acceptable salt thereof, wherein -L²-(R⁷)$_n$ is a group of the following structure:

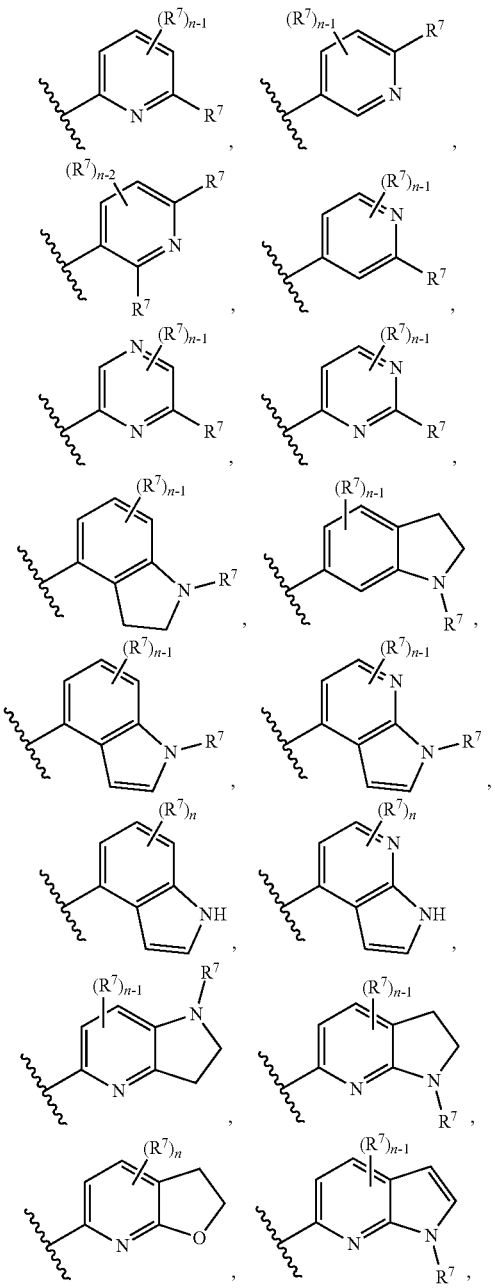

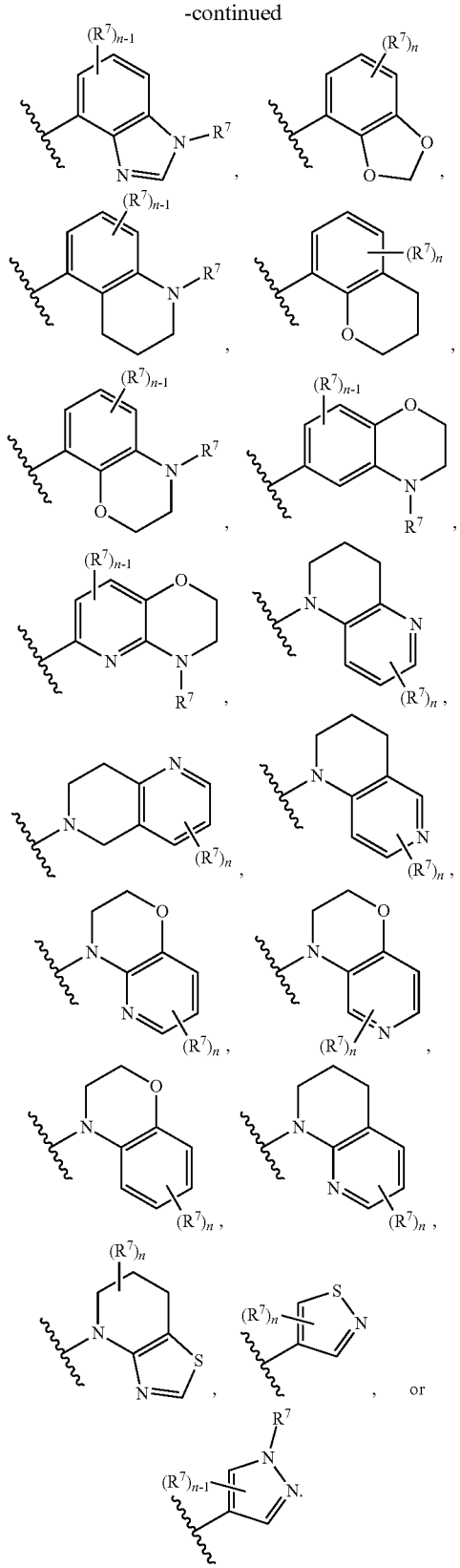
60. The compound of claim 59, or a pharmaceutically acceptable salt thereof, wherein -L²-(R⁷)$_n$ is a group of the following structure:
61. The compound of claim 60, or a pharmaceutically acceptable salt thereof, wherein -L²-(R⁷)$_n$ is a group of the following structure:

-continued

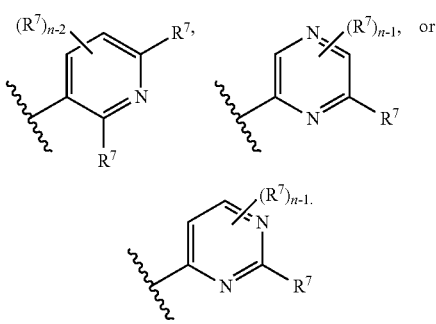

62. The compound of claim 61, or a pharmaceutically acceptable salt thereof, wherein -L²-(R⁷)ₙ is a group of the following structure:

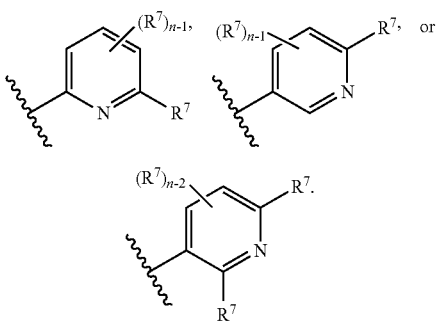

63. The compound of claim 60, or a pharmaceutically acceptable salt thereof, wherein -L²-(R⁷)ₙ is a group of the following structure:

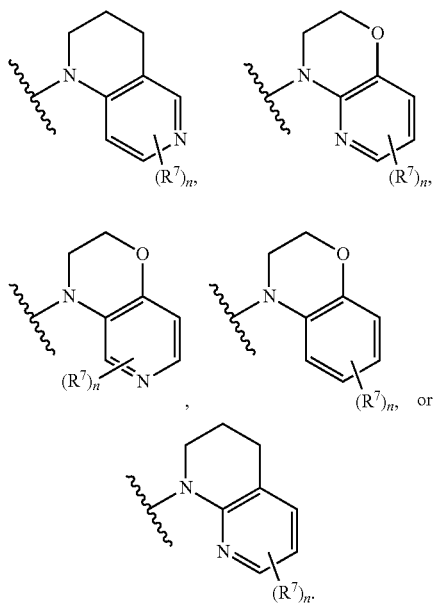

64. The compound of claim 60, or a pharmaceutically acceptable salt thereof, wherein -L²-(R⁷)ₙ is a group of the following structure:

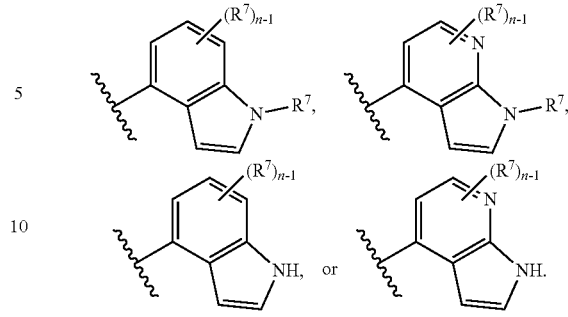

65. The compound of claim 60, or a pharmaceutically acceptable salt thereof, wherein -L²-(R⁷)ₙ is a group of the following structure:

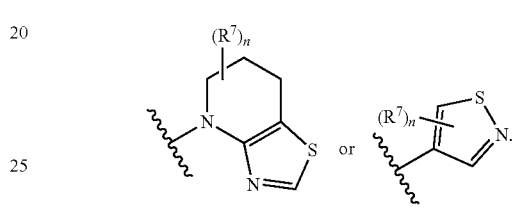

66. The compound of claim 1, or a pharmaceutically acceptable salt thereof, wherein L² is optionally substituted $C_6$-$C_{10}$ aryl.

67. The compound of claim 66, or a pharmaceutically acceptable salt thereof, wherein L² is optionally substituted phenyl.

68. The compound of claim 1, or a pharmaceutically acceptable salt thereof, wherein n is 1.

69. The compound of claim 1, or a pharmaceutically acceptable salt thereof, wherein n is 2.

70. The compound of claim 1, or a pharmaceutically acceptable salt thereof, wherein n is 3.

71. The compound of claim 1, or a pharmaceutically acceptable salt thereof, wherein R⁷ is optionally substituted $C_1$-$C_6$ alkyl.

72. The compound of claim 1, or a pharmaceutically acceptable salt thereof, wherein R⁷ is optionally substituted $C_1$-$C_6$ heteroalkyl.

73. The compound of claim 1, or a pharmaceutically acceptable salt thereof, wherein R⁷ is optionally substituted 4- to 10-membered heterocyclyl.

74. The compound of claim 73, or a pharmaceutically acceptable salt thereof, wherein R⁷ is optionally substituted azetidinyl or optionally substituted morpholinyl.

75. The compound of claim 1, or a pharmaceutically acceptable salt thereof, wherein R⁷ is optionally substituted $C_3$-$C_{10}$ cycloalkyl.

76. The compound of claim 75, or a pharmaceutically acceptable salt thereof, wherein R⁷ is optionally substituted cyclopropyl or optionally substituted cyclobutyl.

77. The compound of claim 1, or a pharmaceutically acceptable salt thereof, wherein R⁷ is —N(R⁷ᴬ)₂.

78. The compound of claim 77, or a pharmaceutically acceptable salt thereof, wherein R⁷ is optionally substituted N-azetidinyl or optionally substituted N-morpholinyl.

79. The compound of claim 1, or a pharmaceutically acceptable salt thereof, wherein two geminal R⁷ groups, together with the atom to which they are attached, combine to form optionally substituted 4- to 10-membered heterocyclyl.

80. The compound of claim 1, or a pharmaceutically acceptable salt thereof, wherein at least one $R^7$ is —$OR^{7A}$.

81. The compound of claim 80, or a pharmaceutically acceptable salt thereof, wherein $R^{7A}$ is optionally substituted $C_{1-6}$ alkyl.

82. The compound of claim 1, or a pharmaceutically acceptable salt thereof, wherein n is 0.

83. The compound of claim 1, or a pharmaceutically acceptable salt thereof, wherein at least one $R^7$ is difluoromethyl, cyclopropyl, 2,2-difluorocyclopropyl, difluoromethoxy, 2,6-dimethylmorpholin-4-yl, N-azetidinyl, 3-fluorocyclobutyl, 2-methoxyethyl, ethoxy, methoxy, 2,2-difluoroethoxy, 2,2-difluoroethyl, trifluoromethyl, isopropyl, methyl, acetyl, fluoro, chloro, 1-methylpyrazol-3-yl, dimethylamino, N-methyl-N-(2-methoxyethyl)-amino, N-ethyl-N-(2-methoxyethyl)-amino, N-(2-propyl)-N-(2-methoxyethyl)-amino, 2-methoxyethylamino, 3-aza-8-oxa-bicyclo[4.3.0]non-3-yl, 3-aza-7-oxa-bicyclo[4.3.0]non-3-yl, 1-fluorocyclobut-1-yl, 3-fluoropyrrolidin-1-yl, 3-methoxypyrrolidin-1-yl, oxetan-3-yl, N-methylindolin-4-yl, 2,2-difluoro-3-methylcycloprop-1-yl, 3-methoxyazetidin-1-yl, 3-methoxypiperidin-1-yl, 1,2-dimethyl-7-azaindol-4-yl, 1-methyl-7-azaindol-4-yl, 2,3-methylenedioxyphenyl, N-methyl-N-(3-oxetanyl)amino, 3-oxetanyloxy, 1,1-difluoro-5-azaspiro[2.3]hex-5-yl, 1-fluoromethyl-cyclopropyl, N-(3-tetrahydrofuranyl)methylamino, N-indolinyl, N-1,4-oxazepanyl, 2-fluoro-2-propyl, 1,1-difluoro-2-propyl, 2,2-difluoro-1-methylcycloprop-1-yl, 1-methylcyclopropyl, 4,4-difluoropiperidin-1-yl, 2-methoxyethoxy, 3,3-difluorocyclobut-1-yl, N-methyl-N-1-methoxyprop-2-ylamino, 1-methoxyprop-2-ylamino, 1-methoxyethyl, 4-methylpiperazinyl, 3-methylmorpholinyl, 2,2-difluoropropoxy, 3-methoxycyclobutyl, methylamino, 4-dimethylamino-3,3-difluoropiperidinyl, 4-methylamino-3,3-difluoropiperidinyl, 3,3-difluoropyrrolidinyl, N-methyl-N-3-methoxycyclobutylamino, 1-methylpyrazol-5-yl, 6-oxa-3-azabicyclo[3.1.1]hept-3-yl, cyclopropyloxy, 2,6-dimethylpyrid-4-yl, 2-methylpyrrolidinyl, 4-oxabicyclo[4.1.0]hept-1-yl, N-methyl-N-(2,6-dimethyltetrahydropyran-4-yl)amino, or N-methyl-N-3-methyloxetan-3-ylmethylamino.

84. The compound of claim 1, or a pharmaceutically acceptable salt thereof, wherein $R^1$ is hydrogen.

85. The compound of claim 1, or a pharmaceutically acceptable salt thereof, wherein

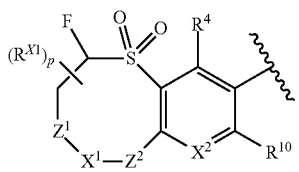

is a group of the following structure

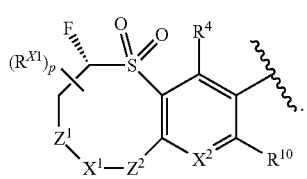

86. The compound of claim 1, or a pharmaceutically acceptable salt thereof, wherein

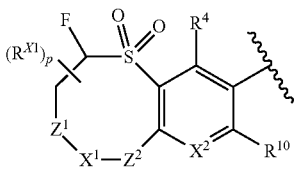

is a group of the following structure

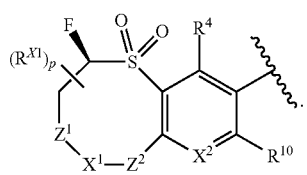

87. A compound selected from the group consisting of

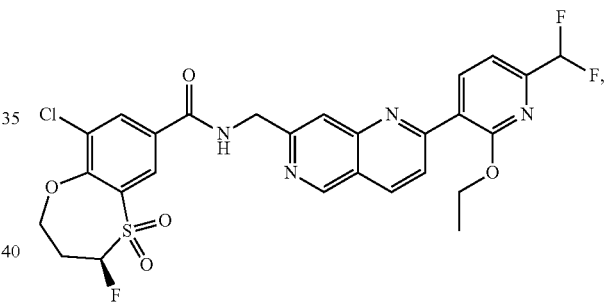

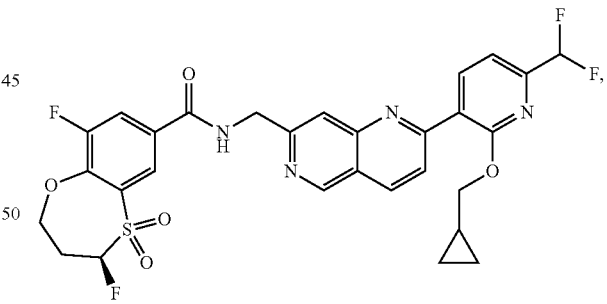

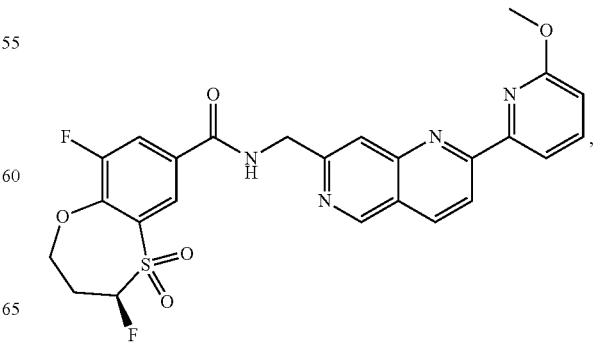

453
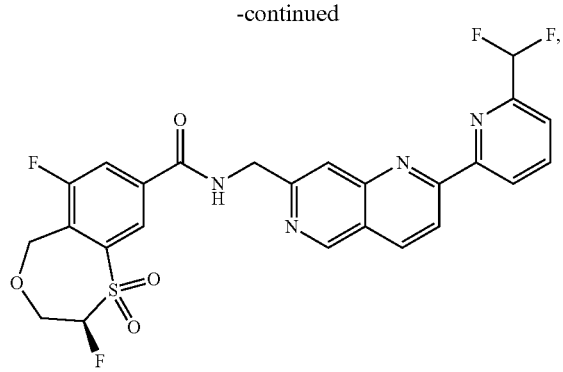
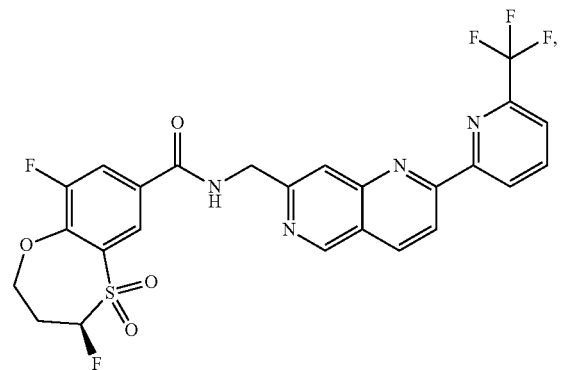
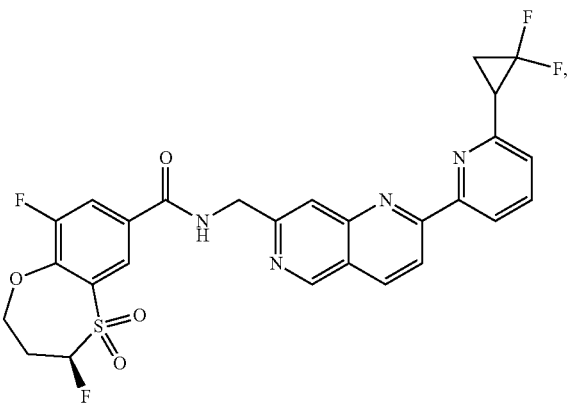
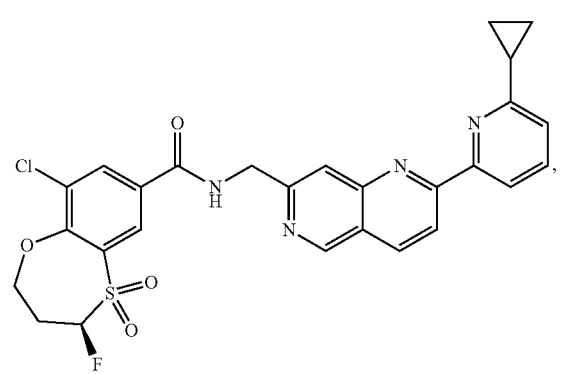
454
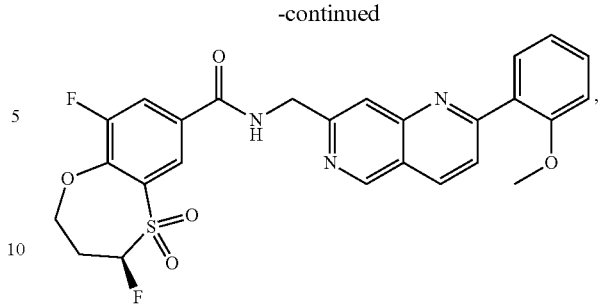
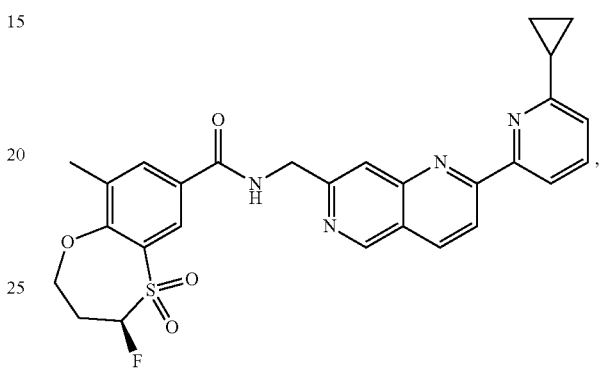
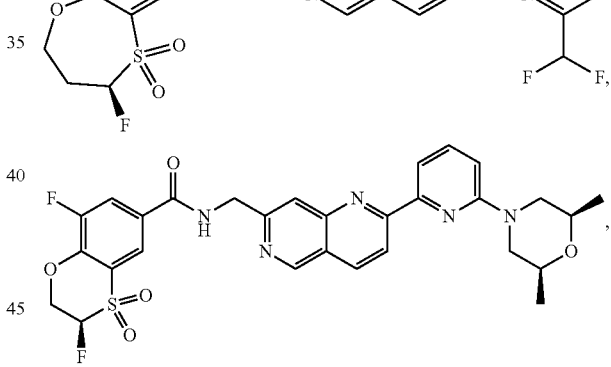
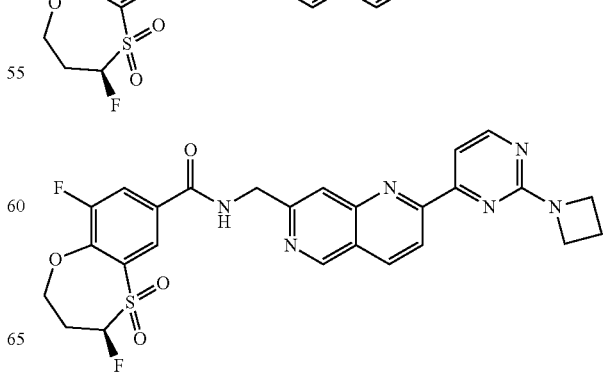

455
-continued
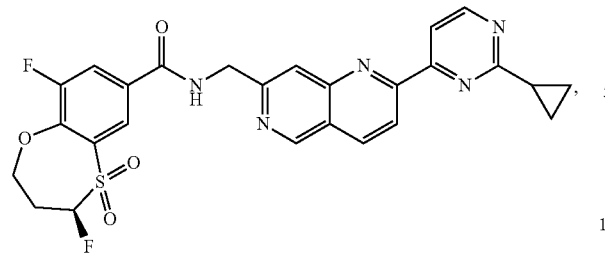
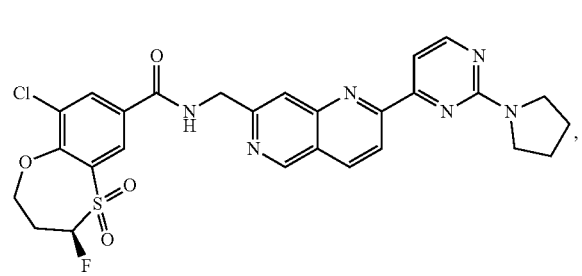
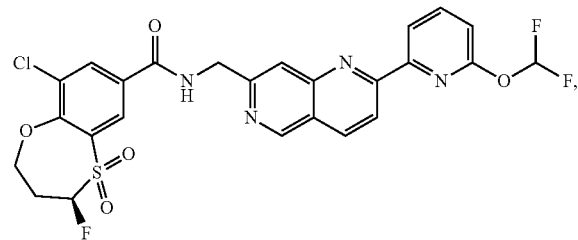
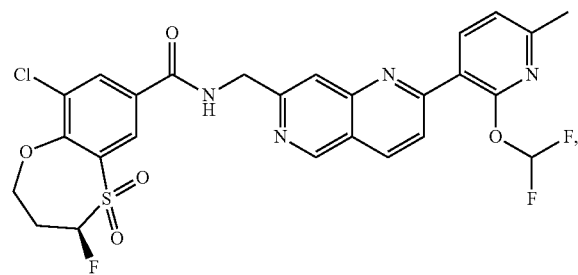
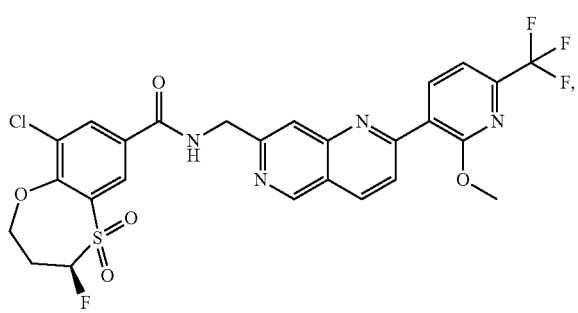
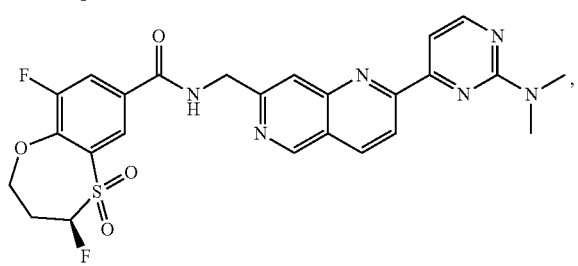
456
-continued
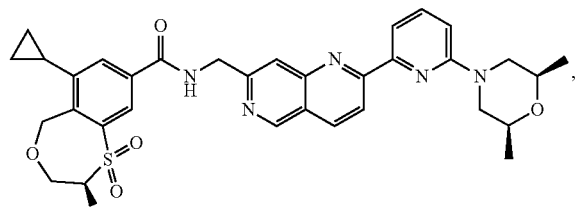
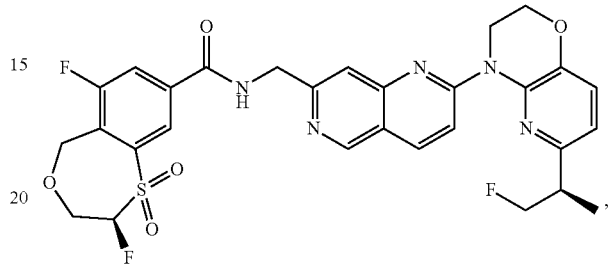
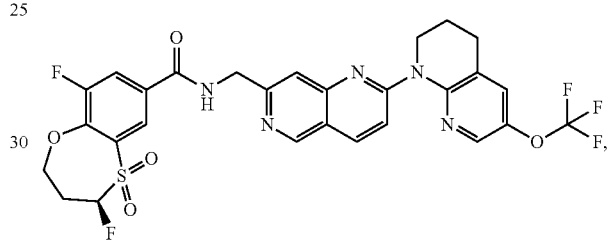
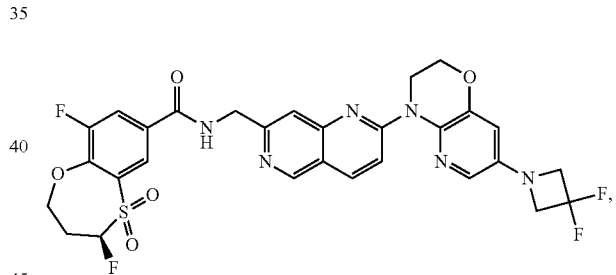
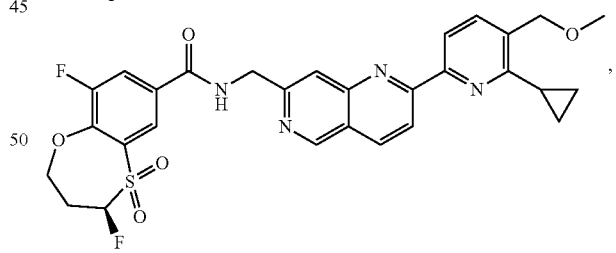
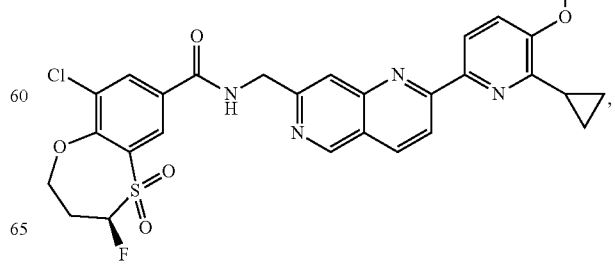

457
-continued
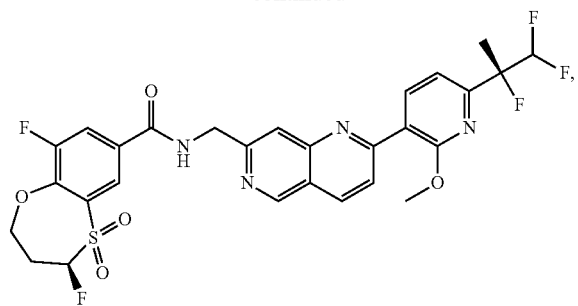
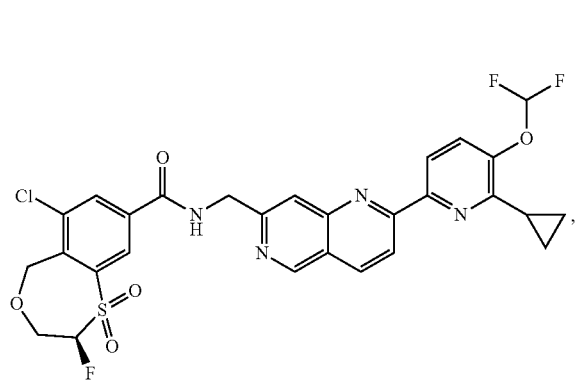
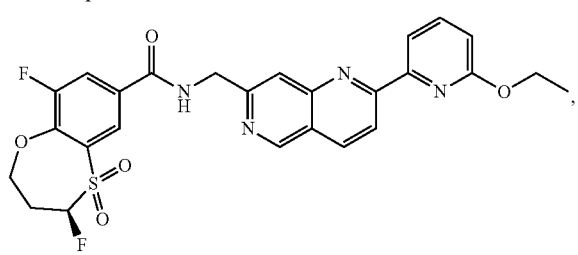
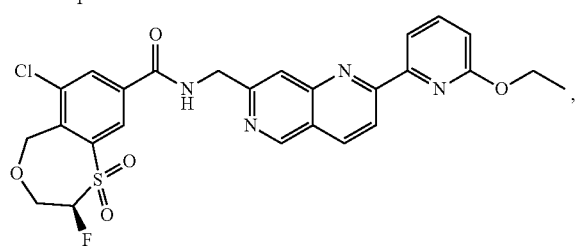
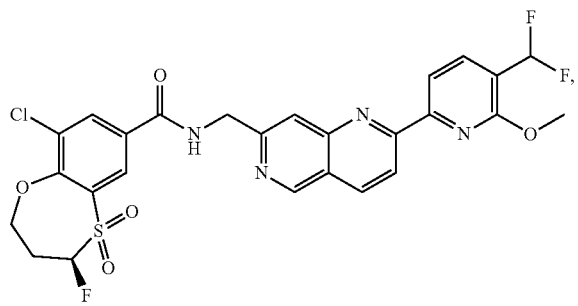
458
-continued
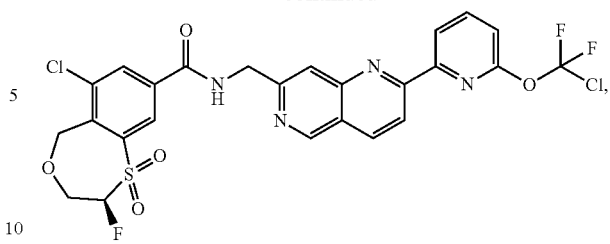
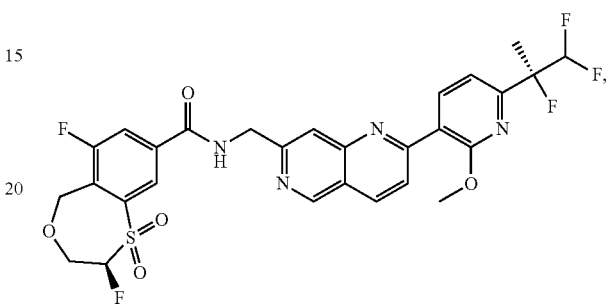
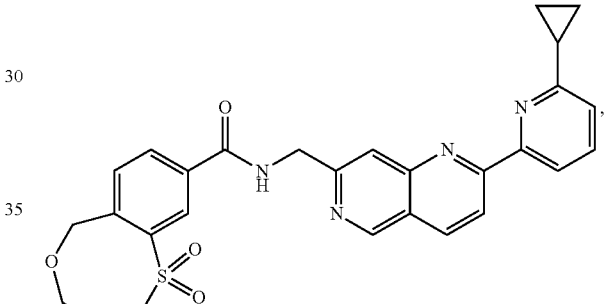
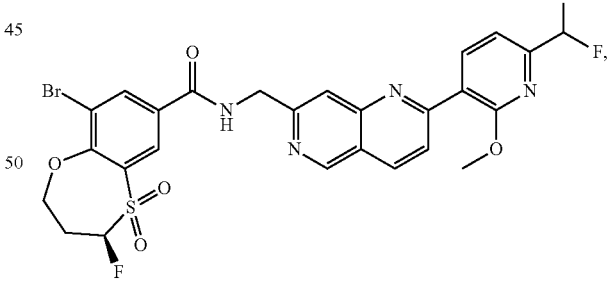
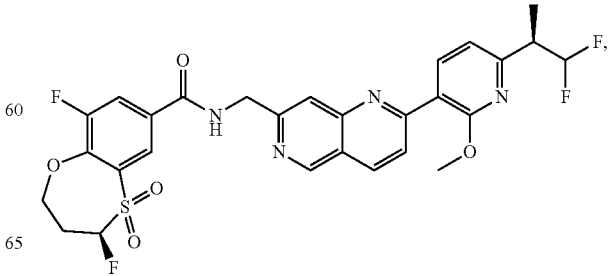

459
-continued
460
-continued
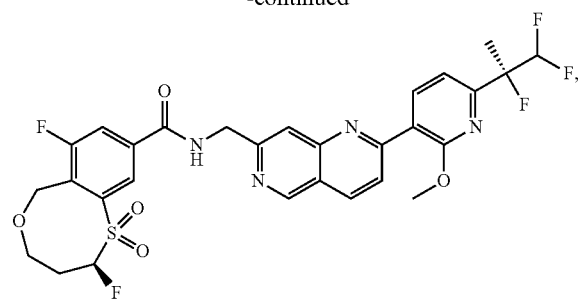
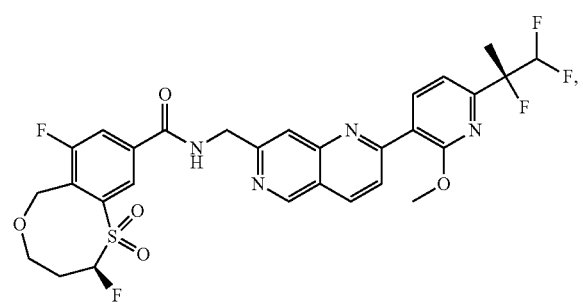
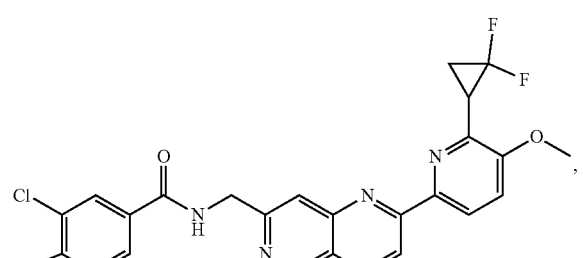
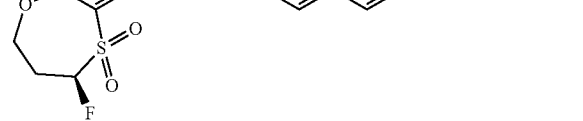
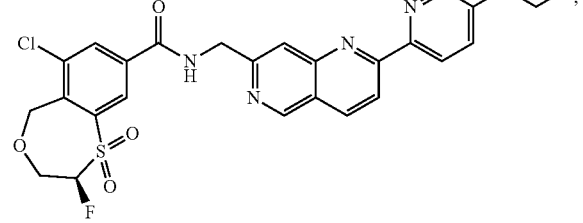
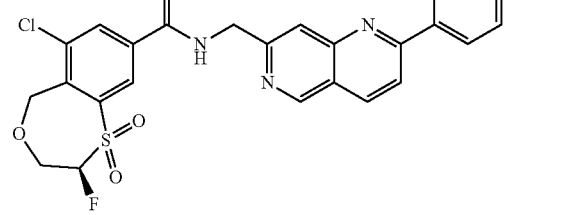

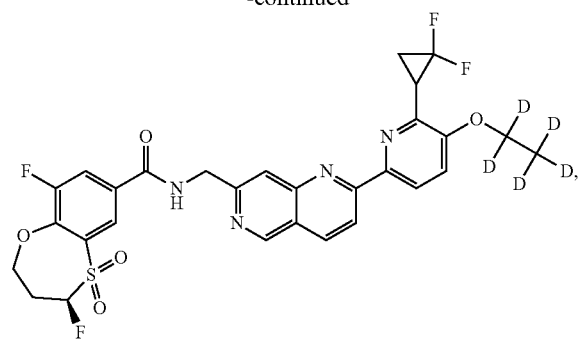
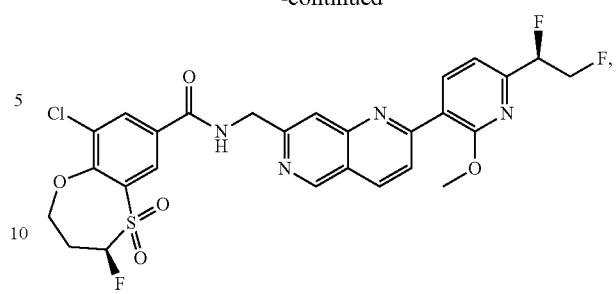
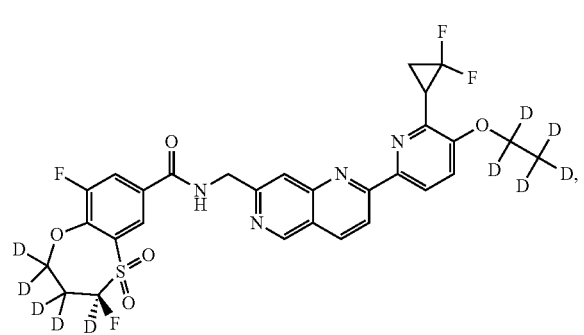
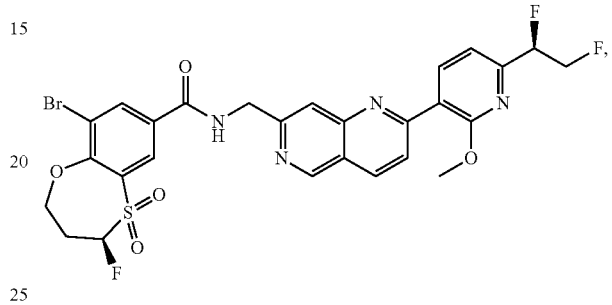
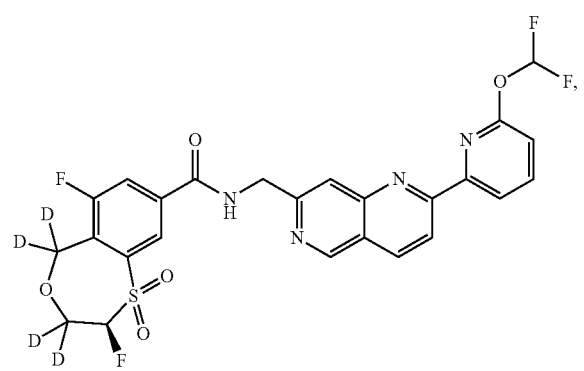
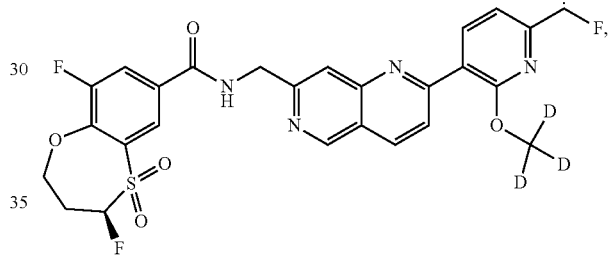
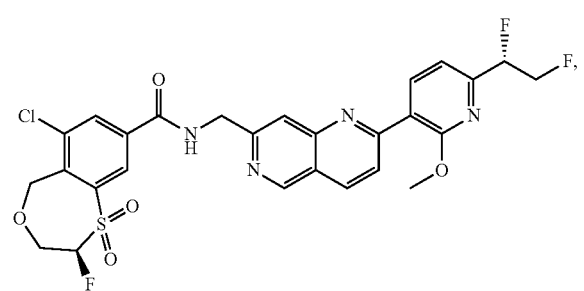
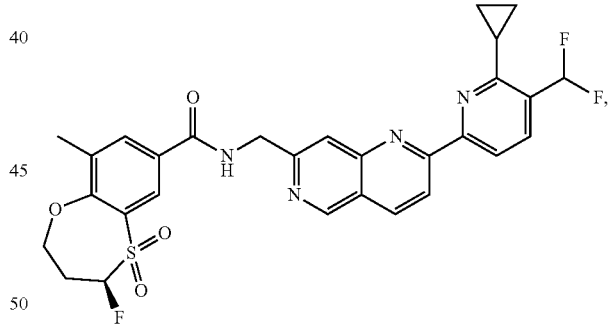
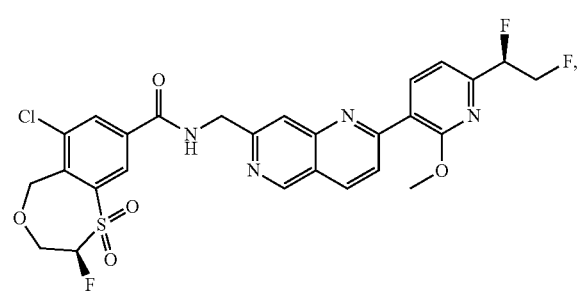
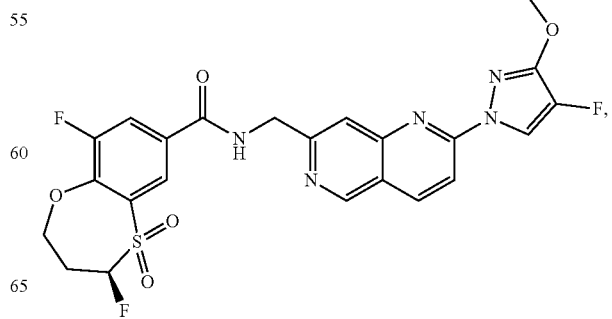

463
-continued
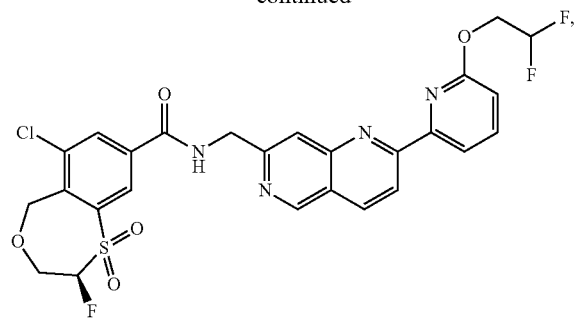
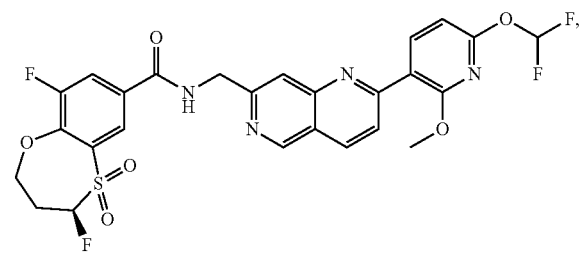
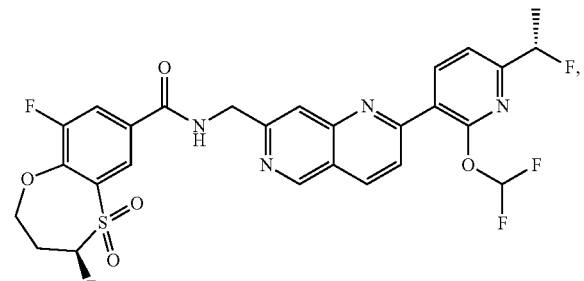
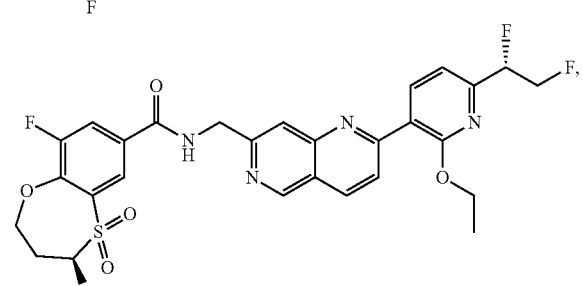
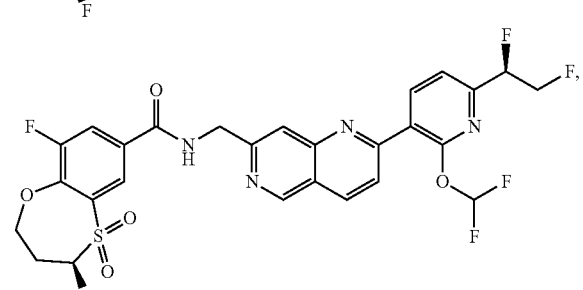
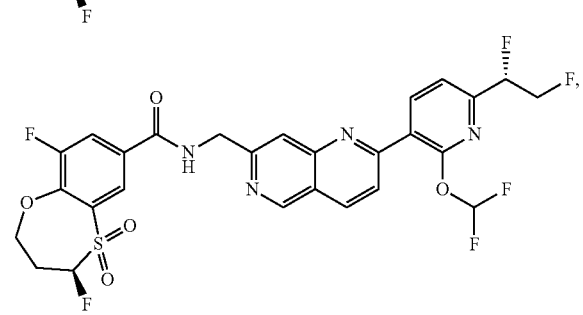
464
-continued
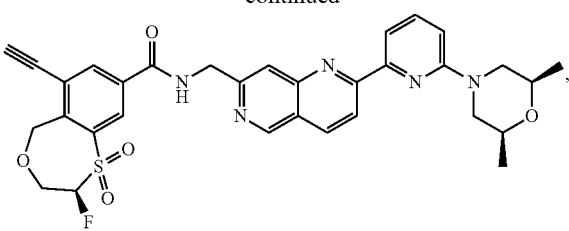
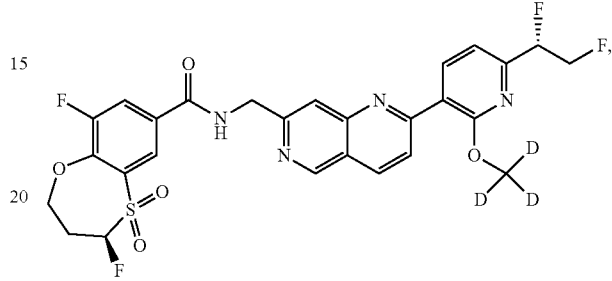
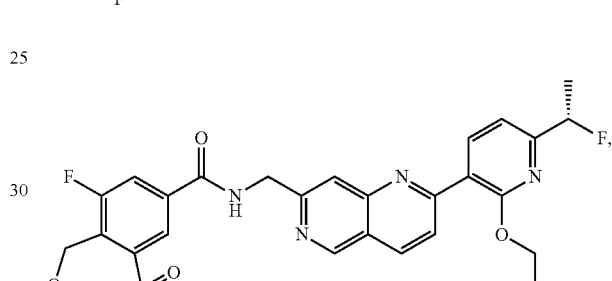
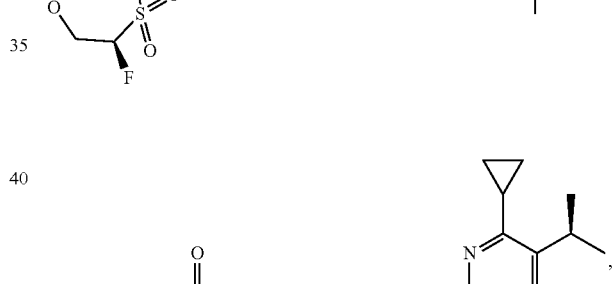
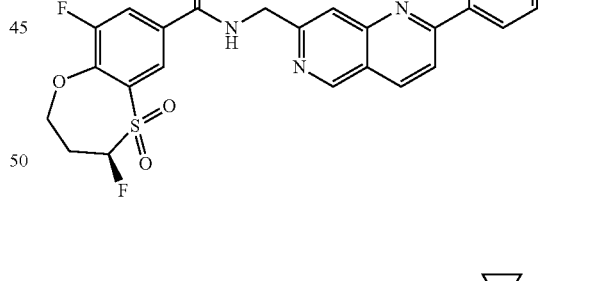
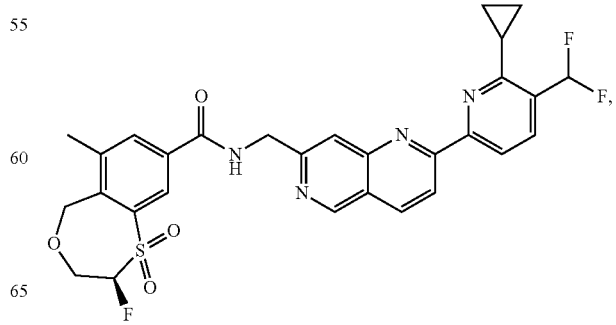

465
-continued
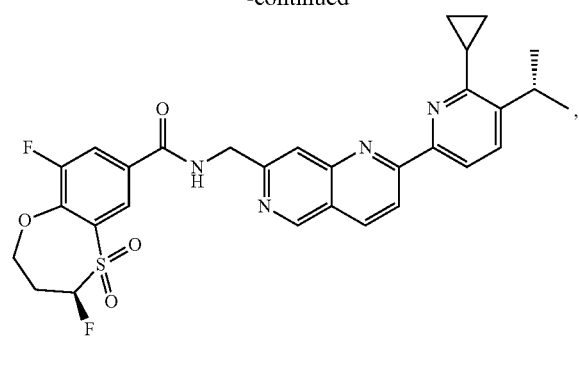
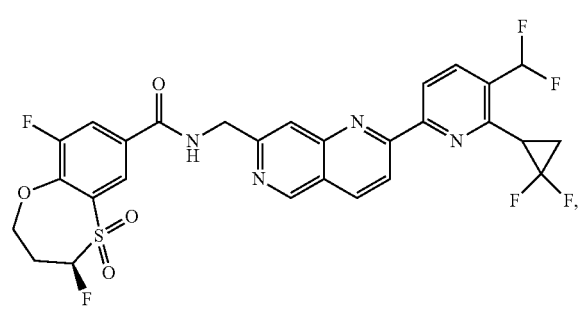
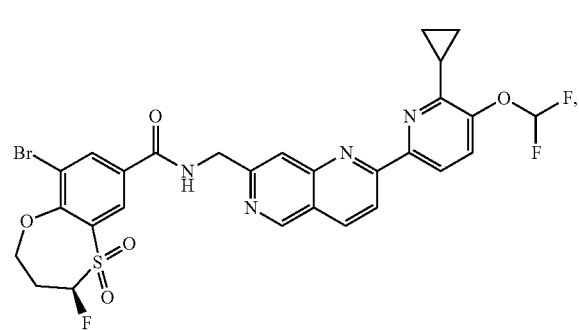
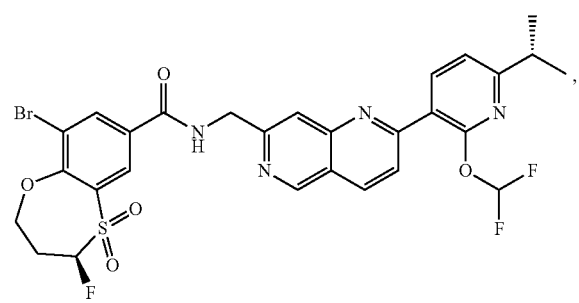
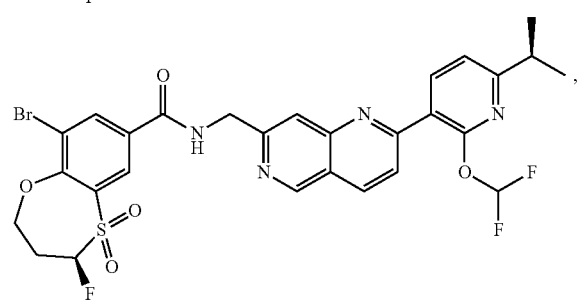
466
-continued
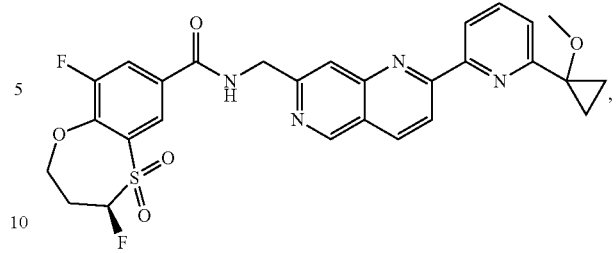
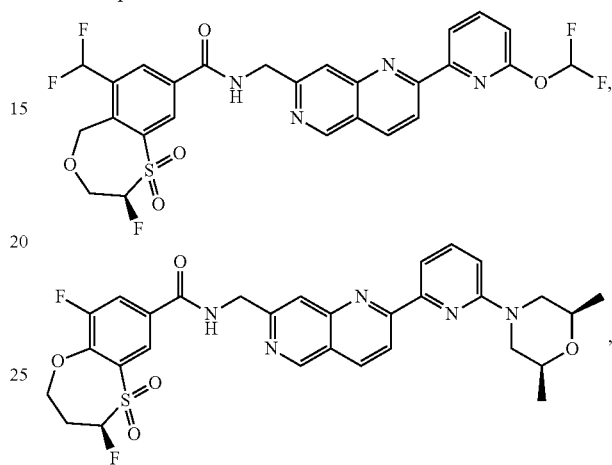
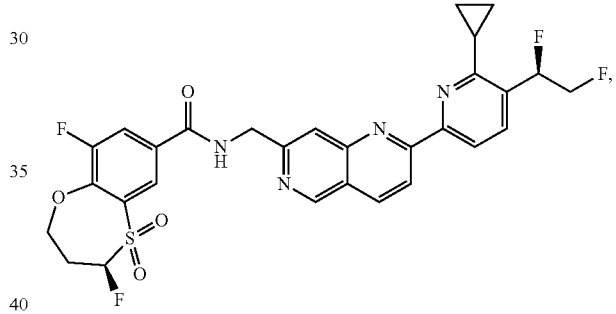
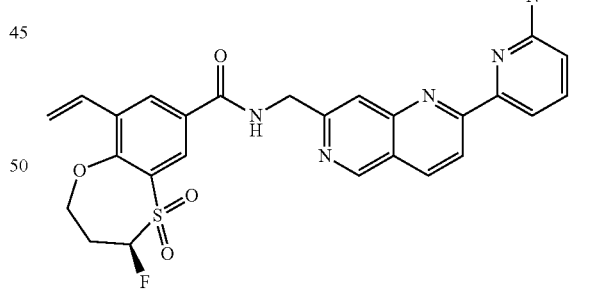
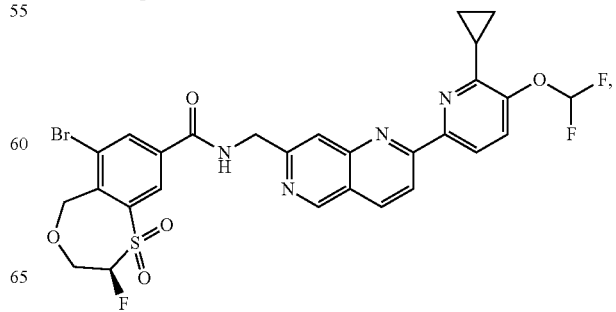

467
-continued
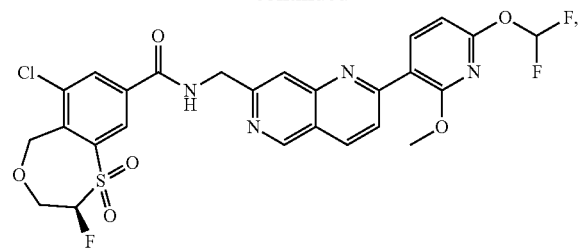
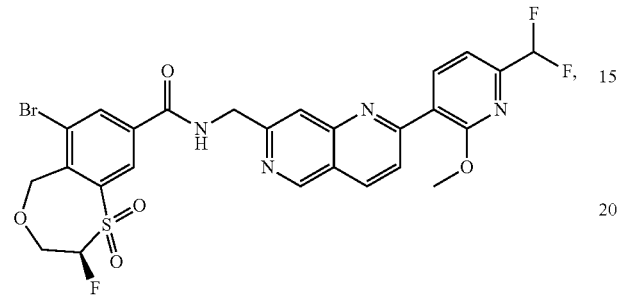
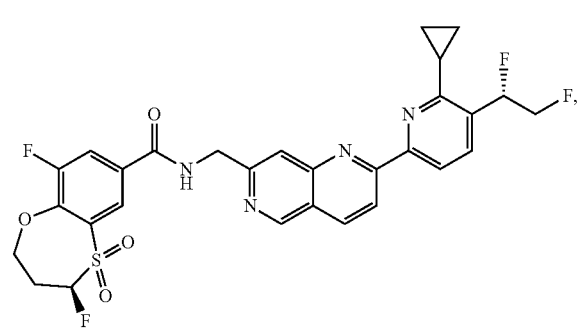
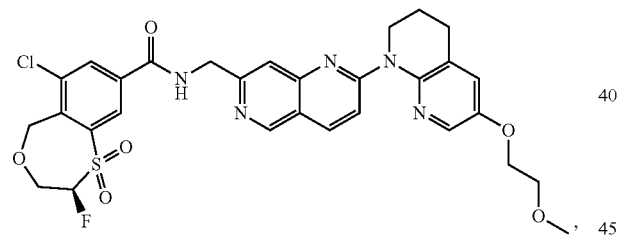
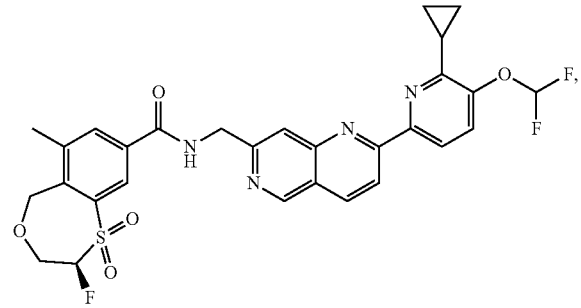
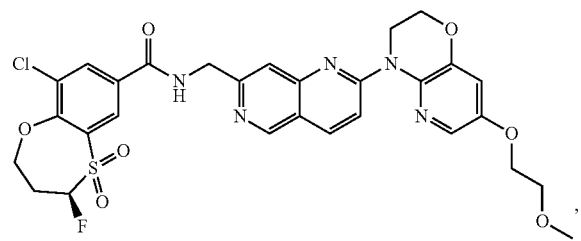
468
-continued
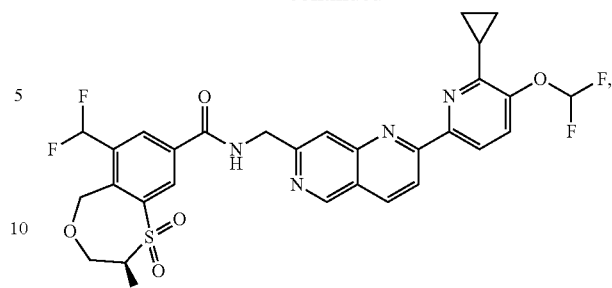
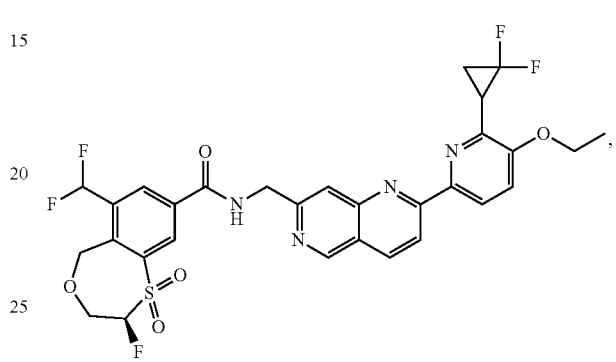
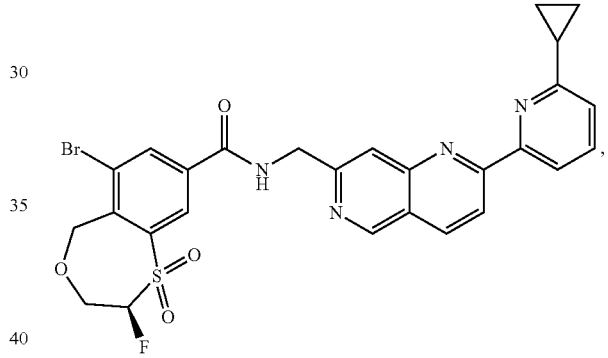
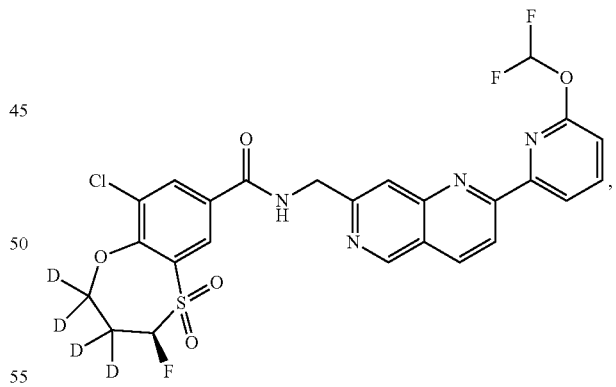
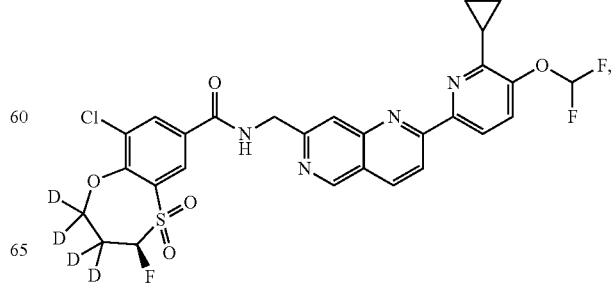

469
-continued
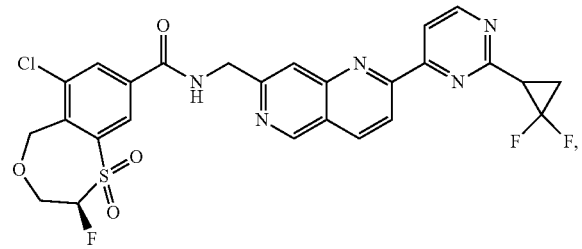
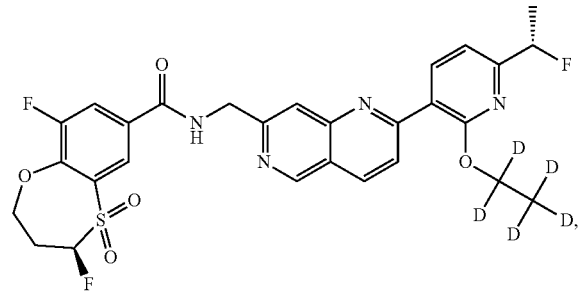
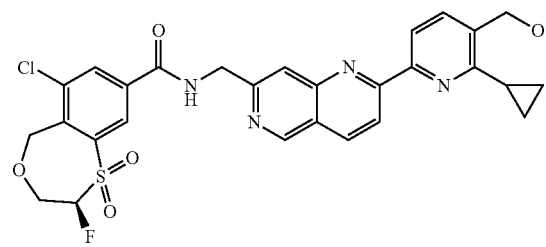
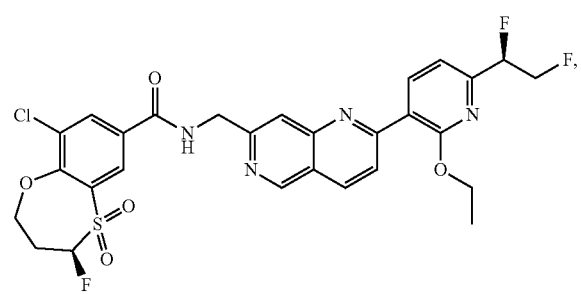
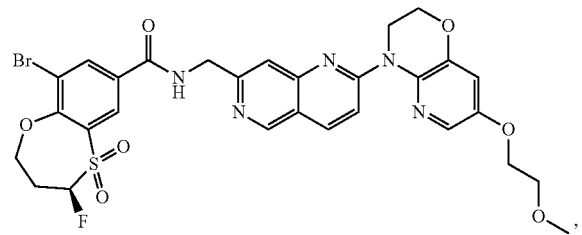
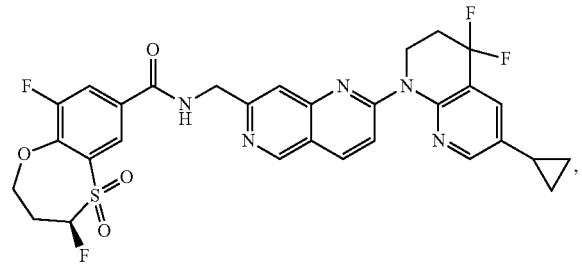
470
-continued
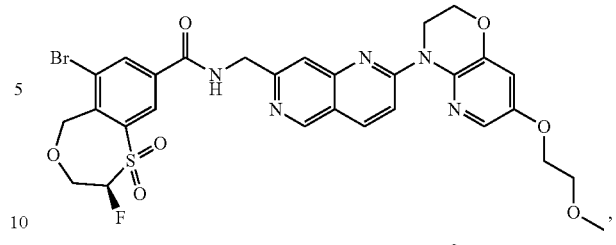
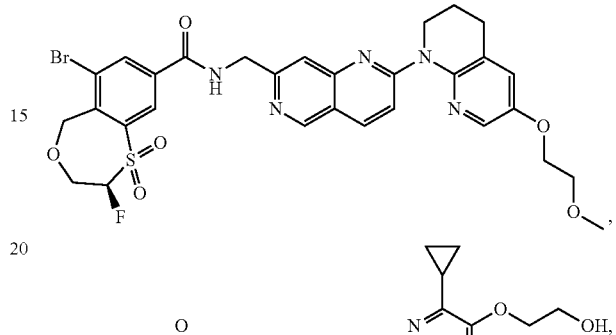
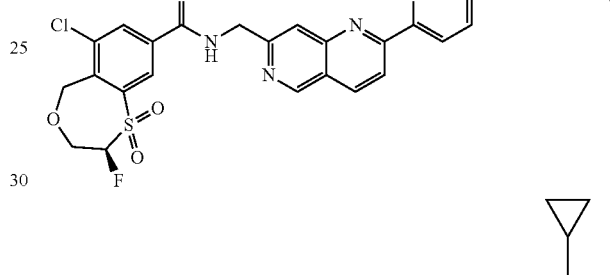
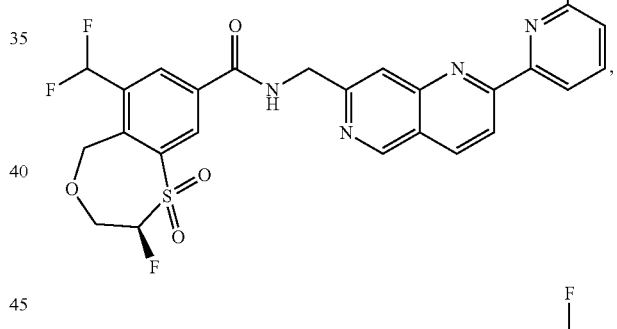
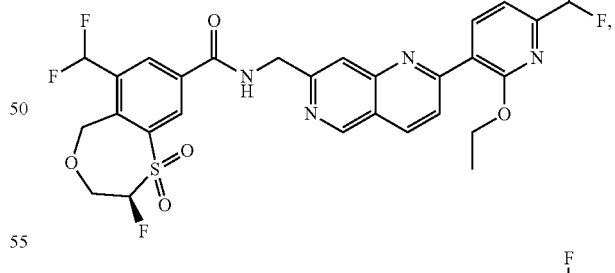
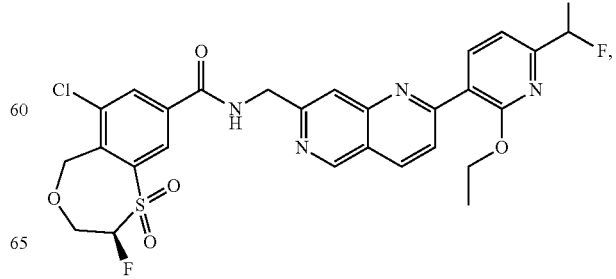

471
-continued
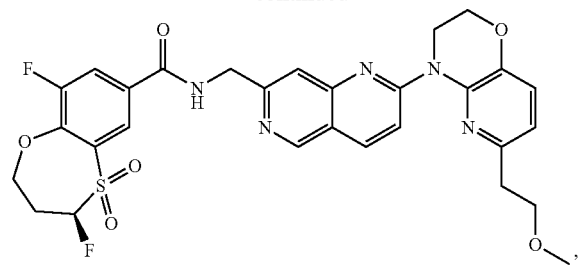
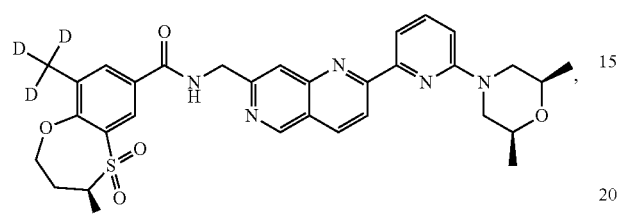
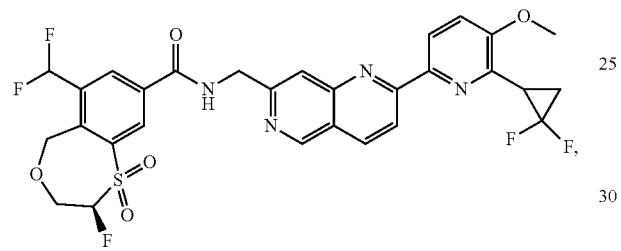
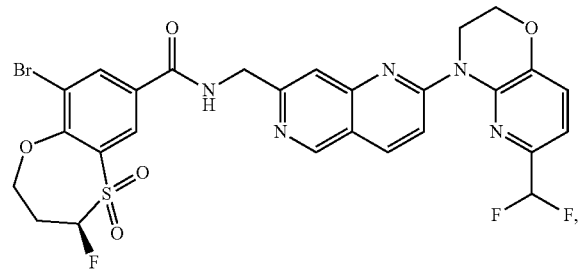
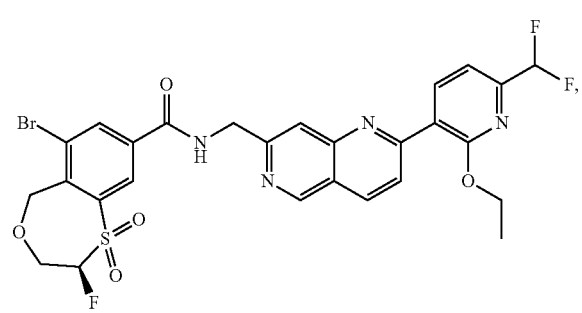
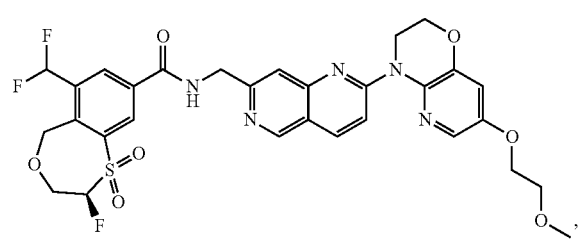
472
-continued
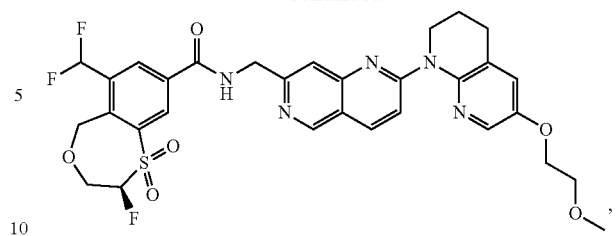
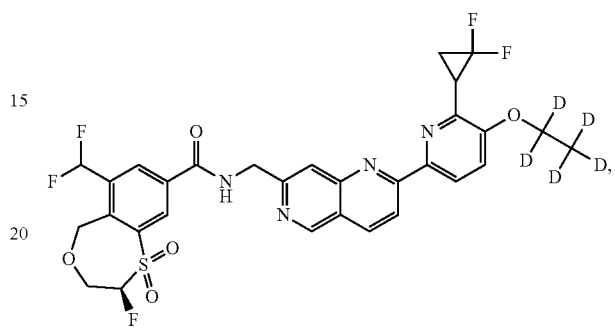
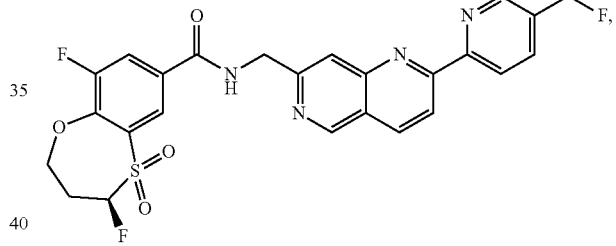
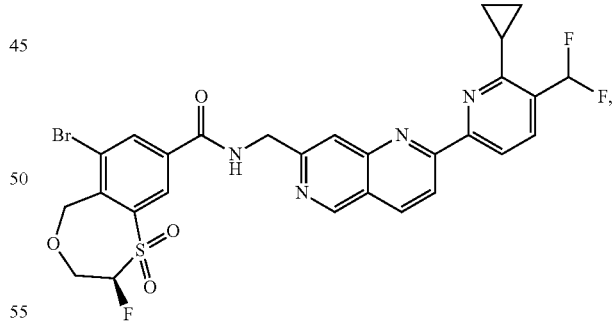
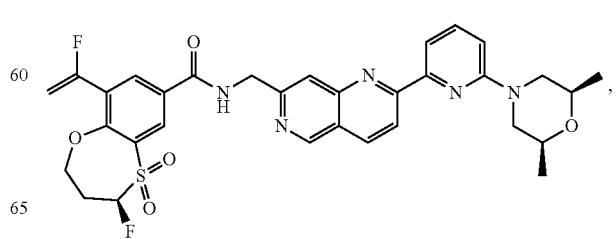

473
-continued
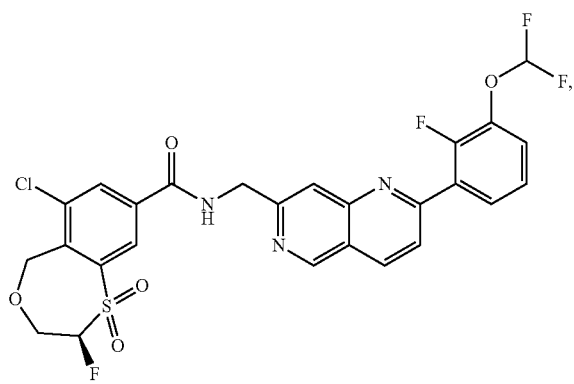
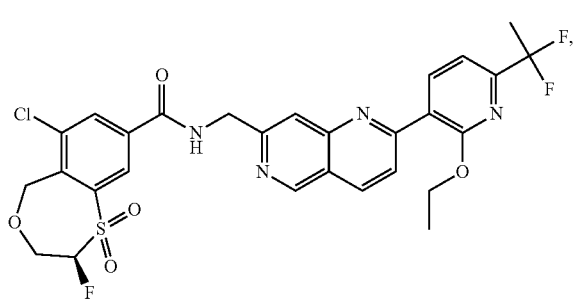
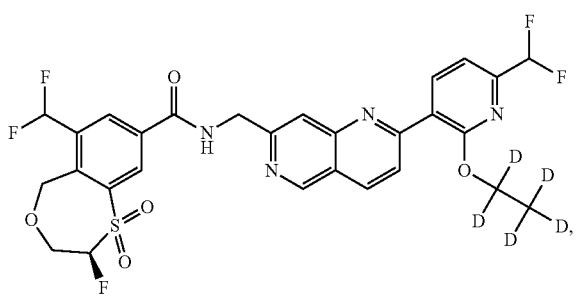
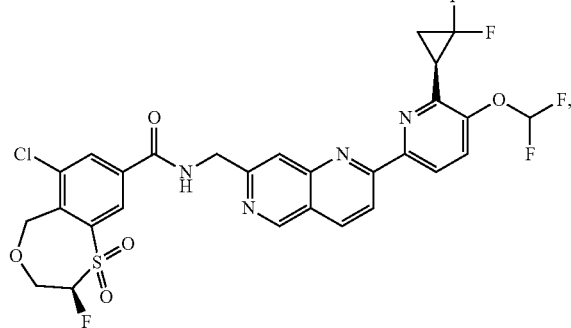
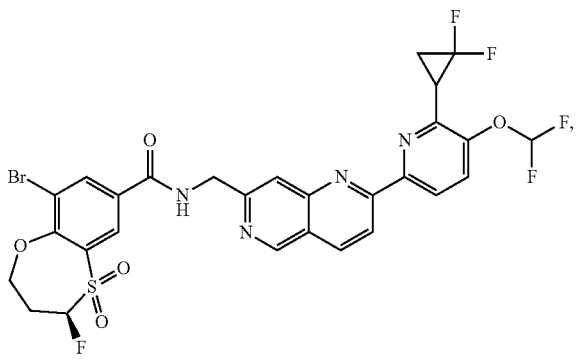
474
-continued
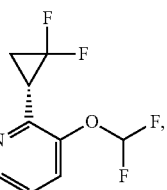
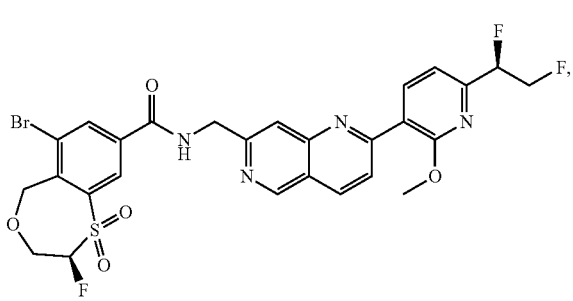
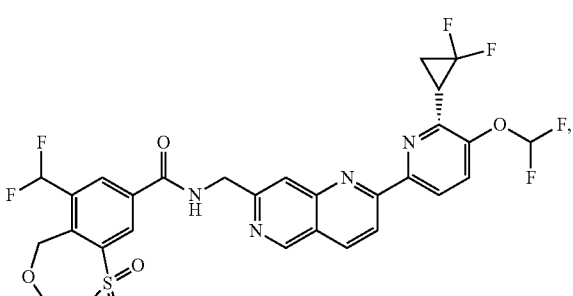
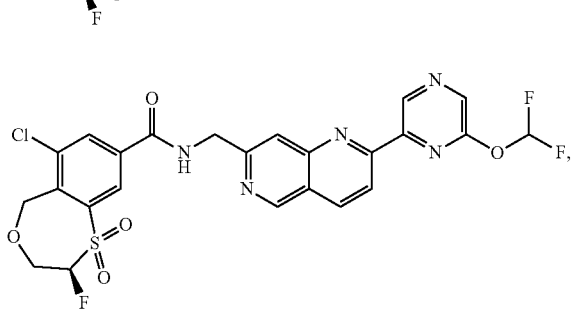
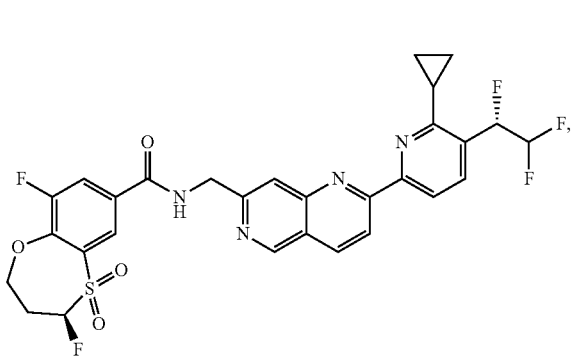

475
-continued
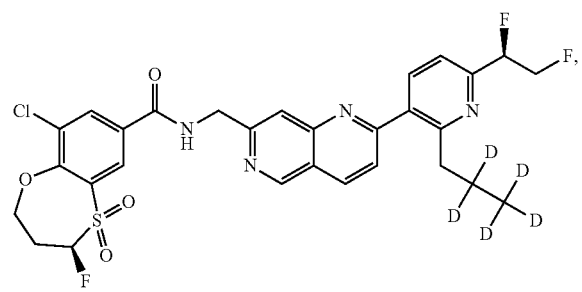
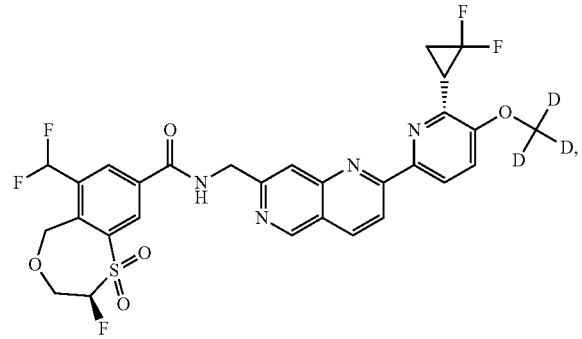
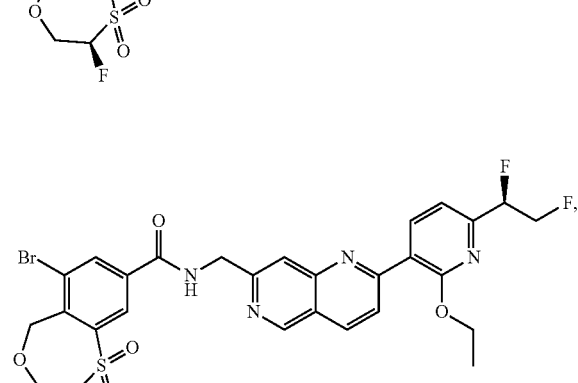
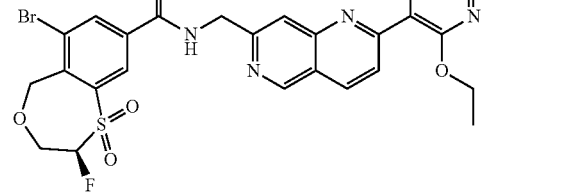
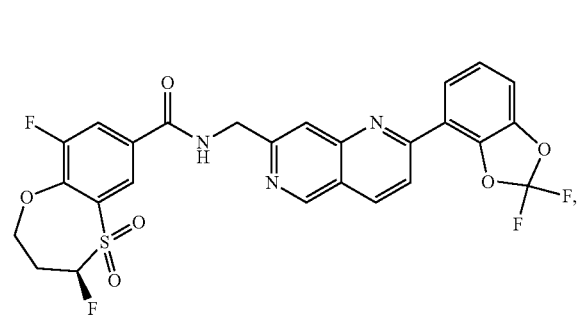
476
-continued
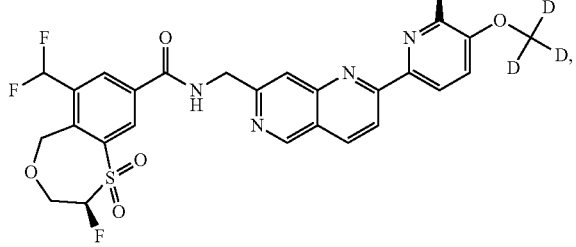
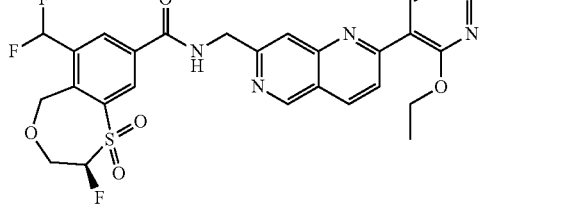
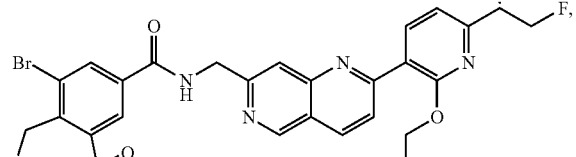
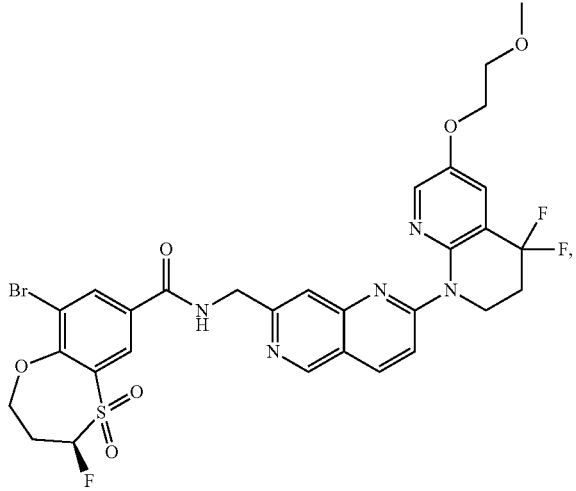
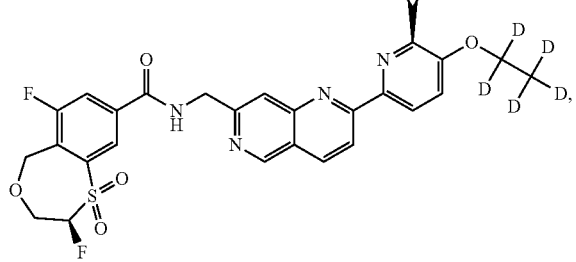

477
-continued
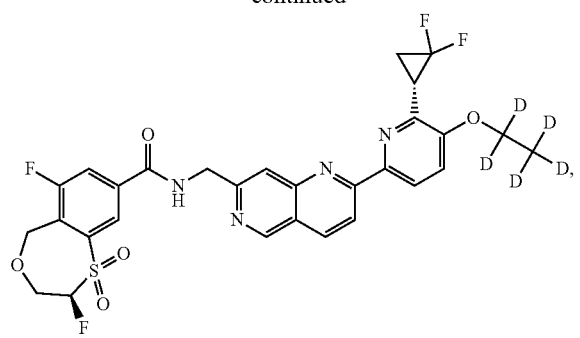
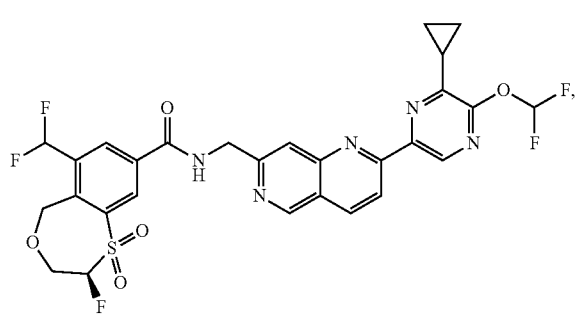
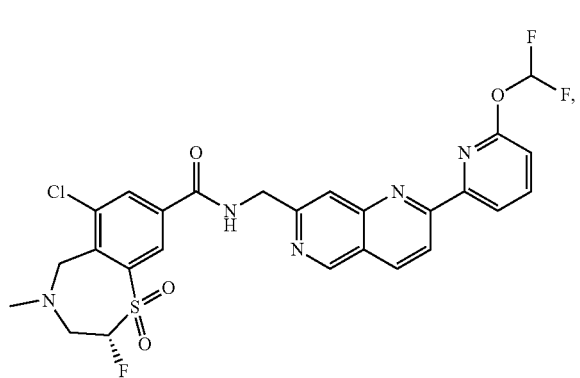
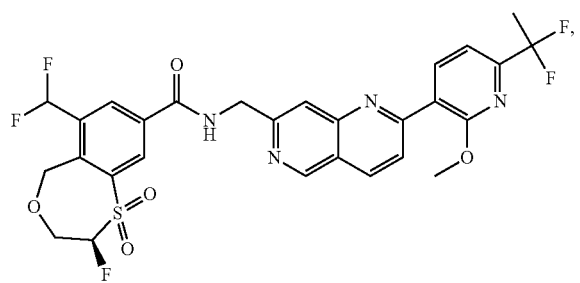
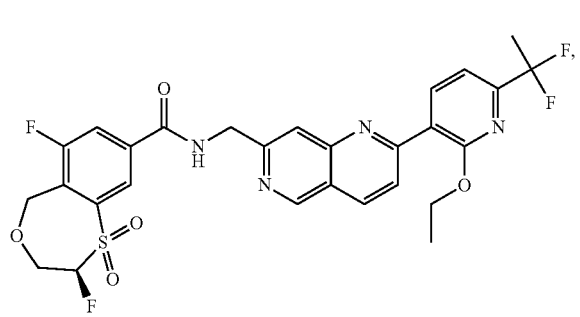
478
-continued
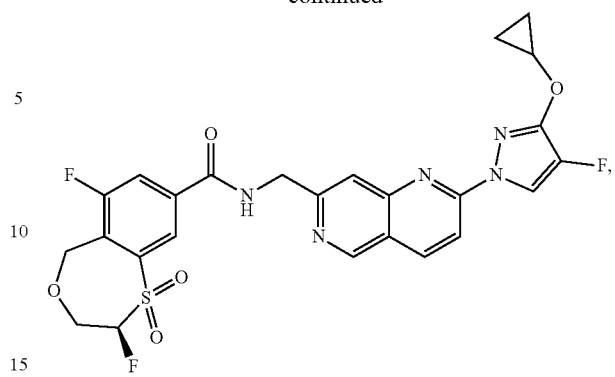
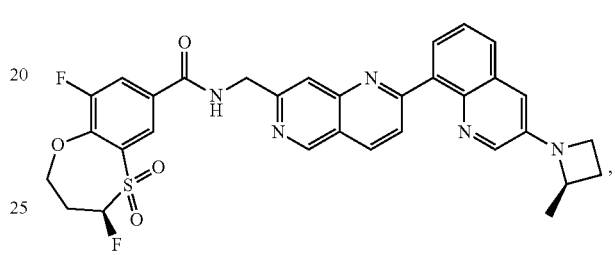
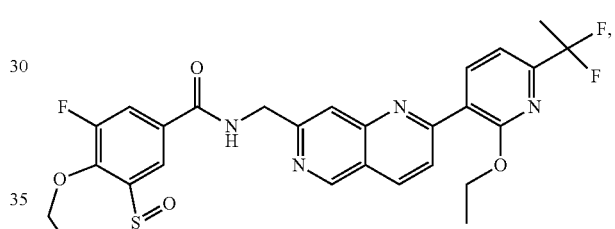
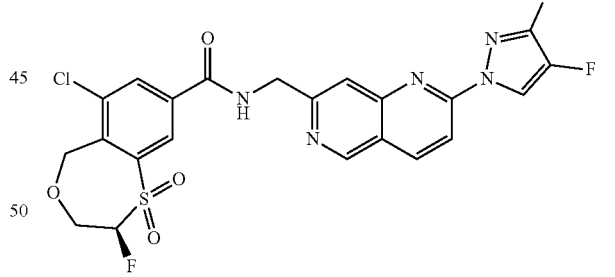
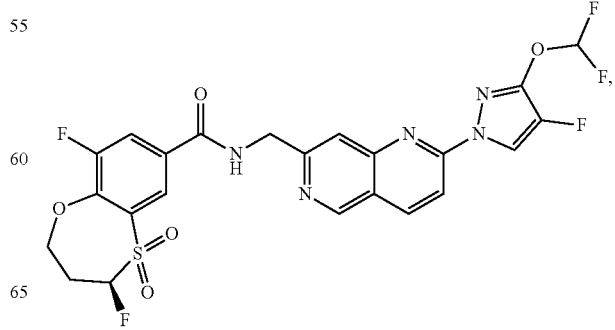

479
-continued
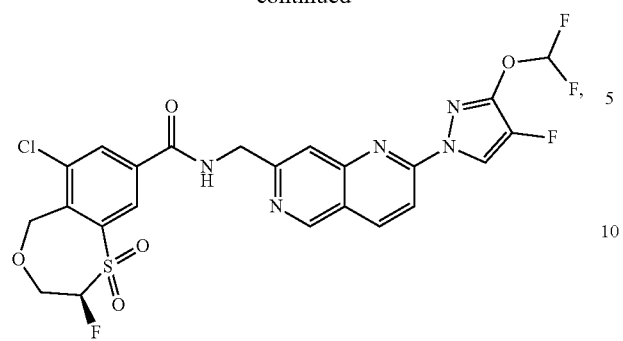
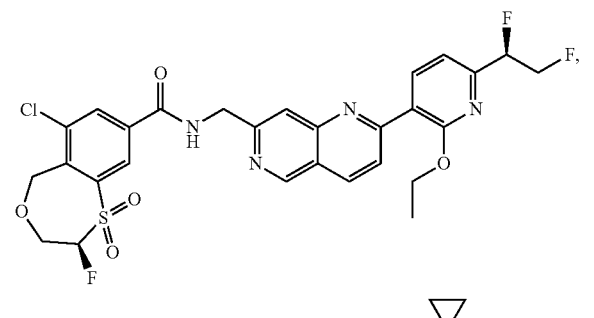
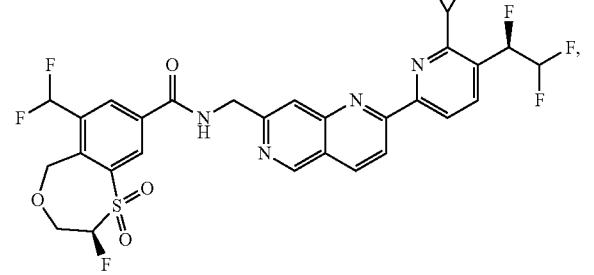
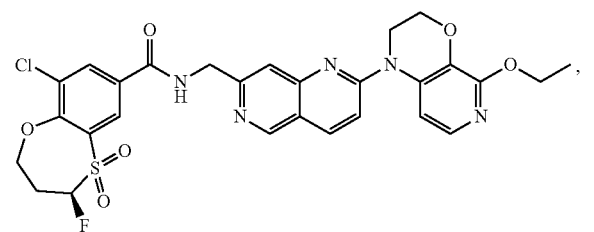
480
-continued
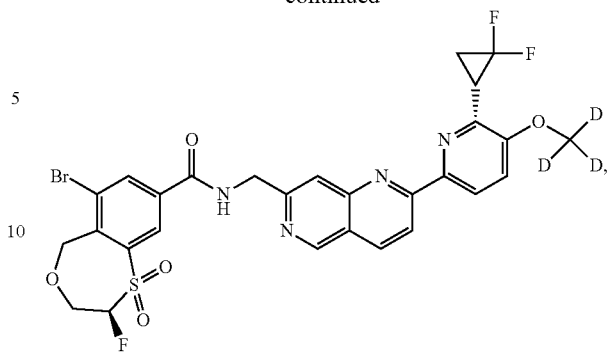
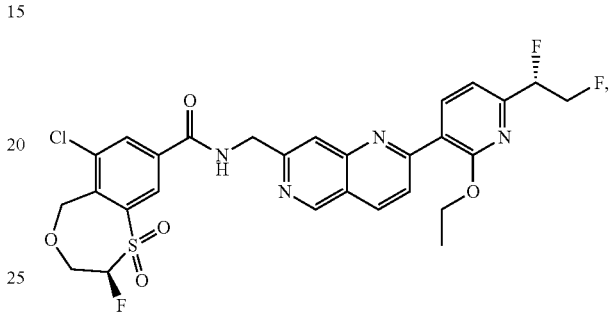
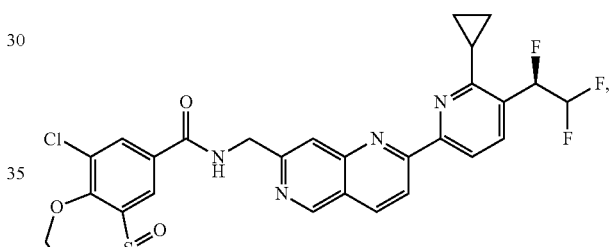
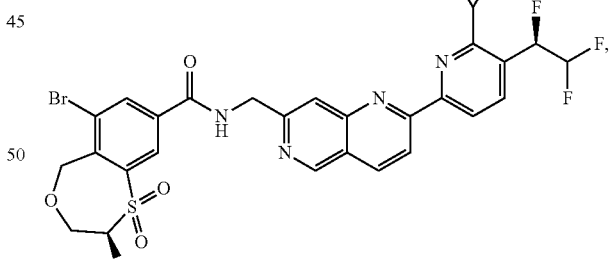
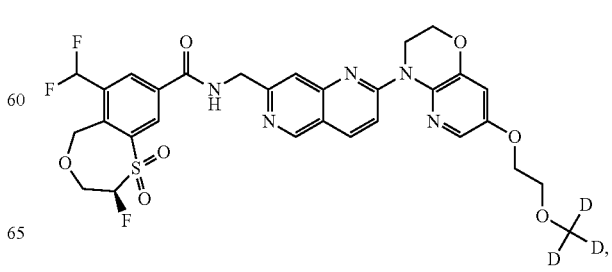

481
-continued
482
-continued
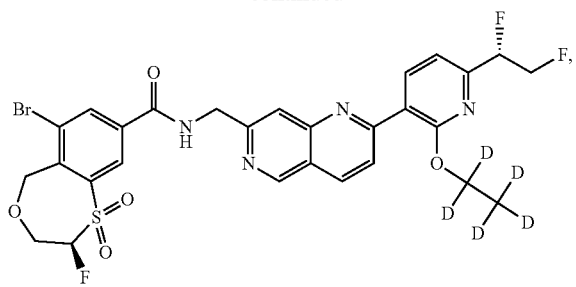
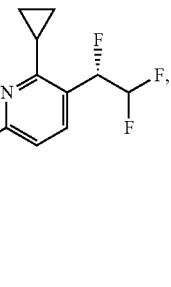

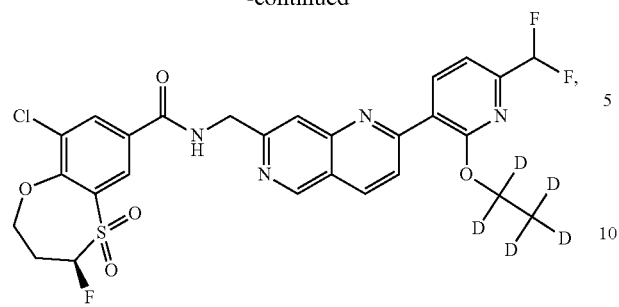
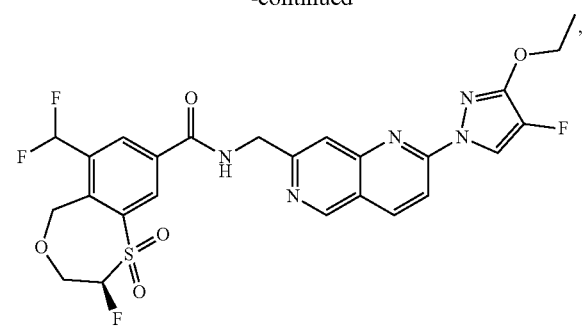
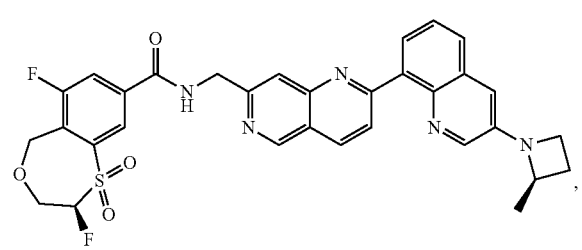
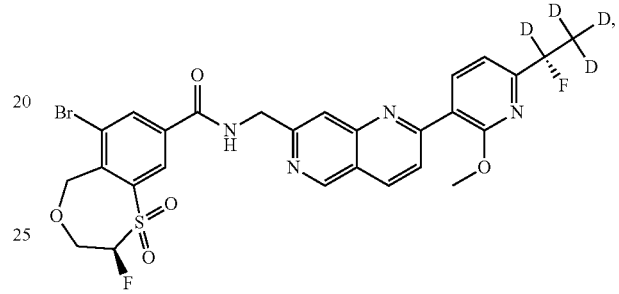
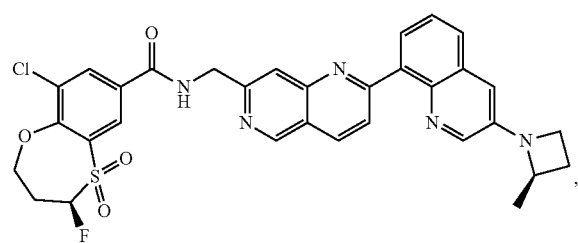
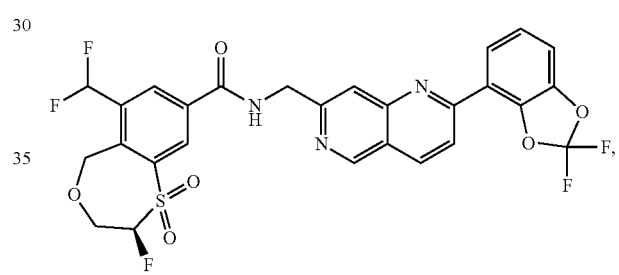
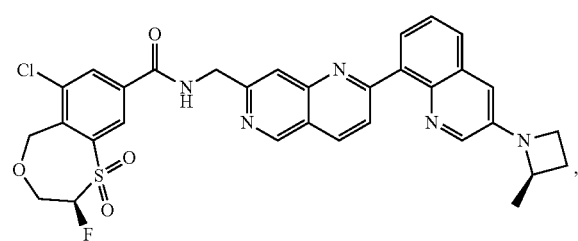
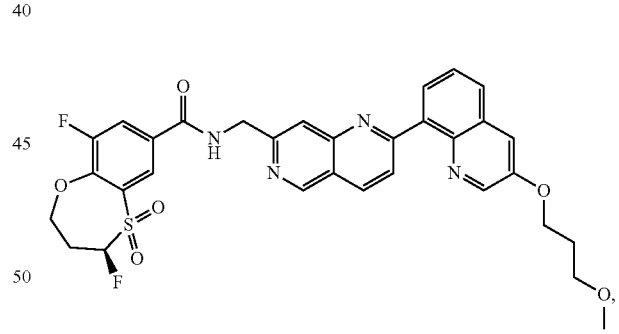
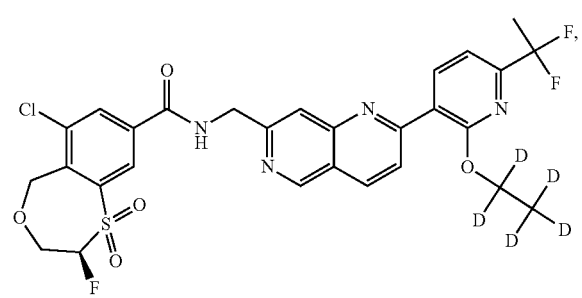
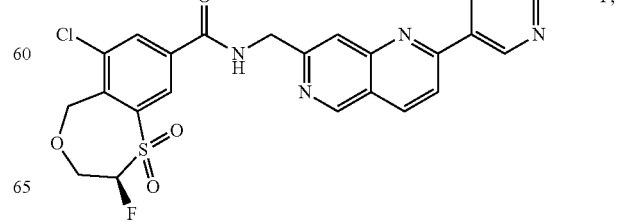

485
-continued
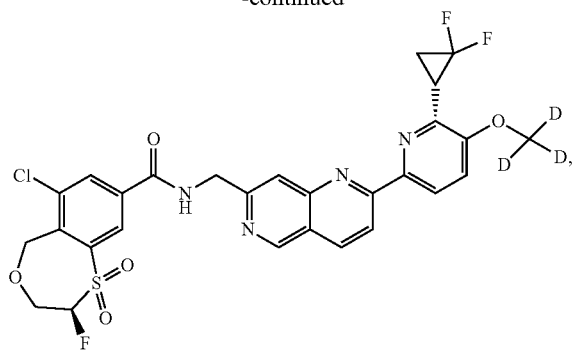
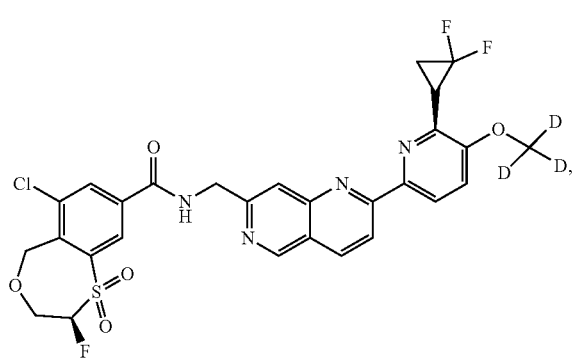
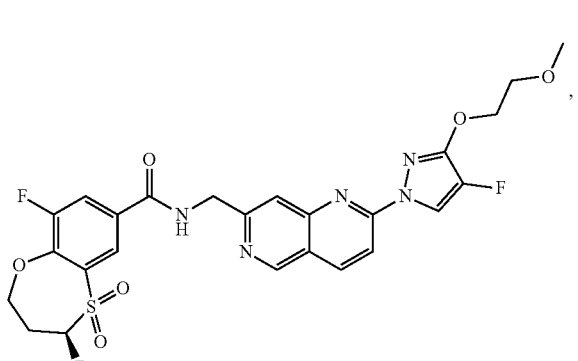
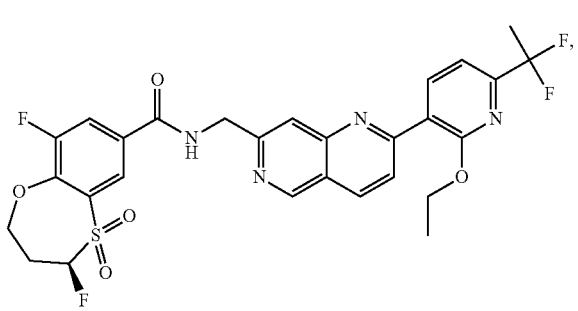
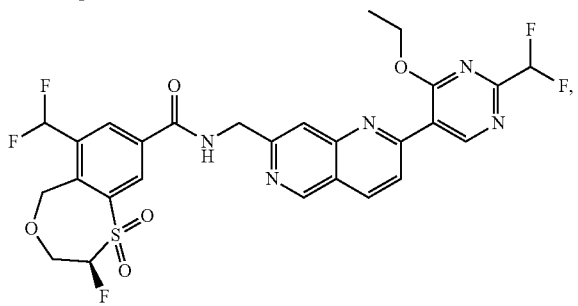
486
-continued
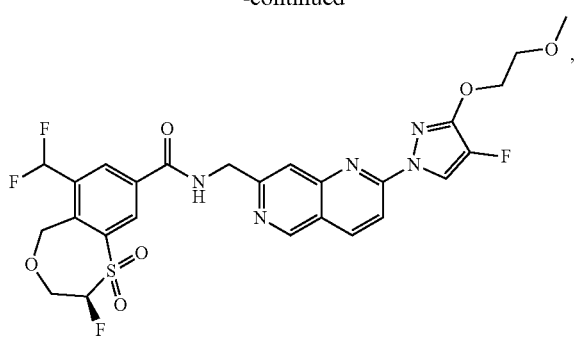
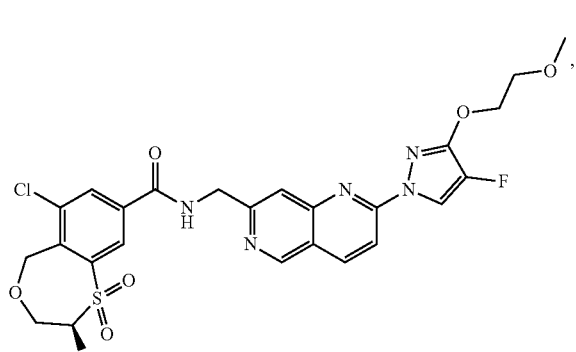
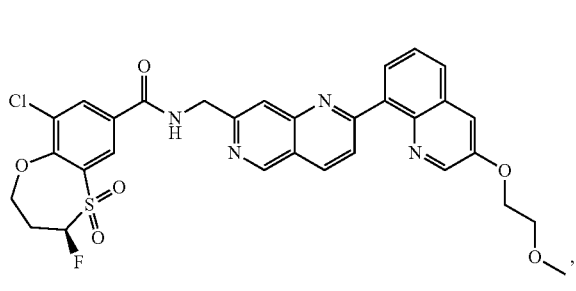
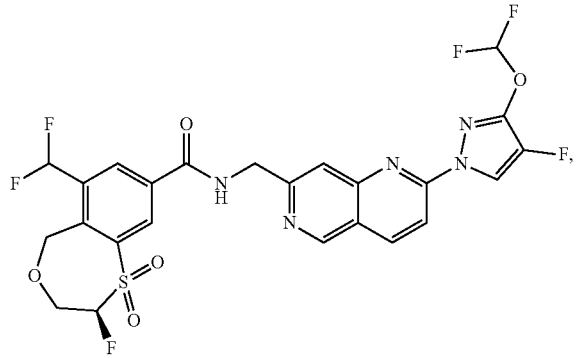
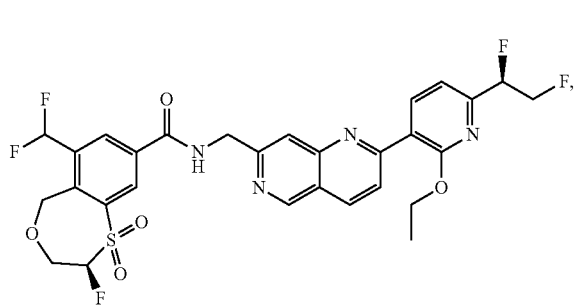

-continued

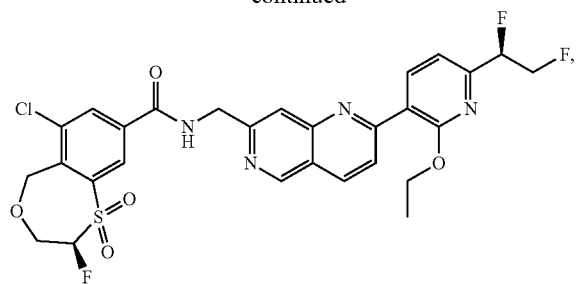

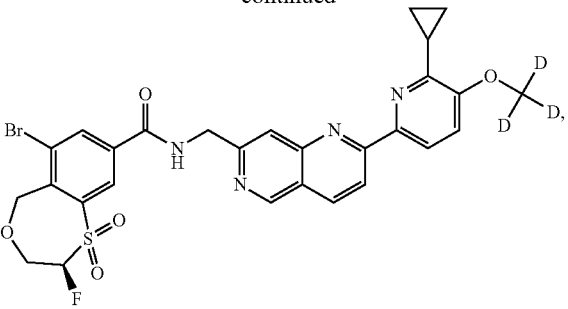

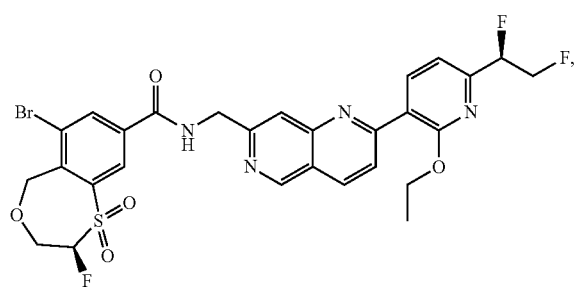

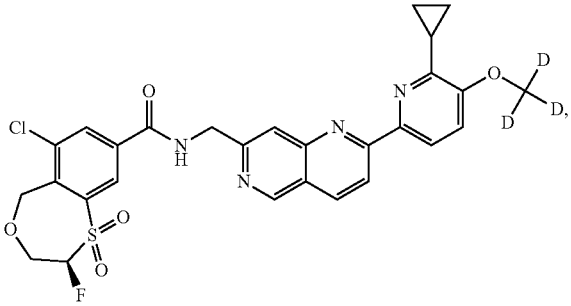

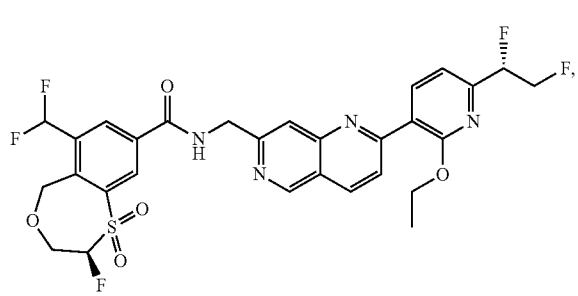

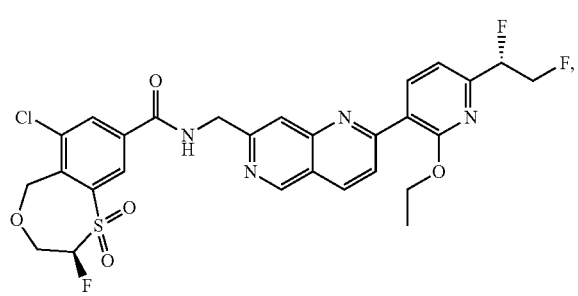

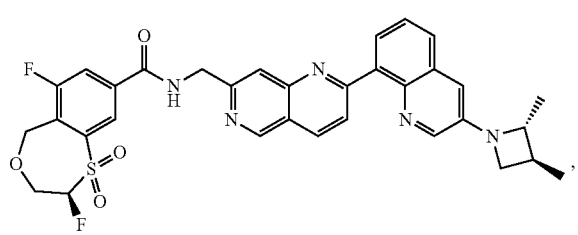

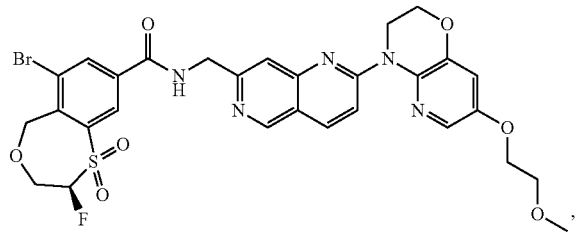

and pharmaceutically acceptable salts thereof.

88. The compound of claim 1, or a pharmaceutically acceptable salt thereof, wherein the compound has a ratio of BRG1 $IC_{50}$ to BRM $IC_{50}$ of at least 5.

89. The compound of claim 1, or a pharmaceutically acceptable salt thereof, wherein the compound has a ratio of BRG1 $IC_{50}$ to BRM $IC_{50}$ of at least 10.

90. The compound of claim 1, or a pharmaceutically acceptable salt thereof, wherein the compound has a ratio of BRG1 $IC_{50}$ to BRM $IC_{50}$ of at least 20.

91. The compound of claim 1, or a pharmaceutically acceptable salt thereof, wherein the compound has a ratio of BRG1 $IC_{50}$ to BRM $IC_{50}$ of at least 30.

92. A pharmaceutical composition comprising a compound of claim 1, and a pharmaceutically acceptable excipient.

93. A method of treating a BAF complex-related disorder in a subject in need thereof, the method comprising administering to the subject an effective amount of a compound of claim 1.

94. The method of claim 93, wherein the BAF complex-related disorder is cancer or a viral infection.

95. A method of treating a disorder related to a BRG1 loss of function mutation in a subject in need thereof, the method comprising administering to the subject an effective amount of a compound of claim 1.

96. The method of claim 95, wherein the disorder related to a BRG1 loss of function mutation is cancer.

97. A method of treating cancer in a subject in need thereof, the method comprising administering to the subject an effective amount of a compound of claim 1, wherein the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

98. The method of claim 97, wherein the cancer is non-small cell lung cancer, colorectal cancer, bladder cancer, cancer of unknown primary, glioma, breast cancer, melanoma, non-melanoma skin cancer, endometrial cancer, soft tissue sarcoma, or penile cancer.

99. The method of claim 98, wherein the cancer is non-small cell lung cancer.

100. The method of claim 98, wherein the cancer is soft tissue sarcoma.

101. The method according to claim 97, further comprising an anticancer therapy, wherein the anticancer therapy is a chemotherapeutic or cytotoxic agent, immunotherapy, surgery, radiotherapy thermotherapy, or photocoagulation.

102. The method according to claim 101, wherein the chemotherapeutic or cytotoxic agent is an antimetabolite, antimitotic, antitumor antibiotic, asparagine-specific enzyme, bisphosphonate, antineoplastic, alkylating agent DNA-Repair enzyme inhibitor, histone deacetylase inhibitor corticosteroid, demethylating agent, immunomodulatory, janus-associated kinase inhibitor, phosphinositide 3-kinase inhibitor, proteasome inhibitor, or tyrosine kinase inhibitor.

\* \* \* \* \*

UNITED STATES PATENT AND TRADEMARK OFFICE
CERTIFICATE OF CORRECTION

PATENT NO. : 12,139,487 B2  
APPLICATION NO. : 18/315526  
DATED : November 12, 2024  
INVENTOR(S) : Shawn E. R. Schiller et al.

Page 1 of 2

It is certified that error appears in the above-identified patent and that said Letters Patent is hereby corrected as shown below:

In the Claims

Claim 10, Line 67, delete "($R^6$)." and insert -- ($R^6$)). --.

Claim 13, Line 39, after " 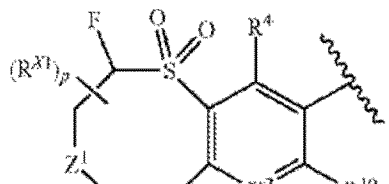 " delete ".".

Claim 16, Lines 60-65, delete " 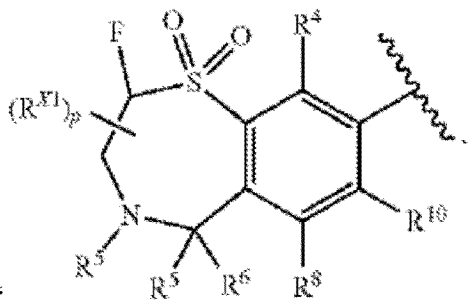 " and insert

-- 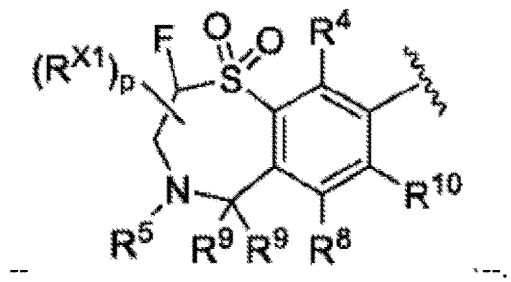 --.

Signed and Sealed this  
Twelfth Day of August, 2025

Coke Morgan Stewart  
*Acting Director of the United States Patent and Trademark Office*

CERTIFICATE OF CORRECTION (continued)
U.S. Pat. No. 12,139,487 B2

Claim 64, Line 10, delete " 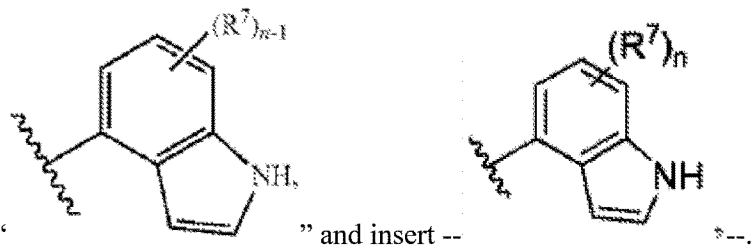 " and insert -- --.

Claim 101, Line 15, delete "radiotherapy" and insert -- radiotherapy, --.

Claim 102, Line 19, delete "agent" and insert -- agent, --.

Claim 102, Line 20, delete "inhibitor" and insert -- inhibitor, --.